(12) United States Patent
Chiu et al.

(10) Patent No.: US 10,501,816 B2
(45) Date of Patent: Dec. 10, 2019

(54) COMPOSITIONS AND METHODS FOR DETECTING HUMAN PEGIVIRUS 2 (HPGV-2)

(71) Applicants: Abbott Laboratories, Abbott Park, IL (US); The Regents of the University of California, Oakland, CA (US)

(72) Inventors: Charles Chiu, San Francisco, CA (US); Deanna Lee, San Francisco, CA (US); Michael Berg, Abbott Park, IL (US); George Dawson, Abbott Park, IL (US); Kelly Coller, Abbott Park, IL (US); Kevin Cheng, Abbott Park, IL (US); John R. Hackett, Jr., Abbott Park, IL (US); Matthew Frankel, Abbott Park, IL (US); Kenn Forberg, Abbott Park, IL (US)

(73) Assignees: ABBOTT LABORATORIES, Abbott Park, IL (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 4 days.

(21) Appl. No.: 15/893,120

(22) Filed: Feb. 9, 2018

(65) Prior Publication Data
US 2018/0230555 A1    Aug. 16, 2018

Related U.S. Application Data

(60) Division of application No. 15/642,992, filed on Jul. 6, 2017, now Pat. No. 9,938,589, which is a continuation of application No. 14/752,262, filed on Jun. 26, 2015, now Pat. No. 9,777,340.

(60) Provisional application No. 62/018,282, filed on Jun. 27, 2014, provisional application No. 62/107,782, filed on Jan. 26, 2015.

(51) Int. Cl.
| | |
|---|---|
| *C07K 14/005* | (2006.01) |
| *A61K 39/12* | (2006.01) |
| *C12Q 1/70* | (2006.01) |
| *G01N 33/569* | (2006.01) |
| *A61K 49/08* | (2006.01) |

(52) U.S. Cl.
CPC .............. *C12Q 1/701* (2013.01); *A61K 39/12* (2013.01); *A61K 49/085* (2013.01); *C07K 14/005* (2013.01); *G01N 33/56983* (2013.01); *C12N 2770/24022* (2013.01); *G01N 2333/183* (2013.01); *G01N 2469/20* (2013.01)

(58) Field of Classification Search
None
See application file for complete search history.

(56) References Cited

U.S. PATENT DOCUMENTS

| | | |
|---|---|---|
| 4,235,877 A | 11/1980 | Fullerton |
| 4,372,945 A | 2/1983 | Likhite |
| 4,474,757 A | 10/1984 | Arnon et al. |
| 4,603,112 A | 7/1986 | Paoletti et al. |
| 4,769,330 A | 9/1988 | Paoletti et al. |
| 4,777,127 A | 10/1988 | Suni et al. |
| 4,946,778 A | 8/1990 | Ladner et al. |
| 5,006,309 A | 4/1991 | Khalil et al. |
| 5,017,487 A | 5/1991 | Stunnenberg et al. |
| 5,063,081 A | 11/1991 | Cozzette et al. |
| 5,089,424 A | 2/1992 | Khalil et al. |
| 5,135,875 A | 8/1992 | Meucci et al. |
| 5,210,015 A | 5/1993 | Gelfand et al. |
| 5,241,070 A | 8/1993 | Law et al. |
| 5,242,828 A | 9/1993 | Berstroem et al. |
| 5,294,404 A | 3/1994 | Grandone et al. |
| 5,352,803 A | 10/1994 | Mattingly |
| 5,359,093 A | 10/1994 | Adamczyk et al. |
| 5,468,646 A | 11/1995 | Mattingly et al. |
| 5,496,925 A | 3/1996 | Mattingly |
| 5,538,848 A | 7/1996 | Livak et al. |
| 5,543,524 A | 8/1996 | Mattingly et al. |
| 5,573,904 A | 11/1996 | Mattingly |
| 5,593,896 A | 1/1997 | Adamczyk et al. |
| 5,605,798 A | 2/1997 | Koester |
| 5,695,934 A | 12/1997 | Brenner |
| 5,714,330 A | 2/1998 | Brenner et al. |
| 5,750,341 A | 5/1998 | Macevicz |

(Continued)

FOREIGN PATENT DOCUMENTS

| | | |
|---|---|---|
| EP | 0471293 | 2/1992 |
| JP | H0928386 A | 2/1997 |

(Continued)

OTHER PUBLICATIONS

Chivero et al., Human pegivirus RNA is found in multiple blood mononuclear cells in vivo and serum-derived viral RNA-containing particles are infectious in vitro, Jun. 1, 2014, Journal of General Virology, vol. 95, pp. 1307-1319.*
U.S. Appl. No. 11/671,956, Non-Provisional Application filed Feb. 6, 2007, Volkov, et al.
U.S. Appl. No. 11/697,835, Non-Provisional Application filed Apr. 9, 2007, Mattingly, et al.
U.S. Appl. No. 11/781,116, Non-Provisional Application filed Jul. 20, 2007, Battulga, et al.

(Continued)

*Primary Examiner* — Benjamin P Blumel
(74) *Attorney, Agent, or Firm* — Casimir Jones, S.C.; Jason Bond

(57) ABSTRACT

Provided herein are compositions, methods, and kits for detecting human *Pegivirus* 2 (HPgV-2). In certain embodiments, provided herein are HPgV-2 specific nucleic acid probes and primers, and methods for detecting HPgV-2 nucleic acid. In other embodiments, provided herein are HPgV-2 immunogenic composition compositions, methods of treating a subject with immunogenic HPgV-2 peptides, and methods of detecting HPgV-2 subject antibodies in a sample.

37 Claims, 138 Drawing Sheets

Specification includes a Sequence Listing.

(56) References Cited

U.S. PATENT DOCUMENTS

| | | |
|---|---|---|
| 5,777,324 A | 7/1998 | Hillenkamp |
| 5,783,699 A | 7/1998 | Mattingly et al. |
| 5,863,736 A | 1/1999 | Haaland |
| 5,912,148 A | 6/1999 | Eggerding |
| 5,945,283 A | 8/1999 | Kwok et al. |
| 6,043,031 A | 3/2000 | Koester et al. |
| 6,130,073 A | 10/2000 | Eggerding |
| 6,210,891 B1 | 4/2001 | Nyren et al. |
| 6,225,047 B1 | 5/2001 | Hutchens et al. |
| 6,258,568 B1 | 7/2001 | Nyren |
| 6,306,597 B1 | 10/2001 | Macevicz |
| 6,329,209 B1 | 12/2001 | Wagner et al. |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,833,246 B2 | 12/2004 | Balasubramanian |
| 6,870,042 B1 | 3/2005 | Schlievert et al. |
| 6,969,488 B2 | 11/2005 | Bridgham et al. |
| 7,108,974 B2 | 9/2006 | Ecker et al. |
| 7,115,400 B1 | 10/2006 | Adessi et al. |
| 7,170,050 B2 | 1/2007 | Turner et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,329,492 B2 | 2/2008 | Hardin et al. |
| 7,405,281 B2 | 7/2008 | Xu et al. |
| 8,017,322 B2 | 9/2011 | Ecker et al. |
| 8,017,743 B2 | 9/2011 | Ecker et al. |
| 2003/0170881 A1 | 9/2003 | Davis et al. |
| 2004/0018577 A1 | 1/2004 | Emerson Campbell et al. |
| 2005/0054078 A1 | 3/2005 | Miller et al. |
| 2005/0130173 A1 | 6/2005 | Leamon et al. |
| 2006/0160164 A1 | 7/2006 | Miller et al. |
| 2007/0036511 A1 | 2/2007 | Lundquist et al. |
| 2007/0072196 A1 | 3/2007 | Xu et al. |
| 2007/0077564 A1 | 4/2007 | Roitman et al. |
| 2007/0128133 A1 | 6/2007 | Eid et al. |
| 2007/0134128 A1 | 6/2007 | Korlach |
| 2007/0141598 A1 | 6/2007 | Turner et al. |
| 2007/0161017 A1 | 7/2007 | Eid et al. |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0009007 A1 | 1/2008 | Lyle et al. |
| 2008/0020401 A1 | 1/2008 | Grenier et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0248493 A1 | 10/2008 | Mattingly et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |

FOREIGN PATENT DOCUMENTS

| | | |
|---|---|---|
| JP | H09117287 A | 5/1997 |
| WO | WO 89/01973 | 3/1989 |
| WO | WO 93/03367 | 2/1993 |
| WO | WO 97/22719 | 6/1997 |
| WO | WO 1998/029747 | 7/1998 |
| WO | WO 99/51773 | 10/1999 |
| WO | WO 00/018957 | 4/2000 |
| WO | WO 00/056934 | 9/2000 |
| WO | WO 2006/084132 | 8/2006 |
| WO | WO 2012/075104 | 6/2012 |

OTHER PUBLICATIONS

U.S. Appl. No. 60/878,017, Provisional Application filed Dec. 29, 2006, Holets-McCormack, et al.

U.S. Appl. No. 61/142,048, Provisional Application filed Dec. 31, 2008, Collier, et al.

Adamczyk et al., "Chemiluminescence quenching of pteroic acid-N-sulfonyl-acridinium-9-carboxamide conjugates by folate binding protein," Bioorg. Med. Chem. Lett. 4: 2313-2317 (2004).

Adamczyk et al. "Chemiluminescent acridinium-9-carboxamide boronic acid probes: Application to a homogeneous glycated hemoglobin assay," Bioorg. Med. Chem. Lett. 16: 1324-1328 (2006).

Adamczyk et al., "Homogeneous chemiluminescent assays for free choline in human plasma and whole blood," Anal. Chim. Acta 579(1): 61-67 (2006).

Adamczyk et al., "Intrinsic factor-mediated modulation of cyanocobalamin-N-sulfonly-acridinium-9-carboxamide chemiluminescence," Bioorg Med. Chem. Lett. 14: 3917-3921 (2004).

Adamczyk et al., Linker-Mediated modulation of the Chemiluminescent Signal from N10-(3Sulfopropyl)-N—sulfonylacridinium-9-carboxamide Tracers Bloconjugate Chem. 11: 714-724 (2000).

Adamczyk et al., "Modulation of the Chemiluminescent Signal from N10-(3-Sulfopropyl)-N10-Sulfonylacridinium-9-carboxamides," Tetrahedron 55: 10899-10914 (1999).

Adamczyk et al., "Neopentyl 3-Triflyloxypropanesulfonate. A Reactive Sulfopropylation Reagent for the Preparation of Chemiluminescent Labels," J. Org. Chem. 63: 5636-5639 (1998).

Adamczyk et al., "Regiodependent Luminescent Quenching of Biotinylated N-Sulfonyl-acridinium-9-carboxamides by Avidin," Org. lett. 5: 3779-3782 (2003).

Adamczyk et al., "Synthesis of a Chemiluminescent Acridinium Hydroxylamine (AHA) for the Direct Detection of Abasic Sites in DNA," Org. Lett. 1: 779-781 (1999).

Adessi, et al. "Solid phase DNA amplification: characterisation of primer attachment and amplification mechanisms" Nucleic Acids Research 28(20): e87-(2000).

Astier, et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J Am. Chem. Soc. 128: 1705-1710 (2006).

Bennett, et al., Pharmacogenomics 6(4): 373-382 (2005).

Birren, et al., Genome Analysis vol. 1: Analyzing DNA, Table of Contents (1998).

Brenner, et al., "Gene expression analysis by massively parallel signature sequencing (MPSS) on microbead arrays," Nature Biotechnology 18: 630-634 (2000).

Burtis et al., "TIETZ Textbook of Clinical Chemistry and Molecular Diagnostics (Table of Contents) 4th Edition" xxi-xxxvi (2006).

Chandriani, et al., "Identification of a previously undescribed divergent virus from the Flaviviridae family in an outbreak of equine serum hepatitis" PNAS 110(15): E1407-1415 (2013).

Chivero, et al., "Human pegivirus RNA is found in multiple blood monoclear cells in vivo and serum-derived viral RNA-containing particles are infectious in vitro" Journ of Genl Virology 95: 1307-1319 (2014).

(56) References Cited

OTHER PUBLICATIONS

Cole, et al. "The EBV-Hybridoma Technique and its Application to human lung cancer" Monoclonal Antibodies and Cancer Therapy: 77-96.
Compton, "Nucleic acid sequence-based amplification" Nature: 350: 91-92 (1991).
Cote, "Generation of human monoclonal antibodies reactive with cellular antigen" Proc Natl Acad Sci USA: 80: 2026-2030 (1983).
Drexler, et al., "Evidence for Novel Hepaciviruses in Rodents" PLOS Pathogens 9(6): E1003438
Edgar, "MUSCLE: multiple sequence alignment with high accuracy and high throughput" Nucleic Acids Research 32(5): 1792-1797 (2004)
Emini, et al., "Induction of Hepatitis A Virus-Neutralizing Antibody by a Virus-Specific Synthetic Peptide" J of Virology, 55(3): 836-839 (1985)
Extended European Search Report issued in co-pending European patent application No. 15811499.1 dated Oct. 6, 2017.
Fisher-Hoch, "Protection of rhesus monkeys from fatal Lassa fever by vaccination with a recombinant vaccinia virus containing the Lassa virus glycoprotein gene" Proc Natl Acad Sci. USA 86: 317-321 (1989)_.
Flexner, "Attnuation and immunogenicity in primates of vaccinia virus recombinants expressing human interleukin-2" Vaccine 8:17-21 (1990).
Fridholm, et al. "Human pegivirus genotype 2 isolate h40048, complete genome" Genbank KP259281.1 Mar. 14, 2015.
GenBank Accession AHA61261, polyprotein [GB virus C], Nov. 19, 2013.
GenBank Accession AJS14317, polyprotein precursor [Human pegivirus genotype 2], Mar. 14, 2015.
Gibson et al., "A Novel method for real time quantitative RT-PCT" Genome Methods (Cold Spring Harbor Laboratory Press) 6(10): 995-1001 (1996).
Gluzman "SV40-transformed simian cells support the replication of early SV40 mutants" Cell (Cold Spring Harbor Laboratory) 23: 175-182 (1981).
Gomara, et al., "Diagnostic Value of Anti-GBS-C Antibodies in HIV-Infected Patients" Chem Biol Drug Des. 78(2): 277-282 (Jun. 20, 2011).
Harlow and Lane, Antibodies A Laboratory Manual—Immunoglobulins—Laboratory manuals, Immunochemistry—Laboratory manuals, Cold Spring Harbor Laboratory (1988).
Haugland, Handbook of Fluorescent Probes and Research Chemicals (1996).
Heid et al., "Real time quantitative PCR" Genome Methods (Cold Spring Harbor Laboratory Press) 6(10): 986-994 (1996).
Heringlake, et al., "GB Virus C/Hepatitis G Virus Infection: A Favorable Prognostic Factor in Human Immunodeficiency Virus—Infected patients?" J Infect Dis 177: 1723-1726 (1998).
Holland et al., "Detection of specific polymerase chain reaction product by utilizing the 5'-3' exonuclease activity of Thermus aquaticus DNA polymerase" Proc Natl Acad Sci USA 88: 7276-7280 (1991).
Huse et al., "Generation of a large combinatorial library of the immunoglobulin repertoire in phase lambda" Research Article 1275-1281 (1989).
International Search Report and Written Opinion for Application No. PCT/US2015/38067 dated Dec. 8, 2015 (20 pages).
Jameson, et al., "The antigenic index: a novel algorithm for predicting antigenic determinants" CABIOS 4(1): 181-186 (1988).
Julieta Trinks et al, Human pegivirus moledular epidemiology in Argentina: Potential contribution of Latin American migration to genotype 3 circulation: Argentine HPgV Molecular Epidemiology, Journal of Medical Virology, vol. 86, No. 12, Mar. 10, 2014, pp. 2076-2083.
Kapoor, et al., "Identificationof Rodent Homologs of Hepatitis C Virus and Pegiviruses" mBio 4(2): e00216-13 (2013).
Katoh, et al., "MAFFT Multiple Sequence Alignment Software Version 7: Improvements in Performance and Usability" Mol Biol Evol 30(4): 772-780 (2013).
Kearse et al., "Geneious Basic: An integrated and extendable desktop software platform for the organization and analysis of sequence data" Bioinformatics 28(12): 1647-1649 (2012).
Keys, et al., "Large scale screening of Human sera for HCV RNA and GBV-C RNA" Journ of Med Virology, 86: 473-477 (2014).
Keys, et al., "Large scale screening of human sera for HCV RNA and GBV-C RNA" Journal of Med Virology 86: 473-477 (2014).
Kohler and Milstein, Nature 256: 495-497 (1975).
Korlach et al., "Selective aluminum passivation for targeted immobilization of single DNA polymerase molecules in zero-mode waveguide nanostructures" PNAS 105(4): 1176-1181 (2008).
Kozbor, et al., "The production of monoclonal antibodies from human lymphocytes" Immunology Today, 4(3): 72-78 (1983).
Lindenbach et al., "Chapter 32: Flaviviridae: The viruses and their replication" Fields virology (Lippincott Williams & Wilkins) 991-1041 (2001).
Livak, et al., "Oligonucleotides with fluorescent dyes at opposite ends provide a quenched probe system useful for etecting PCR product and nucleic acid hybridization" PCT Methods and Application (Cold Spring Harbor Laboratory Press) 4: 357-362 (1995).
Luk et al., "Partially double-stranded linear DNA probes: novel design for sensitive detection of genetically polymorphic targets" Journal of Virological Methods 144: 1-11 (2007).
MacLean et al., "Application of 'next-generation' sequencing technologies to microbial genetics" Nature Reviews/Microbiology 7: 287-296 (2009).
Margulies et al., "Genome sequencing in microfabricated high-density picolitre reactors" Nature 437(15): 376-380 (2005).
Mattingly, "Chemiluminescent 10-Methyl-Acridinium-9-(N-Sulphonylcarboxamide) Salts. Synthesis and Kinetics of Light Emission," J Biolumin. Chemilumin, 6: 107-114 (1991).
Mattingly, et al., In Luminescence Biotechnology: Instruments and Applications: Duke, K. V. Ed.: CRC Press: Boca Raton, 77-105 (2002).
McCapra, et al. "Chemiluminescence involving peroxide decompositions," Photochem. Photobiol, 4: 1111-1121 (1965).
Michael G. Berg et al: "Discovery of a Novel Human Pegivirus in Blood Associated with Hepatitis C Virus Co-Infection". Plos Pathogens. vo 1 • 11. No. 12. Dec. 11, 2015 (Dec. 11, 2015). p. e1005325.
Mitra, et al., "Fluorescent in situ sequencing on polymerase colonies" Analytical Biochemistry 320: 55-65 (2003).
Murray, et al. "Codon usage in plant genes" Nucleic Acids Research 17(2): 477-498 (1989).
Needleman and Wunsch, "A General Methods applicable to the search for similarities in the amino acid sequence of two proteins" J Mol. Biol. 48: 443-453 (1970).
Neri et al., "Transferring automation for large-scale development and production of invader SNP assays" Proceedings of SPIE—The Intl Society—Third Wave Technologies, Inc. 3826: 117-125 (2000).
Pearson and Lipman, "Improved tools for biological sequence comparison" PNAS, 85: 2444-2448 (1988).
Piatek, et al., "Molecular beacon sequence analysis for detecting drug resistance in mycobacterium tuberculosis," Nature Biotechnology, 16: 359-363 (1998).
Polak and Van Noorden, Introduction to Immunocytochemistry, 2nd ed., Springer Verlag, N.Y. (1997).
Quan, et al., "Bats are a major natural reservoir for hepaciviruses and pegiviruses" PNAS, 110(20): 8194-8199 (2013).
Razavi, Stable and versatile active acridinium esters 11 Luminescence, 15: 239-244 (2000).
Razavi, "Stable and versatile active acridinium esters II" Luminescence, 15: 245-249 (2000).
REM! N. Charrel et al: "The Complete Coding Sequence of a European Isolate of GB-C/Hepatitis G Virus". Biochemical and Biophysical Research Communications. vo 1 • 255. No. 2. Feb. 1, 1999 (Feb. 1, 1999). pp. 432-437.
Rolland, "From Genes to gene medicines" recent advances in nonviral gene delivery, Critical Reviews in Therapeutic Drug Carrier Systems, 15(2): 143-198 (1998).

(56) References Cited

OTHER PUBLICATIONS

Ruby, et al., "Price: Software for the targeted Assembly of components of (meta) Genomic sequence data," G3—Genes, Genomes, Genetics, 3: 865-880 (2013).

Sambrook, et al. Molecular Cloning: A Laboratory Manual, Second Edition, Cold Spring harbor, N.Y. (1989).

Shendure et al., "Accurate multiplex polony sequencing of an evolved bacterial genome" Science 309: 1728-1732 (2005).

Smith and Waterman, Advances in Applied Mathematics, 2: 482-489 (1981).

Sohn, et al., "Capacitance cytometry: measuring biological cells one by one," PNAS, 97(20): 10687-10690 (2000).

Souza, et al., "Effect of primer selection on estimates of GB Virus C (GBV-C) Prevalence and Response to antiretroviral therapy for optimal testing for GBV-C Viremia," Journ of Clin Microbiol. 44(9): 3105-3113 (2006).

Stapleton, et al., The GB viruses: a review and proposed classification of GBV-A, GBV-C (HGV), and GBV-D in genus pegivirus within the family flaviviridae, Journ of Gen Virology, 92: 233-246 (2011).

Thelwell et al., "Mode of action and application of Scorpion primers to mutation detection" Nucleic Acids Research 28(19): 3752-3761 (2000).

Tyagi et al., "Molecular Beacons: probes that fluoresce upon hybridization" Nature Biotechnology 14: 303-308 (1996).

Tyagi et al., "Multicolor molecular beacons for allele discrimination" Nature Biotechnology 16: 49-53 (1998).

Tyagi, et al., "Multicolor molecular beacons for allele discrimination" Nature Biotech, 16: 49-53 (1998).

Voelkerding et al., "Next generation Sequencing: from basic research to diagnostics" Clinical Chemistry 55(4) 641-658 (2009).

Wallemacq, et al., "Evaluation of the New AxSYM cyclosporine assay: comparison with TDx monoclonal whole blood and emit cyclosporine assays," Clin Chem 45: 432-435 (1999).

Wilson et al., "The structure of an antigenic determinant in a protein" Cell 37: 767-778 (1984).

Yatscoff, et al., "Abbott TDx Monoclonal Antibody Assay Evaluated for measuring cyclosporine in whole blood" Clin Chem 36(11): 1969-1973 (1990).

Office Action of related Chinese Application No. 201580045396.4, dated Jul. 19, 2018, 14 pages.

Office Action of related Japanese Application No. 2016-575478, dated May 21, 2019, 3 pages.

* cited by examiner

FIG. 1A

Human Pegivirus 2 (UC0125.US) Nucleic Acid Sequence - SEQ ID NO:1

```
   1 GTGTTTGACA ATGCCATGAG GGATCATGAC ACTGGGGTGA GCGGAGGCAG CACCGAAGTC
  61 GGGTGAACTC GACTCCCAGT GCGACCACCT GGCTTGGTCG TTCATGGAGG GCATGCCCAC
 121 GGGAACGCTG ATCGTGCAAA GGGATGGGTC CCTGCACTGG TGCCATGCGC GGCACCACTC
 181 CGTACAGCCT GATAGGGTGG CGGCGGGCCC CCCCAGTGTG ACGTCCGTGG AGCGCAACAT
 241 GGGGTGTTCA ACTGATCAAA CCATTTGTTC TCCAGTCGTG GGGGCCGACT ATAATACCTC
 301 CTCGGGCTGC CGGGCCTTAA ATGGGAGCTA CCACTGCGGT GGTGGCTCTT GCCGGTCACC
 361 AAGTCGTGTG CAGGTTGCGA GACGAGTCTT GCAGCTGTGC GCATTCCTTG CGCTGATCGG
 421 ATCCGGTATG TGTTCGATCC GGTCCAAAAC TGAAGGGCGC ATTGAGTCAG GCAAATATT
 481 GCAGTCTCAG CGCGCATGTT GGACTGGTGA GGGTTTTGCT TTCTTTTCTA ACTGTTGCAA
 541 TCAATCTGAT ATTATGTGGT GTTTGCACCG TTGGTGTGTG ACAAGACCTG GCTGTTTAGT
 601 GTGCACGGGC AATGCCACCC ATCCTATCTG CTGGGACTAT CTTGGATCCG GTGTAAGTCG
 661 GCGGCCTGCA CGTCAATGG GTGAGGGAGC TGAAGCGCTT CTTCGCTTGA TCGGCATTGC
 721 AGGTTGGCTT GGACTGTTAG CTGAGTCCCT TGGTATGTCC GAAGTCTATG CAGCTATTCT
 781 TTGCTTTGGA TTTATTGCTT GGTATGGCTG GGGTATACCT AAAACACTGG TGTGCACCGT
 841 CTGCCCTGCA GTGAACATTT CTCCCTATAG CTTCTTATCT CCAGATACTA TCGCATTTGG
 901 TACGTGGATA CTACAACTAC CTGGTCTTTT GTGGCAAATG TTTGTTAGCT TCCCTATACT
 961 CTACAGCACT TGGATTCTTT GGTTGTTGCT CAGCGGCAAG ACTGTTGCTG TGATAGCAAT
1021 CCTTCTGGCT AGTCCTACGG TTATGGCGTA CAAGCATCAA TCTGAAAGCT ACCTCAAATA
1081 CTGTACCATA ACCAATACTT CAACTTCTAT GAACTGTGAC TGCCCCTTTG AACCTTTAC
1141 TCGCAATACT GAGTCTCGTT CTCCATACC TAGATTCTGT CCTGTTAAAA TCAATAGCTC
1201 TACATTTATT TGTTCATGGG GGTCGTGGTG GTGGTTTGCT GAAAACATCA CGCGTCCATA
1261 CACGGACGTT GGCATGCCAC CAGCACCGAT TTCCGCTTTG TGCTATATCT ATTCTAACAA
1321 TGACCCACCT CCTTGGTATC ATAACACAAC TATCATACCT CAGAACTGTC GCAACTCTAC
1381 GGTGGATCCT ACCACAGCTC CATGCCGTGA CAAGTGGGGC AACGCAACTG CTTGTATTCT
1441 TGACCGCCGG TCGCGGTTCT GCGGGGACTG CTATGGCGGT TGTTTCTATA CTAATGGTAG
1501 TCATGATCGA TCCTGGGATC GATGCGGGAT TGGTTACCGT GATGGACTCA TAGAGTTCGT
1561 GCAGCTCGGT CAGATTCGAC CTAACATCTC GAATACGACC ATTGAGCTCC TCGCTGGCGC
1621 CTCGCTTGTG ATCGCATCCG GTCTTCGGCC TGGGTTTGGT TGCAGCCGAG CGCATGGCGT
1681 GGTGCACTGC TATAGGTGTC CTTCATACCG TGACCTTGAA CAGTTTGGTC CTGGGCTTGG
1741 GAAATGGGTG CCATTGCCCG GCGAGCCTGT CCCGGAGTTG TGTATCAACC CTCAGTGGGC
1801 GAGGCGCGGC TTCCGGATGT CTAATAATCC TCTGAGCTTG CTACAGACCT TCGTTGAGGA
1861 CATTTTCCTA GCGCCTTTTT GTAATCCGAC GCCTGGCCGT GTACGTGTGT GTAACAATAC
1921 CGCTTTCTAT CCAAGAGGAG GCGGCTTTGT GCAGCTCATC GGGGACGTCC AGGTGCTAAC
1981 CCCTAACACT GCATCTTTAC ACTCTCTGCT GACTTTGATA TCTCTTATCT TGTTGGTGTG
2041 TGTTGTTTCT GGTGCGCGAT TCGTTCCACT AATAATCATA TTTTTCTGGA GCGCGCGCCA
2101 TGTATATGCT TCTTGTTACT TAAGCTGTGA TTGGGCTGTT TGCAACGATG CGTTCTGTTT
2161 CACATCTGGC ACTTGTGCCA CCTTCAATGA CGTCTTGTGT CTGCCGGTTG CGACGCGCAT
2221 ATCGTCCTGT GGTCATGCTG TGCCACCTCC CGACCGTGGT TGGGAGGTGC CTGCGGCGAT
2281 GTCATGGGTG ATTTCGCGGA CTACTGGCCT GACGTTCGAT GTCTTTTCCT TCATTCAGTA
2341 CCTTCCTACT GTGCCTGGCA ACAACACCAA TATCATTTAC TGTGGTGAAC CAACCTTCCT
2401 CGGGGACATC ACGGGCATCT ATTGGCCTTA CTTTTTGCCT GGCGCAATCC TCTTGTACTT
2461 GACTCCCTTC CTAGGTTAA GGTTAATGCT TGCCGGCTTC AATATAGATG GCTTGTTTCC
2521 CATACGGCAT GCCACGGCTG CACTGAGGTT TTCGACTTCT CGTGTGACCT TGTGTGTCGT
2581 AGTTGCTTTC CTAATCTATA TATTATCTCA CCCTGTTAAT GCTGCGCTCA ATAGAATGTT
2641 CTTAGCATCT GCAAATTTAG AGATGATCTT ATCTTTTGAT ACCTATCATG AGACTGTTCT
2701 TTATATCCTT TGTCTATTGC TCTACCTCCA GGTGTCGCCC CGTGCGGGCT TGGCCGCTAT
2761 GGTGGCCATC AAGCTATCTC GAGGCCTGTT ATTCGCTGTG GTGTTGGCGC ACGGTGTGTG
2821 CCGACCTGGG CGGGTATTTG GTCTTGAGGT TTGCGCGGAC ATCTCTTGGT TGGTGGAGTT
2881 TACTGGCAAT TGCACTTGGT ACATGTCCTG TGTCTTCTCT TTTTGGTGCG CAGTGTTTGC
2941 CTTCACCAGT CCACTTGGAC GACACTATAA GATTCAGATC TATCGGTACT GGGCGCAGGT
3001 CTATGCCAGA CTCGTCCTCG CTGTCGGTTG TGGTCCTCTC GGTCGAGAGT TCCATTTCCG
3061 TGCAAGTGTG GGCGTGCTGT GGTGTGGAGC TTGCATGCTC TGGCCCCGTG AGTGCTCTGA
3121 AATCAGCCTG GTCTTCATTC TGTGTGCTCT GACAGTGGAC ACCATAGACA CATGGTTAGT
```

FIG. 1B

```
3181 AGCGTGCTTG TCCGCAGGGC CGAGTGCGCG AACCCTTGCA ATTCTGGCCG ATGACATGGC
3241 GCGCATTGGT GACCACCGGG CGTTGCGCGC CGTGTTACGT TGCTTTGGAT CACGCGGCAC
3301 ATACATATAC AACCACATGG GCCAAGTCTC GGAACGGGTG GCGCAAGCAG TCAGGGATCT
3361 CGGCGGTTGC TTGGAACCAG TCGTGTTGGA GGAGCCCACC TTTACTGAGA TCGTGGATGA
3421 CACAATGAGT TTGGTGTGTG GACAATTGCT TGGAGGTAAA CCTGTGGTGG CCCGCTGCGG
3481 CACGCGTGTC TTGGTGGGAC ACCTCAACCC TGAAGATCTG CCACCTGGTT TCCAGCTGAG
3541 TGCTCCGGTG GTTATTACCA GGCCAAGCAT TGGTACGTGG TCCTTCCTTA AGGCGACACT
3601 CACAGGGCGT GCTGAAACAC CAGGGTCCGG CCAGATCGTG GTGTTGTCTT CCCTGACAGG
3661 TCGGTCAATG GGTACCGCAG TGAATGGCAC ACTGTATGCG ACCGGCCATG GTGCCGGCGC
3721 GCGCGGCCTA GCCACGTGCG CTGGTTTGAG GACGCCACTT TACACGGCAT TATCTGATGA
3781 TGTCGTGGCC TATTCTTGCC TTCCGGGCAT GAGTTCCCTA GACCCTGCT GCTGTTCGCC
3841 GAGCCGGGTT TGGGTGATGA ATAACAACGG AGGGTTGGTG TGTGGCAGAG TGGAGAATGA
3901 CGACGTCTGT TTGGACTGTC CCACGCACAT AGATCAACTG CGGGGTGCTT CGGGCTCACC
3961 AGTTTTGTGT GATCACGGTC ATGCATACGC GTTGATGCTC GGTGGTTACT CTACCAGTGG
4021 TATTTGTGCA CGCGTCCGGA CGGTCCGGCC ATGGCATAAC GCCTATTCCT CCTCGGGGGG
4081 GCAAGGCGGA ATGCAGGCGC CAGCTGTGAC ACCAACATAC TCTGAAATCA CCTACTATGC
4141 CCCTACTGGT TCTGGTAAGT CAACAAAATA TCCAGTGGAC CTAGTCAAAC AGGGACACAA
4201 AGTATTGGTC CTTTTACCAA GTGTGGCTGT AGTCAAAAGT ATGGCCCCTT ATATTAAGGA
4261 GACATATAAG ATCAGACCCG AAATTAGAGC TGGCACAGGT CCTGACGGTG TGACGGTCAT
4321 CACTGGTGAG AACTTGGCGT ACATGACCTA TGGCCGCTTC CTTGTGGATC CGGAGACGAA
4381 TCTGCGGGGC TATGCTGTAG TCATTTGCGA CGAGTGTCAC GACACATCAT CCACCACGCT
4441 ACTCGGCATT GGCGCAGTGC GCATGTATGC CGAGAAAGCT GGAGTGAAGA CCGTTGTATT
4501 CGCCACAGCC ACCCCTGCTG GCATTCAAGT ACAGTCACAT TCCAACATTG ATGAATACTT
4561 ATTGACTGAC ACAGGCGACG TGGAATTTTA CGGCGCCAAA ATCAAAATGG ACAACATCAG
4621 AACTGGTAGA CATGTTATCT TTTGCCACTC GAAGGCCAGG TGTGCGGAAC TAACGCAGCA
4681 GCTCTCCGGC CTTGGCATTC GTGCAGTGAG TTTTTGGCGC GGCTGTGACA TCAAAACCAT
4741 TCCCGCCTCA GACTCCATTG TTGTGGTGGC AACTGATGCA TTGTCCACGG GCTACACAGG
4801 AAACTTTGAT TCGGTCATCG ACTGCGGGTG TTGCGTGGAG CAAACTGTGA CAATTGACAT
4861 GGACCCTACG TTCTCCATCT CGGCCCGAGT GGTGCCATGT ACTGCTGCAT TGCGCATGCA
4921 GCGGCGCGGA CGTACCGGTC GTGGTAGAAG GGGAGCGTAC TACACAACTT CTCCAGGAGC
4981 AGCACCCTGC GTCAGCGTTC CCGATGCTAA CGTCTGGCAA GCAGTGGAGA GCGCCATGGT
5041 CTTTTATGAT TGGAGTGCTA CCAGGATACA ACAGTGCCTG GCGGCATACC ATGATTTGGG
5101 GTGCACACCA CGCATCAGCT GTGACCCACA CACTCCAGTG CGGGTGATGG ACACACTGAG
5161 GGCGTACCTG CGCAGACCTG AGGTGACGAC TGCAGCTCTC GCAGGAGAGC AGTGGCCGCT
5221 GCTTTATGGT GCGCAGTTGT GCATCTGCAA AGAGACCGAG GCCCACGGTC CTGATGATAG
5281 CATCAAGTGG AAGTGCTTAC TCAACAACAG TAACAAAACA CCCCTGTTGT ATGCCTTAGA
5341 CAATCCTACA CTGGAATTCA CAACCCAACA TGACTTGACT CGCCGTATAG CCGGCGCTCT
5401 ATCGAGCACA GTGTTCGTGG AGACAGGCTA CGGCCCCATC CTCCTTGCTG GCGCCGCTTT
5461 GGCTGCCTCC TTCGCCTTTG CGGGCGCCAC TGGAGCTTTA GTGCCGTCGG CTGTTTGGAG
5521 CGTTGAGGTC AGGCCTGCTG GCGTGACCCG TCCCGACGCG ACAGACGAGA CCGCGGCCTA
5581 CGCACAGCGC TTGTACCAAG CCTGTGCAGA TTCAGGAATT TTCGCCAGCT GCAGGGTAC
5641 GGCGAGTGCG CGCTGGGCA AACTGGCCGA CGCCAGTAGG GGTGCTAGTC AATATCTGGC
5701 AGCCGCGCCT CCTTCACCCG CCCCCCTGGT ACAGGTGTTG CAGTTCCTCG AGACCAACTT
5761 TAGCTCCATT GCATCTTTCG GCCTGCTCTG TGCTGGCTGC CAGGCTGGCG AGTGCTTCAC
5821 TGCGCTTGCT GGCTTGGTGT CCGGTGCTAC AGCTGGCTTG GGGGGTGCCC ATAAGTGGCT
5881 ATTAGCTATT GCAGGAACTT GGCTGGTTAG CTTGCAGACC GGGTCCCGTG GCGGCATGGT
5941 TGCGGGCCTC TCGATTCTAG CGGGCTGTTG CATCGGTAGT GTCACCGGGC TTGACTTCCT
6001 GTTTGGGTGC CTTACAGGTT GGGAAGCCGT GGTCGGCGCT GCGGTTGCGA CACAGAAGAT
6061 CTTGTCTGGT TCAGCTGATA TGACCACTCT GGTAGATCTC TTACCTGCTC TTTTCTCCCC
6121 CGGTGCCGGC ATAGCTGGCA TCGTGCTTGT CTTCATCTTA AGCAATTCAA GTGTAACCAC
6181 ATGGGCTAAT CGGCTATTAT CCATGTGTGC CAAACAAACC ATTTGTGAAA ACTACTTCTT
6241 AAGTGAAAGA TTTGGCCAAC AATTAAGCAA ACTTTCCCTG TGGCGCTCTG TGTACCATTG
6301 GGCGCAGGCA CGTGAGGGAT ACACACAGTG CGGCGTGATC AGCGGGATCT GGAGCTTCGC
6361 CTTGTCGCATT CTACGCGCTG TGTGGGATTG GGCGGCCAAG CATGTGCCAC GGTTCCGTGT
6421 GCCTATGATT GGCTGCTCAC CTGCGTGGTG CGGGCGCTGG CTTGGTACCG GCACCTTGTT
```

FIG. 1C

```
6481 GACCACCTGT GCGTGTGGAG AACGTGTGTC CCTTCAGTGC CTTTGCTCAA CATCTGACCC
6541 ACAACTCAGT GTGGGCCGTT GGTGTCGGTG TAGTTGGAGT GTTGGGTTCC CATTCAACCC
6601 GACTACGACA GGCACTGGCA CCTTACGGCC GGACATCAGT GACGCCAACA AATTGGGTTT
6661 CCGGTATGGC GTTGCCGACA TCGTGGAGCT AGAGCGGCGG GGCGACAAAT GGCACGTCTG
6721 TGCAGCATCA TGTTGCTTGG ACCGGGCCAG CGTTGCATCC GCTGTGAAGG CCCCACCGGT
6781 CACGGCTAAT GGTATACCTA TTAATAGCTT TTCTCCACCA CAAACTTATT GCCTATCTCT
6841 CTGTTCCTTT GATACAGTTT GCATGTCTAC TAACTTATGT AACCAGCTA AGACCCTGAG
6901 TGTGTGCCAA GAGGAGGCGG TTGAGCTGCT GGAAGAGACA GTTGACACAG CACAAGTAGT
6961 GATGAGCCAA AATCTGGCAG CGCGTAGACG CGCTGAGTAT GATGCATGGC AGGTTCGCCA
7021 AGCAGTTGGC GACGAGTACA CGCGTTTGGC AGACGAGGAT GTTGACATGA CAGCGTCGGT
7081 GAAACCCCCA GTGGCCAGGG CTGCTGTGGG TAGCTCAACG TTGGATGATG TTAGCGTGCT
7141 GACTGTCTTA CGCGAACTCG GCGACCAGTG CCAAAATGCT ATCAAATTTG TAGTTCAGGC
7201 GGCTTCACGG TTTGTTCCAC CAGTGCCCAA GCCACGCACG CGTGTCTCGG GTGTCTTGGA
7261 GCGCGTGCGC ATGTGCATGC GCACGCCTCC AATCAAGTTT GAGGCCACCG CAGTACCAAT
7321 TCATAATATA ATCCCAGAAG AGTGTCATAT TGTGCTACGC TGTACCGGCT GTTGTGACCA
7381 GGCCTTGACC GTTCCGTACG GCACTTGCTC TCTGACTTTA ACCAAATATT TGACTAACAA
7441 ACACAGTCAC TATATTCCAA AAGAGAAGAT AGAAGAAGAC ACAGAAATAG CTGTCATTTG
7501 CGCCGTACCA ACAAAGCGCG CAAGTAAACT TATCACTTTC AGAGCAGGTG ACCGATCAGT
7561 CTCATGTTGT CACCCCTTGC AAACTCCTAT TAGGGCCCTG CTTCAAAAGT ATGGGTTACC
7621 TATTGGGAAG TGGTCCGACT GCAACGGGCC CCTTGGTGAC GACGCCCGAG TCTGTGACGT
7681 CAATGGAGTG ACAACTTATG AACCATGCAT GCAATCCTAC AATTGGTTCC GATCGATTGT
7741 GGCACCAACA ACCCCACCTT TACCTGCAAC CCGGAGCGTG GCTGGCATTT TGCGCGCAGA
7801 CACATCGCGC GTCTACACCA CAACAGCGGT TGATGTCTCC GAGCGGCAGG CTAAGGTCAC
7861 GATTGATCAA AAGTCAGCCA AGGTGGACCA GTGTCTCCGA GACACATACA ATTGCTGCCT
7921 TGCCAAGGCA AAGACCTTCA GACAATCTGG CATGTCATAT GAGGATGCTG TGTCAAAGAT
7981 GCGCGCAAAC ACCACGCGTG ATCATAACAA CGGCATCACT TATACAGATT TGGTCTCTGG
8041 ACGCGCAAAA CCTGTCGTTC AGAAAATTGT AGATCAGATG CGCGCTGGAG TGTACGACGC
8101 TCCAATGCGC ATTATTCCAA AACCTGAAGT GTTTCCACGA GACAAGTCAA CACGGAAGCC
8161 ACCACGGTTC ATCGTTTTCC CTGGGTGTGC CGCACGAGTC GCGGAGAAAA TGATCCTGGG
8221 CGATCCTGGC GCGATAACCA AGCACGTGCT AGGTGATGCC TACGGGTTTG CCACTCCGCC
8281 GCATGAGCGC GCGCGCCTAC TGGAACAATG GTGGAACCGC GCAACGGAGC CACAAGCTAT
8341 CGCGGTTGAT GCAGTCTGCT TTGATAGCAC CATCACGGCA GAGGACATGG ATCGTGAGGC
8401 CAACATCGTG GCTGCAGCGC ATACGGACGC GGAAGGTGTT CACGGCCTAT ACAATTATTA
8461 CAAAAGAAGC CCCATGTGTG ATATCACAGG AAAAGTTGTC GGGGTGCGTA GCTGTCGAGC
8521 CTCAGGTACG CTTACAACAA GCAGTGGCAA CACGCTTACT TGCTACCTCA AGGTTCGCGC
8581 AGCTTGCACG CGCGCCGGCA TTAAACCAAT TGGCTTACTA ATTCATGGAG ATGACACCCT
8641 CATTATCACA GAACGTTGCG CTCAGGAAAC TCTCGATGAG TTCAGCAACG CGCTTGATGA
8701 CTATGGGTTT ACTCACACCA TGCAGGTGTC TGGGGACCTC TCGTCTATCG AGTGCTGCAG
8761 CGCACGTGTG GACAGCGTTT GCCTCCGGGG AGGTATGCGT CGCATGCTCG TGCCACAAGC
8821 TCGACGTGCG ATTGCACGCG TTCTCGGGGA AAAGGGCGAT CCACTGGGTG TTATCAGCAG
8881 CTATATTGTC ATGTATCCTA CTGCGGCTGT GACTGTCTAC GTTCTGATGC CCTGTTGTG
8941 CATGCTCATT CGAAATGAGC CATCGCAGAC GGGGACACTT GTAACGTTGA CGGTCCACGG
9001 TAACAGTGTG AGCGTGCCAG TGTGGCTGCT TCCAACCATT ATTGCAAATT TACATGGCCG
9061 TGACGCACTA CAGGTTGTCC GTCACAGTGC AGCTTCCATG GCGGAACTGT CCTCAGCGTT
9121 GGCCTTCTTT GGCATGAGAG GGTTGAACTG CTGGAGGCGG AGACGCCGTG CCATCAGGAC
9181 TGATATGATC AAGTTGGGCG GGTGGAATGC GAATTTCGCG CAGATGTTAC TGTGGTCACC
9241 GGAGGTAAGA ACACCACAGC CCGAACCAAA GGGCATGTGT CTCTTGCCAC CGGAACTATG
9301 GGAGCGTCCG TACGAAAATT TGCACTTGAG CACGATCGAC CGCAATCGTG GTGCTAGTCG
9361 CTTACGGTTT TGGTTGGTTG CTAGTGCTAT ACTCGCTCTG CTTTGCTTGT AAATCCTAAA
9421 TCAATGTAGT ACCAGGACTA CAAGGCAGGA GGTGAAGTCA GCTGTACCCA CGGCTGGCTG
9481 AAACCGGGGC TTGACGACCC CCCCTATCCG AGTTGGGCAA GGTAACATCA CGGGTGTGAC
9541 GACCCCGCCC CCCCATGTCG CGCGCAAGCG CACGGGCAAG GCAGCTAGGC TGAGAGTCTG
9601 GGCAACTCTC CCGTACCCCA CCCGAGGCTA CGCCTCGTCC TGGCGAGGAC CGTAAACATA
9661 CGTCGTCAGC GTGGTGACCT GACGTATCTT GTTAACCACT TAATGGTCGT AACTCGACCC
9721 CCGTGCCGGG GATCTAAGCG CGGCACCGCG AYGAGAGGGG TCAACGGCCC CTTTCATT
```

FIG. 2A

Human Pegivirus 2 (UC0125.US) Genes and Untranslated Regions

S Protein and Gene Sequence

S Protein Amino Acid Sequence: (SEQ ID NO:2)
MEGMPTGTLIVQRDGSLHWCHARHHSVQPDRVAAGPPSVTSVERNMGCSTDQTICSPVVGADYNTSSGCRALNGSYH
CGGGSCRSPSRVQVARRVLQLCAFLALIGSGMCSIRSKTEGRIESGQ S protein gene sequence: nucleotides 104-475 of SEQ ID NO:1.

E1 Protein and Gene Sequence

E1 Amino Acid Sequence: (SEQ ID NO:3)
ILQSQRACWTGEGFAFFSNCCNQSDIMWCLHRWCVTRPGCLVCTGNATHPICWDYLGSGVSRRPARRMGEGAEALLR
LIGIAGWLGLLAESLGMSEVYAAILCFGFIAWYGWGIPKTLVCTVCPA
VNISPYSFLSPDTIAFGTWILQLPGLLWQMFVSFPILYSTWILWLLLSGKTVAVIAILLASPTVMA E1 gene sequence: nucleotides 476-1048 of SEQ ID NO:1.

E2 Protein and Gene Sequence

E2 Amino Acid Sequence: (SEQ ID NO:4)
YKHQSESYLKYCTITNTSTSMNCDCPFGTFTRNTESRFSIPRFCPVKINSSTFICSWGSWWWFAENITRPYTDVGMP
PAPISALCYIYSNNDPPPWYHNTTIIPQNCRNSTVDPTTAPCRDKWGNATACILDRRSRFCGDCYGGCFYTNGSHDR
SWDRCGIGYRDGLIEFVQLGQIRPNISNTTIELLAGASLVIASGLRPGFGCSRAHGVVHCYRCPSYRDLEQFGPGLG
KWVPLPGEPVPELCINPQWARRGFRMSNNPLSLLQTFVEDIFLAPFCNPTPGRVRVCNNTAFYPRGGGFVQLIGDVQ
VLTPNTASLHSLLTLISLILLVCVVSGARFVPLIIIFFWSARHVYA E2 gene sequence: nucleotides 1049-2110 of SEQ ID NO:1.

X Protein and Gene Sequence

X Protein Amino Acid Sequence: (SEQ ID NO:5)
SCYLSCDWAVCNDAFCFTSGTCATFNDVLCLPVATRISSCGHAVPPPDRGWEVPAAMSWVISRTTGLTFDVFSFIQY
LPTVPGNNTNIIYCGEPTFLGDITGIYWPYFLPGAILLYLTPFLGLRLMLAGFNIDGLFPIRHATAALRFSTSRVTL
CVVVAFLIYILSHPVNAALNRMFLASANLEMILSFDTYHETVLYILCLLLYLQVSPRAGLAAMVAIKLSRGLLFAVV
LAHGVC X Protein gene sequence: nucleotides 2111-2821 of SEQ ID NO:1.

FIG. 2B

NS2 Protein and Gene Sequence

NS2 Amino Acid Sequence: (SEQ ID NO:6)
RPGRVFGLEVCADISWLVEFTGNCTWYMSCVFSFWCAVFAFTSPLGRHYKIQIYRYWAQVYARLVLAVGCGPLGREF
HFRASVGVLWCGACMLWPRECSEISLVFILCALTVDTIDTWLVACLSAGPSARTLAILADDMARIGDHRALRAVLRC
FGSRGTYIYNHMGQVSERVAQAVRDLGGCLEPVVLEEPTFTEIVDDTMSLVCGQLLGGKPVVARCGTRVLVGHLNPE
DLPPGFQLS NS2 gene sequence: nucleotides 2822-3541 of SEQ ID NO:1.

NS3 Protein and Gene Sequence

NS3 Amino Acid Sequence: (SEQ ID NO:7)
APVVITRPSIGTWSFLKATLTGRAETPGSGQIVVLSSLTGRSMGTAVNGTLYATGHGAGARGLATCAGLRTPLYTAL
SDDVVAYSCLPGMSSLDPCCCSPSRVWVMNNNGGLVCGRVENDDVCLDCPTHIDQLRGASGSPVLCDHGHAYALMLG
GYSTSGICARVRTVRPWHNAYSSSGGQGGMQAPAVTPTYSEITYYAPTGSGKSTKYPVDLVKQGHKVLVLLPSVAVV
KSMAPYIKETYKIRPEIRAGTGPDGVTVITGENLAYMTYGRFLVDPETNLRGYAVVICDECHDTSSTTLLGIGAVRM
YAEKAGVKTVVFATATPAGIQVQSHSNIDEYLLTDTGDVEFYGAKIKMDNIRTGRHVIFCHSKARCAELTQQLSGLG
IRAVSFWRGCDIKTIPASDSIVVVATDALSTGYTGNFDSVIDCGCCVEQTVTIDMDPTFSISARVVPCTAALRMQRR
GRTGRGRRGAYYTTSPGAAPCVSVPDANVWQAVESAMVFYDWSATRIQQCLAAYHDLGCTPRISCDPHTPVRVMDTL
RAYLRRPEVTTAALAGEQWPLLYGAQLCICKETEAHGPDDSIKWKCLLNNSNKTPLLYALDNPTLEFTTQHDLTRRI
AGALSSTVFVET NS3 gene sequence: nucleotides 3542-5425 of SEQ ID NO:1

NS4A Protein and Gene Sequence

NS4A Amino Acid Sequence: (SEQ ID NO:8)
GYGPILLAGAALAASFAFAGATGALVPSAVWSVEVRPAGVT NS4A gene sequence: nucleotides 5426-5548 of SEQ ID NO:1

NS4B Protein and Gene Sequence

NS4B Amino Acid Sequence: (SEQ ID NO:9)
RPDATDETAAYAQRLYQACADSGIFASLQGTASAALGKLADASRGASQYLAAAPPSPAPLVQVLQFLETNFSSIASF
GLLCAGCQAGECFTALAGLVSGATAGLGGAHKWLLAIAGTWLVSLQTGSRGGMVAGLSILAGCCIGSVTGLDFLFGC
LTGWEAVVGAAVATQKILSGSADMTTLVDLLPALFSPGAGIAGIVLVFILSNSSVTTWANRLLSMCAKQTICENYFL
SERFGQQLSKLSLWRSVYHWAQAREGYTQCG NS4B gene sequence: nucleotides 5549-6334 of SEQ ID NO:1

FIG. 2C

NS5A Protein and Gene Sequence

NS5A Amino Acid Sequence: (SEQ ID NO:10)
VISGIWSFALCILRAVWDWAAKHVPRFRVPMIGCSPAWCGRWLGTGTLLTTCACGERVSLQCLCSTSDPQLSVGRWC
RCSWSVGFPFNPTTTGTGTLRPDISDANKLGFRYGVADIVELERRGDKWHVCAASCCLDRASVASAVKAPPVTANGI
PINSFSPPQTYCLSLCSFDTVCMSTNLCNPAKTLSVCQEEAVELLEETVDTAQVVMSQNLAARRRAEYDAWQVRQAV
GDEYTRLADEDVDMTASVKPPVARAAVGSSTLDDVSVLTVLRELGDQCQNAIKFVVQAASRFVPPVPKPRTRVSGVL
ERVRMCMRTPPIKFEATAVPIHNIIPEECHIVLRCTGCCDQALTVPYGTCSLTLTKYLTNKHSHYIPKEKIEEDTEI
AVICAVPTKRASKLITFRAGDRSVSCCHPLQTPIRALLQKYGLPIGKWSDCNGPLGDDARVCDVNGVTTYEPC NS5A gene sequence: nucleotides 6335-7708 of SEQ ID NO:1

NS5B Protein and Gene Sequence

NS5B Amino Acid Sequence: (SEQ ID NO:11)
MQSYNWFRSIVAPTTPPLPATRSVAGILRADTSRVYTTTAVDVSERQAKVTIDQKSAKVDQCLRDTYNCCLAKAKTF
RQSGMSYEDAVSKMRANTTRDHNNGITYTDLVSGRAKPVVQKIVDQMRAGVYDAPMRIIPKPEVFPRDKSTRKPPRF
IVFPGCAARVAEKMILGDPGAITKHVLGDAYGFATPPHERARLLEQWWNRATEPQAIAVDAVCFDSTITAEDMDREA
NIVAAAHTDPEGVHGLYNYYKRSPMCDITGKVVGVRSCRASGTLTTSSGNTLTCYLKVRAACTRAGIKPIGLLIHGD
DTLIITERCAQETLDEFSNALDDYGFTHTMQVSGDLSSIECCSARVDSVCLRGGMRRMLVPQARRAIARVLGEKGDP
LGVISSYIVMYPTAAVTVYVLMPLLCMLIRNEPSQTGTLVTLTVHGNSVSVPVWLLPTIIANLHGRDALQVVRHSAA
SMAELSSALAFFGMRGLNCWRRRRRAIRTDMIKLGGWNANFAQMLLWSPEVRTPQPEPKGMCLLPPELWERPYENLH
LSTIDRNRGASRLRFWLVASAILALLCL NS5B gene sequence: nucleotides 7709-9409 of SEQ ID NO:1

5' UTR sequence

5' UTR Sequence: nucleotides 1-103 of SEQ ID NO:1

3' UTR sequence

3' UTR Sequence: nucleotides 9410-9778 of SEQ ID NO:1

FIG. 3A

Human Pegivirus 2 (UC0125.US) Annotated Genome

CCACCGGGCGTTGCGCGCCGTGTTACGTTGCTTTGGATCACGCGGCACATACATATACAACCACATGGGCCAAGTC
                                   Set 5 Fwd →
TCGGAACGGGTGGCGCAAGCAGTCAGGGATCTCGGCGGTTGCTTGGAACCAGTCGTGTTGGAGGAGCCCACCTT
       ← Probe 5R       ← Set 5 Rev
TACTGAGATCGTGGATGACACAATGAGTTTGGTGTGTGGACAATTGCTTGGAGGTAAACCTGTGGTGGCCCGCTG
              Set 2 Fwd →     ← Probe 2 R
CGGCACGCGTGTCTTGGTGGGACACCTCAACCCTGAAGATCTGCCACCTGGTTTCCAGCTGAGTGCTCCGGTGGTT
          ← Set 2 Rev + Set 7 Fwd →      Probe 7F →
ATTACCAGGCCAAGCATTGGTACGTGGTCCTTCCTTAAGGCGACACTCACAGGGCGTGCTGAAACACCAGCGTCC
   ← Set 7 Rev
GGCCAGATCGTGGTGTTGTCTTCCCTGACAGGTCGGTCAATGGGTACCGCAGTGAATGGCACACTGTATGCGACC

GGCCATGGTGCCGGCGCGCGCGGCCTAGCCACGTGCGCTGGTTTGAGGACGCCACTTTACACGGCATTATCTGAT

GATGTCGTGGCCTATTCTTGCCTTCCGGGCATGAGTTCCCTAGACCCCTGCTGCTGTTCGCCGAGCCGGGTTTGGG
Set 4 Fwd →        ← Probe 4R     Set 3 Fwd →      ← Set 4 Rev
TGATGAATAACAACGGAGGGTTGGTGTGTGGCAGAGTGGAGAATGACGACGTCTGTTTGGACTGTCCCACGCAC
      ← Probe 3R       ← Set 3 Rev
ATAGATCAACTGCGGGGTGCTTCGGGCTCACCAGTTTTGTGTGATCACGGTCATGCATACGCGTTGATGCTCGGTG GTTACTCTACCAGTGGTATTTGTGCACGCGTCCGGACGGTCCGGCCATGGCATAACGCCTATTCCTCCTCGGGGGG
            Set 15 Fwd →
GCAAGGCGGAATGCAGGCGCCAGCTGTGACACCAACATACTCTGAAATCACCTACTATGCCCCTACTGGTTCTGGT
           Set 15 Probe →              ← Set 15 Rev
AAGTCAACAAAATATCCAGTGGACCTAGTCAAACAGGGACACAAAGTATTGGTCCTTTTACCAAGTGTGGCTGTAG

TCAAAAGTATGGCCCCTTATATTAAGGAGACATATAAGATCAGACCCGAAATTAGAGCTGGCACAGGTCCTGACG

GTGTGACGGTCATCACTGGTGAGAACTTGGCGTACATGACCTATGGCCGCTTCCTTGTGGATCCGGAGACGAATCT
            Set 1 Fwd →
GCGGGGCTATGCTGTAGTCATTTGCGACGAGTGTCACGACACATCATCCACCACGCTACTCGGCATTGGCGCAGT
   ← Probe 1 R      ← Set 1 Rev
GCGCATGTATGCCGAGAAAGCTGGAGTGAAGACCGTTGTATTCGCCACAGCCAC FIG. 7A
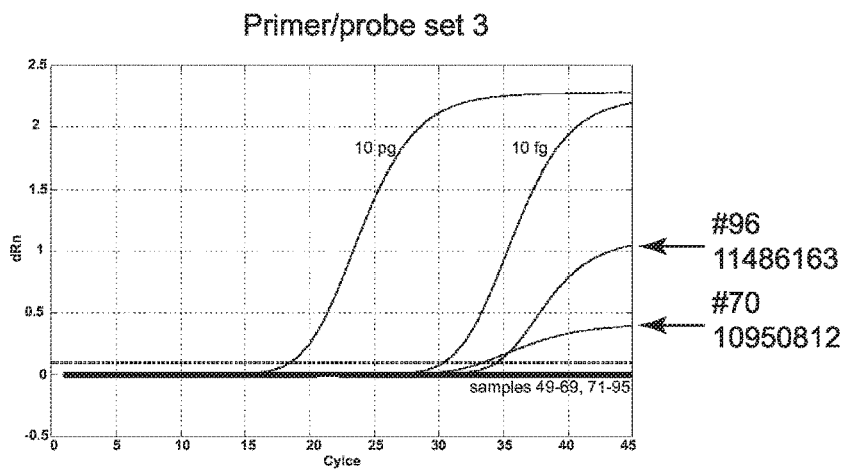
FIG. 7B
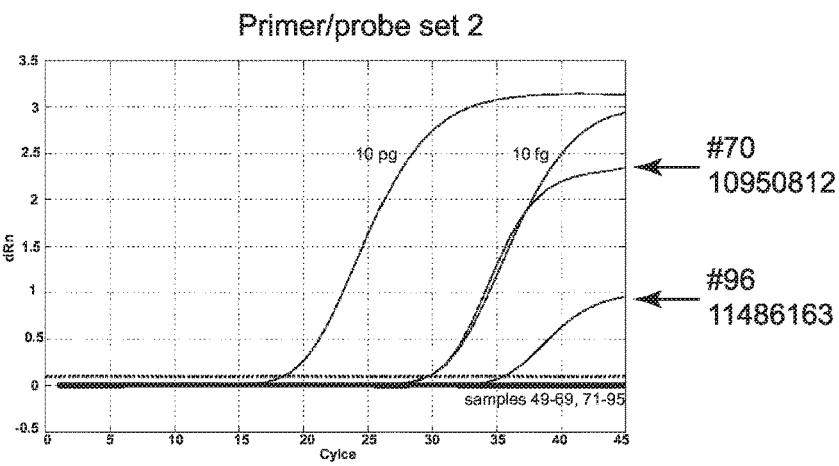
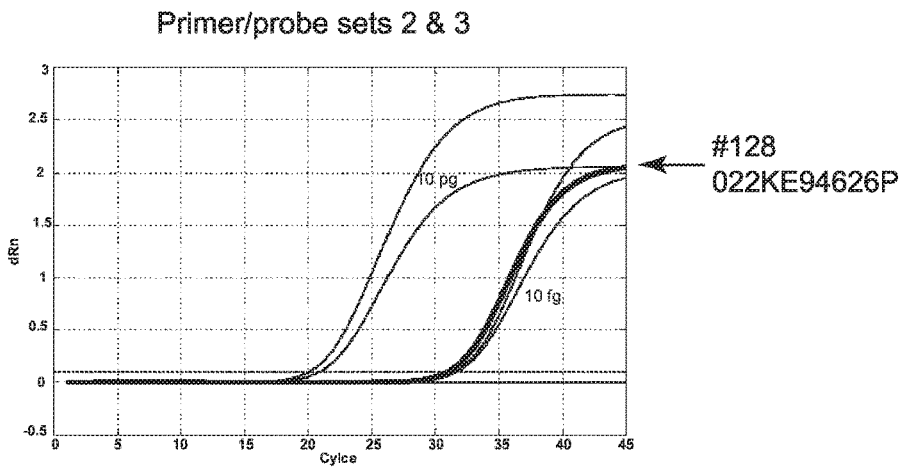

FIG. 9A

Human Pegivirus 2 (ABT0070P.US) Nucleic Acid Sequence - SEQ ID NO:75

```
   1 GTGTTTGACG TGTGACAATG CCATGAGGGA TCATGACACT GGGGTGAGCG GAGGCAGCAC
  61 CGAAGTCGGG TGAACTCGAC TCCCAGTGCG ACCACCTGGC TTGGTCGTTC ATGGAGGGCA
 121 TGCCCACGGG AACGCTGATC GTGCAAAGGG ATGGGTCCCT GCACTGGTGC CATGCGCGGC
 181 ACCACTCCGT ACAGCCTGAT AGGGTGGCGG CGGGCCCCCC CAGTGTGACG TCCGTGGAGC
 241 GCAACATGGG GTGTTCAACT GATCAAACCA TTTGTTCTCC AGTCGTGGAG GCCGACTATA
 301 ATACCTCCTC GGGCTGCCGG GCCTTAAATG GGAGCTACCA CTGCGGTGGT GGCTCTTGCC
 361 GGTCACCAAG TCGTGTGCAG GTTGCAGGAC GAGTCCTGCG GCTGTGCGCA TTCCTTGCGC
 421 TGATCGGATC CGGTATGTGT TCCATCCGGT CCAAAAATGA AGGGCGCATT GAGTCAGGGC
 481 AAATATTGCA GTCTCAGCGC GCATGTTGGA CTGGTGAGGG TTTCGCTTTC TTTTCTAACT
 541 GTTGCAATCA ATCTGACATT ATGTGGTGTT TGCACCGTTG GTGTGTGACA AGACCTGGCT
 601 GTTTGGTGTG CACGGGCAAT GCCACTCATC CTGTCTGCTG GGACTATCTT GGGTCCGGTG
 661 TGAGTCGGCG GCCTGCGCGT CGAATGGGTG AGGGAGCTGA AGTGCTTCTT CGCTTGATCG
 721 GCATTGCAGG TTGGCTCGGG CTCTTAGCTG AGGCTCTTGG TATGTCTGAG ATCTATGCAG
 781 CTTTCCTTTG CTTGGATTT ATTGCTTGGT ATGGCTGGGG TATACCTAAG ACATTGGTGT
 841 GCACAGTCTG CCCTGCAGTG AACATTTCTC CCTATAGCTT CTTATCTCCA GATACTATCG
 901 CATTTGGTAC GTGGCTACTA CAACTGCCTG GTCTTTTGTG GCAAATGTTT GTCAGCTTCC
 961 CTATACTTTA CAGTACTTGG ATTCTTTGGT TGTTGCTCAG CGGCAAGACT GTTGCTGTGA
1021 TAGCGATCCT TTTGGCTAGT CCTACGGTTA TGGCATACAA GCATCAAGCT GATAGCTACC
1081 TCAAATACTG TACCATAACC AATGCTTCAA CTGCTATGAA CTGTGACTGC CCCTTTGGAA
1141 CTTTCACTCG CAATACTGAG TCTGGTTTCA CTATACCTAG ATTCTGTCCT GTTAAACTTA
1201 ATAGCTCTAC ATTTATCTGT TCATGGGGGT CGTGGTGGTG GTTTGCTGAG AACATCACAC
1261 GTCCATACTC GGACGTTGGC ATGCCGCCAG CACCGATTTC CGCTTTGTGC TATATCTATT
1321 CAAACAATGA CCCACCTTCT TGGTATCGTA ACACAACTAT CATACCTCAG AACTGTTACA
1381 ACTCTACGGC TGATCCTACC ACAGCTCCAT GCCGTGACAA GTGGGGCAAT GCAACTGCTT
1441 GTATTCTTGA CCGCCGGTCG CGGTTCTGCG GGACTGCTA TGGCGGTTGC TTCTACACTA
1501 ATGGTAGTCA TGACCGATCC TGGGATCGAT GCGGAATTGG TTACCGTGAT GGACTCATAG
1561 AGTTCGTGCA GCTCGGTCAG ATTCGACCTA ACATCGCGAA TACGACCATT GAGCTCCTCG
1621 CTGGCGCCTC GCTTGTGATC GCATCCGGTC TTCGGGCTGG GTATGGTTGC AGCCGAGCGC
1681 ACGGCGTGGT GCACTGCTTT AAGTGTCCTT CATACCGTGA CCTTGAACGG TTCGGGCCCG
1741 GGCTTGGGAA ATGGGTGCCA TTGCCTGGCG AGCCTGTCCC GGAGTTGTGT ATTAACCCGC
1801 AGTGGGCGAG GCGCGGCTTC CGGGTGTCTA ATAATCCCTT AAGCGTGCTA CAGACCTTCG
1861 TTGAGGACAT TTTCTTAGCG CCTTTCTGCA ATCCGACGCC TGGCCGTGTA CGTGTGTGTA
1921 ACAATACTGC TTTCTACCCG AGAGGAGGCG GCTTTGTGCA GCTCATCGGA GACGTCCAGG
1981 TGTTAACCCC CAACTCTACA TCTTTGCACT CTCTGCTGAC TTTGATATCC CTTATCTTGT
2041 TAGTGTGTGT TGTTTCTGGC GCGCGATTCG TTCCATTGGG AATCATATTC TTCTGGAGCG
2101 TGCGCCACGT ATATGCTTCT TGTTACTTAA GCTGTGATTG GCTGTTTGC AACGATGCGT
2161 TCTGTTTCAC ATCTGGCACT TGTGCTACCT TCAACGACGT CTTGTGTCTG CCGGTTGCGG
2221 CGCGCATATC GTCCTGTGGC CATGCTGTGC CACCGCCCGA CCGTGGTTGG GAGGTGCCCG
2281 CAGCGATGTC ATGGGCGATT TCGCGTACTA CCGGCTTGAC GTTCGATGTC TTTTCCTTCA
2341 TCCAGTACCT TCCTACTGTG CCTGGCAACA ATTCCGATAT CATTTACTGT GGTGAACCAA
2401 GCTTCTTCGG GGACATCACG GGTATCTATT GGCCTTACTT TTTGCCTGGC ATGTTGCTCT
2461 TGTACTTGAC TCCCCTCCTG GGTTTAAGGT TAATGCTTGC CGGCTTTAAT ATAGATGGCT
2521 TGTTTCCCAT ACGGCATGCC ACGGCTGCAC TGAGGTTCTC GACTTCGCGT GTGACCTTGA
2581 GTGTCGTATT TGCTTTCCTA ATCTATATAT TATCTCATCC TGTTAATGCT GCGCTCAATA
2641 GAATGTTCCT AGCATCTGCA AATCTAGAGA TGATCTTATC CTTTGATACC TATCATGAGA
2701 CTGTTCTTTA CGTCGTTTGT CTATTGCTCT ACCTCCAGGT GTCGCCCGT GCGGGCTTGG
2761 CTGCTATGGT GGCCATCAAG CTATCTCGAG GCCTGTTATT CGCTGTGGTG TTGGCGCACG
2821 GAGTGTGCCG ACCTGGGCGG GTATTTGGTC TTGAGGTTTG CGCGGACATC TCTTGGTTGG
2881 TGGAGTTTAC TGGCAACTGC ACTTGGTACA TGTCCTGTGT CTTCTCTTTT TGGTGCGCAG
2941 TGTTTGCCTT CACCAGTCCA CTTGGACGAC AGTATAAGCT TCAGATCTAT CGGTACTGGG
3001 CGCAGGCCTA TGCCAGACTC ATCCTCGCTG TCGGTTGTGG TCCTCTCGGG AGGGAGTTCC
3061 ATTTCCGTGC GAGCGTGGGC GTGCTCTGGT GTGGTGCTTG CATGCTCTGG CCCCGTGAGT
```

FIG. 9B

```
3121 GCTCTGAAAT CAGCTTGGTC TTTATTCTGT GTGCTCTGAC TGTGGACACC ATAGACACAT
3181 GGTTAGTAGC GTGCTTGTCC GCAGGGCCAA GCGCGCGAAC CCTTGCAACT CTGGCCGATG
3241 ACATGGCGCG CATTGGTGAC CACCGGGCGT TGCGCGCCGT GTTGCGTTGC TTTGGATCAC
3301 GTGGCACATA CATATACAAC CACATGGGCC AGGTCTCAGA ACGGGTGGCG CAAGCAGTCA
3361 GGGATTTCGG CGGTTGCTTG GAACCAGTCG TGTTGGAGGA GCCCACCTTT ACTGAGGTCG
3421 TGGATGATAC AATGAATTTG GTGTGTGGAC AATTGCTTGG AGGTAAACCC GTGGTGGCCC
3481 GCTGCGGCAC GCGTGTCTTA GTGGGACACC TCAACCCTGA AGACCTGCCA CCTGGTTTCC
3541 AGCTGAGTGC TCCGGTGGTT ATTACCAAAC CAAGCATTGG TACGTGGCCC TTTCTTAAGG
3601 CGACACTCAC AGGGCGTGCT GAAACACCGG GATCCGGCCA GATCGTGGTG TTGTCTTCCC
3661 TGACAGGTCG GTCAATGGGT ACTGCAGTGA ATGGCACACT GTATGCGACC GGCCACGGTG
3721 CTGGTGCGCG CGGCCTAGCC ACGTGCGCTG GTTGAGGAC GCCACTTTAC ACGGCATTAT
3781 CTGAAGATGT CGTGGCCTAC TCTTGCCTTC CGGGCATGAG CTCCCTAGAG TCCTGCAACT
3841 GCTCGCCCAG CCGGGTTTGG GTGGTGAACA ACAACGGAGG GTTGGTGTGT GGCAGAGTGG
3901 AGAAAGACGA CGTCTGTTTG GACTGTCCCA CGCACATAGA TCAACTGCGG GGTGCTTCGG
3961 GGTCGCCGGT TTTGTGTGAT CACGGTCATG CATACGCGTT GATGCTCGGT GGCTACTCTA
4021 CCAGTGGTAT TTGTGCGCGT GTCCGGATAG TCCGGCCATG GCAGAACGCC TATTCCTCCT
4081 CAGGGGGGCA AGGCGGAATG CAGGCGCCAG CTGTGACACC AACATACTCT GAAATCACCT
4141 ACTATGCCCC TACTGGTTCT GGTAAATCAA CAAAATATCC AGTGGACCTA GTCAAGCAGG
4201 GACACAAAGT ATTAGTCCTT TTACCAAGTG TGGCTGTCGT CAAAAGTATG GCTCCTTACA
4261 TTAAGGAAAA ATATAAGATT AGACCTGAAA TTAGAGCTGG CACAGGGCCT GACGGTGTGA
4321 CGGTCATCAC TGGCGAGAAC TTGGCGTACA TGACCTATGG CCGTTTCCTT GTAGATCCGG
4381 AAACGAATCT GCGGGGTTAC GCTGTAGTCA TCTGCGACGA GTGCCATGAC ACATCATCCA
4441 CCACGCTACT CGGCATCGGC GCAGTGCGCA TGTATGCTGA GAAAGCTGGA GTGAAGACCG
4501 TTGTATTCGC CACAGCCACT CCTGCTGGCA TTCAAGTGCA GTCACATCCC AACATTGATG
4561 AATATCTATT GACTGATACA GGCGACGTGG AATTCTACGG CGCTAAAATT AAATTGGACA
4621 ACATCAGAAC TGGTAGACAT GTTATCTTTT GCCACTCGAA GGCCAGGTGT GCGGAACTAA
4681 CGCAGCAGCT CTCCGGCCTT GGTGTTCGTG CAGTGAGTTT TTGGCGCGGC TGTGACATCA
4741 AGAGCATTCC CGCCTCAGAC TCTATTGTTG TAGTGGCAAC TGATGCATTG TCCACAGGCT
4801 ACACAGGGAA CTTTGATTCG GTCATTGACT GCGGGTGTTG CGTAGAGCAA ACTGTAACAA
4861 TTGACATGGA CCCCACGTTC TCCATCTCGG CCCGAGTGGT GCCATGACT GCTGCATTGC
4921 GTATGCAGCG GCGCGGACGC ACCGGTCGTG GCAGGAGGGG AGCGTACTAC ACAACCACTC
4981 CAGGAGCAGC ACCCTGCGTC AGCGTTCCCG ATGCTAACGT CTGGCAATCA GTGGAGTCAG
5041 CCATGGTCTT TTATGATTGG AGTGCTGCCA GGATAGAGCA ATGCCTGGCG GCATACCATG
5101 ATTTAGGGTG CACACCACGC ATCAGTTGTG ACCCACACAC TCCAGTGCGG GTGATGGACA
5161 CACTGAGGGC GTATCTGCGC AGACCTGAGG TGACGACCGC GGCTCTCGCA GGAGAGCAGT
5221 GGCCGCTGCT TTACGCGTG CAGTTGTGCA TCTGCAAAGA GACCGAGGCC CACGGTCCAG
5281 ACGATGGCAT CAAGTGGAAA TGCTTACTCA ATAACAACAA CAAAACACCC CTGTTGTATG
5341 CCTTAGACAA TCCTACACTG GAATTCACTA CCCAACATGA CTTGACTCGC CGTATAGCTG
5401 GCGCTTTATC GAGCACAGTG TTCGTGGAGA CAGGCTACGG CCCCATCCTC CTCGCTGGCG
5461 CTGCTTTGGC TGCCTCCTTT GCCTTTGCGG GCGCCACTGG AGCTTAGTG CCGTCGGCCG
5521 TTTGGAGCGT TGAAAACGGG CTTGCTGGCG TGACCCGTCC CGATGCGACA GACGAGACCG
5581 CGGCCTACGC GCAGCGCTTG TACCAAGCCT GCGCAGATTC AGGAATTCTC GCCAGCTTGC
5641 AGGGTACGGC GAGTGCGGCA CTGAGCAGAC TGGCCGATGC CAGTAAGGGT GCTAGTCAAT
5701 ATCTGGCAGC CGCGCCTCCT TCGCCCGCCC CCTGGTACA GGTGCTGCAG TTCCTCGAGA
5761 CCAATTTTAG CTCCATTGCA TCTTTCGGTC TGCTCTGTGC CGGCTGTCAG GCCGGCGAGT
5821 GCTTCACTGC GCTTGCCGGG TTGGTGTCCG GTGCTACAGC TGGCTTGGGA GGTGCCCATA
5881 AGTGGTTGTT AGCTATTGCA GGAACTTGGC TAGTTAGCTT GCAGACTGGG CCCCGTGGCG
5941 GCATGGTTGC GGGTCTCTCA GTTCTAGCAG GCTGTTGCAT CGGTAGTGTC ACCGGGCTTG
6001 ACTTCCTGTT TGGGTGCCTT ACAGGTTGGG AGGCCGTGGT CGGTGCTGCG GTTGCAACGC
6061 AGAAAATCTT GTCTGGTTCG GCTGACATGA CCACTCTGGT AGATCTCCTA CCTGCTCTCT
6121 TCTCCCCTGG CGCCGGCATA GCTGGCGTCG TGCTTGTCTT TATTCTAAGC AACTCAAGTG
6181 TAACCATGTG GGCTAATCGG CTATTGTCCA TGTGTGCAAA ACAAACTATT TGTGAAAATT
6241 ACTTCTTAAC TGAGAAATTT GGCCAACAAT TAAGCAAACT TTCCCTGTGG CGCTCTGTGT
6301 ACCATTGGGC GCAGGCACGT GAAGGATACA CACAGTGCGG TGTGGTCAGC GGGATCTGGA
6361 GCTTTGTCTT GTGCATTCTA CGTGCTGTGT GGGATTGGGC GGCTAAACAT GTGCCACGGT
6421 TCCGTGTGCC TATGATTGGC TGCTCACCTG CGTGGTGCGG GCGCTGGCTT GGTACTGGCA
```

FIG. 9C

```
6481 CCTTGTTGAC CACCTGTGGG TGTGGAGAAC GTGTATCCCT TCAGTGCCTT TGCTCGACAT
6541 CTGACCCAAC ACTCAGTGTG GCCGTTGGT GTTGGTGTAG TTGGCGTGTT GGGTTCCCAT
6601 TCAACCCGAC GACGACAGCC ACCGGCACTT TACGGCCGGA CATCAGTGAC GCCACCAAAT
6661 TGGGCTTCCG GTATGGTGTC GCCGAGATCG TGGAGCTAGA GCGGCGGGGC AACAAATGGC
6721 ATGTCTGTGC AGCATCATGT TGCTTGGACC GGGCCAGCGT TGCATCCGCC GTGAGGGCCC
6781 CACCGGTCAC GGCCGATGGC ATACCTATCA GTACCTTTTC TCCACCACAA ACTTACAAAC
6841 TCTCTCTTTG TTCTTTTGAT TCAGTTTGCA TGACTACTAA CTTATGTAAT CCAGCTAAGA
6901 CCCTGAGTGT GTGCTCGCAG GAGGCTGTTG AGCTACTGGA AGAAACAGTT GACAGAGCAC
6961 AAGTAGTGAT GTGTCAAAAT CTGGAGGCGC GAAGACGCGC TGAGTTTGAT GCATGGCAAG
7021 TTCGCGAAGC AATTCGCGAC GAGTACACGC GTTTGGCAGA CGAGGATGTT GACGCGACAA
7081 CGTCGGTGAA ACCCCGGTG GCCAAGGCTG CTGTGGGTAG CTCGACGTTG GATGATGTTA
7141 GCGTGCTGAC TGTCTTGCGC GAACTCGGTG ACCAGTGCCA AAATGCTATC AAATTTGTAG
7201 TTCAGGCGGC TTCACGGTTT GTTCCACCAG TGCCCAAGCC ACGCACGCGT GTCTCGGGTG
7261 TGTTGGAGCG TGTGCGCATG TGCATGCGCA CGCCACCAAT CAAGTTTGAG GCTGCCGCAG
7321 TACCAATTCA TGATATAATC CCAGAAGAGT GTCACATTGT GCTACGCTGT ACCGGCTGCA
7381 ACGACCAGGC CTTGACTGTT CCGTACGGCA CTTGCACTCA GTCTTTAATC AAGCATTTGA
7441 CTAGTAAACA CAGTCACTAC ATTCCAAAAC AGAAGATAGA AGAGGACACA GAAGTAACTG
7501 TCATTTGCGC CGTACCAACA ACGCGCGCAA GCAAACTCAT CACATTCAGA GCAGGTGATC
7561 GATCAGTCTC ATGTTGTCAC CCCTTGCAAA CCCCTATTAG GGCCCTGCTT CTAAAGTACG
7621 GGTTACCTAT CGGGAAGTGG TCTGACTGCA ACGGGCCCCT TGGTGACGAT GCTCGAGTCT
7681 GTGACGTCAA TGGAGTAACA ACTTATGAAC CATGCATGCA ATCCTACAGT TGGTTTCGAC
7741 CGATTGTGGC ACCAACAACC CCACCTTTGC CTGCAACCCG GACCGTGGCT GGCATTTTAC
7801 GCGCAGACAC ATCGCGCGTT TACACCACAA CGGCGGTTGA CGTCTCCGAG CGGCAGGCCA
7861 AGGTCACAAT TGATCAAACA TCAGCCAAGG TGGATCAGTG TTTCCGAGAC ACATACAATT
7921 GCTGCCTTGC TAAGGCAAAG ACCTTCAGAC AATCTGGCAT GTCATATGAG GATGCTGTGT
7981 CAAAGATGCG CGCAAACACC ACGCGTGACC ATAACAACGG CATCACTTAT TCAGATTTGG
8041 TCTCTGGACG CGCAAAACCT GTCGTCAGA AAATTGTAAA TCAAATGCGC GCCGGAGTGT
8101 ACGACGCTCC GATGCGCATT ATCCCAAAAC CTGAAGTGTT CCCTCGAGAC AAAACAACAC
8161 GGAAGCCACC GAGGTTCATC GTTTTCCCTG GGTGCGCCGC GCGAGTCGCG GAGAAAATGA
8221 TCCTGGGTGA TCCTGGCGCG ATAACCAAGC ACGTGCTAGG TGATGCCTAC GGGTTTGCCA
8281 CTCCGCCGCA TGAGCGCGCG CGCCTGTTGG AACAATGGTG GAACCGCGCA ACGGAGCCAC
8341 AAGCTATCGC GGTTGATGCG ATCTGCTTTG ATAGCACCAT CACGGCAGAG GACATGGATC
8401 GTGAGGCTAA CATCGTGGCT GCAGCGCATA CGGACCCTGA AGGTGTTCAC GGCCTATATA
8461 ATTATTACAA AAGAAGCCCC ATGTGTGACA TCACGGGGAA GGTTGTCGGA GTGCGTTGCT
8521 GTCGAGCCTC GGGTACGCTT ACAACAAGCA GTGGCAACAC GCTTACTTGC TACCTTAAGG
8581 TTCGTGCAGC TTGCACGCGC TCCGGCATTA AACCAATTGG CTTACTAATT CATGGAGATG
8641 ACACCCTCAT CGTCACAGAA CGTTGCGCTC AAGAGACTCT CGATGAGTTC AGCAACGCAC
8701 TTGATGACTA TGGGTTCCCA CACACCATCC AGGCGTCTGG GGACCTCTCG TCTATCGAGT
8761 GCTGTAGCGC ACGTGTGGAC AGCGTTTGCC TCCGGGGAGG TATGCGTCGC ATGCTTGTGC
8821 CACAAGCTCG ACGTGCGATT GCACGCGTTC TCGGGGAAAA GGGCGATCCA CTGGGTACCA
8881 TCGGTAGCTA TGTTGTCATG TATCCCACTG CGGCCGTGAC TGTCTACGTG CTATTGCCCC
8941 TGTTGTGCAT GCTCATACGA AATGAGCCAT CACAGACGGG GACACTTGTG ACGCTGACGG
9001 TCCACGGTAA CAGTGTGAGT GTGCCAGCGT GGCTGCTTCC AACCATCATT GCAAATTTAC
9061 ATGGTCGTGA CGCACTACAG GTAGTCCGTC ACAGTGCAGC TTCCATGGCG GAATTGTCAT
9121 CAGCGTTGGC CTTCTTTGGC ATGAGAGGGT TGAATTGCTG GAGGCGGAGA CGCCGTGCCA
9181 TTAGGGCTGA TATGATCAAG TCGGCGGGT GGAATGCGAA TTTCGCGCAG ATGTTACTGT
9241 GGTCACCGGA GGTAAGAACA CCACAACCCG AACCAAGGGG TCTGTGTCTT TTGCCGCCGG
9301 AACTGTGGGA GCGTCCGTAC GAAAATTTGC ACTTGAGCAC GATCGACCGC AATCGTGGTG
9361 CTAGTCGCTT ACGGTTTTGG TTGGTTGCTA GTGCTATACT CGCTCTGCTT TGCTTGTAAA
9421 TCTTAAATCA A
```

FIG. 10A

Human Pegivirus 2 (ABT0070P.US) Genes and Untranslated Regions

S Protein and Gene Sequence

S Protein Amino Acid Sequence: (SEQ ID NO:76)
MEGMPTGTLIVQRDGSLHWCHARHHSVQPDRVAAGPPSVTSVERNMGCSTDQTICSPVVEADYNTSSGCRALNGSYH
CGGGSCRSPSRVQVAGRVLRLCAFLALIGSGMCSIRSKNEGRIESGQ S protein gene sequence: nucleotides 111-482 of SEQ ID NO:75.

E1 Protein and Gene Sequence

E1 Amino Acid Sequence: (SEQ ID NO:77)
ILQSQRACWTGEGFAFFSNCCNQSDIMWCLHRWCVTRPGCLVCTGNATHPVCWDYLGSGVSRRPARRMGEGAEVLLR
LIGIAGWLGLLAEALGMSEIYAAFLCFGFIAWYGWGIPKTLVCTVCPAVNISPYSFLSPDTIAFGTWLLQLPGLLWQ
MFVSFPILYSTWILWLLLSGKTVAVIAILLASPTVMA E1 gene sequence: nucleotides 483-1055 of SEQ ID NO:75.

E2 Protein and Gene Sequence

E2 Amino Acid Sequence: (SEQ ID NO:78)
YKHQADSYLKYCTITNASTAMNCDCPFGTFTRNTESGFTIPRFCPVKLNSSTFICSWGSWWWFAENITRPYSDVGMP
PAPISALCYIYSNNDPPSWYRNTTIIPQNCYNSTADPTTAPCRDKWGNATACILDRRSRFCGDCYGGCFYTNGSHDR
SWDRCGIGYRDGLIEFVQLGQIRPNIANTTIELLAGASLVIASGLRAGYGCSRAHGVVHCFKCPSYRDLERFGPGLG
KWVPLPGEPVPELCINPQWARRGFRVSNNPLSVLQTFVEDIFLAPFCNPTPGRVRVCNNTAFYPRGGGFVQLIGDVQ
VLTPNSTSLHSLLTLISLILLVCVVSGARFVPLGIIFFWSVRHVYA E2 gene sequence: nucleotides 1056-2117 of SEQ ID NO:75.

X Protein and Gene Sequence

X Protein Amino Acid Sequence: (SEQ ID NO:79)
SCYLSCDWAVCNDAFCFTSGTCATFNDVLCLPVAARISSCGHAVPPPDRGWEVPAAMSWAISRTTGLTFDVFSFIQY
LPTVPGNNSDIIYCGEPSFFGDITGIYWPYFLPGMLLYLTPLLGLRLMLAGFNIDGLFPIRHATAALRFSTSRVTL
SVVFAFLIYILSHPVNAALNRMFLASANLEMILSFDTYHETVLYVVCLLLYLQVSPRAGLAAMVAIKLSRGLLFAVV
LAHGVC X Protein gene sequence: nucleotides 2118-2828 of SEQ ID NO:75.

FIG. 10B

NS2 Protein and Gene Sequence

NS2 Amino Acid Sequence: (SEQ ID NO:80)
RPGRVFGLEVCADISWLVEFTGNCTWYMSCVFSFWCAVFAFTSPLGRQYKLQIYRYWAQAYARLILAVGCGPLGREF
HFRASVGVLWCGACMLWPRECSEISLVFILCALTVDTIDTWLVACLSAGPSARTLATLADDMARIGDHRALRAVLRC
FGSRGTYIYNHMGQVSERVAQAVRDFGGCLEPVVLEEPTFTEVVDDTMNLVCGQLLGGKPVVARCGTRVLVGHLNPE
DLPPGFQLS NS2 gene sequence: nucleotides 2829-3548 of SEQ ID NO:75.

NS3 Protein and Gene Sequence

NS3 Amino Acid Sequence: (SEQ ID NO:81)
APVVITKPSIGTWPFLKATLTGRAETPGSGQIVVLSSLTGRSMGTAVNGTLYATGHGAGARGLATCAGLRTPLYTAL
SEDVVAYSCLPGMSSLESCNCSPSRVWVVNNNGGLVCGRVEKDDVCLDCPTHIDQLRGASGSPVLCDHGHAYALMLG
GYSTSGICARVRIVRPWQNAYSSSGGQGGMQAPAVTPTYSEITYYAPTGSGKSTKYPVDLVKQGHKVLVLLPSVAVV
KSMAPYIKEKYKIRPEIRAGTGPDGVTVITGENLAYMTYGRFLVDPETNLRGYAVVICDECHDTSSTTLLGIGAVRM
YAEKAGVKTVVFATATPAGIQVQSHPNIDEYLLTDTGDVEFYGAKIKLDNIRTGRHVIFCHSKARCAELTQQLSGLG
VRAVSFWRGCDIKSIPASDSIVVVATDALSTGYTGNFDSVIDCGCCVEQTVTIDMDPTFSISARVVPCTAALRMQRR
GRTGRGRRGAYYTTTPGAAPCVSVPDANVWQSVESAMVFYDWSAARIEQCLAAYHDLGCTPRISCDPHTPVRVMDTL
RAYLRRPEVTTAALAGEQWPLLYGVQLCICKETEAHGPDDGIKWKCLLNNNNKTPLLYALDNPTLEFTTQHDLTRRI
AGALSSTVFVET NS3 gene sequence: nucleotides 3549-5432 of SEQ ID NO:75

NS4A Protein and Gene Sequence

NS4A Amino Acid Sequence: (SEQ ID NO:82)
GYGPILLAGAALAASFAFAGATGALVPSAVWSVENGLAGVT NS4A gene sequence: nucleotides 5433-5555 of SEQ ID NO:75

NS4B Protein and Gene Sequence

NS4B Amino Acid Sequence: (SEQ ID NO:83)
RPDATDETAAYAQRLYQACADSGILASLQGTASAALSRLADASKGASQYLAAAPPSPAPLVQVLQFLETNFSSIASF
GLLCAGCQAGECFTALAGLVSGATAGLGGAHKWLLAIAGTWLVSLQTGPRGGMVAGLSVLAGCCIGSVTGLDFLFGC
LTGWEAVVGAAVATQKILSGSADMTTLVDLLPALFSPGAGIAGVVLVFILSNSSVTMWANRLLSMCAKQTICENYFL
TEKFGQQLSKLSLWRSVYHWAQAREGYTQCG NS4B gene sequence: nucleotides 5556-6341 of SEQ ID NO:75

FIG. 10C

NS5A Protein and Gene Sequence

<u>NS5A Amino Acid Sequence:</u> (SEQ ID NO:84)
VVSGIWSFVLCILRAVWDWAAKHVPRFRVPMIGCSPAWCGRWLGTGTLLTTCGCGERVSLQCLCSTSDPTLSVGRWC
WCSWRVGFPFNPTTTATGTLRPDISDATKLGFRYGVAEIVELERRGNKWHVCAASCCLDRASVASAVRAPPVTADGI
PISTFSPPQTYKLSLCSFDSVCMTTNLCNPAKTLSVCSQEAVELLEETVDRAQVVMCQNLEARRRAEFDAWQVREAI
RDEYTRLADEDVDATTSVKPPVAKAAVGSSTLDDVSVLTVLRELGDQCQNAIKFVVQAASRFVPPVPKPRTRVSGVL
ERVRMCMRTPPIKFEAAAVPIHDIIPEECHIVLRCTGCNDQALTVPYGTCTQSLIKHLTSKHSHYIPKQKIEEDTEV
TVICAVPTTRASKLITFRAGDRSVSCCHPLQTPIRALLLKYGLPIGKWSDCNGPLGDDARVCDVNGVTTYEPC <u>NS5A gene sequence:</u> nucleotides 6342-7715 of SEQ ID NO:75

NS5B Protein and Gene Sequence

<u>NS5B Amino Acid Sequence:</u> (SEQ ID NO:85)
MQSYSWFRPIVAPTTPPLPATRTVAGILRADTSRVYTTTAVDVSERQAKVTIDQTSAKVDQCFRDTYNCCLAKAKTF
RQSGMSYEDAVSKMRANTTRDHNNGITYSDLVSGRAKPVVQKIVNQMRAGVYDAPMRIIPKPEVFPRDKTTRKPPRF
IVFPGCAARVAEKMILGDPGAITKHVLGDAYGFATPPHERARLLEQWWNRATEPQAIAVDAICFDSTITAEDMDREA
NIVAAAHTDPEGVHGLYNYYKRSPMCDITGKVVGVRCCRASGTLTTSSGNTLTCYLKVRAACTRSGIKPIGLLIHGD
DTLIVTERCAQETLDEFSNALDDYGFPHTIQASGDLSSIECCSARVDSVCLRGGMRRMLVPQARRAIARVLGEKGDP
LGTIGSYVVMYPTAAVTVYVLLPLLCMLIRNEPSQTGTLVTLTVHGNSVSPAWLLPTIIANLHGRDALQVVRHSAA
SMAELSSALAFFGMRGLNCWRRRRAIRADMIKSGGWNANFAQMLLWSPEVRTPQPEPRGLCLLPPELWERPYENLH
LSTIDRNRGASRLRFWLVASAILALLCL <u>NS5B gene sequence:</u> nucleotides 7716-9416 of SEQ ID NO:75

5' UTR sequence

<u>5' UTR Sequence:</u> nucleotides 1-110 of SEQ ID NO:75

3' UTR sequence

<u>3' UTR Sequence:</u> nucleotides 9417-9431 of SEQ ID NO:75

```
Majority    TCAGAGCAGGTGACCGATCAGTCTCATGTTGTCACCCCCTTGCAAACTCCTATTAGGGCCCTGCTTCAAAAGTACGGGTTA
                        7610      7620      7630      7640      7650      7660      7670      7680

UC0125-US   TCAGAGCAGGTGACCGATCAGTCTCATGTTGTCACCCCCTTGCAAACTCCTATTAGGGCCCTGCTTCAAAAGTATGGGTTA    7618
ABT0070P-US TCAGAGCAGGTGATCGATCAGTCTCATGTTGTCACCCCCTTGCAAACCCCTATTAGGCCCCTGCTTCTAAAGTACGGGTTA    7625
ABT0096P-US TCAGAGCAGGTGACCGATCAGTCTCATGTTGTCACCCCCTTGCAAACTCCTGTTAGGCCCTGCTTGAAAAGTACGGGTTA     7629
ABT0128A-US NNNNNNNNNNNNNNNNNNNNNNNNNNNNNNNNNNNNNNNNNNNNNNNNNNNNNNNNNNNNNNNNNNNNNNNNNNNNNNNN     7588

Majority    CCTATCGGGAAGTGTCCGACTGCAACGGGCGCCCCTTGGTGACGATGCCCGAGTCTGTGACGTCAATGGAGTAACAACTTA
                        7690      7700      7710      7720      7730      7740      7750      7760

UC0125-US   CCTATTGGGAAGTGGTCCGACTGCAACGGCGGCCCCTTGGTGACGACGCCCGAGTCTGTGACGTCAATGGAGTGACAACTTA   7698
ABT0070P-US CCTATCGGGAAGTGGTCTGACTGCAACGGGCCCCTTGGTGACGATGCTCGAGTCTGTGACGTCAATGGAGTAACAACTTA     7705
ABT0096P-US CCTATCGGGAAGTGGTCCGACTGCAACGGGCCCCGCTTGGTGACGATGCCCGAGTCTGTGACGTCAATGGAGTAACAACTTA   7709
ABT0128A-US NNNNNNNNNNNNNNNNNNNNNNNNNNNNNNNNNNNNNNNNNNNNNNNNNNNNNNNNNNNNNNNNNNNNNNNNNNNNNNNN     7668

Majority    TGAACCATGCATGCAATGCTACAGTTGGTTCCGACCGATTGTGGCACCAACAACAACCCCACCTTTACCTGCAACCCGGAGCG
                        7770      7780      7790      7800      7810      7820      7830      7840

UC0125-US   TGAACCATGCATGCAATGCTACAATTGGTTCCGATCGATCGATTGTGTGGCACCAACAACACCCCACCTTTACCTGCAACCCGGAGCG  7778
ABT0070P-US TGAACCATGCATGCAATCCTACAGTTGGTTCGACCGATTGTGGCACCAACAACACCCCACCCTTGCCTGCAACCCGGACCG    7785
ABT0096P-US TGAACCATGCATGGAGTCCTACAGTTGGTTCCGACCAATTGTGGCACCAACAACCCCACCCCACCTTTACCTGCAACCCGGAGTG   7789
ABT0128A-US NNNNNNNNNNNNNNNNNNNNNNNNNNNNNNNNNNNNNNNNNNNNNNNNNNNNNNNNNNNNNNNNNNNNNNNNNNNNNNNN     7748

Majority    TGGCTGGCATTTTACGCGGCAGACACATCGCGCGTTTACACCACAACGCGGTTGATGTCTCCGAGCGGCAGGCTAAGGTC
                        7850      7860      7870      7880      7890      7900      7910      7920

UC0125-US   TGGCTGGCATTTTGCGCGCAGACACATGCGCGGTCTACACCACAACGCGGTTGATGTCTCCGAGCGGCAGGCTAAGGTC      7858
ABT0070P-US TGGCTGGCATTTTACGCGGCAGACACATCGCGCGCTTTACACCACAACGCGGTTGACGTCTCCGAGCGGCAGGCCAAGGTC    7865
ABT0096P-US TGGCTGGCATTTTACGCGGCAGACACATCGCGGCGTTTACACCACAACGCGGTTGACGTCCCCGAGCGGCAGGCTAAGGTC    7869
ABT0128A-US NNNNNNNNNNNNNNNNNNNNNNNNNNNNNNNNNNNNNNNNNNNNNNNNNNNNNNNNNNNNNNNNNNNNNNNNNNNNNNNN     7828

Majority    ACAATTGATCAAACATCAGCCAAGGTGGATCAGTGTTCCGAXXXXXXXXXXTGCTGCCTTGCCAAGGCAAAGACCCXX
                        7930      7940      7950      7960      7970      7980      7990      8000

UC0125-US   ACGATTGATCAAAAGTCAGCCAAGGTGGACCAGTGCTCCGAGACACACAATACAATTGCTGCCTTGCCAAGGCAAAGACCTTT   7938
ABT0070P-US ACAATTGATCAAACATCAGCCAAGGTGGATCAGTGTTCCGAGATCCAGAGACACATAACAATTGCTGCCTTCTAAGGCAAAGACCTT  7945
ABT0096P-US ACAATCGATCAAACATCAGCCAAGGTGGATCAGTGTTCCGANNNNNNNNNNNNNNNNNNNNNTTCTGCCTTGCCAAGGCAGAGACNN  7949
ABT0128A-US NNNNNNNNNNNNNNNNNNNNNNNNNNNNNNNNNNNNNNNNNNNNNNNNNNNNNNNNNNNNNNNNNNNNNNNNNNNNNNNN      7908
```

Phylogenetic analysis of 31 flavivirus polyproteins.

NS3

Phylogenetic analysis of 31 flavivirus NS3 proteins.

Phylogenetic analysis of 31 flavivirus NS5B proteins.

FIG. 13A

Human Pegivirus 2 (Consensus Sequence) Nucleic Acid Sequence - SEQ ID NO:299

```
   1 AACTGTTGTT GTAGCAATGC GCATATTGCT ACTTCGGTAC GCCTAATTGG TAGGCGCCCG
  61 GCCGACCGGC CCCGCAAGGG CCTAGTAGGA CGTGTGACAA TGCCATGAGG GATCATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GGAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGGTGTTCAA CTGATCAAAC CATTTGTTCT
 361 CCAGTCGTGG GGGCCGACTA TAATACCTCC TCGGGCTGCC GGGCCTTAAA TGGGAGCTAC
 421 CACTGCGGTG GTGGCTCTTG CCGGTCACCA AGTCGTGTGC AGGTTGCGAG ACGAGTCTTG
 481 CAGCTGTGCG CATTCCTTGC GCTGATCGGA TCCGGTATGT GTTCGATCCG GTCCAAAACT
 541 GAAGGGCGCA TTGAGTCAGG GCAAATATTG CAGTCTCAGC GCGCATGTTG GACTGGTGAG
 601 GGTTTTGCTT TCTTTTCTAA CTGTTGCAAT CAATCTGATA TTATGTGGTG TTTGCACCGT
 661 TGGTGTGTGA CAAGACCTGG CTGTTTAGTG TGCACGGGCA ATGCCACTCA TCCTGTCTGC
 721 TGGGACTATC TTGGGTCCGG TGTAAGTCGG CGGCCTGCGC GTCGAATGGG TGAGGGAGCT
 781 GAAGTGCTTC TTCGCTTGAT CGGCATTGCA GGTTGGCTCG GGCTGTTAGC TGAGGCTCTT
 841 GGTATGTCCG AAATCTATGC AGCTATTCTT TGCTTTGGAT TTATTGCTTG GTATGGCTGG
 901 GGTATACCTA AAACATTGGT GTGCACAGTT CGCCTGCAG TGAACATTTC TCCCTATAGC
 961 TTCTTATCTC CAGATACTAT CGCATTTGGT ACGTGGATAC TACAACTACC TGGTCTTTTG
1021 TGGCAAATGT TTGTCAGCTT CCCTATACTT TACAGCACTT GGATTCTTTG GTTGTTGCTC
1081 AGCGGCAAGA CTGTTGCTGT GATAGCGATC CTTTTGGCTA GTCCTACGGT TATGGCGTAC
1141 AAGCATCAAT CTGAAAGCTA CCTCAAATAC TGTACCATAA CCAATGCTTC AACTGCTATG
1201 AACTGTGACT GCCCCTTTGG AACCTTTACT CGCAATACTG AGTCTCGTTT CTCTATACCT
1261 AGATTCTGTC CTGTTAAAAT TAAXAGCTCT ACATTTATCT GTTCATGGGG GTCGTGGTGG
1321 TGGTTTGCTG AGAACATCAC ACGTCCATAC TCGGACGTTG GCATGCCACC AGCACCGATT
1381 TCCGCTTTGT GCTATATCTA TTCAAACAAT GACCCACCTC CTTGGTATCA TAACACAACT
1441 ATCATACCTC AGAACTGTCG CAACTCTACG GTTGATCCTA CCACAGCTCC ATGCCGTGAC
1501 AAGTGGGGCA ATGCAACTGC TTGTATTCTT GACCGCCGGT CGCGGTTCTG CGGGGACTGC
1561 TATGGCGGTT GXTTCTATAC TAATGGTAGT CATGATCGAT CCTGGGATCG ATGCGGGATT
1621 GGTTACCGTG ATGGACTCAT AGAGTTCGTG CAGCTCGGTC AGATTCGACC TAACATCTCG
1681 AATACGACCA TTGAGCTCCT CGCTGGCGCC TCGCTTGTGA TCGCATCCGG TCTTCGGCCT
1741 GGGTXTGGTT GCAGCCGAGC GCATGGCGTG GTGCACTGCT ATAGGTGTCC TTCATACCGT
1801 GACCTTGAAC AGTTXGGTCC TGGGCTTGGG AAATGGCTGC CATTGCCCGG CGAGCCTGTC
1861 CCGGAGTTGT GTATCAACCC TCAGTGGGCG AGGCGCGGCT TCCGGATGTC TAATAATCCT
1921 CTGAGCTTGC TACAGACCTT CGTTGAGGAC ATTTTCCTAG CGCCTTTTTG TAATCCGACG
1981 CCTGGCCGTG TACGTGTGTG TAACAATACC GCTTTCTATC CAACAGGAGG CGGCTTTGTG
2041 CAGCTCATCG GXGACGTCCA GGTGCTAACC CCTAACACTG CATCTTTACA CTCTCTGCTG
2101 ACTTTGATAT CTCTTATCTT GTTGGTGTGT GTTGTTTCTG GTGCGCGATT CGTTCCACTA
2161 ATAATCATAT TTTTCTGGAG CGCGCGCCAT GTATATGCTT CTTGTTACTT AAGCTGTGAT
2221 TGGGCTGTTT GCAACGATGC GTTCTGTTTC ACATCTGGCA CTTGTGCTAC CTTCAATGAC
2281 GTCTTGTGTC TGCCGGTTGC GACGCGCATA TCGTCCTGTG GCCATGCGTT GCCACCGCCC
2341 GACCGTGGTT GGGAGGTGCC TGCGGCGATG TCATGGGTGA TTTCGCGGAC TACTGGCTTG
2401 ACGTTCGATG TCTTTTCCTT CATXCAGTAT CTTCCTACTG TGCCTGGCAA CAACACCGAT
2461 ATCATTTACT GTGGTGAACC AACCTTCTTC GGGGACATCA CGGGCATCTA TTGGCCTTAC
2521 TTTTTGCCTG GCGTGTTGCT CTTGTACTTG ACTCCCTTCC TXGGTTTAAG GTTAATGCTT
2581 GCCGGCTTTA ATATAGATGG CTTGTTTCCC ATACGGCATG CCACGGCTGC ACTGAGGTTC
2641 TCGACTTCGC GTGTGACCTT GAGTGTCGTA TCTGCTTTTC TAATCTATAT ATTATCTCAC
2701 CCTGTTAATG CTGCGCTCAA TAGAATTTGC TTAGCATCTG CAAATTTAGA GATGATCTTA
2761 TCCTTTGATA CCTATCATGA GACTGTTCTT TAXATCGTTT GTCTATTGCT CTACCTCCAG
2821 GTGTCGCCCC GTGCGGGCTT GGCCGCTATG GTGCCCATCA AGCTATCTCG AGGCCTGTTA
2881 TTCGCTGTGG TGTTGGCGCA CGGAGTGTGC CGACCTGGGC GGGTATTTGG TCTTGAGGTT
2941 TGCGCGGACA TCTCTTGGTT GGTGGAGTTT ACTGGCAACT GCACTTGGTA CATGTCCTGT
3001 GTCTTCTCTT TTTGGTGCGC AGTGTTTGCC TTCACCAGTC CACTTGGACG ACAGTATAAG
3061 CTTCAGATCT ATCGGTACTG GGCGCAGGTC TATGCCAGAC TCATCCTCGC TGTCGGTTGT
3121 GGTCCTCTCG GGCGAGAGTT CCATTCCGC GCAAGCGTGG GCGTGCTTTG GTGTGGTGCT
3181 TGCATGCTCT GGCCCCGTGA GTGCTCTGAA ATCGCTTGG TCTTCATTCT GTGTGCTCTG
3241 ACAGTGGACA CCATAGACAC ATGGTTAGTA GCGTGCTTGT CCGCAGGGCC XAGTGCGCGA
3301 ACCCTTGCAA CXCTGGCCGA TGACATGGCG CGCATXGGTG ACCACCGGGC GTTGCGCGCC
```

FIG. 13B

```
3361 GTGTTGCGTT GCTTTGGATC ACGTGGCACA TACATATACA ACCACATGGG CCAGGTCTCA
3421 GAACGGGTGG CGCAAGCAGT CAGGGATCTC GGCGGTTGCT TGGAACCAGT CGTGTTGGAG
3481 GAGCCCACCT TTACTGAGXT CGTGGATGAT ACAATGAGTT TGGTGTGTGG ACAATTGCTT
3541 GGAGGTAAAC CCGTGGTGGC CCGCTGCGGC ACGCGTGTCT TGGTGGGACA CCTCAACCCT
3601 GAAGATCTGC CACCTGGTTT CCAGCTGAGT GCTCCGGTGG TTATTACCAA ACCAAGCATT
3661 GGTACGTGGT CCTTCCTTAA GGCGACACTC ACAGGGCGTG CTGAAACACC XGGATCCGGC
3721 CAGATCGTGG TGTTGTCTTC CCTGACAGGT CGGTCAATGG GTACTGCAGT GAATGGCACA
3781 CTGTATGCGA CCGGCCATGG TGCCGGTGCG CGCGGCCTAG CCACGTGCGC TGGTTTGAGG
3841 ACGCCACTTT ACACGGCATT ATCTGATGAT GTCGTGGCCT ACTCTTGCCT TCCGGGCATG
3901 AGTTCCCTAG AGCCCTGCXG CTGTTCGCCG AGCCGGGTTT GGGTGATGAA CAACAACGGA
3961 GGGTTGGTGT GTGGCAGAGT GGAGAAXGAC GACGTCTGTT TGGACTGTCC CACGCACATA
4021 GATCAACTGC GGGGTGCTTC GGGGTCACCG GTTTTGTGTG ATCACGGTCA TGCATACGCG
4081 TTGATGCTCG GTGGTTACTC TACCAGTGGT ATTTGTGCGC GTGTCCGGAT AGTCCGGCCA
4141 TGGCAGAACG CCTATTCCTC CTCAGGGGGG CAAGGCGGAA TGCAGGCGCC AGCTGTGACA
4201 CCAACATACT CTGAAATCAC CTACTATGCC CCTACTGGTT CTGGTAAGTC AACAAAATAT
4261 CCAGTGGACC TAGTCAAACA GGGACACAAA GTATTGGTCC TTATACCAAG TGTGGCTGTC
4321 GTCAAAAGTA TGGCCCCTTA CATTAAGGAG ACATATAAGA TTAGACCTGA AATTAGAGCT
4381 GGCACAGGXC CTGACGGTGT GACGGTCATC ACTGGTGAGA ACTTGGCGTA CATGACCTAT
4441 GGCCGCTTCC TTGTGGATCC GGAGACGAAT CTGCGGGGTT ATGCCGTAGT CATTTGCGAC
4501 GAGTGCCACG ACACATCATC CACCACGCTA CTCGGCATTG GCGCAGTGCG CATGTATGCC
4561 GAGAAAGCTG GAGTGAAGAC CGTTGTATTC GCCACAGCCA CTCCTGCTGG CATTCAAGTA
4621 CAGCCACATC CCAACATTGA TGAATATTTA TTGACTGACA CAGGCGACGT GGAATTCTAC
4681 GGCGCCAAAA TCAAATTGGA CAACATCAGA ACTGGTAGAC ATGTTATCTT TTGCCACTCG
4741 AAGGCCAGGT GTGCGGAACT AACGCAGCAG CTCTCCGGCC TTGGTGTTCG TGCAGTGAGT
4801 TTTTGGCGCG GCTGTGACAT CAAAACCATT CCCGCCTCAG ACTCTATTGT TGTAGTGGCA
4861 ACTGATGCAT TGTCCACAGG CTACACAGGX AACTTTGATT CGGTCATCGA CTGCGGGTGT
4921 TGCGTAGAGC AAACTGTGAC AATTGACATG GACCCTACGT TCTCCATCTC GGCCCGAGTG
4981 GTGCCATGTA CTGCTGCATT GCGTATGCAG CGGCGCGGAC GTACCGGTCG TGGCAGAAGG
5041 GGAGCGTACT ACACAACCAC TCCAGGAGCA GCACCCTGCG TCAGCGTTCC CGATGCTAAC
5101 GTCTGGCAAG CAGTGGAGAG CGCCATGGTC TTTTATGATT GGAGTGCTGC CAGGATACAX
5161 CAGTGCCTGG CGGCATACCA TGATTTAGGG TGCACACCAC GCATCAGTTG TGACCCACAC
5221 ACTCCAGTGC GGGTGATGGA CACACTGAGG GCGTACCTGC GCAGACCTGA GGTGACGACT
5281 GCGGCTCTCG CAGGAGAGCA GTGGCCGCTG CTTTACGGTG TGCAGTTGTG CATCTGCAAA
5341 GAGACCGAGG CCCACGGTCC AGACGATXGC ATCAAGTGGA AGTGCTTACT CAACAACAGT
5401 AACAAAACAC CCCTGTTGTA TGCCTTAGAC AATCCTACAC TGGAATTCAC TACCCAACAT
5461 GACTTGACTC GCCGTATAGC CGGCGCTTTA TCGAGCACAG TGTTCGTGGA GACAGGCTAC
5521 GGCCCCATCC TCCTTGCTGG CGCCGCTTTG GCTGCCTCCT TCGCCTTTGC GGGCGCCACT
5581 GGAGCTTTAG TGCCGTCGGC CGTTTGGAGC GTTGACAACG GCTTGCTGG CGTGACCCGT
5641 CCCGACGCGA CAGACGAGAC CGCGGCCTAC GCGCAGCGCT TGTACCAAGC CTGCGCAGAT
5701 TCAGGAXTTX TCGCCGACTT GCAGGGXACG GCGAGTGCGG CGCTGXGCAA ACTGCCGAT
5761 GCCAGTAGGG GTGCTAGTCA ATATCTGGCA GCCGCGCCTC CTTCGCCCGC CCCCCTGGTA
5821 CAGGTGCTGC AGTTCCTXGA GACCAACTTT AGCTCCATTG CATCTTTCGG TCTGCTCTGT
5881 GCTGGCTGTC AGGCTGGCGA GTGCTTCACT GCGCTTGCCG GGTTGGTGTC CGGTGCTACA
5941 GCTGGCTTGG GAGGTGCCCA TAAGTGGTTG TTAGCTATTG CAGGAACTTG GCTAGTTAGC
6001 TTGCAGACTG GGCCCCGTGG CGGCATGGTT GCGGGXCTCT CGGTTCTAGC AGGCTGTTGC
6061 ATCGGTAGTG TCACCGGGCT TGACTTCCTG TTTGGGTGCC TTACAGGTTG GGAGGCCGTG
6121 GTCGGTGCTG CGGTTGCGAC ACAGAAGATC TTGTCTGGTT CGGCTGATAT GACCACTCTG
6181 GTAGATCTCT TACCTGCTCT CTTCTCCCCT GGXGCCGGCA TAGCTGGCAT CGTGCTTGTC
6241 TTTATTCTAA GCAACTCAAG TGTAACCACG TGGGCTAATC GGCTATTGTC CATGTGTGCA
6301 AAACAAACXA TTTGTGAAAA CTACTTCTTA ACTGAGAAAT TTGGCCAACA ATTAAGCAAA
6361 CTTTCCCTGT GGCGCTCTGT GTACCATTGG GCGCAGGCAC GTGAGGGATA CACACAGTGC
6421 GGXGTGGTCA GCGGGATCTG GAGCTTTGTC TTGTGCATTC TACGCGCTGT GTGGGATTGG
6481 GCGGCXAAXC ATGTGCCACG GTTCCGTGTG CCTATGATTG GCTGCTCACC TGCGTGGTGC
6541 GGGCGCTGGC TTGGTACCGG CACCTTGTTG ACCACCTGTG GGTGTGGAGA ACGTGTGTCC
6601 CTTCAGTGCC TTTGCTCAAC ATCTGACCCA ACACTCAGTG TGGGCCGTTG GTGTCGGTGT
6661 AGTTGGAGTG TTGGGTTCCC ATTCAACCCG ACTACGACAG CCACCGGCAC TTTACGGCCG
6721 GACATCAGTG ACGCCACTAA ATTGGGTTTC CGGTATGGTG TTGCCGAGAT CGTGGAGCTA
6781 GAGCGGCGGG GCGACAAATG GCATGTCTGT GCAGCATCAT GTTGCTTGGA CCGAGCCAGC
```

FIG. 13C

```
6841 GTTGCATCCG CCGTGAAGGC CCCACCGGTC ACGGCCAATG GTATACCTAT CAGTACCTTT
6901 TCTCCACCAC AAACTTACAG CCTCTCTCTC TGTTCTTTTG ATTCAGTTTG CATGTCTACT
6961 AACTTATGTA ACCCAGCTAA GACCCTGAGT GTGTGCTCXC AGGAGGCTGT TGAGCTACTG
7021 GAAGAAACAG TTGACACAGC ACAAGTAATG ATGTGTCAAA ATCTGGAGGC GCGAAGACGC
7081 GCXGAGTATG ATGCATGGCA AGTTCGCCAA GCAGTTGGCG ACGAGTACAC GCGTTTGGCA
7141 GACGAGGATG TTGACACGAC AACGTCGGTG AAACCCCGG TGGCCAGGGC TGCTGTGGGT
7201 AGCTCAACGT TGGATGATGT TAGCGTGCTG ACTGTCTTGC GCGAACTCGG CGACCAATGC
7261 CAAAATGCTA TCAAATTTGT AGTTCAGGCG GCTTCACGGT TTGTTCCACC AGTGCCCAAG
7321 CCACGCACGC GTGTCTCGGG TGTGTTGGAG CGTGTGCGCA TGTGCATGCG CACGCCACCA
7381 ATCAAGTTTG AGGCCACCGC AGTACCAATT CATAACATAA TCCCAGAAGA GTGTCACATT
7441 GTGCTACGCT GTACCGGCTG TAACGACCAG GCCTTGACTG TTCCGTACGG CACTTGCACT
7501 CAGACTTTAA TCAAACATTT GACTAACAAA CACAGCCACT ACATTCCAAA ACAGAAGATA
7561 GAAGAAGACA CAGAAGTAAC TGTCATTTGC GCCGTACCAA CAAAGCGCGC AAGTAAACTC
7621 ATCACTTTCA GAGCAGGTGA TCGATCAGTC TCATGTTGTC ACCCCTTGCA AACTCCTATT
7681 AGGGCCCTGC TTCTAAAGTA CGGGTTACCT ATCGGGAAGT GGTCCGACTG CAACGGGCCC
7741 CTTGGTGACG ACGCCCGAGT CTGTGACGTC AATGGAGTAA CAACTTATGA ACCATGCATG
7801 CAATCCTACA GTTGGTTCCG ACCGATTGTG GCACCAACAA CCCCACCTTT ACCTGCAACC
7861 CGGAGCGTGG CTGGCATTTT ACGCGCAGAC ACATCGCGCG TTTACACCAC AACGGCGGTT
7921 GACGTCTCCG AGCGGCAGGC TAAGGTCACA ATTGATCAAA CATCAGCCAA GGTGGATCAG
7981 TGTTTCCGAG ACACATACAA TTGCTGCCTT GCTAAGGCAA AGACCTTCAG ACAATCTGGC
8041 ATGTCATATG AGGATGCTGT GTCAAAGATG CGCGCAAACA CCACGCGTGA CCATAACAAX
8101 GGCATCACTT ATTCAGATTT GGTCTCTGGA CGCGCAAAAC CTGTCGTTCA GAAAATTGTA
8161 GATCAAATGC GCGCTGGAGT GTACGACGCT CCAATGCGCA TTATCCCAAA ACCTGAAGTG
8221 TTCCCTCGAG ACAAGTCAAC ACGGAAGCCA CCXCGGTTCA TCGTTTTCCC TGGGTGCGCC
8281 GCGCGAGTCG CGGAGAAAAT GATCCTGGGC GATCCTGGCG CGATAACCAA GCACGTGCTA
8341 GGTGATGCCT ACGGGTTTGC CACTCCGCCG CATGAGCGCG CGCGCCTATT GGAACAATGG
8401 TGGAACCGCG CAACGGAGCC ACAAGCTATC GCGGTTGATG CGATCTGCTT TGATAGCACC
8461 ATCACGGCAG AGGACATGGA TCGTGAGGCC AACATCXTGG CTGCAGCGCA TXCGGACCCT
8521 GAAGGTGTTC ACGGCCTATA CAATTATTAC AAAAGAAGCC CCATGTGTGA CATCACAGGA
8581 AAAGTTGTCG GGGTGCGTTG CTGTCGAGCC TCAGGTACGC TTACAACAAG CAGTGGCAAC
8641 ACGCTTACTT GCTACCTCAA GGTTCGTGCA GCTTGCACGC GCGCCGGCAT TAAACCAATT
8701 GGCTTACTAA TTCATGGAGA TGACACCCTC ATTATCACAG AACGTTGCGC TCAAGAAACT
8761 CTCGATGAGT TCAGCAACGC ACTTGATGAC TATGGGTTCC CTCACACCAT CCAGGTGTCT
8821 GGGGACCTCT CGTCTGTCGA GTGCTGTAGC GCACGTGTGG ACAGCGTTTG CCTCCGGGGA
8881 GGTATGCGTC GCATGCTCGT GCCACAAGCT CGACGTGCGA TTGCACGCGT TCTCGGGGAA
8941 AAGGGCGATC CACTGGGTGT CATCAGCAGC TATATTGTCA TGTATCCTAC TGCGGCXGTG
9001 ACTGTCTACG TGCTATTGCC CCTGTTGTGC ATGCTCATTC GAAATGAGCC ATCGCAGACG
9061 GGGACACTTG TXACGCTGAC GGTCCACGGT AACAGTGTGA GCGTGCCAGT GTGGCTGCTT
9121 CCAACCATCA TTGXAAATTT ACATGGXCGT GACGCACTAC AGGTAGTCCG TCACAGTGCA
9181 GCTTCCATGG CGGAACTGTC ATCAGCGTTG GCCTTCTTTG GCATGAGAGG GTTGAACTGC
9241 TGGAGGCGGA GACGCCGTGC CATCAGGACT GATATGATCA AGTTGGGCGG GTGGAATGCG
9301 AATTTCGCGC AGATGTTACT GTGGTCACCG GAGGTXAGXA CACCACAXCC CGAACCAAXG
9361 GGXXTGTGTC TCTTXCCACC GGAACTATGG GAGCGTCCGT ACGAAAATTT GCACTTGAGC
9421 ACGATCGACC GCAATCGTGG TGCTAGTCGC TTACGGTTTT GGTTGGTTGC TAGTGCTATA
9481 CTCGCTCTGC TTTGCTTGTA AATCCTAAAT CAATGTAGTA CCAGGACTAC AAGGCAGGAG
9541 GTGAAGTCAG CTGTACCCAC GGCTGGCTGA AACCGGGGCT TGACGACCCC CCTATCCGA
9601 GTTGGGCAAG GTAACATCAC GGGTGTGACG ACCCCGCCCC CCATGTCGC GCGTAAGCGC
9661 ACGGGCAAGG CAGCTAGGCT GAGAGTCTGG GCAACTCTCC CGTACCCCAC CCGAGGCTAC
9721 GCCTCGTCCT GGCGAGGACC GTAAACATAC GTCGTCAGCG TGGTGACCTG ACGTATCTTG
9781 TTACCACTT AATGGTCGTA ACTCGACCCC CGTGCCGGGG ATCTAAGCGC GGCACCGCGA
9841 TGAGGGGGGT CAACGGCCCC TTTCATT
```

FIG. 14A

Human Pegivirus 2 (Consensus Sequence) Genes and Untranslated Regions

5' UTR Sequence

5' UTR Sequence: nucleotides 1-327 of SEQ ID NO:299

S Protein and Gene Sequence

S Protein Amino Acid Sequence: (SEQ ID NO:304)

MGCSTDQTICSPVVGADYNTSSGCRALNGSYHCGGGSCRSPSRVQVARRVLQLCAFLALIGSGMCSIRSKTEGRIESGQ

S protein gene sequence: nucleotides 328-564 of SEQ ID NO:299.

E1 Protein and Gene Sequence

E1 Protein Amino Acid Sequence: (SEQ ID NO:305)

ILQSQRACWTGEGFAFFSNCCNQSDIMWCLBRWCVTRPGCLVCTGNATHPVCWDYLGSGVSRRPARRMGEGAEVLLRLIGIAGWLGLLAEALG
MSEIYAAILCFGFIAWYGWGIPKTLVCTVCPAVNISPYSFLSPDTIAFGTWILQLPGLLWQMFVSFPILYSTWILWLLLSGKTVAVIAILLAS
PTVMA

E1 protein gene sequence: nucleotides 565-1137 of SEQ ID NO:299.

E2 Protein and Gene Sequence

E1 Protein Amino Acid Sequence: (SEQ ID NO:306)

YKHQSESYLKYCTITNASTAMNCDCPFGTFTRNTESRFSIPRFCPVKIXSSTFICSWGSWWWFAENITRPYSDVGMPPAPISALCYIYSNNDP
PPWYHNTTIIPQNCRNSTVDPTTAPCRDKWGNATACILDRRSRFCGDCYGGXFYTNGSHDRSWDRCGIGYRDGLIEFVQLGQIRPNISNTTIE
LLAGASLVIASGLRPGXGCSRAHGVVHCYRCPSYRDLEQXGPGLGKWVPLPGEPVPELCINPQWARRGFRMSNNPLSLLQTFVEDIFLAPFCN
PTPGRVRVCNNTAFYPRGGGFVQLIGDVQVLTPNTASLHSLLTLISLILLVCVVSGARFVPLIIIFFWSARHVYA

E2 protein gene sequence: nucleotides 1138-2199 of SEQ ID NO:299.

X Protein and Gene Sequence

X Protein Amino Acid Sequence: (SEQ ID NO:307)

SCYLSCDWAVCNDAFCFTSGTCATFNDVLCLPVATRISSCGHAVPPPDRGWEVPAAMSWVISRTTGLTFDVFSFXQYLPTVPGNNTDIIYCGE
PTFFGDITGIYWPYFLPGVLLLYLTPFLGLRLMLAGFNIDGLFPIRHATAALRFSTSRVTLSVVSAFLIYILSHPVNAALNRMFLASANLEMI
LSFDTYHETVLXIVCLLLYLQVSPRAGLAAMVAIKLSRGLLFAVVLAHGVC

X protein gene sequence: nucleotides 2200-2910 of SEQ ID NO:299.

FIG. 14B

NS2 Protein and Gene Sequence

NS2 Protein Amino Acid Sequence: (SEQ ID NO:308)

RPGRVFGLEVCADISWLVEFTGNCTWYMSCVFSFWCAVFAFTSPLGRQYKLQIYRYWAQVYARLILAVGCGPLGREFHFRASVGVLWCGACML
WPRECSEISLVFILCALTVDTIDTWLVACLSAGPSARTLATLADDMARKGDHRALRAVLRCFGSRGTYIYNHMGQVSERVAQAVRDLGGCLEP
VVLEEPTFTEXVDDTMSLVCGQLLGGKPVVARCGTRVLVGHLNPEDLPPGFQLS

NS2 protein gene sequence: nucleotides 2911-3630 of SEQ ID NO:299.

NS3 Protein and Gene Sequence

NS3 Protein Amino Acid Sequence: (SEQ ID NO:309)

APVVITEPSIGTWSFLKATLTGRAETPGSGQIVVLSSLTGRSMGTAVNGTLYATGHGAGARGLATCAGLRTPLYTALSDDVVAYSCLPGMSSL
EPCXCSPSRVWVMNNNGGLVCGRVEXDDVCLDCPTHIDQLRGASGSPVLCDHGHAYALMLGGYSTSGICARVRIVRPWQNAYSSSGGQGGMQA
PAVTPTYSEITYYAPTGSGKSTKYPVDLVKQGHKVLVLIPSVAVVKSMAPYIKETYKIRPEIRAGTGPDGVTVITGENLAYMTYGRFLVDPET
NLRGYAVVICDECHDTSSTTLLGIGAVRMYAEKAGVKTVVFATATPAGIQVQPHPNIDEYLLTDTGDVEFYGAKIKLDNIRTGRHVIFCHSKA
RCAELTQQLSGLGVPAVSFWRGCDIKTIPASDSIVVVATDALSTGYTGNFDSVIDCGCCVEQTVTIDMDPTFSISARVVPCTAALRMQRRGRT
GRGRRGAYYTTTPGAAPCVSVPDANVWQAVESAMVFYDWSAARIXQCLAAYHDLGCTPRISCDPHTPVRVMDTLRAYLRRPEVTTAALAGEQW
PLLYGVQLCICKETEAHGPDDXIKWKCLLNNSNKTPLLYALDNPTLEFTTQHDLTRRIAGALSSTVFVET

NS3 protein gene sequence: nucleotides 3631-5514 of SEQ ID NO:299.

NS4A Protein and Gene Sequence

NS4A Protein Amino Acid Sequence: (SEQ ID NO:310)

GYGPILLAGAALAASFAFAGATGALVPSAVWSVDNGLAGVT

NS4A protein gene sequence: nucleotides 5515-5637 of SEQ ID NO:299.

NS4B Protein and Gene Sequence

NS4B Protein Amino Acid Sequence: (SEQ ID NO:311)

RPDATDETAAYAQRLYQACADSGXXASLQGTASAALXKLADASRGASQYLAAAPPSPAPLVQVLQFLETNFSSIASFGLLCAGCQAGECFTAL
AGLVSGATAGLGGAHKWLLAIAGTWLVSLQTGFRGGMVAGLSVLAGCCIGSVTGLDFLFGCLTGWEAVVGAAVATQKILSGSADMTTLVDLLP
ALFSPGAGIAGIVLVFILSNSSVTTWANRLLSMCAKQTICENYFLTEKFGQQLSKLSLWRSVYHWAQAREGYTQCG

NS4B protein gene sequence: nucleotides 5638-6423 of SEQ ID NO:299.

FIG. 14C

NS5A Protein and Gene Sequence

NS5A Protein Amino Acid Sequence: (SEQ ID NO:312)

```
VVSGIWSFVLCILRAVWDWAAXHVPRFRVPMIGCSPAWCGRWLGTGTLLTTCGCGERVSLQCLCSTSDPTLSVGRWCRCSWSVGFPFNPTTTA
TGTLRPDISDATKLGFRYGVAEIVELERRGDKWHVCAASCCLDRASVASAVKAPPVTANGIPISTFSPPQTYSLSLCSFDSVCMSTNLCNPAK
TLSVCSQEAVELLEETVDTAQVMMCQNLEARRRAEYDAWQVRQAVGDEYTRLADEDVDTTTSVKPPVARAAVGSSTLDDVSVLTVLRELGDQC
QNAIKFVVQAASRFVPPVPKPRTRVSGVLERVRMCMRTPPIKFEATAVPIHNIIPEECHIVLRCTGCNDQALTVPYGTCTQTLIKHLTNKHSH
YIPKQKIEEDTEVTVICAVPTKRASKLITFRAGDRSVSCCHPLQTPIRALLLKYGLPIGKWSDCNGPLGDDARVCDVNGVTTYEPC
```

NS5A protein gene sequence: nucleotides 6424-7797 of SEQ ID NO:299.

NS5B Protein and Gene Sequence

NS5B Protein Amino Acid Sequence: (SEQ ID NO:313)

```
MQSYSWFRPIVAPTTPPLPATRSVAGILRADTSRVYTTTAVDVSERQAKVTIDQTSAKVDQCFRDTYNCCLAKAKTFRQSGMSYEDAVSKMRA
NTTRDHNXGITYSDLVSGRAKPVVQKIVDQMRAGVYDAPMRIIPKPEVFPRDKSTRKPPRFIVFPGCAARVAEKMILGDPGAITKHVLGDAYG
FATPPHERARLLEQWNPATEPQAIAVDAICFDSTITAEDMDREANIXAAAHXDPEGVHGLYNYYKRSPMCDITGKVVGVRCCRASGTLTTSS
GNTLTCYLKVRAACTRAGIKPIGLLIHGDDTLIITERCAQETLDEFSNALDDYGFPHTIQVSGDLSSVECCSARVDSVCLRGGMRRMLVPQAR
RAIARVLGEKGDPLGVISSYIVMYPTAAVTVYVLLPLLCMLIRNEPSQTGTLVTLTVHGNSVSVPVWLLPTIIXNLHGRDALQVVRHSAASMA
ELSSALAFFGMRGLNCWRRRERAIRTDMIKLGGWNANFAQMLLWSPEVXTPXPEPXGXCLXPPELWERPYENLHLSTIDRNRGASRLRFWLVA
SAILALLCL
```

NS5B protein gene sequence: nucleotides 7798-9498 of SEQ ID NO:299.

3' UTR Sequence

3' UTR Consensus Sequence: nucleotides 9499-9867 of SEQ ID NO:299.

FIG. 15A

Human Pegivirus 2 (ABT0070p) Nucleic Acid Sequence - SEQ ID NO:300

```
   1 AACTGTTGTT GTAGCAATGC GCATATTGCT ACTTCGGTAC GCCTAATTGG TAGGCGCCCG
  61 GCCGACCGGC CCCGCAAGGG CCTAGTAGGA CGTGTGACAA TGCCATGAGG GATCATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGGTGTTCAA CTGATCAAAC CATTTGTTCT
 361 CCAGTCGTGG AGGCCGACTA TAATACCTCC TCGGGCTGCC GGGCCTTAAA TGGGAGCTAC
 421 CACTGCGGTG GTGGCTCTTG CCGGTCACCA AGTCGTGTGC AGGTTGCAGG ACGAGTCCTG
 481 CGGCTGTGCG CATTCCTTGC GCTGATCGGA TCCGGTATGT GTTCCATCCG GTCCAAAAAT
 541 GAAGGGCGCA TTGAGTCAGG GCAAATATTG CAGTCTCAGC GCGCATGTTG GACTGGTGAG
 601 GGTTTCGCTT TCTTTTCTAA CTGTTGCAAT CAATCTGACA TTATGTGGTG TTTGCACCGT
 661 TGGTGTGTGA CAAGACCTGG CTGTTTGGTG TGCACGGGCA ATGCCACTCA TCCTGTCTGC
 721 TGGGACTATC TTGGGTCCGG TGTGAGTCGG CGGCCTGCGC GTCAATGGG TGAGGGAGCT
 781 GAAGTGCTTC TTCGCTTGAT CGGCATTGCA GGTTGGCTCG GGCTCTTAGC TGAGGCTCTT
 841 GGTATGTCTG AGATCTATGC AGCTTTCCTT TGCTTTGGAT TTATTGCTTG GTATGGCTGG
 901 GGTATACCTA AGACATTGGT GTGCACAGTC TGCCCTGCAG TGAACATTTC TCCCTATAGC
 961 TTCTTATCTC CAGATACTAT CGCATTTGGT ACGTGGCTAC TACAACTGCC TGGTCTTTTG
1021 TGGCAAATGT TTGTCAGCTT CCCTATACTT TACAGTACTT GGATTCTTTG GTTGTTGCTC
1081 AGCGGCAAGA CTGTTGCTGT GATAGCGATC CTTTTGGCTA GTCCTACGGT TATGGCATAC
1141 AAGCATCAAG CTGATAGCTA CCTCAAATAC TGTACCATAA CCAATGCTTC AACTGCTATG
1201 AACTGTGACT GCCCCTTTGG AACTTTCACT CGCAATACTG AGTCTGGTTT CACTATACCT
1261 AGATTCTGTC CTGTTAAACT TAATAGCTCT ACATTTATCT GTTCATGGGG GTCGTGGTGG
1321 TGGTTTGCTG AGAACATCAC ACGTCCATAC TCGGACGTTG GCATGCCGCC AGCACCGATT
1381 TCCGCTTTGT GCTATATCTA TTCAAACAAT GACCCACCTT CTTGGTATCG TAACACAACT
1441 ATCATACCTC AGAACTGTTA CAACTCTACG GCTGATCCTA CCACAGCTCC ATGCCGTGAC
1501 AAGTGGGGCA ATGCAACTGC TTGTATTCTT GACCGCCGGT CGCGGTTCTG CGGGGACTGC
1561 TATGGCGGTT GCTTCTACAC TAATGGTAGT CATGACCGAT CCTGGGATCG ATGCGGAATT
1621 GGTTACCGTG ATGGACTCAT AGAGTTCGTG CAGCTCGGTC AGATTCGACC TAACATCGCG
1681 AATACGACCA TTGAGCTCCT CGCTGGCGCC TCGCTTGTGA TCGCATCCGG TCTTCGGGCT
1741 GGGTATGGTT GCAGCCGAGC GCACGGCGTG GTGCACTGCT TTAAGTGTCC TTCATACCGT
1801 GACCTTGAAC GGTTCGGGCC CGGGCTTGGG AAATGGGTGC CATTGCCTGG CGAGCCTGTC
1861 CCGGAGTTGT GTATTAACCC GCAGTGGGCG AGGCGCGGCT TCCGGGTGTC TAATAATCCC
1921 TTAAGCGTGC TACAGACCTT CGTTGAGGAC ATTTTCTTAG CGCCTTTCTG CAATCCGACG
1981 CCTGGCCGTG TACGTGTGTG TAACAATACT GCTTTCTACC CGAGAGGAGG CGGCTTTGTG
2041 CAGCTCATCG GAGACGTCCA GGTGTTAACC CCCAACTCTA CATCTTTGCA CTCTCTGCTG
2101 ACTTTGATAT CCCTTATCTT GTTAGTGTGT GTTGTTTCTG GCGCGCGATT CGTTCCATTG
2161 GGAATCATAT TCTTCTGGAG CGTGCGCCAC GTATATGCTT CTTGTTACTT AAGCTGTGAT
2221 TGGGCTGTTT GCAACGATGC GTTCTGTTTC ACATCTGGCA CTTGTGCTAC CTTCAACGAC
2281 GTCTTGTGTC TGCCGGTTGC GGCGCGCATA TCGTCCTGTG GCCATGCTGT GCCACCGCCC
2341 GACCGTGGTT GGGAGGTGCC CGCAGCGATG TCATGGGCGA TTTCGCGTAC TACCGGCTTG
2401 ACGTTCGATG TCTTTTCCTT CATCCAGTAC CTTCCTACTG TGCCTGGCAA CAATTCCGAT
2461 ATCATTTACT GTGGTGAACC AAGCTTCTTC GGGGACATCA CGGGTATCTA TTGGCCTTAC
2521 TTTTTGCCTG GCATGTTGCT CTTGTACTTG ACTCCCCTCC TGGGTTAAG GTTAATGCTT
2581 GCCGGCTTTA ATATAGATGG CTTGTTTCCC ATACGGCATG CCACGGCTGC ACTGAGGTTC
2641 TCGACTTCGC GTGTGACCTT GAGTGTCGTA TTTGCTTTCC TAATCTATAT ATTATCTCAT
2701 CCTGTTAATG CTGCGCTCAA TAGAATGTTC CTAGCATCTG CAAATCTAGA GATGATCTTA
2761 TCCTTTGATA CCTATCATGA GACTTCTTT TACGTCGTTT GTCTATTGCT CTACCTCCAG
2821 GTGTCGCCCC GTGCGGGCTT GGCTGCTATG GTGGCCATCA AGCTATCTCG AGGCCTGTTA
2881 TTCGCTGTGG TGTTGGCGCA CGGAGTGTGC CGACCTGGGC GGGTATTTGG TCTTGAGGTT
2941 TGCGCGGACA CTCTCTTGGT TGGTGGAGTT ACTGGCAACT GCACTTGGTA CATGTCCTGT
3001 GTCTTCTCTT TTTGGTGCGC AGTGTTTGCC TTCACCAGTC CACTTGGACG ACAGTATAAG
3061 CTTCAGATCT ATCGGTACTG GGCGCAGGCC TATGCCAGAC TCATCCTCGC TGTCGGTTGT
3121 GGTCCTCTCG GGAGGGAGTT CCATTCCGT GCGAGCGTGG GCGTGCTCTG GTGTGGTGCT
3181 TGCATGCTCT GGCCCCGTGA GTGCTCTGAA ATCAGCTTGG TCTTTATTCT GTGTGCTCTG
3241 ACTGTGGACA CCATAGACAC ATGGTTAGTA GCGTGCTTGT CCGCAGGGCC AAGCGCGCGA
3301 ACCCTTGCAA CTCTGGCCGA TGACATGGCG CGCATTGGTG ACCACCGGGC GTTGCGCGCC
```

FIG. 15B

```
3361 GTGTTGCGTT GCTTTGGATC ACGTGGCACA TACATATACA ACCACATGGG CCAGGTCTCA
3421 GAACGGGTGG CGCAAGCAGT CAGGGATTTC GGCGGTTGCT TGGAACCAGT CGTGTTGGAG
3481 GAGCCCACCT TTACTGAGGT CGTGGATGAT ACAATGAATT TGGTGTGTGG ACAATTGCTT
3541 GGAGGTAAAC CCGTGGTGGC CCGCTGCGGC ACGCGTGTCT TAGTGGGACA CCTCAACCCT
3601 GAAGACCTGC CACCTGGTTT CCAGCTGAGT GCTCCGGTGG TTATTACCAA ACCAAGCATT
3661 GGTACGTGGC CCTTTCTTAA GGCGACACTC ACAGGGCGTG CTGAAACACC GGGATCCGGC
3721 CAGATCGTGG TGTTGTCTTC CCTGACAGGT CGGTCAATGG GTACTGCAGT GAATGGCACA
3781 CTGTATGCGA CCGGCCACGG TGCTGGTGCG CGCGGCCTAG CCACGTGCGC TGGTTTGAGG
3841 ACGCCACTTT ACACGGCATT ATCTGAAGAT GTCGTGGCCT ACTCTTGCCT TCCGGGCATG
3901 AGCTCCCTAG AGTCCTGCAA CTGCTCGCCC AGCCGGGTTT GGGTGGTGAA CAACAACGGA
3961 GGGTTGGTGT GTGGCAGAGT GGAGAAAGAC GACGTCTGTT TGGACTGTCC CACGCACATA
4021 GATCAACTGC GGGGTGCTTC GGGGTCGCCG GTTTTGTGTG ATCACGGTCA TGCATACGCG
4081 TTGATGCTCG GTGGCTACTC TACCAGTGGT ATTTGTGCGC GTGTCCGGAT AGTCCGGCCA
4141 TGGCAGAACG CCTATTCCTC CTCAGGGGGG CAAGGCGGAA TGCAGGCGCC AGCTGTGACA
4201 CCAACATACT CTGAAATCAC CTACTATGCC CCTACTGGTT CTGGTAAATC AACAAAATAT
4261 CCAGTGGACC TAGTCAAGCA GGGACACAAA GTATTAGTCC TTTTACCAAG TGTGGCTGTC
4321 GTCAAAGTA TGGCTCCTTA CATTAAGGAA AAATATAAGA TTAGACCTGA AATTAGAGCT
4381 GGCACAGGGC CTGACGGTGT GACGGTCATC ACTGGCGAGA ACTTGGCGTA CATGACCTAT
4441 GGCCGTTTCC TTGTAGATCC GGAAACGAAT CTGCGGGGTT ACGCTGTAGT CATCTGCGAC
4501 GAGTGCCATG ACACATCATC CACCACGCTA CTCGGCATCG GCGCAGTGCG CATGTATGCT
4561 GAGAAAGCTG GAGTGAAGAC CGTTGTATTC GCCACAGCCA CTCCTGCTGG CATTCAAGTG
4621 CAGTCACATC CCAACATTGA TGAATATCTA TTGACTGATA CAGGCGACGT GGAATTCTAC
4681 GGCGCTAAAA TTAAATTGGA CAACATCAGA ACTGGTAGAC ATGTTATCTT TTGCCACTCG
4741 AAGGCCAGGT GTGCGGAACT AACGCAGCAG CTCTCCGGCC TTGGTGTTCG TGCAGTGAGT
4801 TTTTGGCGCG GCTGTGACAT CAAGAGCATT CCCGCCTCAG ACTCTATTGT TGTAGTGGCA
4861 ACTGATGCAT TGTCCACAGG CTACACAGGG AACTTTGATT CGGTCATTGA CTGCGGGTGT
4921 TGCGTAGAGC AAACTGTAAC AATTGACATG GACCCCACGT TCTCCATCTC GGCCCGAGTG
4981 GTGCCATGCA CTGCTGCATT GCGTATGCAG CGGCGCGGAC GCACCGGTCG TGGCAGGAGG
5041 GGAGCGTACT ACACAACCAC TCCAGGAGCA GCACCCTGCG TCAGCGTTCC CGATGCTAAC
5101 GTCTGGCAAT CAGTGGAGTC AGCCATGGTC TTTTATGATT GGAGTGCTGC CAGGATAGAG
5161 CAATGCCTGG CGGCATACCA TGATTTAGGG TGCACACCAC GCATCAGTTG TGACCCACAC
5221 ACTCCAGTGC GGGTGATGGA CACACTGAGG GCGTATCTGC GCAGACCTGA GGTGACGACC
5281 GCGGCTCTCG CAGGAGAGCA GTGGCCGCTG CTTTACGGCG TGCAGTTGTG CATCTGCAAA
5341 GAGACCGAGG CCCACGGTCC AGACGATGGC ATCAAGTGGA AATGCTTACT CAATAACAAC
5401 AACAAAACAC CCCTGTTGTA TGCCTTAGAC AATCCTACAC TGGAATTCAC TACCCAACAT
5461 GACTTGACTC GCCGTATAGC TGGCGCTTTA TCGAGCACAG TGTTCGTGGA GACAGGCTAC
5521 GGCCCCATCC TCCTCGCTGG CGCTGCTTTG GCTGCCTCCT TGCCTTTGC GGGCGCCACT
5581 GGAGCTTTAG TGCCGTCGGC CGTTTGGAGC GTTGAAAACG GCTTGCTGG CGTGACCCGT
5641 CCCGATGCGA CAGACGAGAC CGCGGCCTAC GCGCAGCGCT TGTACCAAGC CTGCGCAGAT
5701 TCAGGAATTC TCGCCAGCTT GCAGGGTACG GCGAGTGCGG CACTGAGCAG ACTGGCCGAT
5761 GCCAGTAAGG GTGCTAGTCA ATATCTGGCA GCCGCGCCTC CTTCGCCCGC CCCCCTGGTA
5821 CAGGTGCTGC AGTTCCTCGA GACCAATTTT AGCTCCATTG CATCTTTCGG TCTGCTCTGT
5881 GCCGGCTGTC AGGCCGGCGA GTGCTTCACT GCGCTTGCCG GGTTGGTGTC CGGTGCTACA
5941 GCTGGCTTGG GAGGTGCCCA TAAGTGGTTG TTAGCTATTG CAGGAACTTG GCTAGTTAGC
6001 TTGCAGACTG GCCCCGTGG CGGCATGGTT GCGGGTCTCT CAGTTCTAGC AGGCTGTTGC
6061 ATCGGTAGTG TCACCGGGCT TGACTTCCTG TTTGGGTGCC TTACAGGTTG GGAGGCCGTG
6121 GTCGGTGCTG CGGTTGCAAC GCAGAAAATC TTGTCTGGTT CGGCTGACAT GACCACTCTG
6181 GTAGATCTCC TACCTGCTCT CTTCTCCCCT GGCGCCGGCA TAGCTGGCGT CGTGCTTGTC
6241 TTTATTCTAA GCAACTCAAG TGTAACCATG TGGGCTAATC GGCTATTGTC CATGTGTGCA
6301 AAACAAACTA TTTGTGAAAA TTACTTCTTA ACTGAGAAAT TTGGCCAACA ATTAAGCAAA
6361 CTTTCCCTGT GGCGCTCTGT GTACCATTGG GCGCAGGCAC GTGAAGGATA CACACAGTGC
6421 GGTGTGGTCA GCGGGATCTG GAGCTTTGTC TTGTGCATTC TACGTGCTGT GTGGGATTGG
6481 GCGGCTAAAC ATGTGCCACG GTTCCGTGTG CCTATGATTG GCTGCTCACC TGCGTGGTGC
6541 GGGCGCTGGC TTGGTACTGG CACCTTGTTG ACCACCTGTG GGTGTGGAGA ACGTGTATCC
6601 CTTCAGTGCC TTTGCTCGAC ATCTGACCCA ACACTCAGTG TGGGCCGTTG GTGTTGGTGT
6661 AGTTGGCGTG TTGGGTTCCC ATTCAACCCG ACGACGACAG CCACCGGCAC TTTACGGCCG
6721 GACATCAGTG ACGCCACCAA ATTGGGCTTC CGGTATGGTG TCGCCGAGAT CGTGGAGCTA
6781 GAGCGGCGGG GCAACAAATG GCATGTCTGT GCAGCATCAT GTTGCTTGGA CCGGGCCAGC
6841 GTTGCATCCG CCGTGAGGGC CCCACCGGTC ACGGCCGATG GCATACCTAT CAGTACCTTT
```

FIG. 15C

```
6901 TCTCCACCAC AAACTTACAA ACTCTCTCTT TGTTCTTTTG ATTCAGTTTG CATGACTACT
6961 AACTTATGTA ATCCAGCTAA GACCCTGAGT GTGTGCTCGC AGGAGGCTGT TGAGCTACTG
7021 GAAGAAACAG TTGACAGAGC ACAAGTAGTG ATGTGTCAAA ATCTGGAGGC GCGAAGACGC
7081 GCTGAGTTTG ATGCATGACA AGTTCGCGAA GCAATTCGCA ACGAGTACAC GCGTTTGGCA
7141 GACGAGGATG TTGACGCGAC AACGTCGGTG AAACCCCCGG TGGCCAAGGC TGCTGTGGGT
7201 AGCTCGACGT TGGATGATGT TAGCGTGCTG ACTGTCTTGC GCGAACTCGG TGACCAGTGC
7261 CAAAATGCTA TCAAATTTGT AGTTCAGGCG GCTTCACGGT TTGTTCCACC AGTGCCCAAG
7321 CCACGCACGC GTGTCTCGGG TGTGTTGGAG CGTGTGCGCA TGTGCATGCG CACGCCACCA
7381 ATCAAGTTTG AGGCTGCCGC AGTACCAATT CATGATATAA TCCCAGAAGA GTGTCACATT
7441 GTGCTACGCT GTACCGGCTG CAACGACCAG GCCTTGACTG TTCCGTACGG CACTTGCACT
7501 CAGTCTTTAA TCAAGCATTT GACTAGTAAA CACAGTCACT ACATTCCAAA ACAGAAGATA
7561 GAAGAGGACA CAGAAGTAAC TGTCATTTGC GCCGTACCAA CAACGCGCGC AAGCAAACTC
7621 ATCACATTCA GAGCAGGTGA TCGATCAGTC TCATGTTGTC ACCCCTTGCA AACCCCTATT
7681 AGGGCCCTGC TTCTAAAGTA CGGGTTACCT ATCGGGAAGT GGTCTGACTG CAACGGGCCC
7741 CTTGGTGACG ATGCTCGAGT CTGTGACGTC AATGGAGTAA CAACTTATGA ACCATGCATG
7801 CAATCCTACA GTTGGTTTCG ACCGATTGTG GCACCAACAA CCCCACCTTT GCCTGCAACC
7861 CGGACCGTGG CTGGCATTTT ACGCGCAGAC ACATCGCGCG TTTACACCAC AACGGCGGTT
7921 GACGTCTCCG AGCGGCAGGC CAAGGTCACA ATTGATCAAA CATCAGCCAA GGTGGATCAG
7981 TGTTTCCGAG ACACATACAA TTGCTGCCTT GCTAAGGCAA AGACCTTCAG ACAATCTGGC
8041 ATGTCATATG AGGATGCTGT GTCAAAGATG CGCGCAAACA CCACGCGTGA CCATAACAAC
8101 GGCATCACTT ATTCAGATTT GGTCTCTGGA CGCGCAAAAC CTGTCGTTCA GAAAATTGTA
8161 AATCAAATGC GCGCCGGAGT GTACGACGCT CCGATGCGCA TTATCCCAAA ACCTGAAGTG
8221 TTCCCTCGAG ACAAAACAAC ACGGAAGCCA CCGAGGTTCA TCGTTTTCCC TGGGTGCGCC
8281 GCGCGAGTCG CGGAGAAAAT GATCCTGGGT GATCCTGGCG CGATAACCAA GCACGTGCTA
8341 GGTGATGCCT ACGGGTTTGC CACTCCGCCG CATGAGCGCG CGCGCCTGTT GGAACAATGG
8401 TGGAACCGCG CAACGGAGCC ACAAGCTATC GCGGTTGATG CGATCTGCTT TGATAGCACC
8461 ATCACGGCAG AGGACATGGA TCGTGAGGCT AACATCGTGG CTGCAGCGCA TACGGACCCT
8521 GAAGGTGTTC ACGGCCTATA TAATTATTAC AAAAGAAGCC CCATGTGTGA CATCACGGGG
8581 AAGGTTGTCG GAGTGCGTTG CTGTCGAGCC TCGGGTACGC TTACAACAAG CAGTGGCAAC
8641 ACGCTTACTT GCTACCTTAA GGTTCGTGCA GCTTGCACGC GCTCCGGCAT TAAACCAATT
8701 GGCTTACTAA TTCATGGAGA TGACACCCTC ATCGTCACAG AACGTTGCGC TCAAGAGACT
8761 CTCGATGAGT TCAGCAACGC ACTTGATGAC TATGGGTTCC CACACACCAT CCAGGCGTCT
8821 GGGGACCTCT CGTCTATCGA GTGCTGTAGC GCACGTGTGG ACAGCGTTTG CCTCCGGGGA
8881 GGTATGCGTC GCATGCTTGT GCCACAAGCT CGACGTGCGA TTGCACGCGT TCTCGGGGAA
8941 AAGGGCGATC CACTGGGTAC CATCGGTAGC TATGTTGTCA TGTATCCCAC TGCGGCCGTG
9001 ACTGTCTACG TGCTATTGCC CCTGTTGTGC ATGCTCATAC GAAATGAGCC ATCACAGACG
9061 GGGACACTTG TGACGCTGAC GGTCCACGGT AACAGTGTGA GTGTGCCAGC GTGGCTGCTT
9121 CCAACCATCA TTGCAAATTT ACATGGTCGT GACGCACTAC AGGTAGTCCG TCACAGTGCA
9181 GCTTCCATGG CGGAATTGTC ATCAGCGTTG GCCTTCTTTG GCATGAGAGG GTTGAATTGC
9241 TGGAGCGGA GACGCCGTGC CATTAGGGCT GATATGATCA AGTCGGGCGG GTGGAATGCG
9301 AATTTCGCGC AGATGTTACT GTGGTCACCG GAGGTAAGAA CACCACAACC CGAACCAAGG
9361 GGTCTGTGTC TTTTGCCGCC GGAACTGTGG GAGCGTCCGT ACGAAAATTT GCACTTGAGC
9421 ACGATCGACC GCAATCGTGG TGCTAGTCGC TTACGGTTTT GGTTGGTTGC TAGTGCTATA
9481 CTCGCTCTGC TTTGCTTGTA AATCCTAAAT CAATGTAGTA CCAGGACTAC AAGGCAGGAG
9541 GTGAAGTCAG CTGTACCCAC GGCTGGCTGA AACCGGGGCT TGACGACCCC CCTATCCGA
9601 GTTGGGCAAG GTAACATCAC GGGTGTGACG ACCCCGCCCC CCATGTCGC GCGTAAGCGC
9661 ACGGGCAAGG CAGCTAGGCT GAGAGTCTGG GCAACTCTCC CGTACCCCAC CCGAGGCTAC
9721 GCCTCGTCCT GGCGAGGACC GTAAACATAC GTCGTCAGCG TGGTGACCTG ACGTATCTTG
9781 TTAACCACTT AATGGTCGTA ACTCGACCCC CGTGCCGGGG ATCTAAGCGC GGCACCGCGA
9841 TGAGGGGGGT CAACGGCCCC TTTCATT
```

FIG. 16A

Human Pegivirus 2 (ABT0070p) Genes and Untranslated Regions

5' UTR Sequence

5' UTR Sequence: nucleotides 1-327 of SEQ ID NO:300

S Protein and Gene Sequence

S Protein Amino Acid Sequence: (SEQ ID NO:314)

MGCSTDQTICSPVVEADYNTSSGCRALNGSYHCGGGSCRSPSRVQVAGRVLRLCAFLALIGSGMCSIRSKNEGRIESGQ

S protein gene sequence: nucleotides 328-564 of SEQ ID NO:300.

E1 Protein and Gene Sequence

E1 Protein Amino Acid Sequence: (SEQ ID NO:315)

ILQSQRACWTGEGFAFFSNCCNQSDIMWCLHRWCVTRPGCLVCTGNATHPVCWDYLGSGVSRRPARRMGEGAEVLLRLIGIAGWLGLLAEALG
MSEIYAAFLCFGFIAWYGWGIPKTLVCTVCPAVNISPYSFLSPDTIAFGTWLLQLPGLLWQMFVSFPILYSTWILWLLLSGRTVAVIAILLAS
PTVMA

E1 protein gene sequence: nucleotides 565-1137 of SEQ ID NO:300.

E2 Protein and Gene Sequence

E1 Protein Amino Acid Sequence: (SEQ ID NO:316)

YKHQADSYLKYCTITNASTAMNCCCPFGTFTRNTESGFTIPRFCPVKLNSSTFICSWGSWWWFAENITRPYSDVGMPPAPISALCYIYSNNDP
PSWYRNTTIIPQNCYNSTADPTTAPCRDKWGNATACILDRRSRFCGDCYGGCFYTNGSHDRSWDRCGIGYRDGLIEFVQLGQIRPNIANTTIE
LLAGASLVIASGLRAGYGCSRAHGVVHCFKCPSYRDLERFGPGLGKWVPLPGEFVPELCINPQWARRGFRVSNNPLSVLQTFVEDIFLAPFCN
PTPGRVRVCNNTAFYPRGGGFVQLIGDVQVLTPNSTSLHSLLTLISLILLVCVVSGARFVPLGIIFFWSVRHVYA

E2 protein gene sequence: nucleotides 1138-2199 of SEQ ID NO:300.

X Protein and Gene Sequence

X Protein Amino Acid Sequence: (SEQ ID NO:317)

SCYLSCDWAVCNDAFCFTSGTCATFNDVLCLPVAARISSCGHAVPPPDRGWEVPAAMSWAISRTTGLTFDVFSFIQYLPTVPGNNSDIIYCGE
PSFFGDITGIYWPYFLPGMLLLYLTPLLGLPLMLAGFNIDGLFPIRHATAALRFSTSRVTLSVVFAFLIYILSHPVNAALNRMFLASANLEMI
LSFDTYHETVLYVVCLLLYLQVSPRAGLAAMVAIKLSRGLLFAVVLAHGVC

X protein gene sequence: nucleotides 2200-2910 of SEQ ID NO:300.

FIG. 16B

NS2 Protein and Gene Sequence

NS2 Protein Amino Acid Sequence: (SEQ ID NO:318)

RPGRVFGLEVCADISWLVEFTGNCTWYMSCVFSFWCAVFAFTSPLGRQYKLQIYRYWAQAYARLILAVGCGPLGREFHFRASVGVLWCGACML
WPRECSEISLVFILCALTVDTIDTWLVACLSAGPSARTLATLADDMARIGDHRALRAVLRCFGSRGTYIYNHMGQVSERVAQAVRDFGGCLEP
VVLEEPTFTEVVDDTMNLVCGQLLGGKPVVARCGTRVLVGHLNPEDLPPGFQLS

NS2 protein gene sequence: nucleotides 2911-3630 of SEQ ID NO:300.

NS3 Protein and Gene Sequence

NS3 Protein Amino Acid Sequence: (SEQ ID NO:319)

APVVITKPSIGTWPFLKATLTGRAETPGSGQIVVLSSLTGRSMGTAVNGTLYATGHGAGARGLATCAGLRTPLYTALSEDVVAYSCLPGMSSL
ESCNCSPSRVWVVNNNGGLVCGRVEKDDVCLDCPTHIDQLRGASGSPVLCDHGHAYALMLGGYSTSGICARVRIVRPWQNAYSSSGGQGGMQA
PAVTPTYSEITYYAPTGSGKSTKYPVDLVKQGHKVLVLLPSVAVVKSMAPYIKEKYKIRPEIRAGTGPDGVTVITGENLAYMTYGRFLVDPET
NLRGYAVVICDECHDTSSTTLLGIGAVRMYAEKAGVKTVVFATATPAGIQVQSHPNIDEYLLTDTGDVEFYGAKIKLDNIRTGRHVIFCHSKA
RCAELTQQLSGLGVRAVSFWRGCDIKSIPASDSIVVVATDALSTGYTGNFDSVIDCGCCVEQTVTIDMDPTFSISARVVPCTAALPMQRRGRT
GRGRRGAYYTTTPGAAPCVSVPDANVWQSVESAMVFYDWSAARIEQCLAAYHDLGCTPRISCDPHTPVRVMDTLRAYLRRPEVTTAALAGEQW
PLLYGVQLCICKETEAHGPDDGIKWKCLLNNNNKTPLLYALDNPTLEFTTQHDLTRRIAGALSSTVFVET

NS3 protein gene sequence: nucleotides 3631-5514 of SEQ ID NO:300.

NS4A Protein and Gene Sequence

NS4A Protein Amino Acid Sequence: (SEQ ID NO:320)

GYGPILLAGAALAASFAFAGATGALVPSAVWSVENGLAGVT

NS4A protein gene sequence: nucleotides 5515-5637 of SEQ ID NO:300.

NS4B Protein and Gene Sequence

NS4B Protein Amino Acid Sequence: (SEQ ID NO:321)

RPDATDETAAYAQRLYQACADSGILASLQGTASAALSRLADASKGASQYLAAAPPSPAPLVQVLQFLETNFSSIASPGLLCAGCQAGECFTAL
AGLVSGATAGLGGAHWLLAIAGTWLVSLQTGPRGGMVAGLSVLAGCCIGSVTGLDFLFGCLTGWEAVVGAAVATQKILSGSADMTTLVDLLP
ALFSPGAGIAGVVLVFILSNSSVTMWANRLLSMCAKQTICENYFLTEKFGQQLSKLSLWRSVYHWAQAREGYTQCG

NS4B protein gene sequence: nucleotides 5638-6423 of SEQ ID NO:300.

FIG. 16C

NS5A Protein and Gene Sequence

NS5A Protein Amino Acid Sequence: (SEQ ID NO:322)

```
VVSGIWSFVLCILRAVWDWAAKHVPRFRVPMIGCSPAWCGRWLGTGTLLTTCGCGERVSLQCLCSTSDPTLSVGRWCWCSWRVGFPFNPTTTA
TGTLRPDISDATKLGFRYGVAEIVELERRGNKWHVCAASCCLDRASVASAVRAPPVTADGIPISTFSPPQTYKLSLCSFDSVCMTTNLCNPAK
TLSVCSQEAVELLEETVDRAQVVMCQNLEARRRAEFDAWQVREAIRDEYTRLADEDVDATTSVKPPVAKAAVGSSTLDDVSVLTVLRELGDQC
QNAIKFVVQAASRFVPPVPKPRTRVSGVLERVPMCMRTPPIKFEAAAVPIHDIIPEECHIVLRCTGCNDQALTVPYGTCTQSLIKHLTSKHSH
YIPKQKIEEDTEVTVICAVPTTRASKLITFRAGDRSVSCCHPLQTPIRALLLKYGLPIGKWSDCNGPLGDDARVCDVNGVTTYEPC
```

NS5A protein gene sequence: nucleotides 6424-7797 of SEQ ID NO:300.

NS5B Protein and Gene Sequence

NS5B Protein Amino Acid Sequence: (SEQ ID NO:323)

```
MQSYSWFRPIVAPTTPPLPATRTVAGILRADTSRVYTTTAVDVSERQAKVTIDQTSAKVDQCFRDTYNCCLAKARTFRQSGMSYEDAVSKMRA
NTTRDHNNGITYSDLVSGRAKPVVQKIVNQMRAGVYDAPMRIIPKPEVFPRDKTTRKPPRFIVFPGCAARVAEKMILGDPGAITKHVLGDAYG
FATPPHERARLLEQWWNRATEPQAIAVDAICFDSTITAEDMDREANIVAAAHTDPEGVHGLYNYYKRSPMCDITGKVVGVRCCRASGTLTTSS
GNTLTCYLKVRAACTRSGIKPIGLLIHGDDTLIVTERCAQETLDEFSNALDDYGFPHTIQASGDLSSIECCSARVDSVCLRGGMRRMLVPQAR
RAIAPVLGEKGDPLGTIGSYVVMYPTAAVTVYVLLPLLCMLIRNEPSQTGTLVTLTVHGNSVSVPAWLLPTIIANLHGRDALQVVRHSAASMA
ELSSALAFFGMRGLNCWRRRRAIRADMIKSGGWNANFAQMLLWSPEVRTPQFEPRGLCLLPPELWERPYENLHLSTIDRNRGASRLRFWLVA
SAILALLCL
```

NS5B protein gene sequence: nucleotides 7798-9498 of SEQ ID NO:300.

3' UTR Sequence

3' UTR Consensus Sequence: nucleotides 9499-9867 of SEQ ID NO:300.

FIG. 17A

Human Pegivirus 2 (ABT0029A) Nucleic Acid Sequence - SEQ ID NO:301

```
   1 AACTGTTGTT GTAGCAATGC GCATATTGCT ACTTCGGTAC GCCTAATTGG TAGGCGCCCG
  61 GCCGACCGGC CCCGCAAGGG CCTAGTAGGA CGTGTGACAA TGCCATGAGG GATCATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GGAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGGTGTTCAA CTGATCAAAC CATTTGTTCT
 361 CCAGTCGTGG GGGCCGACTA TAATACCTCC TCGGGCTGCC GGGCCTTAAA TGGGAGTTAC
 421 CACTGCGGTG GTGGCTCTTG CCGGTCACCA AGCTGTGTGC AGGTTGCGAG ACGAGTCTTG
 481 CAGCTGTGCG CACTCCTTGC GCTGATCGGA TCCGGTATGT GTTCGATCCG GTCCAAAACT
 541 GAAGGGCGCA TTGAGTCAGG GCAAATATTG CAGTCTCAGC GCGCATGTTG GACTGGTGAG
 601 GGTTTCGCTT TCTTTTCTAA CTGTTGCAAT CAATCTGATA TCATGTGGTG TTTGCACCGT
 661 TGGTGTGTGA CAAGACCTGG CTGTTTGGTG TGCACGGGCA ATGCCACTCA TCCTGTCTGC
 721 TGGGACTATC TCGGGTCCGG CGTAAGTCGG CGGCCTGCTC GTCGAATGGG TGAGGGAGCT
 781 GAAGTGCTTC TTCGCTTGAT CGGCGCTGCA GGCTGGCTTG GCTGTTAGC TGAGGCTCTT
 841 GGTATGTCCG AAATCTATG AGCTATTCTT TGCTTTGGGT TTATTGCTTG GTATGGCTGG
 901 GGTATACCTA AGACATTGGT GTGCACAGTC TGCCCTGCAG TAAACATTTC TCCCTATAGC
 961 TTCTTATCTC CAGATACTAT CGCATTTGGT ACGTGGATAC TACAACTACC TGGTCTTTTG
1021 TGGCAGATGT TTGTCAACTT CCCTATACTT TACAGCACTT GGATTCTTTG GTTGTTGCTC
1081 AGCGGCAAGA CTGTTGCTGT GATAGCGATC CTTCTGGCTA GTCCTACGGT TATGGCGTAC
1141 AAGCATCAAT CTGACAGCTA CCTCAAATAC TGTACCATAA CCAATGCTTC AACTGCTATG
1201 AACTGTGACT GCCCCTTTGG AACCTTTACT CGCAATCACG AGTCTCGTTT CTCTATACCT
1261 AGATTCTGTC CTGTTAAAAT TAAAAGCTCT ACATTTATCT GCTCATGGGG GTCGTGGTGG
1321 TGGTTTGCGG AGAACATCAC GCGTCCATAC WCRGACGTTG GCRTGCCACC AGCACCGATT
1381 TCYGCTTTGT GCTATATCTA TTCWAACAAT GACCCACCTC CTTGGTATCA TAACACAACT
1441 ATCATACCTC AGAAYTGTCG CAACTCTACG GTKGATCCTA CCACARCTCC ATGCCGYGAC
1501 AAGTGGGGYA AYGCAACTGC TTGTATTCTT GACCGCCGKT CGCGGTTCTG CGGGGACTGC
1561 TATGGCGGTT GTTTCTATAC TAATGGTACT CATGATCGAT CCTGGGATCG ATGTGGGATT
1621 GGTTACCGTG ATGGACTCAT AGAGTTSGTG CAGCTCGGTC AGATTSGACC TAACATCTSS
1681 AATACGACCA TTGAGCTCCT CGCWGGCGCC TCGCTTGTGA TCGCATCCGG TCTTCGGCCT
1741 GGGTTTGGTT GCAGCCGAGC GCATGGCGTG GTGCACTGCT ATAGGTGTCC TTCATACCGT
1801 GACCTTGAAC AGTTTGGTCC TGGGCTTGGG AAATGGGTGC CATTGCCCGG CGAGCCTGTC
1861 CCGGAGCTGT GTATCAACCC TCAGTGGGCG AGGCGCGGCT TCCGGATGTC TAATAATCCT
1921 CTGAGCTTGC TACAGACCTT CGTTGAGGAC ATTTTCCTAG CGCCTTTTG TAATCCGACG
1981 CCTGGCCGTG TACGTGTGTG TAACAATACC GCTTTCTATC AAGAGGAGG CGGCTTTGTG
2041 CAGCTCATCG GGACGTCCA GGTGCTAACC CCTAACACTG CATCTTTACA CTCTCTGCTG
2101 ACTTTGATAT CTCTTATCTT GTTGGTGTGT GTTGTTTCTG GTGCGCGATT CGGTCCACTA
2161 ATAATCATAT TTTTCTGGAG CGCGCGCCAY GTATATGCTT CTTGTTACTT AAGCTGKGAT
2221 TGGGCTGTTT GCAACGATGC GTTCTGTTTC ACATCTGGYA CTTGTGCTAC TTTCAATGAC
2281 GTCTTGTGTC TGCCGGTTGC AACGCACATA TCGTCCTGTG CCACGCTGT ACCGCCCCCC
2341 GACCGYGGTT GGGAGGTGCC TGCGGCGATG TCATGGGTGA TTTCGCGGAC TACTGGCTTG
2401 ACGTTCGATG TCTTCTCTTT CATCCGTAT TTCCGTACTG TGCCTGGCAA TAACACTGAT
2461 ATTATCTACT GTGGTGAACC WACCTTCTTT GGGGACATCA CGGGCATTTA TTGGCCTTAC
2521 TTTTTGCCTG GCGTGTTGCT CTTGTACTTG ACTCCCTTCC TGGGTTTTAG GTTAATGCTT
2581 GCTGGCTTTA ATATAGATGG CTTGTTTCCC ATACGGCATG CCACGGCTGC ACTGAGGTTC
2641 TCGACTTCGC GTGCGACCTT GAGTGTCGTA TCTGCTTTTC TAATCTATAT ATTATCTCAC
2701 CCTGTTAAYG CTGCGCTCAA TAGAATGTTC YTAGCATCTG CAAACTTAGA GATGATCTTA
2761 TCCTTTGATA CCTATCACGA GACTGTTCTT TACATCTTTT GTCTATTCCT CTACCTCCAG
2821 GTGTCGCCCC GTGCGGGCTT GGCCGCTATG GTGGCCATCA AGCTATCTCG GGCCTGCTA
2881 TTCGCTCTGG TGTTGGCGCA AGGCGTGTGC CGACCTGGGC GGGTGTTTGG TCTTGAGGTT
2941 TGCGCGGACG TCTCTTGGTT GGTGGAGTTT ACTGGCAACT GCACTTGGTA CATGTCCTGC
3001 ATCTTCTCCT TTTGGTGCGC AGTGTTTGCC TTCACCAGTC CACTTGGACG ACAGTATAAG
3061 CTTCAGATCT ACCGGTACTG GGCACAGGTC TATGCCAGAC TCATCCTCGC TGTCRGTTGT
3121 GGTCCTCTCG GACGAGAGTT CCATTTCCGC GCAAGCGTGG GCGTGCTTTG TGTGGTGCT
3181 TGCATGCTCT GGCCCCGTGA GTGCTCTGAA ATCAGCTTGG CTCTCATTCT GTGTGCTCTG
3241 ACAGTGGACA CCATAGACAC ATGGCTAGTA GCGTGCTTGT CCGCAGGGCC GAGTGCGCGA
3301 GCCCTTGCAA CGCTGGCCGA CGACATGGTG CGCATGGGTG ACCACCGGGC GTTGCGCGCC
```

FIG. 17B

```
3361 GTGTTGCGTT GCTTTGGATC ACGTGGCACA TACATATACA ACCACATGGG CCAGGTCTCA
3421 GAACGGGTGG CGCAAGCAGT CAGGGATCTC GGCGGTTGCT TGGAACCAGT CGTGTTGGAG
3481 GAGCCCACCT TTACTGAGGT CGTGGATGAT ACAATGAGTA AGATATGTGG ACAATTGCTT
3541 GGTGGTAAAC CCGTGGTGGC CCGCTGCGGC ACGCGTGTCT TGGTGGGACA CCTCAACCCT
3601 GAAGATCTGC CACCTGGTTT CCAGCTAAGT GCTCCGGTGG TTATTACCAA ACCAAGCATT
3661 GGTACGTGGT CCTTCCTTAA GGCGACACTC ACAGGGCGCG CTGAAACACC CGGATCCGGC
3721 CAGATCGTGG TGTTGTCTTC CCTGACAGGT CGGTCGATGG GTACTGCAGT GARTGGCACA
3781 CTGTATGCGA CCGGCCATGG TGCTGGTGCA CGCGGCCTAG CCACGTGTGC TGGTTTGAGG
3841 ACGCCTCTCT ACACGGCATT ATCTGATGAT GTCGTGGCCT ACTCTTGCCT TCCGGGCATG
3901 AGTTCCCTAG AGCCCTGCCG CTGTTCGCCG AGCCGGGTTT GGGTGATGAA CAACAATGGA
3961 GGGTTGGTGT GTGGCAGAGT GGAGAATGAA GACGTCTGTT TGGACTGTCC CACGCACATA
4021 GATCAACTGC GGGGTGCTTC GGGTTCACCG GTTTTGTGTG ATCACGGTCA TGCATACGCG
4081 TTGATGCTCG GTGGTTACTC TACCAGTGGT ATTTGTGCGC GTGTCCGGAT AGTCCGGCCA
4141 TGGCAGAACG CCTATTCCTC CTCAGGGGGG CAGGGCGGGA TGCAGGCGCC AGCTGTGACA
4201 CCAACATACT CTGAAATCAC CTACTACGCC CCTACYGGTT CTGGTAAGTC AACAAAATAT
4261 CCAGTGGACC TAGTCAAACA GGGACACAAG GTATTGGTCA TCATACCAAG TGTGTCTGTC
4321 GTCAAGAGTA TGGCCCCTTA CATTAAGGAG ACATATAAGA TTAGACCTGA AATTAGAGCT
4381 GGCACAGGGC CTGACGGTGT GACGGTTATC ACTGGTGAGA ACTTGGCGTA CATGACCTAC
4441 GGCCGCTTCC TCGTGGATCC GGAGACGAAT CTGCGGGGTT ATGCCGTTGT CATTTGCGAC
4501 GAGTGCCATG ACACATCATC TACCACGCTA CTCGGTATTG GCGCAGTGCG CATGTATGCC
4561 GAGAAAGCTG GAGTGAAGAC CGTTGTATTC GCCACAGCCA CTCCTGCTGG CATTCAAGTA
4621 CAGCCACATC CCAACATTGA TGAATATTTA TTGACTGACA CAGGCGACGT GGATTTCTAC
4681 GGCGCCAAAA TCAAATTGGA TAACATCAGA ACTGGTAGAC ATGTTATCTT TTGCCACTCG
4741 AAGGCCAGGT GTGCGGAACT AACGCAGCAG CTCTCCGGCC TTGGTGTTCG TGCAGTGAGT
4801 TTTTGGCGAG GCTGTGACAT CAAAACCATT CCCGCCTCAG ACTCTATTGT CGTAGTGGCA
4861 ACTGATGCAT TGTCCACAGG CTACACAGGG AACTTTGATT CGGTCATCGA CTGCGGGTGT
4921 TGCGTAGAGC AAACTGTGAC AATTGACATG GATCCCACGT TCTCCATCTC AGCCCGAGTG
4981 GTGCCATGTA CTGCTGCATT GCGTATGCAG CGGCGCGGAC GTACTGGTCG CGGCAGAAGG
5041 GGGGCGTACT ACACAACCAC TCCAGGAGCA GCACCCTGTG TCAGCGTTCC CGACGCTAAC
5101 GTCTGGCAAG CAGTGGAGAG CGCCATGGTC TTTTATGATT GGAACGCCGC CAGGATACAG
5161 CAGTGCCTGG CAGCATACCA TGATTTAGGG TGTACACCAC GCCTCAGTTG TGATCCATGC
5221 ACTCCAGTGC GGGTGATGGA CACACTGAGR GCGTACCTGC GCAGACCTGA GGTGACGACT
5281 GCGGCTCTCG CAGGAGAGCA GTGGCCGCTG CTTTACGGTG TGCAGTTGTG CATCTGCAAG
5341 GAGACTGAGG CCCACGGTCC AGACGATRGC ATCAAGTGGA AGTGCTTACT CAACAACAGT
5401 AAYAAAACAC CCCTGTTGTA TGCCTTAGAC AATCCTACAC TGGAATTCAC TACCCAACAT
5461 GACTTGACTC GCCGTATAGC CGGCGCTTTA TCGAGCACAG TGTTCGTGGA GACAGGCTAC
5521 GGCCCCATCC TCCTTGCTGG CGCTGCATTG GCTGCCTCCT TCGCCTTTGC GGGCGCCACT
5581 GGAGCCTTAG TGCCGTCGGC CGTTTGGAGC GTTGATAACG GGGTTGCTGG CGTGACCCGT
5641 CCCGACGCGA CAGACGAGAC CGCGGCCTAC GCGCAGCGCT TGTACCAAGC CTGCGCAGAT
5701 TCAGGACTTC TCGCCAGCTT GCAGGGCACG GCGAGTGCGG CGCTGAGCAA ACTGGCCGAT
5761 GCCAGTAGGG GTGCTAGTCA ATATCTGGCA AGCGCGCCTC CCTCGCCCGC CCCCCTGGTA
5821 CAGGTGCTGC AGTTCCTTGA GACCAACTTT AGCTCCATCG CATCCTTCGG TCTGCTCTGC
5881 GCTGGTTGTC AGGCTGGCGA GTGCTTCACA GCGCTTGCCG GGTTGGTGTC CGGTGCTACG
5941 GCTGGCTTGG GAGGAGCCCA TAAGTGGTTG TTAGCCATTG CAGGAACTTG GCTAGTTAGT
6001 CTGCAGACAG GGGCCCGTGG CGGCATGGTT GCGGGCCTCT CGGTCCTGGC AGGCTGTTGC
6061 ATCGGTAGTG TCACTGGGCT TGACTTCCTG TTTGGGTGCC TTACAGGTTG GGAGGCCGTG
6121 GTTGGTCCTG CGGTTGCGAC ACAGAAAATC TTGTCTGGTT CGGCTGATAT GACCACTCTG
6181 TTAGATCTCT TACCTGCTTT TTTCTCCCCT GGTGCGTCGG TAGCTGGCAT CGTGCTTGTC
6241 TTTATTCTAA GCAACTCAAG TGTAACCACG TGGGCTAATC GGCTATTGTC CATGTGTGCA
6301 AAACAAACCA TTTGTGACAA CTACTTCTTA TCTGACAAAT TTGGCCAACA ATTAAGTAAA
6361 CTTTCCTTGT GGCGCACTCT GTATCGTTGG GCGGAGGCAC GTGAGGGATA CACACAGTGT
6421 GGTGTGGTCG GCGGGATCTG GAGCTTTGTC TTGTGCATTC TACGCGCTGT GTGGGATTGG
6481 GCGGCTAAAC ATGTGCCACG GTTCCGTGTG CCCATGATTG GCTGCTCACC TGCGTGGTGC
6541 GGGCGCTGGC TTGGTACTGG CACCTTGTTG ACCACCTGCG GGTGTGGAGA ACGTGTGTCT
6601 CTTCAGTGTC TTTGCTCAAC GTCTGATCCA TTGCTCAGAG TGGGTCGTTG GTGTCGGTGT
6661 AGTTGGAGTG TTGGGTTCCC ATTCAACCCG ACTACGACAG CCACCGGCAC TTTACGGCCG
6721 GACATTAGCG ACGCCACTAG ATTGGGTTTC CGGTATGGCA TTGCCGAGAT CGTGGAGCTG
6781 GAGCTGCGGG AGCACAAATG GCACGTCTGT GCAGCATCAT GTTGCTTGGA CCGAGCTAGT
6841 GTTGCATCCG CTGTGAAGGC CCCACCGGTC ACAGCCAATG GTATACCTAT CAGTACCTTT
```

FIG. 17C

```
6901 TCTCCACCAC AAACTTACAG CCTCTCTCTC TGTTCTTTTG ATTCAGTTTG CATGTCTACT
6961 AATCTATGTA ACCCAGCCAA GACCCTGAGT GTGTGCTCAC AGGAGGCCGT TGAGCTGCTG
7021 GAAGAAACAG TTGACACGGC ACAAGTGATG ATGTGTCAAA ATCTGGAGGC GCGAAGACGC
7081 GCCGAATATG ATGCATGGCA AGTTCGCCAC GCAGTTGGCG ACGAGTACAC GCGTTTGGCA
7141 GACGAGGATG TTGACACGAC AACGTCGGTG AAACCCCGG CGGCCAGGGC TGCTGTGGAT
7201 AGCTCAACGT TGGAAGATGT TAGCGTGCTG ACTGTTTTGC GCGAGCTCGG CGACCAATGC
7261 CAAAATGCTA TCAAATTTGT AGTTCAGGCG GCTTCACGGT TTGTTCCACC TGTGCCCAGA
7321 CCGCGCACGC GCGTCTCGGG CGTGTTGGAG CGTGTGCGCA TGTGCATGCG CACGCCACCA
7381 ATCAAGTTTG AGGCCACCGC AGTACCAATT CATAACATAA TCCCAGAAGA GTGTCACATC
7441 GTGCTACGCT GTACTGGCTG TAACGACCAG GCCTTGACTG TTCCGTACGG CACTTGCACT
7501 CAGTCTTTAA TTAGACATTT GACCAACAAA CACAACCACT ATATTCCAAA ACAGAAGATA
7561 GAAGAAGACA CAGAAGTAAC TGTCATTTGC GCCGTACCAA CAAAGCGCGC AAGTAAACTC
7621 ATCACTTTCA GAGCAGGTGA TCGATCAGTC TCATGTTGCC ACCCCTTACA AACTCCTATT
7681 AGGGCCCTGC TTCTAAAGTA CGGGTTACCT ATCGGGACGT GGTCCGACTG CAACGGACCC
7741 CTTGGTGACG ACGCCCGAGT CTGTGACGTC AATGGAGTGA CAACTTATGA ACCATGCATG
7801 CAATCCTACA GTTGGTTCCG ACCAATTGTG GCACCTACAA CCCCACCTTT ACCTGTAACC
7861 CGGAGCGTGG CTGGGATTTT ACGCGCAGAC ACATCGCGCG TTTACACCAC AACGGCGGTC
7921 GACGTCTCCG AGCGGCAGTC TAAGGTCACA ATTGATCAAA CATCAGCCAA GGTGGACCAG
7981 TGGTTCCGTG ACACATACAA CTGTTGCCTT GCTAAGGCAA AAACCTTCAG ACAATCTGGC
8041 ATGTCATATG AGGATGCTGT GTCAAAAATG CGCGCAAACA CCACGCGTGA CCATAACACT
8101 GGCATCACTT ATTCAGATTT GGTCTCTGGA CGCGCAAAAC CTGCCGTTCA AAAAATTGTA
8161 GATCAAATGC GTGCTGGAGT GTACGACGCT CCAATGCGCA TTATCCCAAA ACCTGAAGTG
8221 TTCCCCCGAG ACAAGTCAAC ACGGAAGCCA CCGCGGTTCA TCGTTTTTCC TGGGTGCGCC
8281 GCGCGAGTCG CGGAGAAAAT GATCCTGGGC GATCCTGGCG CGATAACCAA GCACGTGCTA
8341 GGTGATGCCT ACGGGTTTGC CACTCCGCCG CATGAACGCG CGCGCCTATT GGAGCAATGG
8401 TGGAACCGTG CAACGGAGCC ACAAGCTATC GCGGTTGATG CGATCTGCTT TGATAGCACC
8461 ATCACAGCAG AGGACATGGA TCGCGAGGCC AACATCCTGG CTGCGGCGCA TTCGGACCCT
8521 GAAGGTGTTC ACGGCCTATA CAATTATTAC AAAAGAAGCC CCATGTGTGA TATCACAGGA
8581 AATGTTGTCG GAGTGCGTTG CTGTAGAGCC TCAGGTACGC TTACAACAAG CAGTGGCAAC
8641 ACGCTTACTT GCTACCTCAA GGTTCGTGCA GCTTGCACGC GCGCCGGCAT TAAACCAATT
8701 GGCTTGCTAA TTCATGGGGA TGATACCCTC ATCATCACAG AACGTTGCGC TCAAGAGACT
8761 CTCGATGAGT TCAGCAATGC ACTTAATGAC TACGGGTTCC CTCACACCTT CCAGGCGTCT
8821 GGGGACCTCT CGTCAGTTGA GTGCTGTAGC GCACGTGTGG ACAGCGTTTG CCTCCGGGGA
8881 GGTATGCGTC GCATGCTCGT GCCACAAGCT CGACGTGCGA TTGCACGCGT TCTCGGGGAA
8941 AAGGGCGATC CACTGGGTGT CATCAGCAGC TATATTGTCA TGTATCCTAC TGCGGCCGTG
9001 ACTGTCTACG TGCTATTGCC CCTGTTGTGC ATGCTCATTC GAAATGAGCC ATCGCAGACG
9061 GGGACACTTG TAACGCTGAC GGTCCACGGT AACAGTGTGA GCGTGCCAGT GTGGCTGCTT
9121 CCAACCATCA TTGTAAATTT ACATGGCCGT GACGCACTGC AGGTAGTTCG TCACACTGCA
9181 GCTTCCATGG CGGAGCTGTC ATCAGCGTTG GCCTCTTTTG GCATGAGAGG GTTGAACTGC
9241 TGGAGGCGGA GACGCCGTGC CATCAGGACT GACATGATCA AGTTGGGCGG GTGGAATGCG
9301 AATTTCGCGC AGATGTTACT GTGGTCACCG GAGGTGAGGA CACCACAACC CGAACCAAGG
9361 GGTGTGTGTC TCTTACCACC GGAACTATGG GAGCGTCCGT ACGAAAATTT GCACTTGAGC
9421 ACGATCGACC GCAATCGTGG TGCTAGTCGC CTACGGTTTT GGTTGGTTGC CAGTGCTATA
9481 CTCGCTCTGC TTTGCTTGTA AATCCTAAAT CAATGTAGTA CCAGGACTAC AAGGCAGGAG
9541 GTGAAGTCAG CTGTACCCAC GGCTGGCTGA AACCGGGGCT TGACGACCCC CCCTATCCGA
9601 GTTGGGCAAG GTAACATCAC GGGTGTGACG ACCCCGCCCC CCATGTCGC GCGTAAGCGC
9661 ACGGGCAAGG CAGCTAGGCT GAGAGTCTGG GCAACTCTCC CGTACCCCAC CCGAGGCTAC
9721 GCCTCGTCCT GGCGAGGACC GTAAACATAC GTCGTCAGCG TGGTGACCTG ACGTATCTTG
9781 TTAACCACTT AATGGTCGTA ACTCGACCCC CGTGCCGGGG ATCTAAGCGC GGCACCGCGA
9841 TGAGGGGGGT CAACGGCCCC TTTCATT
```

FIG. 18A

Human Pegivirus 2 (ABT0029A) Genes and Untranslated Regions

5' UTR Sequence

5' UTR Sequence: nucleotides 1-327 of SEQ ID NO:301

S Protein and Gene Sequence

S Protein Amino Acid Sequence: (SEQ ID NO:324)

MGCSTDQTICSPVVGADYNTSSGCRALNGSYHCGGGSCRSPSCVQVARRVLQLCALLALIGSGMCSIRSKTEGRIESGQ

S protein gene sequence: nucleotides 328-564 of SEQ ID NO:301.

E1 Protein and Gene Sequence

E1 Protein Amino Acid Sequence: (SEQ ID NO:325)

ILQSQRACWTGEGFAFFSNCCNQSDIMWCLHRWCVTRPGCLVCTGNATHPVCWDYLGSGVSRRFARRMGEGAEVLLRLIGAAGWLGLLAEALG
MSEIYAAILCFGFIAWYGWGIPKTLVCTVCPAVNISPYSFLSPDTIAFGTWILQLPGLLWQMFVNFPILYSTWILWLLLSGKTVAVIAILLAS
PTVMA

E1 protein gene sequence: nucleotides 565-1137 of SEQ ID NO:301.

E2 Protein and Gene Sequence

E1 Protein Amino Acid Sequence: (SEQ ID NO:326)

YKHQSDSYLKYCTITNASTAMNCDCPFGTFTRNTESRFSIPRFCPVKIKSSTFICSWGSWWWFAENITRPYXDVGXPPAPISALCYIYSNNDP
PPWYHNTTIIPQNCRNSTVDPTTXPCRDKWGNATACILDRFSRFCGDCYGGCFYTNGTHDRSWDRCGIGYRDGLIEXVQLGQIXPNIXNTTIE
LLAGASLVIASGLRPGFGCSRAHGVVHCYRCPSYRDLEQFGPGLGKWVPLPGEPVPELCINPQWARRGFRMSNNPLSLLQTFVEDIFLAPFCN
FTPGRVFVCNNTAFYPRGGGFVQLIGDVQVLTPNTASLHSLLTLISLILLVCVVSGARFGPLIIFFWSARHVYA

E2 protein gene sequence: nucleotides 1138-2199 of SEQ ID NO:301.

X Protein and Gene Sequence

X Protein Amino Acid Sequence: (SEQ ID NO:327)

SCYLSXDWAVCNDAFCFTSGTCATFNDVLCLFVATHISSCGHAVFFPDRGWEVPAAMSWVISRTTGLTFDVFSFIQYFPTVFGNNTDIIYCGE
PTFFGDITGIYWPYFLPGVLLYLTPFLGFRLMLAGFNIDGLFPIRHATAALRFSTSRATLSVVSAFLIYILSHPVNAALNRMFLASANLEMI
LSFDTYHETVLYIFCLFLYLQVSPRAGLAAMVAIKLSRGLLFALVLAQGVC

X protein gene sequence: nucleotides 2200-2910 of SEQ ID NO:301.

FIG. 18B

NS2 Protein and Gene Sequence

<u>NS2 Protein Amino Acid Sequence:</u> (SEQ ID NO:328)

RPGRVPGLEVCADVSWLVEFTGNCTWYMSCIPSFWCAVFAPTSPLGRQYKLQIYRYWAQVYARLILAVXCGPLGREFHFRASVGVLWCGACML
WPRECSEISLALILCALTVDTIDTWLVACLSAGPSARALATLADDMVRMGDHRALRAVLRCFGSRGTYIYNHMGQVSERVAQAVRDLGGCLEP
VVLEEPTFTEVVDDTMSKICGQLLGGKPVVARCGTRVLVGHLNPEDLPPGFQLS

<u>NS2 protein gene sequence</u>: nucleotides 2911-3630 of SEQ ID NO:301.

NS3 Protein and Gene Sequence

<u>NS3 Protein Amino Acid Sequence:</u> (SEQ ID NO:329)

APVVITKPSIGTWSFLKATLTGRAETPGSGQIVVLSSLTGRSMGTAVXGTLYATGHGAGARGLATCAGLRTPLYTALSDDVVAYSCLPGMSSL
EPCRCSPSRVWVMNNNGGLVCGRVENEDVCLDCPTHIDQLRGASGSPVLCDHGHAYALMLGGYSTSGICARVRIVRPWQNAYSSSGGQGGMQA
PAVTPTYSEITYYAPTGSGKSTKYPVDLVKQGHKVLVIIPSVSVVKSMAPYIKETYKIRPEIRAGTGPDGVTVITGENLAYMTYGRFLVDPET
NLRGYAVVICDECHDTSSTTLLGIGAVRMYAEKAGVKTVVFATATPAGIQVQPHPNIDEYLLTDTGDVDFYGAKIKLDNIRTGRHVIPCHSKA
RCAELTQQLSGLGVRAVSFWRGCDIKTIPASDSIVVVATDALSTGYTGNFDSVIDCGCCVEQTVTIDMDPTFSISARVVPCTAALRMQPRGRT
GRGRRGAYYTTTPGAAPCVSVPDANVWQAVESAMVFYDWNAARIQQCLAAYHDLGCTPRLSCDPCTPVRVMDTLRAYLRRPEVTTAALAGEQW
PLLYGVQLCICKETEAHGPDDXIKWFCLLNNSNKTPLLYALDNPTLEFTTQHDLTRRIAGALSSTVFVET

<u>NS3 protein gene sequence</u>: nucleotides 3631-5514 of SEQ ID NO:301.

NS4A Protein and Gene Sequence

<u>NS4A Protein Amino Acid Sequence:</u> (SEQ ID NO:330)

GYGPILLAGAALAASFAFAGATGALVPSAVWSVDNGVAGVT

<u>NS4A protein gene sequence</u>: nucleotides 5515-5637 of SEQ ID NO:301.

NS4B Protein and Gene Sequence

<u>NS4B Protein Amino Acid Sequence:</u> (SEQ ID NO:331)

RPDATDETAAYAQRLYQACADSGLLASLQGTASAALSKLADASRGASQYLASAPPSPAPLVQVLQFLETNFSSIASFGLLCAGCQAGECFTAL
AGLVSGATAGLGGAHKWLLAIAGTWLVSLQTGARGGMVAGLSVLAGCCIGSVTGLDPLFGCLTGWEAVVGAAVATQKILSGSADMTTLLDLLP
AFFSPGAGVAGIVLVFILSNSSVTTWANRLLSMCAKQTICDNYFLSDKFGQQLSKLSLWRTLYRWAEAREGYTQCG

<u>NS4B protein gene sequence</u>: nucleotides 5638-6423 of SEQ ID NO:301.

FIG. 18C

NS5A Protein and Gene Sequence

NS5A Protein Amino Acid Sequence: (SEQ ID NO:332)

```
VVGGIWSFVLCILPAVWDWAAKHVPRFRVPMIGCSPAWCGRWLGTGTLLTTCGCGERVSLQCLCSTSDPLLRVGRWCRCSWSVGFPFNPTTTA
TGTLRPDISDATRLGFRYGIAEIVELELREHKWHVCAASCCLDRASVASAVKAPPVTANGIPISTFSPPQTYSLSLCSFDSVCMSTNLCNPAK
TLSVCSQEAVELLEETVDTAQVMMCQNLEARRRAEYDAWQVRHAVGDEYTRLADEDVDTTTSVKPPAARAAVDSSTLEDVSVLTVLRELGDQC
QNAIKFVVQAASRFVPPVPRPRTRVSGVLERVRMCMRTPPIKFEATAVPIHNIIPEECHIVLRCTGCNDQALTVPYGTCTQSLIRHLTNKHNH
YIPKQKIEEDTEVTVICAVPTKRASKLITFRAGDRSVSCCHPLQTPIRALLLKYGLPIGTWSDCNGPLGDDARVCDVNGVTTYEPC
```

NS5A protein gene sequence: nucleotides 6424-7797 of SEQ ID NO:301.

NS5B Protein and Gene Sequence

NS5B Protein Amino Acid Sequence: (SEQ ID NO:333)

```
MQSYSWFRPIVAPTTPPLPVTRSVAGILRADTSRVYTTTAVDVSERQSKVTIDQTSAKVDQWFRDTYNCCLAKAKTFRQSGMSYEDAVSKMRA
NTTRDHNTGITYSDLVSGRAKPAVQKIVDQMRAGVYDAPMRIIPKPEVFPRDKSTRKPPRFIVFPGCAARVAEKMILGDPGAITKHVLGDAYG
FATPPHERARLLEQWWNRATEPQAIAVDAICFDSTITAEDMDREANILAAAHSDPEGVHGLYNYYKRSPMCDITGNVVGVRCCRASGTLTTSS
GNTLTCYLKVRAACTRAGIKPIGLLIHGDDTLIITERCAQETLDEFSNALNDYGFPHTFQASGDLSSVECCSARVDSVCLRGGMRRMLVPQAR
RAIARVLGEKGDPLGVISSYIVMYPTAAVTVYVLLPLLCMLIRNEPSQTGTLVTLVHGNSVSVPVWLLPTIIVNLHGRDALQVVRHTAASMA
ELSSALAPFGMRGLNCWRRRRRAIRTDMIKLGGWNANFAQMLLWSPEVRTPQPEPRGVCLLPPELWERPYENLHLSTIDRNRGASRLRFWLVA
SAILALLCL
```

NS5B protein gene sequence: nucleotides 7798-9498 of SEQ ID NO:301.

3' UTR Sequence

3' UTR Consensus Sequence: nucleotides 9499-9867 of SEQ ID NO:301.

FIG. 19A

Human Pegivirus 2 (ABT0239AN) Nucleic Acid Sequence - SEQ ID NO:302

```
   1 NNNNNNNNNN NTAGCAATGC GCATATTGCT ACTTCGGTAC GCCTGATTGG TAGGCGCCCG
  61 GCCGACCGGC CCCGCAAGGG CCTAGTAGGA CGTGTGACAA TGCCATGAGG GATCATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GGAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGGTGTTCAA CTGATCAAAC CATTTGTTCT
 361 CCAGTCGTGG GGGCCGACTA TAATACCTCC TCGGGCTGCC GGGCCTTAAA TGGGAGCGAC
 421 CACTGCGGTG GAAGCTCTTG CCGGTCACCA AGTCGTGTGC AGGCTGCTAG ACGAGTCTTG
 481 CAGCTGTGCG CATTCCTTGC GTTGATCGGA TCCGGTATGT GTTCGATCCG GTCCAAAACT
 541 GAAGGGCGCA TTGAGTCGGG GCAAATATTG CAGTCTCAGC GCGCATGTTG GACTGGTGAG
 601 GGTTTTGCTT TCTTTTCTAA CTGTTGCAAT CAATCTGATA TTATGTGGTG TTTGCACCGT
 661 TGGTGTGTGA CAAGACCTGG CTGTTTAGTG TGCACGGGCA ATGCCACCCA TCCTGTCTGC
 721 TGGGACTATC TTGGGTCCGG TGTAAGTCGG CGGCCTGCGC GCCGATTGGG CGAGGGTGCT
 781 GAAATGCTTC TTCGCTTGAT CGGCATTGCA GGTTGGCTCG GCTTGTTAGC TGAGGCTCTT
 841 GGTATGTCCG AAATGTATGC AGCTATCCTT TGCTTTGGGT TTATTGCTTG GTATGGCTGG
 901 GGTATACCTA AAACATTGGT GTGCACAGTC TGCCCTGCGG TAAACATTTC TCCCTATAGC
 961 TTTTTATCTC CAGACACTAT CGCATTTGGT ACRTGGATAC TACAACTACC TGGTCTTTTG
1021 TGGCAAATGT TTGTCAACTT TCCTATACTT TACAGCACTT GGATTCTTTG GTTGTTGCTT
1081 AGTGGCAAGA CTGTTGCTGT GATAGCAATC CTTTTGGCTA GTCCTACGGT TATGGCGTAC
1141 AAGCATCCAT CTGAAAGCTA CCTCAAATAC TGTACCATAA CCAATGCTTC AGCTGCTATG
1201 AACTGTGACT GCCCCTTTGG AACCTTACT CGCAATACTG AGTCTCGTTT CTCTATACCT
1261 AGATTCTGTC CTGTTAAAAT TGAGAGTTCT ACATTTATCT GCTCATGGGG GTCGTGGTGG
1321 TGGTTTGCTG AGAACATCAC ACGTCCATAC TCGGACGTCG GCATGCCGCC AGCACCGATT
1381 TCCGCTTTGT GCTATATCTA TTCAAACAAT GACCCACCTC CTTGGTATTA TAATACAACT
1441 ATTATACCTC AGAAYTGTCG CAACTCTWCG GTTGATCCYA CCACAGCTCC ATGCCGTGAC
1501 AAGTGGGGCA ATGCAACTGC TTGTATTCTT GACCGCCGGT CGCGGTTCTG CGGGGACTGC
1561 TATGGCGGCT GCTTCTATAC TAATGGTAGT CATGATCGAT CCTGGGATCG ATGCGGATT
1621 GGTTACCGTG ATGGACTCAT AGAGTTTGTG CAGCTTGGTC AGATTCGACC TAACATCTCG
1681 AACACGACCA TTGAGCTCCT CGCTGGTGCC TCGCTTGTGA TTGCATCCGG TCTTCGGCCT
1741 GGGTACGGTT GCAGTCGAGC GCATGGCGTG GTGCACTGCT ATAGGTGTCC TTCATACCGT
1801 GACCTTGAAC AGTTCGGTCC TGGGCTCGGG AAATGGGTGC CGTTGCCTGG TGAGCCTGTC
1861 CCGGAGTTGT GTATCAACCC TCAATGGGCG AGGCGCGGCT TCCGGGTGTC TAACAATCCT
1921 TTAAGCTTGA TACAGACCTT TGTTGAGGAC ATCTTCCTAG CGCCTTTTTG YAMTCCGACG
1981 CCTGGTCGTG TACGTGTGTG TAACAATACT GCTTTCTATC AAGAGGAGG CGGCTTTGTG
2041 CAGCTCATCG GAGACGTCCA GGTGCTGACC CCTAACACTG CATCTTTACA CTCTCTGCTG
2101 ACCTTGATAT CCCTTATCTT GCTAGTGTGT GTTGTCTCTG GCGCGCGATT CGTCCCATTA
2161 ATCATCATAT TTTTCTGGAG CGTGCGCCAT GTATATGCTT CCTGTTACTT GAGCTGTGAT
2221 TGGGCTGTTT GCAATGATGC ATTCTGTTTC ACTTCTGGTA CTTGTGCTAC CTTCAATGAC
2281 GTCTTGTGTC TGCCGGTTGC GACGCGTATA TCGTCCTGTG GGCATGCTGT GCCACCGCCC
2341 GACCGTGGTT GGGAGGTGCC TGCGGCGCTG TCAYGGGKGA TTTCGCGGAC TACYGGCTTG
2401 ACGTTCGATG TCTTTTCTTT CATTCAGTAT CTTCCTACTG TGCCTGGCAA CAATTCCGAT
2461 ATCATTTACT GTGGTGAACC GACCTTTTTC GGGGATCTCA CGGGCATCTA TTGGCCTTAC
2521 TTTTTGCCTG GTGTGTTGCT TTTGTACTTG ACTCCCTTCC TTGGTTTAAG GTTAATGCTT
2581 GCCGGCTTTA ATATAGATGG CTTATTTCCC ATACGGCATG CCACGGCTGC ACTGAGGTTC
2641 TCGACTTCGC CGTGTGACCCT GAGTGTCGTG GCTGCCTTTC TAATCTATAT ATTATCCCAC
2701 CCTGTTAATG CTGCGCTCAA TAGAATGTTC TTAGCTCTCA CAAATTTAGA GATGATTCTA
2761 TCCTTTGATA CTTATCATGA GACTATCCTT TATATCGTCT GCCTAATGCT CTACCTCCAG
2821 GTGTCACCCC GTGCGGGCTT GGCCGCCATG GTGGCCATCA AGCTATCTCG AGGTCTGTTA
2881 TTCGCTGTGG TGTTGGCGCA CGGAGTGTGC CGACCGGGC GGGTATTTGG TCTTGAGGTT
2941 TGCGCGGACA TCTCCTGGTT GGTGGAGTTT ACTGGCAACT GCACTTGGTA TATGTCCTGT
3001 GTCTTCTCTT TTTGGTGCGC AGTGTTTGCC TTCACCAGTC CACTTGGACG ACAGTATAAG
3061 CTTCAGATCT ATCGGTACTG GGCGCAGGTC TATGCCAGAC TCATCCTCGC TGTCGGTTGT
3121 GGTCCTCTCG GCCGAGAGTT CCATTTCCGC GCAAGCGTGG GCGTACTTTG TGTGTGGCGCT
3181 TGCATGCTCT GGCCCCGTGA GTGCTCTGAA ATCAGCTTGG TCTTCATTCT GTGTGCTCTG
3241 ACAGTGGACA CCATAGACAC ATGGTTAGTA GCGTGCTTGT CCGCAGGGCC AAGTGCGCGA
3301 ACCCTTGCAA CGCTGGCCGA TGACATGGCG CGCATGGGTG ACAACCGGGC GTTGCGCGCC
```

FIG. 19B

```
3361 GTGTTGTGTT GCTTTGGATC ACGTGGCACA TACATATACA ACCACATGGG CCAGGTCTCA
3421 GAACGGGTGG CGCGAGCAGT CAGGGATCTC GGCGGTTGCT TGGAACCAGT CGTGTTGGAG
3481 GAGCCCACCT TTACTGAGRT CGTGGATGAT ACAMTGARTT TAGTGTGTGG ACAATTGCTT
3541 GGAGGTAAAC CTGTGGTGGC CCGCTGCGGC ACGCGTGTCT TGGTGGGACA CCTCAACCCT
3601 GAAGATCTGC CACCTGGTTT CCAGCTGAGT GCTCCGGTGG TTATYACCAA ACCAAGCATT
3661 GGTACGTGGT CCTTCCTTAA GGCGACACTC ACAGGGCGTK STGARACACC GGGATCCGGC
3721 CAGATCGTGG TGCTGTCTTC CCTGACAGGT CGGTCAATGG GTACTGCAGT GAATGRCACA
3781 CTGTATGCGA CCGGCCATGG TGCCGGTGCG CGTGGCCTAG CCACGTGCGC TGGTTTGAGG
3841 ACGCCACTTT ACACGGCATT ATCTGATGAT GTCGTGGCCT ATTCTTGCCT TCCGGGCATG
3901 AGTTCCCTGG AGCCCTGCCG CTGTACGCCG AGCCGGGTTT GGGTGATGAA CAACAATGGA
3961 GGGTTGGTGT GTGGCAGAGT AGAGAAGGAC GACGTCTGTT TGGACTGTCC CACGCACATA
4021 GATCAACTGC GGGGTGCTTC GGGGTCACCG GTTTTGTGTG ATCACGGTCA TGCATACGCG
4081 TTGATGCTCG GTGGTTACTC TACCAGTGGT ATTTGTGCGC GTGTCCGGAT AGTTCAGCCA
4141 TGGCAGAACG CCTATTCCTC CTCCGGGGGG CAAGGCGGAA TGCAGGCGCC AGCTGTGACA
4201 CCAACATACT CTGAAATCAC CTACTATGCC CCTACCGGTT CTGGTAAGTC AACAAAATAT
4261 CCAGTGGACC TGGTCAAACA GGGACACAAG GTATTGGTCA TCATACCAAG TGTGACTGTC
4321 GTTAAAAGTA TGGCCAATTA TATTAAGGAG ACATACAAGA TCAGACCTGA AATTAGAGCT
4381 GGCACTGGCC CTGACGGTGT GACGGTCATC ACTGGTGAAA GCTTGGCGTA CATGACCTAT
4441 GGCCGCTTCC TTGTGGATCC GGAGACGAAT CTGCGAGGCT ACGCCGTAGT CATTTGCGAC
4501 GAGTGCCACG ACACATCATC CACCACGCTA CTCGGCATAG GCGCGGTGCG CATGTTTGCT
4561 GAGAAAGCTG GAGTGAGGAC CGTTGTATTC GCCACAGCCA CCCCTGCTGG CATTCAAGTA
4621 CAGCCACATC CTAACATTGA TGAATATTTA TTGACTGACA CAGGCGACGT GGACTTCTAC
4681 GGCGCCAAAA TCAAATTGGA CAACATCAGA ACTGGTAGAC ATGTTATCTT TTGTCACTCG
4741 AAGGCCAGGT GTGCGGAACT AACGCAGCAG CTCTCCGGCC TTGGTGTTCG TGCAGTGAGT
4801 TTTTGGCGCG GCTGTGACAT CAAAACCATT CCCGCCTCAG ACTCTATTGT TGTAGTGGCA
4861 ACTGATGCAT TGTCCACAGG CTACACAGGA AATTTTGATT CGGTCATCGA CTGCGGGTGT
4921 TGCGTAGAAC AAACTGTGAC AATTGACATG GACCCTACGT TTTCCATCTC GGCGCGAGTG
4981 GTGCCATGCA CTGCTGCATT GCGTATGCAG CGGCGCGGAC GTACCGGTCG TGGCAGAAGG
5041 GGAGCGTATT ACACAACCAC TCCAGGAGCA GCACCTTGCG TCAGCGTTCC CGATGCTAAC
5101 GTCTGGCAAG CAGTGGAAAG CGCCATGGTT TTTTATGACT GGGGTGCTGC CAGGATACAA
5161 CAATGCCTGG CGGCATACCA TGATCTAGGG TGCACACCAC GCATCAGTTG YGATCCACAC
5221 ACTCCAGTGC GGGTGATGGA CACACTGCGG GCGTACCTGC GCAGACCTGA GGTGACGACT
5281 GCAGCTCTCK CAGGAGAGCA GTGGCCGCTG CTTTATGGTG TGCAGTTGTG CATCTGCAAA
5341 GAAACCGAGG CCCATGGTCC AGACGATAGC ATCAAGTGGA AGTGCTTACT CAACAACAGT
5401 AATAAAACAC CCCTGCTGTA TGCCTTAGAC AATCCTACAC TGGATTTCAC TACCCAACAT
5461 GACTTGACTC GCCGTATAGC CGGCGCTCTA TCGAGCACAG TGTTCGTGGA GACAGGCTAC
5521 GGCCCCATCC TCCTCGCTGG CGCCGCTTTG GCTGCCTCCT TCGCCTTTGC GGGTGCTACA
5581 GGAGCTTTAG TGCCGTCGGC CGTTTGGAGT GTTGACAACG GGTTAGCTGG CGTGACCCGT
5641 CCCGACGCGA CAGACGAAAC CGCGGCCTAC GCGCAGCGCT TGTACCAAGC CTGCGCAGAT
5701 TCAGGACTTT TCGCCAGCTT GCAGGGCACA GCGAGTGCGG CGCTGGGCAA ACTGGCTGAT
5761 GCCAGTAGGG GTGCTAGTCA ATATCTGGCA GCCGCGCCTC CTTCGCCCGC CCCCCTGGTG
5821 CAGGTGCTGC ATTTCCTTGA GACCAACTTT AGTTCCATTG CATCTTTCGG TCTGCTCTGT
5881 GCTGGTTGTC AGGCTGGTGA GTGCTTCACT GCGCTTGCCG GGCTGGTGTC CGGTGCTACA
5941 GCTGGCTTGG GAGGTGCCCA TAAGTGGTTG TTAGCTATTG CAGGAACCTG GCTAGTTAGC
6001 TTGCAGACTG GGCCCCGTGG CGGCATGGTT GCGGGTCTCT CGGTTCTAGC AGGCTGTTGC
6061 ATCGGTAGTG TCACCGGGCT CGACTTCCTG TTTGGGTGCC TTACAGGTTG GGAGGCCGTG
6121 GTTGGCGCTC CGGTTGCGAC GCAGAAGATC TTGTCTGGTT CAGCTGATAT GACCACTCTG
6181 GTAGATCTCT TACCTGCTAT CTTCTCCCNN NNNNCCGGCA TAGCTGGCAT CGTGCTTGTC
6241 TTTATTCTAA GTAACTCAAG TGTAACCACG TGGGCTAATC GGCTACTGTC CATGTGTGCA
6301 AAACAAACTA TTTGTGATAA CTACTTCTTA ACTGAGAAAT TTGGCCATCA ATTAAGCAAA
6361 CTTTCCCTGT GGCGCGCTGT GTACCATTGG GCGCAGGCAC GTGAGGGATA CACACAGTGC
6421 GGCGTGGTCA GCGGGATCTG GAGCTTTGTC TTGTGCATCC TGCGGGCTGT GTGGGATTGG
6481 GCGGCCAAGC ATGTGCCACG GTTCCGTGTG CCTATGATCG GCTGCTCACC TGCATGGTGC
6541 GGGCGCTGGC TTGGTACCGG CACCCTGTTG ACCACCTGTG GGTGTGGAGA ACGTGTGTCC
6601 CTTCAGTGCC TCTGCTCAAC GTCTGACCCA ACACTCAGTG TGGGCCGTTG GTGTCGGTGT
6661 AGTTGGAGTG TCGGGTTCCC ATTCAACCCG ACTACGACAG CCACCGGCAA TTTACGGCCG
6721 GACATTAGTG ACGCCACTAA ATTGGGTTTC CGATATGGTA TAGCCGAGAT CGTGGAACTG
6781 GAGCGGCGGG GTGACAAATG GCATGTCTGT GCAGCATCAT GTTGCTTGGA CCGAGCCAGC
6841 GTTGCATCCG CCGTGAAGGC CCCACCGGTC ACGGCCAATG GTATACCTAT CGGTACTTTT
```

FIG. 19C

```
6901 TCTCCACCAC AAACTTACAG CCTCTCTCTC TGTTCTTTTG ATTCAGTTTG CATGTCTAGT
6961 AACTTATGTA ACCCAGCTAA GACCCTGAGT GTGTGCTCCC AGGAGGCTGT CGAGCTACTG
7021 GAAGAAACAG TTGATAAAGC ACAAGTAATG ATGTGTCAAA ATCTGGAGGC GCGAAGACGC
7081 GCAGAGTATG ATGCATGGCA GGTTCGCCAA GCAGTTGGCG ACGAGTACAC GCGTTTGGCA
7141 GACGAGGATG TTGACGCGAC AACGTCGGTG AAACCCCCGG TGGCCAGGGC TGCTGTGGGT
7201 AGCTCAACGT TGGATGACGT TAGCGTGCTG ACTGTCTTGC GCGAACTCGG CGACCAATGC
7261 CAAAATGCTA TCAAATTTGT AGTTCAGGCG GCTTCACGGT TTGTTCCACC AGTGCCCAAG
7321 CCGCGCACGC GCGTCTCGGG TGTGCTGGAG CGTGTGCGCA TGTGCATGCG CACGCCACCA
7381 ATCAAATTTG AGGCCACCGC AGTACCAATT CATAACATAA TCCCAGAAGT GTGTCACATT
7441 GTGCTACGCT GTACCGGCTG TAACGACCAG GCCTGACTG TTCCGTACGG CACTTGCACT
7501 CAGACTTTAA TCAAACATTT GACTAACAAA CACAGCCACT ACATTCCAAA ACAGAAGATA
7561 GAAGAAGACA CAGAAGTAAC TGTCATTTGC GCCGTACCAA CAACGCGCGC AAGTAAGCTC
7621 ATCACTTTCA GAGCAGGTGA TCGATCAGTC TCATGTTGTC ACCCCTTGCA AACTCCTGTT
7681 AGGACCCTGC TTCTAAAGTA TGGGTTGCCT ATCGGGAAGT GGTCCGACTG CAACGGCCCC
7741 CTTGGTGACG ATGCCCGAGT CTGTGACATC AATGGAGTAA CAACTTATGA ACCATGCATG
7801 CAATCCTATA GTTGGTTCCG ACCAATTGTA GCGCCAACAA CCCCACCTTT ACCTGCAACC
7861 CGGAGCGTGG CTGGCATTTT ACGCGCGGAC ACATCGCGCG TTTACACCAC AACGGCGGTT
7921 GACGTCTCCG AGCGGCAGGC TAAGGTCACA ATTGATCAAA CATCAGCCAA GGTGGATCAG
7981 TGTTTCCGAG ACACATACAA TTGCTGCCTT GCTAAGGCAA AGACCTTCAA ACAATCTGGC
8041 ATGTCATATG AGGATGCTGT GTYAAAGATG CGCGCAAACA CCACGCGTGA CCATAACAAT
8101 GGCACCACTT ATTCAGATTT GGTCTCTGGA CGCGCAAAAC CTGTCGTTCA GAAAATTGTA
8161 GATCAAATGC GCGCTGGAGT GTACGACGCT CCAATGCGCA TTATCCCAAA ACCTGAAGTG
8221 TTCCCTCGGG ACAAGTCAAC ACGGAAGCCA CCACGGTTCA TCGTTTTCCC TGGGTGCGCC
8281 GCGCGAGTCG CGGAGAAAAT GATCCTGGGC GATCCTGGCG CGATAACCAA GCACGTGCTT
8341 GGTGATGCCT ATGGGTTTGC CACTCCGCCG CATGAGCGCG CGCGTCTATT GGAACAATGG
8401 TGGAACCGTG CAACGGAGCC ACAAGCTATC GCGGTTGATG CGATCTGCTT TGATAGCACT
8461 ATCACGGCAG AGGACATGGA TCGCGAGGCC AACATCATGG CTGCGGCGCA TTCGGACCCT
8521 GAAGGTGTTC ATGGCCTGTA CAAGTATTAC AAAAGAAGCC CCATGTGTGA CATCACGGGA
8581 AAAGTTGTCG GGGTGCGTTG CTGTCGAGCC TCAGGTACGC TTACAACAAG CAGTGGCAAC
8641 ACGCTTACTT GCTATCTCAA GGTTCGCGCA GCTTGCACGC GCGCCGGCAT TAAACCAATT
8701 GGCTTACTAA TTCATGGAGA TGATACCCTC ATTGTCACAG AACGTTGCGC TCAAGAAACT
8761 CTCGATGAGT TCAGCAGCGC ACTCGATGAC TATGGGTTCC CTCACACCTT GCAGGTGTCT
8821 GGGGACCTCT CGTCTGTTGA GTGCTGTAGC GCACGTGTGG ACAGCGTTTG CCTCCGGGGA
8881 GGTATGCGTC GCATGCTCGT GCCACAAGCT CGACGTGCGA TTGCACGCGT TCTCGGGGAG
8941 AAGGGTGATC CACTGGGTGT CATCAGTAGC TATATCGTCA TGTATCCYAC TGCGGCTGTG
9001 ACTGTCTACG TGCTATTGCC CCTGTTATGC ATGCTCATTC GGAATGAGCC ATCGCAGACG
9061 GGGACGATTG TGACGCTGAC GGTCCACGGY AACAGTGTGA GCGTGCCGGT GTGGCTGCTT
9121 CCAACCATCA TTGTAAATTT ACATGGTCGT GACGCACTAC AGGTAGTCCG TCACAGTGCA
9181 GCTTCCATGG CGGAACTGTC GTCAGCGTTG GCCTTCTTTG GCATGAGAGG GTTGAACTGC
9241 TGGAGGCGGA GACGCCGCGC CATCAGGACT GATATGATCA RGTTGGGCGG GTGGATTGCG
9301 AATTTCGCGC AGATGTTACT GTGGTCACCG GAGGTGAGGA CACCACAGCC CGAACCGAAG
9361 GGCTTGTGTC TCTTACCACC GGAACTATGG GAGCGTCCGT ACGAAAATTT GCAMTTGAGC
9421 ACGGTCGACC GTAATCGTGG TGCTAGTCGC TTACGGTTTT GGCTGGTTGC AAGTGCTATA
9481 CTCGCTCTGC TTTGCTTGTA AATCCTAAAT CAATGTAGTA CCAGGACTAC AAGGCAGGAG
9541 GTGAAGTCAG CTGTACCCAC GGCTGGCTGA AACCGGGGCT TGACGACCCC CCTATCCGA
9601 GTTGGGCAAG GTAACATCAC GGGTGTGACG ACCCCGCCCC CCCATGTCGC GCGTAAGCGC
9661 ACGGGCAAGG CAGCTAGGCT GAGAGTCTGG GCAACTCTCC CGTACCCCAC CCGAGGCTAC
9721 GCCTCGTCCT GGCGAGGACC GTAAACATAC GTCGTCAGCG TGGTGACCTG ACGTATCTTG
9781 TTAACCACTT AATGGTCGTA ACTCGACCCC CGTGCCGGGG ATCTAAGCGC GGCACCGCGA
9841 TGAGGGGGGT CAACGGCCCC TTTCATT
```

FIG. 20A

Human Pegivirus 2 (ABT0239AN) Genes and Untranslated Regions

5' UTR Sequence

5' UTR Sequence: nucleotides 12-327 of SEQ ID NO:302

S Protein and Gene Sequence

S Protein Amino Acid Sequence: (SEQ ID NO:334)

MGCSTDQTICSPVVGADYNTSSGCRALNGSDHCGGSSCRSPSRVQAARRVLQLCAFLALIGSGMCSIRSKTEGRIESGQ

S protein gene sequence: nucleotides 328-564 of SEQ ID NO:302.

E1 Protein and Gene Sequence

E1 Protein Amino Acid Sequence: (SEQ ID NO:335)

ILQSQRACWTGEGPAFFSNCCNQSDIMWCLHRWCVTRPGCLVCTGNATHPVCWDYLGSGVSRRPARRLGEGAEMLLRLIGIAGWLGLLAEALG
MSEMYAAILCFGFIAWYGWGIPKTLVCTVCPAVNISPYSFLSPDTIAFGTWILQLPGLLWQMFVNFPILYSTWILWLLLSGKTVAVIAILLAS
PTVMA

E1 protein gene sequence: nucleotides 565-1137 of SEQ ID NO:302.

E2 Protein and Gene Sequence

E1 Protein Amino Acid Sequence: (SEQ ID NO:336)

YKHPSESYLKYCTITNASAAMNCDCPFGTFTRNTESRFSIPRFCPVKIESSTFICSWGSWWWFAENITRPYSDVGMPPAPISALCYIYSNNDP
PPWYYNTTIIPQNCRNSXVDPTTAPCRDKWGNATACILDRRSRFCGDCYGGCFYTNGSHDRSWDRCGIGYRDGLIEFVQLGQIRPNISNTTIE
LLAGASLVIASGLRPGYGCSRAHGVVHCYRCPSYRDLEQFGPGLGKWVPLFGEPVPELCINPQWARRGFRVSNNPLSLIQTFVEDIFLAPFCX
PTPGRVRVCNNTAFYPRGGGFVQLIGDVQVLTPNTASLHSLLTLISLILLVCVVSGARFVPLIIIFFWSVRHVYA

E2 protein gene sequence: nucleotides 1138-2199 of SEQ ID NO:302.

X Protein and Gene Sequence

X Protein Amino Acid Sequence: (SEQ ID NO:337)

SCYLSCDWAVCNDAFCFTSGTCATFNDVLCLPVATRISSCGHAVPPPDRGWEVPAALSXXISRTTGLTFDVFSFIQYLPTVPGNNSDIIYCGE
PTFFGDLTGIYWPYFLPGVLLLYLTPPFLGLRLMLAGFNIDGLFPIRHATAALRFSTSRVTLSVVAAFLIYILSHPVNAALNRMFLASANLEMI
LSFDTYHETILYIVCLMLYLQVSPRAGLAAMVAIKLSRGLLFAVVLAHGVC

X protein gene sequence: nucleotides 2200-2910 of SEQ ID NO:302.

FIG. 20B

NS2 Protein and Gene Sequence

NS2 Protein Amino Acid Sequence: (SEQ ID NO:338)

RPGRVFGLEVCADISWLVEFTGNCTWYMSCVFSFWCAVFAFTSPLGRQYKLQIYRYWAQVYARLILAVGCGPLGREFHFRASVGVLWCGACML
WPRECSEISLVFILCALTVDTIDTWLVACLSAGPSAPTLATLADDMARMGDNRALPAVLCCFGSRGTYIYNHMGQVSERVARAVRDLGGCLEP
VVLEEPTFTEXVDDTXXLVCGQLLGGKPVVARCGTRVLVGHLNPEDLPPGFQLS

NS2 protein gene sequence: nucleotides 2911-3630 of SEQ ID NO:302.

NS3 Protein and Gene Sequence

NS3 Protein Amino Acid Sequence: (SEQ ID NO:339)

APVVITKPSIGTWSFLKATLTGRKETPGSGQIVVLSSLTGRSMGTAVNXTLYATGHGAGARGLATCAGLRTPLYTALSDDVVAYSCLPGMSSL
EPCRCTPSRVWVMNNNGGLVCGRVEKDDVCLDCPTHIDQLRGASGSPVLCDRHGHAYALMLGGYSTSGICARVRIVQPWQNAYSSSGQGGMQA
PAVTPTYSEITYYAPTGSSGKSTKYPVDLVKQGHKVLVIIPSVTVVKSMANYIKETYKIRPEIRAGTGPDGVTVITGESLAYMTYGRFLVDPET
NLRGYAVVICDECHDTSSTTLLGIGAVRMFAEKAGVRTVVFATATPAGIQVQPHPNIDEYLLTDTGDVDFYGAKIKLDNIRTGRHVIFCHSKA
RCAELTQQLSGLGVRAVSFWRGCDIKTIPASDSIVVVATDALSTGYTGNFDSVIDCGCCVEQTVTIDMDPTFSISARVVPCTAALRMQRRGRT
GRGPRGAYYTTTPGAAPCVSVPDANVWQAVESAMVFYDWGAARIQQCLAAYHDLGCTPRISCDPHTPVRVMDTLRAYLRRPEVTTAALXGEQW
PLLYGVQLCICKETEAHGPDDSIKWKCLLNNSNKTPLLYALDNPTLDFTTQHDLTRRIAGALSSTVFVET

NS3 protein gene sequence: nucleotides 3631-5514 of SEQ ID NO:302.

NS4A Protein and Gene Sequence

NS4A Protein Amino Acid Sequence: (SEQ ID NO:340)

GYGPILLAGAALAASFAFAGATGALVPSAVWSVDNGLAGVT

NS4A protein gene sequence: nucleotides 5515-5637 of SEQ ID NO:302.

NS4B Protein and Gene Sequence

NS4B Protein Amino Acid Sequence: (SEQ ID NO:341)

RPDATDETAAYAQRLYQACADSGLFASLQGTASAALGKLADASRGASQYLAAAPPSPAPLVQVLHFLETNFSSIASFGLLCAGCQAGECFTAL
AGLVSGATAGLGGAHKWLLAIAGTWLVSLQTGPRGGMVAGLSVLAGCCIGSVTGLDFLFGCLTGWEAVVGAAVATQKILSGSADMTTLVDLLP
AIFSXXXGIAGIVLVFILSNSSVTTWANPLLSMCAKQTICDNYFLTEKFGHQLSKLSLWRAVYHWAQAREGYTQCG

NS4B protein gene sequence: nucleotides 5638-6423 of SEQ ID NO:302.

FIG. 20C

NS5A Protein and Gene Sequence

NS5A Protein Amino Acid Sequence: (SEQ ID NO:342)

VVSGIWSFVLCILRAVWDWAAKHVPRFRVPMIGCSPAWCGRWLGTGTLLTTCGCGERVSLQCLCSTSDPTLSVGRWCRCSWSVGFPFNPTTTA
TGNLRPDISDATKLGFPRYGIAEIVELERRGDKWHVCAASCCLDRASVASAVKAPPVTANGIPIGTFSPPQTYSLSLCSFDSVCMSSNLCNPAK
TLSVCSQEAVELLEETVDKAQVMMCQNLEARRRAEYDAWQVRQAVGDEYTRLADEDVDATTSVKPPVARAAVGSSTLDDVSVLTVRELGDQC
QNAIKFVVQAASRFVPFVPKPRTRVSGVLERVRMCMRTPPIKFEATAVPIHNIIPEVCHIVLRCTGCNDQALTVPYGTCTQTLIKHLTNKHSH
YIPKQKIEEDTEVTVICAVPTTRASKLITFRAGDRSVSCCHPLQTPVRTLLLKYGLPIGKWSDCNGPLGDDARVCDINGVTTYEPC

NS5A protein gene sequence: nucleotides 6424-7797 of SEQ ID NO:302.

NS5B Protein and Gene Sequence

NS5B Protein Amino Acid Sequence: (SEQ ID NO:343)

MQSYSWFRPIVAPTTPPLPATRSVAGILRADTSRVYTTTAVDVSERQAKVTIDQTSAKVDQCFRDTYNCCLAKAKTFKQSGMSYEDAVKKMRA
NTTRDHNNGTTYSDLVSGPAKPVVQKIVDQMRAGVYDAPMRIIPKPEVFPRDKSTRKPPRFIVFPGCAARVAEKMILGDPGAITKHVLGDAYG
FATPPHERARLLEQWWNRATEPQATAVDAICFDSTITAEDMDREANIMAAAHSDPEGVHGLYKYYKRSPMCDITGKVVGVRCCRASGTLTTSS
GNTLTCYLKVRAACTRAGIKPIGLLIHGDDTLIVTERCAQETLDEFSSALDDYGFPHTLQVSGDLSSVECCSARVDSVCLRGGMRRMLVPQAR
RAIARVLGEKGDPLGVISSYIVMYPTAAVTVYVLLPLLCMLIRNEPSQTGTIVTLTVHGNSVSVPVWLLPTIIVNLHGRDALQVVRHSAASMA
ELSSALAFFGMRGLNCWRRRRAIRTDMIKLGGWIANFAQMLLWSPEVRTFQPEPKGLCLLPPELWERPYENLXLSTVDRNRGASRLRFWLVA
SAILALLCL

NS5B protein gene sequence: nucleotides 7798-9498 of SEQ ID NO:302.

3' UTR Sequence

3' UTR Consensus Sequence: nucleotides 9499-9867 of SEQ ID NO:302.

FIG. 21A

Human Pegivirus 2 (UC0125) Nucleic Acid Sequence - SEQ ID NO:303

```
   1 NNNNNNNNNN NNNNNNNNNN NNNTATTGCT ACTTCGGTAC GCCTAATTGG TAGGCGCCCG
  61 GCCGACCGGC CCCGCAAGGG CCTAGTAGGA CGTGTGACAA TGCCATGAGG GATCATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGGTGTTCAA CTGATCAAAC CATTTGTTCT
 361 CCAGTCGTGG GGGCCGACTA TAATACCTCC TCGGGCTGCC GGGCCTTAAA TGGGAGCTAC
 421 CACTGCGGTG GTGGCTCTTG CCGGTCACCA AGTCGTGTGC AGGTTGCGAG ACGAGTCTTG
 481 CAGCTGTGCG CATTCCTTGC GCTGATCGGA TCCGGTATGT GTTCGATCCG GTCCAAAACT
 541 GAAGGGCGCA TTGAGTCAGG GCAAATATTG CAGTCTCAGC GCGCATGTTG GACTGGTGAG
 601 GGTTTTGCTT TCTTTTCTAA CTGTTGCAAT CAATCTGATA TTATGTGGTG TTTGCACCGT
 661 TGGTGTGTGA CAAGACCTGG CTGTTTAGTG TGCACGGGCA ATGCCACCCA TCCTATCTGC
 721 TGGGACTATC TTGGATCCGG TGTAAGTCGG CGGCCTGCAC GTCGAATGGG TGAGGGAGCT
 781 GAAGCGCTTC TTCGCTTGAT CGGCATTGCA GGTTGGCTTG ACTGTTAGC TGAGTCCCTT
 841 GGTATGTCCG AAGTCTATGC AGCTATTCTT TGCTTTGGAT TTATTGCTTG GTATGGCTGG
 901 GGTATACCTA AAACACTGGT GTGCACCGTC TGCCCTGCAG TGAACATTTC TCCCTATAGC
 961 TTCTTATCTC CAGATACTAT CGCATTTGGT ACGTGGATAC TACAACTACC TGGTCTTTTG
1021 TGGCAAATGT TTGTTAGCTT CCCTATACTC TACAGCACTT GGATTCTTTG GTTGTTGCTC
1081 AGCGGCAAGA CTGTTGCTGT GATAGCAATC CTTCTGGCTA GTCCTACGGT TATGGCGTAC
1141 AAGCATCAAT CTGAAAGCTA CCTCAAATAC TGTACCATAA CCAATACTTC AACTTCTATG
1201 AACTGTGACT GCCCCTTTGG AACCTTTACT CGCAATACTG AGTCTCGTTT CTCCATACCT
1261 AGATTCTGTC CTGTTAAAAT CAATAGCTCT ACATTTATTT GTTCATGGGG GTCGTGGTGG
1321 TGGTTTGCTG AAAACATCAC GCGTCCATAC ACGGACGTTG GCATGCCACC AGCACCGATT
1381 TCCGCTTTGT GCTATATCTA TTCTAACAAT GACCCACCTC CTTGGTATCA TAACACAACT
1441 ATCATACCTC AGAACTGTCG CAACTCTACG GTGGATCCTA CCACAGCTCC ATGCCGTGAC
1501 AAGTGGGGCA ACGAACTGC TTGTATTCTT GACCGCCGGT CGCGGTTCTG CGGGGACTGC
1561 TATGGCGGTT GTTTCTATAC TAATGGTAGT CATGATCGAT CCTGGGATCG ATGCGGGATT
1621 GGTTACCGTG ATGGACTCAT AGAGTTCGTG CAGCTCGGTC AGATTCGACC TAACATCTCG
1681 AATACGACCA TTGAGCTCCT CGCTGGCGCC TCGCTTGTGA TCGCATCCGG TCTTCGGCCT
1741 GGGTTTGGTT GCAGCCGAGC GCATGGCGTG GTGCACTGCT ATAGGTGTCC TTCATACCGT
1801 GACCTTGAAC AGTTTGGTCC TGGGCTTGGG AAATGGGTGC CATTGCCCGG CGAGCCTGTC
1861 CCGGAGTTGT GTATCAACCC TCAGTGGGCG AGGCGCGGCT TCCGGATGTC TAATAATCCT
1921 CTGAGCTTGC TACAGACCTT CGTTGAGGAC ATTTTCCTAG CGCCTTTTTG TAATCCGACG
1981 CCTGGCCGTG TACGTGTGTG TAACAATACC GCTTTCTATC AAGAGGAGG CGGCTTTGTG
2041 CAGCTCATCG GGGACGTCCA GGTGCTAACC CCTAACACTG CATCTTTACA CTCTCTGCTG
2101 ACTTTGATAT CTCTTATCTT GTTGGTGTGT GTTGTTTCTG GTGCGCGATT CGTTCCACTA
2161 ATAATCATAT TTTTCTGGAG CGCGCGCCAT GTATATGCTT CTTGTTACTT AAGCTGTGAT
2221 TGGGCTGTTT GCAACGATGC GTTCTGTTTC ACATCTGGCA CTTGTGCCAC CTTCAATGAC
2281 GTCTTGTGTC TGCCGGTTGC GACGCGCATA TCGTCCTGTG GTCATGCTGT GCCACCTCCC
2341 GACCGTGGTT GGGAGGTGCC TGCGGCGATG TCATGGGTGA TTTCGCGGAC TACTGGCCTG
2401 ACGTTCGATG TCTTTTCCTT CATTCAGTAC CTTCCTACTG TGCCTGGCAA CAACACCAAT
2461 ATCATTTACT GTGGTGAACC AACCTTCCTC GGGGACATCA CGGGCATCTA TTGGCCTTAC
2521 TTTTTGCCTG GCGCAATCCT CTTGTACTTG ACTCCCTTCC TAGGTTTAAG GTTAATGCTT
2581 GCCGGCTTCA ATATAGATGG CTTGTTTCCC ATACGGCATG CCACGGCTGC ACTGAGGTTT
2641 TCGACTTCTC GTGTGACCTT GTGTGTCGTA GTTGCTTTCC TAATCTATAT ATTATCTCAC
2701 CCTGTTAATG CTGCGCTCAA TAGAATGTTC TTAGCATCTG CAAATTTAGA GATGATCTTA
2761 TCTTTTGATA CCTATCATGA GACTGTTCTT TATATCCTTT GTCTATTGCT CTACCTCCAG
2821 GTGTCGCCCC GTGCGGGCTT GGCCGCTATG GTGGCCATCA AGCTATCTCG AGGCCTGTTA
2881 TTCGCTGTGG TGTTGGCGCA CGGTGTGTGC CGACCTGGGC GGGTATTTGG TCTTGAGGTT
2941 TGCGCGGACA TCTCTTGGTT GGTGGAGTTT ACTGGCAATT GCACTTGGTA CATGTCCTGT
3001 GTCTTCTCTT TTTGGTGCGC AGTGTTTGCC TTCACCAGTC CACTTGGACG ACACTATAAG
3061 ATTCAGATCT ATCGGTACTG GGCGCAGGTC TATGCCAGAC TCGTCCTCGC TGTCGGTTGT
3121 GGTCCTCTCG GTCGAGAGTT CCATTCCGT GCAAGTGTGG GCGTGCTGTG TGTGGAGCT
3181 TGCATGCTCT GGCCCGTGA GTGCTCTGAA ATCAGCCTGG TCTTCATTCT GTGTGCTCTG
3241 ACAGTGGACA CCATAGACAC ATGGTTAGTA GCGTGCTTGT CCGCAGGGCC GAGTGCGCGA
```

FIG. 21B

```
3301 ACCCTTGCAA TTCTGGCCGA TGACATGGCG CGCATTGGTG ACCACCGGGC GTTGCGCGCC
3361 GTGTTACGTT GCTTTGGATC ACGCGGCACA TACATATACA ACCACATGGG CCAAGTCTCG
3421 GAACGGGTGG CGCAAGCAGT CAGGGATCTC GGCGGTTGCT TGGAACCAGT CGTGTTGGAG
3481 GAGCCCACCT TTACTGAGAT CGTGGATGAC ACAATGAGTT TGGTGTGTGG ACAATTGCTT
3541 GGAGGTAAAC CTGTGGTGGC CCGCTGCGGC ACGCGTGTCT TGGTGGGACA CCTCAACCCT
3601 GAAGATCTGC CACCTGGTTT CCAGCTGAGT GCTCCGGTGG TTATTACCAG GCCAAGCATT
3661 GGTACGTGGT CCTTCCTTAA GGCGACACTC ACAGGGCGTG CTGAAACACC AGGGTCCGGC
3721 CAGATCGTGG TGTTGTCTTC CCTGACAGGT CGGTCAATGG GTACCGCAGT GAATGGCACA
3781 CTGTATGCGA CCGGCCATGG TGCCGGCGCG CGCGGCCTAG CCACGTGCGC TGGTTTGAGG
3841 ACGCCACTTT ACACGGCATT ATCTGATGAT GTCGTGGCCT ATTCTTGCCT TCCGGGCATG
3901 AGTTCCCTAG ACCCCTGCTG CTGTTCGCCG AGCCGGGTTT GGGTGATGAA TAACAACGGA
3961 GGGTTGGTGT GTGGCAGAGT GGAGAATGAC GACGTCTGTT TGGACTGTCC CACGCACATA
4021 GATCAACTGC GGGGTGCTTC GGGCTCACCA GTTTTGTGTG ATCACGGTCA TGCATACGCG
4081 TTGATGCTCG GTGGTTACTC TACCAGTGGT ATTTGTGCAC GCGTCCGGAC GGTCCGGCCA
4141 TGGCATAACG CCTATTCCTC CTCGGGGGGG CAAGGCGGAA TGCAGGCGCC AGCTGTGACA
4201 CCAACATACT CTGAAATCAC CTACTATGCC CCTACTGGTT CTGGTAAGTC AACAAAATAT
4261 CCAGTGGACC TAGTCAAACA GGGACACAAA GTATTGGTCC TTTTACCAAG TGTGGCTGTA
4321 GTCAAAAGTA TGGCCCCTTA TATTAAGGAG ACATATAAGA TCAGACCCGA AATTAGAGCT
4381 GGCACAGGTC CTGACGGTGT GACGGTCATC ACTGGTGAGA ACTTGGCGTA CATGACCTAT
4441 GGCCGCTTCC TTGTGGATCC GGAGACGAAT CTGCGGGGCT ATGCTGTAGT CATTTGCGAC
4501 GAGTGTCACG ACACATCATC CACCACGCTA CTCGGCATTG GCGCAGTGCG CATGTATGCC
4561 GAGAAAGCTG GAGTGAAGAC CGTTGTATTC GCCACAGCCA CCCCTGCTGG CATTCAAGTA
4621 CAGTCACATT CCAACATTGA TGAATACTTA TTGACTGACA CAGGCGACGT GGAATTTTAC
4681 GGCGCCAAAA TCAAAATGGA CAACATCAGA ACTGGTAGAC ATGTTATCTT TGCCACTCG
4741 AAGGCCAGGT GTGCGGAACT AACGCAGCAG CTCTCCGGCC TTGGCATTCG TGCAGTGAGT
4801 TTTTGGCGCG GCTGTGACAT CAAAACCATT CCCGCCTCAG ACTCCATTGT TGTGGTGGCA
4861 ACTGATGCAT TGTCCACGGG CTACACAGGA AACTTTGATT CGGTCATCGA CTGCGGGTGT
4921 TGCGTGGAGC AAACTGTGAC AATTGACATG GACCCTACGT TCTCCATCTC GGCCCGAGTG
4981 GTGCCATGTA CTGCTGCATT GCGCATGCAG CGGCGCGGAC GTACCGGTCG TGGTAGAAGG
5041 GGAGCGTACT ACACAACTTC TCCAGGAGCA GCACCCTGCG TCAGCGTTCC CGATGCTAAC
5101 GTCTGGCCAG CAGTGGACAG CGCCATGGTC TTTTATGATT GGAGTGCTAC CAGGATACAA
5161 CAGTGCCTGG CGGCATACCA TGATTTGGGG TGCACACCAC GCATCAGCTG TGACCCACAC
5221 ACTCCAGTGC GGGTGATGGA CACACTGAGG GCGTACCTGC GCAGACCTGA GGTGACGACT
5281 GCAGCTCTCG CAGGAGAGCA GTGGCCGCTG CTTTATGGTG CGCAGTTGTG CATCTGCAAA
5341 GAGACCGAGG CCCACGGTCC TGATGATAGC ATCAAGTGGA AGTGCTTACT CAACAACAGT
5401 AACAAAACAC CCCTGTTGTA TGCCTTAGAC AATCCTACAC TGGAATTCAC AACCCAACAT
5461 GACTTGACTC GCCGTATAGC CGGCGCTCTA TCGAGCACAG TGTTCGTGGA GACAGGCTAC
5521 GGCCCCATCC TCCTTGCTGG CGCCGCTTTG GCTGCCTCCT TCGCCTTTGC GGGCGCCACT
5581 GGAGCTTTAG TGCCGTCGGC TGTTTGGAGC GTTGAGGTCA GGCCTGCTGG CGTGACCCGT
5641 CCCGACGCGA CAGACGAGAC CGCGGCCTAC GCACAGCGCT TGTACCAAGC CTGTGCAGAT
5701 TCAGGAATTT CGCCAGCTT GCAGGGTACG GCGAGTGCGG CGCTGGGCAA ACTGGCCGAC
5761 GCCAGTAGGG TGCTAGTCA ATATCTGGCA GCCGCGCCTC CTTCACCCGC CCCCCTGGTA
5821 CAGGTGTTGC AGTTCCTCGA GACCAACTTT AGCTCCATTG CATCTTTCGG CCTGCTCTGT
5881 GCTGGCTGCC AGGCTGGCGA GTGCTTCACT GCGCTTGCTG GCTTGGTGTC CGGTGCTACA
5941 GCTGGCTTGG GGGTGCCCA TAAGTGGCTA TTAGCTATTG CAGGAACTTG GCTGGTTAGC
6001 TTGCAGACCG GGTCCGTGG CGGCATGGTT GCGGGCCTCT CGATTCTAGC GGGCTGTTGC
6061 ATCGGTAGTG TCACCGGGCT TGACTTCCTG TTTGGGTGCC TTACAGGTTG GGAAGCCGTG
6121 GTCGGCGCTG CGGTTGCGAC ACAGAAGATC TTGTCTGGTT CAGCTGATAT GACCACTCTG
6181 GTAGATCTCT TACCTGCTCT TTTCTCCCCC GGTGCCGGCA TAGCTGGCAT CGTGCTTGTC
6241 TTCATCTTAA GCAATTCAAG TGTAACCACA TGGGCTAATC GGCTATTATC CATGTGTGCC
6301 AAACAAACCA TTTGTGAAAA CTACTTCTTA AGTGAAAGAT TTGGCCAACA ATTAAGCAAA
6361 CTTTCCCTGT GGCGCTCTGT GTACCATTGG GCGCAGGCAC GTGAGGGATA CACACAGTGC
6421 GGCGTGATCA GCGGGATCTG GAGCTTCGCC TTGTGCATTC TACGCGCTGT GTGGGATTGG
6481 GCGGCCAAGC ATGTGCCACG GTTCCGTGTG CCTATGATTG GCTGCTCACC TGCGTGGTGC
6541 GGGCGCTGGC TTGGTACCGG CACCTTGTTG ACCACCTGTG CGTGTGGAGA ACGTGTGTCC
6601 CTTCAGTGCC TTTGCTCAAC ATCTGACCCA CAACTCAGTG TGGGCCGTTG GTGTCGGTGT
6661 AGTTGGAGTG TTGGGTTCCC ATTCAACCCG ACTACGACAG GCACTGGCAC CTTACGGCCG
6721 GACATCAGTG ACGCCAACAA ATTGGGTTTC CGGTATGGCG TTCCGACAT CGTGGAGCTA
6781 GAGCGGCGGG GCGACAAATG GCACGTCTGT GCAGCATCAT GTTGCTTGGA CCGGGCCAGC
```

FIG. 21C

```
6841 GTTGCATCCG CTGTGAAGGC CCCACCGGTC ACGGCTAATG GTATACCTAT TAATAGCTTT
6901 TCTCCACCAC AAACTTATTG CCTATCTCTC TGTTCCTTTG ATACAGTTTG CATGTCTACT
6961 AACTTATGTA ACCCAGCTAA GACCCTGAGT GTGTGCCAAG AGGAGGCGGT TGAGCTGCTG
7021 GAAGAGACAG TTGACACAGC ACAAGTAGTG ATGAGCCAAA ATCTGGCAGC GCGTAGACGC
7081 GCTGAGTATG ATGCATGGCA GGTTCGCCAA GCAGTTGGCG ACGAGTACAC GCGTTTGGCA
7141 GACGAGGATG TTGACATGAC AGCGTCGGTG AAACCCCCAG TGGCCAGGGC TGCTGTGGGT
7201 AGCTCAACGT TGGATGATGT TAGCGTGCTG ACTGTCTTAC GCGAACTCGG CGACCAGTGC
7261 CAAAATGCTA TCAAATTTGT AGTTCAGGCG GCTTCACGGT TTGTTCCACC AGTGCCCAAG
7321 CCACGCACGC GTGTCTCGGG TGTCTTGGAG CGCGTGCGCA TGTGCATGCG CACGCCTCCA
7381 ATCAAGTTTG AGGCCACCGC AGTACCAATT CATAATATAA TCCCAGAAGA GTGTCATATT
7441 GTGCTACGCT GTACCGGCTG TTGTGACCAG GCCTTGACCG TTCCGTACGG CACTTGCTCT
7501 CTGACTTTAA CCAAATATTT GACTAACAAA CACAGTCACT ATATTCCAAA AGAGAAGATA
7561 GAAGAAGACA CAGAAATAGC TGTCATTTGC GCCGTACCAA CAAAGCGCGC AAGTAAACTT
7621 ATCACTTTCA GAGCAGGTGA CCGATCAGTC TCATGTTGTC ACCCCTTGCA AACTCCTATT
7681 AGGGCCCTGC TTCAAAAGTA TGGGTTACCT ATTGGGAAGT GGTCCGACTG CAACGGGCCC
7741 CTTGGTGACG ACGCCCGAGT CTGTGACGTC AATGGAGTGA CAACTTATGA ACCATGCATG
7801 CAATCCTACA ATTGGTTCCG ATCGATTGTG GCACCAACAA CCCCACCTTT ACCTGCAACC
7861 CGGAGCGTGG CTGGCATTTT GCGCGCAGAC ACATCGCGCG TCTACACCAC AACAGCGGTT
7921 GATGTCTCCG AGCGGCAGGC TAAGGTCACG ATTGATCAAA AGTCAGCCAA GGTGGACCAG
7981 TGTCTCCGAG ACACATACAA TTGCTGCCTT GCCAAGGCAA AGACCTTCAG ACAATCTGGC
8041 ATGTCATATG AGGATGCTGT GTCAAAGATG CGCGCAAACA CCACGCGTGA TCATAACAAC
8101 GGCATCACTT ATACAGATTT GGTCTCTGGA CGCGCAAAAC CTGTCGTTCA GAAAATTGTA
8161 GATCAGATGC GCGCTGGAGT GTACGACGCT CCAATGCGCA TTATTCCAAA ACCTGAAGTG
8221 TTTCCACGAG ACAAGTCAAC ACGGAAGCCA CCACGGTTCA TCGTTTTCCC TGGGTGTGCC
8281 GCACGAGTCG CGGAGAAAAT GATCCTGGGC GATCCTGGCG CGATAACCAA GCACGTGCTA
8341 GGTGATGCCT ACGGGTTTGC CACTCCGCCG CATGAGCGCG CGCGCCTACT GGAACAATGG
8401 TGGAACCGCG CAACGGAGCC ACAAGCTATC GCGGTTGATG CAGTCTGCTT TGATAGCACC
8461 ATCACGGCAG AGGACATGGA TCGTGAGGCC AACATCGTGG CTGCAGCGCA TACGGACCCG
8521 GAAGGTGTTC ACGGCCTATA CAATTATTAC AAAAGAAGCC CCATGTGTGA TATCACAGGA
8581 AAAGTTGTCG GGGTGCGTAG CTGTCGAGCC TCAGGTACGC TTACAACAAG CAGTGGCAAC
8641 ACGCTTACTT GCTACCTCAA GGTTCGCGCA GCTTGCACGC GCGCCGGCAT TAAACCAATT
8701 GGCTTACTAA TTCATGGAGA TGACACCCTC ATTATCACAG AACGTTGCGC TCAGGAAACT
8761 CTCGATGAGT TCAGCAACGC GCTTGATGAC TATGGGTTTA CTCACACCAT GCAGGTGTCT
8821 GGGGACCTCT CGTCTATCGA GTGCTGCAGC GCACGTGTGG ACAGCGTTTG CCTCCGGGGA
8881 GGTATGCGTC GCATGCTCGT GCCACAAGCT CGACGTGCGA TTGCACGCGT CTCGGGGAA
8941 AAGGGCGATC CACTGGGTGT TATCAGCAGC TATATTGTCA TGTATCCTAC TGCGGCTGTG
9001 ACTGTCTACG TTCTGATGCC CCTGTTGTGC ATGCTCATTC GAAATGAGCC ATCGCAGACG
9061 GGGACACTTG TAACGTTGAC GGTCCACGGT AACAGTGTGA GCGTGCCAGT GTGGCTGCTT
9121 CCAACCATTA TTGCAAATTT ACATGGCCGT GACGCACTAC AGGTTGTCCG TCACAGTGCA
9181 GCTTCCATGG CGGAACTGTC CTCAGCGTTG GCCTTCTTTG GCATGAGAGG GTTGAACTGC
9241 TGGAGGCGGA GACGCCGTGC CATCAGGACT GATATGATCA AGTTGGCGG GTGGAATGCG
9301 AATTTCGCGC AGATGTTACT GTGGTCACCG GAGGTAAGAA CACCACAGCC CGAACCAAAG
9361 GGCATGTGTC TCTTGCCACC GGAACTATGG GAGCGTCCGT ACGAAAATTT GCACTTGAGC
9421 ACGATCGACC GCAATCGTGG TGCTAGTCGC TTACGGTTTT GGTTGGTTGC TAGTGCTATA
9481 CTCGCTCTGC TTTGCTTGTA AATCCTAAAT CAATGTAGTA CCAGGACTAC AAGGCAGGAG
9541 GTGAAGTCAG CTGTACCCAC GGCTGGCTGA AACCGGGGCT TGACGACCCC CCTATCCGA
9601 GTTGGGCAAG GTAACATCAC GGGTGTGACG ACCCCGCCCC CCCATGTCGC GCGCAAGCGC
9661 ACGGGCAAGG CAGCTAGGCT GAGAGTCTGG GCAACTCTCC CGTACCCCAC CCGAGGCTAC
9721 GCCTCGTCCT GGCGAGGACC GTAAACATAC GTCGTCAGCG TGGTGACCTG ACGTATCTTG
9781 TTAACCACTT AATGGTCGTA ACTCGACCCC CGTGCCGGGG ATCTAAGCGC GGCACCGCGA
9841 TGAGAGGGGT CAACGGCCCC TTTCATT
```

FIG. 22A

Human Pegivirus 2 (UC0125) Genes and Untranslated Regions

5' UTR Sequence

5' UTR Sequence: nucleotides 24-327 of SEQ ID NO:303

S Protein and Gene Sequence

S Protein Amino Acid Sequence: (SEQ ID NO:344)

MGCSTDQTICSPVVGADYNTSSGCRALNGSYHCGGGSCRSPSRVQVARRVLQLCAFLALIGSGMCSIRSKTEGRIESGQ

S protein gene sequence: nucleotides 328-564 of SEQ ID NO:303.

E1 Protein and Gene Sequence

E1 Protein Amino Acid Sequence: (SEQ ID NO:345)

ILQSQRACWTGEGFAFFSNCCNQSDIMWCLHRWCVTRPGCLVCTGNATHPICWDYLGSGVSRRPARRMGEGAEALLRLIGIAGWLGLLAESLG
MSEVYAAILCFGFIAWYGWGIPKTLVCTVCPAVNISPYSFLSPDTIAFGTWILQLPGLLWQMFVSFPILYSTWILWLLLSGKTVAVIAILLAS
PTVMA

E1 protein gene sequence: nucleotides 565-1137 of SEQ ID NO:303.

E2 Protein and Gene Sequence

E1 Protein Amino Acid Sequence: (SEQ ID NO:346)

YKHQSESYLKYCTITNTSTSMNCDCPFGTFTRNTESRFSIPRFCPVKINSSTFICSWGSWWWFAENITRFYTDVGMPPAPISALCYIYSNNDP
PPWYHNTTIIPQNCRNSTVDPTTAPCRDKWGNATACILDRRSRFCGDCYGGCFYTNGSHDRSWDRCGIGYRDGLIEFVQLGQIRPNISNTTIE
LLAGASLVIASGLRPGFGCSRAHGVVHCYRCPSYRDLEQFGPGLGKWVPLPGEPVPELCINPQWARRGFRMSNNPLSLLQTFVEDIFLAPFCN
PTPGRVRVCNNTAFYPRGGGFVQLIGDVQVLTPNTASLHSLLTLISLILLVCVVSGARFVPLIIIFFWSARHVYA

E2 protein gene sequence: nucleotides 1138-2199 of SEQ ID NO:303.

X Protein and Gene Sequence

X Protein Amino Acid Sequence: (SEQ ID NO:347)

SCYLSCDWAVCNDAFCFTSGTCATFNDVLCLPVATRISSCGHAVPPPDRGWEVPAAMSWVISRTTGLTFDVFSFIQYLPTVPGNNTNIIYCGE
PTFLGDITGIYWPYFLPGAILLYLTPFLGLRLMLAGFNIDGLFPIRHATAALRFSTSRVTLCVVVAFLIYILSHPVNAALNRMFLASANLEMI
LSFDTYHETVLYIILCLLLYLQVSPRAGLAAMVAIKLSRGLLFAVVLAHGVC

X protein gene sequence: nucleotides 2200-2910 of SEQ ID NO:303.

FIG. 22B

NS2 Protein and Gene Sequence

NS2 Protein Amino Acid Sequence: (SEQ ID NO:348)

RPGRVFGLEVCADISWLVEFTGNCTWYMSCVFSFWCAVFAFTSPLGRHYKIQIYRYWAQVYARLVLAVGCGPLGREFHFRASVGVLWCGACML
WPRECSEISLVFILCALTVDTIDTWLVACLSAGPSARTLAILADDMARIGDHRALRAVLRCFGSRGTYIYNHMGQVSERVAQAVRDLGGCLEP
VVLEEPTFTEIVDDTMSLVCGQLLGGKPVVARCGTRVLVGHLNPEDLPPGFQLS

NS2 protein gene sequence: nucleotides 2911-3630 of SEQ ID NO:303.

NS3 Protein and Gene Sequence

NS3 Protein Amino Acid Sequence: (SEQ ID NO:349)

APVVITRPSIGTWSFLKATLTGRAETPGSCQIVVLSSLTGRSMCTAVNGTLYATCHGACARCLATCAGLRTPLYTALSDDVVAYSCLPGMSSL
DPCCCSPSRVWVMNNNGGLVCGRVENDDVCLDCPTHIDQLRGASGSPVLCDHGHAYALMLGGYSTSGICARVRTVRPWHNAYSSSGGQGGMQA
PAVTPTYSEITYYAPTGSGKSTKYPVDLVKQGHKVLVLLPSVAVVKSMAPYIKETYKIRPEIRAGTGPDGVTVITGENLAYMTYGRFLVDPET
NLRGYAVVICDECHDTSSTTLLGIGAVRMYAEKAGVKTVVFATATPAGIQVQSHSNIDEYLLTDTGDVEFYGAKIKMDNIRTGRHVIFCHSKA
RCAELTQQLSGLGIRAVSFWRGCDIKTIPASDSIVVVATDALSTGYTGNFDSVIDCGCCVEQTVTIDMDPTFSISARVVPCTAALRMQRRGRT
GRGRRGAYYTTSPGAAPCVSVPDANVWQAVESAMVFYDWSATRIQQCLAAYHDLGCTPRISCDPHTPVRVMDTLRAYLRRPEVTTAALAGEQW
PLLYGAQLCICKETEAHGPDDSIKWKCLLNNSNKTPLLYALDNPTLEFTTQHDLTRRIAGALSSTVFVET

NS3 protein gene sequence: nucleotides 3631-5514 of SEQ ID NO:303.

NS4A Protein and Gene Sequence

NS4A Protein Amino Acid Sequence: (SEQ ID NO:350)

GYGPILLAGAALAASFAFAGATGALVPSAVWSVEVRPAGVT

NS4A protein gene sequence: nucleotides 5515-5637 of SEQ ID NO:303.

NS4B Protein and Gene Sequence

NS4B Protein Amino Acid Sequence: (SEQ ID NO:351)

RPDATDETAAYAQRLYQACADSGIFASLQGTASAALGKLADASRGASQYLAAAPPSPAPLVQVLQFLETNFSSIASFGLLCAGCQAGECFTAL
AGLVSGATAGLGGAHKWLLAIAGTWLVSLQTGSRGGMVAGLSILAGCCIGSVTGLDFLFGCLTGWEAVVGAAVATQKILSGSADMTTLVDLLP
ALFSPGAGIAGIVLVFILSNSSVTTWANRLLSMCAKQTICENYFLSERFGQQLSKLSLWRSVYHWAQAREGYTQCG

NS4B protein gene sequence: nucleotides 5638-6423 of SEQ ID NO:303.

FIG. 22C

NS5A Protein and Gene Sequence

NS5A Protein Amino Acid Sequence: (SEQ ID NO:352)

```
VISGIWSFALCILRAVWDWAAKHVPRFRVPMIGCSPAWCGRWLGTGTLLTTCACGERVSLQCLCSTSDPQLSVGRWCRCSWSVGFPFNPTTTG
TGTLRPDISDANKLGFRYGVADIVELERRGDKWHVCAASCCLDRASVASAVKAPPVTANGIPINSFSPPQTYCLSLCSFDTVCMSTNLCNPAK
TLSVCQEEAVELLEETVDTAQVVMSQNLAARRRAEYDAWQVRQAVGDEYTRLADEDVDMTASVKPPVARAAVGSSTLDDVSVLTVLRELGDQC
QNAIKFVVQAASRFVPPVPKPRTRVSGVLERVRMCMRTPPIKFEATAVPIHNIIPEECHIVLRCTGCCDQALTVPYGTCSLTLTKYLTNKHSH
YIPKERIEEDTEIAVICAVPTKRASKLITFRAGDRSVSCCHPLQTPIRALLQKYGLPIGKWSDCNGPLGDDARVCDVNGVTTYEPC
```

NS5A protein gene sequence: nucleotides 6424-7797 of SEQ ID NO:303.

NS5B Protein and Gene Sequence

NS5B Protein Amino Acid Sequence: (SEQ ID NO:353)

```
MQSYNWFRSIVAPTTPPLPATRSVAGILRADTSRVYTTTAVDVSERQAKVTIDQKSAKVDQCLRDTYNCCLAKAKTFRQSGMSYEDAVSKMRA
NTTRDHNNGITYTDLVSGRAKPVVQKIVDQMRAGVYDAPMRIIPKPEVFPRDKSTRKPPRFIVFPGCAARVAEKMILGDPGAITKHVLGDAYG
FATPPHERARLLEQWWNRATEPQAIAVDAVCFDSTITAEDMDREANIVAAHTDPEGVHGLYNYYKRSPMCDITGKVVGVRSCRASGTLTTSS
GNTLTCYLKVRAACTRAGIKPIGLLIHGDDTLIITERCAQETLDEFSNALDDYGFTHTMQVSGDLSSIECCSARVDSVCLRGGMRRMLVPQAR
RAIARVLGEKGDPLGVISSYIVMYPTAAVTVYVLMPLLCMLIRNEPSQTGTLVTLTVHGNSVSVPVWLLPTIIANLHGRDALQVVRHSAASMA
ELSSALAFFGMRGLNCWRRKPRAIRTDMIKLGGWNANFAQMLLWSPEVRTPQPEPKGMCLLPFELWERPYENLHLSTIDRNHGASRLRFWLVA
SAILALLCL
```

NS5B protein gene sequence: nucleotides 7798-9498 of SEQ ID NO:303.

3' UTR Sequence

3' UTR Consensus Sequence: nucleotides 9499-9867 of SEQ ID NO:303

1. HPgV-2 transefcted cell lysate
2. HPgV-2 E2 transfected cell supernatant

1. Pre-column concentrate
2. Column flow-through
3. Wash 1 flow-through
4. Wash 2 flow-through
5. Concentrated elute 1. Pre-column concentrate
2. Column flow-through
3. Wash 1
4. Wash 2
5. Wash 3
6. Concentrated elute

FIG. 29A

Human Pegivirus 2 (ABT0030P.US) Nucleic Acid Sequence - SEQ ID NO:419

```
   1 AACTGTTGTT GTAGCAATGC GCATATTGCT ACTTCGGTAC GCCTAATTGG TAGGCGCCCG
  61 GCCGACCGGC CCCGCAAGGG CCTAGTAGGA CGTGTGACAA TGCCATGAGG GATTATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GGAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGTGTTCAA CTGATCAAAC CATTTGTTCT
 361 CCAGTCGTGG GGGCCGACTA TAATACCTCC TCGGGCTGCC GGGCCTTAAA TGGGAGCTAC
 421 CACTGCGGTG GTGGCTCTTG CCGGTCACCA AGTCGTGTGC AGGTTGCGAG ACGAGTCTTG
 481 CAGCTGAGCG CATTCCTTGC GTTGATCGGA TCCGGTATGT GTTCGATCCG GTCCAAAACT
 541 GAAGGGCGCA TTGAGTCGGG GCAAATATTG CAGTCTCAGC GCGCATGTTG GACTGGTGAG
 601 GGTTTTGCTT TCTTTTCTAA CTGTTGCAAT CAATCTGATA TCATGTGGTG TTTGCACCGT
 661 TGGTGTGTGA CAAGACCTGG CTGTTTAGTG TGCACGGGCA ATGCCACTCA TCCTGTCTGC
 721 TGGGACTATC TTGGGTCCGG TGTAAGCCGG CGGCCTGCGC GTCGAATGGG TGAGGGAGCT
 781 GAAGCGCTTC TTCGCTTGAT CGGCATTGCA GGTTGGCTCG GCTGCTAGC TGAGGCTCTT
 841 GGTATGTCCG AACTCTACGC AGCTATTCTT TGCTTTGGAT TTATTGCTTG GTATGGTTGG
 901 GGTATACCTA AAACATTGGT GTGCACAGTC TGCCCTGCAG TAAACATTTC TCCCTATAGC
 961 TTCTTATCTC CAGACACTAT CGCATTTGGT ACGTGGATAC TACAACTACC TGGTCTTTTG
1021 TGGCAAATGT TTGTCAGCTT TCCTATACTT TACAGCACTT GGATTCTTTG GTTGTTGCTC
1081 AGCGGCAAAA CTGTTGCTGT GATAGCAATT CTTTTGGCGA GTCCTACGGT TATGGCATAC
1141 AAGCATCAAT CTGACAGCTA CCTCAAATAC TGTACCATAA CCAATGCTTC AACTGCTATG
1201 AACTGTGACT GCCCCTTTGG AACCTTTACT CGCAATACTG AGTCTCGTTT CTCTATACCT
1261 AGATTCTGTC CTGTTAAAAT TAATAGCTCT ACATTTATCT GCTCATGGGG GTCGTGGTGG
1321 TGGTTTGCTG AGAACATCAC GCGTCCATAC TCGGACGTTG GCATGCCACC GGCACCGATT
1381 TCTGCTTTGT GCTATATCTA TTCAAACAAT GACCCTCCTC CTTGGTACCA TAATACAACT
1441 ATCATACCTC AGAACTGTCG CAACTCCACG GCTGATCCCA CCACAGCCCC ATGCCGTGAC
1501 AAGTGGGGCA CGCAACTGC TTGTATTCTT GACCGCCGGT CGCGGTTCTG CGGGGACTGC
1561 TATGGCGGCT GCTTCTATAC TAATGGTAGT CATGATCGAT CCTGGGATCG ATGCGGGATT
1621 GGTTACCGTG ATGGACTCAT AGAGTTCGTG CAGCTCGGTC AGATTCGACC CAACATCTCG
1681 AATACGACCA TTGAGCTCCT CGCTGGCGCC TCGCTAGTGA TTGCATCCGG TCTTCGGGCT
1741 GGGTACGGTT GCAGCCGAGC GCATGGCGTG GTGCACTGCT ATAAGTGTCC TTCATACCGT
1801 GACCTTGAAC AATTTGGTCC CGGGCTCGGG AAATGGGTGC CATTGCCTGG CGAGCCTGTC
1861 CCGGAGTTGT GTATTAACCC CCAGTGGGCG AGGCGCGGCT TCCGGGTGTC TAACAATCCT
1921 TTGCACTTGA TACAGACCTT TGTTGAGGAC ATCTTCCTAG CACCTTTTTG CAGTCCGACG
1981 CCTGGCCGTG TACGTGTGTG TAACAATACT GCTTTCTATC CGACAGGAGG TGGTTTTGTG
2041 CAGCTCATCG GAGACGTCCA GGTGCTAACC CCTAACACTG CATCTTTACA CTCTCTGCTG
2101 ACTTTAATAT CCCTTATCTT GCTAGTGTGT GTTGTTTCTG CGCGCGGTT CATCCCATTA
2161 ATCATCATAT TTTTCTGGAG CGTGCGCCAC GTATATGCTT CTTGTTACTT AAGCTGTGAT
2221 TGGGCTGTTT GCAACGATGC GTTCTGTTTC ACATCTGGCA CTTGTGCTAC CTTCAATGAC
2281 GTCTTGTGTC TGCCGGTTGC GGCGCGCATA TCGTCCTGTG GCCACGCTGT GCCACCTCCC
2341 GACCGTGGTT GGGAGGTGCC TGCGGCGATG TCATGGGCGA TTTCGCGGAC TACTGGTTTG
2401 ACGTTCGATG TCTTCTCCTT TATTCAGTAT TTCCCTACAG TGCCTGGCAA CAACACCGAT
2461 ATCATTTACT GTGGTGAACC AACCTTCTTC GGGGACATCA CAGGCATCTA TTGGCCTTAC
2521 TTTTTGCCTG GCTTGTTGCT CTTGTACTTG ACTCCTCTAC TGGGTTTTAG GTTAATGCTT
2581 GCCGGCTTCA ATATAGATGG CTTGTTTCCC ATACGGCATG CCACGGCTGC GCTGAGGTTC
2641 TCGACCTCAC GTGCGACCAT GTGTGTCGTA TCTGCTTTCC TAATCTATAT ATTATCTCAT
2701 CCTGTTAATG CTGCGCTCAA TAGAATGTTC CTAGCATCTG CAAACTTAGA GATGATCTTA
2761 TCTTTTGATA CCTATCATGA GACTATCCTT TACATCGCTT GTCTATTGCT CTACCTCCAG
2821 GTGTCGCCCC GCGCGGGCTT GGCCGCTATG GTGGCCATCA AGCTGTCTCG AGGCCTGCTA
2881 TTCGCTGTGG TGTTGGCGCA CGGCGTGTGC CGACCTGGGC GGGTATTTGG TCTTGAGGTT
2941 TGCGCGGACA TCTCATGGTT GGTGGAGTTT ACTGGCAACT GCACTTGGTA CATGTCCTGT
3001 GTCTTCTCTT TTTGGTGCGC AGTGTTTGCC TTCACCAGTC CACTTGGACG ACACTATAAG
3061 CTTCAGATCT ACCGGTACTG GGCGCAGGTC TATGCCAGAC TCATCCTTGC TGTCGGTTGT
3121 GGTCCTCTCG GACGAGAGTT CCATTTCCGT GCAAGCGTGG GTGTGCTTTG TGTGGTGCT
3181 TGCATGCTCT GGCCCCGTGA GTGCTCTGAA ATCAGCTTGG TCTTCATTCT GTGTGCTCTG
```

FIG. 29B

```
3241 ACAGTGGACA CCATAGACAC ATGGTTAGTA GCGTGCTTGT CCGCAGGGCC GAGTGCGCGA
3301 ACCCTTGCAA CACTGGCCGA TGACATGGCG CGCTTTGGTG ACCACCGGGC GTTGCGCGCC
3361 GTGTTGCGTT GCTTTGGATC ACGTGGCACA TACATATACA ACCACATGGG CCAGGTCTCA
3421 GAACGGGTGG CGCAAGCAGT CAGGGATTTC GGCGGTTGCT TGGAACCAGT CGTGTTGGAG
3481 GAGCCCACCT TTACTGAGGT CGTGGATGAC ACAATGAATT TAGTGTGTGG ACAATTGCTT
3541 GGAGGTAAGC CTGTGGTGGC CCGCTGCGGC ACGCGTGTCT TGGTGGGACA CCTCAACCCT
3601 GAAGATCTGC CACCTGGTTT CCAGCTGAGT GCTCCGGTCA TTATCACCAA ACCAAGCATT
3661 GGTACGTGGT CCTTCCTTAA GGCGACACTC ACAGGGCGTG CTGAAACACC GGGATCCGGC
3721 CAGATCGTGG TGTTGTCTTC CCTGACAGGT CGGTCAATGG GTACTGCAGT GAGTGGCACA
3781 CTGTATGCGA CCGGCCATGG TGCTGGTGCG CGCGGCCTAG CCACGTGCGC CGGTTTGAGG
3841 ACGCCACTTT ACACGGCATT ATCTGATGAT GTCGTGGCCT ACTCTTGCCT CCCGGGCATG
3901 AGTTCCCTAG AGCCCTGCCG CTGTGCGCCG AGCCGGGTTT GGGTGATGAA CAACAATGGA
3961 GGGTTGGTGT GTGGCAGAGT GGAGAATGAG GACGTCTGTT TGGACTGTCC CACGCACATA
4021 GATCAACTGC GGGGTGCTTC GGGATCGCCG GTCTTGTGTG ATCACGGTCA TGCATACGCG
4081 CTGATGCTCG GTGGTTACTC TACCAGTGGT ATTTGTGCGC GTGTCCGGAT AGTCCGGCCA
4141 TGGCAGAACG CCTATTCCTC CTCAGGGGGG CAAGGCGGGA TGCAGGCGCC AGCTGTGACA
4201 CCAACATACT CTGAAATCAC CTACTATGCC CCTACTGGTT CTGGTAAGTC AACAAAATAT
4261 CCAGTGGACC TGGTCAAACA GGGACACAAA GTATTGGTCC TTATACCAAG TGTGGCTGTC
4321 GTCAAAAGCA TGGCCCCTTA CATTAAGGAG ACATATAAGA TTAGACCTGA AATTAGAGCT
4381 GGCACAGGCC CTGACGGTGT GACGGTCATC ACTGGTGAGA ACTTGGCGTA CATGACCTAT
4441 GGCCGCTTCC TTGTGGATCC GGAGACGAAT CTGCAGGGTT ATGCCGTAGT CATTTGCGAC
4501 GAGTGCCACG ACACATCATC CACCACGCTA CTCGGCATTG GCGCAGTGCG CATGTATGCC
4561 GAGAAAGCTG AGTGAGGAC CGTTGTATTC GCCACAGCCA CTCCTGCTGG CATTCAAGTA
4621 CAGCCACACC CCAACATTGA TGAATATTTA TTGACTAATG AAGGCGACGT GGACTTCTAC
4681 GGCGCCAAAA TCAAATTGGA CAACATCAGA ACTGGTAGAC ATGTTATCTT TGTCACTCG
4741 AAGGCCAGGT GCGCGGAACT AACGCAGCAG CTCTCCGGCC TTGGCGTTCA TGCAGTGAGT
4801 TTTTGGCGCG GCTGTGACAT CAAAACCATT CCCGCCTCAG GCTCTATTGT TGTAGTGGCA
4861 ACTGATGCAT TGTCCACAGG CTTCACAGGA AATTTTGATT CGGTCATCGA CTGCGGGTGT
4921 TGCGTAGAGC AAACTGTGAC AATTGACATG GACCCCACGT TCTCCATCTC GGCCCGAGTG
4981 GTGCCATGTA CTGCTGCATT GCGTATGCAG CGGCGCGGAC GCACCGGTCG TGGCAGAAGG
5041 GGAGCGTACT ACACAACCAC TCCAGGAGCA GCACCCTGCG TCAGCGTTCC CGATGCTAAC
5101 GTCTGGCAAG CAGCGGAGAG CGCCATGGTC TTTTATGATT GGAATGCTGC TAGGATACAG
5161 CAGTGCCTGG CGGCATACCA TGACTTAGGG TGCACACCAC GCATCGGTTG TGACCCACAC
5221 ACTCCAGTGC GGGTGATGGA CACACTGAGG GCGTACCTGC GCAGACCTGA GGTGACGACT
5281 GCAGCTCTCG CGGGAGAGCA GTGGCCGCTG CTTTATGGTG TGCAGTTGTG CATCTGCAAA
5341 GAGACCGAGG CCCACGGTCC AGATGATGGC ATCAAGTGGA AGTGCTTACT CAACAATACT
5401 AATAAAACAC CCTGTTGTA TGCCTTAGAC AATCCTACAC TGGAATTCAC TACCCAACAT
5461 GACTTGACTC GCCGTATAGC CGGCGCTTTA TCGAGCACAG TGTTCGTGGA AGCAGGCTAC
5521 GGCCCCATCC TCCTTGCTGG CGCCGCTTTG GCAGCCTCCT TCGCCTTTGC GGGCGCCACT
5581 GGAGCTTTAG TGCCGTCGGC CGTTTGGAGC GTTGACAACG GGCCTGCTGG CGTGACCCGT
5641 CCCGACGCGA CAGACGAGAC TGCGGCCTAC GCGCAGCGCT TGTACCAAGC CTGCGCAGAT
5701 TCAGGAATTC TCGCCAGCTT GCAGGGCACA GCGTGTGCGG CGCTGAGCAA ACTGGCCGAT
5761 GCCAGTAGGG GTGCTAGTCA ATATCTGGCA GCCGCGCCTC CTTCGCCCGC CCCCCTGGTG
5821 CAGGTGCTGC AGTTCCTCGA GACTAACTTT AGCTCCATTG CATCCTTCGG TCTGCTCTGT
5881 GCTGGTTGTC AGGCTGGCGA GTGCTTCACC GCACTTGCCG GGTTGGTGTC CGGCGCTACA
5941 GCAGGCTTGG GAGGTGCCCA TAAGTGGTTG TTGGCTATTG CAGGAACTTG GCTGGTTAGC
6001 CTGCAGACCG GGCCCGTGG CGGCATGGTT GCGGGCCTCT CGGTTCTAGC AGGCTGTTGC
6061 ATCGGCAGTG TCACCGGGCT TGACTTCCTG TTTGGGTGCC TTACGGGTTG GGAGGCCGTG
6121 GTCGGTGCTG CGGTTGCGAC ACAGAAAATC TTGTCTGGTT CGGCTGACAT GACCACTCTG
6181 GTAGATCTCT TACCTGCTAT CTTCTCTCCT GGTGCCGGCA TAGCCGGCGT CGTGCTCGTC
6241 TTTATTCTAA GCAACTCAAG TGTAACCACG TGGGCTAATC GGCTATTGTC CATGTGTGCA
6301 AAACAAACCA TTTGTGAAAA TTACTTCTTG ACTGAGAGAT TTGGCCAACA ATTAAGCAAA
6361 CTTTCCCTGT GGCGCGCTGT GTACCATTGG GCACAGGCGC GCGAGGGATA CACACAGTGC
6421 GGTGTGGTCG GCGGGATCTG GAGCTTTGCC TTGTGCGTCC TGCGAGCTGT GTGGGATTGG
6481 GCGGCTAGGC ATGTGCCACG GTTCCGTGTG CCCATGATTG GCTGCTCACC TGCATGGTGC
6541 GGGCGCTGGC TTGGTACCGG CACCTTGTTG ACCACCTGTG GGTGTGGAGA ACGTGTGTCC
```

FIG. 29C

```
6601 CTTCAGTGCC TTTGCTCGAC GTCTGACCCA ACACTCAGTG TGGGCCGTTG GTGTCGGTGC
6661 AGTTGGAGTG TTGGGTTCCC ATTCAACCCG ACTACGACAG CCACCGGCAC TTTACGGCCG
6721 GACATTAGCG ACGCCACTAA ATTGGGTTTC CGGTATGGTG TTGCTGAGAT TGTGGAGCTA
6781 GAGTGGCGGG ACAACAAATG GCACGTCTGC GCAGCATCAT GTTGCGTGGA CCGAGCTAGT
6841 GTTGCATCTG CCGTGAAGGC CCCACCGGTC ACAGCCAATG GCATACCTAT CAGTACTTTT
6901 TCTCCACCAG AAACTTACAA ACTCTCTCTC TGTTCTTTTG ATTCAGTCTG CATGTCTAAC
6961 TCAAGTAACC CAGCTAAGAC CCTGAGTGTG TGCTCACAGG AGGCTGTTGA GCTGCTGGAA
7021 GAAACAGTTG ATACAGCACA AGCAGTGATG TGTAAGAATC TGGAGGCGCG AAGACGCGCT
7081 GAATATGATG CATGGCAGGT TCGTCAAGCA GTTGGCGACG AGTACACGCG CTTGGCTGAC
7141 GAGGATGTTG ACACAACAGC GTCGGTGAAA CCCCCGGTGG CCAGGGCTGC TGTGGGTAGC
7201 TCAACGTTGG ATGATGTTAA CGTGCTGACT GTCTTGCGCG AGCTCGGTGA CCAATGCCAA
7261 AATGCTATCA AATTTGTAGT CCAGGCGGCT TCACGGTTTG TTCCACCAGT GCCCAGGCCG
7321 CGCACGCGTG TCTCGGGTGT GTTGGAGCGC GTGCGCATGT GCATGCGCAC GCCACCAATC
7381 AAGTTTGAGG CCACCGCAGT ACCAATTCAT AACATAATCC CAGAAGAGTG TCACATTGTG
7441 CTACGCTGTA CCGGCTGTAG TGACCAGGCC TTGACTGTTC CGTACGGCAC TTGCACTCAG
7501 ACTTTAACCA AACATTTGAC TAACAAACAC AGCCATTACA TTCCAAAACA GAAGATAGAA
7561 GAAGACACAG AAGTAACTGT TATCTGCGCC GTACCAACAA CGCGCGCATC TAAACTCATC
7621 ACTTTCAGAG CAGGTGATCG ATCAGTCTCT TGTTGTCACC CCTTACAAAC TCCTATTAGG
7681 GCCCTGCTTC TAAAGTACGG GTTACCTATC GGGAAGTGGT CTGACTGCAA CGGCCCCTT
7741 GGTGACGACG CCCGAGTCTG TGACGTCAAT GGAGTAACAA CTTATGAACC ATGCATGCAA
7801 TCCTACAGTT GGTTCCGACC GATTGTGGCA CCAACAACCC CACCTTTGCC TGCAACCCGG
7861 AGCGTGGCTG GCATTTTACG CGCAGACACA TCGCGCGTTT ACACCACAAC GGCGGTTGAC
7921 GTCTCCGAGA GGCAGGCTAA GGTCACAATC GATCAAACAT CAGCCAAGGT GGATCAGTGT
7981 TTCCGAGACA CCTACAATTG TTGCCTTGCT AAGGCAAAGA CCTTCAAACA ATCTGGCATG
8041 TCATATGAGG ATGCTGTGTC AAAGATGCGC GCAAACACCA CGCGTGATCA TAACCATGGC
8101 ACTACTTATT CAGATTTGGT CTCTGGACGC GCAAAACCTG TCGTTCAGAA AATTGTAAAT
8161 CAAATGCGCG CTGGAGTGTA CGACGCTCCA ATGCGCATTA TCCCAAAACC TGAGGTGTTC
8221 CCTCGAGACA AGGAAACACG GAAGCCACCA CGGTTCATTG TTTTTCCTGG GTGCGCCGCA
8281 CGAGTCGCGG AGAAAATGAT CCTGGGCGAT CCTGGTGCGA TAACCAAGCA CGTGCTAGGT
8341 GATGCCTACG GGTTTGCCAC TCCGCCCCAC GAGCGCGCGC GCCTGTTGGA ACAATGGTGG
8401 AACCGCGCAA CAGAGCCACA AGCTATCGCG GTTGATGCGA TCTGCTTTGA TAGCACTATC
8461 ACGGCAGAGG ACATGGATCG TGAAGCCAAC ATCGTGGCTG CAGCGCATGC GGACCCTGAA
8521 GGTGTTCACG GCCTATACAA TTATTACAAA AGAAGCCCCA TGTGTGACAT CACAGGAAAT
8581 ATTGTCGGGG TGCGTTGCTG CCGAGCCTCA GGTACGCTTA CAACAAGCAG TGGCAACACG
8641 CTTACTTGCT ACCTCAAGGT TCGCGCGGCT TGCACGCGGG CCGGCATTAA ACCAATTGGC
8701 TTACTAATTC ATGGAGATGA CACCCTCATT ATCACAGAAC GTTGCGCTCA AGAAACTCTC
8761 GATGAGTTCA GCAGGGCACT TGATGACTAT GGGTTCCCCC ACACCTTCCA GGCGTCTGGG
8821 GACCTCTCGT CTATCGAGTG CTGCAGCGCA CACGTGGACA GTGTTTGCCT CCGGGGAGGT
8881 ATGCGTCGCA TGCTCGTGCC ACAAGCTCGA CGTGCGATTG CACGCGTTCT CGGGGAAAAG
8941 GGCGATCCAC TGGGTGTCAT CAGCAGCTAT ATTGTCATGT ATCCTACTGC GGCCGTGACT
9001 GTCTATGTGC TATTGCCTCT GTTGTGCATG CTCATTCGAA ATGAGCCATC GCAGACGGGG
9061 ACATTTGTGA CGTTGACGGT CCACGGCAAC AGTGTGAGCG TGCCAGTGTG GCTGCTTCCA
9121 ACCATCATTG TAAATTTACA TGGTCGTGAC GCACTACAAG TAGTCCGTCA CACTGCAGCT
9181 TCCATGGCGG AGCTGTCCTC AGCGTTGGCC TTCTTTGGCA TGAGAGGGTT GAACTGCTGG
9241 AGGCGGAGAC GCCGTGCCAT CAGGGCTGAT ATGATCAAGT TGGGCGGGTG GAATGCGAAC
9301 TTCGCGCAGA TGTTACTGTG GTCACCGGAG GTGAGAACAC CACAGCCCGA ACCAAAGGGC
9361 ATGTGTCTCT TACCACCGGA ACTATGGGAG CGTCCGTACG AAAATTTGCA TTTGAGCACG
9421 ATCGACCGCA ATCGTGGTGC TAGTCGCTTA CGGTTTTGGT TGGTTGCTAG TGCTATACTC
9481 GCTCTGCTTT GCTTGTAAAT CCTAAATCAA TGTAGTACCA GGACTACAAG GCAGGAGGTG
9541 AAGTCAGCTG TACCCACGGC TGGCTGAAAC CGGGGCTTGA CGACCCCCCC TATCNNNNNN
9601 NNNNNNNNNN NNNNNNNNNN NNNNNNNNNN NNNNNCCCCC ATGTCGCGCG TAAGCGCACG
9661 GGCAAGGCAG CTAGGCTGAG AGTCTGGGCA ACTCTCCCGT ACCCCACCCG AGGCTACGCC
9721 TCGTCCTGGC GAGGACCGTA AACATACGTC GTCAGCGTGG TGACCTGACG TATCTTGTTA
9781 ACCACTTAAT GGTCGTAACT CGACCCCCGT GCTGGGGATC TAAGCGCGGC ACCGCGATGA
9841 GAAGGGTCAA NNNNNNNNNN NNNN
```

FIG. 30A

Human Pegivirus 2 (ABT0030P.US) Genes and Untranslated Regions

S Protein and Gene Sequence

S Protein Amino Acid Sequence: (SEQ ID NO:420)
MGCSTDQTICSPVVGADYNTSSGCRALNGSYHCGGGSCRSPSRVQVARRVLQLSAFLALIGSGMCSIRSKTEGRIESGQ S protein gene sequence: nucleotides 328-564 of SEQ ID NO:419.

E1 Protein and Gene Sequence

E1 Amino Acid Sequence: (SEQ ID NO:421)
ILQSQRACWTGEGFAFFSNCCNQSDIMWCLHRWCVTRPGCLVCTGNATHPVCWDYLGSGVSRRPARRMGEGAEALLRLIGIAG
WLGLLAEALGMSELYAAILCFGFIAWYGWGIPKTLVCTVCPAVNISPYSFLSPDTIAFGTWILQLPGLLWQMFVSFPILYSTW
ILWLLLSGKTVAVIAILLASPTVMA E1 gene sequence: nucleotides 565-1137 of SEQ ID NO:419.

E2 Protein and Gene Sequence

E2 Amino Acid Sequence: (SEQ ID NO:422)
YKHQSDSYLKYCTITNASTAMNCDCPFGTFTRNTESRFSIPRFCPVKINSSTFICSWGSWWWFAENITRPYSDVGMPPAPISA
LCYIYSNNDPPPWYHNTTIIPQNCRNSTADPTTAPCRDKWGNATACILDRRSRFCGDCYGGCFYTNGSHDRSWDRCGIGYRDG
LIEFVQLGQIRPNISNTTIELLAGASLVIASGLRAGYGCSRAHGVVHCYKCPSYRDLEQFGPGLGKWVPLPGEPVPELCINPQ
WARRGFRVSNNPLHLIQTFVEDIFLAPFCSPTPGRVRVCNNTAFYPTGGGFVQLIGDVQVLTPNTASLHSLLTLISLILLVCV
VSGARFIPLIIIFFWSVRHVYA E2 gene sequence: nucleotides 1138-2199 of SEQ ID NO:419.

X Protein and Gene Sequence

X Protein Amino Acid Sequence: (SEQ ID NO:423)
SCYLSCDWAVCNDAFCFTSGTCATFNDVLCLPVAARISSCGHAVPPPDRGWEVPAAMSWAISRTTGLTFDVFSFIQYFPTVPG
NNTDIIYCGEPTFFGDITGIYWPYFLPGLLLLYLTPLLGFRLMLAGFNIDGLFPIRHATAALRFSTSRATMCVVSAFLIYILS
HPVNAALNRMFLASANLEMILSFDTYHETILYIACLLLYLQVSPRAGLAAMVAIKLSRGLLFAVVLAHGVC X Protein gene sequence: nucleotides 2200-2910 of SEQ ID NO:419.

FIG. 30B

NS2 Protein and Gene Sequence

NS2 Amino Acid Sequence: (SEQ ID NO:424)
RPGRVFGLEVCADISWLVEFTGNCTWYMSCVFSFWCAVFAFTSPLGRHYKLQIYRYWAQVYARLILAVGCGPLGREFHFRASV
GVLWCGACMLWPRECSEISLVFILCALTVDTIDTWLVACLSAGPSARTLATLADDMARFGDHRALRAVLRCFGSRGTYIYNHM
GQVSERVAQAVRDFGGCLEPVVLEEPTFTEVVDDTMNLVCGQLLGGKPVVARCGTRVLVGHLNPEDLPPGFQLS NS2 gene sequence: nucleotides 2911-3630 of SEQ ID NO:419.

NS3 Protein and Gene Sequence

NS3 Amino Acid Sequence: (SEQ ID NO:425)
APVIITKPSIGTWSFLKATLTGRAETPGSGQIVVLSSLTGRSMGTAVSGTLYATGHGAGARGLATCAGLRTPLYTALSDDVVA
YSCLPGMSSLEPCRCAPSRVWVMNNNGGLVCGRVENEDVCLDCPTHIDQLRGASGSPVLCDHGHAYALMLGGYSTSGICARVR
IVRPWQNAYSSSGGQGGMQAPAVTPTYSEITYYAPTGSGKSTKYPVDLVKQGHKVLVLIPSVAVVKSMAPYIKETYKIRPEIR
AGTGPDGVTVITGENLAYMTYGRFLVDPETNLQGYAVVICDECHDTSSTTLLGIGAVRMYAEKAGVRTVVFATATPAGIQVQP
HPNIDEYLLTNEGDVDFYGAKIKLDNIRTGRHVIFCHSKARCAELTQQLSGLGVHAVSFWRGCDIKTIPASGSIVVVATDALS
TGFTGNFDSVIDCGCCVEQTVTIDMDPTFSISARVVPCTAALRMQRRGRTGRGRRGAYYTTTPGAAPCVSVPDANVWQAAESA
MVFYDWNAARIQQCLAAYHDLGCTPRIGCDPHTPVRVMDTLRAYLRRPEVTTAALAGEQWPLLYGVQLCICKETEAHGPDDGI
KWKCLLNNTNKTPLLYALDNPTLEFTTQHDLTRRIAGALSSTVFVEA NS3 gene sequence: nucleotides 3631-5514 of SEQ ID NO:419

NS4A Protein and Gene Sequence

NS4A Amino Acid Sequence: (SEQ ID NO:426)
GYGPILLAGAALAASFAFAGATGALVPSAVWSVDNGPAGVT NS4A gene sequence: nucleotides 5515-5637 of SEQ ID NO:419

NS4B Protein and Gene Sequence

NS4B Amino Acid Sequence: (SEQ ID NO:427)
RPDATDETAAYAQRLYQACADSGILASLQGTACAALSKLADASRGASQYLAAAPPSPAPLVQVLQFLETNFSSIASFGLLCAG
CQAGECFTALAGLVSGATAGLGGAHKWLLAIAGTWLVSLQTGPRGGMVAGLSVLAGCCIGSVTGLDFLFGCLTGWEAVVGAAV
ATQKILSGSADMTTLVDLLPAIFSPGAGIAGVVLVFILSNSSVTTWANRLLSMCAKQTICENYFLTERFGQQLSKLSLWRAVY
HWAQAREGYTQCG NS4B gene sequence: nucleotides 5638-6423 of SEQ ID NO:419

FIG. 30C

NS5A Protein and Gene Sequence

NS5A Amino Acid Sequence: (SEQ ID NO:428)
VVGGIWSFALCVLRAVWDWAARHVPRFRVPMIGCSPAWCGRWLGTGTLLTTCGCGERVSLQCLCSTSDPTLSVGRWCRCSWSV
GFPFNPTTTATGTLRPDISDATKLGFRYGVAEIVELEWRDNKWHVCAASCCVDRASVASAVKAPPVTANGIPISTFSPPETYK
LSLCSFDSVCMSNSSNPAKTLSVCSQEAVELLEETVDTAQAVMCKNLEARRRAEYDAWQVRQAVGDEYTRLADEDVDTTASVK
PPVARAAVGSSTLDDVNVLTVLRELGDQCQNAIKFVVQAASRFVPPVPRPRTRVSGVLERVRMCMRTPPIKFEATAVPIHNII
PEECHIVLRCTGCSDQALTVPYGTCTQTLTKHLTNKHSHYIPKQKIEEDTEVTVICAVPTTRASKLITFRAGDRSVSCCHPLQ
TPIRALLLKYGLPIGKWSDCNGPLGDDARVCDVNGVTTYEPC NS5A gene sequence: nucleotides 6424-7794 of SEQ ID NO:419

NS5B Protein and Gene Sequence

NS5B Amino Acid Sequence: (SEQ ID NO:429)
MQSYSWFRPIVAPTTPPLPATRSVAGILRADTSRVYTTTAVDVSERQAKVTIDQTSAKVDQCFRDTYNCCLAKAKTFKQSGMS
YEDAVSKMRANTTRDHNHGTTYSDLVSGRAKPVVQKIVNQMRAGVYDAPMRIIPKPEVFPRDKETRKPPRFIVFPGCAARVAE
KMILGDPGAITKHVLGDAYGFATPPHERARLLEQWWNRATEPQAIAVDAICFDSTITAEDMDREANIVAAAHADPEGVHGLYN
YYKRSPMCDITGNIVGVRCCRASGTLTTSSGNTLTCYLKVRAACTRAGIKFIGLLIHGDDTLIITERCAQETLDEFSRALDDY
GFPHTFQASGDLSSIECCSAHVDSVCLRGGMRRMLVPQARRAIARVLGEKGDPLGVISSYIVMYPTAAVTVYVLLPLLCMLIR
NEPSQTGTFVTLTVHGNSVSVPVWLLPTIIVNLHGRDALQVVRHTAASMAELSSALAFFGMRGLNCWRRRRRAIRADMIKLGG
WNANFAQMLLWSPEVRTPQPEPKGMCLLPPELWERPYENLHLSTIDRNRGASRLRFWLVASAILALLCL NS5B gene sequence: nucleotides 7795-9495 of SEQ ID NO:419

5' UTR sequence

5' UTR Sequence: nucleotides 1-327 of SEQ ID NO:419

3' UTR sequence

3' UTR Sequence: nucleotides 9496-9864 of SEQ ID NO:419

FIG. 31A

Human Pegivirus 2 (ABT0041P.US) Nucleic Acid Sequence - SEQ ID NO:430

```
   1 NNNNNNNNNN NNNNNAATGC GCATATTGCT ACTTCGGTAC GCCTAATTGG TAGGCGCCCG
  61 GCCGACCGGC CCCGCAAGGG CCTAGTAGGA CGTGTGACAA TGCCATGAGG GATCATGACA
 121 CTGGGGTGAG CGGAGGCAGC ACCGAAGTCG GGTGAACTCG ACTCCCAGTG CGACCACCTG
 181 GCTTGGTCGT TCATGGAGGG CATGCCCACG GGAACGCTGA TCGTGCAAAG GGATGGGTCC
 241 CTGCACTGGT GCCATGCGCG GCACCACTCC GTACAGCCTG ATAGGGTGGC GGCGGGCCCC
 301 CCCAGTGTGA CGTCCGTGGA GCGCAACATG GGGTGTTCAA CTGATCAAAC CATTTGTTCT
 361 CCAGTCGTGG GGGCCGACTA TAATACCTCC TCGGGCTGCC GGGCCTTAAA TGGGAGCTAC
 421 CACTGCGGTG GTGGCTCTTG CCGGTCACCA AGTCGTGTGC AGGTCGCGGG ACGAGTCTTG
 481 CGGCTGTGCG CATTCCTTGC GTTGATCGGA TCCGGTATGT GTTCGATCCG GTCCAAAACT
 541 GAAGGGCGCA TTGAGTCAGG GCAAATATTG CAGTCTCAGC GCGCATGTTG GACTGGTGAG
 601 GGTTTCGCTT TCTTTTCTAA CTGTTGCAAT CAATCTGATA TTATGTGGTG TTTGCACCGT
 661 TGGTGTGTGA CAAGACCTGG CTGTTTAGTG TGCACGGGCA ATGCCACTCA TCCTATCTGC
 721 TGGGACTATC TTGGGTCCGG TGTAAGTCGG CGGCCTGCAC GTCGAATGGG TGAGGGAGCT
 781 GAAGTGCTTC TTCGCTTGAT CGGCATTGCA GGTTGGCTCG GCTGTTAGC TGAGACTCTT
 841 GGTATGTCCG AATTCTATGC AGCTATTCTA TGCTTTGGAT TTATTGCTTG GTATGGCTGG
 901 GGTATACCTA AAACATTGGT GTGCACGGTC TGCCCTGCAG TGAACATTTC TCCCTATAGC
 961 TTCTTATCTC CAGATACTAT CGCATTTGGT ACGTGGATAC TACAACTACC TGGTCTTTTG
1021 TGGCAAATGT TTGTCAACTT TCCTATACTT TACAGCACTT GGATTCTTTG GTTGTTGCTC
1081 AGCGGCAAGA CTGTTGCTGT GATAGCAATC CTTTTGGCTA GTCCTACGGT TATGGCATAC
1141 AAGCATCAAT CTGAAAGCTA CCTCAAATAC TGTACCATAA CCAATGCTTC AACTGCTATG
1201 AATTGTGACT GCCCCTTTGG AACCTTTACT CGTAATACTG AGTCTCGTTT CTCTATACCT
1261 AGATTCTGTC CTGTTAAAAT TGACAGCTCT ACATTATCT GCTCGTGGGG GTCGTGGTGG
1321 TGGTTTGCTG AGAACATCAC GCGTCCATAC TCGGACGTTG GCATGCCGCC AGCACCGATC
1381 TCCGCTTTGT GCTATATCTA TGCAAACAAT GACCCACCTC CTTGGTATCA TAACACAACT
1441 ATCATACCTC AGAACTGTCG CAACTCCTCG GCTGATCCTA CCACTGCTCC ATGCCGTGAC
1501 AAGTGGGGCA ATGCAACTGC TTGTATTCTT GACCGCCGGT CGCGGTTCTG CGGGGACTGC
1561 TATGGCGGTT GTTTCTATAC TAATGGCACT CACGATCGAT CCTGGGATCG ATGCGGGATT
1621 GGTTACCGTG ATGGACTCAT AGAGTTTGTG CAGCTTGGTC AGATTCGACC AACATCTCG
1681 AATACGACCA TTGAACTCCT CGCTGGCGCC TCGCTTGTGA TCGCATCCGG TCTTCGGCCT
1741 GGCTACGGTT GCAGCCGTGC GCATGGCGTG GTGCACTGCT ATAGGTGTCC TTCATATCGT
1801 GACCTTGAAC AGTTTGGTCC CGGGCTCGGG AAATGGGTGC CACTGCCTGG CGAGCCTGTC
1861 CCGGAGTTGT GTATTAACCC TCAGTGGGCG AGACGCGGCT TCCGGGTATC TAACAACCCT
1921 TTAAGCTTGC TGCAGACCTT CGTTGAGGAC ATTTTCCTAG CACCTTTTTG CAACCCGACG
1981 CCTGGCCGTG TACGTGTGTG TAACAATACT GCTTTCTATC CGAAGGGAGG CGGCTTTGTG
2041 CAGCTCATCG GAGACGTCCA GGTGTTAACC CCTAACACTG CATCTTTACA CTCTCTGCTG
2101 ACTTTAATAT CCCTTATTTT GTTAGTGTGT GTTGTTTCTG GCGCGCGATT CGTCCCATTG
2161 TTTATCATAT TTTTCTGGAG CGTGCGTCAC GTATATGCTT CTTGTTACTT AAGCTGTGAT
2221 TGGGCTGTTT GCAACGATGC GTTCTGTTTC ACATCTGGCA CTTGTGCTAC TTTCAATGAC
2281 GTCTTGTGTC TGCCGGTTGC GACGCGCGTA TCGTCCTGCG GCATGCTGT ACCACCTCCC
2341 GACCGTGGTT GGGAGGTGCC TGCGGCGATG TCATGGGCGA TCTCACGAAC TACTGGCTTG
2401 ACGTTCGATG TCTTTTCCTT CATCCAGTAC TTTCCTACTG TGCCTGGCAA CAACACTGAT
2461 ATCATTTACT GTGGTGACCC AACTTTCTTC GGGGACATCA CGGGCATCTA TTGGCCTTAC
2521 TTTTTGCCTG GCATGTTGCT CTTGTACTTG ACTCCTTTCC TGGGTTTAAG GTTAATGCTT
2581 GCTGGCTTCA ATATAGATGG CTTGTTTCCC ATACGGCACG CCACGGCTGC ACTGAGGTTC
2641 TCGACTTCGC GTGTGACCTT GAGTGTCGTA CTTGCTTTCT TAATCTATAT ACTATCTCAC
2701 CCTGTTAATG CTGCGCTCAA TAGAATGTTC CTAGCATCTG CAAATTTAGA GATGATCTTA
2761 TCCTTTGACA CCTATCATGA CTATTCTT TACATTCTTT GCCTGTTGCT CTACCTCCAG
2821 GTGTCGCCCC GCGCTGGGCT GGCCGCTATG GTGGCCGTCA AGCTATCTCG AGGCCTGTTA
2881 TTCGCCGTGG TGTTGGCGCA CGGAGTGTGC CGACCCGGGC GGGTATTTGG TCTTGAGGTC
2941 TGCGCGGACA TCACTTGGTT GGTGGAGTTT ACTGGCAACT GCACTTGGTA CATGTCCTGT
3001 GTTTTCTCAT TTTGGTGCGC AGTGTTCGCC TTCACCAGTC CACTTGGACG ACGGTATAAG
3061 CTTCAGATCT ACCGGTACTG GGCGCAGGTC TATGCCAGAA TCATCCTCGC TGTCGGTTGT
3121 GGTCCTCTCG GACGGGAGTT CCATTTCCGT GCAGGCGTGG GTGCGTTTTG TGTGGTGCT
3181 TGCATGCTCT GGCCCCGTGA GTGCTCTGAA ATCAGCTTGG TCTTCATTCT GTGTGCTCTG
```

FIG. 31B

```
3241 ACGATGGACA CCATAGACAN NNNNNNNNNN NNNNNNNNNN NNNNNNNNNN NNNNNNNNNN
3301 NNNNNNNNNN NNNNNNNNNN NNNNNNNNNN NNNNNNNNNN NNNNNNNNNN NNNNNNNNNN
3361 GTGTTGCGTT GCTTTGGATC ACGTGGCACA TACATATACA ACCACATGGG CCAGGTCTCA
3421 GAACGGGTGG CGCAAGCAGT CAGGGATTTC GGCGGTTGCT TGGAACCAGT CGTGTTGGAG
3481 GAGCCCACCT TTACTGAGGT CGTGGATGAT ACAATGAGTC TAGTGTGTGG ACAATTGCTT
3541 GGAGGTAAAC CTGTGGTGGC CCGCTGCGGC ACGCGTGTCT TGGTGGGACA CCTCAACCCT
3601 GAAGACTTGC CACCTGGTTT CCAGCTGAGT GCTCCGGTGG TTATCACCAA ACCAAGCATT
3661 GGTACGTGGT CCTTCCTTAA GGCGACACTC ACAGGGCGTG CTGAGACACC GGGATCCGGC
3721 CAGATCGTGG TGTTGTCTTC CCTGACAGGT CGGTCAATGG GTACCGCAGT GAATGGCACA
3781 CTGTATGCGA CCGGCCATGG TGCTGGTGCG CGCGGCCTAG CCACGTGCGC TGGCTTGAGG
3841 ACGCCACTTT ACACGGCACT ATCAGATGAT GTCGTGGCCT ACTCTTGCCT TCCGGGCATG
3901 AGTTCCCTGG AGCCCTGCTG CTGTTCGCCG AGCCGGGTTT GGGTGATGAA CAACAATGGA
3961 GGGTTGGTGT GTGGCAGAGT GGAGAAGGAC GACGTCTGTT TGGACTGTCC CACGCACATA
4021 GATCAGCTGC GGGGTGCCTC GGGGTCACCG GTTTTGTGTG ATCACGGTCA CGCATACGCG
4081 TTGATGCTCG GTGGCTACTC TACCAGCGGT ATTTGTGCGC GTGTCCGGAT AGTCCGGCCA
4141 TGGCAGAACG CCTATTCCTC CTCAGGGGGG CAAGGCGGAA TGCAGGCGCC AGCTGTGACA
4201 CCAACATACT CTGAAATCAC CTACTATGCC CCTACTGGTT CTGGTAAGTC AACAAAATAT
4261 CCAGTGGACC TAGTCAAACA GGGACACAAG GTCTTGGTTC TTATACCAAG CGTGGCTGTC
4321 GTCAAAAGCA TGGCCCCTTA CATTAAGGAG ACATATAAGA TTAGACCTGA AATTAGAGCT
4381 GGCACAGGGC CTGACGGTGT GACGGTCATC ACTGGTGAGA ACTTGGCGTA CATGACCTAT
4441 GGCCGTTTCC TCGTGGATCC GGAGACGAAT CTGCGGGGTT ATGCCGTAGT CATTTGCGAC
4501 GAGTGTCACG ATACATCATC CACCACGCTA CTCGGCATTG GCGCAGTGCG CATGTATGCC
4561 GAGCAAGCTG GAGTGAAGAC CGTTGTATTC GCCACAGCCA CTCCTGCTGG TATCCAAGTA
4621 CAGCCACATC CAAACATTGA TGAATATTTA TTGACTGACA CAGGCGACGT GGATTTCTAC
4681 GGCGCCAAAA TCAAATTGGA CAACATTAGA ACTGGTAGAC ATGTTATCTT TTGTCACTCG
4741 AAAGCCAAGT GTGCGGAACT AACGCAGCAG CTCTCCGGCC TTGGTGTTCG TGCAGTGAGT
4801 TTTTGGCGCG GCTGTGACAT CAAAACCATT CCCGCCTCAG ACTCTATTGT TGTGGTGGCA
4861 ACTGATGCAT TGTCCACAGG CTACACAGGA AATTTTGATT CGGTCATTGA CTGCGGGTGT
4921 TGCGTAGAGC AAACTGTGAC AATTGACATG GACCCACGT TCTCCATCTC GGCCCGAGTA
4981 GTGCCATGCA CTGCTGCATT GCGAATGCAG CGGCGCGGAC GCACCGGTCG TGGCAGAAGG
5041 GGAGCGTACT ACACAACCAC TCCAGGAGCA GCACCCTGCG TCAACGTTCC CGATGCTAAC
5101 GTCTGGCAAG CAGTGGAGTC AGCCATGGTC TTCTATGATT GGAATGCTGC CAGGATACAG
5161 CAGTGTCTGG CGGCATACCA TGATTTAGGG TGTACACCAC GCATCAGTTG TGACCCACAC
5221 ACTCCAGTGC GGGTGATGGA CACACTGAGG GCGTACCTGC GCAGACCTGA GGTGACGACT
5281 GCGGCTCTCG CAGGAGAGCA GTGGCCGCTG CTATACGGTG TGCAGTTGTG CATCTGCAAA
5341 GAGACCGAGG CCCACGGTCC AGATGATGGC ATCAAGTGGA AATGTTTACT CAATAACAAC
5401 AATAAAACAC CCCTGTTGTA TGCCTTAGAC AATCCTACAC TGGAATTCAC TACCCAACAT
5461 GACTTGACTC GCCGTATAGC CGGCGCTCTA TCGAGCACAG TGTTCGTGGA ACAGGCTAT
5521 GGCCCCATCC TCCTCGCTGG CGCCGCTTTG GCTGCCTCCT TCGCCTTTGC GGGCGCCACT
5581 GGAGCTTTAG TGCCGTCGGC CGTTTGGAGT GTTGACAACG GGCCTACTGG CGTGACCCGT
5641 CCCGACGCGA CAGACGAGAC CGTGGCCTAC GCGCAGCGCT TGTACCACGC CTGCGCAGAT
5701 TCAGGAATTC TCGCCAGCTT GCAGGGCACG GCGTGTGCGG CACTGAGTAA ACTGGCCGAT
5761 GCCAGTAGGG GTGCTAGTCA ATATCTGGCA ACCGCGCCTC CTTCGCCCGC CCCCCTGGTA
5821 CAGGTGCTGC AGTTCCTCGA GACCAACTTT GCTCCATTG CATCTTTCGG TCTGCTCTGT
5881 GCTGGTTGTC AGGCTGGTGA GTGCTTCACT GCGCTTGCCG GGTTGGTGTC CGGTGCTACA
5941 GCTGGCTTGG GAGGTGCCCA TAAGTGGTTG TTAGCTATTG CAGGAACTTG GCTAGTTAGC
6001 CTGCAGACCG GCCCCGTGG CGGCATGGTT GCGGGTCTCT CGGTTCTAGC GGGCTGTTGC
6061 ATCGGCGGTG TCACCGGGCT TGACTTCCTG TTTGGGTGCC TTACAGGTTG GGAGGCCGTG
6121 GTCGGTGCTG CCGTTGCGAC ACAGAAGATC TTGTCTGGTT CGGCTGATAT GACCACTCTG
6181 GTAGATCTCT TACCTGCTCT CTTTTCCCCT GGTGCTGGCA TAGCTGGCAT CGTGCTTGTC
6241 TTTATTCTAA GCAACACAAG TGTAACCGCA TGGGCCAATC GGCTATTGTC CATGTGTGCA
6301 AAACAAACCA TTTGTGAAAA CTACTTCTTA ACTGAGAAAT TTGGCCAACA ATTAAGCAAA
6361 CTTTCCTTGT GGCGTGCTGT GTACCATTGG GCGCAGGCAC ATGAGGGGTA CACACAGTGC
6421 GGTGTGGTTG CGGGATCTG GAGCTTTGTC CTGTGCATTC TACGCGCTGC GTGGGATTGG
6481 GCGGCCAAGC ATGTGCCACG GTTCCGTGTG CCTATGATTG GCTGCTCACC TGCGTGGTGC
6541 GGGCGCTGGC TTGGTACTGG CACCTTGTTG ACCACCTGTG GGTGTGGAGA ACGTGTATCC
```

FIG. 31C

```
6601 CTTCAATGCC TTTGTTCAAC ATCTGACCCA ATACTCAGTG TGGGCCGTTG GTGCCGGTGT
6661 AGTTGGAGTG TTGGGTTTCC ATTCAACCCG ACCACGACAG CCACCGGCAC TTTACGGCCG
6721 GACATCGGCG ACGCCACCAG ATTGGGTTTC CGGTATGGCA TCGCCGAGAT CGTGGAGCTA
6781 GAACGGCGGG GCGACAAATG GCATGTCTGT GCAGCATCTT GTTGCTTGGA CCGAGCTAGC
6841 GTTGCATCCG CTGTGAAGGC CCCTCCGGTC ACGGCTAATG CATACCTAT CAGTCCTTTC
6901 TCTCCACCAC AAACTTACAA ACTCTCTCTC TGCTCTTTTG ATTCAGTTTG CATGTCTATC
6961 AACTCATGTA ATCCATCTAA GATCCTGAGT GTGTGCTCAC AGGAAGCCGT TGAGCTGCTG
7021 GAAGAAACAG TCGACACGGC ACAAACAATG ATGTGTAAAA ATCTGGAGGC GCGAAGACGC
7081 GCCGAATTTG ACGCATGGCA AGTCCGCCAA GCAGTTGGCG ACGAGTACAC ACGCTTGGCA
7141 GATGAGGATG TCGACACGAT AACGTCGGTG AAACCCCGG TGGCCAGGGC TGCTGTGGGT
7201 AGCTCAACGT TGGATGATGT TGGCGTGCTG ACTGTCTTGC GCGAGCTCGG CGACCAATGC
7261 CAAAATGCTA TCAAATTTGT AGTTGAAGCG GCCTCACGGT TTGTTCCACC AGTGCCCAAG
7321 CCGCGCACGC GTGTCTCGGG TGTGCTGGAG CGTGTGCGCA TGTGCATGCG CACGCCACCA
7381 ATGAAGTTTG AGGCCGCCGC AGTACCAATC CACAACATAA TCCCAGAAAA ATGTCACATT
7441 GTGCTACGCT GTACCGGCTG TAGTGACCAG GCCTTGACTG TTCCGTACGG CACTTGCACT
7501 CAGACTTTAA GCAGCCATTT GACTAACAAA CACAGTCACT ACATTCCAAA ACAGAAGATA
7561 GAAGAAGACA CAGAAGTAAC TGTCATTTGC GCCGTACCAA CAAAGCGCGC AAGCAAACTC
7621 ATTACTTTCA GAGTAGGTGA TCGATCAGTC TCATGTTGTC ACCCCTTGCA AACTCCTGTT
7681 AGGGCCCTGC TTCTAAAGTA CGGGTTGCCT ATCGGGAAGT GGTCCGACTG CAACGGCCCA
7741 CTTGGTGACG ACGCTCGAGT CTGTGACGTC AATGGAGTGA CAACTTATGA ACCATGCATG
7801 CAATCCTACA GTTGGTTTCG ACCGATTGTG GCACCAACAA CCCCACCTTT GCCTGTAACC
7861 CGGAGCGTGG CTGGCATTTT ACGCGCAGAC ACATCGCGCG TTTACACCAC AACAGCGGTT
7921 GATGTCTCCG AGCGGCAGGC TAAGGTCACA ATTGATCAAA AGTCAGCCAA GGTGGATCAG
7981 TGTTTCCGAG ACACATACAA CTGTTGCCTT GCTAAGGCAA AGACCTTCAG ACAATCTGGC
8041 ATGTCATATG AGGATGCTGT GTCAAAGATG CGCGCAAACA CCACGCGTGA TCATAACACT
8101 GGCATCACTT ATACAGATTT GGTCTCTGGA CGCGCAAAAC CTGCTGTTCA GAAAATTGTA
8161 GATCAAATGC GCTCTGGAGT GTACGACGCT CCAATGCGCA TTATCCCAAA GCCTGAAGTG
8221 TTTCCTCGAG ACAAGTCAAC ACGGAAGCCA CCACGGTTCA TCGTTTTCCC TGGGTGCGCC
8281 GCACGAGTCG CGGAGAAAAT GATCCTGGGC GATCCTGGTG CGATAACCAA GCACGTGCTG
8341 GGTGATGCCT ACGGGTTTGC CACTCCGCCG CATGAGCGTG CGCGCCTATT GGAACAATGG
8401 TGGAACCGCG CGACGGAGCC ACAGGCTATC GCGGTTGATG CGATCTGCTT TGATAGCACC
8461 ATCACGGCGG AGGACATGGA TCGCGAGGCC CACATCGTGG CTGCAGCGCA CGCGGACCCA
8521 GAAGGTGTTC ATGGCCTATA CAATTATTAC AAAAGAAGCC CCATGTGTGA CATCACAGGA
8581 AAAGTTGTCG GGGTGCGTTG CTGTCAGCC TCAGGTACGC TTACAACAAG CAGTGGCAAC
8641 ACGCTTACTT GCTACCTCAA GGTTCGCGCG GCTTGCACGC GCGCCGGCAT TAAACCAATT
8701 GGCTTACTAA TTCATGGAGA TGACACCCTC ATTATCACGG AACGTTGCAC TCAAGAAACT
8761 CTCGATGAGT TCAGCAACGC ACTTGATGAC TACGGGTTTC CTCACACCTT CCAGGTGTCT
8821 GGGGACCTCT CGTCTATCGA GTGCTGTAGT GCACGTGTGG ACAGCGTTTG CCTCCAGGA
8881 GGTATGCGTC GCATGCTTGT GCCACAAGCT CGACGTGCGA TCGCACGCGT TCTCGGAGAA
8941 AAGGGTGATC CACTGGGTGT TATCAGCAGC TATATTGTCA TGTACCCTAC TGCAGCCGTG
9001 ACTGTCTACG TACTACTGCC CCTGTTGTGC ATGCTCATTC GGAATGAGCC ATCGCAGACG
9061 GGGACATTGG TGACGCTGAC GGTCCACGGT AACAGTGTGA GCGTGCCAGT GTGGCTGCTT
9121 CCAACCATCA TTGCAAATTT ACATGGCCGT GACGCACTAC AGGTGGTCCG CCACAGTGCA
9181 GCTTCCATGG CGGAACTGTC GTCAGCGTTG GCCTTCTTTG CATGAGAGG GTTGAACTGC
9241 TGGCGGCGGA GACGCCGTGC CATCAGGACT GACATGATCA AATTGGGCGG GTGGAATGCG
9301 AATTTCGCGC AGATGTTACT GTGGTCACCG GAGGTAAGAA CACCACAGCC CGAACCAAAG
9361 GGCATGTGTC TTTTGCCACC GGAACTATGG GAGCGTCCGT ACGAAAATTT GCACTTGAGC
9421 ACGATCGACC GCGACCGTGG TGCTAGTCGC TTACGGTTTT GGTTGGTTGC TAGTGCTGTA
9481 CTCGCTCTGC TTTGCTTGTA AATCCTAAAT CAATGTAGTA CCAGGACTAC AAGGCAGGAG
9541 GNNNNNNNNN NNNNNNNNNN NNNNNNNNNN NNNNNNNNNN NNNNNNNNNN NNNNNNNNNN
9601 NNNNNNNNNN NNNNNNNNNN NNNNNNNNNN NNNNNCCCC CCATGTCGC GCGTAAGCGC
9661 ACGGGCAAGG CAGCTAGGCT GAGAGTCTGG GCAACTCTCC CGTACCCAC CCGAGGCTAC
9721 GCCTCGTCCT GGCGAGGACC GTAAACATAC GTCGTCAGCG TGGTGACCTG ACGTATCTTG
9781 TTACCACTT AATGGTCGTA ACTCGACCCC CGTGCCGGGG ATCTAAGCGC GGCACCGCGA
9841 TGAGGGGGGT CAACGGNNNN NNNNNNN
```

FIG. 32A

Human Pegivirus 2 (ABT0041P.US) Genes and Untranslated Regions

S Protein and Gene Sequence

S Protein Amino Acid Sequence: (SEQ ID NO:431)
MGCSTDQTICSPVVGADYNTSSGCRALNGSYHCGGGSCRSPSRVQVAGRVLRLCAFLALIGSGMCSIRSKTEGRIESGQ S protein gene sequence: nucleotides 328-564 of SEQ ID NO:430

E1 Protein and Gene Sequence

E1 Amino Acid Sequence: (SEQ ID NO:432)
ILQSQRACWTGEGFAFFSNCCNQSDIMWCLHRWCVTRPGCLVCTGNATHPICWDYLGSGVSRRPARRMGEGAEVLLRLIGIAG
WLGLLAETLGMSEFYAAILCFGFIAWYGWGIPKTLVCTVCPAVNISPYSFLSPDTIAFGTWILQLPGLLWQMFVNFPILYSTW
ILWLLLSGKTVAVIAILLASPTVMA E1 gene sequence: nucleotides 565-1137 of SEQ ID NO:430

E2 Protein and Gene Sequence

E2 Amino Acid Sequence: (SEQ ID NO:433)
YKHQSESYLKYCTITNASTAMNCDCPFGTFTRNTESRFSIPRFCPVKIDSSTFICSWGSWWWFAENITRPYSDVGMPPAPISA
LCYIYANNDPPPWYHNTTIIPQNCRNSSADPTTAPCRDKWGNATACILDRRSRFCGDCYGGCFYTNGTHDRSWDRCGIGYRDG
LIEFVQLGQIRPNISNTTIELLAGASLVIASGLRPGYGCSRAHGVVHCYRCPSYRDLEQFGPGLGKWVPLPGEPVPELCINPQ
WARRGFRVSNNPLSLLQTFVEDIFLAPFCNPTPGRVRVCNNTAFYPKGGGFVQLIGDVQVLTPNTASLHSLLTLISLILLVCV
VSGARFVPLFIIFFWSVRHVYA E2 gene sequence: nucleotides 1138-2199 of SEQ ID NO:430

X Protein and Gene Sequence

X Protein Amino Acid Sequence: (SEQ ID NO:434)
SCYLSCDWAVCNDAFCFTSGTCATFNDVLCLPVATRVSSCGHAVPPPDRGWEVPAAMSWAISRTTGLTFDVFSFIQYFPTVPG
NNTDIIYCGDPTFFGDITGIYWPYFLPGMLLLYLTPFLGLRLMLAGFNIDGLFPIRHATAALRFSTSRVTLSVVLAFLIYILS
HPVNAALNRMFLASANLEMILSFDTYHETILYILCLLLYLQVSPRAGLAAMVAVKLSRGLLFAVVLAHGVC X Protein gene sequence: nucleotides 2200-2910 of SEQ ID NO:430

FIG. 32B

NS2 Protein and Gene Sequence

NS2 Amino Acid Sequence: (SEQ ID NO:435)
RPGRVFGLEVCADITWLVEFTGNCTWYMSCVFSFWCAVFAFTSPLGRRYKLQIYRYWAQVYARIILAVGCGPLGREFHFRAGV
GAFWCGACMLWPRECSEISLVFILCALTMDTIDXXXXXXXXXXXXXXXXXXXXXXXXXXXXXXXXVLRCFGSRGTYIYNHM
GQVSERVAQAVRDFGGCLEPVVLEEPTFTEVVDDTMSLVCGQLLGGKPVVARCGTRVLVGHLNPEDLPPGFQLS NS2 gene sequence: nucleotides 2911-3630 of SEQ ID NO:430

NS3 Protein and Gene Sequence

NS3 Amino Acid Sequence: (SEQ ID NO:436)
APVVITKPSIGTWSFLKATLTGRAETPGSGQIVVLSSLTGRSMGTAVNGTLYATGHGAGARGLATCAGLRTPLYTALSDDVVA
YSCLPGMSSLEPCCCSPSRVWVMNNNGGLVCGRVEKDDVCLDCPTHIDQLRGASGSPVLCDHGHAYALMLGGYSTSGICARVR
IVRPWQNAYSSSGGQGGMQAPAVTPTYSEITYYAPTGSGKSTKYPVDLVKQGHKVLVLIPSVAVVKSMAPYIKETYKIRPEIR
AGTGPDGVTVITGENLAYMTYGRFLVDPETNLRGYAVVICDECHDTSSTTLLGIGAVRMYAEQAGVKTVVFATATPAGIQVQP
HPNIDEYLLTDTGDVDFYGAKIKLDNIRTGRHVIFCHSKAKCAELTQQLSGLGVRAVSFWRGCDIKTIPASDSIVVVATDALS
TGYTGNFDSVIDCGCCVEQTVTIDMDPTFSISARVVPCTAALRMQRRGRTGRGRRGAYYTTTPGAAPCVNVPDANVWQAVESA
MVFYDWNAARIQQCLAAYHDLGCTPRISCDPHTPVRVMDTLRAYLRRPEVTTAALAGEQWPLLYGVQLCICKETEAHGPDDGI
KWKCLLNNNNKTPLLYALDNPTLEFTTQHDLTRRIAGALSSTVFVET NS3 gene sequence: nucleotides 3631-5514 of SEQ ID NO:430

NS4A Protein and Gene Sequence

NS4A Amino Acid Sequence: (SEQ ID NO:437)
 GYGPILLAGAALAASFAFAGATGALVPSAVWSVDNGPTGVT NS4A gene sequence: nucleotides 5515-5637 of SEQ ID NO:430

NS4B Protein and Gene Sequence

NS4B Amino Acid Sequence: (SEQ ID NO:438)
RPDATDETVAYAQRLYHACADSGILASLQGTACAALSKLADASRGASQYLATAPPSPAPLVQVLQFLETNFSSIASFGLLCAG
CQAGECFTALAGLVSGATAGLGGAHKWLLAIAGTWLVSLQTGPRGGMVAGLSVLAGCCIGGVTGLDFLFGCLTGWEAVVGAAV
ATQKILSGSADMTTLVDLLPALFSPGAGIAGIVLVFILSNTSVTAWANRLLSMCAKQTICENYFLTEKFGQQLSKLSLWRAVY
HWAQAHEGYTQCG NS4B gene sequence: nucleotides 5638-6423 of SEQ ID NO:430

FIG. 32C

NS5A Protein and Gene Sequence

NS5A Amino Acid Sequence: (SEQ ID NO:439)
VVGGIWSFVLCILRAAWDWAAKHVPRFRVPMIGCSPAWCGRWLGTGTLLTTCGCGERVSLQCLCSTSDPILSVGRWCRCSWSV
GFPFNPTTTATGTLRPDIGDATRLGFRYGIAEIVELERRGDKWHVCAASCCLDRASVASAVKAPPVTANGIPISPFSPPQTYK
LSLCSFDSVCMSINSCNPSKILSVCSQEAVELLEETVDTAQTMMCKNLEARRRAEFDAWQVRQAVGDEYTRLADEDVDTITSV
KPPVARAAVGSSTLDDVGVLTVLRELGDQCQNAIKFVVEAASRFVPPVPKPRTRVSGVLERVRMCMRTPPMKFEAAAVPIHNI
IPEKCHIVLRCTGCSDQALTVPYGTCTQTLSSHLTNKHSHYIPKQKIEEDTEVTVICAVPTKRASKLITFRVGDRSVSCCHPL
QTPVRALLLKYGLPIGKWSDCNGPLGDDARVCDVNGVTTYEPC NS5A gene sequence: nucleotides 6424-7797 of SEQ ID NO:430

NS5B Protein and Gene Sequence

NS5B Amino Acid Sequence: (SEQ ID NO:440)
MQSYSWFRPIVAPTTPPLPVTRSVAGILRADTSRVYTTTAVDVSERQAKVTIDQKSAKVDQCFRDTYNCCLAKAKTFRQSGMS
YEDAVSKMRANTTRDHNTGITYTDLVSGRAKPAVQKIVDQMRSGVYDAPMRIIPKPEVFPRDKSTRKPPRFIVFPGCAARVAE
KMILGDPGAITKHVLGDAYGFATPPHERARLLEQWWNRATEPQAIAVDAICFDSTITAEDMDREAHIVAAAHADPEGVHGLYN
YYKRSPMCDITGKVVGVRCCRASGTLTTSSGNTLTCYLKVRAACTRAGIKPIGLLIHGDDTLIITERCTQETLDEFSNALDDY
GFPHTFQVSGDLSSIECCSARVDSVCLRGGMRRMLVPQARRAIARVLGEKGDPLGVISSYIVMYPTAAVTVYVLLPLLCMLIR
NEPSQTGTLVTLTVHGNSVSVPVWLLPTIIANLHGRDALQVVRHSAASMAELSSALAFFGMRGLNCWRRRRRAIRTDMIKLGG
WNANFAQMLLWSPEVRTPQPEPKGMCLLPPELWERPYENLHLSTIDRDRGASRLRFWLVASAVLALLCL NS5B gene sequence: nucleotides 7798-9498 of SEQ ID NO:430

5' UTR sequence

5' UTR Sequence: nucleotides 1-327 of SEQ ID NO:430

3' UTR sequence

3' UTR Sequence: nucleotides 9499-9867 of SEQ ID NO:430

SEQUENCE LISTING

```
<160> NUMBER OF SEQ ID NOS: 440

<210> SEQ ID NO 1
<211> LENGTH: 9778
<212> TYPE: DNA
<213> ORGANISM: Human Pegivirus 2

<400> SEQUENCE: 1
gtgtttgaca atgccatgag ggatcatgac actggggtga gcggaggcag caccgaagtc      60
gggtgaactc gactcccagt gcgaccacct ggcttggtcg ttcatggagg gcatgcccac     120
gggaacgctg atcgtgcaaa gggatgggtc cctgcactgg tgccatgcgc ggcaccactc     180
cgtacagcct gatagggtgg cggcgggccc ccccagtgtg acgtccgtgg agcgcaacat     240
ggggtgttca actgatcaaa ccatttgttc tccagtcgtg ggggccgact ataataccct     300
ctcgggctgc cgggccttaa atgggagcta ccactgcggt ggtggctctt gccggtcacc     360
aagtcgtgtg caggttgcga gacgagtctt gcagctgtgc gcattccttg cgctgatcgg     420
atccggtatg tgttcgatcc ggtccaaaac tgaagggcgc attgagtcag ggcaaatatt     480
gcagtctcag cgcgcatgtt ggactggtga gggttttgct ttcttttcta actgttgcaa     540
tcaatctgat attatgtggt gtttgcaccg ttggtgtgtg acaagacctg gctgtttagt     600
gtgcacgggc aatgccaccc atcctatctg ctgggactat cttggatccg gtgtaagtcg     660
gcggcctgca cgtcgaatgg gtgagggagc tgaagcgctt cttcgcttga tcggcattgc     720
aggttggctt ggactgttag ctgagtccct tggtatgtcc gaagtctatg cagctattct     780
ttgcttggga tttattgctt ggtatggctg gggtatacct aaaacactgg tgtgcaccgt     840
ctgccctgca gtgaacattt ctccctatag cttcttatct ccagatacta tcgcatttgg     900
tacgtggata ctacaactac ctggtctttt gtggcaaatg tttgttagct tccctatact     960
ctacagcact tggattcttt ggttgttgct cagcggcaag actgttgctg tgatagcaat    1020
ccttctggct agtcctacgg ttatggcgta caagcatcaa tctgaaagct acctcaaata    1080
ctgtaccata accaatactt caacttctat gaactgtgac tgccccttg gaacctttac    1140 tcgcaatact gagtctcgtt tctccatacc tagattctgt cctgttaaaa tcaatagctc    1200
tacatttatt tgttcatggg ggtcgtggtg gtggtttgct gaaaacatca cgcgtccata    1260
cacggacgtt ggcatgccac cagcaccgat ttccgctttg tgctatatct attctaacaa    1320
tgacccacct ccttggtatc ataacacaac tatcatacct cagaactgtc gcaactctac    1380
ggtggatcct accacagctc catgccgtga caagtggggc aacgcaactg cttgtattct    1440
```

```
tgaccgccgg tcgcggttct gcggggactg ctatggcggt tgtttctata ctaatggtag   1500
tcatgatcga tcctgggatc gatgcgggat tggttaccgt gatggactca tagagttcgt   1560
gcagctcggt cagattcgac ctaacatctc gaatacgacc attgagctcc tcgctggcgc   1620
ctcgcttgtg atcgcatccg gtcttcggcc tgggtttggt tgcagccgag cgcatggcgt   1680
ggtgcactgc tataggtgtc cttcataccg tgaccttgaa cagtttggtc ctgggcttgg   1740
gaaatgggtg ccattgcccg gcgagcctgt cccggagttg tgtatcaacc ctcagtgggc   1800
gaggcgcggc ttccggatgt ctaataatcc tctgagcttg ctacagacct tcgttgagga   1860
cattttccta gcgcctttt gtaatccgac gcctggccgt gtacgtgtgt gtaacaatac   1920
cgctttctat ccaagaggag gcggctttgt gcagctcatc ggggacgtcc aggtgctaac   1980
ccctaacact gcatctttac actctctgct gactttgata tctcttatct tgttggtgtg   2040
tgttgtttct ggtgcgcgat tcgttccact aataatcata ttttctgga gcgcgcgcca   2100 tgtatatgct tcttgttact taagctgtga ttgggctgtt tgcaacgatg cgttctgttt   2160
cacatctggc acttgtgcca ccttcaatga cgtcttgtgt ctgccggttg cgacgcgcat   2220
atcgtcctgt ggtcatgctg tgccacctcc cgaccgtggt tgggaggtgc ctgcggcgat   2280
gtcatgggtg atttcgcgga ctactggcct gacgttcgat gtcttttcct tcattcagta   2340
ccttcctact gtgcctggca acaacaccaa tatcatttac tgtggtgaac caaccttcct   2400
cggggacatc acgggcatct attggcctta cttttgcct ggcgcaatcc tcttgtactt   2460
gactcccttc ctaggtttaa ggttaatgct tgccggcttc aatatagatg gcttgtttcc   2520
catacggcat gccacggctg cactgaggtt ttcgacttct cgtgtgacct tgtgtgtcgt   2580
agttgctttc ctaatctata tattatctca ccctgttaat gctgcgctca atagaatgtt   2640
cttagcatct gcaaatttag agatgatctt atcttttgat acctatcatg agactgttct   2700
ttatatcctt tgtctattgc tctacctcca ggtgtcgccc cgtgcgggct tggccgctat   2760
ggtggccatc aagctatctc gaggcctgtt attcgctgtg gtgttggcgc acggtgtgtg   2820
ccgacctggg cgggtatttg gtcttgaggt ttgcgcggac atctcttggt tggtggagtt   2880
tactggcaat tgcacttggt acatgtcctg tgtcttctct ttttggtgcg cagtgtttgc   2940
cttcaccagt ccacttggac gacactataa gattcagatc tatcggtact gggcgcaggt   3000
ctatgccaga ctcgtcctcg ctgtcggttg tggtcctctc ggtcgagagt tccatttccg   3060
tgcaagtgtg ggcgtgctgt ggtgtggagc ttgcatgctc tggccccgtg agtgctctga   3120
aatcagcctg gtcttcattc tgtgtgctct gacagtggac accatagaca catggttagt   3180
agcgtgcttg tccgcagggc cgagtgcgcg aacccttgca attctggccg atgacatggc   3240
gcgcattggt gaccaccggg cgttgcgcgc cgtgttacgt tgctttggat cacgcggcac   3300
atacatatac aaccacatgg ccaagtctct ggaacgggtg gcgcaagcag tcagggatct   3360
cggcggttgc ttggaaccag tcgtgttgga ggagcccacc tttactgaga tcgtggatga   3420
cacaatgagt ttggtgtgtg acaattgct tggaggtaaa cctgtggtgg cccgctgcgg   3480
cacgcgtgtc ttggtgggac acctcaaccc tgaagatctg ccacctggtt tccagctgag   3540
tgctccggtg gttattacca ggccaagcat tggtacgtgg tccttcctta aggcgacact   3600
cacagggcgt gctgaaacac cagggtccgg ccagatcgtg gtgttgtctt ccctgacagg   3660
tcggtcaatg ggtaccgcag tgaatggcac actgtatgcg accggccatg gtgccggcgc   3720
gcgcggccta gccacgtgcg ctggtttgag gacgccactt tacacggcat tatctgatga   3780
```

```
tgtcgtggcc tattcttgcc ttccgggcat gagttcccta gaccsctgct gctgttcgcc    3840
gagccgggtt tgggtgatga ataacaacgg agggttggtg tgtggcagag tggagaatga    3900
cgacgtctgt ttggactgtc ccacgcacat agatcaactg cggggtgctt cgggctcacc    3960
agttttgtgt gatcacggtc atgcatacgc gttgatgctc ggtggttact ctaccagtgg    4020
tatttgtgca cgcgtccgga cggtccggcc atggcataac gcctattcct cctcgggggg    4080
gcaaggcgga atgcaggcgc cagctgtgac accaacatac tctgaaatca cctactatgc    4140
ccctactggt tctggtaagt caacaaaata tccagtggac ctagtcaaac agggacacaa    4200
agtattggtc cttttaccaa gtgtggctgt agtcaaaagt atggccccct atattaagga    4260
gacatataag atcagacccg aaattagagc tggcacaggt cctgacggtg tgacggtcat    4320
cactggtgag aacttggcgt acatgaccta tggccgcttc cttgtggatc cggagacgaa    4380
tctgcggggc tatgctgtag tcatttgcga cgagtgtcac gacacatcat ccaccacgct    4440
actcggcatt ggcgcagtgc gcatgtatgc cgagaaagct ggagtgaaga ccgttgtatt    4500
cgccacagcc accoctgctg gcattcaagt acagtcacat tccaacattg atgaatactt    4560
attgactgac acaggcgacg tggaatttta cggcgccaaa atcaaaatgg acaacatcag    4620
aactggtaga catgttatct tttgccactc gaaggccagg tgtgcggaac taacgcagca    4680
gctctccggc cttggcattc gtgcagtgag ttttggcgc ggctgtgaca tcaaaaccat    4740
tcccgcctca gactccattg ttgtggtggc aactgatgca ttgtccacgg gctacacagg    4800
aaactttgat tcggtcatcg actgcgggtg ttgcgtggag caaactgtga caattgacat    4860
ggaccctacg ttctccatct cggcccgagt ggtgccatgt actgctgcat gcgcatgca    4920 gcggcgcgga cgtaccggtc gtggtagaag gggagcgtac tacacaactt ctccaggagc    4980
agcaccctgc gtcagcgttc ccgatgctaa cgtctggcaa gcagtggaga cgccatggt    5040 cttttatgat tggagtgcta ccaggataca acagtgcctg gcggcatacc atgatttggg    5100
gtgcacacca cgcatcagct gtgacccaca cactccagtg cgggtgatgg acacactgag    5160
ggcgtacctg cgcagacctg aggtgacgac tgcagctctc gcaggagagc agtggccgct    5220
gcttcagggt gcgcagttgt gcatctgcaa agagaccgag gcccacggtc ctgatgatag    5280
catcaagtgg aagtgcttac tcaacaacag taacaaaaca cccctgttgt atgccttaga    5340
caatcctaca ctggaattca caacccaaca tgacttgact cgccgtatag ccggcgctct    5400
atcgagcaca gtgttcgtgg agacaggcta cggccccatc ctccttgctg gcgccgcttt    5460
ggctgcctcc ttcgcctttg cgggcgccac tggagcttta gtgccgtcgg ctgtttggag    5520
cgttgaggtc aggcctgctg gcgtgacccg tccccgacgcg acagacgaga ccgcggccta    5580
cgcacagcgc ttgtaccaag cctgtgcaga ttcaggaatt ttcgccagct tgcagggtac    5640
ggcgagtgcg gcgctgggca aactggccga cgccagtagg ggtgctagtc aatatctggc    5700
agccgcgcct ccttcacccg ccccccctggt acaggtgttg cagttcctcg agaccaactt    5760
tagctccatt gcatctttcg gcctgctctg tgctggctgc caggctggcg agtgcttcac    5820
tgcgcttgct ggcttggtgt ccggtgctac agctggcttg ggggtgccc ataagtggct    5880 attagctatt gcaggaactt ggctggttag cttgcagacc gggtcccgtg gcggcatggt    5940
tgcgggcctc tcgattctag cgggctgttg catcggtagt gtcaccgggc ttgacttcct    6000
gtttgggtgc cttacaggtt gggaagccgt ggtcggcgct gcggttgcga cacagaagat    6060
cttgtctggt tcagctgata tgaccactct ggtagatctc ttacctgctc ttttctcccc    6120
cggtgccggc atagctggca tcgtgcttgt cttcatctta agcaattcaa gtgtaaccac    6180
```

```
atgggctaat cggctattat ccatgtgtgc caaacaaacc atttgtgaaa actacttctt    6240
aagtgaaaga tttggccaac aattaagcaa actttccctg tggcgctctg tgtaccattg    6300
ggcgcaggca cgtgagggat acacacagtg cggcgtgatc agcgggatct ggagcttcgc    6360
cttgtgcatt ctacgcgctg tgtgggattg ggcggccaag catgtgccac ggttccgtgt    6420
gcctatgatt ggctgctcac ctgcgtggtg cgggcgctgg cttggtaccg gcaccttgtt    6480
gaccacctgt gcgtgtggag aacgtgtgtc ccttcagtgc ctttgctcaa catctgaccc    6540
acaactcagt gtgggccgtt ggtgtcggtg tagttggagt gttgggttcc cattcaaccc    6600
gactacgaca ggcactggca ccttacgccc ggacatcagt gacgccaaca aattgggttt    6660
ccggtatggc gttgccgaca tcgtggagct agagcggcgg ggcgacaaat ggcacgtctg    6720
tgcagcatca tgttgcttgg accgggccag cgttgcatcc gctgtgaagg ccccaccggt    6780
cacggctaat ggtataccta ttaatagctt ttctccacca caaacttatt gcctatctct    6840
ctgttccttt gatacagttt gcatgtctac taacttatgt aacccagcta agaccctgag    6900
tgtgtgccaa gaggaggcgg ttgagctgct ggaagagaca gttgacacag cacaagtagt    6960
gatgagccaa aatctggcag cgcgtagacg cgctgagtat gatgcatggc aggttcgcca    7020
agcagttggc gacgagtaca cgcgtttggc agacgaggat gttgacatga cagcgtcggt    7080
gaaaccccca gtggccaggg ctgctgtggg tagctcaacg ttggatgatg ttagcgtgct    7140
gactgtctta cgcgaactcg gcgaccagtg ccaaaatgct atcaaatttg tagttcaggc    7200
ggcttcacgg tttgttccac cagtgcccaa gccacgcacg cgtgtctcgg gtgtcttgga    7260
gcgcgtgcgc atgtgcatgc gcacgcctcc aatcaagttt gaggccaccg cagtaccaat    7320
tcataatata atcccagaag agtgtcatat tgtgctacgc tgtaccggct gttgtgacca    7380
ggccttgacc gttccgtacg gcacttgctc tctgacttta accaaatatt tgactaacaa    7440
acacagtcac tatattccaa aagagaagat agaagaagac acagaaatag ctgtcatttg    7500
cgccgtacca acaaagcgcg caagtaaact tatcactttc agagcaggtg accgatcagt    7560
ctcatgttgt cacccctttgc aaactcctat tagggccctg cttcaaaagt atgggttacc    7620
tattgggaag tggtccgact gcaacgggcc ccttggtgac gacgcccgag tctgtgacgt    7680
caatggagtg acaacttatg aaccatgcat gcaatcctac aattggttcc gatcgattgt    7740
ggcaccaaca accccacctt tacctgcaac ccggagcgtg gctggcattt gcgcgcagag    7800
cacatcgcgc gtctacacca acagcggt tgatgtctcc gagcggcagg ctaaggtcac    7860
gattgatcaa aagtcagcca aggtggacca gtgtctccga gacacataca attgctgcct    7920
tgccaaggca aagaccttca gacaatctgg catgtcatat gaggatgctg tgtcaaagat    7980
gcgcgcaaac accacgcgtg atcataacaa cggcatcact tatacagatt tggtctctgg    8040
acgcgcaaaa cctgtcgttc agaaaattgt agatcagatg cgcgctggag tgtacgacgc    8100
tccaatgcgc attattccaa aacctgaagt gtttccacga acaagtcaa cacggaagcc    8160 accacggttc atcgttttcc ctgggtgtgc cgcacgagtc gcggagaaaa tgatcctggg    8220
cgatcctggc gcgataacca agcacgtgct aggtgatgcc tacgggtttg ccactccgcc    8280
gcatgagcgc gcgcgcctac tggaacaatg gtggaaccgc gcaacggagc acaaagctat    8340
cgcggttgat gcagtctgct ttgatagcac catcacggca gaggacatgg atcgtgaggc    8400
caacatcgtg gctgcagcgc atacggaccc ggaaggtgtt cacggcctat acaattatta    8460
caaaagaagc cccatgtgtg atatcacagg aaaagttgtc ggggtgcgta gctgtcgagc    8520
```

-continued

```
ctcaggtacg cttacaacaa gcagtggcaa cacgcttact tgctacctca aggttcgcgc    8580
agcttgcacg cgcgccggca ttaaaccaat tggcttacta attcatggag atgacaccct    8640
cattatcaca gaacgttgcg ctcaggaaac tctcgatgag ttcagcaacg cgcttgatga    8700
ctatgggttt actcacacca tgcaggtgtc tggggacctc tcgtctatcg agtgctgcag    8760
cgcacgtgtg gacagcgttt gcctccgggg aggtatgcgt cgcatgctcg tgccacaagc    8820
tcgacgtgcg attgcacgcg ttctcgggga aagggcgat ccactgggtg ttatcagcag     8880
ctatattgtc atgtatccta ctgcggctgt gactgtctac gttctgatgc ccctgttgtg    8940
catgctcatt cgaaatgagc catcgcagac ggggacactt gtaacgttga cggtccacgg    9000
taacagtgtg agcgtgccag tgtggctgct tccaaccatt attgcaaatt tacatggccg    9060
tgacgcacta caggttgtcc gtcacagtgc agcttccatg gcggaactgt cctcagcgtt    9120
ggccttcttt ggcatgagag ggttgaactg ctggaggcgg agacgccgtg ccatcaggac    9180
tgatatgatc aagttgggcg ggtggaatgc gaatttcgcg cagatgttac tgtggtcacc    9240
ggaggtaaga acaccacagc ccgaaccaaa gggcatgtgt ctcttgccac cggaactatg    9300
ggagcgtccg tacgaaaatt tgcacttgag cacgatcgac cgcaatcgtg gtgctagtcg    9360
cttacggttt tggttggttg ctagtgctat actcgctctg ctttgcttgt aaatcctaaa    9420
tcaatgtagt accaggacta caaggcagga ggtgaagtca gctgtaccca cggctggctg    9480
aaaccggggc ttgacgaccc ccctatccg  agttgggcaa ggtaacatca cgggtgtgac    9540
gaccccgccc cccatgtcg  cgcgcaagcg cacgggcaag gcagctaggc tgagagtctg    9600
ggcaactctc ccgtacccca cccgaggcta cgcctcgtcc tggcgaggac cgtaaacata    9660
cgtcgtcagc gtggtgacct gacgtatctt gttaaccact taatggtcgt aactcgaccc    9720
ccgtgccggg gatctaagcg cggcaccgcg aygagagggg tcaacggccc ctttcatt     9778
```

<210> SEQ ID NO 2
<211> LENGTH: 124
<212> TYPE: PRT
<213> ORGANISM: Human Pegivirus 2

<400> SEQUENCE: 2

```
Met Glu Gly Met Pro Thr Gly Thr Leu Ile Val Gln Arg Asp Gly Ser
1               5                   10                  15

Leu His Trp Cys His Ala Arg His His Ser Val Gln Pro Asp Arg Val
            20                  25                  30

Ala Ala Gly Pro Pro Ser Val Thr Ser Val Glu Arg Asn Met Gly Cys
        35                  40                  45

Ser Thr Asp Gln Thr Ile Cys Ser Pro Val Val Gly Ala Asp Tyr Asn
    50                  55                  60

Thr Ser Ser Gly Cys Arg Ala Leu Asn Gly Ser Tyr His Cys Gly Gly
65                  70                  75                  80

Gly Ser Cys Arg Ser Pro Ser Arg Val Gln Val Ala Arg Arg Val Leu
                85                  90                  95

Gln Leu Cys Ala Phe Leu Ala Leu Ile Gly Ser Gly Met Cys Ser Ile
            100                 105                 110

Arg Ser Lys Thr Glu Gly Arg Ile Glu Ser Gly Gln
        115                 120
```

<210> SEQ ID NO 3
<211> LENGTH: 191
<212> TYPE: PRT
<213> ORGANISM: Human Pegivirus 2

<400> SEQUENCE: 3

```
Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
            20                  25                  30

Trp Cys Val Thr Arg Pro Gly Cys Leu Val Cys Thr Gly Asn Ala Thr
        35                  40                  45

His Pro Ile Cys Trp Asp Tyr Leu Gly Ser Gly Val Ser Arg Arg Pro
    50                  55                  60

Ala Arg Arg Met Gly Glu Gly Ala Glu Ala Leu Leu Arg Leu Ile Gly
65                  70                  75                  80

Ile Ala Gly Trp Leu Gly Leu Leu Ala Glu Ser Leu Gly Met Ser Glu
                85                  90                  95

Val Tyr Ala Ala Ile Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Ile Leu Gln Leu Pro Gly Leu Leu Trp Gln Met Phe Val Ser Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
            180                 185                 190
```

<210> SEQ ID NO 4
<211> LENGTH: 354
<212> TYPE: PRT
<213> ORGANISM: Human Pegivirus 2

<400> SEQUENCE: 4

```
Tyr Lys His Gln Ser Glu Ser Tyr Leu Lys Tyr Cys Thr Ile Thr Asn
1               5                   10                  15

Thr Ser Thr Ser Met Asn Cys Asp Cys Pro Phe Gly Thr Phe Thr Arg
            20                  25                  30

Asn Thr Glu Ser Arg Phe Ser Ile Pro Arg Phe Cys Pro Val Lys Ile
        35                  40                  45

Asn Ser Ser Thr Phe Ile Cys Ser Trp Gly Ser Trp Trp Phe Ala
    50                  55                  60

Glu Asn Ile Thr Arg Pro Tyr Thr Asp Val Gly Met Pro Pro Ala Pro
65                  70                  75                  80

Ile Ser Ala Leu Cys Tyr Ile Tyr Ser Asn Asn Asp Pro Pro Trp
                85                  90                  95

Tyr His Asn Thr Thr Ile Ile Pro Gln Asn Cys Arg Asn Ser Thr Val
            100                 105                 110

Asp Pro Thr Thr Ala Pro Cys Arg Asp Lys Trp Gly Asn Ala Thr Ala
        115                 120                 125

Cys Ile Leu Asp Arg Arg Ser Arg Phe Cys Gly Asp Cys Tyr Gly Gly
    130                 135                 140

Cys Phe Tyr Thr Asn Gly Ser His Asp Arg Ser Trp Asp Arg Cys Gly
145                 150                 155                 160

Ile Gly Tyr Arg Asp Gly Leu Ile Glu Phe Val Gln Leu Gly Gln Ile
                165                 170                 175
```

```
Arg Pro Asn Ile Ser Asn Thr Thr Ile Glu Leu Leu Ala Gly Ala Ser
            180                 185                 190

Leu Val Ile Ala Ser Gly Leu Arg Pro Gly Phe Gly Cys Ser Arg Ala
            195                 200                 205

His Gly Val Val His Cys Tyr Arg Cys Pro Ser Tyr Arg Asp Leu Glu
            210                 215                 220

Gln Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
            245                 250                 255

Met Ser Asn Asn Pro Leu Ser Leu Leu Gln Thr Phe Val Glu Asp Ile
            260                 265                 270

Phe Leu Ala Pro Phe Cys Asn Pro Thr Pro Gly Arg Val Arg Val Cys
            275                 280                 285

Asn Asn Thr Ala Phe Tyr Pro Arg Gly Gly Gly Phe Val Gln Leu Ile
            290                 295                 300

Gly Asp Val Gln Val Leu Thr Pro Asn Thr Ala Ser Leu His Ser Leu
305                 310                 315                 320

Leu Thr Leu Ile Ser Leu Ile Leu Leu Val Cys Val Val Ser Gly Ala
            325                 330                 335

Arg Phe Val Pro Leu Ile Ile Ile Phe Phe Trp Ser Ala Arg His Val
            340                 345                 350

Tyr Ala

<210> SEQ ID NO 5
<211> LENGTH: 237
<212> TYPE: PRT
<213> ORGANISM: Human Pegivirus 2

<400> SEQUENCE: 5

Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
            20                  25                  30

Val Ala Thr Arg Ile Ser Ser Cys Gly His Ala Val Pro Pro Pro Asp
            35                  40                  45

Arg Gly Trp Glu Val Pro Ala Ala Met Ser Trp Val Ile Ser Arg Thr
50                  55                  60

Thr Gly Leu Thr Phe Asp Val Phe Ser Phe Ile Gln Tyr Leu Pro Thr
65                  70                  75                  80

Val Pro Gly Asn Asn Thr Asn Ile Ile Tyr Cys Gly Glu Pro Thr Phe
            85                  90                  95

Leu Gly Asp Ile Thr Gly Ile Tyr Trp Pro Tyr Phe Leu Pro Gly Ala
            100                 105                 110

Ile Leu Leu Tyr Leu Thr Pro Phe Leu Gly Leu Arg Leu Met Leu Ala
            115                 120                 125

Gly Phe Asn Ile Asp Gly Leu Phe Pro Ile Arg His Ala Thr Ala Ala
            130                 135                 140

Leu Arg Phe Ser Thr Ser Arg Val Thr Leu Cys Val Val Ala Phe
145                 150                 155                 160

Leu Ile Tyr Ile Leu Ser His Pro Val Asn Ala Ala Leu Asn Arg Met
            165                 170                 175

Phe Leu Ala Ser Ala Asn Leu Glu Met Ile Leu Ser Phe Asp Thr Tyr
            180                 185                 190
```

```
His Glu Thr Val Leu Tyr Ile Leu Cys Leu Leu Tyr Leu Gln Val
        195                 200                 205

Ser Pro Arg Ala Gly Leu Ala Ala Met Val Ala Ile Lys Leu Ser Arg
210                 215                 220

Gly Leu Leu Phe Ala Val Val Leu Ala His Gly Val Cys
225                 230                 235

<210> SEQ ID NO 6
<211> LENGTH: 240
<212> TYPE: PRT
<213> ORGANISM: Human Pegivirus 2

<400> SEQUENCE: 6

Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
                20                  25                  30

Ser Phe Trp Cys Ala Val Phe Ala Phe Thr Ser Pro Leu Gly Arg His
        35                  40                  45

Tyr Lys Ile Gln Ile Tyr Arg Tyr Trp Ala Gln Val Tyr Ala Arg Leu
50                  55                  60

Val Leu Ala Val Gly Cys Gly Pro Leu Gly Arg Glu Phe His Phe Arg
65                  70                  75                  80

Ala Ser Val Gly Val Leu Trp Cys Gly Ala Cys Met Leu Trp Pro Arg
                85                  90                  95

Glu Cys Ser Glu Ile Ser Leu Val Phe Ile Leu Cys Ala Leu Thr Val
            100                 105                 110

Asp Thr Ile Asp Thr Trp Leu Val Ala Cys Leu Ser Ala Gly Pro Ser
        115                 120                 125

Ala Arg Thr Leu Ala Ile Leu Ala Asp Asp Met Ala Arg Ile Gly Asp
130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Leu Gly Gly Cys Leu Glu Pro Val Val Leu Glu Glu Pro
            180                 185                 190

Thr Phe Thr Glu Ile Val Asp Asp Thr Met Ser Leu Val Cys Gly Gln
        195                 200                 205

Leu Leu Gly Gly Lys Pro Val Val Ala Arg Cys Gly Thr Arg Val Leu
210                 215                 220

Val Gly His Leu Asn Pro Glu Asp Leu Pro Pro Gly Phe Gln Leu Ser
225                 230                 235                 240

<210> SEQ ID NO 7
<211> LENGTH: 628
<212> TYPE: PRT
<213> ORGANISM: Human Pegivirus 2

<400> SEQUENCE: 7

Ala Pro Val Val Ile Thr Arg Pro Ser Ile Gly Thr Trp Ser Phe Leu
1               5                   10                  15

Lys Ala Thr Leu Thr Gly Arg Ala Glu Thr Pro Gly Ser Gly Gln Ile
                20                  25                  30

Val Val Leu Ser Ser Leu Thr Gly Arg Ser Met Gly Thr Ala Val Asn
        35                  40                  45
```

```
Gly Thr Leu Tyr Ala Thr Gly His Gly Ala Gly Arg Gly Leu Ala
 50                  55                  60

Thr Cys Ala Gly Leu Arg Thr Pro Leu Tyr Thr Ala Leu Ser Asp Asp
 65                  70                  75                  80

Val Val Ala Tyr Ser Cys Leu Pro Gly Met Ser Ser Leu Asp Pro Cys
                 85                  90                  95

Cys Cys Ser Pro Ser Arg Val Trp Val Met Asn Asn Asn Gly Gly Leu
            100                 105                 110

Val Cys Gly Arg Val Glu Asn Asp Val Cys Leu Asp Cys Pro Thr
        115                 120                 125

His Ile Asp Gln Leu Arg Gly Ala Ser Gly Ser Pro Val Leu Cys Asp
130                 135                 140

His Gly His Ala Tyr Ala Leu Met Leu Gly Gly Tyr Ser Thr Ser Gly
145                 150                 155                 160

Ile Cys Ala Arg Val Arg Thr Val Arg Pro Trp His Asn Ala Tyr Ser
                165                 170                 175

Ser Ser Gly Gly Gln Gly Gly Met Gln Ala Pro Ala Val Thr Pro Thr
            180                 185                 190

Tyr Ser Glu Ile Thr Tyr Tyr Ala Pro Thr Gly Ser Gly Lys Ser Thr
        195                 200                 205

Lys Tyr Pro Val Asp Leu Val Lys Gln Gly His Lys Val Leu Val Leu
210                 215                 220

Leu Pro Ser Val Ala Val Val Lys Ser Met Ala Pro Tyr Ile Lys Glu
225                 230                 235                 240

Thr Tyr Lys Ile Arg Pro Glu Ile Arg Ala Gly Thr Gly Pro Asp Gly
                245                 250                 255

Val Thr Val Ile Thr Gly Glu Asn Leu Ala Tyr Met Thr Tyr Gly Arg
            260                 265                 270

Phe Leu Val Asp Pro Glu Thr Asn Leu Arg Gly Tyr Ala Val Val Ile
        275                 280                 285

Cys Asp Glu Cys His Asp Thr Ser Ser Thr Thr Leu Leu Gly Ile Gly
290                 295                 300

Ala Val Arg Met Tyr Ala Glu Lys Ala Gly Val Lys Thr Val Val Phe
305                 310                 315                 320

Ala Thr Ala Thr Pro Ala Gly Ile Gln Val Gln Ser His Ser Asn Ile
                325                 330                 335

Asp Glu Tyr Leu Leu Thr Asp Thr Gly Asp Val Glu Phe Tyr Gly Ala
            340                 345                 350

Lys Ile Lys Met Asp Asn Ile Arg Thr Gly Arg His Val Ile Phe Cys
        355                 360                 365

His Ser Lys Ala Arg Cys Ala Glu Leu Thr Gln Gln Leu Ser Gly Leu
370                 375                 380

Gly Ile Arg Ala Val Ser Phe Trp Arg Gly Cys Asp Ile Lys Thr Ile
385                 390                 395                 400

Pro Ala Ser Asp Ser Ile Val Val Ala Thr Asp Ala Leu Ser Thr
                405                 410                 415

Gly Tyr Thr Gly Asn Phe Asp Ser Val Ile Asp Cys Gly Cys Cys Val
            420                 425                 430

Glu Gln Thr Val Thr Ile Asp Met Asp Pro Thr Phe Ser Ile Ser Ala
        435                 440                 445

Arg Val Val Pro Cys Thr Ala Ala Leu Arg Met Gln Arg Arg Gly Arg
450                 455                 460
```

```
Thr Gly Arg Gly Arg Arg Gly Ala Tyr Tyr Thr Ser Pro Gly Ala
465                 470                 475                 480

Ala Pro Cys Val Ser Val Pro Asp Ala Asn Val Trp Gln Ala Val Glu
            485                 490                 495

Ser Ala Met Val Phe Tyr Asp Trp Ser Ala Thr Arg Ile Gln Gln Cys
            500                 505                 510

Leu Ala Ala Tyr His Asp Leu Gly Cys Thr Pro Arg Ile Ser Cys Asp
            515                 520                 525

Pro His Thr Pro Val Arg Val Met Asp Thr Leu Arg Ala Tyr Leu Arg
        530                 535                 540

Arg Pro Glu Val Thr Thr Ala Ala Leu Ala Gly Glu Gln Trp Pro Leu
545                 550                 555                 560

Leu Tyr Gly Ala Gln Leu Cys Ile Cys Lys Glu Thr Glu Ala His Gly
                565                 570                 575

Pro Asp Asp Ser Ile Lys Trp Lys Cys Leu Leu Asn Asn Ser Asn Lys
            580                 585                 590

Thr Pro Leu Leu Tyr Ala Leu Asp Asn Pro Thr Leu Glu Phe Thr Thr
        595                 600                 605

Gln His Asp Leu Thr Arg Arg Ile Ala Gly Ala Leu Ser Ser Thr Val
    610                 615                 620

Phe Val Glu Thr
625

<210> SEQ ID NO 8
<211> LENGTH: 41
<212> TYPE: PRT
<213> ORGANISM: Human Pegivirus 2

<400> SEQUENCE: 8

Gly Tyr Gly Pro Ile Leu Leu Ala Gly Ala Ala Leu Ala Ala Ser Phe
1               5                   10                  15

Ala Phe Ala Gly Ala Thr Gly Ala Leu Val Pro Ser Ala Val Trp Ser
            20                  25                  30

Val Glu Val Arg Pro Ala Gly Val Thr
        35                  40

<210> SEQ ID NO 9
<211> LENGTH: 262
<212> TYPE: PRT
<213> ORGANISM: Human Pegivirus 2

<400> SEQUENCE: 9

Arg Pro Asp Ala Thr Asp Glu Thr Ala Ala Tyr Ala Gln Arg Leu Tyr
1               5                   10                  15

Gln Ala Cys Ala Asp Ser Gly Ile Phe Ala Ser Leu Gln Gly Thr Ala
            20                  25                  30

Ser Ala Ala Leu Gly Lys Leu Ala Asp Ala Ser Arg Gly Ala Ser Gln
        35                  40                  45

Tyr Leu Ala Ala Ala Pro Pro Ser Pro Ala Pro Leu Val Gln Val Leu
    50                  55                  60

Gln Phe Leu Glu Thr Asn Phe Ser Ser Ile Ala Ser Phe Gly Leu Leu
65                  70                  75                  80

Cys Ala Gly Cys Gln Ala Gly Glu Cys Phe Thr Ala Leu Ala Gly Leu
                85                  90                  95

Val Ser Gly Ala Thr Ala Gly Leu Gly Gly Ala His Lys Trp Leu Leu
            100                 105                 110
```

Ala Ile Ala Gly Thr Trp Leu Val Ser Leu Gln Thr Gly Ser Arg Gly
            115                 120                 125

Gly Met Val Ala Gly Leu Ser Ile Leu Ala Gly Cys Cys Ile Gly Ser
        130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Val Asp Leu Leu Pro Ala Leu Phe Ser Pro Gly
            180                 185                 190

Ala Gly Ile Ala Gly Ile Val Leu Val Phe Ile Leu Ser Asn Ser Ser
            195                 200                 205

Val Thr Thr Trp Ala Asn Arg Leu Leu Ser Met Cys Ala Lys Gln Thr
    210                 215                 220

Ile Cys Glu Asn Tyr Phe Leu Ser Glu Arg Phe Gly Gln Gln Leu Ser
225                 230                 235                 240

Lys Leu Ser Leu Trp Arg Ser Val Tyr His Trp Ala Gln Ala Arg Glu
                245                 250                 255

Gly Tyr Thr Gln Cys Gly
            260

<210> SEQ ID NO 10
<211> LENGTH: 458
<212> TYPE: PRT
<213> ORGANISM: Human Pegivirus 2

<400> SEQUENCE: 10

Val Ile Ser Gly Ile Trp Ser Phe Ala Leu Cys Ile Leu Arg Ala Val
1               5                   10                  15

Trp Asp Trp Ala Ala Lys His Val Pro Arg Phe Arg Val Pro Met Ile
            20                  25                  30

Gly Cys Ser Pro Ala Trp Cys Gly Arg Trp Leu Gly Thr Gly Thr Leu
        35                  40                  45

Leu Thr Thr Cys Ala Cys Gly Glu Arg Val Ser Leu Gln Cys Leu Cys
    50                  55                  60

Ser Thr Ser Asp Pro Gln Leu Ser Val Gly Arg Trp Cys Arg Cys Ser
65                  70                  75                  80

Trp Ser Val Gly Phe Pro Phe Asn Pro Thr Thr Thr Gly Thr Gly Thr
                85                  90                  95

Leu Arg Pro Asp Ile Ser Asp Ala Asn Lys Leu Gly Phe Arg Tyr Gly
            100                 105                 110

Val Ala Asp Ile Val Glu Leu Glu Arg Arg Gly Asp Lys Trp His Val
        115                 120                 125

Cys Ala Ser Cys Cys Leu Asp Arg Ala Ser Val Ala Ser Ala Val
    130                 135                 140

Lys Ala Pro Pro Val Thr Ala Asn Gly Ile Pro Ile Asn Ser Phe Ser
145                 150                 155                 160

Pro Pro Gln Thr Tyr Cys Leu Ser Leu Cys Ser Phe Asp Thr Val Cys
                165                 170                 175

Met Ser Thr Asn Leu Cys Asn Pro Ala Lys Thr Leu Ser Val Cys Gln
            180                 185                 190

Glu Glu Ala Val Glu Leu Leu Glu Thr Val Asp Thr Ala Gln Val
        195                 200                 205

Val Met Ser Gln Asn Leu Ala Ala Arg Arg Ala Glu Tyr Asp Ala
    210                 215                 220

```
Trp Gln Val Arg Gln Ala Val Gly Asp Glu Tyr Thr Arg Leu Ala Asp
225                 230                 235                 240

Glu Asp Val Asp Met Thr Ala Ser Val Lys Pro Pro Val Ala Arg Ala
            245                 250                 255

Ala Val Gly Ser Ser Thr Leu Asp Asp Val Ser Val Leu Thr Val Leu
        260                 265                 270

Arg Glu Leu Gly Asp Gln Cys Gln Asn Ala Ile Lys Phe Val Val Gln
    275                 280                 285

Ala Ala Ser Arg Phe Val Pro Pro Val Pro Lys Pro Arg Thr Arg Val
290                 295                 300

Ser Gly Val Leu Glu Arg Val Arg Met Cys Met Arg Thr Pro Pro Ile
305                 310                 315                 320

Lys Phe Glu Ala Thr Ala Val Pro Ile His Asn Ile Ile Pro Glu Glu
            325                 330                 335

Cys His Ile Val Leu Arg Cys Thr Gly Cys Cys Asp Gln Ala Leu Thr
            340                 345                 350

Val Pro Tyr Gly Thr Cys Ser Leu Thr Leu Thr Lys Tyr Leu Thr Asn
        355                 360                 365

Lys His Ser His Tyr Ile Pro Lys Glu Lys Ile Glu Glu Asp Thr Glu
    370                 375                 380

Ile Ala Val Ile Cys Ala Val Pro Thr Lys Arg Ala Ser Lys Leu Ile
385                 390                 395                 400

Thr Phe Arg Ala Gly Asp Arg Ser Val Ser Cys Cys His Pro Leu Gln
            405                 410                 415

Thr Pro Ile Arg Ala Leu Leu Gln Lys Tyr Gly Leu Pro Ile Gly Lys
            420                 425                 430

Trp Ser Asp Cys Asn Gly Pro Leu Gly Asp Asp Ala Arg Val Cys Asp
        435                 440                 445

Val Asn Gly Val Thr Thr Tyr Glu Pro Cys
    450                 455

<210> SEQ ID NO 11
<211> LENGTH: 567
<212> TYPE: PRT
<213> ORGANISM: Human Pegivirus 2

<400> SEQUENCE: 11

Met Gln Ser Tyr Asn Trp Phe Arg Ser Ile Val Ala Pro Thr Thr Pro
1               5                   10                  15

Pro Leu Pro Ala Thr Arg Ser Val Ala Gly Ile Leu Arg Ala Asp Thr
            20                  25                  30

Ser Arg Val Tyr Thr Thr Thr Ala Val Asp Val Ser Glu Arg Gln Ala
        35                  40                  45

Lys Val Thr Ile Asp Gln Lys Ser Ala Lys Val Asp Gln Cys Leu Arg
    50                  55                  60

Asp Thr Tyr Asn Cys Cys Leu Ala Lys Ala Lys Thr Phe Arg Gln Ser
65                  70                  75                  80

Gly Met Ser Tyr Glu Asp Ala Val Ser Lys Met Arg Ala Asn Thr Thr
            85                  90                  95

Arg Asp His Asn Asn Gly Ile Thr Tyr Thr Asp Leu Val Ser Gly Arg
            100                 105                 110

Ala Lys Pro Val Val Gln Lys Ile Val Asp Gln Met Arg Ala Gly Val
        115                 120                 125

Tyr Asp Ala Pro Met Arg Ile Ile Pro Lys Pro Glu Val Phe Pro Arg
```

```
            130                 135                 140
Asp Lys Ser Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His
                180                 185                 190

Glu Arg Ala Arg Leu Leu Glu Gln Trp Trp Asn Arg Ala Thr Glu Pro
                195                 200                 205

Gln Ala Ile Ala Val Asp Ala Val Cys Phe Asp Ser Thr Ile Thr Ala
                210                 215                 220

Glu Asp Met Asp Arg Glu Ala Asn Ile Val Ala Ala His Thr Asp
225                 230                 235                 240

Pro Glu Gly Val His Gly Leu Tyr Asn Tyr Tyr Lys Arg Ser Pro Met
                245                 250                 255

Cys Asp Ile Thr Gly Lys Val Val Gly Val Arg Ser Cys Arg Ala Ser
                260                 265                 270

Gly Thr Leu Thr Thr Ser Ser Gly Asn Thr Leu Thr Cys Tyr Leu Lys
                275                 280                 285

Val Arg Ala Ala Cys Thr Arg Ala Gly Ile Lys Pro Ile Gly Leu Leu
290                 295                 300

Ile His Gly Asp Thr Leu Ile Ile Thr Glu Arg Cys Ala Gln Glu
305                 310                 315                 320

Thr Leu Asp Glu Phe Ser Asn Ala Leu Asp Asp Tyr Gly Phe Thr His
                325                 330                 335

Thr Met Gln Val Ser Gly Asp Leu Ser Ser Ile Glu Cys Cys Ser Ala
                340                 345                 350

Arg Val Asp Ser Val Cys Leu Arg Gly Met Arg Arg Met Leu Val
                355                 360                 365

Pro Gln Ala Arg Arg Ala Ile Ala Arg Val Leu Gly Glu Lys Gly Asp
370                 375                 380

Pro Leu Gly Val Ile Ser Ser Tyr Ile Val Met Tyr Pro Thr Ala Ala
385                 390                 395                 400

Val Thr Val Tyr Val Leu Met Pro Leu Leu Cys Met Leu Ile Arg Asn
                405                 410                 415

Glu Pro Ser Gln Thr Gly Thr Leu Val Thr Leu Thr Val His Gly Asn
                420                 425                 430

Ser Val Ser Val Pro Val Trp Leu Leu Pro Thr Ile Ile Ala Asn Leu
                435                 440                 445

His Gly Arg Asp Ala Leu Gln Val Val Arg His Ser Ala Ala Ser Met
450                 455                 460

Ala Glu Leu Ser Ser Ala Leu Ala Phe Phe Gly Met Arg Gly Leu Asn
465                 470                 475                 480

Cys Trp Arg Arg Arg Arg Ala Ile Arg Thr Asp Met Ile Lys Leu
                485                 490                 495

Gly Gly Trp Asn Ala Asn Phe Ala Gln Met Leu Leu Trp Ser Pro Glu
                500                 505                 510

Val Arg Thr Pro Gln Pro Glu Pro Lys Gly Met Cys Leu Leu Pro Pro
                515                 520                 525

Glu Leu Trp Glu Arg Pro Tyr Glu Asn Leu His Leu Ser Thr Ile Asp
                530                 535                 540

Arg Asn Arg Gly Ala Ser Arg Leu Arg Phe Trp Leu Val Ala Ser Ala
545                 550                 555                 560
```

Ile Leu Ala Leu Leu Cys Leu
            565

<210> SEQ ID NO 12
<211> LENGTH: 24
<212> TYPE: DNA
<213> ORGANISM: Artificial sequence
<220> FEATURE:
<223> OTHER INFORMATION: Synthetic

<400> SEQUENCE: 12
tattgctact tcggtacgcc taat                                              24

<210> SEQ ID NO 13
<211> LENGTH: 24
<212> TYPE: DNA
<213> ORGANISM: Artificial sequence
<220> FEATURE:
<223> OTHER INFORMATION: Synthetic

<400> SEQUENCE: 13
aagggcctag taggacgtgt gaca                                              24

<210> SEQ ID NO 14
<211> LENGTH: 24
<212> TYPE: DNA
<213> ORGANISM: Artificial sequence
<220> FEATURE:
<223> OTHER INFORMATION: Synthetic

<400> SEQUENCE: 14
cactggggtg agcggaggca gcac                                              24

<210> SEQ ID NO 15
<211> LENGTH: 24
<212> TYPE: DNA
<213> ORGANISM: Artificial sequence
<220> FEATURE:
<223> OTHER INFORMATION: Synthetic

<400> SEQUENCE: 15
gaggcagcac cgaagtcggg tgaa                                              24

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
tgccacccat cctatctgct                                                   20

<210> SEQ ID NO 17
<211> LENGTH: 24
<212> TYPE: DNA
<213> ORGANISM: Artificial sequence
<220> FEATURE:
<223> OTHER INFORMATION: Synthetic

<400> SEQUENCE: 17
tattgcttgg tatggctggg gtat                                              24

<210> SEQ ID NO 18
<211> LENGTH: 23

```
<212> TYPE: DNA
<213> ORGANISM: Artificial sequence
<220> FEATURE:
<223> OTHER INFORMATION: Synthetic

<400> SEQUENCE: 18
atggctgggg tatacctaar aca                                              23

<210> SEQ ID NO 19
<211> LENGTH: 19
<212> TYPE: DNA
<213> ORGANISM: Artificial sequence
<220> FEATURE:
<223> OTHER INFORMATION: Synthetic

<400> SEQUENCE: 19
tggcgtacaa gcatcaatc                                                   19

<210> SEQ ID NO 20
<211> LENGTH: 22
<212> TYPE: DNA
<213> ORGANISM: Artificial sequence
<220> FEATURE:
<223> OTHER INFORMATION: Synthetic

<400> SEQUENCE: 20
accgatttcc gctttgtgct at                                               22

<210> SEQ ID NO 21
<211> LENGTH: 18
<212> TYPE: DNA
<213> ORGANISM: Artificial sequence
<220> FEATURE:
<223> OTHER INFORMATION: Synthetic

<400> SEQUENCE: 21
cctgggcttg ggaaatgg                                                    18

<210> SEQ ID NO 22
<211> LENGTH: 23
<212> TYPE: DNA
<213> ORGANISM: Artificial sequence
<220> FEATURE:
<223> OTHER INFORMATION: Synthetic

<400> SEQUENCE: 22
catgggtgat ttcgcggact act                                              23

<210> SEQ ID NO 23
<211> LENGTH: 24
<212> TYPE: DNA
<213> ORGANISM: Artificial sequence
<220> FEATURE:
<223> OTHER INFORMATION: Synthetic

<400> SEQUENCE: 23
cctcggggac atcacgggca tcta                                             24

<210> SEQ ID NO 24
<211> LENGTH: 24
<212> TYPE: DNA
<213> ORGANISM: Artificial sequence
<220> FEATURE:
<223> OTHER INFORMATION: Synthetic

<400> SEQUENCE: 24
```
ctgttaatgc tgcgctcaat agaa                                              24

<210> SEQ ID NO 25
<211> LENGTH: 24
<212> TYPE: DNA
<213> ORGANISM: Artificial sequence
<220> FEATURE:
<223> OTHER INFORMATION: Synthetic

<400> SEQUENCE: 25
gcgggtattt ggtcttgagg tttg                                              24

<210> SEQ ID NO 26
<211> LENGTH: 24
<212> TYPE: DNA
<213> ORGANISM: Artificial sequence
<220> FEATURE:
<223> OTHER INFORMATION: Synthetic

<400> SEQUENCE: 26
tttggatcac gcggcacata cata                                              24

<210> SEQ ID NO 27
<211> LENGTH: 22
<212> TYPE: DNA
<213> ORGANISM: Artificial sequence
<220> FEATURE:
<223> OTHER INFORMATION: Synthetic

<400> SEQUENCE: 27
acgggtggcg caagcagtca gg                                                22

<210> SEQ ID NO 28
<211> LENGTH: 20
<212> TYPE: DNA
<213> ORGANISM: Artificial sequence
<220> FEATURE:
<223> OTHER INFORMATION: Synthetic

<400> SEQUENCE: 28
gaggagccca cctttactga                                                   20

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
gaagatctgc cacctggttt                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
tccttcctta aggcgacact                                                   20

<210> SEQ ID NO 31
<211> LENGTH: 24
<212> TYPE: DNA
<213> ORGANISM: Artificial sequence

```
<220> FEATURE:
<223> OTHER INFORMATION: Synthetic

<400> SEQUENCE: 31
gagccgggtt tgggtgatga ataa                                              24

<210> SEQ ID NO 32
<211> LENGTH: 20
<212> TYPE: DNA
<213> ORGANISM: Artificial sequence
<220> FEATURE:
<223> OTHER INFORMATION: Synthetic

<400> SEQUENCE: 32
tgggtgatga ataacaacgg                                                   20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
aatgacgacg tctgtttgga                                                   20

<210> SEQ ID NO 34
<211> LENGTH: 24
<212> TYPE: DNA
<213> ORGANISM: Artificial sequence
<220> FEATURE:
<223> OTHER INFORMATION: Synthetic

<400> SEQUENCE: 34
acgcgttgat gctcggtggt tact                                              24

<210> SEQ ID NO 35
<211> LENGTH: 20
<212> TYPE: DNA
<213> ORGANISM: Artificial sequence
<220> FEATURE:
<223> OTHER INFORMATION: Synthetic

<400> SEQUENCE: 35
ccagctgtga caccaacata                                                   20

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
agtcatttgc gacgagtgtc                                                   20

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
ggcccacggt cctgatgata                                                   20
```

```
<210> SEQ ID NO 38
<211> LENGTH: 20
<212> TYPE: DNA
<213> ORGANISM: Artificial sequence
<220> FEATURE:
<223> OTHER INFORMATION: Synthetic

<400> SEQUENCE: 38
ggcccayggt ccagacgatr                                               20

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
ggcccatggt ccggatgatg                                               20

<210> SEQ ID NO 40
<211> LENGTH: 20
<212> TYPE: DNA
<213> ORGANISM: Artificial sequence
<220> FEATURE:
<223> OTHER INFORMATION: Synthetic

<400> SEQUENCE: 40
ccgtttggag ygttgayaac                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic

<400> SEQUENCE: 41
ctgtttggag cgttgaggtc                                               20

<210> SEQ ID NO 42
<211> LENGTH: 24
<212> TYPE: DNA
<213> ORGANISM: Artificial sequence
<220> FEATURE:
<223> OTHER INFORMATION: Synthetic

<400> SEQUENCE: 42
tacyggcacc ttgttgacca cctg                                          24

<210> SEQ ID NO 43
<211> LENGTH: 21
<212> TYPE: DNA
<213> ORGANISM: Artificial sequence
<220> FEATURE:
<223> OTHER INFORMATION: Synthetic

<400> SEQUENCE: 43
ctagagcggc ggggcgacaa a                                             21

<210> SEQ ID NO 44
<211> LENGTH: 24
<212> TYPE: DNA
<213> ORGANISM: Artificial sequence
<220> FEATURE:
<223> OTHER INFORMATION: Synthetic
```

<400> SEQUENCE: 44
gaggcggttg agctgctgga agag                                                  24

<210> SEQ ID NO 45
<211> LENGTH: 24
<212> TYPE: DNA
<213> ORGANISM: Artificial sequence
<220> FEATURE:
<223> OTHER INFORMATION: Synthetic

<400> SEQUENCE: 45
tagttcaggc ggcttcacgg tttg                                                  24

<210> SEQ ID NO 46
<211> LENGTH: 18
<212> TYPE: DNA
<213> ORGANISM: Artificial sequence
<220> FEATURE:
<223> OTHER INFORMATION: Synthetic

<400> SEQUENCE: 46
tgcgccgtac caacaaag                                                         18

<210> SEQ ID NO 47
<211> LENGTH: 24
<212> TYPE: DNA
<213> ORGANISM: Artificial sequence
<220> FEATURE:
<223> OTHER INFORMATION: Synthetic

<400> SEQUENCE: 47
tgtcacccct tgcaaactcc tatt                                                  24

<210> SEQ ID NO 48
<211> LENGTH: 19
<212> TYPE: DNA
<213> ORGANISM: Artificial sequence
<220> FEATURE:
<223> OTHER INFORMATION: Synthetic

<400> SEQUENCE: 48
agtgtacgac gctccaatg                                                        19

<210> SEQ ID NO 49
<211> LENGTH: 22
<212> TYPE: DNA
<213> ORGANISM: Artificial sequence
<220> FEATURE:
<223> OTHER INFORMATION: Synthetic

<400> SEQUENCE: 49
gcacgagtcg cggagaaaat ga                                                    22

<210> SEQ ID NO 50
<211> LENGTH: 20
<212> TYPE: DNA
<213> ORGANISM: Artificial sequence
<220> FEATURE:
<223> OTHER INFORMATION: Synthetic

<400> SEQUENCE: 50
acgagtcgcg gagaaaatga                                                       20

<210> SEQ ID NO 51

```
<211> LENGTH: 18
<212> TYPE: DNA
<213> ORGANISM: Artificial sequence
<220> FEATURE:
<223> OTHER INFORMATION: Synthetic

<400> SEQUENCE: 51
cgcgcctact ggaacaat                                              18

<210> SEQ ID NO 52
<211> LENGTH: 24
<212> TYPE: DNA
<213> ORGANISM: Artificial sequence
<220> FEATURE:
<223> OTHER INFORMATION: Synthetic

<400> SEQUENCE: 52
acgcgcttga tgactatggg ttta                                       24

<210> SEQ ID NO 53
<211> LENGTH: 20
<212> TYPE: DNA
<213> ORGANISM: Artificial sequence
<220> FEATURE:
<223> OTHER INFORMATION: Synthetic

<400> SEQUENCE: 53
ttgacggtcc acggtaacag                                            20

<210> SEQ ID NO 54
<211> LENGTH: 20
<212> TYPE: DNA
<213> ORGANISM: Artificial sequence
<220> FEATURE:
<223> OTHER INFORMATION: Synthetic

<400> SEQUENCE: 54
gaggagccca cctttactga                                            20

<210> SEQ ID NO 55
<211> LENGTH: 20
<212> TYPE: DNA
<213> ORGANISM: Artificial sequence
<220> FEATURE:
<223> OTHER INFORMATION: Synthetic

<400> SEQUENCE: 55
tacctccaag caattgtcca                                            20

<210> SEQ ID NO 56
<211> LENGTH: 26
<212> TYPE: DNA
<213> ORGANISM: Artificial sequence
<220> FEATURE:
<223> OTHER INFORMATION: Synthetic

<400> SEQUENCE: 56
caccaaactc attgtgtcat ccacga                                     26

<210> SEQ ID NO 57
<211> LENGTH: 20
<212> TYPE: DNA
<213> ORGANISM: Artificial sequence
<220> FEATURE:
<223> OTHER INFORMATION: Synthetic

<400> SEQUENCE: 57
```
gaagatctgc cacctggttt                                              20

<210> SEQ ID NO 58
<211> LENGTH: 20
<212> TYPE: DNA
<213> ORGANISM: Artificial sequence
<220> FEATURE:
<223> OTHER INFORMATION: Synthetic

<400> SEQUENCE: 58
agtgtcgcct taaggaagga                                              20

<210> SEQ ID NO 59
<211> LENGTH: 20
<212> TYPE: DNA
<213> ORGANISM: Artificial sequence
<220> FEATURE:
<223> OTHER INFORMATION: Synthetic

<400> SEQUENCE: 59
ccaccggagc actcagctgg                                              20

<210> SEQ ID NO 60
<211> LENGTH: 20
<212> TYPE: DNA
<213> ORGANISM: Artificial sequence
<220> FEATURE:
<223> OTHER INFORMATION: Synthetic

<400> SEQUENCE: 60
tccttcctta aggcgacact                                              20

<210> SEQ ID NO 61
<211> LENGTH: 20
<212> TYPE: DNA
<213> ORGANISM: Artificial sequence
<220> FEATURE:
<223> OTHER INFORMATION: Synthetic

<400> SEQUENCE: 61
agggaagaca acaccacgat                                              20

<210> SEQ ID NO 62
<211> LENGTH: 20
<212> TYPE: DNA
<213> ORGANISM: Artificial sequence
<220> FEATURE:
<223> OTHER INFORMATION: Synthetic

<400> SEQUENCE: 62
aaacaccagg gtccggccag                                              20

<210> SEQ ID NO 63
<211> LENGTH: 20
<212> TYPE: DNA
<213> ORGANISM: Artificial sequence
<220> FEATURE:
<223> OTHER INFORMATION: Synthetic

<400> SEQUENCE: 63
tgggtgatga ataacaacgg                                              20

<210> SEQ ID NO 64
<211> LENGTH: 20
<212> TYPE: DNA

```
<213> ORGANISM: Artificial sequence
<220> FEATURE:
<223> OTHER INFORMATION: Synthetic

<400> SEQUENCE: 64
gatctatgtg cgtgggacag                                              20

<210> SEQ ID NO 65
<211> LENGTH: 22
<212> TYPE: DNA
<213> ORGANISM: Artificial sequence
<220> FEATURE:
<223> OTHER INFORMATION: Synthetic

<400> SEQUENCE: 65
ccactctgcc acacaccaac cc                                           22

<210> SEQ ID NO 66
<211> LENGTH: 20
<212> TYPE: DNA
<213> ORGANISM: Artificial sequence
<220> FEATURE:
<223> OTHER INFORMATION: Synthetic

<400> SEQUENCE: 66
aatgacgacg tctgtttgga                                              20

<210> SEQ ID NO 67
<211> LENGTH: 20
<212> TYPE: DNA
<213> ORGANISM: Artificial sequence
<220> FEATURE:
<223> OTHER INFORMATION: Synthetic

<400> SEQUENCE: 67
catgaccgtg atcacacaaa                                              20

<210> SEQ ID NO 68
<211> LENGTH: 20
<212> TYPE: DNA
<213> ORGANISM: Artificial sequence
<220> FEATURE:
<223> OTHER INFORMATION: Synthetic

<400> SEQUENCE: 68
ctggtgagcc cgaagcaccc                                              20

<210> SEQ ID NO 69
<211> LENGTH: 20
<212> TYPE: DNA
<213> ORGANISM: Artificial sequence
<220> FEATURE:
<223> OTHER INFORMATION: Synthetic

<400> SEQUENCE: 69
ccagctgtga caccaacata                                              20

<210> SEQ ID NO 70
<211> LENGTH: 21
<212> TYPE: DNA
<213> ORGANISM: Artificial sequence
<220> FEATURE:
<223> OTHER INFORMATION: Synthetic

<400> SEQUENCE: 70
tttgactaca gccacacttg g                                            21
```

<210> SEQ ID NO 71
<211> LENGTH: 26
<212> TYPE: DNA
<213> ORGANISM: Artificial sequence
<220> FEATURE:
<223> OTHER INFORMATION: Synthetic

<400> SEQUENCE: 71
ccagtggacc tagtcaaaca gggaca                                          26

<210> SEQ ID NO 72
<211> LENGTH: 20
<212> TYPE: DNA
<213> ORGANISM: Artificial sequence
<220> FEATURE:
<223> OTHER INFORMATION: Synthetic

<400> SEQUENCE: 72
agtcatttgc gacgagtgtc                                                 20

<210> SEQ ID NO 73
<211> LENGTH: 20
<212> TYPE: DNA
<213> ORGANISM: Artificial sequence
<220> FEATURE:
<223> OTHER INFORMATION: Synthetic

<400> SEQUENCE: 73
acggtcttca ctccagcttt                                                 20

<210> SEQ ID NO 74
<211> LENGTH: 20
<212> TYPE: DNA
<213> ORGANISM: Artificial sequence
<220> FEATURE:
<223> OTHER INFORMATION: Synthetic

<400> SEQUENCE: 74
tcggcataca tgcgcactgc                                                 20

<210> SEQ ID NO 75
<211> LENGTH: 9431
<212> TYPE: DNA
<213> ORGANISM: Human Pegivirus 2

<400> SEQUENCE: 75
gtgtttgacg tgtgacaatg ccatgaggga tcatgacact ggggtgagcg gaggcagcac      60
cgaagtcggg tgaactcgac tcccagtgcg accacctggc ttggtcgttc atggagggca    120
tgcccacggg aacgctgatc gtgcaaaggg atgggtccct gcactggtgc catgcgcggc    180
accactccgt acagcctgat agggtggcgg cgggcccccc cagtgtgacg tccgtggagc    240
gcaacatggg gtgttcaact gatcaaacca tttgttctcc agtcgtggag ccgactata     300 atacctcctc gggctgccgg gccttaaatg ggagctacca ctgcggtggt ggctcttgcc    360
ggtcaccaag tcgtgtgcag gttgcaggac gagtcctgcg gctgtgcgca ttccttgcgc    420
tgatcggatc cggtatgtgt tccatccggt ccaaaaatga agggcgcatt gagtcagggc    480
aaatattgca gtctcagcgc gcatgttgga ctggtgaggg tttcgctttc ttttctaact    540
gttgcaatca atctgacatt atgtggtgtt tgcaccgttg gtgtgtgaca agacctggct    600
gtttggtgtg cacgggcaat gccactcatc ctgtctgctg ggactatctt gggtccggtg    660

```
tgagtcggcg gcctgcgcgt cgaatgggtg agggagctga agtgcttctt cgcttgatcg    720
gcattgcagg ttggctcggg ctcttagctg aggctcttgg tatgtctgag atctatgcag    780 cttttcctttg ctttggattt attgcttggt atggctgggg tatacctaag acattggtgt    840
gcacagtctg ccctgcagtg aacatttctc cctatagctt cttatctcca gatactatcg    900
catttggtac gtggctacta caactgcctg gtcttttgtg gcaaatgttt gtcagcttcc    960
ctatacttta cagtacttgg attctttggt tgttgctcag cggcaagact gttgctgtga   1020
tagcgatcct tttggctagt cctacggtta tggcatacaa gcatcaagct gatagctacc   1080
tcaaatactg taccataacc aatgcttcaa ctgctatgaa ctgtgactgc ccctttggaa   1140
ctttcactcg caatactgag tctggttttca ctataccctag attctgtcct gttaaactta   1200
atagctctac atttatctgt tcatgggggt cgtggtggtg gtttgctgag aacatcacac   1260
gtccatactc ggacgttggc atgccgccag caccgatttc cgctttgtgc tatatctatt   1320
caaacaatga cccaccttct tggtatcgta acacaactat catacctcag aactgttaca   1380
actctacggc tgatcctacc acagctccat gccgtgacaa gtggggcaat gcaactgctt   1440
gtattcttga ccgccggtcg cggttctgcg gggactgcta tggcggttgc ttctacacta   1500
atggtagtca tgaccgatcc tgggatcgat gcggaattgg ttaccgtgat ggactcatag   1560
agttcgtgca gctcggtcag attcgaccta acatcgcgaa tacgaccatt gagctcctcg   1620
ctggcgcctc gcttgtgatc gcatccggtc ttcgggctgg gtatggttgc agccgagcgc   1680
acggcgtggt gcactgcttt aagtgtcctt cataccgtga ccttgaacgg ttcgggcccg   1740
ggcttgggaa atgggtgcca ttgcctggcg agcctgtccc ggagtgtgt attaacccgc    1800 agtgggcgag gcgcggcttc cgggtgtcta ataatcccctt aagcgtgcta cagaccttcg   1860
ttgaggacat tttcttagcg cctttctgca atccgacgcc tggccgtgta cgtgtgtgta   1920
acaatactgc tttctacccg agaggaggcg gctttgtgca gctcatcgga gacgtccagg   1980
tgttaacccc caactctaca tctttgcact ctctgctgac tttgatatcc cttatcttgt   2040
tagtgtgtgt tgtttctggc gcgcgattcg ttccattggg aatcatattc ttctggagcg   2100
tgcgccacgt atatgcttct tgttacttaa gctgtgattg ggctgttgtc aacgatgcgt   2160
tctgtttcac atctggcact tgtgctacct tcaacgacgt cttgtgtctg ccggttgcgg   2220
cgcgcatatc gtcctgtggc catgctgtgc caccgcccga ccgtggttgg gaggtgcccg   2280
cagcgatgtc atgggcgatt tcgcgtacta ccggcttgac gttcgatgtc ttttccttca   2340
tccagtacct tcctactgtg cctggcaaca attccgatat catttactgt ggtgaaccaa   2400
gcttcttcgg ggacatcacg ggtatctatt ggccttactt tttgcctggc atgttgctct   2460
tgtacttgac tccctcctg ggtttaaggt taatgcttgc cggctttaat atagatggct   2520
tgtttcccat acggcatgcc acggctgcac tgaggttctc gacttcgcgt gtgaccttga   2580
gtgtcgtatt tgctttccta atctatatat tatctcatcc tgttaatgct gcgctcaata   2640
gaatgttcct agcatctgca aatctagaga tgatcttatc ctttgatacc tatcatgaga   2700
ctgttcttta cgtcgtttgt ctattgctct acctccaggt gtcgccccgt gcgggcttgg   2760
ctgctatggt ggccatcaag ctatctcgag gcctgttatt cgctgtggtg ttggcgcacg   2820
gagtgtgccg acctgggcgg gtatttggtc ttgaggtttg cgcggacatc tcttggttgg   2880
tggagtttac tggcaactgc acttggtaca tgtcctgtgt cttctctttt tggtgcgcag   2940
tgtttgcctt caccagtcca cttgacgac agtataagct tcagatctat cggtactggg   3000
cgcaggccta tgccagactc atcctcgctg tcggttgtgg tcctctcggg agggagttcc   3060
```

```
atttccgtgc gagcgtgggc gtgctctggt gtggtgcttg catgctctgg ccccgtgagt    3120
gctctgaaat cagcttggtc tttattctgt gtgctctgac tgtggacacc atagacacat    3180
ggttagtagc gtgcttgtcc gcagggccaa gcgcgcgaac ccttgcaact ctggccgatg    3240
acatggcgcg cattggtgac caccgggcgt tgcgcgccgt gttgcgttgc tttggatcac    3300
gtggcacata catatacaac cacatgggcc aggtctcaga acgggtggcg caagcagtca    3360
gggatttcgg cggttgcttg gaaccagtcg tgttggagga gcccacctttt actgaggtcg    3420 tggatgatac aatgaatttg gtgtgtggac aattgcttgg aggtaaaccc gtggtggccc    3480
gctgcggcac gcgtgtctta gtgggacacc tcaaccctga agacctgcca cctggtttcc    3540
agctgagtgc tccggtggtt attaccaaac caagcattgg tacgtggccc tttcttaagg    3600
cgacactcac agggcgtgct gaaacaccgg gatccggcca gatcgtggtg ttgtcttccc    3660
tgacaggtcg gtcaatgggt actgcagtga atggcacact gtatgcgacc ggccacggtg    3720
ctggtgcgcg cggcctagcc acgtgcgctg gtttgaggac gccactttac acggcattat    3780
ctgaagatgt cgtggcctac tcttgccttc cgggcatgag ctccctagag tcctgcaact    3840
gctcgcccag ccgggtttgg gtggtgaaca acaacgagg gttggtgtgt ggcagagtgg    3900
agaaagacga cgtctgtttg gactgtccca cgcacataga tcaactgcgg ggtgcttcgg    3960
ggtcgccggt tttgtgtgat cacggtcatg catacgcgtt gatgctcggt ggctactcta    4020
ccagtggtat ttgtgcgcgt gtccggatag tccggccatg gcagaacgcc tattcctcct    4080
caggggggca aggcggaatg caggcgccag ctgtgacacc aacatactct gaaatcacct    4140
actatgcccc tactggttct ggtaaatcaa caaaatatcc agtggaccta gtcaagcagg    4200
gacacaaagt attagtcctt ttaccaagtg tggctgtcgt caaaagtatg gctccttaca    4260
ttaaggaaaa atataagatt agacctgaaa ttagagctgg cacagggcct gacggtgtga    4320
cggtcatcac tggcgagaac ttggcgtaca tgacctatgg ccgtttcctt gtagatccgg    4380
aaacgaatct gcggggttac gctgtagtca tctgcgacga gtgccatgac acatcatcca    4440
ccacgctact cggcatcggc gcagtgcgca tgtatgctga aaagctgga gtgaagaccg    4500 ttgtattcgc cacagccact cctgctggca ttcaagtgca gtcacatccc aacattgatg    4560
aatatctatt gactgataca ggcgacgtgg aattctacgg cgctaaaatt aaattggaca    4620
acatcagaac tggtagacat gttatctttt gccactcgaa ggccaggtgt gcggaactaa    4680
cgcagcagct ctccggcctt ggtgttcgtg cagtgagttt ttggcgcggc tgtgacatca    4740
agagcattcc cgcctcagac tctattgttg tagtggcaac tgatgcattg tccacaggct    4800
acacagggaa ctttgattcg gtcattgact gcgggtgttg cgtagagcaa actgtaacaa    4860
ttgacatgga cccacgttc tccatctcgg cccgagtggt gccatgcact gctgcattgc    4920
gtatgcagcg gcgcggacgc accggtcgtg gcaggagggg agcgtactac acaaccactc    4980
caggagcagc accctgcgtc agcgttcccg atgctaacgt ctggcaatca gtggagtcag    5040
ccatggtctt ttatgattgg agtgctgcca ggatagagca atgcctggcg gcataccatg    5100
atttagggtg cacaccacgc atcagttgtg acccacacac tccagtgcgg gtgatggaca    5160
cactgagggc gtatctgcgc agacctgagg tgacgaccgc ggctctcgca ggagagcagt    5220
ggccgctgct ttacggcgtg cagttgtgca tctgcaaaga gaccgaggcc cacggtccag    5280
acgatggcat caagtggaaa tgcttactca ataacaacaa caaaacaccc ctgttgtatg    5340
ccttagacaa tcctacactg gaattcacta cccaacatga cttgactcgc cgtatagctg    5400
```

```
gcgctttatc gagcacagtg ttcgtggaga caggctacgg ccccatcctc ctcgctggcg   5460
ctgctttggc tgcctccttt gcctttgcgg gcgccactgg agctttagtg ccgtcggccg   5520
tttggagcgt tgaaaacggg cttgctggcg tgacccgtcc cgatgcgaca gacgagaccg   5580
cggcctacgc gcagcgcttg taccaagcct gcgcagattc aggaattctc gccagcttgc   5640
agggtacggc gagtgcggca ctgagcagac tggccgatgc cagtaagggt gctagtcaat   5700
atctggcagc cgcgcctcct tcgcccgccc ccctggtaca ggtgctgcag ttcctcgaga   5760
ccaattttag ctccattgca tctttcggtc tgctctgtgc cggctgtcag gccggcgagt   5820
gcttcactgc gcttgccggg ttggtgtccg gtgctacagc tggcttggga ggtgcccata   5880
agtggttgtt agctattgca ggaacttggc tagttagctt gcagactggg ccccgtggcg   5940
gcatggttgc gggtctctca gttctagcag gctgttgcat cggtagtgtc accgggcttg   6000
acttcctgtt tgggtgcctt acaggttggg aggccgtggt cggtgctgcg gttgcaacgc   6060
agaaaatctt gtctggttcg gctgacatga ccactctggt agatctccta cctgctctct   6120
tctcccctgg cgccggcata gctggcgtcg tgcttgtctt tattctaagc aactcaagtg   6180
taaccatgtg ggctaatcgg ctattgtcca tgtgtgcaaa acaaactatt tgtgaaaatt   6240
acttcttaac tgagaaattt ggccaacaat taagcaaact ttccctgtgg cgctctgtgt   6300
accattgggc gcaggcacgt gaaggataca cacagtgcgg tgtggtcagc gggatctgga   6360
gctttgtctt gtgcattcta cgtgctgtgt gggattgggc ggctaaacat gtgccacggt   6420
tccgtgtgcc tatgattggc tgctcacctg cgtggtgcgg gcgctggctt ggtactggca   6480
ccttgttgac cacctgtggg tgtggagaac gtgtatccct tcagtgcctt tgctcgacat   6540
ctgacccaac actcagtgtg ggccgttggt gttggtgtag ttggcgtgtt gggttcccat   6600
tcaacccgac gacgacagcc accggcactt tacggccgga catcagtgac gccaccaaat   6660
tgggcttccg gtatggtgtc gccgagatcg tggagctaga gcggcggggc aacaaatggc   6720
atgtctgtgc agcatcatgt tgcttggacc gggccagcgt tgcatccgcc gtgagggccc   6780
caccggtcac ggccgatggc atacctatca gtaccttttc tccaccacaa acttacaaac   6840
tctctctttg ttcttttgat tcagtttgca tgactactaa cttatgtaat ccagctaaga   6900
ccctgagtgt gtgctcgcag gaggctgttg agctactgga agaaacagtt gacagagcac   6960
aagtagtgat gtgtcaaaat ctggaggcgc gaagacgcgc tgagtttgat gcatggcaag   7020
ttcgcgaagc aattcgcgac gagtacacgc gtttggcaga cgaggatgtt gacgcgacaa   7080
cgtcggtgaa accccggtg gccaaggctg ctgtgggtag ctcgacgttg gatgatgtta   7140
gcgtgctgac tgtcttgcgc gaactcggtg accagtgcca aaatgctatc aaatttgtag   7200
ttcaggcggc ttcacggttt gttccaccag tgcccaagcc acgcacgcgt gtctcgggtg   7260
tgttggagcg tgtgcgcatg tgcatgcgca cgccaccaat caagtttgag gctgccgcag   7320
taccaattca tgatataatc ccagaagagt gtcacattgt gctacgctgt accggctgca   7380
acgaccaggc cttgactgtt ccgtacgcat cttgcactca gtctttaatc aagcatttga   7440
ctagtaaaca cagtcactac attccaaaac agaagataga agaggacaca gaagtaactg   7500
tcatttgcgc cgtaccaaca acgcgcgcaa gcaaactcat cacattcaga gcaggtgatc   7560
gatcagtctc atgttgtcac cccttgcaaa cccctattag ggccctgctt ctaaagtacg   7620
ggttacctat cgggaagtgg tctgactgca acgggcccct tggtgacgat gctcgagtct   7680
gtgacgtcaa tggagtaaca acttatgaac catgcatgca atcctacagt tggtttcgac   7740
cgattgtggc accaacaacc ccacctttgc ctgcaacccg gaccgtggct ggcattttac   7800
```

```
gcgcagacac atcgcgcgtt tacaccacaa cggcggttga cgtctccgag cggcaggcca    7860
aggtcacaat tgatcaaaca tcagccaagg tggatcagtg tttccgagac acatacaatt    7920
gctgccttgc taaggcaaag accttcagac aatctggcat gtcatatgag gatgctgtgt    7980
caaagatgcg cgcaaacacc acgcgtgacc ataacaacgg catcacttat tcagatttgg    8040
tctctggacg cgcaaaacct gtcgttcaga aaattgtaaa tcaaatgcgc gccggagtgt    8100
acgacgctcc gatgcgcatt atcccaaaac ctgaagtgtt ccctcgagac aaaacaacac    8160
ggaagccacc gaggttcatc gttttccctg gtgcgccgc gcgagtcgcg gagaaaatga    8220
tcctgggtga tcctggcgcg ataaccaagc acgtgctagg tgatgcctac gggtttgcca    8280
ctccgccgca tgagcgcgcg cgcctgttgg aacaatggtg gaaccgcgca acggagccac    8340
aagctatcgc ggttgatgcg atctgctttg atagcaccat cacggcagag gacatggatc    8400
gtgaggctaa catcgtggct gcagcgcata cggaccctga aggtgttcac ggcctatata    8460
attattacaa aagaagcccc atgtgtgaca tcacggggaa ggttgtcgga gtgcgttgct    8520
gtcgagcctc gggtacgctt acaacaagca gtggcaacac gcttacttgc taccttaagg    8580
ttcgtgcagc ttgcacgcgc tccggcatta aaccaattgg cttactaatt catggagatg    8640
acaccctcat cgtcacagaa cgttgcgctc aagagactct cgatgagttc agcaacgcac    8700
ttgatgacta tgggttccca cacaccatcc aggcgtctgg ggacctctcg tctatcgagt    8760
gctgtagcgc acgtgtggac agcgtttgcc tccggggagg tatgcgtcgc atgcttgtgc    8820
cacaagctcg acgtgcgatt gcacgcgttc tcggggaaaa gggcgatcca ctgggtacca    8880
tcggtagcta tgttgtcatg tatcccactg cggccgtgac tgtctacgtg ctattgcccc    8940
tgttgtgcat gctcatacga aatgagccat cacagacggg gacacttgtg acgctgacgg    9000
tccacggtaa cagtgtgagt gtgccagcgt ggctgcttcc aaccatcatt gcaaatttac    9060
atggtcgtga cgcactacag gtagtccgtc acagtgcagc ttccatggcg gaattgtcat    9120
cagcgttggc cttcttttggc atgagagggt tgaattgctg gaggcggaga cgccgtgcca    9180
ttagggctga tatgatcaag tcgggcgggt ggaatgcgaa tttcgcgcag atgttactgt    9240
ggtcaccgga ggtaagaaca ccacaacccg aaccaagggg tctgtgtctt ttgccgccgg    9300
aactgtggga gcgtccgtac gaaaatttgc acttgagcac gatcgaccgc aatcgtggtg    9360
ctagtcgctt acggttttgg ttggttgcta gtgctatact cgctctgctt tgcttgtaaa    9420
tcttaaatca a                                                        9431
```

<210> SEQ ID NO 76
<211> LENGTH: 124
<212> TYPE: PRT
<213> ORGANISM: Human Pegivirus 2

<400> SEQUENCE: 76

```
Met Glu Gly Met Pro Thr Gly Thr Leu Ile Val Gln Arg Asp Gly Ser
1               5                   10                  15

Leu His Trp Cys His Ala Arg His His Ser Val Gln Pro Asp Arg Val
            20                  25                  30

Ala Ala Gly Pro Pro Ser Val Thr Ser Val Glu Arg Asn Met Gly Cys
        35                  40                  45

Ser Thr Asp Gln Thr Ile Cys Ser Pro Val Val Glu Ala Asp Tyr Asn
    50                  55                  60

Thr Ser Ser Gly Cys Arg Ala Leu Asn Gly Ser Tyr His Cys Gly Gly
65                  70                  75                  80
```

Gly Ser Cys Arg Ser Pro Ser Arg Val Gln Val Ala Gly Arg Val Leu
                85                  90                  95

Arg Leu Cys Ala Phe Leu Ala Leu Ile Gly Ser Gly Met Cys Ser Ile
            100                 105                 110

Arg Ser Lys Asn Glu Gly Arg Ile Glu Ser Gly Gln
        115                 120

<210> SEQ ID NO 77
<211> LENGTH: 191
<212> TYPE: PRT
<213> ORGANISM: Human Pegivirus 2

<400> SEQUENCE: 77

Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
            20                  25                  30

Trp Cys Val Thr Arg Pro Gly Cys Leu Val Cys Thr Gly Asn Ala Thr
        35                  40                  45

His Pro Val Cys Trp Asp Tyr Leu Gly Ser Gly Val Ser Arg Arg Pro
    50                  55                  60

Ala Arg Arg Met Gly Glu Gly Ala Glu Val Leu Leu Arg Leu Ile Gly
65                  70                  75                  80

Ile Ala Gly Trp Leu Gly Leu Leu Ala Glu Ala Leu Gly Met Ser Glu
                85                  90                  95

Ile Tyr Ala Ala Phe Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Leu Leu Gln Leu Pro Gly Leu Leu Trp Gln Met Phe Val Ser Phe Pro
145                 150                 155                 160

Ile Leu Tyr Ser Thr Trp Ile Leu Trp Leu Leu Leu Ser Gly Lys Thr
                165                 170                 175

Val Ala Val Ile Ala Ile Leu Leu Ala Ser Pro Thr Val Met Ala
            180                 185                 190

<210> SEQ ID NO 78
<211> LENGTH: 354
<212> TYPE: PRT
<213> ORGANISM: Human Pegivirus 2

<400> SEQUENCE: 78

Tyr Lys His Gln Ala Asp Ser Tyr Leu Lys Tyr Cys Thr Ile Thr Asn
1               5                   10                  15

Ala Ser Thr Ala Met Asn Cys Asp Cys Pro Phe Gly Thr Phe Thr Arg
            20                  25                  30

Asn Thr Glu Ser Gly Phe Thr Ile Pro Arg Phe Cys Pro Val Lys Leu
        35                  40                  45

Asn Ser Ser Thr Phe Ile Cys Ser Trp Gly Ser Trp Trp Trp Phe Ala
    50                  55                  60

Glu Asn Ile Thr Arg Pro Tyr Ser Asp Val Gly Met Pro Pro Ala Pro
65                  70                  75                  80

Ile Ser Ala Leu Cys Tyr Ile Tyr Ser Asn Asn Asp Pro Pro Ser Trp
                85                  90                  95

Tyr Arg Asn Thr Thr Ile Ile Pro Gln Asn Cys Tyr Asn Ser Thr Ala
            100                 105                 110

Asp Pro Thr Thr Ala Pro Cys Arg Asp Lys Trp Gly Asn Ala Thr Ala
            115                 120                 125

Cys Ile Leu Asp Arg Arg Ser Arg Phe Cys Gly Asp Cys Tyr Gly Gly
            130                 135                 140

Cys Phe Tyr Thr Asn Gly Ser His Asp Arg Ser Trp Asp Arg Cys Gly
145                 150                 155                 160

Ile Gly Tyr Arg Asp Gly Leu Ile Glu Phe Val Gln Leu Gly Gln Ile
                165                 170                 175

Arg Pro Asn Ile Ala Asn Thr Thr Ile Glu Leu Leu Ala Gly Ala Ser
            180                 185                 190

Leu Val Ile Ala Ser Gly Leu Arg Ala Gly Tyr Gly Cys Ser Arg Ala
            195                 200                 205

His Gly Val Val His Cys Phe Lys Cys Pro Ser Tyr Arg Asp Leu Glu
            210                 215                 220

Arg Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
                245                 250                 255

Val Ser Asn Asn Pro Leu Ser Val Leu Gln Thr Phe Val Glu Asp Ile
            260                 265                 270

Phe Leu Ala Pro Phe Cys Asn Pro Thr Pro Gly Arg Val Arg Val Cys
            275                 280                 285

Asn Asn Thr Ala Phe Tyr Pro Arg Gly Gly Phe Val Gln Leu Ile
            290                 295                 300

Gly Asp Val Gln Val Leu Thr Pro Asn Ser Thr Ser Leu His Ser Leu
305                 310                 315                 320

Leu Thr Leu Ile Ser Leu Ile Leu Leu Val Cys Val Val Ser Gly Ala
                325                 330                 335

Arg Phe Val Pro Leu Gly Ile Ile Phe Phe Trp Ser Val Arg His Val
            340                 345                 350

Tyr Ala

<210> SEQ ID NO 79
<211> LENGTH: 237
<212> TYPE: PRT
<213> ORGANISM: Human Pegivirus 2

<400> SEQUENCE: 79

Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
            20                  25                  30

Val Ala Ala Arg Ile Ser Ser Cys Gly His Ala Val Pro Pro Pro Asp
            35                  40                  45

Arg Gly Trp Glu Val Pro Ala Ala Met Ser Trp Ala Ile Ser Arg Thr
    50                  55                  60

Thr Gly Leu Thr Phe Asp Val Phe Ser Phe Ile Gln Tyr Leu Pro Thr
65                  70                  75                  80

Val Pro Gly Asn Asn Ser Asp Ile Ile Tyr Cys Gly Glu Pro Ser Phe
                85                  90                  95

Phe Gly Asp Ile Thr Gly Ile Tyr Trp Pro Tyr Phe Leu Pro Gly Met
            100                 105                 110

```
Leu Leu Leu Tyr Leu Thr Pro Leu Gly Leu Arg Leu Met Leu Ala
            115                 120                 125

Gly Phe Asn Ile Asp Gly Leu Phe Pro Ile Arg His Ala Thr Ala Ala
130                 135                 140

Leu Arg Phe Ser Thr Ser Arg Val Thr Leu Ser Val Val Phe Ala Phe
145                 150                 155                 160

Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
            180                 185                 190

His Glu Thr Val Leu Tyr Val Val Cys Leu Leu Tyr Leu Gln Val
            195                 200                 205

Ser Pro Arg Ala Gly Leu Ala Ala Met Val Ala Ile Lys Leu Ser Arg
210                 215                 220

Gly Leu Leu Phe Ala Val Val Leu Ala His Gly Val Cys
225                 230                 235

<210> SEQ ID NO 80
<211> LENGTH: 240
<212> TYPE: PRT
<213> ORGANISM: Human Pegivirus 2

<400> SEQUENCE: 80

Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
            20                  25                  30

Ser Phe Trp Cys Ala Val Phe Ala Phe Thr Ser Pro Leu Gly Arg Gln
            35                  40                  45

Tyr Lys Leu Gln Ile Tyr Arg Tyr Trp Ala Gln Ala Tyr Ala Arg Leu
    50                  55                  60

Ile Leu Ala Val Gly Cys Gly Pro Leu Gly Arg Glu Phe His Phe Arg
65                  70                  75                  80

Ala Ser Val Gly Val Leu Trp Cys Gly Ala Cys Met Leu Trp Pro Arg
                85                  90                  95

Glu Cys Ser Glu Ile Ser Leu Val Phe Ile Leu Cys Ala Leu Thr Val
            100                 105                 110

Asp Thr Ile Asp Thr Trp Leu Val Ala Cys Leu Ser Ala Gly Pro Ser
        115                 120                 125

Ala Arg Thr Leu Ala Thr Leu Ala Asp Asp Met Ala Arg Ile Gly Asp
    130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Phe Gly Gly Cys Leu Glu Pro Val Val Leu Glu Glu Pro
            180                 185                 190

Thr Phe Thr Glu Val Val Asp Asp Thr Met Asn Leu Val Cys Gly Gln
        195                 200                 205

Leu Leu Gly Gly Lys Pro Val Val Ala Arg Cys Gly Thr Arg Val Leu
    210                 215                 220

Val Gly His Leu Asn Pro Glu Asp Leu Pro Pro Gly Phe Gln Leu Ser
225                 230                 235                 240
```

```
<210> SEQ ID NO 81
<211> LENGTH: 628
<212> TYPE: PRT
<213> ORGANISM: Human Pegivirus 2

<400> SEQUENCE: 81

Ala Pro Val Val Ile Thr Lys Pro Ser Ile Gly Thr Trp Pro Phe Leu
1               5                   10                  15

Lys Ala Thr Leu Thr Gly Arg Ala Glu Thr Pro Gly Ser Gly Gln Ile
            20                  25                  30

Val Val Leu Ser Ser Leu Thr Gly Arg Ser Met Gly Thr Ala Val Asn
        35                  40                  45

Gly Thr Leu Tyr Ala Thr Gly His Gly Ala Gly Ala Arg Gly Leu Ala
    50                  55                  60

Thr Cys Ala Gly Leu Arg Thr Pro Leu Tyr Thr Ala Leu Ser Glu Asp
65                  70                  75                  80

Val Val Ala Tyr Ser Cys Leu Pro Gly Met Ser Ser Leu Glu Ser Cys
                85                  90                  95

Asn Cys Ser Pro Ser Arg Val Trp Val Val Asn Asn Gly Gly Leu
            100                 105                 110

Val Cys Gly Arg Val Glu Lys Asp Asp Val Cys Leu Asp Cys Pro Thr
        115                 120                 125

His Ile Asp Gln Leu Arg Gly Ala Ser Gly Ser Pro Val Leu Cys Asp
    130                 135                 140

His Gly His Ala Tyr Ala Leu Met Leu Gly Gly Tyr Ser Thr Ser Gly
145                 150                 155                 160

Ile Cys Ala Arg Val Arg Ile Val Arg Pro Trp Gln Asn Ala Tyr Ser
                165                 170                 175

Ser Ser Gly Gly Gln Gly Gly Met Gln Ala Pro Ala Val Thr Pro Thr
            180                 185                 190

Tyr Ser Glu Ile Thr Tyr Tyr Ala Pro Thr Gly Ser Gly Lys Ser Thr
        195                 200                 205

Lys Tyr Pro Val Asp Leu Val Lys Gln Gly His Lys Val Leu Val Leu
    210                 215                 220

Leu Pro Ser Val Ala Val Val Lys Ser Met Ala Pro Tyr Ile Lys Glu
225                 230                 235                 240

Lys Tyr Lys Ile Arg Pro Glu Ile Arg Ala Gly Thr Gly Pro Asp Gly
                245                 250                 255

Val Thr Val Ile Thr Gly Glu Asn Leu Ala Tyr Met Thr Tyr Gly Arg
            260                 265                 270

Phe Leu Val Asp Pro Glu Thr Asn Leu Arg Gly Tyr Ala Val Val Ile
        275                 280                 285

Cys Asp Glu Cys His Asp Thr Ser Ser Thr Leu Leu Gly Ile Gly
    290                 295                 300

Ala Val Arg Met Tyr Ala Glu Lys Ala Gly Val Lys Thr Val Val Phe
305                 310                 315                 320

Ala Thr Ala Thr Pro Ala Gly Ile Gln Val Gln Ser His Pro Asn Ile
                325                 330                 335

Asp Glu Tyr Leu Leu Thr Asp Thr Gly Asp Val Glu Phe Tyr Gly Ala
            340                 345                 350

Lys Ile Lys Leu Asp Asn Ile Arg Thr Gly Arg His Val Ile Phe Cys
        355                 360                 365

His Ser Lys Ala Arg Cys Ala Glu Leu Thr Gln Gln Leu Ser Gly Leu
    370                 375                 380
```

```
Gly Val Arg Ala Val Ser Phe Trp Arg Gly Cys Asp Ile Lys Ser Ile
385                 390                 395                 400

Pro Ala Ser Asp Ser Ile Val Val Ala Thr Asp Ala Leu Ser Thr
            405                 410                 415

Gly Tyr Thr Gly Asn Phe Asp Ser Val Ile Asp Cys Gly Cys Cys Val
                420                 425                 430

Glu Gln Thr Val Thr Ile Asp Met Asp Pro Thr Phe Ser Ile Ser Ala
            435                 440                 445

Arg Val Val Pro Cys Thr Ala Ala Leu Arg Met Gln Arg Gly Arg
    450                 455                 460

Thr Gly Arg Gly Arg Gly Ala Tyr Tyr Thr Thr Pro Gly Ala
465                 470                 475                 480

Ala Pro Cys Val Ser Val Pro Asp Ala Asn Val Trp Gln Ser Val Glu
                485                 490                 495

Ser Ala Met Val Phe Tyr Asp Trp Ser Ala Ala Arg Ile Glu Gln Cys
                500                 505                 510

Leu Ala Ala Tyr His Asp Leu Gly Cys Thr Pro Arg Ile Ser Cys Asp
                515                 520                 525

Pro His Thr Pro Val Arg Val Met Asp Thr Leu Arg Ala Tyr Leu Arg
                530                 535                 540

Arg Pro Glu Val Thr Thr Ala Ala Leu Ala Gly Glu Gln Trp Pro Leu
545                 550                 555                 560

Leu Tyr Gly Val Gln Leu Cys Ile Cys Lys Glu Thr Glu Ala His Gly
                565                 570                 575

Pro Asp Asp Gly Ile Lys Trp Lys Cys Leu Leu Asn Asn Asn Lys
            580                 585                 590

Thr Pro Leu Leu Tyr Ala Leu Asp Asn Pro Thr Leu Glu Phe Thr Thr
                595                 600                 605

Gln His Asp Leu Thr Arg Arg Ile Ala Gly Ala Leu Ser Ser Thr Val
                610                 615                 620

Phe Val Glu Thr
625

<210> SEQ ID NO 82
<211> LENGTH: 41
<212> TYPE: PRT
<213> ORGANISM: Human Pegivirus 2

<400> SEQUENCE: 82

Gly Tyr Gly Pro Ile Leu Leu Ala Gly Ala Leu Ala Ala Ser Phe
1               5                   10                  15

Ala Phe Ala Gly Ala Thr Gly Ala Leu Val Pro Ser Ala Val Trp Ser
            20                  25                  30

Val Glu Asn Gly Leu Ala Gly Val Thr
            35                  40

<210> SEQ ID NO 83
<211> LENGTH: 262
<212> TYPE: PRT
<213> ORGANISM: Human Pegivirus 2

<400> SEQUENCE: 83

Arg Pro Asp Ala Thr Asp Glu Thr Ala Ala Tyr Ala Gln Arg Leu Tyr
1               5                   10                  15

Gln Ala Cys Ala Asp Ser Gly Ile Leu Ala Ser Leu Gln Gly Thr Ala
            20                  25                  30
```

```
Ser Ala Ala Leu Ser Arg Leu Ala Asp Ala Ser Lys Gly Ala Ser Gln
            35                  40                  45

Tyr Leu Ala Ala Ala Pro Pro Ser Pro Ala Pro Leu Val Gln Val Leu
 50                  55                  60

Gln Phe Leu Glu Thr Asn Phe Ser Ser Ile Ala Ser Phe Gly Leu Leu
 65                  70                  75                  80

Cys Ala Gly Cys Gln Ala Gly Glu Cys Phe Thr Ala Leu Ala Gly Leu
                 85                  90                  95

Val Ser Gly Ala Thr Ala Gly Leu Gly Ala His Lys Trp Leu Leu
                100                 105                 110

Ala Ile Ala Gly Thr Trp Leu Val Ser Leu Gln Thr Gly Pro Arg Gly
            115                 120                 125

Gly Met Val Ala Gly Leu Ser Val Leu Ala Gly Cys Cys Ile Gly Ser
        130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Val Asp Leu Leu Pro Ala Leu Phe Ser Pro Gly
            180                 185                 190

Ala Gly Ile Ala Gly Val Val Leu Val Phe Ile Leu Ser Asn Ser Ser
        195                 200                 205

Val Thr Met Trp Ala Asn Arg Leu Leu Ser Met Cys Ala Lys Gln Thr
            210                 215                 220

Ile Cys Glu Asn Tyr Phe Leu Thr Glu Lys Phe Gly Gln Gln Leu Ser
225                 230                 235                 240

Lys Leu Ser Leu Trp Arg Ser Val Tyr His Trp Ala Gln Ala Arg Glu
                245                 250                 255

Gly Tyr Thr Gln Cys Gly
                260

<210> SEQ ID NO 84
<211> LENGTH: 458
<212> TYPE: PRT
<213> ORGANISM: Human Pegivirus 2

<400> SEQUENCE: 84

Val Val Ser Gly Ile Trp Ser Phe Val Leu Cys Ile Leu Arg Ala Val
1               5                   10                  15

Trp Asp Trp Ala Ala Lys His Val Pro Arg Phe Arg Val Pro Met Ile
                20                  25                  30

Gly Cys Ser Pro Ala Trp Cys Gly Arg Trp Leu Gly Thr Gly Thr Leu
            35                  40                  45

Leu Thr Thr Cys Gly Cys Gly Glu Arg Val Ser Leu Gln Cys Leu Cys
         50                 55                  60

Ser Thr Ser Asp Pro Thr Leu Ser Val Gly Arg Trp Cys Trp Cys Ser
65                  70                  75                  80

Trp Arg Val Gly Phe Pro Phe Asn Pro Thr Thr Ala Thr Gly Thr
                85                  90                  95

Leu Arg Pro Asp Ile Ser Asp Ala Thr Lys Leu Gly Phe Arg Tyr Gly
                100                 105                 110

Val Ala Glu Ile Val Glu Leu Glu Arg Arg Gly Asn Lys Trp His Val
            115                 120                 125

Cys Ala Ala Ser Cys Cys Leu Asp Arg Ala Ser Val Ala Ser Ala Val
        130                 135                 140
```

```
Arg Ala Pro Pro Val Thr Ala Asp Gly Ile Pro Ile Ser Thr Phe Ser
145                 150                 155                 160

Pro Pro Gln Thr Tyr Lys Leu Ser Leu Cys Ser Phe Asp Ser Val Cys
            165                 170                 175

Met Thr Thr Asn Leu Cys Asn Pro Ala Lys Thr Leu Ser Val Cys Ser
        180                 185                 190

Gln Glu Ala Val Glu Leu Leu Glu Thr Val Asp Arg Ala Gln Val
            195                 200                 205

Val Met Cys Gln Asn Leu Glu Ala Arg Arg Ala Glu Phe Asp Ala
    210                 215                 220

Trp Gln Val Arg Glu Ala Ile Arg Asp Glu Tyr Thr Arg Leu Ala Asp
225                 230                 235                 240

Glu Asp Val Asp Ala Thr Thr Ser Val Lys Pro Pro Val Ala Lys Ala
                245                 250                 255

Ala Val Gly Ser Ser Thr Leu Asp Asp Val Ser Val Leu Thr Val Leu
            260                 265                 270

Arg Glu Leu Gly Asp Gln Cys Gln Asn Ala Ile Lys Phe Val Val Gln
        275                 280                 285

Ala Ala Ser Arg Phe Val Pro Pro Val Pro Lys Pro Arg Thr Arg Val
290                 295                 300

Ser Gly Val Leu Glu Arg Val Arg Met Cys Met Arg Thr Pro Pro Ile
305                 310                 315                 320

Lys Phe Glu Ala Ala Ala Val Pro Ile His Asp Ile Pro Glu Glu
                325                 330                 335

Cys His Ile Val Leu Arg Cys Thr Gly Cys Asn Asp Gln Ala Leu Thr
                340                 345                 350

Val Pro Tyr Gly Thr Cys Thr Gln Ser Leu Ile Lys His Leu Thr Ser
            355                 360                 365

Lys His Ser His Tyr Ile Pro Lys Gln Lys Ile Glu Glu Asp Thr Glu
        370                 375                 380

Val Thr Val Ile Cys Ala Val Pro Thr Thr Arg Ala Ser Lys Leu Ile
385                 390                 395                 400

Thr Phe Arg Ala Gly Asp Arg Ser Val Ser Cys Cys His Pro Leu Gln
                405                 410                 415

Thr Pro Ile Arg Ala Leu Leu Leu Lys Tyr Gly Leu Pro Ile Gly Lys
            420                 425                 430

Trp Ser Asp Cys Asn Gly Pro Leu Gly Asp Asp Ala Arg Val Cys Asp
        435                 440                 445

Val Asn Gly Val Thr Thr Tyr Glu Pro Cys
    450                 455
```

<210> SEQ ID NO 85
<211> LENGTH: 567
<212> TYPE: PRT
<213> ORGANISM: Human Pegivirus 2

<400> SEQUENCE: 85

```
Met Gln Ser Tyr Ser Trp Phe Arg Pro Ile Val Ala Pro Thr Thr Pro
1               5                   10                  15

Pro Leu Pro Ala Thr Arg Thr Val Ala Gly Ile Leu Arg Ala Asp Thr
            20                  25                  30

Ser Arg Val Tyr Thr Thr Thr Ala Val Asp Val Ser Glu Arg Gln Ala
        35                  40                  45

Lys Val Thr Ile Asp Gln Thr Ser Ala Lys Val Asp Gln Cys Phe Arg
```

```
            50                  55                  60
Asp Thr Tyr Asn Cys Cys Leu Ala Lys Ala Lys Thr Phe Arg Gln Ser
 65                  70                  75                  80

Gly Met Ser Tyr Glu Asp Ala Val Ser Lys Met Arg Ala Asn Thr Thr
                     85                  90                  95

Arg Asp His Asn Asn Gly Ile Thr Tyr Ser Asp Leu Val Ser Gly Arg
                    100                 105                 110

Ala Lys Pro Val Val Gln Lys Ile Val Asn Gln Met Arg Ala Gly Val
                115                 120                 125

Tyr Asp Ala Pro Met Arg Ile Ile Pro Lys Pro Glu Val Phe Pro Arg
            130                 135                 140

Asp Lys Thr Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His
                180                 185                 190

Glu Arg Ala Arg Leu Leu Glu Gln Trp Trp Asn Arg Ala Thr Glu Pro
            195                 200                 205

Gln Ala Ile Ala Val Asp Ala Ile Cys Phe Asp Ser Thr Ile Thr Ala
            210                 215                 220

Glu Asp Met Asp Arg Glu Ala Asn Ile Val Ala Ala His Thr Asp
225                 230                 235                 240

Pro Glu Gly Val His Gly Leu Tyr Asn Tyr Tyr Lys Arg Ser Pro Met
                245                 250                 255

Cys Asp Ile Thr Gly Lys Val Val Gly Val Arg Cys Cys Arg Ala Ser
                260                 265                 270

Gly Thr Leu Thr Thr Ser Ser Gly Asn Thr Leu Thr Cys Tyr Leu Lys
            275                 280                 285

Val Arg Ala Ala Cys Thr Arg Ser Gly Ile Lys Pro Ile Gly Leu Leu
            290                 295                 300

Ile His Gly Asp Asp Thr Leu Ile Val Thr Glu Arg Cys Ala Gln Glu
305                 310                 315                 320

Thr Leu Asp Glu Phe Ser Asn Ala Leu Asp Asp Tyr Gly Phe Pro His
                325                 330                 335

Thr Ile Gln Ala Ser Gly Asp Leu Ser Ser Ile Glu Cys Cys Ser Ala
                340                 345                 350

Arg Val Asp Ser Val Cys Leu Arg Gly Gly Met Arg Arg Met Leu Val
            355                 360                 365

Pro Gln Ala Arg Arg Ala Ile Ala Arg Val Leu Gly Glu Lys Gly Asp
            370                 375                 380

Pro Leu Gly Thr Ile Gly Ser Tyr Val Val Met Tyr Pro Thr Ala Ala
385                 390                 395                 400

Val Thr Val Tyr Val Leu Leu Pro Leu Leu Cys Met Leu Ile Arg Asn
                405                 410                 415

Glu Pro Ser Gln Thr Gly Thr Leu Val Thr Leu Thr Val His Gly Asn
                420                 425                 430

Ser Val Ser Val Pro Ala Trp Leu Leu Pro Thr Ile Ile Ala Asn Leu
            435                 440                 445

His Gly Arg Asp Ala Leu Gln Val Val Arg His Ser Ala Ala Ser Met
            450                 455                 460

Ala Glu Leu Ser Ser Ala Leu Ala Phe Phe Gly Met Arg Gly Leu Asn
465                 470                 475                 480
```

-continued

```
Cys Trp Arg Arg Arg Arg Ala Ile Arg Ala Asp Met Ile Lys Ser
                485                 490                 495

Gly Gly Trp Asn Ala Asn Phe Ala Gln Met Leu Leu Trp Ser Pro Glu
            500                 505                 510

Val Arg Thr Pro Gln Pro Glu Pro Arg Gly Leu Cys Leu Leu Pro Pro
        515                 520                 525

Glu Leu Trp Glu Arg Pro Tyr Glu Asn Leu His Leu Ser Thr Ile Asp
    530                 535                 540

Arg Asn Arg Gly Ala Ser Arg Leu Arg Phe Trp Leu Val Ala Ser Ala
545                 550                 555                 560

Ile Leu Ala Leu Leu Cys Leu
                565

<210> SEQ ID NO 86
<211> LENGTH: 45
<212> TYPE: PRT
<213> ORGANISM: Human Pegivirus 2

<400> SEQUENCE: 86

Gly Gly Ser Cys Arg Ser Pro Ser Arg Val Gln Val Ala Arg Arg Val
1               5                   10                  15

Leu Gln Leu Ser Ala Phe Leu Ala Leu Ile Gly Ser Gly Met Ser Ser
            20                  25                  30

Ile Arg Ser Lys Thr Glu Gly Arg Ile Glu Ser Gly Gln
        35                  40                  45

<210> SEQ ID NO 87
<211> LENGTH: 41
<212> TYPE: PRT
<213> ORGANISM: Human Pegivirus 2

<400> SEQUENCE: 87

Arg Asp Gly Ser Leu His Trp Ser His Ala Arg His His Ser Val Gln
1               5                   10                  15

Pro Asp Arg Val Ala Ala Gly Pro Pro Ser Val Thr Ser Val Glu Arg
            20                  25                  30

Asn Met Gly Ser Ser Thr Asp Gln Thr
        35                  40

<210> SEQ ID NO 88
<211> LENGTH: 31
<212> TYPE: PRT
<213> ORGANISM: Human Pegivirus 2

<400> SEQUENCE: 88

Ser Met Asn Ser Asp Ser Pro Phe Gly Thr Phe Thr Arg Asn Thr Glu
1               5                   10                  15

Ser Arg Phe Ser Ile Pro Arg Phe Ser Pro Val Lys Ile Asn Ser
            20                  25                  30

<210> SEQ ID NO 89
<211> LENGTH: 40
<212> TYPE: PRT
<213> ORGANISM: Human Pegivirus 2

<400> SEQUENCE: 89

Gln Ala Pro Ala Val Thr Pro Thr Tyr Ser Glu Ile Thr Tyr Tyr Ala
1               5                   10                  15

Pro Thr Gly Ser Gly Lys Ser Thr Lys Tyr Pro Val Asp Leu Val Lys
```

```
                 20                  25                  30

Gln Gly His Lys Val Leu Val Leu
         35                  40

<210> SEQ ID NO 90
<211> LENGTH: 32
<212> TYPE: PRT
<213> ORGANISM: Human Pegivirus 2

<400> SEQUENCE: 90

Val Lys Ser Met Ala Pro Tyr Ile Lys Glu Thr Tyr Lys Ile Arg Pro
1               5                   10                  15

Glu Ile Arg Ala Gly Thr Gly Pro Asp Gly Val Thr Val Ile Thr Gly
            20                  25                  30

<210> SEQ ID NO 91
<211> LENGTH: 21
<212> TYPE: PRT
<213> ORGANISM: Human Pegivirus 2

<400> SEQUENCE: 91

Pro Glu Thr Asn Leu Arg Gly Tyr Ala Val Val Ile Ser Asp Glu Ser
1               5                   10                  15

His Asp Thr Ser Ser
            20

<210> SEQ ID NO 92
<211> LENGTH: 34
<212> TYPE: PRT
<213> ORGANISM: Human Pegivirus 2

<400> SEQUENCE: 92

Pro Cys Thr Ala Ala Leu Arg Met Gln Arg Arg Gly Arg Thr Gly Arg
1               5                   10                  15

Gly Arg Arg Gly Ala Tyr Tyr Thr Thr Ser Pro Gly Ala Ala Pro Cys
            20                  25                  30

Val Ser

<210> SEQ ID NO 93
<211> LENGTH: 32
<212> TYPE: PRT
<213> ORGANISM: Human Pegivirus 2

<400> SEQUENCE: 93

Leu Ser Glu Arg Phe Gly Gln Gln Leu Ser Lys Leu Ser Leu Trp Arg
1               5                   10                  15

Ser Val Tyr His Trp Ala Gln Ala Arg Glu Gly Tyr Thr Gln Cys Gly
            20                  25                  30

<210> SEQ ID NO 94
<211> LENGTH: 40
<212> TYPE: PRT
<213> ORGANISM: Human Pegivirus 2

<400> SEQUENCE: 94

Asn Pro Thr Thr Thr Gly Thr Gly Thr Leu Arg Pro Asp Ile Ser Asp
1               5                   10                  15

Ala Asn Lys Leu Gly Phe Arg Tyr Gly Val Ala Asp Ile Val Glu Leu
            20                  25                  30

Glu Arg Arg Gly Asp Lys Trp His
        35                  40
```

<210> SEQ ID NO 95
<211> LENGTH: 33
<212> TYPE: PRT
<213> ORGANISM: Human Pegivirus 2

<400> SEQUENCE: 95

Gln Asn Leu Ala Ala Arg Arg Arg Ala Glu Tyr Asp Ala Trp Gln Val
1               5                   10                  15

Arg Gln Ala Val Gly Asp Glu Tyr Thr Arg Leu Ala Asp Glu Asp Val
            20                  25                  30

Asp

<210> SEQ ID NO 96
<211> LENGTH: 31
<212> TYPE: PRT
<213> ORGANISM: Human Pegivirus 2

<400> SEQUENCE: 96

Arg Phe Val Pro Pro Val Pro Lys Pro Arg Thr Arg Val Ser Gly Val
1               5                   10                  15

Leu Glu Arg Val Arg Met Cys Met Arg Thr Pro Pro Ile Lys Phe
            20                  25                  30

<210> SEQ ID NO 97
<211> LENGTH: 22
<212> TYPE: PRT
<213> ORGANISM: Human Pegivirus 2

<400> SEQUENCE: 97

Asn Thr Thr Arg Asp His Asn Asn Gly Ile Thr Tyr Thr Asp Leu Val
1               5                   10                  15

Ser Gly Arg Ala Lys Pro
            20

<210> SEQ ID NO 98
<211> LENGTH: 35
<212> TYPE: PRT
<213> ORGANISM: Human Pegivirus 2

<400> SEQUENCE: 98

Asp Ala Pro Met Arg Ile Ile Pro Lys Pro Glu Val Phe Pro Arg Asp
1               5                   10                  15

Lys Ser Thr Arg Lys Pro Pro Arg Phe Ile Val Phe Pro Gly Cys Ala
            20                  25                  30

Ala Arg Val
        35

<210> SEQ ID NO 99
<211> LENGTH: 20
<212> TYPE: PRT
<213> ORGANISM: Human Pegivirus 2

<400> SEQUENCE: 99

Met Pro Leu Leu Cys Met Leu Ile Arg Asn Glu Pro Ser Gln Thr Gly
1               5                   10                  15

Thr Leu Val Thr
            20

<210> SEQ ID NO 100
<211> LENGTH: 45

<212> TYPE: PRT
<213> ORGANISM: Human Pegivirus 2

<400> SEQUENCE: 100

Gly Gly Ser Cys Arg Ser Pro Ser Arg Val Gln Val Ala Arg Arg Val
1               5                   10                  15

Leu Gln Leu Ser Ala Phe Leu Ala Leu Ile Gly Ser Gly Met Ser Ser
            20                  25                  30

Ile Arg Ser Lys Thr Glu Gly Arg Ile Glu Ser Gly Gln
        35                  40                  45

<210> SEQ ID NO 101
<211> LENGTH: 23
<212> TYPE: PRT
<213> ORGANISM: Human Pegivirus 2

<400> SEQUENCE: 101

Gly Gly Ser Cys Arg Ser Pro Ser Arg Val Gln Val Ala Arg Arg Val
1               5                   10                  15

Leu Gln Leu Ser Ala Phe Leu
            20

<210> SEQ ID NO 102
<211> LENGTH: 26
<212> TYPE: PRT
<213> ORGANISM: Human Pegivirus 2

<400> SEQUENCE: 102

Ser Ala Phe Leu Ala Leu Ile Gly Ser Gly Met Ser Ser Ile Arg Ser
1               5                   10                  15

Lys Thr Glu Gly Arg Ile Glu Ser Gly Gln
            20                  25

<210> SEQ ID NO 103
<211> LENGTH: 20
<212> TYPE: PRT
<213> ORGANISM: Human Pegivirus 2

<400> SEQUENCE: 103

Ala Arg Arg Val Leu Gln Leu Ser Ala Phe Leu Ala Leu Ile Gly Ser
1               5                   10                  15

Gly Met Ser Ser
            20

<210> SEQ ID NO 104
<211> LENGTH: 45
<212> TYPE: PRT
<213> ORGANISM: Human Pegivirus 2

<400> SEQUENCE: 104

Gly Gly Ser Cys Arg Ser Pro Ser Arg Val Gln Val Ala Arg Arg Val
1               5                   10                  15

Leu Gln Leu Cys Ala Phe Leu Ala Leu Ile Gly Ser Gly Met Cys Ser
            20                  25                  30

Ile Arg Ser Lys Thr Glu Gly Arg Ile Glu Ser Gly Gln
        35                  40                  45

<210> SEQ ID NO 105
<211> LENGTH: 23
<212> TYPE: PRT
<213> ORGANISM: Human Pegivirus 2

```
<400> SEQUENCE: 105

Gly Gly Ser Cys Arg Ser Pro Ser Arg Val Gln Val Ala Arg Val
1               5                   10                  15

Leu Gln Leu Cys Ala Phe Leu
            20

<210> SEQ ID NO 106
<211> LENGTH: 26
<212> TYPE: PRT
<213> ORGANISM: Human Pegivirus 2

<400> SEQUENCE: 106

Cys Ala Phe Leu Ala Leu Ile Gly Ser Gly Met Cys Ser Ile Arg Ser
1               5                   10                  15

Lys Thr Glu Gly Arg Ile Glu Ser Gly Gln
            20                  25

<210> SEQ ID NO 107
<211> LENGTH: 20
<212> TYPE: PRT
<213> ORGANISM: Human Pegivirus 2

<400> SEQUENCE: 107

Ala Arg Arg Val Leu Gln Leu Cys Ala Phe Leu Ala Leu Ile Gly Ser
1               5                   10                  15

Gly Met Cys Ser
            20

<210> SEQ ID NO 108
<211> LENGTH: 45
<212> TYPE: PRT
<213> ORGANISM: Human Pegivirus 2

<400> SEQUENCE: 108

Gly Gly Ser Cys Arg Ser Pro Ser Arg Val Gln Val Ala Gly Arg Val
1               5                   10                  15

Leu Arg Leu Cys Ala Phe Leu Ala Leu Ile Gly Ser Gly Met Cys Ser
                20                  25                  30

Ile Arg Ser Lys Asn Glu Gly Arg Ile Glu Ser Gly Gln
            35                  40                  45

<210> SEQ ID NO 109
<211> LENGTH: 23
<212> TYPE: PRT
<213> ORGANISM: Human Pegivirus 2

<400> SEQUENCE: 109

Gly Gly Ser Cys Arg Ser Pro Ser Arg Val Gln Val Ala Gly Arg Val
1               5                   10                  15

Leu Arg Leu Cys Ala Phe Leu
            20

<210> SEQ ID NO 110
<211> LENGTH: 16
<212> TYPE: PRT
<213> ORGANISM: Human Pegivirus 2

<400> SEQUENCE: 110

Met Cys Ser Ile Arg Ser Lys Asn Glu Gly Arg Ile Glu Ser Gly Gln
1               5                   10                  15
```

```
<210> SEQ ID NO 111
<211> LENGTH: 20
<212> TYPE: PRT
<213> ORGANISM: Human Pegivirus 2

<400> SEQUENCE: 111

Val Ala Gly Arg Val Leu Arg Leu Cys Ala Phe Leu Ala Leu Ile Gly
1               5                   10                  15

Ser Gly Met Cys
            20

<210> SEQ ID NO 112
<211> LENGTH: 41
<212> TYPE: PRT
<213> ORGANISM: Human Pegivirus 2

<400> SEQUENCE: 112

Arg Asp Gly Ser Leu His Trp Ser His Ala Arg His His Ser Val Gln
1               5                   10                  15

Pro Asp Arg Val Ala Ala Gly Pro Pro Ser Val Thr Ser Val Glu Arg
            20                  25                  30

Asn Met Gly Ser Ser Thr Asp Gln Thr
        35                  40

<210> SEQ ID NO 113
<211> LENGTH: 23
<212> TYPE: PRT
<213> ORGANISM: Human Pegivirus 2

<400> SEQUENCE: 113

Arg Asp Gly Ser Leu His Trp Ser His Ala Arg His His Ser Val Gln
1               5                   10                  15

Pro Asp Arg Val Ala Ala Gly
            20

<210> SEQ ID NO 114
<211> LENGTH: 41
<212> TYPE: PRT
<213> ORGANISM: Human Pegivirus 2

<400> SEQUENCE: 114

Arg Asp Gly Ser Leu His Trp Cys His Ala Arg His His Ser Val Gln
1               5                   10                  15

Pro Asp Arg Val Ala Ala Gly Pro Pro Ser Val Thr Ser Val Glu Arg
            20                  25                  30

Asn Met Gly Ser Ser Thr Asp Gln Thr
        35                  40

<210> SEQ ID NO 115
<211> LENGTH: 23
<212> TYPE: PRT
<213> ORGANISM: Human Pegivirus 2

<400> SEQUENCE: 115

Arg Asp Gly Ser Leu His Trp Cys His Ala Arg His His Ser Val Gln
1               5                   10                  15

Pro Asp Arg Val Ala Ala Gly
            20

<210> SEQ ID NO 116
<211> LENGTH: 22
<212> TYPE: PRT
```

```
<213> ORGANISM: Human Pegivirus 2

<400> SEQUENCE: 116

Val Ala Ala Gly Pro Pro Ser Val Thr Ser Val Glu Arg Asn Met Gly
1               5                   10                  15

Ser Ser Thr Asp Gln Thr
            20

<210> SEQ ID NO 117
<211> LENGTH: 21
<212> TYPE: PRT
<213> ORGANISM: Human Pegivirus 2

<400> SEQUENCE: 117

Arg His His Ser Val Gln Pro Asp Arg Val Ala Ala Gly Pro Pro Ser
1               5                   10                  15

Val Thr Ser Val Glu
            20

<210> SEQ ID NO 118
<211> LENGTH: 31
<212> TYPE: PRT
<213> ORGANISM: Human Pegivirus 2

<400> SEQUENCE: 118

Ser Met Asn Ser Asp Ser Pro Phe Gly Thr Phe Thr Arg Asn Thr Glu
1               5                   10                  15

Ser Arg Phe Ser Ile Pro Arg Phe Ser Pro Val Lys Ile Asn Ser
            20                  25                  30

<210> SEQ ID NO 119
<211> LENGTH: 31
<212> TYPE: PRT
<213> ORGANISM: Human Pegivirus 2

<400> SEQUENCE: 119

Ser Met Asn Cys Asp Cys Pro Phe Gly Thr Phe Thr Arg Asn Thr Glu
1               5                   10                  15

Ser Arg Phe Ser Ile Pro Arg Phe Cys Pro Val Lys Ile Asn Ser
            20                  25                  30

<210> SEQ ID NO 120
<211> LENGTH: 19
<212> TYPE: PRT
<213> ORGANISM: Human Pegivirus 2

<400> SEQUENCE: 120

Ser Met Asn Ser Asp Ser Pro Phe Gly Thr Phe Thr Arg Asn Thr Glu
1               5                   10                  15

Ser Arg Phe

<210> SEQ ID NO 121
<211> LENGTH: 19
<212> TYPE: PRT
<213> ORGANISM: Human Pegivirus 2

<400> SEQUENCE: 121

Ser Met Asn Cys Asp Cys Pro Phe Gly Thr Phe Thr Arg Asn Thr Glu
1               5                   10                  15

Ser Arg Phe
```

```
<210> SEQ ID NO 122
<211> LENGTH: 15
<212> TYPE: PRT
<213> ORGANISM: Human Pegivirus 2

<400> SEQUENCE: 122

Ser Arg Phe Ser Ile Pro Arg Phe Ser Pro Val Lys Ile Asn Ser
1               5                   10                  15

<210> SEQ ID NO 123
<211> LENGTH: 16
<212> TYPE: PRT
<213> ORGANISM: Human Pegivirus 2

<400> SEQUENCE: 123

Phe Gly Thr Phe Thr Arg Asn Thr Glu Ser Arg Phe Ser Ile Pro Arg
1               5                   10                  15

<210> SEQ ID NO 124
<211> LENGTH: 31
<212> TYPE: PRT
<213> ORGANISM: Human Pegivirus 2

<400> SEQUENCE: 124

Ala Met Asn Cys Asp Cys Pro Phe Gly Thr Phe Thr Arg Asn Thr Glu
1               5                   10                  15

Ser Gly Phe Thr Ile Pro Arg Phe Cys Pro Val Lys Leu Asn Ser
            20                  25                  30

<210> SEQ ID NO 125
<211> LENGTH: 19
<212> TYPE: PRT
<213> ORGANISM: Human Pegivirus 2

<400> SEQUENCE: 125

Ala Met Asn Cys Asp Cys Pro Phe Gly Thr Phe Thr Arg Asn Thr Glu
1               5                   10                  15

Ser Gly Phe

<210> SEQ ID NO 126
<211> LENGTH: 15
<212> TYPE: PRT
<213> ORGANISM: Human Pegivirus 2

<400> SEQUENCE: 126

Ser Gly Phe Thr Ile Pro Arg Phe Cys Pro Val Lys Leu Asn Ser
1               5                   10                  15

<210> SEQ ID NO 127
<211> LENGTH: 16
<212> TYPE: PRT
<213> ORGANISM: Human Pegivirus 2

<400> SEQUENCE: 127

Phe Gly Thr Phe Thr Arg Asn Thr Glu Ser Gly Phe Thr Ile Pro Arg
1               5                   10                  15

<210> SEQ ID NO 128
<211> LENGTH: 31
<212> TYPE: PRT
<213> ORGANISM: Human Pegivirus 2

<400> SEQUENCE: 128

Ala Met Asn Cys Asp Cys Pro Phe Gly Thr Phe Thr Arg Asn Thr Glu
```

```
                1               5                  10                  15
Ser Gly Phe Ser Ile Ser Ile Asp Ser Val Leu Leu Lys Ser Ile
                20                  25                  30
```

<210> SEQ ID NO 129
<211> LENGTH: 40
<212> TYPE: PRT
<213> ORGANISM: Human Pegivirus 2

<400> SEQUENCE: 129

```
Gln Ala Pro Ala Val Thr Pro Thr Tyr Ser Glu Ile Thr Tyr Tyr Ala
1               5                  10                  15
Pro Thr Gly Ser Gly Lys Ser Thr Lys Tyr Pro Val Asp Leu Val Lys
                20                  25                  30
Gln Gly His Lys Val Leu Val Leu
            35                  40
```

<210> SEQ ID NO 130
<211> LENGTH: 24
<212> TYPE: PRT
<213> ORGANISM: Human Pegivirus 2

<400> SEQUENCE: 130

```
Gln Ala Pro Ala Val Thr Pro Thr Tyr Ser Glu Ile Thr Tyr Tyr Ala
1               5                  10                  15
Pro Thr Gly Ser Gly Lys Ser Thr
                20
```

<210> SEQ ID NO 131
<211> LENGTH: 20
<212> TYPE: PRT
<213> ORGANISM: Human Pegivirus 2

<400> SEQUENCE: 131

```
Gly Lys Ser Thr Lys Tyr Pro Val Asp Leu Val Lys Gln Gly His Lys
1               5                  10                  15
Val Leu Val Leu
            20
```

<210> SEQ ID NO 132
<211> LENGTH: 23
<212> TYPE: PRT
<213> ORGANISM: Human Pegivirus 2

<400> SEQUENCE: 132

```
Ile Thr Tyr Tyr Ala Pro Thr Gly Ser Gly Lys Ser Thr Lys Tyr Pro
1               5                  10                  15
Val Asp Leu Val Lys Gln Gly
            20
```

<210> SEQ ID NO 133
<211> LENGTH: 32
<212> TYPE: PRT
<213> ORGANISM: Human Pegivirus 2

<400> SEQUENCE: 133

```
Val Lys Ser Met Ala Pro Tyr Ile Lys Glu Thr Tyr Lys Ile Arg Pro
1               5                  10                  15
Glu Ile Arg Ala Gly Thr Gly Pro Asp Gly Val Thr Val Ile Thr Gly
                20                  25                  30
```

```
<210> SEQ ID NO 134
<211> LENGTH: 18
<212> TYPE: PRT
<213> ORGANISM: Human Pegivirus 2

<400> SEQUENCE: 134

Val Lys Ser Met Ala Pro Tyr Ile Lys Glu Thr Tyr Lys Ile Arg Pro
1               5                   10                  15

Glu Ile

<210> SEQ ID NO 135
<211> LENGTH: 17
<212> TYPE: PRT
<213> ORGANISM: Human Pegivirus 2

<400> SEQUENCE: 135

Pro Glu Ile Arg Ala Gly Thr Gly Pro Asp Gly Val Thr Val Ile Thr
1               5                   10                  15

Gly

<210> SEQ ID NO 136
<211> LENGTH: 19
<212> TYPE: PRT
<213> ORGANISM: Human Pegivirus 2

<400> SEQUENCE: 136

Ile Lys Glu Thr Tyr Lys Ile Arg Pro Glu Ile Arg Ala Gly Thr Gly
1               5                   10                  15

Pro Asp Gly

<210> SEQ ID NO 137
<211> LENGTH: 32
<212> TYPE: PRT
<213> ORGANISM: Human Pegivirus 2

<400> SEQUENCE: 137

Val Lys Ser Met Ala Pro Tyr Ile Lys Glu Lys Tyr Lys Ile Arg Pro
1               5                   10                  15

Glu Ile Arg Ala Gly Thr Gly Pro Asp Gly Val Thr Val Ile Thr Gly
                20                  25                  30

<210> SEQ ID NO 138
<211> LENGTH: 18
<212> TYPE: PRT
<213> ORGANISM: Human Pegivirus 2

<400> SEQUENCE: 138

Val Lys Ser Met Ala Pro Tyr Ile Lys Glu Lys Tyr Lys Ile Arg Pro
1               5                   10                  15

Glu Ile

<210> SEQ ID NO 139
<211> LENGTH: 19
<212> TYPE: PRT
<213> ORGANISM: Human Pegivirus 2

<400> SEQUENCE: 139

Ile Lys Glu Lys Tyr Lys Ile Arg Pro Glu Ile Arg Ala Gly Thr Gly
1               5                   10                  15

Pro Asp Gly
```

<210> SEQ ID NO 140
<211> LENGTH: 40
<212> TYPE: PRT
<213> ORGANISM: Human Pegivirus 2

<400> SEQUENCE: 140

Leu Val Asp Pro Glu Thr Asn Leu Arg Gly Tyr Ala Val Val Ile Cys
1               5                   10                  15

Asp Glu Cys His Asp Thr Ser Ser Thr Thr Leu Leu Gly Ile Gly Ala
            20                  25                  30

Val Arg Met Tyr Ala Glu Lys Ala
        35                  40

<210> SEQ ID NO 141
<211> LENGTH: 24
<212> TYPE: PRT
<213> ORGANISM: Human Pegivirus 2

<400> SEQUENCE: 141

Leu Val Asp Pro Glu Thr Asn Leu Arg Gly Tyr Ala Val Val Ile Cys
1               5                   10                  15

Asp Glu Cys His Asp Thr Ser Ser
            20

<210> SEQ ID NO 142
<211> LENGTH: 25
<212> TYPE: PRT
<213> ORGANISM: Human Pegivirus 2

<400> SEQUENCE: 142

Thr Asn Leu Arg Gly Tyr Ala Val Val Ile Cys Asp Glu Cys His Asp
1               5                   10                  15

Thr Ser Ser Thr Thr Leu Leu Gly Ile
            20                  25

<210> SEQ ID NO 143
<211> LENGTH: 20
<212> TYPE: PRT
<213> ORGANISM: Human Pegivirus 2

<400> SEQUENCE: 143

Asp Thr Ser Ser Thr Thr Leu Leu Gly Ile Gly Ala Val Arg Met Tyr
1               5                   10                  15

Ala Glu Lys Ala
            20

<210> SEQ ID NO 144
<211> LENGTH: 21
<212> TYPE: PRT
<213> ORGANISM: Human Pegivirus 2

<400> SEQUENCE: 144

Pro Glu Thr Asn Leu Arg Gly Tyr Ala Val Val Ile Ser Asp Glu Ser
1               5                   10                  15

His Asp Thr Ser Ser
            20

<210> SEQ ID NO 145
<211> LENGTH: 14
<212> TYPE: PRT
<213> ORGANISM: Human Pegivirus 2

<400> SEQUENCE: 145

```
Pro Glu Thr Asn Leu Arg Gly Tyr Ala Val Val Ile Ser Asp
1               5                   10
```

<210> SEQ ID NO 146
<211> LENGTH: 11
<212> TYPE: PRT
<213> ORGANISM: Human Pegivirus 2

<400> SEQUENCE: 146

```
Val Ile Ser Asp Glu Ser His Asp Thr Ser Ser
1               5                   10
```

<210> SEQ ID NO 147
<211> LENGTH: 21
<212> TYPE: PRT
<213> ORGANISM: Human Pegivirus 2

<400> SEQUENCE: 147

```
Pro Glu Thr Asn Leu Arg Gly Tyr Ala Val Val Ile Cys Asp Glu Cys
1               5                   10                  15

His Asp Thr Ser Ser
            20
```

<210> SEQ ID NO 148
<211> LENGTH: 14
<212> TYPE: PRT
<213> ORGANISM: Human Pegivirus 2

<400> SEQUENCE: 148

```
Pro Glu Thr Asn Leu Arg Gly Tyr Ala Val Val Ile Cys Asp
1               5                   10
```

<210> SEQ ID NO 149
<211> LENGTH: 17
<212> TYPE: PRT
<213> ORGANISM: Human Pegivirus 2

<400> SEQUENCE: 149

```
Arg Arg Gly Phe Ala Val Val Ile Cys Val Glu Cys His Glu His Ile
1               5                   10                  15

Thr
```

<210> SEQ ID NO 150
<211> LENGTH: 34
<212> TYPE: PRT
<213> ORGANISM: Human Pegivirus 2

<400> SEQUENCE: 150

```
Pro Cys Thr Ala Ala Leu Arg Met Gln Arg Arg Gly Arg Thr Gly Arg
1               5                   10                  15

Gly Arg Arg Gly Ala Tyr Tyr Thr Thr Ser Pro Gly Ala Ala Pro Cys
            20                  25                  30

Val Ser
```

<210> SEQ ID NO 151
<211> LENGTH: 20
<212> TYPE: PRT
<213> ORGANISM: Human Pegivirus 2

<400> SEQUENCE: 151

```
Pro Cys Thr Ala Ala Leu Arg Met Gln Arg Arg Gly Arg Thr Gly Arg
1               5                   10                  15
```

```
Gly Arg Arg Gly
            20

<210> SEQ ID NO 152
<211> LENGTH: 18
<212> TYPE: PRT
<213> ORGANISM: Human Pegivirus 2

<400> SEQUENCE: 152

Gly Arg Arg Gly Ala Tyr Tyr Thr Thr Ser Pro Gly Ala Ala Pro Cys
1               5                   10                  15

Val Ser

<210> SEQ ID NO 153
<211> LENGTH: 19
<212> TYPE: PRT
<213> ORGANISM: Human Pegivirus 2

<400> SEQUENCE: 153

Arg Arg Gly Arg Thr Gly Arg Gly Arg Gly Ala Tyr Tyr Thr Thr
1               5                   10                  15

Ser Pro Gly

<210> SEQ ID NO 154
<211> LENGTH: 33
<212> TYPE: PRT
<213> ORGANISM: Human Pegivirus 2

<400> SEQUENCE: 154

Pro Cys Thr Ala Ala Leu Arg Met Gln Arg Arg Gly Arg Thr Gly Arg
1               5                   10                  15

Gly Arg Arg Gly Ala Tyr Tyr Thr Thr Thr Pro Gly Ala Ala Pro Cys
            20                  25                  30

Val

<210> SEQ ID NO 155
<211> LENGTH: 17
<212> TYPE: PRT
<213> ORGANISM: Human Pegivirus 2

<400> SEQUENCE: 155

Gly Arg Arg Gly Ala Tyr Tyr Thr Thr Thr Pro Gly Ala Ala Pro Cys
1               5                   10                  15

Val

<210> SEQ ID NO 156
<211> LENGTH: 19
<212> TYPE: PRT
<213> ORGANISM: Human Pegivirus 2

<400> SEQUENCE: 156

Arg Arg Gly Arg Thr Gly Arg Gly Arg Arg Gly Ala Tyr Tyr Thr Thr
1               5                   10                  15

Thr Pro Gly

<210> SEQ ID NO 157
<211> LENGTH: 32
<212> TYPE: PRT
<213> ORGANISM: Human Pegivirus 2

<400> SEQUENCE: 157
```

Leu Ser Glu Arg Phe Gly Gln Gln Leu Ser Lys Leu Ser Leu Trp Arg
1               5                   10                  15

Ser Val Tyr His Trp Ala Gln Ala Arg Glu Gly Tyr Thr Gln Cys Gly
            20                  25                  30

<210> SEQ ID NO 158
<211> LENGTH: 18
<212> TYPE: PRT
<213> ORGANISM: Human Pegivirus 2

<400> SEQUENCE: 158

Leu Ser Glu Arg Phe Gly Gln Gln Leu Ser Lys Leu Ser Leu Trp Arg
1               5                   10                  15

Ser Val

<210> SEQ ID NO 159
<211> LENGTH: 17
<212> TYPE: PRT
<213> ORGANISM: Human Pegivirus 2

<400> SEQUENCE: 159

Arg Ser Val Tyr His Trp Ala Gln Ala Arg Glu Gly Tyr Thr Gln Cys
1               5                   10                  15

Gly

<210> SEQ ID NO 160
<211> LENGTH: 19
<212> TYPE: PRT
<213> ORGANISM: Human Pegivirus 2

<400> SEQUENCE: 160

Leu Ser Lys Leu Ser Leu Trp Arg Ser Val Tyr His Trp Ala Gln Ala
1               5                   10                  15

Arg Glu Gly

<210> SEQ ID NO 161
<211> LENGTH: 32
<212> TYPE: PRT
<213> ORGANISM: Human Pegivirus 2

<400> SEQUENCE: 161

Leu Thr Glu Lys Phe Gly Gln Gln Leu Ser Lys Leu Ser Leu Trp Arg
1               5                   10                  15

Ser Val Tyr His Trp Ala Gln Ala Arg Glu Gly Tyr Thr Gln Cys Gly
            20                  25                  30

<210> SEQ ID NO 162
<211> LENGTH: 18
<212> TYPE: PRT
<213> ORGANISM: Human Pegivirus 2

<400> SEQUENCE: 162

Leu Thr Glu Lys Phe Gly Gln Gln Leu Ser Lys Leu Ser Leu Trp Arg
1               5                   10                  15

Ser Val

<210> SEQ ID NO 163
<211> LENGTH: 40
<212> TYPE: PRT
<213> ORGANISM: Human Pegivirus 2

<400> SEQUENCE: 163

Asn Pro Thr Thr Thr Gly Thr Gly Thr Leu Arg Pro Asp Ile Ser Asp
1               5                   10                  15

Ala Asn Lys Leu Gly Phe Arg Tyr Gly Val Ala Asp Ile Val Glu Leu
            20                  25                  30

Glu Arg Arg Gly Asp Lys Trp His
            35                  40

<210> SEQ ID NO 164
<211> LENGTH: 24
<212> TYPE: PRT
<213> ORGANISM: Human Pegivirus 2

<400> SEQUENCE: 164

Phe Asn Pro Thr Thr Thr Gly Thr Gly Thr Leu Arg Pro Asp Ile Ser
1               5                   10                  15

Asp Ala Asn Lys Leu Gly Phe Arg
            20

<210> SEQ ID NO 165
<211> LENGTH: 20
<212> TYPE: PRT
<213> ORGANISM: Human Pegivirus 2

<400> SEQUENCE: 165

Gly Phe Arg Tyr Gly Val Ala Asp Ile Val Glu Leu Glu Arg Arg Gly
1               5                   10                  15

Asp Lys Trp His
            20

<210> SEQ ID NO 166
<211> LENGTH: 19
<212> TYPE: PRT
<213> ORGANISM: Human Pegivirus 2

<400> SEQUENCE: 166

Arg Pro Asp Ile Ser Asp Ala Asn Lys Leu Gly Phe Arg Tyr Gly Val
1               5                   10                  15

Ala Asp Ile

<210> SEQ ID NO 167
<211> LENGTH: 40
<212> TYPE: PRT
<213> ORGANISM: Human Pegivirus 2

<400> SEQUENCE: 167

Asn Pro Thr Thr Thr Ala Thr Gly Thr Leu Arg Pro Asp Ile Ser Asp
1               5                   10                  15

Ala Thr Lys Leu Gly Phe Arg Tyr Gly Val Ala Glu Ile Val Glu Leu
            20                  25                  30

Glu Arg Arg Gly Asn Lys Trp His
            35                  40

<210> SEQ ID NO 168
<211> LENGTH: 23
<212> TYPE: PRT
<213> ORGANISM: Human Pegivirus 2

<400> SEQUENCE: 168

Asn Pro Thr Thr Thr Ala Thr Gly Thr Leu Arg Pro Asp Ile Ser Asp
1               5                   10                  15

```
Ala Thr Lys Leu Gly Phe Arg
            20

<210> SEQ ID NO 169
<211> LENGTH: 20
<212> TYPE: PRT
<213> ORGANISM: Human Pegivirus 2

<400> SEQUENCE: 169

Gly Phe Arg Tyr Gly Val Ala Glu Ile Val Glu Leu Glu Arg Arg Gly
1               5                   10                  15

Asn Lys Trp His
            20

<210> SEQ ID NO 170
<211> LENGTH: 19
<212> TYPE: PRT
<213> ORGANISM: Human Pegivirus 2

<400> SEQUENCE: 170

Arg Pro Asp Ile Ser Asp Ala Thr Lys Leu Gly Phe Arg Tyr Gly Val
1               5                   10                  15

Ala Glu Ile

<210> SEQ ID NO 171
<211> LENGTH: 33
<212> TYPE: PRT
<213> ORGANISM: Human Pegivirus 2

<400> SEQUENCE: 171

Gln Asn Leu Ala Ala Arg Arg Arg Ala Glu Tyr Asp Ala Trp Gln Val
1               5                   10                  15

Arg Gln Ala Val Gly Asp Glu Tyr Thr Arg Leu Ala Asp Glu Asp Val
            20                  25                  30
Asp

<210> SEQ ID NO 172
<211> LENGTH: 20
<212> TYPE: PRT
<213> ORGANISM: Human Pegivirus 2

<400> SEQUENCE: 172

Gln Asn Leu Ala Ala Arg Arg Arg Ala Glu Tyr Asp Ala Trp Gln Val
1               5                   10                  15

Arg Gln Ala Val
            20

<210> SEQ ID NO 173
<211> LENGTH: 17
<212> TYPE: PRT
<213> ORGANISM: Human Pegivirus 2

<400> SEQUENCE: 173

Arg Gln Ala Val Gly Asp Glu Tyr Thr Arg Leu Ala Asp Glu Asp Val
1               5                   10                  15

Asp

<210> SEQ ID NO 174
<211> LENGTH: 19
<212> TYPE: PRT
<213> ORGANISM: Human Pegivirus 2
```

<400> SEQUENCE: 174

Arg Ala Glu Tyr Asp Ala Trp Gln Val Arg Gln Ala Val Gly Asp Glu
1               5                   10                  15

Tyr Thr Arg

<210> SEQ ID NO 175
<211> LENGTH: 33
<212> TYPE: PRT
<213> ORGANISM: Human Pegivirus 2

<400> SEQUENCE: 175

Gln Asn Leu Glu Ala Arg Arg Arg Ala Glu Phe Asp Ala Trp Gln Val
1               5                   10                  15

Arg Glu Ala Ile Arg Asp Glu Tyr Thr Arg Leu Ala Asp Glu Asp Val
            20                  25                  30

Asp

<210> SEQ ID NO 176
<211> LENGTH: 20
<212> TYPE: PRT
<213> ORGANISM: Human Pegivirus 2

<400> SEQUENCE: 176

Gln Asn Leu Glu Ala Arg Arg Arg Ala Glu Phe Asp Ala Trp Gln Val
1               5                   10                  15

Arg Glu Ala Ile
            20

<210> SEQ ID NO 177
<211> LENGTH: 17
<212> TYPE: PRT
<213> ORGANISM: Human Pegivirus 2

<400> SEQUENCE: 177

Arg Glu Ala Ile Arg Asp Glu Tyr Thr Arg Leu Ala Asp Glu Asp Val
1               5                   10                  15

Asp

<210> SEQ ID NO 178
<211> LENGTH: 19
<212> TYPE: PRT
<213> ORGANISM: Human Pegivirus 2

<400> SEQUENCE: 178

Arg Ala Glu Phe Asp Ala Trp Gln Val Arg Glu Ala Ile Arg Asp Glu
1               5                   10                  15

Tyr Thr Arg

<210> SEQ ID NO 179
<211> LENGTH: 23
<212> TYPE: PRT
<213> ORGANISM: Human Pegivirus 2

<400> SEQUENCE: 179

Phe Glu Ala Trp Gln Val Arg Glu Ala Ile Arg Asp Glu Tyr Thr Arg
1               5                   10                  15

Leu Ala Asp Glu Asp Val Asp
            20

<210> SEQ ID NO 180
<211> LENGTH: 31
<212> TYPE: PRT
<213> ORGANISM: Human Pegivirus 2

<400> SEQUENCE: 180

Arg Phe Val Pro Pro Val Pro Lys Pro Arg Thr Arg Val Ser Gly Val
1               5                   10                  15

Leu Glu Arg Val Arg Met Cys Met Arg Thr Pro Pro Ile Lys Phe
            20                  25                  30

<210> SEQ ID NO 181
<211> LENGTH: 16
<212> TYPE: PRT
<213> ORGANISM: Human Pegivirus 2

<400> SEQUENCE: 181

Arg Phe Val Pro Pro Val Pro Lys Pro Arg Thr Arg Val Ser Gly Val
1               5                   10                  15

<210> SEQ ID NO 182
<211> LENGTH: 18
<212> TYPE: PRT
<213> ORGANISM: Human Pegivirus 2

<400> SEQUENCE: 182

Ser Gly Val Leu Glu Arg Val Arg Met Cys Met Arg Thr Pro Pro Ile
1               5                   10                  15

Lys Phe

<210> SEQ ID NO 183
<211> LENGTH: 15
<212> TYPE: PRT
<213> ORGANISM: Human Pegivirus 2

<400> SEQUENCE: 183

Lys Pro Arg Thr Arg Val Ser Gly Val Leu Glu Arg Val Arg Met
1               5                   10                  15

<210> SEQ ID NO 184
<211> LENGTH: 17
<212> TYPE: PRT
<213> ORGANISM: Human Pegivirus 2

<400> SEQUENCE: 184

Arg Thr Arg Val Ser Gly Val Leu Glu Arg Val Arg Met Cys Met Thr
1               5                   10                  15

Thr

<210> SEQ ID NO 185
<211> LENGTH: 22
<212> TYPE: PRT
<213> ORGANISM: Human Pegivirus 2

<400> SEQUENCE: 185

Asn Thr Thr Arg Asp His Asn Asn Gly Ile Thr Tyr Thr Asp Leu Val
1               5                   10                  15

Ser Gly Arg Ala Lys Pro
            20

<210> SEQ ID NO 186
<211> LENGTH: 14
<212> TYPE: PRT

<213> ORGANISM: Human Pegivirus 2

<400> SEQUENCE: 186

Asn Thr Thr Arg Asp His Asn Asn Gly Ile Thr Tyr Thr Asp
1               5                   10

<210> SEQ ID NO 187
<211> LENGTH: 11
<212> TYPE: PRT
<213> ORGANISM: Human Pegivirus 2

<400> SEQUENCE: 187

Tyr Thr Asp Leu Val Ser Gly Arg Ala Lys Pro
1               5                   10

<210> SEQ ID NO 188
<211> LENGTH: 22
<212> TYPE: PRT
<213> ORGANISM: Human Pegivirus 2

<400> SEQUENCE: 188

Asn Thr Thr Arg Asp His Asn Asn Gly Ile Thr Tyr Ser Asp Leu Val
1               5                   10                  15

Ser Gly Arg Ala Lys Pro
            20

<210> SEQ ID NO 189
<211> LENGTH: 14
<212> TYPE: PRT
<213> ORGANISM: Human Pegivirus 2

<400> SEQUENCE: 189

Asn Thr Thr Arg Asp His Asn Asn Gly Ile Thr Tyr Ser Asp
1               5                   10

<210> SEQ ID NO 190
<211> LENGTH: 11
<212> TYPE: PRT
<213> ORGANISM: Human Pegivirus 2

<400> SEQUENCE: 190

Tyr Ser Asp Leu Val Ser Gly Arg Ala Lys Pro
1               5                   10

<210> SEQ ID NO 191
<211> LENGTH: 35
<212> TYPE: PRT
<213> ORGANISM: Human Pegivirus 2

<400> SEQUENCE: 191

Asp Ala Pro Met Arg Ile Ile Pro Lys Pro Glu Val Phe Pro Arg Asp
1               5                   10                  15

Lys Ser Thr Arg Lys Pro Pro Arg Phe Ile Val Phe Pro Gly Cys Ala
            20                  25                  30

Ala Arg Val
        35

<210> SEQ ID NO 192
<211> LENGTH: 24
<212> TYPE: PRT
<213> ORGANISM: Human Pegivirus 2

<400> SEQUENCE: 192

```
Asp Ala Pro Met Arg Ile Ile Pro Lys Pro Glu Val Phe Pro Arg Asp
1               5                   10                  15

Lys Ser Thr Arg Lys Pro Pro Arg
            20
```

<210> SEQ ID NO 193
<211> LENGTH: 20
<212> TYPE: PRT
<213> ORGANISM: Human Pegivirus 2

<400> SEQUENCE: 193

```
Asp Lys Ser Thr Arg Lys Pro Pro Arg Phe Ile Val Phe Pro Gly Cys
1               5                   10                  15

Ala Ala Arg Val
            20
```

<210> SEQ ID NO 194
<211> LENGTH: 20
<212> TYPE: PRT
<213> ORGANISM: Human Pegivirus 2

<400> SEQUENCE: 194

```
Ile Pro Lys Pro Glu Val Phe Pro Arg Asp Lys Ser Thr Arg Lys Pro
1               5                   10                  15

Pro Arg Phe Ile
            20
```

<210> SEQ ID NO 195
<211> LENGTH: 35
<212> TYPE: PRT
<213> ORGANISM: Human Pegivirus 2

<400> SEQUENCE: 195

```
Asp Ala Pro Met Arg Ile Ile Pro Lys Pro Glu Val Phe Pro Arg Asp
1               5                   10                  15

Lys Thr Thr Arg Lys Pro Pro Arg Phe Ile Val Phe Pro Gly Cys Ala
            20                  25                  30

Ala Arg Val
        35
```

<210> SEQ ID NO 196
<211> LENGTH: 24
<212> TYPE: PRT
<213> ORGANISM: Human Pegivirus 2

<400> SEQUENCE: 196

```
Asp Ala Pro Met Arg Ile Ile Pro Lys Pro Glu Val Phe Pro Arg Asp
1               5                   10                  15

Lys Thr Thr Arg Lys Pro Pro Arg
            20
```

<210> SEQ ID NO 197
<211> LENGTH: 20
<212> TYPE: PRT
<213> ORGANISM: Human Pegivirus 2

<400> SEQUENCE: 197

```
Asp Lys Thr Thr Arg Lys Pro Pro Arg Phe Ile Val Phe Pro Gly Cys
1               5                   10                  15

Ala Ala Arg Val
            20
```

<210> SEQ ID NO 198
<211> LENGTH: 20
<212> TYPE: PRT
<213> ORGANISM: Human Pegivirus 2

<400> SEQUENCE: 198

Ile Pro Lys Pro Glu Val Phe Pro Arg Asp Lys Thr Thr Arg Lys Pro
1               5                   10                  15

Pro Arg Phe Ile
            20

<210> SEQ ID NO 199
<211> LENGTH: 20
<212> TYPE: PRT
<213> ORGANISM: Human Pegivirus 2

<400> SEQUENCE: 199

Met Pro Leu Leu Cys Met Leu Ile Arg Asn Glu Pro Ser Gln Thr Gly
1               5                   10                  15

Thr Leu Val Thr
            20

<210> SEQ ID NO 200
<211> LENGTH: 15
<212> TYPE: PRT
<213> ORGANISM: Human Pegivirus 2

<400> SEQUENCE: 200

Met Pro Leu Leu Cys Met Leu Ile Arg Asn Glu Pro Ser Gln Thr
1               5                   10                  15

<210> SEQ ID NO 201
<211> LENGTH: 15
<212> TYPE: PRT
<213> ORGANISM: Human Pegivirus 2

<400> SEQUENCE: 201

Met Leu Ile Arg Asn Glu Pro Ser Gln Thr Gly Thr Leu Val Thr
1               5                   10                  15

<210> SEQ ID NO 202
<211> LENGTH: 20
<212> TYPE: PRT
<213> ORGANISM: Human Pegivirus 2

<400> SEQUENCE: 202

Leu Pro Leu Leu Cys Met Leu Ile Arg Asn Glu Pro Ser Gln Thr Gly
1               5                   10                  15

Thr Leu Val Thr
            20

<210> SEQ ID NO 203
<211> LENGTH: 15
<212> TYPE: PRT
<213> ORGANISM: Human Pegivirus 2

<400> SEQUENCE: 203

Leu Pro Leu Leu Cys Met Leu Ile Arg Asn Glu Pro Ser Gln Thr
1               5                   10                  15

<210> SEQ ID NO 204
<211> LENGTH: 20
<212> TYPE: PRT

```
<213> ORGANISM: Human Pegivirus 2

<400> SEQUENCE: 204

Leu Pro Leu Leu Cys Met Leu Ile Arg Asn Glu Pro Ser Gln Thr Gly
1               5                   10                  15

Thr Leu Val Thr
            20

<210> SEQ ID NO 205
<211> LENGTH: 39
<212> TYPE: PRT
<213> ORGANISM: Human Pegivirus 2

<400> SEQUENCE: 205

Ala Glu Ala Ala Pro Lys Ser Gly Glu Leu Asp Ser Gln Cys Asp His
1               5                   10                  15

Leu Ala Trp Ser Phe Met Glu Gly Met Pro Thr Gly Thr Leu Ile Val
            20                  25                  30

Gln Arg Asp Gly Ser Leu His
            35

<210> SEQ ID NO 206
<211> LENGTH: 23
<212> TYPE: PRT
<213> ORGANISM: Human Pegivirus 2

<400> SEQUENCE: 206

Ala Glu Ala Ala Pro Lys Ser Gly Glu Leu Asp Ser Gln Cys Asp His
1               5                   10                  15

Leu Ala Trp Ser Phe Met Glu
            20

<210> SEQ ID NO 207
<211> LENGTH: 19
<212> TYPE: PRT
<213> ORGANISM: Human Pegivirus 2

<400> SEQUENCE: 207

Phe Met Glu Gly Met Pro Thr Gly Thr Leu Ile Val Gln Arg Asp Gly
1               5                   10                  15

Ser Leu His

<210> SEQ ID NO 208
<211> LENGTH: 17
<212> TYPE: PRT
<213> ORGANISM: Human Pegivirus 2

<400> SEQUENCE: 208

Gln Cys Asp His Leu Ala Trp Ser Phe Met Glu Gly Met Pro Thr Gly
1               5                   10                  15

Thr

<210> SEQ ID NO 209
<211> LENGTH: 50
<212> TYPE: PRT
<213> ORGANISM: Human Pegivirus 2

<400> SEQUENCE: 209

Ser Val Glu Val Arg Pro Ala Gly Val Thr Arg Pro Asp Ala Thr Asp
1               5                   10                  15

Glu Thr Ala Ala Tyr Ala Gln Arg Leu Tyr Gln Ala Cys Ala Asp Ser
```

20                  25                  30

Gly Ile Phe Ala Ser Leu Gln Gly Thr Ala Ser Ala Ala Leu Gly Lys
            35                  40                  45

Leu Ala
    50

<210> SEQ ID NO 210
<211> LENGTH: 31
<212> TYPE: PRT
<213> ORGANISM: Human Pegivirus 2

<400> SEQUENCE: 210

Ser Val Glu Val Arg Pro Ala Gly Val Thr Arg Pro Asp Ala Thr Asp
1               5                   10                  15

Glu Thr Ala Ala Tyr Ala Gln Arg Leu Tyr Gln Ala Cys Ala Asp
            20                  25                  30

<210> SEQ ID NO 211
<211> LENGTH: 23
<212> TYPE: PRT
<213> ORGANISM: Human Pegivirus 2

<400> SEQUENCE: 211

Ala Cys Ala Asp Ser Gly Ile Phe Ala Ser Leu Gln Gly Thr Ala Ser
1               5                   10                  15

Ala Ala Leu Gly Lys Leu Ala
            20

<210> SEQ ID NO 212
<211> LENGTH: 32
<212> TYPE: PRT
<213> ORGANISM: Human Pegivirus 2

<400> SEQUENCE: 212

Val Thr Arg Pro Asp Ala Thr Asp Glu Thr Ala Ala Tyr Ala Gln Arg
1               5                   10                  15

Leu Tyr Gln Ala Cys Ala Asp Ser Gly Ile Phe Ala Ser Leu Gln Gly
            20                  25                  30

<210> SEQ ID NO 213
<211> LENGTH: 50
<212> TYPE: PRT
<213> ORGANISM: Human Pegivirus 2

<400> SEQUENCE: 213

Ser Val Glu Asn Gly Leu Ala Gly Val Thr Arg Pro Asp Ala Thr Asp
1               5                   10                  15

Glu Thr Ala Ala Tyr Ala Gln Arg Leu Tyr Gln Ala Cys Ala Asp Ser
            20                  25                  30

Gly Ile Leu Ala Ser Leu Gln Gly Thr Ala Ser Ala Ala Leu Ser Arg
        35                  40                  45

Leu Ala
    50

<210> SEQ ID NO 214
<211> LENGTH: 31
<212> TYPE: PRT
<213> ORGANISM: Human Pegivirus 2

<400> SEQUENCE: 214

Ser Val Glu Asn Gly Leu Ala Gly Val Thr Arg Pro Asp Ala Thr Asp

```
                1               5                  10                 15
Glu Thr Ala Ala Tyr Ala Gln Arg Leu Tyr Gln Ala Cys Ala Asp
            20                  25                 30

<210> SEQ ID NO 215
<211> LENGTH: 23
<212> TYPE: PRT
<213> ORGANISM: Human Pegivirus 2

<400> SEQUENCE: 215

Ala Cys Ala Asp Ser Gly Ile Leu Ala Ser Leu Gln Gly Thr Ala Ser
1               5                   10                  15

Ala Ala Leu Ser Arg Leu Ala
            20

<210> SEQ ID NO 216
<211> LENGTH: 32
<212> TYPE: PRT
<213> ORGANISM: Human Pegivirus 2

<400> SEQUENCE: 216

Val Thr Arg Pro Asp Ala Thr Asp Glu Thr Ala Ala Tyr Ala Gln Arg
1               5                   10                  15

Leu Tyr Gln Ala Cys Ala Asp Ser Gly Ile Leu Ala Ser Leu Gln Gly
            20                  25                  30

<210> SEQ ID NO 217
<211> LENGTH: 39
<212> TYPE: PRT
<213> ORGANISM: Human Pegivirus 2

<400> SEQUENCE: 217

Ala Glu Ala Ala Pro Lys Ser Gly Glu Leu Asp Ser Gln Cys Asp His
1               5                   10                  15

Leu Ala Trp Ser Phe Met Glu Gly Met Pro Thr Gly Thr Leu Ile Val
            20                  25                  30

Gln Arg Asp Gly Ser Leu His
        35

<210> SEQ ID NO 218
<211> LENGTH: 50
<212> TYPE: PRT
<213> ORGANISM: Human Pegivirus 2

<400> SEQUENCE: 218

Ser Val Glu Val Arg Pro Ala Gly Val Thr Arg Pro Asp Ala Thr Asp
1               5                   10                  15

Glu Thr Ala Ala Tyr Ala Gln Arg Leu Tyr Gln Ala Cys Ala Asp Ser
            20                  25                  30

Gly Ile Phe Ala Ser Leu Gln Gly Thr Ala Ser Ala Ala Leu Gly Lys
        35                  40                  45

Leu Ala
    50

<210> SEQ ID NO 219
<211> LENGTH: 18
<212> TYPE: DNA
<213> ORGANISM: Artificial sequence
<220> FEATURE:
<223> OTHER INFORMATION: Synthetic

<400> SEQUENCE: 219
```
gagtcacgcg gggtgctt                                            18

<210> SEQ ID NO 220
<211> LENGTH: 26
<212> TYPE: DNA
<213> ORGANISM: Artificial sequence
<220> FEATURE:
<223> OTHER INFORMATION: Synthetic

<400> SEQUENCE: 220
cttaatataa ggggccatac ttttga                                   26

<210> SEQ ID NO 221
<211> LENGTH: 20
<212> TYPE: DNA
<213> ORGANISM: Artificial sequence
<220> FEATURE:
<223> OTHER INFORMATION: Synthetic

<400> SEQUENCE: 221
tggaaccagt cgtgttggag                                          20

<210> SEQ ID NO 222
<211> LENGTH: 20
<212> TYPE: DNA
<213> ORGANISM: Artificial sequence
<220> FEATURE:
<223> OTHER INFORMATION: Synthetic

<400> SEQUENCE: 222
gaacagcagc aggggtctag                                          20

<210> SEQ ID NO 223
<211> LENGTH: 20
<212> TYPE: DNA
<213> ORGANISM: Artificial sequence
<220> FEATURE:
<223> OTHER INFORMATION: Synthetic

<400> SEQUENCE: 223
ctagacccct gctgctgttc                                          20

<210> SEQ ID NO 224
<211> LENGTH: 20
<212> TYPE: DNA
<213> ORGANISM: Artificial sequence
<220> FEATURE:
<223> OTHER INFORMATION: Synthetic

<400> SEQUENCE: 224
tgactacagc cacacttggt                                          20

<210> SEQ ID NO 225
<211> LENGTH: 22
<212> TYPE: DNA
<213> ORGANISM: Artificial sequence
<220> FEATURE:
<223> OTHER INFORMATION: Synthetic

<400> SEQUENCE: 225
atatgggagc taccactgcg gt                                       22

<210> SEQ ID NO 226
<211> LENGTH: 26
<212> TYPE: DNA

```
<213> ORGANISM: Artificial sequence
<220> FEATURE:
<223> OTHER INFORMATION: Synthetic

<400> SEQUENCE: 226
taacaggaca gaatctaggt atggag                                          26

<210> SEQ ID NO 227
<211> LENGTH: 24
<212> TYPE: DNA
<213> ORGANISM: Artificial sequence
<220> FEATURE:
<223> OTHER INFORMATION: Synthetic

<400> SEQUENCE: 227
tgtctattgc tctacctcca ggtg                                            24

<210> SEQ ID NO 228
<211> LENGTH: 23
<212> TYPE: DNA
<213> ORGANISM: Artificial sequence
<220> FEATURE:
<223> OTHER INFORMATION: Synthetic

<400> SEQUENCE: 228
ttccaaagca acgtaacacg gcg                                             23

<210> SEQ ID NO 229
<211> LENGTH: 23
<212> TYPE: DNA
<213> ORGANISM: Artificial sequence
<220> FEATURE:
<223> OTHER INFORMATION: Synthetic

<400> SEQUENCE: 229
cgccgtgtta cgttgctttg gaa                                             23

<210> SEQ ID NO 230
<211> LENGTH: 24
<212> TYPE: DNA
<213> ORGANISM: Artificial sequence
<220> FEATURE:
<223> OTHER INFORMATION: Synthetic

<400> SEQUENCE: 230
ttaccagaac cagtaggggc atag                                            24

<210> SEQ ID NO 231
<211> LENGTH: 28
<212> TYPE: DNA
<213> ORGANISM: Artificial sequence
<220> FEATURE:
<223> OTHER INFORMATION: Synthetic

<400> SEQUENCE: 231
acagtcacat tccaacattg atgaatac                                        28

<210> SEQ ID NO 232
<211> LENGTH: 21
<212> TYPE: DNA
<213> ORGANISM: Artificial sequence
<220> FEATURE:
<223> OTHER INFORMATION: Synthetic

<400> SEQUENCE: 232
tgctcccctt ctaccacgac c                                               21
```

<210> SEQ ID NO 233
<211> LENGTH: 22
<212> TYPE: DNA
<213> ORGANISM: Artificial sequence
<220> FEATURE:
<223> OTHER INFORMATION: Synthetic

<400> SEQUENCE: 233
taggcgtgtg gttttccggt ct                                        22

<210> SEQ ID NO 234
<211> LENGTH: 22
<212> TYPE: DNA
<213> ORGANISM: Artificial sequence
<220> FEATURE:
<223> OTHER INFORMATION: Synthetic

<400> SEQUENCE: 234
ccaatcccac acagcgcgta ga                                        22

<210> SEQ ID NO 235
<211> LENGTH: 22
<212> TYPE: DNA
<213> ORGANISM: Artificial sequence
<220> FEATURE:
<223> OTHER INFORMATION: Synthetic

<400> SEQUENCE: 235
tctacgcgct gtgtgggatt gg                                        22

<210> SEQ ID NO 236
<211> LENGTH: 23
<212> TYPE: DNA
<213> ORGANISM: Artificial sequence
<220> FEATURE:
<223> OTHER INFORMATION: Synthetic

<400> SEQUENCE: 236
gggtctcaaa cttgattgga ggc                                       23

<210> SEQ ID NO 237
<211> LENGTH: 24
<212> TYPE: DNA
<213> ORGANISM: Artificial sequence
<220> FEATURE:
<223> OTHER INFORMATION: Synthetic

<400> SEQUENCE: 237
ctatgcccct actggttctg gtaa                                      24

<210> SEQ ID NO 238
<211> LENGTH: 28
<212> TYPE: DNA
<213> ORGANISM: Artificial sequence
<220> FEATURE:
<223> OTHER INFORMATION: Synthetic

<400> SEQUENCE: 238
gtattcatca atgttggaat gtgactgt                                  28

<210> SEQ ID NO 239
<211> LENGTH: 24
<212> TYPE: DNA
<213> ORGANISM: Artificial sequence
<220> FEATURE:

<223> OTHER INFORMATION: Synthetic

<400> SEQUENCE: 239
acttattgac tgacacaggc gacg                                              24

<210> SEQ ID NO 240
<211> LENGTH: 24
<212> TYPE: DNA
<213> ORGANISM: Artificial sequence
<220> FEATURE:
<223> OTHER INFORMATION: Synthetic

<400> SEQUENCE: 240
tgcatgcgca atgcagcagt acat                                              24

<210> SEQ ID NO 241
<211> LENGTH: 25
<212> TYPE: DNA
<213> ORGANISM: Artificial sequence
<220> FEATURE:
<223> OTHER INFORMATION: Synthetic

<400> SEQUENCE: 241
gtgcccataa gtggctatta gctat                                             25

<210> SEQ ID NO 242
<211> LENGTH: 27
<212> TYPE: DNA
<213> ORGANISM: Artificial sequence
<220> FEATURE:
<223> OTHER INFORMATION: Synthetic

<400> SEQUENCE: 242
tgcttaattg ttggccaaat ctttcac                                           27

<210> SEQ ID NO 243
<211> LENGTH: 24
<212> TYPE: DNA
<213> ORGANISM: Artificial sequence
<220> FEATURE:
<223> OTHER INFORMATION: Synthetic

<400> SEQUENCE: 243
acgattccgt gtgcctatga ttgg                                              24

<210> SEQ ID NO 244
<211> LENGTH: 27
<212> TYPE: DNA
<213> ORGANISM: Artificial sequence
<220> FEATURE:
<223> OTHER INFORMATION: Synthetic

<400> SEQUENCE: 244
ctgggttaca taagttagta gacatgc                                           27

<210> SEQ ID NO 245
<211> LENGTH: 21
<212> TYPE: DNA
<213> ORGANISM: Artificial sequence
<220> FEATURE:
<223> OTHER INFORMATION: Synthetic

<400> SEQUENCE: 245
tctccgcctc cagcagttca a                                                 21

```
<210> SEQ ID NO 246
<211> LENGTH: 25
<212> TYPE: DNA
<213> ORGANISM: Artificial sequence
<220> FEATURE:
<223> OTHER INFORMATION: Synthetic

<400> SEQUENCE: 246
agccgcagta ggatacatga caata                                25

<210> SEQ ID NO 247
<211> LENGTH: 26
<212> TYPE: DNA
<213> ORGANISM: Artificial sequence
<220> FEATURE:
<223> OTHER INFORMATION: Synthetic

<400> SEQUENCE: 247
tgtgatatca caggaaaagt tgtcgg                               26

<210> SEQ ID NO 248
<211> LENGTH: 23
<212> TYPE: DNA
<213> ORGANISM: Artificial sequence
<220> FEATURE:
<223> OTHER INFORMATION: Synthetic

<400> SEQUENCE: 248
acagtcacag ccgcagtagg ata                                  23

<210> SEQ ID NO 249
<211> LENGTH: 25
<212> TYPE: DNA
<213> ORGANISM: Artificial sequence
<220> FEATURE:
<223> OTHER INFORMATION: Synthetic

<400> SEQUENCE: 249
gagaaaatga tcctgggcga tcctg                                25

<210> SEQ ID NO 250
<211> LENGTH: 23
<212> TYPE: DNA
<213> ORGANISM: Artificial sequence
<220> FEATURE:
<223> OTHER INFORMATION: Synthetic

<400> SEQUENCE: 250
gccgtgatgg tgctatcaaa gca                                  23

<210> SEQ ID NO 251
<211> LENGTH: 20
<212> TYPE: DNA
<213> ORGANISM: Artificial sequence
<220> FEATURE:
<223> OTHER INFORMATION: Synthetic

<400> SEQUENCE: 251
gggacacctc aaccctgaag                                      20

<210> SEQ ID NO 252
<211> LENGTH: 20
<212> TYPE: DNA
<213> ORGANISM: Artificial sequence
<220> FEATURE:
<223> OTHER INFORMATION: Synthetic
```

<400> SEQUENCE: 252
tcactgcggt acccattgac                                          20

<210> SEQ ID NO 253
<211> LENGTH: 22
<212> TYPE: DNA
<213> ORGANISM: Artificial sequence
<220> FEATURE:
<223> OTHER INFORMATION: Synthetic

<400> SEQUENCE: 253
atatgggagc taccactgcg gt                                       22

<210> SEQ ID NO 254
<211> LENGTH: 26
<212> TYPE: DNA
<213> ORGANISM: Artificial sequence
<220> FEATURE:
<223> OTHER INFORMATION: Synthetic

<400> SEQUENCE: 254
ggtacagtat ttgaggtagc tttcag                                   26

<210> SEQ ID NO 255
<211> LENGTH: 24
<212> TYPE: DNA
<213> ORGANISM: Artificial sequence
<220> FEATURE:
<223> OTHER INFORMATION: Synthetic

<400> SEQUENCE: 255 cttttggtg cgcagtgttt gcct                                     24

<210> SEQ ID NO 256
<211> LENGTH: 24
<212> TYPE: DNA
<213> ORGANISM: Artificial sequence
<220> FEATURE:
<223> OTHER INFORMATION: Synthetic

<400> SEQUENCE: 256
tgtcagggaa gacaacacca cgat                                     24

<210> SEQ ID NO 257
<211> LENGTH: 22
<212> TYPE: DNA
<213> ORGANISM: Artificial sequence
<220> FEATURE:
<223> OTHER INFORMATION: Synthetic

<400> SEQUENCE: 257
acactcacag ggcgtgctga aa                                       22

<210> SEQ ID NO 258
<211> LENGTH: 23
<212> TYPE: DNA
<213> ORGANISM: Artificial sequence
<220> FEATURE:
<223> OTHER INFORMATION: Synthetic

<400> SEQUENCE: 258
acgccaagtt ctcaccagtg atg                                      23

<210> SEQ ID NO 259
<211> LENGTH: 25

```
<212> TYPE: DNA
<213> ORGANISM: Artificial sequence
<220> FEATURE:
<223> OTHER INFORMATION: Synthetic

<400> SEQUENCE: 259
gtgtggctgt agtcaaaagt atggc                                          25

<210> SEQ ID NO 260
<211> LENGTH: 22
<212> TYPE: DNA
<213> ORGANISM: Artificial sequence
<220> FEATURE:
<223> OTHER INFORMATION: Synthetic

<400> SEQUENCE: 260
cagcagtaca tggcaccact cg                                             22

<210> SEQ ID NO 261
<211> LENGTH: 22
<212> TYPE: DNA
<213> ORGANISM: Artificial sequence
<220> FEATURE:
<223> OTHER INFORMATION: Synthetic

<400> SEQUENCE: 261
ttcggtcatc gactgcgggt gt                                             22

<210> SEQ ID NO 262
<211> LENGTH: 25
<212> TYPE: DNA
<213> ORGANISM: Artificial sequence
<220> FEATURE:
<223> OTHER INFORMATION: Synthetic

<400> SEQUENCE: 262
ccagccaagt tcctgcaata gctaa                                          25

<210> SEQ ID NO 263
<211> LENGTH: 22
<212> TYPE: DNA
<213> ORGANISM: Artificial sequence
<220> FEATURE:
<223> OTHER INFORMATION: Synthetic

<400> SEQUENCE: 263
ttcactgcgc ttgctggctt gg                                             22

<210> SEQ ID NO 264
<211> LENGTH: 21
<212> TYPE: DNA
<213> ORGANISM: Artificial sequence
<220> FEATURE:
<223> OTHER INFORMATION: Synthetic

<400> SEQUENCE: 264
ccgtaaggtg ccagtgcctg t                                              21

<210> SEQ ID NO 265
<211> LENGTH: 27
<212> TYPE: DNA
<213> ORGANISM: Artificial sequence
<220> FEATURE:
<223> OTHER INFORMATION: Synthetic

<400> SEQUENCE: 265
```

```
aagcatcaat ctgaaagcta cctcaaa                                            27

<210> SEQ ID NO 266
<211> LENGTH: 25
<212> TYPE: DNA
<213> ORGANISM: Artificial sequence
<220> FEATURE:
<223> OTHER INFORMATION: Synthetic

<400> SEQUENCE: 266
tgaatcttat agtgtcgtcc aagtg                                              25

<210> SEQ ID NO 267
<211> LENGTH: 20
<212> TYPE: DNA
<213> ORGANISM: Artificial sequence
<220> FEATURE:
<223> OTHER INFORMATION: Synthetic

<400> SEQUENCE: 267
ctgtgactgc ccctttggaa                                                    20

<210> SEQ ID NO 268
<211> LENGTH: 20
<212> TYPE: DNA
<213> ORGANISM: Artificial sequence
<220> FEATURE:
<223> OTHER INFORMATION: Synthetic

<400> SEQUENCE: 268
catgccaacg tccgtgtatg                                                    20

<210> SEQ ID NO 269
<211> LENGTH: 24
<212> TYPE: DNA
<213> ORGANISM: Artificial sequence
<220> FEATURE:
<223> OTHER INFORMATION: Synthetic

<400> SEQUENCE: 269
aacccttgca attctggccg atga                                               24

<210> SEQ ID NO 270
<211> LENGTH: 22
<212> TYPE: DNA
<213> ORGANISM: Artificial sequence
<220> FEATURE:
<223> OTHER INFORMATION: Synthetic

<400> SEQUENCE: 270
agatccctga ctgcttgcgc ca                                                 22

<210> SEQ ID NO 271
<211> LENGTH: 22
<212> TYPE: DNA
<213> ORGANISM: Artificial sequence
<220> FEATURE:
<223> OTHER INFORMATION: Synthetic

<400> SEQUENCE: 271
cccacggtcc tgatgatagc at                                                 22

<210> SEQ ID NO 272
<211> LENGTH: 23
<212> TYPE: DNA
<213> ORGANISM: Artificial sequence
```

```
<220> FEATURE:
<223> OTHER INFORMATION: Synthetic

<400> SEQUENCE: 272
gctaaccagc caagttcctg caa                                              23

<210> SEQ ID NO 273
<211> LENGTH: 30
<212> TYPE: DNA
<213> ORGANISM: Artificial sequence
<220> FEATURE:
<223> OTHER INFORMATION: Synthetic

<400> SEQUENCE: 273
aagtgaaaga tttggccaac aattaagcaa                                       30

<210> SEQ ID NO 274
<211> LENGTH: 20
<212> TYPE: DNA
<213> ORGANISM: Artificial sequence
<220> FEATURE:
<223> OTHER INFORMATION: Synthetic

<400> SEQUENCE: 274
ccacgcaggt gagcagccaa                                                  20

<210> SEQ ID NO 275
<211> LENGTH: 25
<212> TYPE: DNA
<213> ORGANISM: Artificial sequence
<220> FEATURE:
<223> OTHER INFORMATION: Synthetic

<400> SEQUENCE: 275
acaattatta caaagaagc cccat                                             25

<210> SEQ ID NO 276
<211> LENGTH: 19
<212> TYPE: DNA
<213> ORGANISM: Artificial sequence
<220> FEATURE:
<223> OTHER INFORMATION: Synthetic

<400> SEQUENCE: 276
agtcacagcc gcagtagga                                                   19

<210> SEQ ID NO 277
<211> LENGTH: 20
<212> TYPE: DNA
<213> ORGANISM: Artificial sequence
<220> FEATURE:
<223> OTHER INFORMATION: Synthetic

<400> SEQUENCE: 277
ttgacatgac agcgtcggtg                                                  20

<210> SEQ ID NO 278
<211> LENGTH: 20
<212> TYPE: DNA
<213> ORGANISM: Artificial sequence
<220> FEATURE:
<223> OTHER INFORMATION: Synthetic

<400> SEQUENCE: 278
agcgcgcatc tgatctacaa                                                  20
```

```
<210> SEQ ID NO 279
<211> LENGTH: 19
<212> TYPE: DNA
<213> ORGANISM: Artificial sequence
<220> FEATURE:
<223> OTHER INFORMATION: Synthetic

<400> SEQUENCE: 279
aacagcggtt gatgtctcc                                                   19

<210> SEQ ID NO 280
<211> LENGTH: 19
<212> TYPE: DNA
<213> ORGANISM: Artificial sequence
<220> FEATURE:
<223> OTHER INFORMATION: Synthetic

<400> SEQUENCE: 280
aaagatgcgc gcaaacacc                                                   19

<210> SEQ ID NO 281
<211> LENGTH: 20
<212> TYPE: DNA
<213> ORGANISM: Artificial sequence
<220> FEATURE:
<223> OTHER INFORMATION: Synthetic

<400> SEQUENCE: 281
agcgcgcatc tgatctacaa                                                  20

<210> SEQ ID NO 282
<211> LENGTH: 24
<212> TYPE: DNA
<213> ORGANISM: Artificial sequence
<220> FEATURE:
<223> OTHER INFORMATION: Synthetic

<400> SEQUENCE: 282
gctagtgcta tactcgctct gctt                                             24

<210> SEQ ID NO 283
<211> LENGTH: 23
<212> TYPE: DNA
<213> ORGANISM: Artificial sequence
<220> FEATURE:
<223> OTHER INFORMATION: Synthetic

<400> SEQUENCE: 283
atgatgcatg gcaggttcgc caa                                              23

<210> SEQ ID NO 284
<211> LENGTH: 23
<212> TYPE: DNA
<213> ORGANISM: Artificial sequence
<220> FEATURE:
<223> OTHER INFORMATION: Synthetic

<400> SEQUENCE: 284
gatcaatcgt gaccttagcc tgc                                              23

<210> SEQ ID NO 285
<211> LENGTH: 23
<212> TYPE: DNA
<213> ORGANISM: Artificial sequence
<220> FEATURE:
<223> OTHER INFORMATION: Synthetic
```

<400> SEQUENCE: 285
aactcggcga ccagtgccaa aat            23

<210> SEQ ID NO 286
<211> LENGTH: 22
<212> TYPE: DNA
<213> ORGANISM: Artificial sequence
<220> FEATURE:
<223> OTHER INFORMATION: Synthetic

<400> SEQUENCE: 286
tgtctgcgcg caaaatgcca gc            22

<210> SEQ ID NO 287
<211> LENGTH: 24
<212> TYPE: DNA
<213> ORGANISM: Artificial sequence
<220> FEATURE:
<223> OTHER INFORMATION: Synthetic

<400> SEQUENCE: 287
ggcaaagacc ttcagacaat ctgg            24

<210> SEQ ID NO 288
<211> LENGTH: 23
<212> TYPE: DNA
<213> ORGANISM: Artificial sequence
<220> FEATURE:
<223> OTHER INFORMATION: Synthetic

<400> SEQUENCE: 288
caccccgaca acttttcctg tga            23

<210> SEQ ID NO 289
<211> LENGTH: 23
<212> TYPE: DNA
<213> ORGANISM: Artificial sequence
<220> FEATURE:
<223> OTHER INFORMATION: Synthetic

<400> SEQUENCE: 289
ttgatcgtgc aaagggatgg gtc            23

<210> SEQ ID NO 290
<211> LENGTH: 23
<212> TYPE: DNA
<213> ORGANISM: Artificial sequence
<220> FEATURE:
<223> OTHER INFORMATION: Synthetic

<400> SEQUENCE: 290
ctaacagtcc aagccaacct gca            23

<210> SEQ ID NO 291
<211> LENGTH: 22
<212> TYPE: DNA
<213> ORGANISM: Artificial sequence
<220> FEATURE:
<223> OTHER INFORMATION: Synthetic

<400> SEQUENCE: 291
gccatgaggg atcatgacac tg            22

<210> SEQ ID NO 292

```
<211> LENGTH: 22
<212> TYPE: DNA
<213> ORGANISM: Artificial sequence
<220> FEATURE:
<223> OTHER INFORMATION: Synthetic

<400> SEQUENCE: 292
tttgcacgat cagcgttccc gt                                          22

<210> SEQ ID NO 293
<211> LENGTH: 26
<212> TYPE: DNA
<213> ORGANISM: Artificial sequence
<220> FEATURE:
<223> OTHER INFORMATION: Synthetic

<400> SEQUENCE: 293
ctgtcctgtt actccatacc tagatt                                      26

<210> SEQ ID NO 294
<211> LENGTH: 21
<212> TYPE: DNA
<213> ORGANISM: Artificial sequence
<220> FEATURE:
<223> OTHER INFORMATION: Synthetic

<400> SEQUENCE: 294
cgacacctgg aggtagagca a                                           21

<210> SEQ ID NO 295
<211> LENGTH: 22
<212> TYPE: DNA
<213> ORGANISM: Artificial sequence
<220> FEATURE:
<223> OTHER INFORMATION: Synthetic

<400> SEQUENCE: 295
cctccaatca agtttgagac cc                                          22

<210> SEQ ID NO 296
<211> LENGTH: 20
<212> TYPE: DNA
<213> ORGANISM: Artificial sequence
<220> FEATURE:
<223> OTHER INFORMATION: Synthetic

<400> SEQUENCE: 296
gtacactcca gcgcgcatct                                             20

<210> SEQ ID NO 297
<211> LENGTH: 20
<212> TYPE: DNA
<213> ORGANISM: Artificial sequence
<220> FEATURE:
<223> OTHER INFORMATION: Synthetic

<400> SEQUENCE: 297
accaagtgtg gctgtagtca                                             20

<210> SEQ ID NO 298
<211> LENGTH: 20
<212> TYPE: DNA
<213> ORGANISM: Artificial sequence
<220> FEATURE:
<223> OTHER INFORMATION: Synthetic

<400> SEQUENCE: 298
``` ccccctgttgt atgcctagcc                                              20

<210> SEQ ID NO 299
<211> LENGTH: 9867
<212> TYPE: DNA
<213> ORGANISM: Human Pegivirus 2
<220> FEATURE:
<221> NAME/KEY: misc_feature
<222> LOCATION: (1284)..(1284)
<223> OTHER INFORMATION: N = A, C, T, or G
<220> FEATURE:
<221> NAME/KEY: misc_feature
<222> LOCATION: (1572)..(1572)
<223> OTHER INFORMATION: N = A, C, T, or G
<220> FEATURE:
<221> NAME/KEY: misc_feature
<222> LOCATION: (1745)..(1745)
<223> OTHER INFORMATION: N = A, C, T, or G
<220> FEATURE:
<221> NAME/KEY: misc_feature
<222> LOCATION: (1815)..(1815)
<223> OTHER INFORMATION: N = A, C, T, or G
<220> FEATURE:
<221> NAME/KEY: misc_feature
<222> LOCATION: (2052)..(2052)
<223> OTHER INFORMATION: N = A, C, T, or G
<220> FEATURE:
<221> NAME/KEY: misc_feature
<222> LOCATION: (2424)..(2424)
<223> OTHER INFORMATION: N = A, C, T, or G
<220> FEATURE:
<221> NAME/KEY: misc_feature
<222> LOCATION: (2562)..(2562)
<223> OTHER INFORMATION: N = A, C, T, or G
<220> FEATURE:
<221> NAME/KEY: misc_feature
<222> LOCATION: (2793)..(2793)
<223> OTHER INFORMATION: N = A, C, T, or G
<220> FEATURE:
<221> NAME/KEY: misc_feature
<222> LOCATION: (3291)..(3291)
<223> OTHER INFORMATION: N = A, C, T, or G
<220> FEATURE:
<221> NAME/KEY: misc_feature
<222> LOCATION: (3312)..(3312)
<223> OTHER INFORMATION: N = A, C, T, or G
<220> FEATURE:
<221> NAME/KEY: misc_feature
<222> LOCATION: (3336)..(3336)
<223> OTHER INFORMATION: N = A, C, T, or G
<220> FEATURE:
<221> NAME/KEY: misc_feature
<222> LOCATION: (3499)..(3499)
<223> OTHER INFORMATION: N = A, C, T, or G
<220> FEATURE:
<221> NAME/KEY: misc_feature
<222> LOCATION: (3711)..(3711)
<223> OTHER INFORMATION: N = A, C, T, or G
<220> FEATURE:
<221> NAME/KEY: misc_feature
<222> LOCATION: (3919)..(3919)
<223> OTHER INFORMATION: N = A, C, T, or G
<220> FEATURE:
<221> NAME/KEY: misc_feature
<222> LOCATION: (3987)..(3987)
<223> OTHER INFORMATION: N = A, C, T, or G
<220> FEATURE:
<221> NAME/KEY: misc_feature
<222> LOCATION: (4389)..(4389)
<223> OTHER INFORMATION: N = A, C, T, or G
<220> FEATURE:
<221> NAME/KEY: misc_feature
<222> LOCATION: (4890)..(4890)
<223> OTHER INFORMATION: N = A, C, T, or G
<220> FEATURE:
<221> NAME/KEY: misc_feature
<222> LOCATION: (5160)..(5160)

-continued

```
<223> OTHER INFORMATION: N = A, C, T, or G
<220> FEATURE:
<221> NAME/KEY: misc_feature
<222> LOCATION: (5368)..(5368)
<223> OTHER INFORMATION: N = A, C, T, or G
<220> FEATURE:
<221> NAME/KEY: misc_feature
<222> LOCATION: (5707)..(5707)
<223> OTHER INFORMATION: N = A, C, T, or G
<220> FEATURE:
<221> NAME/KEY: misc_feature
<222> LOCATION: (5710)..(5710)
<223> OTHER INFORMATION: N = A, C, T, or G
<220> FEATURE:
<221> NAME/KEY: misc_feature
<222> LOCATION: (5727)..(5727)
<223> OTHER INFORMATION: N = A, C, T, or G
<220> FEATURE:
<221> NAME/KEY: misc_feature
<222> LOCATION: (5746)..(5746)
<223> OTHER INFORMATION: N = A, C, T, or G
<220> FEATURE:
<221> NAME/KEY: misc_feature
<222> LOCATION: (5838)..(5838)
<223> OTHER INFORMATION: N = A, C, T, or G
<220> FEATURE:
<221> NAME/KEY: misc_feature
<222> LOCATION: (6036)..(6036)
<223> OTHER INFORMATION: N = A, C, T, or G
<220> FEATURE:
<221> NAME/KEY: misc_feature
<222> LOCATION: (6213)..(6213)
<223> OTHER INFORMATION: N = A, C, T, or G
<220> FEATURE:
<221> NAME/KEY: misc_feature
<222> LOCATION: (6309)..(6309)
<223> OTHER INFORMATION: N = A, C, T, or G
<220> FEATURE:
<221> NAME/KEY: misc_feature
<222> LOCATION: (6423)..(6423)
<223> OTHER INFORMATION: N = A, C, T, or G
<220> FEATURE:
<221> NAME/KEY: misc_feature
<222> LOCATION: (6486)..(6486)
<223> OTHER INFORMATION: N = A, C, T, or G
<220> FEATURE:
<221> NAME/KEY: misc_feature
<222> LOCATION: (6489)..(6489)
<223> OTHER INFORMATION: N = A, C, T, or G
<220> FEATURE:
<221> NAME/KEY: misc_feature
<222> LOCATION: (6999)..(6999)
<223> OTHER INFORMATION: N = A, C, T, or G
<220> FEATURE:
<221> NAME/KEY: misc_feature
<222> LOCATION: (7083)..(7083)
<223> OTHER INFORMATION: N = A, C, T, or G
<220> FEATURE:
<221> NAME/KEY: misc_feature
<222> LOCATION: (8100)..(8100)
<223> OTHER INFORMATION: N = A, C, T, or G
<220> FEATURE:
<221> NAME/KEY: misc_feature
<222> LOCATION: (8253)..(8253)
<223> OTHER INFORMATION: N = A, C, T, or G
<220> FEATURE:
<221> NAME/KEY: misc_feature
<222> LOCATION: (8497)..(8497)
<223> OTHER INFORMATION: N = A, C, T, or G
<220> FEATURE:
<221> NAME/KEY: misc_feature
<222> LOCATION: (8512)..(8512)
<223> OTHER INFORMATION: N = A, C, T, or G
<220> FEATURE:
<221> NAME/KEY: misc_feature
<222> LOCATION: (8997)..(8997)
<223> OTHER INFORMATION: N = A, C, T, or G
<220> FEATURE:
<221> NAME/KEY: misc_feature
```

```
<222> LOCATION: (9072)..(9072)
<223> OTHER INFORMATION: N = A, C, T, or G
<220> FEATURE:
<221> NAME/KEY: misc_feature
<222> LOCATION: (9134)..(9134)
<223> OTHER INFORMATION: N = A, C, T, or G
<220> FEATURE:
<221> NAME/KEY: misc_feature
<222> LOCATION: (9147)..(9147)
<223> OTHER INFORMATION: N = A, C, T, or G
<220> FEATURE:
<221> NAME/KEY: misc_feature
<222> LOCATION: (9336)..(9336)
<223> OTHER INFORMATION: N = A, C, T, or G
<220> FEATURE:
<221> NAME/KEY: misc_feature
<222> LOCATION: (9339)..(9339)
<223> OTHER INFORMATION: N = A, C, T, or G
<220> FEATURE:
<221> NAME/KEY: misc_feature
<222> LOCATION: (9348)..(9348)
<223> OTHER INFORMATION: N = A, C, T, or G
<220> FEATURE:
<221> NAME/KEY: misc_feature
<222> LOCATION: (9359)..(9359)
<223> OTHER INFORMATION: N = A, C, T, or G
<220> FEATURE:
<221> NAME/KEY: misc_feature
<222> LOCATION: (9363)..(9364)
<223> OTHER INFORMATION: N = A, C, T, or G
<220> FEATURE:
<221> NAME/KEY: misc_feature
<222> LOCATION: (9375)..(9375)
<223> OTHER INFORMATION: N = A, C, T, or G

<400> SEQUENCE: 299
aactgttgtt gtagcaatgc gcatattgct acttcggtac gcctaattgg taggcgcccg      60
gccgaccggc cccgcaaggg cctagtagga cgtgtgacaa tgccatgagg gatcatgaca     120
ctggggtgag cggaggcagc accgaagtcg ggtgaactcg actcccagtg cgaccacctg     180
gcttggtcgt tcatggaggg catgcccacg ggaacgctga tcgtgcaaag ggatgggtcc     240
ctgcactggt gccatgcgcg gcaccactcc gtacagcctg atagggtggc ggcgggcccc     300
cccagtgtga cgtccgtgga gcgcaacatg gggtgttcaa ctgatcaaac catttgttct     360
ccagtcgtgg gggccgacta taatacctcc tcgggctgcc gggccttaaa tgggagctac     420
cactgcggtg gtggctcttg ccggtcacca agtcgtgtgc aggttgcgag acgagtcttg     480
cagctgtgcg cattccttgc gctgatcgga tccggtatgt gttcgatccg gtccaaaact     540
gaagggcgca ttgagtcagg gcaaatattg cagtctcagc gcgcatgttg gactggtgag     600
ggttttgctt tcttttctaa ctgttgcaat caatctgata ttatgtggtg tttgcaccgt     660
tggtgtgtga caagacctgg ctgtttagtg tgcacgggca atgccactca tcctgtctgc     720
tgggactatc ttgggtccgg tgtaagtcgg cggcctgcgc gtcgaatggg tgagggagct     780
gaagtgcttc ttcgcttgat cggcattgca ggttggctcg ggctgttagc tgaggctctt     840
ggtatgtccg aaatctatgc agctattctt gctttggat  ttattgcttg gtatggctgg     900
ggtataccta aaacattggt gtgcacagtc tgccctgcag tgaacatttc tccctatagc     960
ttcttatctc cagatactat cgcatttggt acgtggatac tacaactacc tggtcttttg    1020
tggcaaatgt tgtcagctt  ccctatactt tacagcactt ggattcttg gttgttgctc    1080 agcggcaaga ctgttgctgt gatagcgatc cttttggcta gtcctacggt tatggcgtac    1140
aagcatcaat ctgaaagcta cctcaaatac tgtaccataa ccaatgcttc aactgctatg    1200
aactgtgact gccccttgg  aacctttact cgcaatactg agtctcgttt ctctatacct    1260
```

```
agattctgtc ctgttaaaat taanagctct acatttatct gttcatgggg gtcgtggtgg    1320
tggtttgctg agaacatcac acgtccatac tcggacgttg gcatgccacc agcaccgatt    1380
tccgctttgt gctatatcta ttcaaacaat gacccacctc cttggtatca taacacaact    1440
atcataccto agaactgtcg caactctacg gttgatccta ccacagctcc atgccgtgac    1500
aagtggggca atgcaactgc ttgtattctt gaccgccggt cgcggttctg cggggactgc    1560
tatggcggtt gnttctatac taatggtagt catgatcgat cctgggatcg atgcgggatt    1620
ggttaccgtg atggactcat agagttcgtg cagctcggtc agattcgacc taacatctcg    1680
aatacgacca ttgagctcct cgctggcgcc tcgcttgtga tcgcatccgg tcttcggcct    1740
gggtntggtt gcagccgagc gcatggcgtg gtgcactgct ataggtgtcc ttcataccgt    1800
gaccttgaac agttnggtcc tgggcttggg aaatgggtgc cattgcccgg cgagcctgtc    1860
ccggagttgt gtatcaaccc tcagtgggcg aggcgcggct tccggatgtc taataatcct    1920
ctgagcttgc tacagacctt cgttgaggac atttttcctag cgcctttttg taatccgacg    1980
cctggccgtg tacgtgtgtg taacaatacc gctttctatc caagaggagg cggctttgtg    2040
cagctcatcg gngacgtcca ggtgctaacc cctaacactg catctttaca ctctctgctg    2100
actttgatat ctcttatctt gttggtgtgt gttgtttctg gtgcgcgatt cgttccacta    2160
ataatcatat ttttctggag cgcgcgccat gtatatgctt cttgttactt aagctgtgat    2220
tgggctgttt gcaacgatgc gttctgtttc acatctggca cttgtgctac cttcaatgac    2280
gtcttgtgtc tgccggttgc gacgcgcata tcgtcctgtg ccatgctgt gccaccgccc    2340
gaccgtggtt gggaggtgcc tgcggcgatg tcatgggtga tttcgcggac tactggcttg    2400
acgttcgatg tcttttcctt catncagtat cttcctactg tgcctggcaa caacaccgat    2460
atcatttact gtggtgaacc aaccttcttc ggggacatca cgggcatcta ttggccttac    2520
tttttgcctg gcgtgttgct cttgtacttg actcccttcc tnggtttaag gttaatgctt    2580
gccggcttta atatagatgg cttgtttccc atacggcatg ccacggctgc actgaggttc    2640
tcgacttcgc gtgtgacctt gagtgtcgta tctgcttttc taatctatat attatctcac    2700
cctgttaatg ctgcgctcaa tagaatgttc ttagcatctg caaatttaga gatgatctta    2760
tcctttgata cctatcatga gactgttctt tanatcgttt gtctattgct ctacctccag    2820
gtgtcgcccc gtgcgggctt ggccgctatg gtggccatca agctatctcg aggcctgtta    2880
ttcgctgtgg tgttggcgca cggagtgtgc cgacctgggc gggtatttgg tcttgaggtt    2940
tgcgcggaca tctcttggtt ggtggagttt actggcaact gcacttggta catgtcctgt    3000
gtcttctctt tttggtgcgc agtgtttgcc ttcaccagtc cacttggacg acagtataag    3060
cttcagatct atcggtactg ggcgcaggtc tatgccagac tcatcctcgc tgtcggttgt    3120
ggtcctctcg ggcgagagtt ccatttccgc gcaagcgtgg gcgtgctttg gtgtggtgct    3180
tgcatgctct ggccccgtga gtgctctgaa atcagcttgg tcttcattct gtgtgctctg    3240
acagtggaca ccatagacac atggttagta gcgtgccttgt ccgcagggcc nagtgcgcga    3300
acccttgcaa cnctggccga tgacatggcg cgcatnggtg accaccgggc gttgcgcgcc    3360
gtgttgcgtt gctttggatc acgtggcaca tacatataca accacatggg ccaggtctca    3420
gaacgggtgg cgcaagcagt cagggatctc ggcggttgct tggaaccagt cgtgttggag    3480
gagcccacct ttactgagnt cgtggatgat acaatgagtt tggtgtgtgg acaattgctt    3540
ggaggtaaac ccgtggtggc ccgctgcggc acgcgtgtct tggtgggaca cctcaacccct    3600
gaagatctgc cacctggttt ccagctgagt gctccggtgg ttattaccaa accaagcatt    3660
```

```
ggtacgtggt ccttccttaa ggcgacactc acagggcgtg ctgaaacacc nggatccggc   3720
cagatcgtgg tgttgtcttc cctgacaggt cggtcaatgg gtactgcagt gaatggcaca   3780
ctgtatgcga ccggccatgg tgccggtgcg cgcggcctag ccacgtgcgc tggtttgagg   3840
acgccacttt acacggcatt atctgatgat gtcgtggcct actcttgcct tccgggcatg   3900
agttccctag agccctgcng ctgttcgccg agccgggttt gggtgatgaa caacaacgga   3960
gggttggtgt gtggcagagt ggagaangac gacgtctgtt tggactgtcc cacgcacata   4020
gatcaactgc ggggtgcttc ggggtcaccg gttttgtgtg atcacggtca tgcatacgcg   4080
ttgatgctcg gtggttactc taccagtggt atttgtgcgc gtgtccggat agtccggcca   4140
tggcagaacg cctattcctc ctcagggggg caaggcggaa tgcaggcgcc agctgtgaca   4200
ccaacatact ctgaaatcac ctactatgcc cctactggtt ctggtaagtc aacaaaatat   4260
ccagtggacc tagtcaaaca gggacacaaa gtattggtcc ttataccaag tgtggctgtc   4320
gtcaaaagta tggccccctta cattaaggag acatataaga ttagacctga aattagagct   4380
ggcacaggnc ctgacggtgt gacggtcatc actggtgaga acttggcgta catgacctat   4440
ggccgcttcc ttgtggatcc ggagacgaat ctgcggggtt atgccgtagt catttgcgac   4500
gagtgccacg acacatcatc caccacgcta ctcggcattg gcgcagtgcg catgtatgcc   4560
gagaaagctg gagtgaagac cgttgtattc gccacagcca ctcctgctgg cattcaagta   4620
cagccacatc ccaacattga tgaatattta ttgactgaca caggcgacgt ggaattctac   4680
ggcgccaaaa tcaaattgga caacatcaga actggtagac atgttatctt ttgccactcg   4740
aaggccaggt gtgcggaact aacgcagcag ctctccggcc ttggtgttcg tgcagtgagt   4800
ttttggcgcg gctgtgacat caaaaccatt cccgcctcag actctattgt tgtagtggca   4860
actgatgcat tgtccacagg ctacacaggn aactttgatt cggtcatcga ctgcgggtgt   4920
tgcgtagagc aaactgtgac aattgacatg gaccctacgt tctccatctc ggcccgagtg   4980
gtgccatgta ctgctgcatt gcgtatgcag cggcgcggac gtaccggtcg tggcagaagg   5040
ggagcgtact acacaaccac tccaggagca gcaccctgcg tcagcgttcc cgatgctaac   5100
gtctggcaag cagtggagag cgccatggtc ttttatgatt ggagtgctgc caggatacan   5160
cagtgcctgg cggcatacca tgatttaggg tgcacaccac gcatcagttg tgacccacac   5220
actccagtgc gggtgatgga cacactgagg gcgtacctgc gcagacctga ggtgacgact   5280
gcggctctcg caggagagca gtggccgctg ctttacggtg tgcagttgtg catctgcaaa   5340
gagaccgagg cccacggtcc agacgatngc atcaagtgga agtgcttact caacaacagt   5400
aacaaaacac ccctgttgta tgccttagac aatcctacac tggaattcac tacccaacat   5460
gacttgactc gccgtatagc cggcgcttta tcgagcacag tgttcgtgga cacaggctac   5520
ggccccatcc tccttgctgg cgccgctttg gctgcctcct tcgcctttgc gggcgccact   5580
ggagctttag tgccgtcggc cgtttggagc gttgacaacg gcttgctggt gtgaccccgt   5640
cccgacgcga cagacgagac cgcggcctac gcgcagcgct tgtaccaagc ctgcgcagat   5700
tcagganttn tcgccagctt gcagggnacg gcgagtgcgg cgctgngcaa actggccgat   5760
gccagtaggg gtgctagtca atatctggca gccgcgcctc cttcgcccgc cccctggta    5820
caggtgctgc agttcctnga ccaacttttt agctccattg catctttcgg tctgctctgt   5880
gctgctgtc aggctggcga gtgcttcact gcgcttgccg ggttggtgtc cggtgctaca    5940
gctggcttgg gaggtgccca taagtggttg ttagctattg caggaacttg gctagttagc   6000
```

```
ttgcagactg ggccccgtgg cggcatggtt gcgggnctct cggttctagc aggctgttgc    6060
atcggtagtg tcaccgggct tgacttcctg tttgggtgcc ttacaggttg ggaggccgtg    6120
gtcggtgctg cggttgcgac acagaagatc ttgtctggtt cggctgatat gaccactctg    6180
gtagatctct tacctgctct cttctcccct ggngccggca tagctggcat cgtgcttgtc    6240
tttattctaa gcaactcaag tgtaaccacg tgggctaatc ggctattgtc catgtgtgca    6300
aaacaaacna tttgtgaaaa ctacttctta actgagaaat ttggccaaca attaagcaaa    6360
cttccctgt ggcgctctgt gtaccattgg gcgcaggcac gtgagggata cacacagtgc     6420
ggngtggtca gcgggatctg gagctttgtc ttgtgcattc tacgcgctgt gtgggattgg    6480
gcggcnaanc atgtgccacg gttccgtgtg cctatgattg gctgctcacc tgcgtggtgc    6540
gggcgctggc ttggtaccgg caccttgttg accacctgtg ggtgtggaga acgtgtgtcc    6600
cttcagtgcc tttgctcaac atctgaccca acactcagtg tgggccgttg gtgtcggtgt    6660
agttggagtg ttgggttccc attcaacccg actacgacag ccaccggcac tttacggccg    6720
gacatcagtg acgccactaa attgggtttc cggtatggtt ttgccgagat cgtggagcta    6780
gagcggcggg gcgacaaatg gcatgtctgt gcagcatcat gttgcttgga ccgagccagc    6840
gttgcatccg ccgtgaaggc cccaccggtc acggccaatg gtatacctat cagtacctt     6900
tctccaccac aaacttacag cctctctctc tgttcttttg attcagtttg catgtctact    6960
aacttatgta acccagctaa gaccctgagt gtgtgctcnc aggaggctgt tgagctactg    7020
gaagaaacag ttgacacagc acaagtaatg atgtgtcaaa atctggaggc gcgaagacgc    7080
gcngagtatg atgcatggca agttcgccaa gcagttggcg acgagtacac gcgtttggca    7140
gacgaggatg ttgacacgac aacgtcggtg aaaccccggg tggccagggc tgctgtgggt    7200
agctcaacgt tggatgatgt tagcgtgctg actgtcttgc gcgaactcgg cgaccaatgc    7260
caaaatgcta tcaaatttgt agttcaggcg gcttcacggt ttgttccacc agtgcccaag    7320
ccacgcacgc gtgtctcggg tgtgttggag cgtgtgcgca tgtgcatgcg cacgccacca    7380
atcaagtttg aggccaccgc agtaccaatt cataacataa tcccagaaga gtgtcacatt    7440
gtgctacgct gtaccggctg taacgaccag gccttgactg ttccgtacgg cacttgcact    7500
cagactttaa tcaaacattt gactaacaaa cacagccact acattccaaa acagaagata    7560
gaagaagaca cagaagtaac tgtcatttgc gccgtaccaa caaagcgcgc aagtaaactc    7620
atcactttca gagcaggtga tcgatcagtc tcatgttgtc accccttgca aactcctatt    7680
agggccctgc ttctaaagta cgggttacct atcgggaagt ggtccgactg caacgggccc    7740
cttggtgacg acgcccgagt ctgtgacgtc aatggagtaa caacttatga accatgcatg    7800
caatcctaca gttggttccg accgattgtg gcaccaacaa ccccaccttt acctgcaacc    7860
cggagcgtgg ctggcatttt acgcgcagac acatcgcgcg tttacaccac aacggcggtt    7920
gacgtctccg agcggcaggc taaggtcaca attgatcaaa catcagccaa ggtgatcag    7980
tgtttccgag acacatacaa ttgctgcctt gctaaggcaa agaccttcag acaatctggc    8040
atgtcatatg aggatgctgt gtcaaagatg cgcgcaaaca ccacgcgtga ccataacaan    8100
ggcatcactt attcagattt ggtctctgga cgcgcaaaac ctgtcgttca gaaaattgta    8160
gatcaaatgc gcgctggagt gtacgacgct ccaatgcgca ttatcccaaa acctgaagtg    8220
ttccctcgag acaagtcaac acggaagcca ccncggttca tcgttttccc tgggtgcgcc    8280
gcgcgagtcg cggagaaaat gatcctgggc gatcctggcg cgataaccaa gcacgtgcta    8340
ggtgatgcct acgggtttgc cactccgccg catgagcgcg cgcgcctatt ggaacaatgg    8400
```

```
tggaaccgcg caacggagcc acaagctatc gcggttgatg cgatctgctt tgatagcacc    8460
atcacggcag aggacatgga tcgtgaggcc aacatcntgg ctgcagcgca tncggaccct    8520
gaaggtgttc acggcctata caattattac aaaagaagcc ccatgtgtga catcacagga    8580
aaagttgtcg gggtgcgttg ctgtcgagcc tcaggtacgc ttacaacaag cagtggcaac    8640
acgcttactt gctacctcaa ggttcgtgca gcttgcacgc gcgccggcat taaaccaatt    8700
ggcttactaa ttcatggaga tgacaccctc attatcacag aacgttgcgc tcaagaaact    8760
ctcgatgagt tcagcaacgc acttgatgac tatgggttcc ctcacaccat ccaggtgtct    8820
ggggacctct cgtctgtcga gtgctgtagc gcacgtgtgg acagcgtttg cctccgggga    8880
ggtatgcgtc gcatgctcgt gccacaagct cgacgtgcga ttgcacgcgt tctcggggaa    8940
aagggcgatc cactgggtgt catcagcagc tatattgtca tgtatcctac tgcggcngtg    9000
actgtctacg tgctattgcc cctgttgtgc atgctcattc gaaatgagcc atcgcagacg    9060
gggacacttg tnacgctgac ggtccacggt aacagtgtga cgtgccagt gtggctgctt     9120 ccaaccatca ttgnaaattt acatggncgt gacgcactac aggtagtccg tcacagtgca    9180
gcttccatgg cggaactgtc atcagcgttg gccttctttg gcatgagagg gttgaactgc    9240
tggaggcgga gacgccgtgc catcaggact gatatgatca gttgggcgg gtggaatgcg     9300 aatttcgcgc agatgttact gtggtcaccg gaggtnagna caccacancc cgaaccaang    9360
ggnntgtgtc tcttnccacc ggaactatgg gagcgtccgt acgaaaattt gcacttgagc    9420
acgatcgacc gcaatcgtgg tgctagtcgc ttacggtttt ggttggttgc tagtgctata    9480
ctcgctctgc tttgcttgta aatcctaaat caatgtagta ccaggactac aaggcaggag    9540
gtgaagtcag ctgtacccac ggctggctga accggggct tgacgacccc ccctatccga     9600
gttgggcaag gtaacatcac gggtgtgacg accccgcccc ccatgtcgc gcgtaagcgc     9660 acgggcaagg cagctaggct gagagtctgg gcaactctcc cgtacccac ccgaggctac     9720 gcctcgtcct ggcgaggacc gtaaacatac gtcgtcagcg tggtgacctg acgtatcttg    9780
ttaaccactt aatggtcgta actcgacccc cgtgccgggg atctaagcgc ggcaccgcga    9840
tgaggggggt caacggcccc tttcatt                                        9867
```

<210> SEQ ID NO 300
<211> LENGTH: 9867
<212> TYPE: DNA
<213> ORGANISM: Human Pegivirus 2

<400> SEQUENCE: 300

```
aactgttgtt gtagcaatgc gcatattgct acttcggtac gcctaattgg taggcgcccg      60
gccgaccggc cccgcaaggg cctagtagga cgtgtgacaa tgccatgagg gatcatgaca     120
ctggggtgag cggaggcagc accgaagtcg ggtgaactcg actcccagtg cgaccacctg     180
gcttggtcgt tcatggaggg catgcccacg gaacgctga tcgtgcaaag ggatgggtcc      240
ctgcactggt gccatgcgcg gcaccactcc gtacagcctg atagggtggc ggcgggcccc     300
cccagtgtga cgtccgtgga gcgcaacatg gggtgttcaa ctgatcaaac catttgttct    360
ccagtcgtgg aggccgacta taatacctcc tcgggctgcc gggccttaaa tgggagctac     420
cactgcggtg gtggctcttg ccggtcacca agtcgtgtgc aggttgcagg acgagtcctg     480
cggctgtgcg cattccttgc gctgatcgga tccggtatcgt gttccatccg gtccaaaaat    540
gaagggcgca ttgagtcagg gcaaatattg cagtctcagc gcgcatgttg gactggtgag    600
```

```
ggtttcgctt tcttttctaa ctgttgcaat caatctgaca ttatgtggtg tttgcaccgt    660
tggtgtgtga caagacctgg ctgtttggtg tgcacgggca atgccactca tcctgtctgc    720
tgggactatc ttgggtccgg tgtgagtcgg cggcctgcgc gtcgaatggg tgagggagct    780
gaagtgcttc ttcgcttgat cggcattgca ggttggctcg ggctcttagc tgaggctctt    840
ggtatgtctg agatctatgc agctttcctt tgctttggat ttattgcttg gtatggctgg    900
ggtataccta agacattggt gtgcacagtc tgccctgcag tgaacatttc tccctatagc    960
ttcttatctc cagatactat cgcatttggt acgtggctac tacaactgcc tggtcttttg   1020
tggcaaatgt ttgtcagctt ccctatactt tacagtactt ggattcttg gttgttgctc    1080
agcggcaaga ctgttgctgt gatagcgatc cttttggcta gtcctacggt tatggcatac   1140
aagcatcaag ctgatagcta cctcaaatac tgtaccataa ccaatgcttc aactgctatg   1200
aactgtgact gccccttgg aactttcact cgcaatactg agtctggttt cactatacct    1260
agattctgtc ctgttaaact taatagctct acatttatct gttcatgggg gtcgtggtgg   1320
tggtttgctg agaacatcac acgtccatac tcggacgttg gcatgccgcc agcaccgatt   1380
tccgctttgt gctatatcta ttcaaacaat gacccacctt cttggtatcg taacacaact   1440
atcataccte agaactgtta caactctacg gctgatccta ccacagctcc atgccgtgac   1500
aagtggggca atgcaactgc ttgtattctt gaccgccggt cgcggttctg cggggactgc   1560
tatggcggtt gcttctacac taatggtagt catgaccgat cctgggatcg atgcggaatt   1620
ggttaccgtg atggactcat agagttcgtg cagctcggtc agattcgacc taacatcgcg   1680
aatacgacca ttgagctcct cgctggcgcc tcgcttgtga tcgcatccgg tcttcgggct   1740
gggtatggtt gcagccgagc gcacggcgtg gtgcactgct ttaagtgtcc ttcataccgt   1800
gaccttgaac ggttcgggcc cgggcttggg aaatgggtgc cattgcctgg cgagcctgtc   1860
ccggagttgt gtattaaccc gcagtgggcg aggcgcggct tccgggtgtc taataatccc   1920
ttaagcgtgc tacagacctt cgttgaggac atttttcttag cgcctttctg caatccgacg   1980
cctggccgtg tacgtgtgtg taacaatact gctttctacc cgagaggagg cggctttgtg   2040
cagctcatcg gagacgtcca ggtgttaacc cccaactcta catctttgca ctctctgctg   2100
actttgatat cccttatctt gttagtgtgt gttgtttctg gcgcgcgatt cgttccattg   2160
ggaatcatat tcttctggag cgtgcgccac gtatatgctt cttgttactt aagctgtgat   2220
tgggctgttt gcaacgatgc gttctgtttc acatctggca cttgtgctac cttcaacgac   2280
gtcttgtgtc tgccggttgc ggcgcgcata tcgtcctgtg gccatgctgt gccaccgccc   2340
gaccgtggtt gggaggtgcc cgcagcgatg tcatgggcga tttcgcgtac taccggcttg   2400
acgttcgatg tcttttcctt catccagtac cttcctactg tgcctggcaa caattccgat   2460
atcatttact gtggtgaacc aagcttcttc ggggacatca cgggtatcta ttggccttac   2520
ttttgcctg gcatgttgct cttgtacttg actcccctcc tgggtttaag gttaatgctt    2580
gccggcttta atatagatgg cttgtttccc atacggcatg ccacggctgc actgaggttc   2640
tcgacttcgc gtgtgacctt gagtgtcgta tttgctttcc taatctatat attatctcat   2700
cctgttaatg ctgcgctcaa tagaatgttc ctagcatctg caaatctaga gatgatctta   2760
tcctttgata cctatcatga gactgttctt tacgtcgttt gtctattgct ctacctccag   2820
gtgtcgcccc gtgcgggctt ggctgctatg gtgccatca agctatctcg aggcctgtta   2880
ttcgctgtgt tgttggcgca cggagtgtgc gacctgggc gggtatttgg tcttgaggtt   2940
tgcgcggaca tctcttggtt ggtggagttt actggcaact gcacttggta catgtcctgt   3000
```

```
gtcttctctt tttggtgcgc agtgtttgcc ttcaccagtc cacttggacg acagtataag   3060
cttcagatct atcggtactg ggcgcaggcc tatgccagac tcatcctcgc tgtcggttgt   3120
ggtcctctcg ggagggagtt ccatttccgt gcgagcgtgg gcgtgctctg gtgtggtgct   3180
tgcatgctct ggccccgtga gtgctctgaa atcagcttgg tctttattct gtgtgctctg   3240
actgtggaca ccatagacac atggttagta gcgtgcttgt ccgcagggcc aagcgcgcga   3300
acccttgcaa ctctggccga tgacatggcg cgcattggtg accaccgggc gttgcgcgcc   3360
gtgttgcgtt gctttggatc acgtggcaca tacatataca accacatggg ccaggtctca   3420
gaacgggtgg cgcaagcagt cagggatttc ggcggttgct tggaaccagt cgtgttggag   3480
gagcccacct ttactgaggt cgtggatgat acaatgaatt tggtgtgtgg acaattgctt   3540
ggaggtaaac ccgtggtggc ccgctgcggg acgcgtgtct tagtgggaca cctcaaccct   3600
gaagacctgc cacctggttt ccagctgagt gctccggtgg ttattaccaa accaagcatt   3660
ggtacgtggc cctttcttaa ggcgacactc acagggcgtg ctgaaacacc gggatccggc   3720
cagatcgtgg tgttgtcttc cctgacaggt cggtcaatgg gtactgcagt gaatggcaca   3780
ctgtatgcga ccggccacgg tgctggtgcg cgcggcctag ccacgtgcgc tggtttgagg   3840
acgccacttt acacggcatt atctgaagat gtcgtggcct actcttgcct tccgggcatg   3900
agctccctag agtcctgcaa ctgctcgccc agcccgggttt gggtggtgaa caacaacgga   3960
gggttggtgt gtggcagagt ggagaaagac gacgtctgtt tggactgtcc cacgcacata   4020
gatcaactgc ggggtgcttc ggggtcgccg gttttgtgtg atcacggtca tgcatacgcg   4080
ttgatgctcg gtggctactc taccagtggt atttgtgcgc gtgtccggat agtccggcca   4140
tggcagaacg cctattcctc ctcaggggg caaggcggaa tgcaggcgcc agctgtgaca   4200
ccaacatact ctgaaatcac ctactatgcc cctactggtt ctggtaaatc aacaaaatat   4260
ccagtggacc tagtcaagca gggacacaaa gtattagtcc ttttaccaag tgtggctgtc   4320
gtcaaaagta tggctcctta cattaaggaa aaatataaga ttagacctga aattagagct   4380
ggcacagggc ctgacggtgt gacggtcatc actggcgaga acttggcgta catgacctat   4440
ggccgttttcc ttgtagatcc ggaaacgaat ctgcggggtt acgctgtagt catctgcgac   4500
gagtgccatg acacatcatc caccacgcta ctcggcatcg gcgcagtgcg catgtatgct   4560
gagaaagctg gagtgaagac cgttgtattc gccacagcca ctcctgctgg cattcaagtg   4620
cagtcacatc ccaacattga tgaatatcta ttgactgata caggcgacgt ggaattctac   4680
ggcgctaaaa ttaaattgga caacatcaga actggtagca atgttatctt ttgccactcg   4740
aaggccaggt gtgcggaact aacgcagcag ctctccggcc ttggtgttcg tgcagtgagt   4800
ttttggcgcg gctgtgacat caagagcatt cccgcctcag actctattgt tgtagtggca   4860
actgatgcat tgtccacagg ctacacaggg aactttgatt cggtcattga ctgcgggtgt   4920
tgcgtagagc aaactgtaac aattgacatg gaccccacgt tctccatctc ggcccgagtg   4980
gtgccatgca ctgctgcatt gcgtatgcag cggcgcggac gcaccggtcg tggcaggagg   5040
ggagcgtact acacaaccac tccaggagca gcccctgcg tcagcgttcc cgatgctaac   5100
gtctggcaat cagtggagtc agccatggtc ttttatgatt ggagtgctgc caggatagag   5160
caatgcctgg cggcatacca tgatttaggg tgcacaccac gcatcagttg tgacccacac   5220
actccagtgc gggtgatgga cactgagg gcgtatctgc gcagacctga ggtgacgacc   5280
gcggctctcg caggagagca gtggccgctg ctttacggcg tgcagttgtg catctgcaaa   5340
```

```
gagaccgagg cccacggtcc agacgatggc atcaagtgga aatgcttact caataacaac    5400
aacaaaacac ccctgttgta tgccttagac aatcctacac tggaattcac tacccaacat    5460
gacttgactc gccgtatagc tggcgcttta tcgagcacag tgttcgtgga gacaggctac    5520
ggccccatcc tcctcgctgg cgctgctttg gctgcctcct ttgcctttgc gggcgccact    5580
ggagctttag tgccgtcggc cgtttggagc gttgaaaacg ggcttgctgg cgtgacccgt    5640
cccgatgcga cagacgagac cgcggcctac gcgcagcgct tgtaccaagc ctgcgcagat    5700
tcaggaattc tcgccagctt gcagggtacg gcgagtgcgg cactgagcag actggccgat    5760
gccagtaagg gtgctagtca atatctggca gccgcgcctc cttcgcccgc cccctggta    5820
caggtgctgc agttcctcga gaccaatttt agctccattg catctttcgg tctgctctgt    5880
gccggctgtc aggccggcga gtgcttcact gcgcttgccg ggttggtgtc cggtgctaca    5940
gctggcttgg gaggtgccca taagtggttg ttagctattg caggaacttg gctagttagc    6000
ttgcagactg gccccgtgg cggcatggtt gcgggtctct cagttctagc aggctgttgc    6060
atcggtagtg tcaccgggct tgacttcctg tttgggtgcc ttacaggttg ggaggccgtg    6120
gtcggtgctg cggttgcaac gcagaaaatc ttgtctggtt cggctgacat gaccactctg    6180
gtagatctcc tacctgctct cttctcccct ggcgccggca tagctggcgt cgtgcttgtc    6240
tttattctaa gcaactcaag tgtaaccatg tgggctaatc ggctattgtc catgtgtgca    6300
aaacaaacta tttgtgaaaa ttacttctta actgagaaat ttggccaaca attaagcaaa    6360
cttttccctgt ggcgctctgt gtaccattgg gcgcaggcac gtgaaggata cacacagtgc    6420
ggtgtggtca gcgggatctg gagctttgtc ttgtgcattc tacgtgctgt gtgggattgg    6480
gcggctaaac atgtgccacg gttccgtgtg cctatgattg gctgctcacc tgcgtggtgc    6540
gggcgctggc ttggtactgg caccttgttg accacctgtg ggtgtggaga acgtgtatcc    6600
cttcagtgcc tttgctcgac atctgaccca acactcagtg tgggccgttg gtgttggtgt    6660
agttggcgtg ttgggttccc attcaacccg acgacgacag ccaccggcac tttacggccg    6720
gacatcagtg acgccaccaa attgggcttc cggtatggtg tcgccgagat cgtggagcta    6780
gagcggcggc gcaacaaatg gcatgtctgt gcagcatcat gttgcttgga ccgggccagc    6840
gttgcatccg ccgtgagggc cccaccggtc acggccgatg gcataccctat cagtaccttt    6900
tctccaccac aaacttacaa actctctctt tgttcttttg attcagtttg catgactact    6960
aacttatgta atccagctaa gaccctgagt gtgtgctcgc aggaggctgt tgagctactg    7020
gaagaaacag ttgacagagc acaagtagtg atgtgtcaaa atctggaggc gcgaagacgc    7080
gctgagtttg atgcatggca agttcgcgaa gcaattcgcg acgagtacac gcgtttggca    7140
gacgaggatg ttgacgcgac aacgtcggtg aaaccccccgg tggccaaggc tgctgtgggt    7200
agctcgacgt tggatgatgt tagcgtgctg actgtcttgc gcgaactcgg tgaccagtgc    7260
caaaatgcta tcaaatttgt agttcaggcg gcttcacggt ttgttccacc agtgcccaag    7320
ccacgcacgc gtgtctcggg tgtgttggag cgtgtgcgca tgtgcatgcg cacgccacca    7380
atcaagtttg aggctgccgc agtaccaatt catgatataa tcccagaaga gtgtcacatt    7440
gtgctacgct gtaccggctg caacgaccag gccttgactg ttccgtacgg cacttgcact    7500
cagtctttaa tcaagcattt gactagtaaa cacagtcact acattccaaa acagaagata    7560
gaagaggaca cagaagtaac tgtcatttgc gccgtaccaa caacgcgcgc aagcaaactc    7620
atcacattca gagcaggtga tcgatcagtc tcatgttgtc accccttgca aacccctatt    7680
agggccctgc ttctaaagta cgggttacct atcgggaagt ggtctgactg caacgggccc    7740
```

```
cttggtgacg atgctcgagt ctgtgacgtc aatggagtaa caacttatga accatgcatg   7800
caatcctaca gttggtttcg accgattgtg gcaccaacaa ccccaccttt gcctgcaacc   7860
cggaccgtgg ctggcatttt acgcgcagac acatcgcgcg tttacaccac aacggcggtt   7920
gacgtctccg agcggcaggc caaggtcaca attgatcaaa catcagccaa ggtggatcag   7980
tgtttccgag acacatacaa ttgctgcctt gctaaggcaa agaccttcag acaatctggc   8040
atgtcatatg aggatgctgt gtcaaagatg cgcgcaaaca ccacgcgtga ccataacaac   8100
ggcatcactt attcagattt ggtctctgga cgcgcaaaac ctgtcgttca gaaaattgta   8160
aatcaaatgc gcgccggagt gtacgacgct ccgatgcgca ttatcccaaa acctgaagtg   8220
ttccctcgag acaaaacaac acggaagcca ccgaggttca tcgttttccc tgggtgcgcc   8280
gcgcgagtcg cggagaaaat gatcctgggt gatcctggcg cgataaccaa gcacgtgcta   8340
ggtgatgcct acgggtttgc cactccgccg catgagcgcg cgcgcctgtt ggaacaatgg   8400
tggaaccgcg caacggagcc acaagctatc gcggttgatg cgatctgctt tgatagcacc   8460
atcacggcag aggacatgga tcgtgaggct aacatcgtgg ctgcagcgca tacggaccct   8520
gaaggtgttc acggcctata taattattac aaaagaagcc ccatgtgtga catcacgggg   8580
aaggttgtcg gagtgcgttg ctgtcgagcc tcgggtacgc ttacaacaag cagtggcaac   8640
acgcttactt gctaccttaa ggttcgtgca gcttgcacgc gctccggcat taaaccaatt   8700
ggcttactaa ttcatggaga tgacaccctc atcgtcacag aacgttgcgc tcaagagact   8760
ctcgatgagt tcagcaacgc acttgatgac tatgggttcc cacacaccat ccaggcgtct   8820
ggggacctct cgtctatcga gtgctgtagc gcacgtgtgg acagcgtttg cctccgggga   8880
ggtatgcgtc gcatgcttgt gccacaagct cgacgtgcga ttgcacgcgt tctcggggaa   8940
aagggcgatc cactgggtac catcggtagc tatgttgtca tgtatcccac tgcggccgtg   9000
actgtctacg tgctattgcc cctgttgtgc atgctcatac gaaatgagcc atcacagacg   9060
gggacacttg tgacgctgac ggtccacggt aacagtgtga gtgtgccagc gtggctgctt   9120
ccaaccatca ttgcaaattt acatggtcgt gacgcactac aggtagtccg tcacagtgca   9180
gcttccatgg cggaattgtc atcagcgttg gccttctttg gcatgagagg gttgaattgc   9240
tggaggcgga gacgccgtgc cattagggct gatatgatca gtcgggcgg gtggaatgcg   9300 aatttcgcgc agatgttact gtggtcaccg gaggtaagaa caccacaacc cgaaccaagg   9360
ggtctgtgtc ttttgccgcc ggaactgtgg gagcgtccgt acgaaaattt gcacttgagc   9420
acgatcgacc gcaatcgtgg tgctagtcgc ttacggtttt ggttggttgc tagtgctata   9480
ctcgctctgc tttgcttgta aatcctaaat caatgtagta ccaggactac aaggcaggag   9540
gtgaagtcag ctgtacccac ggctggctga accgggggct tgacgacccc ccctatccga   9600
gttgggcaag gtaacatcac gggtgtgacg accccgcccc ccatgtcgc gcgtaagcgc   9660 acgggcaagg cagctaggct gagagtctgg gcaactctcc cgtacccac ccgaggctac   9720 gcctcgtcct ggcgaggacc gtaaacatac gtcgtcagcg tggtgacctg acgtatcttg   9780
ttaaccactt aatggtcgta actcgacccc cgtgccgggg atctaagcgc ggcaccgcga   9840 tgagggggt caacggcccc tttcatt                                       9867
```

<210> SEQ ID NO 301
<211> LENGTH: 9867
<212> TYPE: DNA
<213> ORGANISM: Human Pegivirus 2

```
<400> SEQUENCE: 301
aactgttgtt gtagcaatgc gcatattgct acttcggtac gcctaattgg taggcgcccg      60
gccgaccggc cccgcaaggg cctagtagga cgtgtgacaa tgccatgagg gatcatgaca     120
ctggggtgag cggaggcagc accgaagtcg ggtgaactcg actcccagtg cgaccacctg     180
gcttggtcgt tcatggaggg catgcccacg ggaacgctga tcgtgcaaag ggatgggtcc     240
ctgcactggt gccatgcgcg gcaccactcc gtacagcctg atagggtggc ggcgggcccc     300
cccagtgtga cgtccgtgga gcgcaacatg gggtgttcaa ctgatcaaac catttgttct     360
ccagtcgtgg gggccgacta taatacctcc tcgggctgcc gggccttaaa tgggagttac     420
cactgcggtg gtggctcttg ccggtcacca agctgtgtgc aggttgcgag acgagtcttg     480
cagctgtgcg cactccttgc gctgatcgga tccggtatgt gttcgatccg gtccaaaact     540
gaagggcgca ttgagtcagg gcaaatattg cagtctcagc gcgcatgttg gactggtgag     600
ggtttcgctt tcttttctaa ctgttgcaat caatctgata tcatgtggtg tttgcaccgt     660
tggtgtgtga caagacctgg ctgtttggtg tgcacgggca atgccactca tcctgtctgc     720
tgggactatc tcgggtccgg cgtaagtcgg cggcctgctc gtcgaatggg tgagggagct     780
gaagtgcttc ttcgcttgat cggcgctgca ggctggcttg gctgttagc tgaggctctt     840
ggtatgtccg aaatctatgc agctattctt tgctttgggt ttattgcttg gtatggctgg     900
ggtataccta agacattggt gtgcacagtc tgccctgcag taaacatttc tccctatagc     960
ttcttatctc cagatactat cgcatttggt acgtggatac tacaactacc tggtcttttg    1020
tggcagatgt ttgtcaactt ccctatactt tacagcactt ggattcttg gttgttgctc    1080
agcggcaaga ctgttgctgt gatagcgatc cttctggcta gtcctacggt tatggcgtac    1140
aagcatcaat ctgacagcta cctcaaatac tgtaccataa ccaatgcttc aactgctatg    1200
aactgtgact gccccttggg aacctttact cgcaatactg agtctcgttt ctctatacct    1260
agattctgtc ctgttaaaat taaaagctct acatttatct gctcatgggg gtcgtggtgg    1320
tggtttgcgg agaacatcac gcgtccatac wcrgacgttg gcrtgccacc agcaccgatt    1380
tcygctttgt gctatatcta ttcwaacaat gacccacctc cttggtatca taacacaact    1440
atcataccct agaaytgtcg caactctacg gtkgatccta ccacarctcc atgccgygac    1500
aagtggggya aygcaactgc ttgtattctt gaccgccgkt cgcggttctg cggggactgc    1560
tatggcggtt gtttctatac taatggtact catgatcgat cctgggatcg atgtgggatt    1620
ggttaccgtg atggactcat agagttsgtg cagctcggtc agattsgacc taacatctss    1680
aatacgacca ttgagctcct cgcwggcgcc tcgcttgtga tcgcatccgg tcttcggcct    1740
gggtttggtt gcagccgagc gcatggcgtg gtgcactgct ataggtgtcc ttcataccgt    1800
gaccttgaac agtttggtcc tgggcttggg aaatgggtgc cattgcccgg cgagcctgtc    1860
ccggagctgt gtatcaaccc tcagtgggcg aggcgcggct tccggatgtc taataatcct    1920
ctgagcttgc tacagacctt cgttgaggac attttcctag cgccttttg taatccgacg    1980
cctggccgtg tacgtgtgtg taacaatacc gctttctatc caagaggagg cggctttgtg    2040
cagctcatcg gggacgtcca ggtgctaacc cctaacactg catctttaca ctctctgctg    2100
actttgatat ctcttatctt gttggtgtgt gttgtttctg gtgcgcgatt cggtccacta    2160
ataatcatat ttttctggag cgcgcgccay gtatatgctt cttgttactt aagctgkgat    2220
tgggctgttt gcaacgatgc gttctgtttc acatctggya cttgtgctac tttcaatgac    2280
gtcttgtgtc tgccggttgc aacgcacata tcgtcctgtg gccacgctgt accgcccccc    2340
```

```
gaccgyggtt gggaggtgcc tgcggcgatg tcatgggtga tttcgcggac tactggcttg    2400
acgttcgatg tcttctcttt catccagtat ttccctactg tgcctggcaa taacactgat    2460
attatctact gtggtgaacc waccttcttt ggggacatca cgggcattta ttggccttac    2520
tttttgcctg gcgtgttgct cttgtacttg actcccttcc tgggttttag gttaatgctt    2580
gctggcttta atatagatgg cttgtttccc atacggcatg ccacggctgc actgaggttc    2640
tcgacttcgc gtgcgacctt gagtgtcgta tctgcttttc taatctatat attatctcac    2700
cctgttaayg ctgcgctcaa tagaatgttc ytagcatctg caaacttaga gatgatctta    2760
tcctttgata cctatcacga gactgttctt tacatctttt gtctattcct ctacctccag    2820
gtgtcgcccc gtgcgggctt ggccgctatg gtggccatca agctatctcg gggcctgcta    2880
ttcgctctgg tgttggcgca aggcgtgtgc cgacctgggc gggtgtttgg tcttgaggtt    2940
tgcgcggacg tctcttggtt ggtggagttt actggcaact gcacttggta catgtcctgc    3000
atcttctcct tttggtgcgc agtgtttgcc ttcaccagtc cacttggacg acagtataag    3060
cttcagatct accggtactg ggcacaggtc tatgccagac tcatcctcgc tgtcrgttgt    3120
ggtcctctcg gacgagagtt ccatttccgc gcaagcgtgg gcgtgctttg gtgtggtgct    3180
tgcatgctct ggccccgtga gtgctctgaa atcagcttgg ctctcattct gtgtgctctg    3240
acagtggaca ccatagacac atggctagta gcgtgcttgt ccgcagggcc gagtgcgcga    3300
gcccttgcaa cgctggccga cgacatggtg cgcatgggtg accaccgggc gttgcgcgcc    3360
gtgttgcgtt gctttggatc acgtggcaca tacatataca accacatggg ccaggtctca    3420
gaacgggtgg cgcaagcagt cagggatctc ggcggttgct tggaaccagt cgtgttggag    3480
gagcccacct ttactgaggt cgtggatgat acaatgagta agatatgtgg acaattgctt    3540
ggtggtaaac ccgtggtggc ccgctgcggc acgcgtgtct tggtgggaca cctcaaccct    3600
gaagatctgc cacctggttt ccagctaagt gctccggtgg ttattaccaa accaagcatt    3660
ggtacgtggt ccttccttaa ggcgacactc acagggcgcg ctgaaacacc cggatccggc    3720
cagatcgtgg tgttgtcttc cctgacaggt cggtcgatgg gtactgcagt gartggcaca    3780
ctgtatgcga ccggccatgg tgctggtgca cgcggcctag ccacgtgtgc tggtttgagg    3840
acgcctctct acacggcatt atctgatgat gtcgtggcct actcttgcct tccgggcatg    3900
agttccctag agccctgccg ctgttcgccg agccgggttt gggtgatgaa caacaatgga    3960
gggttggtgt gtggcagagt ggagaatgaa gacgtctgtt tggactgtcc cacgcacata    4020
gatcaactgc ggggtgcttc gggttcaccg gttttgtgtg atcacggtca tgcatacgcg    4080
ttgatgctcg gtggttactc taccagtggt atttgtgcgc gtgtccggat agtccggcca    4140
tggcagaacg cctattcctc ctcaggggg caggggggga tgcaggcgcc agctgtgaca    4200
ccaacatact ctgaaatcac ctactacgcc cctacyggtt ctggtaagtc aacaaaatat    4260
ccagtggacc tagtcaaaca gggacacaag gtattggtca tcataccaag tgtgtctgtc    4320
gtcaagagta tggccccttta cattaaggag acatataaga ttagacctga aattagagct    4380
ggcacagggc ctgacggtgt gacggttatc actggtgaga acttggcgta catgaccctac    4440 ggccgcttcc tcgtggatcc ggagacgaat ctgcggggtt atgccgttgt catttgcgac    4500
gagtgccatg acacatcatc taccacgcta ctcggtattg gcgcagtgcg catgtatgcc    4560
gagaaagctg gagtgaagac cgttgtattc gccacagcca ctcctgctgg cattcaagta    4620
cagccacatc ccaacattga tgaatatttta ttgactgaca caggcgacgt ggatttctac    4680
```

```
ggcgccaaaa tcaaattgga taacatcaga actggtagac atgttatctt ttgccactcg    4740
aaggccaggt gtgcggaact aacgcagcag ctctccggcc ttggtgttcg tgcagtgagt    4800
ttttggcgag gctgtgacat caaaaccatt cccgcctcag actctattgt cgtagtggca    4860
actgatgcat tgtccacagg ctacacaggg aactttgatt cggtcatcga ctgcgggtgt    4920
tgcgtagagc aaactgtgac aattgacatg gatcccacgt tctccatctc agcccgagtg    4980
gtgccatgta ctgctgcatt gcgtatgcag cggcgcggac gtactggtcg cggcagaagg    5040
ggggcgtact acacaaccac tccaggagca gcaccctgtg tcagcgttcc cgacgctaac    5100
gtctggcaag cagtggagag cgccatggtc ttttatgatt ggaacgccgc caggatacag    5160
cagtgcctgg cagcatacca tgatttaggg tgtacaccac gcctcagttg tgatccatgc    5220
actccagtgc gggtgatgga cacactgagr gcgtacctgc gcagacctga ggtgacgact    5280
gcggctctcg caggagagca gtggccgctg ctttacggtg tgcagttgtg catctgcaag    5340
gagactgagg cccacggtcc agacgatrgc atcaagtgga agtgcttact caacaacagt    5400
aayaaaacac ccctgttgta tgccttagac aatcctacac tggaattcac tacccaacat    5460
gacttgactc gccgtatagc cggcgcttta tcgagcacag tgttcgtgga cacaggctac    5520
ggccccatcc tccttgctgg cgctgcattg gctgcctcct tcgcctttgc gggcgccact    5580
ggagccttag tgccgtcggc cgtttggagc gttgataacg gggttgctgg cgtgacccgt    5640
cccgacgcga cagacgagac cgcggcctac gcgcagcgct tgtaccaagc tgcgcagat    5700 tcaggacttc tcgccagctt gcagggcacg gcgagtgcgg cgctgagcaa actggccgat    5760
gccagtaggg gtgctagtca atatctggca agcgcgcctc cctcgcccgc cccctggta    5820 caggtgctgc agttccttga gaccaacttt agctccatcg catccttcgg tctgctctgc    5880
gctggttgtc aggctggcga gtgcttcaca gcgcttgccg ggttggtgtc cggtgctacg    5940
gctggcttgg gaggagccca taagtggttg ttagccattg caggaacttg gctagttagt    6000
ctgcagacag gggcccgtgg cggcatggtt gcgggcctct cggtcctggc aggctgttgc    6060
atcggtagtg tcactgggct tgacttcctg tttgggtgcc ttacaggttg ggaggccgtg    6120
gttggtgctg cggttgcgac acagaaaatc ttgtctggtt cggctgatat gaccactctg    6180
ttagatctct tacctgcttt tttctcccct ggtgccggcg tagctggcat cgtgcttgtc    6240
tttattctaa gcaactcaag tgtaaccacg tgggctaatc ggctattgtc catgtgtgca    6300
aaacaaacca tttgtgacaa ctacttctta tctgacaaat ttggccaaca attaagtaaa    6360
ctttccttgt ggcgcactct gtatcgttgg gcggaggcac gtgagggata cacacagtgt    6420
ggtgtggtcg gcgggatctg gagctttgtc ttgtgcattc tacgcgctgt gtgggattgg    6480
gcggctaaac atgtgccacg gttccgtgtg cccatgattg gctgctcacc tgcgtggtgc    6540
gggcgctggc ttggtactgg caccttgttg accacctgcg ggtgtggaga acgtgtgtct    6600
cttcagtgtc tttgctcaac gtctgatcca ttgctcagag tgggtcgttg gtgtcggtgt    6660
agttggagtg ttgggttccc attcaacccg actacgacag ccaccggcac tttacggccg    6720
gacattagcg acgccactag attgggtttc cggtatggca ttgccgagat cgtggagctg    6780
gagctgcggg agcacaaatg gcacgtctgt gcagcatcat gttgcttgga ccagctagt    6840 gttgcatccg ctgtgaaggc cccaccggtc acagccaatg gtataccat cagtacctt    6900 tctccaccac aaacttacag cctctctctc tgttcttttg attcagtttg catgtctact    6960
aatctatgta acccagccaa gaccctgagt gtgtgctcac aggaggccgt tgagctgctg    7020
gaagaaacag ttgacacggc acaagtgatg atgtgtcaaa atctggaggc gcgaagacgc    7080
```

```
gccgaatatg atgcatggca agttcgccac gcagttggcg acgagtacac gcgtttggca    7140
gacgaggatt ttgacacgac aacgtcggtg aaaccccggg cggccagggc tgctgtggat    7200
```



```
gccgaatatg atgcatggca agttcgccac gcagttggcg acgagtacac gcgtttggca    7140
gacgaggatt ttgacacgac aacgtcggtg aaaccccggg cggccagggc tgctgtggat    7200
agctcaacgt tggaagatgt tagcgtgctg actgttttgc gcgagctcgg cgaccaatgc    7260
caaaatgcta tcaaatttgt agttcaggcg gcttcacggg ttgttccacc tgtgcccaga    7320
ccgcgcacgc gcgtctcggg cgtgttggag cgtgtgcgca tgtgcatgcg cacgccacca    7380
atcaagtttg aggccaccgc agtaccaatt cataacataa tcccagaaga gtgtcacatc    7440
gtgctacgct gtactggctg taacgaccag gccttgactg ttccgtacgg cacttgcact    7500
cagtctttaa ttagacattt gaccaacaaa cacaaccact atattccaaa acagaagata    7560
gaagaagaca cagaagtaac tgtcatttgc gccgtaccaa caaagcgcgc aagtaaactc    7620
atcactttca gagcaggtga tcgatcagtc tcatgttgcc accccttaca aactcctatt    7680
agggccctgc ttctaaagta cgggttacct atcgggacgt ggtccgactg caacggaccc    7740
cttggtgacg acgcccgagt ctgtgacgtc aatggagtga caacttatga accatgcatg    7800
caatcctaca gttggttccg accaattgtg gcacctacaa ccccacccttt acctgtaacc    7860
cggagcgtgg ctgggatttt acgcgcagac acatcgcgcg tttacaccac aacgcggtc    7920
gacgtctccg agcggcagtc taaggtcaca attgatcaaa catcagccaa ggtggaccag    7980
tggttccgtg acacatacaa ctgttgcctt gctaaggcaa aaaccttcag acaatctggc    8040
atgtcatatg aggatgctgt gtcaaaaatg cgcgcaaaca ccacgcgtga ccataacact    8100
ggcatcactt attcagattt ggtctctgga cgcgcaaaac ctgccgttca aaaaattgta    8160
gatcaaatgc gtgctggagt gtacgacgct ccaatgcgca ttatcccaaa acctgaagtg    8220
ttcccccgag acaagtcaac acggaagcca ccgcggttca tcgttttttcc tgggtgcgcc    8280
gcgcgagtcg cggagaaaat gatcctgggc gatcctggcg cgataaccaa gcacgtgcta    8340
ggtgatgcct acgggtttgc cactccgccg catgaacgcg cgcgcctatt ggagcaatgg    8400
tggaaccgtg caacggagcc acaagctatc gcggttgatg cgatctgctt tgatagcacc    8460
atcacagcag aggacatgga tcgcgaggcc aacatcctgg ctgcggcgca ttcggaccct    8520
gaaggtgttc acgcctata caattattac aaaagaagcc ccatgtgtga tatcacagga    8580
aatgttgtcg gagtgcgttg ctgtagagcc tcaggtacgc ttacaacaag cagtggcaac    8640
acgcttactt gctacctcaa ggttcgtgca gcttgcacgc gcgccggcat taaccaatt    8700
ggcttgctaa ttcatgggga tgataccctc atcatcacag aacgttgcgc tcaagagact    8760
ctcgatgagt tcagcaatgc acttaatgac tacgggttcc ctcacacctt ccaggcgtct    8820
ggggacctct cgtcagttga gtgctgtagc gcacgtgtgg acagcgtttg cctccgggga    8880
ggtatgcgtc gcatgctcgt gccacaagct cgacgtgcga ttgcacgcgt tctcgggaa    8940
aagggcgatc cactgggtgt catcagcagc tatattgtca tgtatcctac tgcggccgtg    9000
actgtctacg tgctattgcc cctgttgtgc atgctcattc gaaatgagcc atcgcagacg    9060
gggacacttg taacgctgac ggtccacggt aacagtgtga gcgtgccagt gtggctgctt    9120
ccaaccatca ttgtaaattt acatggccgt gacgcactgc aggtagttcg tcacactgca    9180
gcttccatgg cggagctgtc atcagcgttg gccttctttg gcatgagagg gttgaactgc    9240
tggaggcgga gacgccgtgc catcaggact gacatgatca agttgggcgg gtggaatgcg    9300
aatttcgcgc agatgttact gtggtcaccg gaggtgagga caccacaacc cgaaccaagg    9360
ggtgtgtgtc tcttaccacc ggaactatgg gagcgtccgt acgaaaattt gcacttgagc    9420
```

| | |
|---|---:|
| acgatcgacc gcaatcgtgg tgctagtcgc ctacggtttt ggttggttgc cagtgctata | 9480 |
| ctcgctctgc tttgcttgta aatcctaaat caatgtagta ccaggactac aaggcaggag | 9540 |
| gtgaagtcag ctgtacccac ggctggctga aaccgggggct tgacgacccc ccctatccga | 9600 |
| gttgggcaag gtaacatcac gggtgtgacg accccgcccc cccatgtcgc gcgtaagcgc | 9660 |
| acgggcaagg cagctaggct gagagtctgg gcaactctcc cgtaccccac ccgaggctac | 9720 |
| gcctcgtcct ggcgaggacc gtaaacatac gtcgtcagcg tggtgacctg acgtatcttg | 9780 |
| ttaaccactt aatggtcgta actcgacccc cgtgccgggg atctaagcgc ggcaccgcga | 9840 |
| tgaggggggt caacggcccc tttcatt | 9867 |

<210> SEQ ID NO 302
<211> LENGTH: 9867
<212> TYPE: DNA
<213> ORGANISM: Human Pegivirus 2
<220> FEATURE:
<221> NAME/KEY: misc_feature
<222> LOCATION: (1)..(11)
<223> OTHER INFORMATION: N = A, C, T, or G
<220> FEATURE:
<221> NAME/KEY: misc_feature
<222> LOCATION: (6209)..(6214)
<223> OTHER INFORMATION: N = A, C, T, or G

<400> SEQUENCE: 302

| | |
|---|---:|
| nnnnnnnnnn ntagcaatgc gcatattgct acttcggtac gcctgattgg taggcgcccg | 60 |
| gccgaccggc cccgcaaggg cctagtagga cgtgtgacaa tgccatgagg gatcatgaca | 120 |
| ctggggtgag cggaggcagc accgaagtcg ggtgaactcg actcccagtg cgaccacctg | 180 |
| gcttggtcgt tcatggaggg catgcccacg ggaacgctga tcgtgcaaag ggatgggtcc | 240 |
| ctgcactggt gccatgcgcg gcaccactcc gtacagcctg atagggtggc ggcgggcccc | 300 |
| cccagtgtga cgtccgtgga gcgcaacatg gggtgttcaa ctgatcaaac catttgttct | 360 |
| ccagtcgtgg gggccgacta taatacctcc tcgggctgcc gggccttaaa tgggagcgac | 420 |
| cactgcggtg gaagctcttg ccggtcacca agtcgtgtgc aggctgctag acgagtcttg | 480 |
| cagctgtgcg cattccttgc gttgatcgga tccgtatgt gttcgatccg gtccaaaact | 540 |
| gaagggcgca ttgagtcggg gcaaatattg cagtctcagc gcgcatgttg gactggtgag | 600 |
| ggttttgctt tcttttctaa ctgttgcaat caatctgata ttatgtggtg tttgcaccgt | 660 |
| tggtgtgtga caagacctgg ctgtttagtg tgcacgggca atgccaccca tcctgtctgc | 720 |
| tgggactatc tttgggtccgg tgtaagtcgg cggcctgcgc gccgattggg cgagggtgct | 780 |
| gaaatgcttc ttcgcttgat cggcattgca ggttggctcg gcttgttagc tgaggctctt | 840 |
| ggtatgtccg aaatgtatgc agctatcctt tgctttgggt ttattgcttg gtatggctgg | 900 |
| ggtataccta aaacattggt gtgcacagtc tgccctgcgg taaacatttc tccctatagc | 960 |
| tttttatctc cagacactat cgcatttggt acrtggatac tacaactacc tggtcttttg | 1020 |
| tggcaaatgt ttgtcaactt tcctatactt tacagcactt ggattcttg gttgttgctt | 1080 |
| agtggcaaga ctgttgctgt gatagcaatc cttttggcta gtcctacggt tatggcgtac | 1140 |
| aagcatccat ctgaaagcta cctcaaatac tgtaccataa ccaatgcttc agctgctatg | 1200 |
| aactgtgact gccccttgg aacctttact cgcaatactg agtctcgttt ctctataccct | 1260 |
| agattctgtc ctgttaaaat tgagagttct acatttatct gctcatgggg gtcgtggtgg | 1320 |
| tggtttgcta gaacatcac acgtccatac tcggacgtcg gcatgccgcc agcaccgatt | 1380 |
| tccgctttgt gctatatcta ttcaaacaat gacccacctc cttggtatta taatacaact | 1440 |

```
attataccctc agaaytgtcg caactctwcg gttgatccya ccacagctcc atgccgtgac    1500
aagtggggca atgcaactgc ttgtattctt daccgccggt cgcggttctg cggggactgc    1560
tatggcggct gcttctatac taatggtagt catgatcgat cctgggatcg atgcgggatt    1620
ggttaccgtg atggactcat agagtttgtg cagcttggtc agattcgacc taacatctcg    1680
aacacgacca ttgagctcct cgctggtgcc tcgcttgtga ttgcatccgg tcttcggcct    1740
gggtacggtt gcagtcgagc gcatggcgtg gtgcactgct ataggtgtcc ttcataccgt    1800
gaccttgaac agttcggtcc tgggctcggg aaatgggtgc cgttgcctgg tgagcctgtc    1860
ccggagttgt gtatcaaccc tcaatgggcg aggcgcggct tccgggtgtc taacaatcct    1920
ttaagcttga tacagacctt tgttgaggac atcttcctag cgcctttttg yamtccgacg    1980
cctggtcgtg tacgtgtgtg taacaatact gctttctatc caagaggagg cggctttgtg    2040
cagctcatcg gagacgtcca ggtgctgacc cctaacactg catctttaca ctctctgctg    2100
accttgatat cccttatctt gctagtgtgt gttgtctctg gcgcgcgatt cgtcccatta    2160
atcatcatat ttttctggag cgtgcgccat gtatatgctt cctgttactt gagctgtgat    2220
tgggctgttt gcaatgatgc attctgtttc acttctggta cttgtgctac cttcaatgac    2280
gtcttgtgtc tgccggttgc gacgcgtata tcgtcctgtg ggcatgctgt gccaccgccc    2340
gaccgtggtt gggaggtgcc tgcggcgctg tcayggkga tttcgcggac tacyggcttg    2400
acgttcgatg tcttttcttt cattcagtat cttcctactg tgcctggcaa caattccgat    2460
atcatttact gtggtgaacc gacctttttc ggggatctca cgggcatcta ttggccttac    2520
tttttgcctg gtgtgttgct tttgtacttg actcccttcc ttggtttaag gttaatgctt    2580
gccggcttta atatagatgg cttatttccc atacggcatg ccacggctgc actgaggttc    2640
tcgacttcgc gtgtgaccct gagtgtcgtg gctgcctttc taatctatat attatcccac    2700
cctgttaatg ctgcgctcaa tagaatgttc ttagcatctg caaatttaga gatgattcta    2760
tcctttgata cttatcatga gactatcctt tatatcgtct gcctaatgct ctacctccag    2820
gtgtcacccc gtgcgggctt ggccgccatg gtggccatca agctatctcg aggtctgtta    2880
ttcgctgtgg tgttggcgca cggagtgtgc cgacccgggc gggtatttgg tcttgaggtt    2940
tgcgcggaca tctcctggtt ggtggagttt actggcaact gcacttggta tatgtcctgt    3000
gtcttctctt tttggtgcgc agtgtttgcc ttcaccagtc cacttggacg acagtataag    3060
cttcagatct atcggtactg ggcgcaggtc tatgccagac tcatcctcgc tgtcggttgt    3120
ggtcctctcg gccgagagtt ccatttccgc gcaagcgtgg gcgtactttg tgtgtggcgct   3180 tgcatgctct ggccccgtga gtgctctgaa atcagcttgg tcttcattct gtgtgctctg    3240
acagtggaca ccatagacac atggttagta gcgtgcttgt ccgcagggcc aagtgcgcga    3300
acccttgcaa cgctggccga tgacatggcg cgcatgggtg acaaccgggc gttgcgcgcc    3360
gtgttgtgtt gctttggatc acgtggcaca tacatataca accacatggg ccaggtctca    3420
gaacgggtgg cgcgagcagt cagggatctc ggcggttgct tggaaccagt cgtgttggag    3480
gagcccacct ttactgagrt cgtggatgat acamtgartt tagtgtgtgg acaattgctt    3540
ggaggtaaac ctgtggtggc ccgctgcggc acgcgtgtct tggtgggaca cctcaaccct    3600
gaagatctgc cacctggttt ccagctgagt gctccggtgg ttatyaccaa accaagcatt    3660
ggtacgtggt cctccttaa ggcgacactc acagggcgtk stgaracacc gggatccggc     3720
cagatcgtgg tgctgtcttc cctgacaggt cggtcaatgg gtactgcagt gaatgrcaca    3780
```

```
ctgtatgcga ccggccatgg tgccggtgcg cgtggcctag ccacgtgcgc tggtttgagg    3840
acgccacttt acacggcatt atctgatgat gtcgtggcct attcttgcct tccgggcatg    3900
agttccctgg agccctgccg ctgtacgccg agccgggttt gggtgatgaa caacaatgga    3960
gggttggtgt gtggcagagt agagaaggac gacgtctgtt tggactgtcc cacgcacata    4020
gatcaactgc ggggtgcttc ggggtcaccg gttttgtgtg atcacggtca tgcatacgcg    4080
ttgatgctcg gtggttactc taccagtggt atttgtgcgc gtgtccggat agttcagcca    4140
tggcagaacg cctattcctc ctccgggggg caaggcggaa tgcaggcgcc agctgtgaca    4200
ccaacatact ctgaaatcac ctactatgcc cctaccggtt ctggtaagtc aacaaaatat    4260
ccagtggacc tggtcaaaca gggacacaag gtattggtca tcataccaag tgtgactgtc    4320
gttaaaagta tggccaatta tattaaggag acatacaaga tcagacctga aattagagct    4380
ggcactggcc ctgacggtgt gacggtcatc actggtgaaa gcttggcgta catgacctat    4440
ggccgcttcc ttgtggatcc ggagacgaat ctgcgaggct acgccgtagt catttgcgac    4500
gagtgccacg acacatcatc caccacgcta ctcggcatag gcgcggtgcg catgtttgct    4560
gagaaagctg gagtgaggac cgttgtattc gccacagcca cccctgctgg cattcaagta    4620
cagccacatc ctaacattga tgaatattta ttgactgaca caggcgacgt ggacttctac    4680
ggcgccaaaa tcaaattgga caacatcaga actggtagac atgttatctt ttgtcactcg    4740
aaggccaggt gtgcggaact aacgcagcag ctctccggcc ttggtgttcg tgcagtgagt    4800
ttttggcgcg gctgtgacat caaaaccatt cccgcctcag actctattgt tgtagtggca    4860
actgatgcat tgtccacagg ctacacagga aattttgatt cggtcatcga ctgcgggtgt    4920
tgcgtagaac aaactgtgac aattgacatg gaccctacgt tttccatctc ggcgcgagtg    4980
gtgccatgca ctgctgcatt gcgtatgcag cggcgcggac gtaccggtcg tggcagaagg    5040
ggagcgtatt acacaaccac tccaggagca gcaccttgcg tcagcgttcc cgatgctaac    5100
gtctggcaag cagtggaaag cgccatggtt ttttatgact ggggtgctgc caggatacaa    5160
caatgcctgg cggcatacca tgatctaggg tgcaccaccac gcatcagttg ygatccacac    5220
actccagtgc gggtgatgga cacactgcgg gcgtacctgc gcagacctga ggtgacgact    5280
gcagctctck caggagagca gtggccgctg ctttatggtg tgcagttgtg catctgcaaa    5340
gaaaccgagg cccatggtcc agacgatagc atcaagtgga gtgcttact caacaacagt    5400
aataaaacac ccctgctgta tgccttagac aatcctacac tggatttcac tacccaacat    5460
gacttgactc gccgtatagc cggcgctcta tcgagcacag tgttcgtgga cacaggctac    5520
ggccccatcc tcctcgctgg cgccgctttg gctgcctcct tcgcctttgc gggtgctaca    5580
ggagctttag tgccgtcggc cgtttggagt gttgacaacg ggttagctgg cgtgacccgt    5640
cccgacgcga cagacgaaac cgcggcctac gcgcagcgct tgtaccaagc tgcgcagat    5700
tcaggacttt tcgccagctt gcagggcaca gcgagtgcgg cgctgggcaa actggctgat    5760
gccagtaggg gtgctagtca atatctggca gccgcgcctc cttcgcccgc cccctggtg    5820
caggtgctgc atttccttga gaccaacttt agttccattg catctttcgg tctgctctgt    5880
gctggttgtc aggctggtga gtgcttcact gcgcttgccg ggctggtgtc cggtgctaca    5940
gctggcttgg gaggtgccca taagtggttg ttagctattg caggaacctg gctagttagc    6000
ttgcagactg gccccgtggg cggcatggtt gcgggtctct cggttctagc aggctgttgc    6060
atcggtagtg tcaccgggct cgacttcctg tttgggtgcc ttacaggttg ggaggccgtg    6120
gttggcgctg cggttgcgac gcagaagatc ttgtctggtt cagctgatat gaccactctg    6180
```

```
gtagatctct tacctgctat cttctcccnn nnnnccggca tagctggcat cgtgcttgtc    6240
tttattctaa gtaactcaag tgtaaccacg tgggctaatc ggctactgtc catgtgtgca    6300
aaacaaacta tttgtgataa ctacttctta actgagaaat ttggccatca attaagcaaa    6360 cttccctgt ggcgcgctgt gtaccattgg gcgcaggcac gtgagggata cacacagtgc     6420
ggcgtggtca gcgggatctg gagctttgtc ttgtgcatcc tgcgggctgt gtgggattgg    6480
gcggccaagc atgtgccacg gttccgtgtg cctatgatcg gctgctcacc tgcatggtgc    6540
gggcgctggc ttggtaccgg caccctgttg accacctgtg ggtgtggaga cgtgtgtcc     6600 cttcagtgcc tctgctcaac gtctgaccca cactcagtg tgggccgttg gtgtcggtgt     6660
agttggagtg tcgggttccc attcaacccg actacgacag ccaccggcaa tttacggccg    6720
gacattagtg acgccactaa attgggtttc cgatatggta tagccgagat cgtgaactg     6780 gagcggcggg gtgacaaatg gcatgtctgt gcagcatcat gttgcttgga ccgagccagc    6840
gttgcatccg ccgtgaaggc cccaccggtc acggccaatg gtatacctat cggtactttt    6900
tctccaccac aaacttacag cctctctctc tgttcttttg attcagtttg catgtctagt    6960
aacttatgta acccagctaa gaccctgagt gtgtgctccc aggaggctgt cgagctactg    7020
gaagaaacag ttgataaagc acaagtaatg atgtgtcaaa atctggaggc gcgaagacgc    7080
gcagagtatg atgcatggca ggttcgccaa gcagttggcg acgagtacac gcgtttggca    7140
gacgaggatg ttgacgcgac aacgtcggtg aaaccccgg tggccagggc tgctgtgggt     7200
agctcaacgt tggatgacgt tagcgtgctg actgtcttgc gcgaactcgg cgaccaatgc    7260
caaaatgcta tcaaatttgt agttcaggcg gcttcacggt ttgttccacc agtgcccaag    7320
ccgcgcacgc gcgtctcggg tgtgctggag cgtgtgcgca tgtgcatgcg cacgccacca    7380
atcaaatttg aggccaccgc agtaccaatt cataacataa tcccagaagt gtgtcacatt    7440
gtgctacgct gtaccggctg taacgaccag gccttgactg ttccgtacgg cacttgcact    7500
cagactttaa tcaaacattt gactaacaaa cacagccact acattccaaa acagaagata    7560
gaagaagaca cagaagtaac tgtcatttgc gccgtaccaa caacgcgcgc aagtaagctc    7620
atcactttca gagcaggtga tcgatcagtc tcatgttgtc accccttgca aactcctgtt    7680
aggaccctgc ttctaaagta tgggttgcct atcgggaagt ggtccgactg caacggcccc    7740
cttggtgacg atgcccgagt ctgtgacatc aatggagtaa caacttatga accatgcatg    7800
caatcctata gttggttccg accaattgta gcgccaacaa ccccacccttt acctgcaacc    7860 cggagcgtgg ctggcatttt acgcgcggac acatcgcgcg tttacaccac aacggcggtt    7920
gacgtctccg agcggcaggc taaggtcaca attgatcaaa catcagccaa ggtggatcag    7980
tgtttccgag acacatacaa ttgctgcctt gctaaggcaa agaccttcaa acaatctggc    8040
atgtcatatg aggatgctgt gtyaaagatg cgcgcaaaca ccacgcgtga ccataacaat    8100
ggcaccactt attcagattt ggtctctgga cgcgcaaaac ctgtcgttca gaaaattgta    8160
gatcaaatgc gcgctggagt gtacgacgct ccaatgcgca ttatcccaaa acctgaagtg    8220
ttccctcggg acaagtcaac acggaagcca ccacggttca tcgtttcccc tgggtgcgcc    8280
gcgcgagtcg cggagaaaat gatcctgggc gatcctggcg cgataaccaa gcacgtgctt    8340
ggtgatgcct atgggtttgc cactccgccg catgagcgcg cgcgtctatt ggaacaatgg    8400
tggaaccgtg caacggagcc acaagctatc gcggttgatg cgatctgctt tgatagcact    8460
atcacggcag aggacatgga tcgcgaggcc aacatcatgg ctgcggcgca ttcggaccct    8520
```

```
gaaggtgttc atggcctgta caagtattac aaaagaagcc ccatgtgtga catcacggga    8580
aaagttgtcg gggtgcgttg ctgtcgagcc tcaggtacgc ttacaacaag cagtggcaac    8640
acgcttactt gctatctcaa ggttcgcgca gcttgcacgc gcgccggcat taaaccaatt    8700
ggcttactaa ttcatggaga tgataccctc attgtcacag aacgttgcgc tcaagaaact    8760
ctcgatgagt tcagcagcgc actcgatgac tatgggttcc ctcacacctt gcaggtgtct    8820
ggggacctct cgtctgttga gtgctgtagc gcacgtgtgg acagcgtttg cctccgggga    8880
ggtatgcgtc gcatgctcgt gccacaagct cgacgtgcga ttgcacgcgt tctcggggag    8940
aagggtgatc cactgggtgt catcagtagc tatatcgtca tgtatccyac tgcggctgtg    9000
actgtctacg tgctattgcc cctgttatgc atgctcattc ggaatgagcc atcgcagacg    9060
gggacgattg tgacgctgac ggtccacggy aacagtgtga gcgtgccggt gtggctgctt    9120
ccaaccatca ttgtaaattt acatggtcgt gacgcactac aggtagtccg tcacagtgca    9180
gcttccatgg cggaactgtc gtcagcgttg gccttctttg gcatgagagg gttgaactgc    9240
tggaggcgga gacgccgcgc catcaggact gatatgatca rgttgggcgg gtggattgcg    9300
aatttcgcgc agatgttact gtggtcaccg gaggtgagga caccacagcc cgaaccgaag    9360
ggcttgtgtc tcttaccacc ggaactatgg gagcgtccgt acgaaaattt gcamttgagc    9420
acggtcgacc gtaatcgtgg tgctagtcgc ttacggtttt ggctggttgc aagtgctata    9480
ctcgctctgc tttgcttgta aatcctaaat caatgtagta ccaggactac aaggcaggag    9540
gtgaagtcag ctgtacccac ggctggctga aaccggggct tgacgacccc ccctatccga    9600
gttgggcaag gtaacatcac gggtgtgacg accccgcccc cccatgtcgc gcgtaagcgc    9660
acgggcaagg cagctaggct gagagtctgg gcaactctcc cgtaccccac ccgaggctac    9720
gcctcgtcct ggcgaggacc gtaaacatac gtcgtcagcg tggtgacctg acgtatcttg    9780
ttaaccactt aatggtcgta actcgacccc cgtgccgggg atctaagcgc ggcaccgcga    9840
tgaggggggt caacggcccc tttcatt                                        9867
```

<210> SEQ ID NO 303
<211> LENGTH: 9867
<212> TYPE: DNA
<213> ORGANISM: Human Pegivirus 2
<220> FEATURE:
<221> NAME/KEY: misc_feature
<222> LOCATION: (1)..(23)
<223> OTHER INFORMATION: N=A, C, T or G

<400> SEQUENCE: 303

```
nnnnnnnnnn nnnnnnnnnn nnntattgct acttcggtac gcctaattgg taggcgcccg      60
gccgaccggc cccgcaaggg cctagtagga cgtgtgacaa tgccatgagg gatcatgaca     120
ctggggtgag cggaggcagc accgaagtcg ggtgaactcg actcccagtg cgaccacctg     180
gcttggtcgt tcatggaggg catgcccacg ggaacgctga tcgtgcaaag ggatgggtcc     240
ctgcactggt gccatgcgcg gcaccactcc gtacagcctg atagggtggc ggcgggcccc     300
cccagtgtga cgtccgtgga gcgcaacatg gggtgttcaa ctgatcaaac catttgttct     360
ccagtcgtgg gggccgacta taatacctcc tcgggctgcc gggccttaaa tgggagctac     420
cactgcggtg gtggctcttg ccggtcacca agtcgtgtgc aggttgcgag acgagtcttg     480
cagctgtgcg cattccttgc gctgatcgga tccggtatgt gttcgatccg gtccaaaact     540
gaagggcgca ttgagtcagg gcaaatattg cagtctcagc gcgcatgttg gactggtgag     600
ggttttgctt tcttttctaa ctgttgcaat caatctgata ttatgtggtg tttgcaccgt     660
```

-continued

```
tggtgtgtga caagacctgg ctgtttagtg tgcacgggca atgccaccca tcctatctgc      720
tgggactatc ttggatccgg tgtaagtcgg cggcctgcac gtcgaatggg tgagggagct      780
gaagcgcttc ttcgcttgat cggcattgca ggttggcttg gactgttagc tgagtccctt      840
ggtatgtccg aagtctatgc agctattctt tgctttggat ttattgcttg gtatggctgg      900
ggtataccta aaacactggt gtgcaccgtc tgccctgcag tgaacatttc tccctatagc      960
ttcttatctc cagatactat cgcatttggt acgtggatac tacaactacc tggtcttttg     1020
tggcaaatgt tgttagcttc cctatactc tacagcactt ggattctttg gttgttgctc     1080
agcggcaaga ctgttgctgt gatagcaatc cttctggcta gtcctacggt tatggcgtac     1140
aagcatcaat ctgaaagcta cctcaaatac tgtaccataa ccaatacttc aacttctatg     1200
aactgtgact gccccttttgg aacctttact cgcaatactg agtctcgttt ctccatacct     1260
agattctgtc ctgttaaaat caatagctct acatttattt gttcatgggg gtcgtggtgg     1320
tggtttgctg aaaacatcac gcgtccatac acggacgttg gcatgccacc agcaccgatt     1380
tccgctttgt gctatatcta ttctaacaat gacccacctc cttggtatca taacacaact     1440 atcataccctc agaactgtcg caactctacg gtggatccta ccacagctcc atgccgtgac     1500
aagtggggca acgcaactgc ttgtattctt gaccgccggt cgcggttctg cggggactgc     1560
tatggcggtt gtttctatac taatggtagt catgatcgat cctgggatcg atgcgggatt     1620
ggttaccgtg atggactcat agagttcgtg cagctcggtc agattcgacc taacatctcg     1680
aatacgacca ttgagctcct cgctggcgcc tcgcttgtga tcgcatccgg tcttcggcct     1740
gggtttggtt gcagccgagc gcatggcgtg gtgcactgct ataggtgtcc ttcataccgt     1800
gaccttgaac agtttggtcc tgggcttggg aaatgggtgc cattgcccgg cgagcctgtc     1860
ccggagttgt gtatcaaccc tcagtgggcg aggcgcggct tccggatgtc taataatcct     1920
ctgagcttgc tacagacctt cgttgaggac attttcctag cgcctttttg taatccgacg     1980
cctggccgtg tacgtgtgtg taacaatacc gctttctatc aagaggagg cggctttgtg     2040 cagctcatcg gggacgtcca ggtgctaacc cctaacactg catctttaca ctctctgctg     2100
actttgatat ctcttatctt gttggtgtgt gttgtttctg gtgcgcgatt cgttccacta     2160
ataatcatat ttttctggag cgcgcgccat gtatatgctt cttgttactt aagctgtgat     2220
tgggctgttt gcaacgatgc gttctgtttc acatctggca cttgtgccac cttcaatgac     2280
gtcttgtgtc tgccggttgc gacgcgcata tcgtcctgtg gtcatgctgt gccacctccc     2340
gaccgtggtt gggaggtgcc tgcggcgatg tcatgggtga tttcgcggac tactggcctg     2400
acgttcgatg tcttttcctt cattcagtac cttcctactg tgcctggcaa caacaccaat     2460
atcatttact gtggtgaacc aaccttcctc ggggacatca cgggcatcta ttggccttac     2520
tttttgcctg gcgcaatcct cttgtacttg actcccttcc taggtttaag gttaatgctt     2580
gccggcttca atatagatgg cttgtttccc atacggcatg ccacggctgc actgagggttt     2640 tcgacttctc gtgtgacctt gtgtgtcgta gttgctttcc taatctatat attatctcac     2700
cctgttaatg ctgcgctcaa tagaatgttc ttagcatctg caaatttaga gatgatctta     2760
tcttttgata cctatcatga gactgttctt tatatccttt gtctattgct ctacctccag     2820
gtgtcgcccc gtgcgggctt ggccgctatg gtggccatca agctatctcg aggcctgtta     2880
ttcgctgtgg tgttggcgca cggtgtgtgc cgacctgggc gggtatttgg tcttgaggtt     2940
tgcgcggaca tctcttggtt ggtggagttt actggcaatt gcacttggta catgtcctgt     3000
```

```
gtcttctctt tttggtgcgc agtgtttgcc ttcaccagtc cacttggacg acactataag   3060
attcagatct atcggtactg ggcgcaggtc tatgccagac tcgtcctcgc tgtcggttgt   3120
ggtcctctcg gtcgagagtt ccatttccgt gcaagtgtgg gcgtgctgtg gtgtggagct   3180
tgcatgctct ggccccgtga gtgctctgaa atcagcctgg tcttcattct gtgtgctctg   3240
acagtggaca ccatagacac atggttagta gcgtgcttgt ccgcagggcc gagtgcgcga   3300
acccttgcaa ttctggccga tgacatgcgc gcattggtg accaccgggc gttgcgcgcc    3360
gtgttacgtt gctttggatc acgcggcaca tacatataca accacatggg ccaagtctcg   3420
gaacgggtgg cgcaagcagt cagggatctc ggcggttgct tggaaccagt cgtgttggag   3480
gagcccacct ttactgagat cgtggatgac acaatgagtt tggtgtgtgg acaattgctt   3540
ggaggtaaac ctgtggtggc ccgctgcggc acgcgtgtct tggtgggaca cctcaaccct   3600
gaagatctgc cacctggttt ccagctgagt gctccggtgg ttattaccag gccaagcatt   3660
ggtacgtggt ccttccttaa ggcgacactc acagggcgtg ctgaaacacc agggtccggc   3720
cagatcgtgg tgttgtcttc cctgacaggt cggtcaatgg gtaccgcagt gaatggcaca   3780
ctgtatgcga ccggccatgg tgccggcgcg cgcggcctag ccacgtgcgc tggtttgagg   3840
acgccacttt acacggcatt atctgatgat gtcgtggcct attcttgcct tccgggcatg   3900
agttccctag acccctgctg ctgttcgccg agccgggttt gggtgatgaa taacaacgga   3960
gggttggtgt gtggcagagt ggagaatgac gacgtctgtt tggactgtcc cacgcacata   4020
gatcaactgc ggggtgcttc gggctcacca gttttgtgtg atcacggtca tgcatacgcg   4080
ttgatgctcg gtgttactc taccagtggt atttgtgcac gcgtccggac ggtccggcca   4140
tggcataacg cctattcctc ctcggggggg caaggcggaa tgcaggcgcc agctgtgaca   4200
ccaacatact ctgaaatcac ctactatgcc cctactggtt ctggtaagtc aacaaaatat   4260
ccagtggacc tagtcaaaca gggacacaaa gtattggtcc ttttaccaag tgtggctgta   4320
gtcaaaagta tggcccccta tattaaggag acatataaga tcagacccga aattagagct   4380
ggcacaggtc ctgacggtgt gacggtcatc actggtgaga acttggcgta catgacctat   4440
ggccgcttcc ttgtggatcc ggagacgaat ctgcggggct atgctgtagt catttgcgac   4500
gagtgtcacg acacatcatc caccacgcta ctcggcattg gcgcagtgcg catgtatgcc   4560
gagaaagctg gagtgaagac cgttgtattc gccacagcca cccctgctgg cattcaagta   4620
cagtcacatt ccaacattga tgaatactta ttgactgaca caggcgacgt ggaattttac   4680
ggcgccaaaa tcaaaatgga caacatcaga actggtagac atgttatctt ttgccactcg   4740
aaggccaggt gtgcggaact aacgcagcag ctctccggcc ttggcattcg tgcagtgagt   4800
ttttggcgcg gctgtgacat caaaaccatt cccgcctcag actccattgt tgtggtggca   4860
actgatgcat tgtccacggg ctacacagga aactttgatt cggtcatcga ctgcgggtgt   4920
tgcgtggagc aaactgtgac aattgacatg gaccctacgt tctccatctc ggcccgagtg   4980
gtgccatgta ctgctgcatt gcgcatgcag cggcgcggac gtaccggtcg tggtagaagg   5040
ggagcgtact acacaacttc tccaggagca gcaccctgcg tcagcgttcc cgatgctaac   5100
gtctggcaag cagtggagag cgccatggtc ttttatgatt ggagtgctac caggatacaa   5160
cagtgcctgg cggcatacca tgatttgggg tgcacaccac gcatcagctg tgacccacac   5220
actccagtgc gggtgatgga cactgagg gcgtacctgc gcagacctga ggtgacgact   5280
gcagctctcg caggagagca gtggccgctg ctttatggtg cgcagttgtg catctgcaaa   5340
gagaccgagg cccacggtcc tgatgatagc atcaagtgga agtgcttact caacaacagt   5400
```

```
aacaaaacac ccctgttgta tgccttagac aatcctacac tggaattcac aacccaacat   5460
gacttgactc gccgtatagc cggcgctcta tcgagcacag tgttcgtgga gacaggctac   5520
ggccccatcc tccttgctgg cgccgctttg gctgcctcct tcgcctttgc gggcgccact   5580
ggagctttag tgccgtcggc tgtttggagc gttgaggtca ggcctgctgg cgtgacccgt   5640
cccgacgcga cagacgagac cgcggcctac gcacagcgct tgtaccaagc ctgtgcagat   5700
tcaggaattt tcgccagctt gcagggtacg gcgagtgcgg cgctgggcaa actgccgac    5760
gccagtaggg gtgctagtca atatctggca gccgcgcctc cttcacccgc cccctggta    5820
caggtgttgc agttcctcga gaccaacttt agctccattg catctttcgg cctgctctgt   5880
gctggctgcc aggctggcga gtgcttcact gcgcttgctg gcttggtgtc cggtgctaca   5940
gctggcttgg ggggtgccca taagtggcta ttagctattg caggaacttg gctggttagc   6000
ttgcagaccg ggtcccgtgg cggcatggtt gcgggcctct cgattctagc gggctgttgc   6060
atcggtagtg tcaccgggct tgacttcctg tttgggtgcc ttacaggttg ggaagccgtg   6120
gtcggcgctg cggttgcgac acagaagatc ttgtctggtt cagctgatat gaccactctg   6180
gtagatctct tacctgctct tttctccccc ggtgccggca tagctggcat cgtgcttgtc   6240
ttcatcttaa gcaattcaag tgtaaccaca tgggctaatc ggctattatc catgtgtgcc   6300
aaacaaacca tttgtgaaaa ctacttctta agtgaaagat ttggccaaca attaagcaaa   6360
cttccctgt ggcgctctgt gtaccattgg gcgcaggcac gtgagggata cacacagtgc    6420
ggcgtgatca gcgggatctg gagcttcgcc ttgtgcattc tacgcgctgt gtgggattgg   6480
gcggccaagc atgtgccacg gttccgtgtg cctatgattg gctgctcacc tgcgtggtgc   6540
gggcgctggc ttggtaccgg caccttgttg accacctgtg cgtgtggaga acgtgtgtcc   6600
cttcagtgcc tttgctcaac atctgaccca caactcagtg tgggccgttg gtgtcggtgt   6660
agttggagtg ttgggttccc attcaacccg actacgacag gcactggcac cttacggccg   6720
gacatcagtg acgccaacaa attgggtttc cggtatggcg ttgccgacat cgtggagcta   6780
gagcggcggg gcgacaaatg gcacgtctgt gcagcatcat gttgcttgga ccgggccagc   6840
gttgcatccg ctgtgaaggc cccaccggtc acggctaatg gtatacctat taatagcttt   6900
tctccaccac aaacttattg cctatctctc tgttcctttg atacagtttg catgtctact   6960
aacttatgta acccagctaa gaccctgagt gtgtgccaag aggaggcggt tgagctgctg   7020
gaagagacag ttgacacagc acaagtagtg atgagccaaa atctggcagc gcgtagacgc   7080
gctgagtatg atgcatggca ggttcgccaa gcagttggcg acgagtacac gcgtttggca   7140
gacgaggatg ttgacatgac agcgtcggtg aaacccccag tggccagggc tgctgtgggt   7200
agctcaacgt tggatgatgt tagcgtgctg actgtcttac gcgaactcgg cgaccagtgc   7260
caaaatgcta tcaaatttgt agttcaggcg gcttcacggt ttgttccacc agtgcccaag   7320
ccacgcacgc gtgtctcggg tgtcttggag cgcgtgcgca tgtgcatgcg cacgcctcca   7380
atcaagtttg aggccaccgc agtaccaatt cataatataa tcccagaaga gtgtcatatt   7440
gtgctacgct gtaccggctg ttgtgaccag gccttgaccg ttccgtacgg cacttgctct   7500
ctgactttaa ccaaatattt gactaacaaa cacagtcact atattccaaa agagaagata   7560
gaagaagaca cagaaatagc tgtcatttgc gccgtaccaa caaagcgcgc aagtaaactt   7620
atcactttca gagcaggtga ccgatcagtc tcatgttgtc accccttgca aactcctatt   7680
agggccctgc ttcaaaagta tgggttacct attgggaagt ggtccgactg caacgggccc   7740
```

```
cttggtgacg acgcccgagt ctgtgacgtc aatggagtga caacttatga accatgcatg    7800
caatcctaca attggttccg atcgattgtg gcaccaacaa ccccacctt acctgcaacc    7860 cggagcgtgg ctggcatttt gcgcgcagac acatcgcgcg tctacaccac aacagcggtt    7920
gatgtctccg agcggcaggc taaggtcacg attgatcaaa agtcagccaa ggtggaccag    7980
tgtctccgag acacatacaa ttgctgcctt gccaaggcaa agaccttcag acaatctggc    8040
atgtcatatg aggatgctgt gtcaaagatg cgcgcaaaca ccacgcgtga tcataacaac    8100
ggcatcactt atacagattt ggtctctgga cgcgcaaaac ctgtcgttca gaaaattgta    8160
gatcagatgc gcgctggagt gtacgacgct ccaatgcgca ttattccaaa acctgaagtg    8220
tttccacgag acaagtcaac acggaagcca ccacggttca tcgttttccc tgggtgtgcc    8280
gcacgagtcg cggagaaaat gatcctgggc gatcctggcg cgataaccaa gcacgtgcta    8340
ggtgatgcct acgggtttgc cactccgccg catgagcgcg cgcgcctact ggaacaatgg    8400
tggaaccgcg caacggagcc acaagctatc gcggttgatg cagtctgctt tgatagcacc    8460
atcacggcag aggacatgga tcgtgaggcc aacatcgtgg ctgcagcgca tacgacccg    8520 gaaggtgttc acggcctata caattattac aaaagaagcc ccatgtgtga tatcacagga    8580
aaagttgtcg gggtgcgtag ctgtcgagcc tcaggtacgc ttacaacaag cagtggcaac    8640
acgcttactt gctacctcaa ggttcgcgca gcttgcacgc gcgccggcat taaaccaatt    8700
ggcttactaa ttcatggaga tgacaccctc attatcacag aacgttgcgc tcaggaaact    8760
ctcgatgagt tcagcaacgc gcttgatgac tatgggttta ctcacaccat gcaggtgtct    8820 gggggacctct cgtctatcga gtgctgcagc gcacgtgtgg acagcgtttg cctccgggga    8880
ggtatgcgtc gcatgctcgt gccacaagct cgacgtgcga ttgcacgcgt tctcggggaa    8940
aagggcgatc cactgggtgt tatcagcagc tatattgtca tgtatcctac tgcggctgtg    9000
actgtctacg ttctgatgcc cctgttgtgc atgctcattc gaaatgagcc atcgcagacg    9060
gggacacttg taacgttgac ggtccacggt aacagtgtga gcgtgccagt gtggctgctt    9120
ccaaccatta ttgcaaattt acatggccgt gacgcactac aggttgtccg tcacagtgca    9180
gcttccatgg cggaactgtc ctcagcgttg gccttctttg gcatgagagg gttgaactgc    9240
tggaggcgga gacgccgtgc catcaggact gatatgatca agttgggcgg gtggaatgcg    9300
aatttcgcgc agatgttact gtggtcaccg gaggtaagaa caccacagcc cgaaccaaag    9360
ggcatgtgtc tcttgccacc ggaactatgg gagcgtccgt acgaaaattt gcacttgagc    9420
acgatcgacc gcaatcgtgg tgctagtcgc ttacggtttt ggttggttgc tagtgctata    9480
ctcgctctgc tttgcttgta aatcctaaat caatgtagta ccaggactac aaggcaggag    9540
gtgaagtcag ctgtacccac ggctggctga accgggggct tgacgacccc ccctatccga    9600
gttgggcaag gtaacatcac gggtgtgacg accccgcccc ccatgtcgc gcgcaagcgc    9660 acggcaagg cagctaggct gagagtctgg gcaactctcc cgtacccac ccgaggctac    9720 gcctcgtcct ggcgaggacc gtaaacatac gtcgtcagcg tggtgacctg acgtatcttg    9780
ttaaccactt aatggtcgta actcgacccc cgtgccgggg atctaagcgc ggcaccgcga    9840
tgagaggggt caacggcccc tttcatt                                       9867
```

<210> SEQ ID NO 304
<211> LENGTH: 79
<212> TYPE: PRT
<213> ORGANISM: Human Pegivirus 2

<400> SEQUENCE: 304

```
Met Gly Cys Ser Thr Asp Gln Thr Ile Cys Ser Pro Val Val Gly Ala
1               5                   10                  15

Asp Tyr Asn Thr Ser Ser Gly Cys Arg Ala Leu Asn Gly Ser Tyr His
            20                  25                  30

Cys Gly Gly Gly Ser Cys Arg Ser Pro Ser Arg Val Gln Val Ala Arg
        35                  40                  45

Arg Val Leu Gln Leu Cys Ala Phe Leu Ala Leu Ile Gly Ser Gly Met
    50                  55                  60

Cys Ser Ile Arg Ser Lys Thr Glu Gly Arg Ile Glu Ser Gly Gln
65                  70                  75
```

<210> SEQ ID NO 305
<211> LENGTH: 191
<212> TYPE: PRT
<213> ORGANISM: Human Pegivirus 2

<400> SEQUENCE: 305

```
Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
            20                  25                  30

Trp Cys Val Thr Arg Pro Gly Cys Leu Val Cys Thr Gly Asn Ala Thr
        35                  40                  45

His Pro Val Cys Trp Asp Tyr Leu Gly Ser Gly Val Ser Arg Arg Pro
    50                  55                  60

Ala Arg Arg Met Gly Glu Gly Ala Glu Val Leu Leu Arg Leu Ile Gly
65                  70                  75                  80

Ile Ala Gly Trp Leu Gly Leu Leu Ala Glu Ala Leu Gly Met Ser Glu
                85                  90                  95

Ile Tyr Ala Ala Ile Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Ile Leu Gln Leu Pro Gly Leu Leu Trp Gln Met Phe Val Ser Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
            180                 185                 190
```

<210> SEQ ID NO 306
<211> LENGTH: 354
<212> TYPE: PRT
<213> ORGANISM: Human Pegivirus 2
<220> FEATURE:
<221> NAME/KEY: MISC_FEATURE
<222> LOCATION: (49)..(49)
<223> OTHER INFORMATION: Xaa = any amino acid
<220> FEATURE:
<221> NAME/KEY: MISC_FEATURE
<222> LOCATION: (145)..(145)
<223> OTHER INFORMATION: Xaa = any amino acid
<220> FEATURE:
<221> NAME/KEY: MISC_FEATURE
<222> LOCATION: (203)..(203)
<223> OTHER INFORMATION: Xaa = any amino acid
<220> FEATURE:
<221> NAME/KEY: MISC_FEATURE
<222> LOCATION: (226)..(226)
<223> OTHER INFORMATION: Xaa = any amino acid

<400> SEQUENCE: 306

Tyr Lys His Gln Ser Glu Ser Tyr Leu Lys Tyr Cys Thr Ile Thr Asn
1               5                   10                  15

Ala Ser Thr Ala Met Asn Cys Asp Cys Pro Phe Gly Thr Phe Thr Arg
            20                  25                  30

Asn Thr Glu Ser Arg Phe Ser Ile Pro Arg Phe Cys Pro Val Lys Ile
        35                  40                  45

Xaa Ser Ser Thr Phe Ile Cys Ser Trp Gly Ser Trp Trp Trp Phe Ala
    50                  55                  60

Glu Asn Ile Thr Arg Pro Tyr Ser Asp Val Gly Met Pro Pro Ala Pro
65                  70                  75                  80

Ile Ser Ala Leu Cys Tyr Ile Tyr Ser Asn Asn Asp Pro Pro Pro Trp
                85                  90                  95

Tyr His Asn Thr Thr Ile Ile Pro Gln Asn Cys Arg Asn Ser Thr Val
            100                 105                 110

Asp Pro Thr Thr Ala Pro Cys Arg Asp Lys Trp Gly Asn Ala Thr Ala
        115                 120                 125

Cys Ile Leu Asp Arg Arg Ser Arg Phe Cys Gly Asp Cys Tyr Gly Gly
    130                 135                 140

Xaa Phe Tyr Thr Asn Gly Ser His Asp Arg Ser Trp Asp Arg Cys Gly
145                 150                 155                 160

Ile Gly Tyr Arg Asp Gly Leu Ile Glu Phe Val Gln Leu Gly Gln Ile
                165                 170                 175

Arg Pro Asn Ile Ser Asn Thr Thr Ile Glu Leu Leu Ala Gly Ala Ser
            180                 185                 190

Leu Val Ile Ala Ser Gly Leu Arg Pro Gly Xaa Gly Cys Ser Arg Ala
        195                 200                 205

His Gly Val Val His Cys Tyr Arg Cys Pro Ser Tyr Arg Asp Leu Glu
    210                 215                 220

Gln Xaa Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
                245                 250                 255

Met Ser Asn Asn Pro Leu Ser Leu Leu Gln Thr Phe Val Glu Asp Ile
            260                 265                 270

Phe Leu Ala Pro Phe Cys Asn Pro Thr Pro Gly Arg Val Arg Val Cys
        275                 280                 285

Asn Asn Thr Ala Phe Tyr Pro Arg Gly Gly Gly Phe Val Gln Leu Ile
    290                 295                 300

Gly Asp Val Gln Val Leu Thr Pro Asn Thr Ala Ser Leu His Ser Leu
305                 310                 315                 320

Leu Thr Leu Ile Ser Leu Ile Leu Leu Val Cys Val Val Ser Gly Ala
                325                 330                 335

Arg Phe Val Pro Leu Ile Ile Ile Phe Phe Trp Ser Ala Arg His Val
            340                 345                 350

Tyr Ala

<210> SEQ ID NO 307
<211> LENGTH: 237
<212> TYPE: PRT
<213> ORGANISM: Human Pegivirus 2
<220> FEATURE:

<221> NAME/KEY: MISC_FEATURE
<222> LOCATION: (75)..(75)
<223> OTHER INFORMATION: Xaa = any amino acid
<220> FEATURE:
<221> NAME/KEY: MISC_FEATURE
<222> LOCATION: (198)..(198)
<223> OTHER INFORMATION: Xaa = any amino acid

<400> SEQUENCE: 307

```
Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
            20                  25                  30

Val Ala Thr Arg Ile Ser Ser Cys Gly His Ala Val Pro Pro Pro Asp
        35                  40                  45

Arg Gly Trp Glu Val Pro Ala Ala Met Ser Trp Val Ile Ser Arg Thr
    50                  55                  60

Thr Gly Leu Thr Phe Asp Val Phe Ser Phe Xaa Gln Tyr Leu Pro Thr
65                  70                  75                  80

Val Pro Gly Asn Asn Thr Asp Ile Ile Tyr Cys Gly Glu Pro Thr Phe
                85                  90                  95

Phe Gly Asp Ile Thr Gly Ile Tyr Trp Pro Tyr Phe Leu Pro Gly Val
            100                 105                 110

Leu Leu Leu Tyr Leu Thr Pro Phe Leu Gly Leu Arg Leu Met Leu Ala
        115                 120                 125

Gly Phe Asn Ile Asp Gly Leu Phe Pro Ile Arg His Ala Thr Ala Ala
130                 135                 140

Leu Arg Phe Ser Thr Ser Arg Val Thr Leu Ser Val Val Ser Ala Phe
145                 150                 155                 160

Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
            180                 185                 190

His Glu Thr Val Leu Xaa Ile Val Cys Leu Leu Tyr Leu Gln Val
        195                 200                 205

Ser Pro Arg Ala Gly Leu Ala Ala Met Val Ala Ile Lys Leu Ser Arg
    210                 215                 220

Gly Leu Leu Phe Ala Val Val Leu Ala His Gly Val Cys
225                 230                 235
```

<210> SEQ ID NO 308
<211> LENGTH: 240
<212> TYPE: PRT
<213> ORGANISM: Human Pegivirus 2
<220> FEATURE:
<221> NAME/KEY: MISC_FEATURE
<222> LOCATION: (142)..(142)
<223> OTHER INFORMATION: Xaa = any amino acid
<220> FEATURE:
<221> NAME/KEY: MISC_FEATURE
<222> LOCATION: (197)..(197)
<223> OTHER INFORMATION: Xaa = any amino acid

<400> SEQUENCE: 308

```
Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
            20                  25                  30

Ser Phe Trp Cys Ala Val Phe Ala Phe Thr Ser Pro Leu Gly Arg Gln
        35                  40                  45
```

```
Tyr Lys Leu Gln Ile Tyr Arg Tyr Trp Ala Gln Val Tyr Ala Arg Leu
     50                  55                  60

Ile Leu Ala Val Gly Cys Gly Pro Leu Gly Arg Glu Phe His Phe Arg
 65                  70                  75                  80

Ala Ser Val Gly Val Leu Trp Cys Gly Ala Cys Met Leu Trp Pro Arg
                 85                  90                  95

Glu Cys Ser Glu Ile Ser Leu Val Phe Ile Leu Cys Ala Leu Thr Val
            100                 105                 110

Asp Thr Ile Asp Thr Trp Leu Val Ala Cys Leu Ser Ala Gly Pro Ser
        115                 120                 125

Ala Arg Thr Leu Ala Thr Leu Ala Asp Asp Met Ala Arg Xaa Gly Asp
    130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Leu Gly Gly Cys Leu Glu Pro Val Val Leu Glu Glu Pro
            180                 185                 190

Thr Phe Thr Glu Xaa Val Asp Asp Thr Met Ser Leu Val Cys Gly Gln
        195                 200                 205

Leu Leu Gly Gly Lys Pro Val Val Ala Arg Cys Gly Thr Arg Val Leu
    210                 215                 220

Val Gly His Leu Asn Pro Glu Asp Leu Pro Pro Gly Phe Gln Leu Ser
225                 230                 235                 240

<210> SEQ ID NO 309
<211> LENGTH: 628
<212> TYPE: PRT
<213> ORGANISM: Human Pegivirus 2
<220> FEATURE:
<221> NAME/KEY: MISC_FEATURE
<222> LOCATION: (97)..(97)
<223> OTHER INFORMATION: Xaa = any amino acid
<220> FEATURE:
<221> NAME/KEY: MISC_FEATURE
<222> LOCATION: (119)..(119)
<223> OTHER INFORMATION: Xaa = any amino acid
<220> FEATURE:
<221> NAME/KEY: MISC_FEATURE
<222> LOCATION: (510)..(510)
<223> OTHER INFORMATION: Xaa = any amino acid
<220> FEATURE:
<221> NAME/KEY: MISC_FEATURE
<222> LOCATION: (580)..(580)
<223> OTHER INFORMATION: Xaa = any amino acid

<400> SEQUENCE: 309

Ala Pro Val Val Ile Thr Lys Pro Ser Ile Gly Thr Trp Ser Phe Leu
 1               5                  10                  15

Lys Ala Thr Leu Thr Gly Arg Ala Glu Thr Pro Gly Ser Gly Gln Ile
             20                  25                  30

Val Val Leu Ser Ser Leu Thr Gly Arg Ser Met Gly Thr Ala Val Asn
         35                  40                  45

Gly Thr Leu Tyr Ala Thr Gly His Gly Ala Gly Ala Arg Gly Leu Ala
     50                  55                  60

Thr Cys Ala Gly Leu Arg Thr Pro Leu Tyr Thr Ala Leu Ser Asp Asp
 65                  70                  75                  80

Val Val Ala Tyr Ser Cys Leu Pro Gly Met Ser Ser Leu Glu Pro Cys
                 85                  90                  95
```

```
Xaa Cys Ser Pro Ser Arg Val Trp Val Met Asn Asn Asn Gly Gly Leu
            100                 105                 110

Val Cys Gly Arg Val Glu Xaa Asp Asp Val Cys Leu Asp Cys Pro Thr
            115                 120                 125

His Ile Asp Gln Leu Arg Gly Ala Ser Gly Ser Pro Val Leu Cys Asp
        130                 135                 140

His Gly His Ala Tyr Ala Leu Met Leu Gly Gly Tyr Ser Thr Ser Gly
145                 150                 155                 160

Ile Cys Ala Arg Val Arg Ile Val Arg Pro Trp Gln Asn Ala Tyr Ser
                165                 170                 175

Ser Ser Gly Gly Gln Gly Gly Met Gln Ala Pro Ala Val Thr Pro Thr
            180                 185                 190

Tyr Ser Glu Ile Thr Tyr Tyr Ala Pro Thr Gly Ser Gly Lys Ser Thr
        195                 200                 205

Lys Tyr Pro Val Asp Leu Val Lys Gln Gly His Lys Val Leu Val Leu
    210                 215                 220

Ile Pro Ser Val Ala Val Lys Ser Met Ala Pro Tyr Ile Lys Glu
225                 230                 235                 240

Thr Tyr Lys Ile Arg Pro Glu Ile Arg Ala Gly Thr Gly Pro Asp Gly
                245                 250                 255

Val Thr Val Ile Thr Gly Glu Asn Leu Ala Tyr Met Thr Tyr Gly Arg
            260                 265                 270

Phe Leu Val Asp Pro Glu Thr Asn Leu Arg Gly Tyr Ala Val Val Ile
        275                 280                 285

Cys Asp Glu Cys His Asp Thr Ser Ser Thr Leu Leu Gly Ile Gly
290                 295                 300

Ala Val Arg Met Tyr Ala Glu Lys Ala Gly Val Lys Thr Val Val Phe
305                 310                 315                 320

Ala Thr Ala Thr Pro Ala Gly Ile Gln Val Gln Pro His Pro Asn Ile
                325                 330                 335

Asp Glu Tyr Leu Leu Thr Asp Thr Gly Asp Val Glu Phe Tyr Gly Ala
            340                 345                 350

Lys Ile Lys Leu Asp Asn Ile Arg Thr Gly Arg His Val Ile Phe Cys
        355                 360                 365

His Ser Lys Ala Arg Cys Ala Glu Leu Thr Gln Gln Leu Ser Gly Leu
    370                 375                 380

Gly Val Arg Ala Val Ser Phe Trp Arg Gly Cys Asp Ile Lys Thr Ile
385                 390                 395                 400

Pro Ala Ser Asp Ser Ile Val Val Ala Thr Asp Ala Leu Ser Thr
                405                 410                 415

Gly Tyr Thr Gly Asn Phe Asp Ser Val Ile Asp Cys Gly Cys Cys Val
            420                 425                 430

Glu Gln Thr Val Thr Ile Asp Met Asp Pro Thr Phe Ser Ile Ser Ala
        435                 440                 445

Arg Val Val Pro Cys Thr Ala Ala Leu Arg Met Gln Arg Arg Gly Arg
    450                 455                 460

Thr Gly Arg Gly Arg Arg Gly Ala Tyr Tyr Thr Thr Pro Gly Ala
465                 470                 475                 480

Ala Pro Cys Val Ser Val Pro Asp Ala Asn Val Trp Gln Ala Val Glu
                485                 490                 495

Ser Ala Met Val Phe Tyr Asp Trp Ser Ala Ala Arg Ile Xaa Gln Cys
            500                 505                 510

Leu Ala Ala Tyr His Asp Leu Gly Cys Thr Pro Arg Ile Ser Cys Asp
```

```
            515                 520                 525
Pro His Thr Pro Val Arg Val Met Asp Thr Leu Arg Ala Tyr Leu Arg
        530                 535                 540

Arg Pro Glu Val Thr Thr Ala Leu Ala Gly Glu Gln Trp Pro Leu
545                 550                 555                 560

Leu Tyr Gly Val Gln Leu Cys Ile Cys Lys Glu Thr Glu Ala His Gly
                    565                 570                 575

Pro Asp Asp Xaa Ile Lys Trp Lys Cys Leu Leu Asn Asn Ser Asn Lys
                580                 585                 590

Thr Pro Leu Leu Tyr Ala Leu Asp Asn Pro Thr Leu Glu Phe Thr Thr
                595                 600                 605

Gln His Asp Leu Thr Arg Arg Ile Ala Gly Ala Leu Ser Ser Thr Val
        610                 615                 620

Phe Val Glu Thr
625

<210> SEQ ID NO 310
<211> LENGTH: 41
<212> TYPE: PRT
<213> ORGANISM: Human Pegivirus 2

<400> SEQUENCE: 310

Gly Tyr Gly Pro Ile Leu Leu Ala Gly Ala Leu Ala Ala Ser Phe
1               5                   10                  15

Ala Phe Ala Gly Ala Thr Gly Ala Leu Val Pro Ser Ala Val Trp Ser
                20                  25                  30

Val Asp Asn Gly Leu Ala Gly Val Thr
                35                  40

<210> SEQ ID NO 311
<211> LENGTH: 262
<212> TYPE: PRT
<213> ORGANISM: Human Pegivirus 2
<220> FEATURE:
<221> NAME/KEY: MISC_FEATURE
<222> LOCATION: (24)..(25)
<223> OTHER INFORMATION: Xaa = any amino acid
<220> FEATURE:
<221> NAME/KEY: MISC_FEATURE
<222> LOCATION: (37)..(37)
<223> OTHER INFORMATION: Xaa = any amino acid

<400> SEQUENCE: 311

Arg Pro Asp Ala Thr Asp Glu Thr Ala Ala Tyr Ala Gln Arg Leu Tyr
1               5                   10                  15

Gln Ala Cys Ala Asp Ser Gly Xaa Xaa Ala Ser Leu Gln Gly Thr Ala
                20                  25                  30

Ser Ala Ala Leu Xaa Lys Leu Ala Asp Ala Ser Arg Gly Ala Ser Gln
                35                  40                  45

Tyr Leu Ala Ala Ala Pro Pro Ser Pro Ala Pro Leu Val Gln Val Leu
            50                  55                  60

Gln Phe Leu Glu Thr Asn Phe Ser Ser Ile Ala Ser Phe Gly Leu Leu
65                  70                  75                  80

Cys Ala Gly Cys Gln Ala Gly Glu Cys Phe Thr Ala Leu Ala Gly Leu
                85                  90                  95

Val Ser Gly Ala Thr Ala Gly Leu Gly Gly Ala His Lys Trp Leu Leu
                100                 105                 110

Ala Ile Ala Gly Thr Trp Leu Val Ser Leu Gln Thr Gly Pro Arg Gly
            115                 120                 125
```

```
Gly Met Val Ala Gly Leu Ser Val Leu Ala Gly Cys Cys Ile Gly Ser
    130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Val Asp Leu Leu Pro Ala Leu Phe Ser Pro Gly
            180                 185                 190

Ala Gly Ile Ala Gly Ile Val Leu Val Phe Ile Leu Ser Asn Ser Ser
        195                 200                 205

Val Thr Thr Trp Ala Asn Arg Leu Leu Ser Met Cys Ala Lys Gln Thr
    210                 215                 220

Ile Cys Glu Asn Tyr Phe Leu Thr Glu Lys Phe Gly Gln Gln Leu Ser
225                 230                 235                 240

Lys Leu Ser Leu Trp Arg Ser Val Tyr His Trp Ala Gln Ala Arg Glu
                245                 250                 255

Gly Tyr Thr Gln Cys Gly
            260

<210> SEQ ID NO 312
<211> LENGTH: 458
<212> TYPE: PRT
<213> ORGANISM: Human Pegivirus 2
<220> FEATURE:
<221> NAME/KEY: MISC_FEATURE
<222> LOCATION: (22)..(22)
<223> OTHER INFORMATION: Xaa = any amino acid

<400> SEQUENCE: 312

Val Val Ser Gly Ile Trp Ser Phe Val Leu Cys Ile Leu Arg Ala Val
1               5                   10                  15

Trp Asp Trp Ala Ala Xaa His Val Pro Arg Phe Arg Val Pro Met Ile
                20                  25                  30

Gly Cys Ser Pro Ala Trp Cys Gly Arg Trp Leu Gly Thr Gly Thr Leu
            35                  40                  45

Leu Thr Thr Cys Gly Cys Gly Glu Arg Val Ser Leu Gln Cys Leu Cys
        50                  55                  60

Ser Thr Ser Asp Pro Thr Leu Ser Val Gly Arg Trp Cys Arg Cys Ser
65                  70                  75                  80

Trp Ser Val Gly Phe Pro Phe Asn Pro Thr Thr Thr Ala Thr Gly Thr
                85                  90                  95

Leu Arg Pro Asp Ile Ser Asp Ala Thr Lys Leu Gly Phe Arg Tyr Gly
            100                 105                 110

Val Ala Glu Ile Val Glu Leu Glu Arg Arg Gly Asp Lys Trp His Val
        115                 120                 125

Cys Ala Ala Ser Cys Cys Leu Asp Arg Ala Ser Val Ala Ser Ala Val
    130                 135                 140

Lys Ala Pro Pro Val Thr Ala Asn Gly Ile Pro Ile Ser Thr Phe Ser
145                 150                 155                 160

Pro Pro Gln Thr Tyr Ser Leu Ser Leu Cys Ser Phe Asp Ser Val Cys
                165                 170                 175

Met Ser Thr Asn Leu Cys Asn Pro Ala Lys Thr Leu Ser Val Cys Ser
            180                 185                 190

Gln Glu Ala Val Glu Leu Leu Glu Glu Thr Val Asp Thr Ala Gln Val
        195                 200                 205
```

```
Met Met Cys Gln Asn Leu Glu Ala Arg Arg Ala Glu Tyr Asp Ala
    210                 215                 220

Trp Gln Val Arg Gln Ala Val Gly Asp Glu Tyr Thr Arg Leu Ala Asp
225                 230                 235                 240

Glu Asp Val Asp Thr Thr Thr Ser Val Lys Pro Pro Val Ala Arg Ala
                245                 250                 255

Ala Val Gly Ser Ser Thr Leu Asp Asp Val Ser Val Leu Thr Val Leu
            260                 265                 270

Arg Glu Leu Gly Asp Gln Cys Gln Asn Ala Ile Lys Phe Val Val Gln
        275                 280                 285

Ala Ala Ser Arg Phe Val Pro Pro Val Pro Lys Pro Arg Thr Arg Val
    290                 295                 300

Ser Gly Val Leu Glu Arg Val Arg Met Cys Met Arg Thr Pro Pro Ile
305                 310                 315                 320

Lys Phe Glu Ala Thr Ala Val Pro Ile His Asn Ile Ile Pro Glu Glu
                325                 330                 335

Cys His Ile Val Leu Arg Cys Thr Gly Cys Asn Asp Gln Ala Leu Thr
            340                 345                 350

Val Pro Tyr Gly Thr Cys Thr Gln Thr Leu Ile Lys His Leu Thr Asn
        355                 360                 365

Lys His Ser His Tyr Ile Pro Lys Gln Lys Ile Glu Glu Asp Thr Glu
    370                 375                 380

Val Thr Val Ile Cys Ala Val Pro Thr Lys Arg Ala Ser Lys Leu Ile
385                 390                 395                 400

Thr Phe Arg Ala Gly Asp Arg Ser Val Ser Cys Cys His Pro Leu Gln
                405                 410                 415

Thr Pro Ile Arg Ala Leu Leu Leu Lys Tyr Gly Leu Pro Ile Gly Lys
            420                 425                 430

Trp Ser Asp Cys Asn Gly Pro Leu Gly Asp Asp Ala Arg Val Cys Asp
        435                 440                 445

Val Asn Gly Val Thr Thr Tyr Glu Pro Cys
    450                 455

<210> SEQ ID NO 313
<211> LENGTH: 567
<212> TYPE: PRT
<213> ORGANISM: Human Pegivirus 2
<220> FEATURE:
<221> NAME/KEY: MISC_FEATURE
<222> LOCATION: (101)..(101)
<223> OTHER INFORMATION: Xaa = any amino acid
<220> FEATURE:
<221> NAME/KEY: MISC_FEATURE
<222> LOCATION: (234)..(234)
<223> OTHER INFORMATION: Xaa = any amino acid
<220> FEATURE:
<221> NAME/KEY: MISC_FEATURE
<222> LOCATION: (239)..(239)
<223> OTHER INFORMATION: Xaa = any amino acid
<220> FEATURE:
<221> NAME/KEY: MISC_FEATURE
<222> LOCATION: (446)..(446)
<223> OTHER INFORMATION: Xaa = any amino acid
<220> FEATURE:
<221> NAME/KEY: MISC_FEATURE
<222> LOCATION: (514)..(514)
<223> OTHER INFORMATION: Xaa = any amino acid
<220> FEATURE:
<221> NAME/KEY: MISC_FEATURE
<222> LOCATION: (517)..(517)
<223> OTHER INFORMATION: Xaa = any amino acid
<220> FEATURE:
<221> NAME/KEY: MISC_FEATURE
```

```
<222> LOCATION: (521)..(521)
<223> OTHER INFORMATION: Xaa = any amino acid
<220> FEATURE:
<221> NAME/KEY: MISC_FEATURE
<222> LOCATION: (523)..(523)
<223> OTHER INFORMATION: Xaa = any amino acid
<220> FEATURE:
<221> NAME/KEY: MISC_FEATURE
<222> LOCATION: (526)..(526)
<223> OTHER INFORMATION: Xaa = any amino acid

<400> SEQUENCE: 313
```

Met Gln Ser Tyr Ser Trp Phe Arg Pro Ile Val Ala Pro Thr Thr Pro
1               5                   10                  15

Pro Leu Pro Ala Thr Arg Ser Val Ala Gly Ile Leu Arg Ala Asp Thr
            20                  25                  30

Ser Arg Val Tyr Thr Thr Thr Ala Val Asp Val Ser Glu Arg Gln Ala
        35                  40                  45

Lys Val Thr Ile Asp Gln Thr Ser Ala Lys Val Asp Gln Cys Phe Arg
    50                  55                  60

Asp Thr Tyr Asn Cys Cys Leu Ala Lys Ala Lys Thr Phe Arg Gln Ser
65                  70                  75                  80

Gly Met Ser Tyr Glu Asp Ala Val Ser Lys Met Arg Ala Asn Thr Thr
                85                  90                  95

Arg Asp His Asn Xaa Gly Ile Thr Tyr Ser Asp Leu Val Ser Gly Arg
            100                 105                 110

Ala Lys Pro Val Val Gln Lys Ile Val Asp Gln Met Arg Ala Gly Val
        115                 120                 125

Tyr Asp Ala Pro Met Arg Ile Ile Pro Lys Pro Glu Val Phe Pro Arg
    130                 135                 140

Asp Lys Ser Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His
            180                 185                 190

Glu Arg Ala Arg Leu Leu Glu Gln Trp Trp Asn Arg Ala Thr Glu Pro
        195                 200                 205

Gln Ala Ile Ala Val Asp Ala Ile Cys Phe Asp Ser Thr Ile Thr Ala
    210                 215                 220

Glu Asp Met Asp Arg Glu Ala Asn Ile Xaa Ala Ala His Xaa Asp
225                 230                 235                 240

Pro Glu Gly Val His Gly Leu Tyr Asn Tyr Tyr Lys Arg Ser Pro Met
                245                 250                 255

Cys Asp Ile Thr Gly Lys Val Val Gly Val Arg Cys Cys Arg Ala Ser
            260                 265                 270

Gly Thr Leu Thr Thr Ser Ser Gly Asn Thr Leu Thr Cys Tyr Leu Lys
        275                 280                 285

Val Arg Ala Ala Cys Thr Arg Ala Gly Ile Lys Pro Ile Gly Leu Leu
    290                 295                 300

Ile His Gly Asp Asp Thr Leu Ile Ile Thr Glu Arg Cys Ala Gln Glu
305                 310                 315                 320

Thr Leu Asp Glu Phe Ser Asn Ala Leu Asp Asp Tyr Gly Phe Pro His
                325                 330                 335

Thr Ile Gln Val Ser Gly Asp Leu Ser Ser Val Glu Cys Cys Ser Ala
            340                 345                 350

```
Arg Val Asp Ser Val Cys Leu Arg Gly Gly Met Arg Met Leu Val
        355                 360                 365

Pro Gln Ala Arg Arg Ala Ile Ala Arg Val Leu Gly Glu Lys Gly Asp
    370                 375                 380

Pro Leu Gly Val Ile Ser Ser Tyr Ile Val Met Tyr Pro Thr Ala Ala
385                 390                 395                 400

Val Thr Val Tyr Val Leu Leu Pro Leu Leu Cys Met Leu Ile Arg Asn
                405                 410                 415

Glu Pro Ser Gln Thr Gly Thr Leu Val Thr Leu Thr Val His Gly Asn
                420                 425                 430

Ser Val Ser Val Pro Val Trp Leu Leu Pro Thr Ile Ile Xaa Asn Leu
        435                 440                 445

His Gly Arg Asp Ala Leu Gln Val Val Arg His Ser Ala Ala Ser Met
    450                 455                 460

Ala Glu Leu Ser Ser Ala Leu Ala Phe Phe Gly Met Arg Gly Leu Asn
465                 470                 475                 480

Cys Trp Arg Arg Arg Arg Ala Ile Arg Thr Asp Met Ile Lys Leu
                485                 490                 495

Gly Gly Trp Asn Ala Asn Phe Ala Gln Met Leu Leu Trp Ser Pro Glu
                500                 505                 510

Val Xaa Thr Pro Xaa Pro Glu Pro Xaa Gly Xaa Cys Leu Xaa Pro Pro
        515                 520                 525

Glu Leu Trp Glu Arg Pro Tyr Glu Asn Leu His Leu Ser Thr Ile Asp
    530                 535                 540

Arg Asn Arg Gly Ala Ser Arg Leu Arg Phe Trp Leu Val Ala Ser Ala
545                 550                 555                 560

Ile Leu Ala Leu Leu Cys Leu
                565

<210> SEQ ID NO 314
<211> LENGTH: 79
<212> TYPE: PRT
<213> ORGANISM: Human Pegivirus 2

<400> SEQUENCE: 314

Met Gly Cys Ser Thr Asp Gln Thr Ile Cys Ser Pro Val Val Glu Ala
1               5                   10                  15

Asp Tyr Asn Thr Ser Ser Gly Cys Arg Ala Leu Asn Gly Ser Tyr His
                20                  25                  30

Cys Gly Gly Gly Ser Cys Arg Ser Pro Ser Arg Val Gln Val Ala Gly
            35                  40                  45

Arg Val Leu Arg Leu Cys Ala Phe Leu Ala Leu Ile Gly Ser Gly Met
        50                  55                  60

Cys Ser Ile Arg Ser Lys Asn Glu Gly Arg Ile Glu Ser Gly Gln
65                  70                  75

<210> SEQ ID NO 315
<211> LENGTH: 191
<212> TYPE: PRT
<213> ORGANISM: Human Pegivirus 2

<400> SEQUENCE: 315

Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
                20                  25                  30
```

```
Trp Cys Val Thr Arg Pro Gly Cys Leu Val Cys Gly Asn Ala Thr
            35                  40                  45

His Pro Val Cys Trp Asp Tyr Leu Gly Ser Gly Val Ser Arg Pro
    50                  55                  60

Ala Arg Arg Met Gly Glu Gly Ala Glu Val Leu Leu Arg Leu Ile Gly
65                  70                  75                  80

Ile Ala Gly Trp Leu Gly Leu Leu Ala Glu Ala Leu Gly Met Ser Glu
                85                  90                  95

Ile Tyr Ala Ala Phe Leu Cys Phe Gly Phe Ile Ala Trp Tyr Gly Trp
                100                 105                 110

Gly Ile Pro Lys Thr Leu Val Cys Thr Val Cys Pro Ala Val Asn Ile
                115                 120                 125

Ser Pro Tyr Ser Phe Leu Ser Pro Asp Thr Ile Ala Phe Gly Thr Trp
    130                 135                 140

Leu Leu Gln Leu Pro Gly Leu Leu Trp Gln Met Phe Val Ser Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
                180                 185                 190

<210> SEQ ID NO 316
<211> LENGTH: 354
<212> TYPE: PRT
<213> ORGANISM: Human Pegivirus 2

<400> SEQUENCE: 316

Tyr Lys His Gln Ala Asp Ser Tyr Leu Lys Tyr Cys Thr Ile Thr Asn
1               5                   10                  15

Ala Ser Thr Ala Met Asn Cys Asp Cys Pro Phe Gly Thr Phe Thr Arg
                20                  25                  30

Asn Thr Glu Ser Gly Phe Thr Ile Pro Arg Phe Cys Pro Val Lys Leu
            35                  40                  45

Asn Ser Ser Thr Phe Ile Cys Ser Trp Gly Ser Trp Trp Phe Ala
    50                  55                  60

Glu Asn Ile Thr Arg Pro Tyr Ser Asp Val Gly Met Pro Pro Ala Pro
65                  70                  75                  80

Ile Ser Ala Leu Cys Tyr Ile Tyr Ser Asn Asn Asp Pro Pro Ser Trp
                85                  90                  95

Tyr Arg Asn Thr Thr Ile Ile Pro Gln Asn Cys Tyr Asn Ser Thr Ala
                100                 105                 110

Asp Pro Thr Thr Ala Pro Cys Arg Asp Lys Trp Gly Asn Ala Thr Ala
            115                 120                 125

Cys Ile Leu Asp Arg Arg Ser Arg Phe Cys Gly Asp Cys Tyr Gly Gly
    130                 135                 140

Cys Phe Tyr Thr Asn Gly Ser His Asp Arg Ser Trp Asp Arg Cys Gly
145                 150                 155                 160

Ile Gly Tyr Arg Asp Gly Leu Ile Glu Phe Val Gln Leu Gly Gln Ile
                165                 170                 175

Arg Pro Asn Ile Ala Asn Thr Thr Ile Glu Leu Leu Ala Gly Ala Ser
            180                 185                 190

Leu Val Ile Ala Ser Gly Leu Arg Ala Gly Tyr Gly Cys Ser Arg Ala
        195                 200                 205

His Gly Val Val His Cys Phe Lys Cys Pro Ser Tyr Arg Asp Leu Glu
    210                 215                 220
```

```
Arg Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
            245                 250                 255

Val Ser Asn Asn Pro Leu Ser Val Leu Gln Thr Phe Val Glu Asp Ile
        260                 265                 270

Phe Leu Ala Pro Phe Cys Asn Pro Thr Pro Gly Arg Val Arg Val Cys
            275                 280                 285

Asn Asn Thr Ala Phe Tyr Pro Arg Gly Gly Gly Phe Val Gln Leu Ile
        290                 295                 300

Gly Asp Val Gln Val Leu Thr Pro Asn Ser Thr Ser Leu His Ser Leu
305                 310                 315                 320

Leu Thr Leu Ile Ser Leu Ile Leu Leu Val Cys Val Val Ser Gly Ala
            325                 330                 335

Arg Phe Val Pro Leu Gly Ile Ile Phe Phe Trp Ser Val Arg His Val
            340                 345                 350

Tyr Ala

<210> SEQ ID NO 317
<211> LENGTH: 237
<212> TYPE: PRT
<213> ORGANISM: Human Pegivirus 2

<400> SEQUENCE: 317

Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
            20                  25                  30

Val Ala Ala Arg Ile Ser Ser Cys Gly His Ala Val Pro Pro Pro Asp
        35                  40                  45

Arg Gly Trp Glu Val Pro Ala Ala Met Ser Trp Ala Ile Ser Arg Thr
    50                  55                  60

Thr Gly Leu Thr Phe Asp Val Phe Ser Phe Ile Gln Tyr Leu Pro Thr
65                  70                  75                  80

Val Pro Gly Asn Asn Ser Asp Ile Ile Tyr Cys Gly Glu Pro Ser Phe
                85                  90                  95

Phe Gly Asp Ile Thr Gly Ile Tyr Trp Pro Tyr Phe Leu Pro Gly Met
            100                 105                 110

Leu Leu Leu Tyr Leu Thr Pro Leu Leu Gly Leu Arg Leu Met Leu Ala
        115                 120                 125

Gly Phe Asn Ile Asp Gly Leu Phe Pro Ile Arg His Ala Thr Ala Ala
130                 135                 140

Leu Arg Phe Ser Thr Ser Arg Val Thr Leu Ser Val Val Phe Ala Phe
145                 150                 155                 160

Leu Ile Tyr Ile Leu Ser His Pro Val Asn Ala Ala Leu Asn Arg Met
            165                 170                 175

Phe Leu Ala Ser Ala Asn Leu Glu Met Ile Leu Ser Phe Asp Thr Tyr
        180                 185                 190

His Glu Thr Val Leu Tyr Val Val Cys Leu Leu Leu Tyr Leu Gln Val
    195                 200                 205

Ser Pro Arg Ala Gly Leu Ala Ala Met Val Ala Ile Lys Leu Ser Arg
210                 215                 220

Gly Leu Leu Phe Ala Val Val Leu Ala His Gly Val Cys
225                 230                 235
```

<210> SEQ ID NO 318
<211> LENGTH: 240
<212> TYPE: PRT
<213> ORGANISM: Human Pegivirus 2

<400> SEQUENCE: 318

```
Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
            20                  25                  30

Ser Phe Trp Cys Ala Val Phe Ala Phe Thr Ser Pro Leu Gly Arg Gln
        35                  40                  45

Tyr Lys Leu Gln Ile Tyr Arg Tyr Trp Ala Gln Ala Tyr Ala Arg Leu
    50                  55                  60

Ile Leu Ala Val Gly Cys Gly Pro Leu Gly Arg Glu Phe His Phe Arg
65                  70                  75                  80

Ala Ser Val Gly Val Leu Trp Cys Gly Ala Cys Met Leu Trp Pro Arg
                85                  90                  95

Glu Cys Ser Glu Ile Ser Leu Val Phe Ile Leu Cys Ala Leu Thr Val
            100                 105                 110

Asp Thr Ile Asp Thr Trp Leu Val Ala Cys Leu Ser Ala Gly Pro Ser
        115                 120                 125

Ala Arg Thr Leu Ala Thr Leu Ala Asp Asp Met Ala Arg Ile Gly Asp
    130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Phe Gly Gly Cys Leu Glu Pro Val Val Leu Glu Glu Pro
            180                 185                 190

Thr Phe Thr Glu Val Val Asp Asp Thr Met Asn Leu Val Cys Gly Gln
        195                 200                 205

Leu Leu Gly Gly Lys Pro Val Val Ala Arg Cys Gly Thr Arg Val Leu
    210                 215                 220

Val Gly His Leu Asn Pro Glu Asp Leu Pro Pro Gly Phe Gln Leu Ser
225                 230                 235                 240
```

<210> SEQ ID NO 319
<211> LENGTH: 628
<212> TYPE: PRT
<213> ORGANISM: Human Pegivirus 2

<400> SEQUENCE: 319

```
Ala Pro Val Val Ile Thr Lys Pro Ser Ile Gly Thr Trp Pro Phe Leu
1               5                   10                  15

Lys Ala Thr Leu Thr Gly Arg Ala Glu Thr Pro Gly Ser Gly Gln Ile
            20                  25                  30

Val Val Leu Ser Ser Leu Thr Gly Arg Ser Met Gly Thr Ala Val Asn
        35                  40                  45

Gly Thr Leu Tyr Ala Thr Gly His Gly Ala Gly Arg Gly Leu Ala
    50                  55                  60

Thr Cys Ala Gly Leu Arg Thr Pro Leu Tyr Thr Ala Leu Ser Glu Asp
65                  70                  75                  80

Val Val Ala Tyr Ser Cys Leu Pro Gly Met Ser Ser Leu Glu Ser Cys
                85                  90                  95
```

```
Asn Cys Ser Pro Ser Arg Val Trp Val Asn Asn Gly Gly Leu
                100                 105             110

Val Cys Gly Arg Val Glu Lys Asp Val Cys Leu Asp Cys Pro Thr
            115             120             125

His Ile Asp Gln Leu Arg Gly Ala Ser Gly Ser Pro Val Leu Cys Asp
        130             135             140

His Gly His Ala Tyr Ala Leu Met Leu Gly Gly Tyr Ser Thr Ser Gly
145             150             155                         160

Ile Cys Ala Arg Val Arg Ile Val Arg Pro Trp Gln Asn Ala Tyr Ser
                165             170             175

Ser Ser Gly Gly Gln Gly Gly Met Gln Ala Pro Ala Val Thr Pro Thr
            180             185             190

Tyr Ser Glu Ile Thr Tyr Tyr Ala Pro Thr Gly Ser Gly Lys Ser Thr
            195             200             205

Lys Tyr Pro Val Asp Leu Val Lys Gln Gly His Lys Val Leu Val Leu
        210             215             220

Leu Pro Ser Val Ala Val Val Lys Ser Met Ala Pro Tyr Ile Lys Glu
225             230             235                         240

Lys Tyr Lys Ile Arg Pro Glu Ile Arg Ala Gly Thr Gly Pro Asp Gly
                245             250             255

Val Thr Val Ile Thr Gly Glu Asn Leu Ala Tyr Met Thr Tyr Gly Arg
            260             265             270

Phe Leu Val Asp Pro Glu Thr Asn Leu Arg Gly Tyr Ala Val Val Ile
            275             280             285

Cys Asp Glu Cys His Asp Thr Ser Ser Thr Thr Leu Leu Gly Ile Gly
290             295             300

Ala Val Arg Met Tyr Ala Glu Lys Ala Gly Val Lys Thr Val Val Phe
305             310             315             320

Ala Thr Ala Thr Pro Ala Gly Ile Gln Val Gln Ser His Pro Asn Ile
            325             330             335

Asp Glu Tyr Leu Leu Thr Asp Thr Gly Asp Val Glu Phe Tyr Gly Ala
            340             345             350

Lys Ile Lys Leu Asp Asn Ile Arg Thr Gly Arg His Val Ile Phe Cys
            355             360             365

His Ser Lys Ala Arg Cys Ala Glu Leu Thr Gln Gln Leu Ser Gly Leu
            370             375             380

Gly Val Arg Ala Val Ser Phe Trp Arg Gly Cys Asp Ile Lys Ser Ile
385             390             395             400

Pro Ala Ser Asp Ser Ile Val Val Ala Thr Asp Ala Leu Ser Thr
            405             410             415

Gly Tyr Thr Gly Asn Phe Asp Ser Val Ile Asp Cys Gly Cys Cys Val
            420             425             430

Glu Gln Thr Val Thr Ile Asp Met Asp Pro Thr Phe Ser Ile Ser Ala
            435             440             445

Arg Val Val Pro Cys Thr Ala Ala Leu Arg Met Gln Arg Arg Gly Arg
            450             455             460

Thr Gly Arg Gly Arg Arg Gly Ala Tyr Tyr Thr Thr Thr Pro Gly Ala
465             470             475             480

Ala Pro Cys Val Ser Val Pro Asp Ala Asn Val Trp Gln Ser Val Glu
            485             490             495

Ser Ala Met Val Phe Tyr Asp Trp Ser Ala Ala Arg Ile Glu Gln Cys
            500             505             510
```

```
Leu Ala Ala Tyr His Asp Leu Gly Cys Thr Pro Arg Ile Ser Cys Asp
            515                 520                 525

Pro His Thr Pro Val Arg Val Met Asp Thr Leu Arg Ala Tyr Leu Arg
    530                 535                 540

Arg Pro Glu Val Thr Thr Ala Ala Leu Ala Gly Glu Gln Trp Pro Leu
545                 550                 555                 560

Leu Tyr Gly Val Gln Leu Cys Ile Cys Lys Glu Thr Glu Ala His Gly
                565                 570                 575

Pro Asp Asp Gly Ile Lys Trp Lys Cys Leu Leu Asn Asn Asn Asn Lys
            580                 585                 590

Thr Pro Leu Leu Tyr Ala Leu Asp Asn Pro Thr Leu Glu Phe Thr Thr
        595                 600                 605

Gln His Asp Leu Thr Arg Arg Ile Ala Gly Ala Leu Ser Ser Thr Val
    610                 615                 620

Phe Val Glu Thr
625

<210> SEQ ID NO 320
<211> LENGTH: 41
<212> TYPE: PRT
<213> ORGANISM: Human Pegivirus 2

<400> SEQUENCE: 320

Gly Tyr Gly Pro Ile Leu Leu Ala Gly Ala Leu Ala Ala Ser Phe
1               5                   10                  15

Ala Phe Ala Gly Ala Thr Gly Ala Leu Val Pro Ser Ala Val Trp Ser
                20                  25                  30

Val Glu Asn Gly Leu Ala Gly Val Thr
                35                  40

<210> SEQ ID NO 321
<211> LENGTH: 262
<212> TYPE: PRT
<213> ORGANISM: Human Pegivirus 2

<400> SEQUENCE: 321

Arg Pro Asp Ala Thr Asp Glu Thr Ala Ala Tyr Ala Gln Arg Leu Tyr
1               5                   10                  15

Gln Ala Cys Ala Asp Ser Gly Ile Leu Ala Ser Leu Gln Gly Thr Ala
                20                  25                  30

Ser Ala Ala Leu Ser Arg Leu Ala Asp Ala Ser Lys Gly Ala Ser Gln
            35                  40                  45

Tyr Leu Ala Ala Pro Pro Ser Pro Ala Pro Leu Val Gln Val Leu
    50                  55                  60

Gln Phe Leu Glu Thr Asn Phe Ser Ser Ile Ala Ser Phe Gly Leu Leu
65                  70                  75                  80

Cys Ala Gly Cys Gln Ala Gly Glu Cys Phe Thr Ala Leu Ala Gly Leu
                85                  90                  95

Val Ser Gly Ala Thr Ala Gly Leu Gly Gly Ala His Lys Trp Leu Leu
            100                 105                 110

Ala Ile Ala Gly Thr Trp Leu Val Ser Leu Gln Thr Gly Pro Arg Gly
        115                 120                 125

Gly Met Val Ala Gly Leu Ser Val Leu Ala Gly Cys Cys Ile Gly Ser
    130                 135                 140

Val Thr Gly Leu Asp Phe Leu Phe Gly Cys Leu Thr Gly Trp Glu Ala
145                 150                 155                 160
```

```
Val Val Gly Ala Ala Val Ala Thr Gln Lys Ile Leu Ser Gly Ser Ala
                165                 170                 175
Asp Met Thr Thr Leu Val Asp Leu Leu Pro Ala Leu Phe Ser Pro Gly
            180                 185                 190
Ala Gly Ile Ala Gly Val Val Leu Val Phe Ile Leu Ser Asn Ser Ser
        195                 200                 205
Val Thr Met Trp Ala Asn Arg Leu Leu Ser Met Cys Ala Lys Gln Thr
    210                 215                 220
Ile Cys Glu Asn Tyr Phe Leu Thr Glu Lys Phe Gly Gln Gln Leu Ser
225                 230                 235                 240
Lys Leu Ser Leu Trp Arg Ser Val Tyr His Trp Ala Gln Ala Arg Glu
                245                 250                 255
Gly Tyr Thr Gln Cys Gly
            260

<210> SEQ ID NO 322
<211> LENGTH: 458
<212> TYPE: PRT
<213> ORGANISM: Human Pegivirus 2

<400> SEQUENCE: 322

Val Val Ser Gly Ile Trp Ser Phe Val Leu Cys Ile Leu Arg Ala Val
1               5                   10                  15
Trp Asp Trp Ala Ala Lys His Val Pro Arg Phe Arg Val Pro Met Ile
            20                  25                  30
Gly Cys Ser Pro Ala Trp Cys Gly Arg Trp Leu Gly Thr Gly Thr Leu
        35                  40                  45
Leu Thr Thr Cys Gly Cys Gly Glu Arg Val Ser Leu Gln Cys Leu Cys
    50                  55                  60
Ser Thr Ser Asp Pro Thr Leu Ser Val Gly Arg Trp Cys Trp Cys Ser
65                  70                  75                  80
Trp Arg Val Gly Phe Pro Phe Asn Pro Thr Thr Thr Ala Thr Gly Thr
                85                  90                  95
Leu Arg Pro Asp Ile Ser Asp Ala Thr Lys Leu Gly Phe Arg Tyr Gly
            100                 105                 110
Val Ala Glu Ile Val Glu Leu Glu Arg Arg Gly Asn Lys Trp His Val
        115                 120                 125
Cys Ala Ala Ser Cys Cys Leu Asp Arg Ala Ser Val Ala Ser Ala Val
    130                 135                 140
Arg Ala Pro Pro Val Thr Ala Asp Gly Ile Pro Ile Ser Thr Phe Ser
145                 150                 155                 160
Pro Pro Gln Thr Tyr Lys Leu Ser Leu Cys Ser Phe Asp Ser Val Cys
                165                 170                 175
Met Thr Thr Asn Leu Cys Asn Pro Ala Lys Thr Leu Ser Val Cys Ser
            180                 185                 190
Gln Glu Ala Val Glu Leu Leu Glu Thr Val Asp Arg Ala Gln Val
        195                 200                 205
Val Met Cys Gln Asn Leu Glu Ala Arg Arg Ala Glu Phe Asp Ala
    210                 215                 220
Trp Gln Val Arg Glu Ala Ile Arg Asp Glu Tyr Thr Arg Leu Ala Asp
225                 230                 235                 240
Glu Asp Val Asp Ala Thr Thr Ser Val Lys Pro Val Ala Lys Ala
                245                 250                 255
Ala Val Gly Ser Ser Thr Leu Asp Asp Val Ser Val Leu Thr Val Leu
            260                 265                 270
```

Arg Glu Leu Gly Asp Gln Cys Gln Asn Ala Ile Lys Phe Val Val Gln
                275                 280                 285

Ala Ala Ser Arg Phe Val Pro Val Pro Lys Pro Arg Thr Arg Val
            290                 295                 300

Ser Gly Val Leu Glu Arg Val Arg Met Cys Met Arg Thr Pro Pro Ile
305                 310                 315                 320

Lys Phe Glu Ala Ala Val Pro Ile His Asp Ile Ile Pro Glu Glu
                325                 330                 335

Cys His Ile Val Leu Arg Cys Thr Gly Cys Asn Asp Gln Ala Leu Thr
                340                 345                 350

Val Pro Tyr Gly Thr Cys Thr Gln Ser Leu Ile Lys His Leu Thr Ser
                355                 360                 365

Lys His Ser His Tyr Ile Pro Lys Gln Lys Ile Glu Glu Asp Thr Glu
                370                 375                 380

Val Thr Val Ile Cys Ala Val Pro Thr Thr Arg Ala Ser Lys Leu Ile
385                 390                 395                 400

Thr Phe Arg Ala Gly Asp Arg Ser Val Ser Cys Cys His Pro Leu Gln
                405                 410                 415

Thr Pro Ile Arg Ala Leu Leu Leu Lys Tyr Gly Leu Pro Ile Gly Lys
                420                 425                 430

Trp Ser Asp Cys Asn Gly Pro Leu Gly Asp Asp Ala Arg Val Cys Asp
                435                 440                 445

Val Asn Gly Val Thr Thr Tyr Glu Pro Cys
                450                 455

<210> SEQ ID NO 323
<211> LENGTH: 567
<212> TYPE: PRT
<213> ORGANISM: Human Pegivirus 2

<400> SEQUENCE: 323

Met Gln Ser Tyr Ser Trp Phe Arg Pro Ile Val Ala Pro Thr Thr Pro
1               5                   10                  15

Pro Leu Pro Ala Thr Arg Thr Val Ala Gly Ile Leu Arg Ala Asp Thr
                20                  25                  30

Ser Arg Val Tyr Thr Thr Thr Ala Val Asp Val Ser Glu Arg Gln Ala
            35                  40                  45

Lys Val Thr Ile Asp Gln Thr Ser Ala Lys Val Asp Gln Cys Phe Arg
    50                  55                  60

Asp Thr Tyr Asn Cys Cys Leu Ala Lys Ala Lys Thr Phe Arg Gln Ser
65                  70                  75                  80

Gly Met Ser Tyr Glu Asp Ala Val Ser Lys Met Arg Ala Asn Thr Thr
                85                  90                  95

Arg Asp His Asn Asn Gly Ile Thr Tyr Ser Asp Leu Val Ser Gly Arg
                100                 105                 110

Ala Lys Pro Val Val Gln Lys Ile Val Asn Gln Met Arg Ala Gly Val
            115                 120                 125

Tyr Asp Ala Pro Met Arg Ile Ile Pro Lys Pro Glu Val Phe Pro Arg
130                 135                 140

Asp Lys Thr Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His

```
            180                 185                 190
Glu Arg Ala Arg Leu Glu Gln Trp Trp Asn Arg Ala Thr Glu Pro
        195                 200                 205
Gln Ala Ile Ala Val Asp Ala Ile Cys Phe Asp Ser Thr Ile Thr Ala
        210                 215                 220
Glu Asp Met Asp Arg Glu Ala Asn Ile Val Ala Ala His Thr Asp
225                 230                 235                 240
Pro Glu Gly Val His Gly Leu Tyr Asn Tyr Tyr Lys Arg Ser Pro Met
            245                 250                 255
Cys Asp Ile Thr Gly Lys Val Gly Val Arg Cys Arg Ala Ser
            260                 265                 270
Gly Thr Leu Thr Thr Ser Ser Gly Asn Thr Leu Thr Cys Tyr Leu Lys
        275                 280                 285
Val Arg Ala Ala Cys Thr Arg Ser Gly Ile Lys Pro Ile Gly Leu Leu
        290                 295                 300
Ile His Gly Asp Asp Thr Leu Ile Val Thr Glu Arg Cys Ala Gln Glu
305                 310                 315                 320
Thr Leu Asp Glu Phe Ser Asn Ala Leu Asp Asp Tyr Gly Phe Pro His
            325                 330                 335
Thr Ile Gln Ala Ser Gly Asp Leu Ser Ser Ile Glu Cys Cys Ser Ala
            340                 345                 350
Arg Val Asp Ser Val Cys Leu Arg Gly Gly Met Arg Arg Met Leu Val
            355                 360                 365
Pro Gln Ala Arg Arg Ala Ile Ala Arg Val Leu Gly Glu Lys Gly Asp
        370                 375                 380
Pro Leu Gly Thr Ile Gly Ser Tyr Val Val Met Tyr Pro Thr Ala Ala
385                 390                 395                 400
Val Thr Val Tyr Val Leu Leu Pro Leu Leu Cys Met Leu Ile Arg Asn
            405                 410                 415
Glu Pro Ser Gln Thr Gly Thr Leu Val Thr Leu Thr Val His Gly Asn
            420                 425                 430
Ser Val Ser Val Pro Ala Trp Leu Leu Pro Thr Ile Ile Ala Asn Leu
        435                 440                 445
His Gly Arg Asp Ala Leu Gln Val Val Arg His Ser Ala Ala Ser Met
        450                 455                 460
Ala Glu Leu Ser Ser Ala Leu Ala Phe Phe Gly Met Arg Gly Leu Asn
465                 470                 475                 480
Cys Trp Arg Arg Arg Arg Ala Ile Arg Ala Asp Met Ile Lys Ser
            485                 490                 495
Gly Gly Trp Asn Ala Asn Phe Ala Gln Met Leu Leu Trp Ser Pro Glu
            500                 505                 510
Val Arg Thr Pro Gln Pro Glu Pro Arg Gly Leu Cys Leu Leu Pro Pro
            515                 520                 525
Glu Leu Trp Glu Arg Pro Tyr Glu Asn Leu His Leu Ser Thr Ile Asp
            530                 535                 540
Arg Asn Arg Gly Ala Ser Arg Leu Arg Phe Trp Leu Val Ala Ser Ala
545                 550                 555                 560
Ile Leu Ala Leu Leu Cys Leu
            565
```

<210> SEQ ID NO 324
<211> LENGTH: 79
<212> TYPE: PRT
<213> ORGANISM: Human Pegivirus 2

<400> SEQUENCE: 324

Met Gly Cys Ser Thr Asp Gln Thr Ile Cys Ser Pro Val Val Gly Ala
1               5                   10                  15

Asp Tyr Asn Thr Ser Ser Gly Cys Arg Ala Leu Asn Gly Ser Tyr His
            20                  25                  30

Cys Gly Gly Gly Ser Cys Arg Ser Pro Ser Cys Val Gln Val Ala Arg
        35                  40                  45

Arg Val Leu Gln Leu Cys Ala Leu Leu Ala Leu Ile Gly Ser Gly Met
    50                  55                  60

Cys Ser Ile Arg Ser Lys Thr Glu Gly Arg Ile Glu Ser Gly Gln
65                  70                  75

<210> SEQ ID NO 325
<211> LENGTH: 191
<212> TYPE: PRT
<213> ORGANISM: Human Pegivirus 2

<400> SEQUENCE: 325

Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
            20                  25                  30

Trp Cys Val Thr Arg Pro Gly Cys Leu Val Cys Thr Gly Asn Ala Thr
        35                  40                  45

His Pro Val Cys Trp Asp Tyr Leu Gly Ser Gly Val Ser Arg Arg Pro
    50                  55                  60

Ala Arg Arg Met Gly Glu Gly Ala Glu Val Leu Leu Arg Leu Ile Gly
65                  70                  75                  80

Ala Ala Gly Trp Leu Gly Leu Leu Ala Glu Ala Leu Gly Met Ser Glu
                85                  90                  95

Ile Tyr Ala Ala Ile Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Ile Leu Gln Leu Pro Gly Leu Leu Trp Gln Met Phe Val Asn Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
            180                 185                 190

<210> SEQ ID NO 326
<211> LENGTH: 354
<212> TYPE: PRT
<213> ORGANISM: Human Pegivirus 2
<220> FEATURE:
<221> NAME/KEY: MISC_FEATURE
<222> LOCATION: (72)..(72)
<223> OTHER INFORMATION: Xaa = any amino acid
<220> FEATURE:
<221> NAME/KEY: MISC_FEATURE
<222> LOCATION: (76)..(76)
<223> OTHER INFORMATION: Xaa = any amino acid
<220> FEATURE:
<221> NAME/KEY: MISC_FEATURE
<222> LOCATION: (117)..(117)
<223> OTHER INFORMATION: Xaa = any amino acid

```
<220> FEATURE:
<221> NAME/KEY: MISC_FEATURE
<222> LOCATION: (170)..(170)
<223> OTHER INFORMATION: Xaa = any amino acid
<220> FEATURE:
<221> NAME/KEY: MISC_FEATURE
<222> LOCATION: (177)..(177)
<223> OTHER INFORMATION: Xaa = any amino acid
<220> FEATURE:
<221> NAME/KEY: MISC_FEATURE
<222> LOCATION: (181)..(181)
<223> OTHER INFORMATION: Xaa = any amino acid

<400> SEQUENCE: 326
```

Tyr Lys His Gln Ser Asp Ser Tyr Leu Lys Tyr Cys Thr Ile Thr Asn
1               5                   10                  15

Ala Ser Thr Ala Met Asn Cys Asp Cys Pro Phe Gly Thr Phe Thr Arg
            20                  25                  30

Asn Thr Glu Ser Arg Phe Ser Ile Pro Arg Phe Cys Pro Val Lys Ile
        35                  40                  45

Lys Ser Ser Thr Phe Ile Cys Ser Trp Gly Ser Trp Trp Phe Ala
    50                  55                  60

Glu Asn Ile Thr Arg Pro Tyr Xaa Asp Val Gly Xaa Pro Pro Ala Pro
65                  70                  75                  80

Ile Ser Ala Leu Cys Tyr Ile Tyr Ser Asn Asn Asp Pro Pro Trp
            85                  90                  95

Tyr His Asn Thr Thr Ile Ile Pro Gln Asn Cys Arg Asn Ser Thr Val
            100                 105                 110

Asp Pro Thr Thr Xaa Pro Cys Arg Asp Lys Trp Gly Asn Ala Thr Ala
            115                 120                 125

Cys Ile Leu Asp Arg Arg Ser Arg Phe Cys Gly Asp Cys Tyr Gly Gly
130                 135                 140

Cys Phe Tyr Thr Asn Gly Thr His Asp Arg Ser Trp Asp Arg Cys Gly
145                 150                 155                 160

Ile Gly Tyr Arg Asp Gly Leu Ile Glu Xaa Val Gln Leu Gly Gln Ile
                165                 170                 175

Xaa Pro Asn Ile Xaa Asn Thr Thr Ile Glu Leu Leu Ala Gly Ala Ser
            180                 185                 190

Leu Val Ile Ala Ser Gly Leu Arg Pro Gly Phe Gly Cys Ser Arg Ala
        195                 200                 205

His Gly Val Val His Cys Tyr Arg Cys Pro Ser Tyr Arg Asp Leu Glu
    210                 215                 220

Gln Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
                245                 250                 255

Met Ser Asn Asn Pro Leu Ser Leu Leu Gln Thr Phe Val Glu Asp Ile
            260                 265                 270

Phe Leu Ala Pro Phe Cys Asn Pro Thr Pro Gly Arg Val Arg Val Cys
        275                 280                 285

Asn Asn Thr Ala Phe Tyr Pro Arg Gly Gly Phe Val Gln Leu Ile
    290                 295                 300

Gly Asp Val Gln Val Leu Thr Pro Asn Thr Ala Ser Leu His Ser Leu
305                 310                 315                 320

Leu Thr Leu Ile Ser Leu Ile Leu Leu Val Cys Val Val Ser Gly Ala
            325                 330                 335

Arg Phe Gly Pro Leu Ile Ile Ile Phe Phe Trp Ser Ala Arg His Val

<210> SEQ ID NO 327
<211> LENGTH: 237
<212> TYPE: PRT
<213> ORGANISM: Human Pegivirus 2
<220> FEATURE:
<221> NAME/KEY: MISC_FEATURE
<222> LOCATION: (6)..(6)
<223> OTHER INFORMATION: Xaa = any amino acid

<400> SEQUENCE: 327

Ser Cys Tyr Leu Ser Xaa Asp Trp Ala Val Cys Asn Asp Ala Phe Cys
1               5                   10                  15

Phe Thr Ser Gly Thr Cys Ala Thr Phe Asn Asp Val Leu Cys Leu Pro
            20                  25                  30

Val Ala Thr His Ile Ser Ser Cys Gly His Ala Val Pro Pro Pro Asp
        35                  40                  45

Arg Gly Trp Glu Val Pro Ala Ala Met Ser Trp Val Ile Ser Arg Thr
    50                  55                  60

Thr Gly Leu Thr Phe Asp Val Phe Ser Phe Ile Gln Tyr Phe Pro Thr
65                  70                  75                  80

Val Pro Gly Asn Asn Thr Asp Ile Ile Tyr Cys Gly Glu Pro Thr Phe
                85                  90                  95

Phe Gly Asp Ile Thr Gly Ile Tyr Trp Pro Tyr Phe Leu Pro Gly Val
            100                 105                 110

Leu Leu Leu Tyr Leu Thr Pro Phe Leu Gly Phe Arg Leu Met Leu Ala
        115                 120                 125

Gly Phe Asn Ile Asp Gly Leu Phe Pro Ile Arg His Ala Thr Ala Ala
    130                 135                 140

Leu Arg Phe Ser Thr Ser Arg Ala Thr Leu Ser Val Val Ser Ala Phe
145                 150                 155                 160

Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
            180                 185                 190

His Glu Thr Val Leu Tyr Ile Phe Cys Leu Phe Leu Tyr Leu Gln Val
        195                 200                 205

Ser Pro Arg Ala Gly Leu Ala Ala Met Val Ala Ile Lys Leu Ser Arg
    210                 215                 220

Gly Leu Leu Phe Ala Leu Val Leu Ala Gln Gly Val Cys
225                 230                 235

<210> SEQ ID NO 328
<211> LENGTH: 240
<212> TYPE: PRT
<213> ORGANISM: Human Pegivirus 2
<220> FEATURE:
<221> NAME/KEY: MISC_FEATURE
<222> LOCATION: (69)..(69)
<223> OTHER INFORMATION: Xaa = any amino acid

<400> SEQUENCE: 328

Arg Pro Gly Arg Val Phe Gly Leu Glu Val Cys Ala Asp Val Ser Trp
1               5                   10                  15

Leu Val Glu Phe Thr Gly Asn Cys Thr Trp Tyr Met Ser Cys Ile Phe
            20                  25                  30

```
Ser Phe Trp Cys Ala Val Phe Ala Phe Thr Ser Pro Leu Gly Arg Gln
         35                  40                  45

Tyr Lys Leu Gln Ile Tyr Arg Tyr Trp Ala Gln Val Tyr Ala Arg Leu
 50                  55                  60

Ile Leu Ala Val Xaa Cys Gly Pro Leu Gly Arg Glu Phe His Phe Arg
 65                  70                  75                  80

Ala Ser Val Gly Val Leu Trp Cys Gly Ala Cys Met Leu Trp Pro Arg
                 85                  90                  95

Glu Cys Ser Glu Ile Ser Leu Ala Leu Ile Leu Cys Ala Leu Thr Val
                100                 105                 110

Asp Thr Ile Asp Thr Trp Leu Val Ala Cys Leu Ser Ala Gly Pro Ser
            115                 120                 125

Ala Arg Ala Leu Ala Thr Leu Ala Asp Asp Met Val Arg Met Gly Asp
130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Leu Gly Gly Cys Leu Glu Pro Val Val Leu Glu Glu Pro
            180                 185                 190

Thr Phe Thr Glu Val Val Asp Asp Thr Met Ser Lys Ile Cys Gly Gln
        195                 200                 205

Leu Leu Gly Gly Lys Pro Val Val Ala Arg Cys Gly Thr Arg Val Leu
    210                 215                 220

Val Gly His Leu Asn Pro Glu Asp Leu Pro Pro Gly Phe Gln Leu Ser
225                 230                 235                 240

<210> SEQ ID NO 329
<211> LENGTH: 628
<212> TYPE: PRT
<213> ORGANISM: Human Pegivirus 2
<220> FEATURE:
<221> NAME/KEY: MISC_FEATURE
<222> LOCATION: (48)..(48)
<223> OTHER INFORMATION: Xaa = any amino acid
<220> FEATURE:
<221> NAME/KEY: MISC_FEATURE
<222> LOCATION: (580)..(580)
<223> OTHER INFORMATION: Xaa = any amino acid

<400> SEQUENCE: 329

Ala Pro Val Val Ile Thr Lys Pro Ser Ile Gly Thr Trp Ser Phe Leu
 1               5                  10                  15

Lys Ala Thr Leu Thr Gly Arg Ala Glu Thr Pro Gly Ser Gly Gln Ile
                 20                  25                  30

Val Val Leu Ser Ser Leu Thr Gly Arg Ser Met Gly Thr Ala Val Xaa
             35                  40                  45

Gly Thr Leu Tyr Ala Thr Gly His Gly Ala Gly Ala Arg Gly Leu Ala
 50                  55                  60

Thr Cys Ala Gly Leu Arg Thr Pro Leu Tyr Thr Ala Leu Ser Asp Asp
 65                  70                  75                  80

Val Val Ala Tyr Ser Cys Leu Pro Gly Met Ser Ser Leu Glu Pro Cys
                 85                  90                  95

Arg Cys Ser Pro Ser Arg Val Trp Val Met Asn Asn Asn Gly Gly Leu
                100                 105                 110

Val Cys Gly Arg Val Glu Asn Glu Asp Val Cys Leu Asp Cys Pro Thr
            115                 120                 125
```

```
His Ile Asp Gln Leu Arg Gly Ala Ser Gly Ser Pro Val Leu Cys Asp
    130                 135                 140

His Gly His Ala Tyr Ala Leu Met Leu Gly Gly Tyr Ser Thr Ser Gly
145                 150                 155                 160

Ile Cys Ala Arg Val Arg Ile Val Arg Pro Trp Gln Asn Ala Tyr Ser
                165                 170                 175

Ser Ser Gly Gly Gln Gly Gly Met Gln Ala Pro Ala Val Thr Pro Thr
                180                 185                 190

Tyr Ser Glu Ile Thr Tyr Tyr Ala Pro Thr Gly Ser Gly Lys Ser Thr
        195                 200                 205

Lys Tyr Pro Val Asp Leu Val Lys Gln Gly His Lys Val Leu Val Ile
    210                 215                 220

Ile Pro Ser Val Ser Val Val Lys Ser Met Ala Pro Tyr Ile Lys Glu
225                 230                 235                 240

Thr Tyr Lys Ile Arg Pro Glu Ile Arg Ala Gly Thr Gly Pro Asp Gly
                245                 250                 255

Val Thr Val Ile Thr Gly Glu Asn Leu Ala Tyr Met Thr Tyr Gly Arg
                260                 265                 270

Phe Leu Val Asp Pro Glu Thr Asn Leu Arg Gly Tyr Ala Val Val Ile
    275                 280                 285

Cys Asp Glu Cys His Asp Thr Ser Ser Thr Thr Leu Leu Gly Ile Gly
    290                 295                 300

Ala Val Arg Met Tyr Ala Glu Lys Ala Gly Val Lys Thr Val Val Phe
305                 310                 315                 320

Ala Thr Ala Thr Pro Ala Gly Ile Gln Val Gln Pro His Pro Asn Ile
                325                 330                 335

Asp Glu Tyr Leu Leu Thr Asp Thr Gly Asp Val Asp Phe Tyr Gly Ala
                340                 345                 350

Lys Ile Lys Leu Asp Asn Ile Arg Thr Gly Arg His Val Ile Phe Cys
            355                 360                 365

His Ser Lys Ala Arg Cys Ala Glu Leu Thr Gln Gln Leu Ser Gly Leu
    370                 375                 380

Gly Val Arg Ala Val Ser Phe Trp Arg Gly Cys Asp Ile Lys Thr Ile
385                 390                 395                 400

Pro Ala Ser Asp Ser Ile Val Val Ala Thr Asp Ala Leu Ser Thr
                405                 410                 415

Gly Tyr Thr Gly Asn Phe Asp Ser Val Ile Asp Cys Gly Cys Cys Val
                420                 425                 430

Glu Gln Thr Val Thr Ile Asp Met Asp Pro Thr Phe Ser Ile Ser Ala
            435                 440                 445

Arg Val Val Pro Cys Thr Ala Ala Leu Arg Met Gln Arg Arg Gly Arg
    450                 455                 460

Thr Gly Arg Gly Arg Arg Gly Ala Tyr Tyr Thr Thr Thr Pro Gly Ala
465                 470                 475                 480

Ala Pro Cys Val Ser Val Pro Asp Ala Asn Val Trp Gln Ala Val Glu
                485                 490                 495

Ser Ala Met Val Phe Tyr Asp Trp Asn Ala Ala Arg Ile Gln Gln Cys
                500                 505                 510

Leu Ala Ala Tyr His Asp Leu Gly Cys Thr Pro Arg Leu Ser Cys Asp
            515                 520                 525

Pro Cys Thr Pro Val Arg Val Met Asp Thr Leu Arg Ala Tyr Leu Arg
    530                 535                 540

Arg Pro Glu Val Thr Thr Ala Ala Leu Ala Gly Glu Gln Trp Pro Leu
```

```
                545                 550                 555                 560
Leu Tyr Gly Val Gln Leu Cys Ile Cys Lys Glu Thr Glu Ala His Gly
                    565                 570                 575

Pro Asp Asp Xaa Ile Lys Trp Lys Cys Leu Leu Asn Asn Ser Asn Lys
                580                 585                 590

Thr Pro Leu Leu Tyr Ala Leu Asp Asn Pro Thr Leu Glu Phe Thr Thr
                595                 600                 605

Gln His Asp Leu Thr Arg Arg Ile Ala Gly Ala Leu Ser Ser Thr Val
            610                 615                 620

Phe Val Glu Thr
625

<210> SEQ ID NO 330
<211> LENGTH: 41
<212> TYPE: PRT
<213> ORGANISM: Human Pegivirus 2

<400> SEQUENCE: 330

Gly Tyr Gly Pro Ile Leu Leu Ala Gly Ala Ala Leu Ala Ala Ser Phe
1               5                   10                  15

Ala Phe Ala Gly Ala Thr Gly Ala Leu Val Pro Ser Ala Val Trp Ser
            20                  25                  30

Val Asp Asn Gly Val Ala Gly Val Thr
        35                  40

<210> SEQ ID NO 331
<211> LENGTH: 262
<212> TYPE: PRT
<213> ORGANISM: Human Pegivirus 2

<400> SEQUENCE: 331

Arg Pro Asp Ala Thr Asp Glu Thr Ala Ala Tyr Ala Gln Arg Leu Tyr
1               5                   10                  15

Gln Ala Cys Ala Asp Ser Gly Leu Leu Ala Ser Leu Gln Gly Thr Ala
            20                  25                  30

Ser Ala Ala Leu Ser Lys Leu Ala Asp Ala Ser Arg Gly Ala Ser Gln
        35                  40                  45

Tyr Leu Ala Ser Ala Pro Pro Ser Pro Ala Pro Leu Val Gln Val Leu
    50                  55                  60

Gln Phe Leu Glu Thr Asn Phe Ser Ser Ile Ala Ser Phe Gly Leu Leu
65                  70                  75                  80

Cys Ala Gly Cys Gln Ala Gly Glu Cys Phe Thr Ala Leu Ala Gly Leu
                85                  90                  95

Val Ser Gly Ala Thr Ala Leu Gly Gly Ala His Lys Trp Leu Leu
            100                 105                 110

Ala Ile Ala Gly Thr Trp Leu Val Ser Leu Gln Thr Gly Ala Arg Gly
        115                 120                 125

Gly Met Val Ala Gly Leu Ser Val Leu Ala Gly Cys Cys Ile Gly Ser
    130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Leu Asp Leu Leu Pro Ala Phe Phe Ser Pro Gly
            180                 185                 190

Ala Gly Val Ala Gly Ile Val Leu Val Phe Ile Leu Ser Asn Ser Ser
```

-continued

```
            195                 200                 205
Val Thr Thr Trp Ala Asn Arg Leu Leu Ser Met Cys Ala Lys Gln Thr
210                 215                 220

Ile Cys Asp Asn Tyr Phe Leu Ser Asp Lys Phe Gly Gln Gln Leu Ser
225                 230                 235                 240

Lys Leu Ser Leu Trp Arg Thr Leu Tyr Arg Trp Ala Glu Ala Arg Glu
                245                 250                 255

Gly Tyr Thr Gln Cys Gly
            260

<210> SEQ ID NO 332
<211> LENGTH: 458
<212> TYPE: PRT
<213> ORGANISM: Human Pegivirus 2

<400> SEQUENCE: 332

Val Val Gly Gly Ile Trp Ser Phe Val Leu Cys Ile Leu Arg Ala Val
1               5                   10                  15

Trp Asp Trp Ala Ala Lys His Val Pro Arg Phe Arg Val Pro Met Ile
                20                  25                  30

Gly Cys Ser Pro Ala Trp Cys Gly Arg Trp Leu Gly Thr Gly Thr Leu
            35                  40                  45

Leu Thr Thr Cys Gly Cys Gly Glu Arg Val Ser Leu Gln Cys Leu Cys
        50                  55                  60

Ser Thr Ser Asp Pro Leu Leu Arg Val Gly Arg Trp Cys Arg Cys Ser
65                  70                  75                  80

Trp Ser Val Gly Phe Pro Phe Asn Pro Thr Thr Thr Ala Thr Gly Thr
                85                  90                  95

Leu Arg Pro Asp Ile Ser Asp Ala Thr Arg Leu Gly Phe Arg Tyr Gly
            100                 105                 110

Ile Ala Glu Ile Val Glu Leu Glu Leu Arg Glu His Lys Trp His Val
        115                 120                 125

Cys Ala Ala Ser Cys Cys Leu Asp Arg Ala Ser Val Ala Ser Ala Val
130                 135                 140

Lys Ala Pro Pro Val Thr Ala Asn Gly Ile Pro Ile Ser Thr Phe Ser
145                 150                 155                 160

Pro Pro Gln Thr Tyr Ser Leu Ser Leu Cys Ser Phe Asp Ser Val Cys
                165                 170                 175

Met Ser Thr Asn Leu Cys Asn Pro Ala Lys Thr Leu Ser Val Cys Ser
            180                 185                 190

Gln Glu Ala Val Glu Leu Leu Glu Thr Val Asp Thr Ala Gln Val
        195                 200                 205

Met Met Cys Gln Asn Leu Glu Ala Arg Arg Ala Glu Tyr Asp Ala
210                 215                 220

Trp Gln Val Arg His Ala Val Gly Asp Glu Tyr Thr Arg Leu Ala Asp
225                 230                 235                 240

Glu Asp Val Asp Thr Thr Ser Val Lys Pro Ala Ala Arg Ala
                245                 250                 255

Ala Val Asp Ser Ser Thr Leu Glu Asp Val Ser Val Leu Thr Val Leu
            260                 265                 270

Arg Glu Leu Gly Asp Gln Cys Gln Asn Ala Ile Lys Phe Val Val Gln
        275                 280                 285

Ala Ala Ser Arg Phe Val Pro Pro Val Pro Arg Pro Arg Thr Arg Val
            290                 295                 300
```

Ser Gly Val Leu Glu Arg Val Arg Met Cys Met Arg Thr Pro Pro Ile
305                 310                 315                 320

Lys Phe Glu Ala Thr Ala Val Pro Ile His Asn Ile Ile Pro Glu Glu
            325                 330                 335

Cys His Ile Val Leu Arg Cys Thr Gly Cys Asn Asp Gln Ala Leu Thr
            340                 345                 350

Val Pro Tyr Gly Thr Cys Thr Gln Ser Leu Ile Arg His Leu Thr Asn
            355                 360                 365

Lys His Asn His Tyr Ile Pro Lys Gln Lys Ile Glu Glu Asp Thr Glu
370                 375                 380

Val Thr Val Ile Cys Ala Val Pro Thr Lys Arg Ala Ser Lys Leu Ile
385                 390                 395                 400

Thr Phe Arg Ala Gly Asp Arg Ser Val Ser Cys Cys His Pro Leu Gln
            405                 410                 415

Thr Pro Ile Arg Ala Leu Leu Leu Lys Tyr Gly Leu Pro Ile Gly Thr
            420                 425                 430

Trp Ser Asp Cys Asn Gly Pro Leu Gly Asp Asp Ala Arg Val Cys Asp
            435                 440                 445

Val Asn Gly Val Thr Thr Tyr Glu Pro Cys
450                 455

<210> SEQ ID NO 333
<211> LENGTH: 567
<212> TYPE: PRT
<213> ORGANISM: Human Pegivirus 2

<400> SEQUENCE: 333

Met Gln Ser Tyr Ser Trp Phe Arg Pro Ile Val Ala Pro Thr Thr Pro
1               5                   10                  15

Pro Leu Pro Val Thr Arg Ser Val Ala Gly Ile Leu Arg Ala Asp Thr
            20                  25                  30

Ser Arg Val Tyr Thr Thr Thr Ala Val Asp Val Ser Glu Arg Gln Ser
            35                  40                  45

Lys Val Thr Ile Asp Gln Thr Ser Ala Lys Val Asp Gln Trp Phe Arg
50                  55                  60

Asp Thr Tyr Asn Cys Cys Leu Ala Lys Ala Lys Thr Phe Arg Gln Ser
65                  70                  75                  80

Gly Met Ser Tyr Glu Asp Ala Val Ser Lys Met Arg Ala Asn Thr Thr
            85                  90                  95

Arg Asp His Asn Thr Gly Ile Thr Tyr Ser Asp Leu Val Ser Gly Arg
            100                 105                 110

Ala Lys Pro Ala Val Gln Lys Ile Val Asp Gln Met Arg Ala Gly Val
            115                 120                 125

Tyr Asp Ala Pro Met Arg Ile Ile Pro Lys Pro Glu Val Phe Pro Arg
130                 135                 140

Asp Lys Ser Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
            165                 170                 175

Thr Lys His Val Leu Gly Asp Ala Tyr Gly Phe Ala Thr Pro Pro His
            180                 185                 190

Glu Arg Ala Arg Leu Leu Glu Gln Trp Trp Asn Arg Ala Thr Glu Pro
            195                 200                 205

Gln Ala Ile Ala Val Asp Ala Ile Cys Phe Asp Ser Thr Ile Thr Ala
210                 215                 220

```
Glu Asp Met Asp Arg Glu Ala Asn Ile Leu Ala Ala His Ser Asp
225                 230                 235                 240
Pro Glu Gly Val His Gly Leu Tyr Asn Tyr Tyr Lys Arg Ser Pro Met
                245                 250                 255
Cys Asp Ile Thr Gly Asn Val Val Gly Val Arg Cys Cys Arg Ala Ser
            260                 265                 270
Gly Thr Leu Thr Thr Ser Ser Gly Asn Thr Leu Thr Cys Tyr Leu Lys
        275                 280                 285
Val Arg Ala Ala Cys Thr Arg Ala Gly Ile Lys Pro Ile Gly Leu Leu
    290                 295                 300
Ile His Gly Asp Asp Thr Leu Ile Ile Thr Glu Arg Cys Ala Gln Glu
305                 310                 315                 320
Thr Leu Asp Glu Phe Ser Asn Ala Leu Asn Asp Tyr Gly Phe Pro His
                325                 330                 335
Thr Phe Gln Ala Ser Gly Asp Leu Ser Ser Val Glu Cys Cys Ser Ala
            340                 345                 350
Arg Val Asp Ser Val Cys Leu Arg Gly Gly Met Arg Met Leu Val
        355                 360                 365
Pro Gln Ala Arg Arg Ala Ile Ala Arg Val Leu Gly Glu Lys Gly Asp
    370                 375                 380
Pro Leu Gly Val Ile Ser Ser Tyr Ile Val Met Tyr Pro Thr Ala Ala
385                 390                 395                 400
Val Thr Val Tyr Val Leu Leu Pro Leu Leu Cys Met Leu Ile Arg Asn
                405                 410                 415
Glu Pro Ser Gln Thr Gly Thr Leu Val Thr Leu Thr Val His Gly Asn
            420                 425                 430
Ser Val Ser Val Pro Val Trp Leu Leu Pro Thr Ile Ile Val Asn Leu
        435                 440                 445
His Gly Arg Asp Ala Leu Gln Val Val Arg His Thr Ala Ala Ser Met
    450                 455                 460
Ala Glu Leu Ser Ser Ala Leu Ala Phe Phe Gly Met Arg Gly Leu Asn
465                 470                 475                 480
Cys Trp Arg Arg Arg Arg Ala Ile Arg Thr Asp Met Ile Lys Leu
                485                 490                 495
Gly Gly Trp Asn Ala Asn Phe Ala Gln Met Leu Leu Trp Ser Pro Glu
            500                 505                 510
Val Arg Thr Pro Gln Pro Glu Pro Arg Gly Val Cys Leu Leu Pro Pro
        515                 520                 525
Glu Leu Trp Glu Arg Pro Tyr Glu Asn Leu His Leu Ser Thr Ile Asp
    530                 535                 540
Arg Asn Arg Gly Ala Ser Arg Leu Arg Phe Trp Leu Val Ala Ser Ala
545                 550                 555                 560
Ile Leu Ala Leu Leu Cys Leu
                565

<210> SEQ ID NO 334
<211> LENGTH: 79
<212> TYPE: PRT
<213> ORGANISM: Human Pegivirus 2

<400> SEQUENCE: 334

Met Gly Cys Ser Thr Asp Gln Thr Ile Cys Ser Pro Val Val Gly Ala
1               5                   10                  15

Asp Tyr Asn Thr Ser Ser Gly Cys Arg Ala Leu Asn Gly Ser Asp His
```

```
                 20                  25                  30
Cys Gly Gly Ser Ser Cys Arg Ser Pro Ser Arg Val Gln Ala Ala Arg
             35                  40                  45

Arg Val Leu Gln Leu Cys Ala Phe Leu Ala Leu Ile Gly Ser Gly Met
         50                  55                  60

Cys Ser Ile Arg Ser Lys Thr Glu Gly Arg Ile Glu Ser Gly Gln
 65                  70                  75

<210> SEQ ID NO 335
<211> LENGTH: 191
<212> TYPE: PRT
<213> ORGANISM: Human Pegivirus 2

<400> SEQUENCE: 335

Ile Leu Gln Ser Gln Arg Ala Cys Trp Thr Gly Glu Gly Phe Ala Phe
 1               5                  10                  15

Phe Ser Asn Cys Cys Asn Gln Ser Asp Ile Met Trp Cys Leu His Arg
             20                  25                  30

Trp Cys Val Thr Arg Pro Gly Cys Leu Val Cys Thr Gly Asn Ala Thr
         35                  40                  45

His Pro Val Cys Trp Asp Tyr Leu Gly Ser Gly Val Ser Arg Arg Pro
     50                  55                  60

Ala Arg Arg Leu Gly Glu Gly Ala Glu Met Leu Leu Arg Leu Ile Gly
 65                  70                  75                  80

Ile Ala Gly Trp Leu Gly Leu Leu Ala Glu Ala Leu Gly Met Ser Glu
                 85                  90                  95

Met Tyr Ala Ala Ile Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Ile Leu Gln Leu Pro Gly Leu Leu Trp Gln Met Phe Val Asn Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
            180                 185                 190

<210> SEQ ID NO 336
<211> LENGTH: 354
<212> TYPE: PRT
<213> ORGANISM: Human Pegivirus 2
<220> FEATURE:
<221> NAME/KEY: MISC_FEATURE
<222> LOCATION: (111)..(111)
<223> OTHER INFORMATION: Xaa = any amino acid
<220> FEATURE:
<221> NAME/KEY: MISC_FEATURE
<222> LOCATION: (279)..(279)
<223> OTHER INFORMATION: Xaa = any amino acid

<400> SEQUENCE: 336

Tyr Lys His Pro Ser Glu Ser Tyr Leu Lys Cys Thr Ile Thr Asn
 1               5                  10                  15

Ala Ser Ala Ala Met Asn Cys Asp Cys Pro Phe Gly Thr Phe Thr Arg
             20                  25                  30

Asn Thr Glu Ser Arg Phe Ser Ile Pro Arg Phe Cys Pro Val Lys Ile
         35                  40                  45
```

Glu Ser Ser Thr Phe Ile Cys Ser Trp Gly Ser Trp Trp Phe Ala
50              55              60

Glu Asn Ile Thr Arg Pro Tyr Ser Asp Val Gly Met Pro Pro Ala Pro
65              70              75              80

Ile Ser Ala Leu Cys Tyr Ile Tyr Ser Asn Asn Asp Pro Pro Trp
            85              90              95

Tyr Tyr Asn Thr Thr Ile Ile Pro Gln Asn Cys Arg Asn Ser Xaa Val
            100             105             110

Asp Pro Thr Thr Ala Pro Cys Arg Asp Lys Trp Gly Asn Ala Thr Ala
            115             120             125

Cys Ile Leu Asp Arg Arg Ser Arg Phe Cys Gly Asp Cys Tyr Gly Gly
130             135             140

Cys Phe Tyr Thr Asn Gly Ser His Asp Arg Ser Trp Asp Arg Cys Gly
145             150             155             160

Ile Gly Tyr Arg Asp Gly Leu Ile Glu Phe Val Gln Leu Gly Gln Ile
            165             170             175

Arg Pro Asn Ile Ser Asn Thr Thr Ile Glu Leu Leu Ala Gly Ala Ser
            180             185             190

Leu Val Ile Ala Ser Gly Leu Arg Pro Gly Tyr Gly Cys Ser Arg Ala
195             200             205

His Gly Val Val His Cys Tyr Arg Cys Pro Ser Tyr Arg Asp Leu Glu
210             215             220

Gln Phe Gly Pro Gly Leu Gly Lys Trp Val Pro Leu Pro Gly Glu Pro
225             230             235             240

Val Pro Glu Leu Cys Ile Asn Pro Gln Trp Ala Arg Gly Phe Arg
            245             250             255

Val Ser Asn Asn Pro Leu Ser Leu Ile Gln Thr Phe Val Glu Asp Ile
            260             265             270

Phe Leu Ala Pro Phe Cys Xaa Pro Thr Pro Gly Arg Val Arg Val Cys
            275             280             285

Asn Asn Thr Ala Phe Tyr Pro Arg Gly Gly Gly Phe Val Gln Leu Ile
            290             295             300

Gly Asp Val Gln Val Leu Thr Pro Asn Thr Ala Ser Leu His Ser Leu
305             310             315             320

Leu Thr Leu Ile Ser Leu Ile Leu Leu Val Cys Val Val Ser Gly Ala
            325             330             335

Arg Phe Val Pro Leu Ile Ile Ile Phe Phe Trp Ser Val Arg His Val
            340             345             350

Tyr Ala

<210> SEQ ID NO 337
<211> LENGTH: 237
<212> TYPE: PRT
<213> ORGANISM: Human Pegivirus 2
<220> FEATURE:
<221> NAME/KEY: MISC_FEATURE
<222> LOCATION: (59)..(60)
<223> OTHER INFORMATION: Xaa = any amino acid

<400> SEQUENCE: 337

Ser Cys Tyr Leu Ser Cys Asp Trp Ala Val Cys Asn Asp Ala Phe Cys
1               5               10              15

Phe Thr Ser Gly Thr Cys Ala Thr Phe Asn Asp Val Leu Cys Leu Pro
            20              25              30

Val Ala Thr Arg Ile Ser Ser Cys Gly His Ala Val Pro Pro Pro Asp

```
                35                  40                  45
Arg Gly Trp Glu Val Pro Ala Ala Leu Ser Xaa Xaa Ile Ser Arg Thr
 50                  55                  60

Thr Gly Leu Thr Phe Asp Val Phe Ser Phe Ile Gln Tyr Leu Pro Thr
65                  70                  75                  80

Val Pro Gly Asn Asn Ser Asp Ile Ile Tyr Cys Gly Glu Pro Thr Phe
                85                  90                  95

Phe Gly Asp Leu Thr Gly Ile Tyr Trp Pro Tyr Phe Leu Pro Gly Val
            100                 105                 110

Leu Leu Leu Tyr Leu Thr Pro Phe Leu Gly Leu Arg Leu Met Leu Ala
            115                 120                 125

Gly Phe Asn Ile Asp Gly Leu Phe Pro Ile Arg His Ala Thr Ala Ala
            130                 135                 140

Leu Arg Phe Ser Thr Ser Arg Val Thr Leu Ser Val Val Ala Ala Phe
145                 150                 155                 160

Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
            180                 185                 190

His Glu Thr Ile Leu Tyr Ile Val Cys Leu Met Leu Tyr Leu Gln Val
            195                 200                 205

Ser Pro Arg Ala Gly Leu Ala Ala Met Val Ala Ile Lys Leu Ser Arg
210                 215                 220

Gly Leu Leu Phe Ala Val Val Leu Ala His Gly Val Cys
225                 230                 235

<210> SEQ ID NO 338
<211> LENGTH: 240
<212> TYPE: PRT
<213> ORGANISM: Human Pegivirus 2
<220> FEATURE:
<221> NAME/KEY: MISC_FEATURE
<222> LOCATION: (197)..(197)
<223> OTHER INFORMATION: Xaa = any amino acid
<220> FEATURE:
<221> NAME/KEY: MISC_FEATURE
<222> LOCATION: (202)..(203)
<223> OTHER INFORMATION: Xaa = any amino acid

<400> SEQUENCE: 338

Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
                20                  25                  30

Ser Phe Trp Cys Ala Val Phe Ala Phe Thr Ser Pro Leu Gly Arg Gln
            35                  40                  45

Tyr Lys Leu Gln Ile Tyr Arg Tyr Trp Ala Gln Val Tyr Ala Arg Leu
 50                  55                  60

Ile Leu Ala Val Gly Cys Gly Pro Leu Gly Arg Glu Phe His Phe Arg
65                  70                  75                  80

Ala Ser Val Gly Val Leu Trp Cys Gly Ala Cys Met Leu Trp Pro Arg
                85                  90                  95

Glu Cys Ser Glu Ile Ser Leu Val Phe Ile Leu Cys Ala Leu Thr Val
            100                 105                 110

Asp Thr Ile Asp Thr Trp Leu Val Ala Cys Leu Ser Ala Gly Pro Ser
            115                 120                 125

Ala Arg Thr Leu Ala Thr Leu Ala Asp Asp Met Ala Arg Met Gly Asp
```

```
                130             135             140
Asn Arg Ala Leu Arg Ala Val Leu Cys Cys Phe Gly Ser Arg Gly Thr
145                 150                 155                 160

Tyr Ile Tyr Asn His Met Gly Gln Val Ser Glu Arg Val Ala Arg Ala
                165                 170                 175

Val Arg Asp Leu Gly Gly Cys Leu Glu Pro Val Val Leu Glu Glu Pro
            180                 185                 190

Thr Phe Thr Glu Xaa Val Asp Asp Thr Xaa Xaa Leu Val Cys Gly Gln
                195                 200                 205

Leu Leu Gly Gly Lys Pro Val Val Ala Arg Cys Gly Thr Arg Val Leu
            210                 215                 220

Val Gly His Leu Asn Pro Glu Asp Leu Pro Pro Gly Phe Gln Leu Ser
225                 230                 235                 240

<210> SEQ ID NO 339
<211> LENGTH: 628
<212> TYPE: PRT
<213> ORGANISM: Human Pegivirus 2
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (49)..(49)
<223> OTHER INFORMATION: Xaa = any amino acid
<220> FEATURE:
<221> NAME/KEY: MISC_FEATURE
<222> LOCATION: (554)..(554)
<223> OTHER INFORMATION: Xaa = any amino acid

<400> SEQUENCE: 339

Ala Pro Val Val Ile Thr Lys Pro Ser Ile Gly Thr Trp Ser Phe Leu
1               5                   10                  15

Lys Ala Thr Leu Thr Gly Arg Xaa Glu Thr Pro Gly Ser Gly Gln Ile
                20                  25                  30

Val Val Leu Ser Ser Leu Thr Gly Arg Ser Met Gly Thr Ala Val Asn
            35                  40                  45

Xaa Thr Leu Tyr Ala Thr Gly His Gly Ala Gly Arg Gly Leu Ala
    50                  55                  60

Thr Cys Ala Gly Leu Arg Thr Pro Leu Tyr Thr Ala Leu Ser Asp Asp
65                  70                  75                  80

Val Val Ala Tyr Ser Cys Leu Pro Gly Met Ser Ser Leu Glu Pro Cys
                85                  90                  95

Arg Cys Thr Pro Ser Arg Val Trp Val Met Asn Asn Asn Gly Gly Leu
                100                 105                 110

Val Cys Gly Arg Val Glu Lys Asp Asp Val Cys Leu Asp Cys Pro Thr
            115                 120                 125

His Ile Asp Gln Leu Arg Gly Ala Ser Gly Ser Pro Val Leu Cys Asp
130                 135                 140

His Gly His Ala Tyr Ala Leu Met Leu Gly Gly Tyr Ser Thr Ser Gly
145                 150                 155                 160

Ile Cys Ala Arg Val Arg Ile Val Gln Pro Trp Gln Asn Ala Tyr Ser
                165                 170                 175

Ser Ser Gly Gly Gln Gly Gly Met Gln Ala Pro Ala Val Thr Pro Thr
            180                 185                 190

Tyr Ser Glu Ile Thr Tyr Tyr Ala Pro Thr Gly Ser Gly Lys Ser Thr
                195                 200                 205
```

```
Lys Tyr Pro Val Asp Leu Val Lys Gln Gly His Lys Val Leu Val Ile
    210                 215                 220
Ile Pro Ser Val Thr Val Val Lys Ser Met Ala Asn Tyr Ile Lys Glu
225                 230                 235                 240
Thr Tyr Lys Ile Arg Pro Glu Ile Arg Ala Gly Thr Gly Pro Asp Gly
                245                 250                 255
Val Thr Val Ile Thr Gly Glu Ser Leu Ala Tyr Met Thr Tyr Gly Arg
                260                 265                 270
Phe Leu Val Asp Pro Glu Thr Asn Leu Arg Gly Tyr Ala Val Val Ile
            275                 280                 285
Cys Asp Glu Cys His Asp Thr Ser Ser Thr Thr Leu Leu Gly Ile Gly
290                 295                 300
Ala Val Arg Met Phe Ala Glu Lys Ala Gly Val Arg Thr Val Val Phe
305                 310                 315                 320
Ala Thr Ala Thr Pro Ala Gly Ile Gln Val Gln Pro His Pro Asn Ile
                325                 330                 335
Asp Glu Tyr Leu Leu Thr Asp Thr Gly Asp Val Asp Phe Tyr Gly Ala
            340                 345                 350
Lys Ile Lys Leu Asp Asn Ile Arg Thr Gly Arg His Val Ile Phe Cys
355                 360                 365
His Ser Lys Ala Arg Cys Ala Glu Leu Thr Gln Gln Leu Ser Gly Leu
    370                 375                 380
Gly Val Arg Ala Val Ser Phe Trp Arg Gly Cys Asp Ile Lys Thr Ile
385                 390                 395                 400
Pro Ala Ser Asp Ser Ile Val Val Ala Thr Asp Ala Leu Ser Thr
                405                 410                 415
Gly Tyr Thr Gly Asn Phe Asp Ser Val Ile Asp Cys Gly Cys Cys Val
                420                 425                 430
Glu Gln Thr Val Thr Ile Asp Met Asp Pro Thr Phe Ser Ile Ser Ala
            435                 440                 445
Arg Val Val Pro Cys Thr Ala Ala Leu Arg Met Gln Arg Arg Gly Arg
    450                 455                 460
Thr Gly Arg Gly Arg Arg Gly Ala Tyr Tyr Thr Thr Thr Pro Gly Ala
465                 470                 475                 480
Ala Pro Cys Val Ser Val Pro Asp Ala Asn Val Trp Gln Ala Val Glu
                485                 490                 495
Ser Ala Met Val Phe Tyr Asp Trp Gly Ala Ala Arg Ile Gln Gln Cys
            500                 505                 510
Leu Ala Ala Tyr His Asp Leu Gly Cys Thr Pro Arg Ile Ser Cys Asp
            515                 520                 525
Pro His Thr Pro Val Arg Val Met Asp Thr Leu Arg Ala Tyr Leu Arg
    530                 535                 540
Arg Pro Glu Val Thr Thr Ala Ala Leu Xaa Gly Glu Gln Trp Pro Leu
545                 550                 555                 560
Leu Tyr Gly Val Gln Leu Cys Ile Cys Lys Glu Thr Glu Ala His Gly
                565                 570                 575
Pro Asp Asp Ser Ile Lys Trp Lys Cys Leu Leu Asn Asn Ser Asn Lys
            580                 585                 590
Thr Pro Leu Leu Tyr Ala Leu Asp Asn Pro Thr Leu Asp Phe Thr Thr
            595                 600                 605
Gln His Asp Leu Thr Arg Arg Ile Ala Gly Ala Leu Ser Ser Thr Val
    610                 615                 620

Phe Val Glu Thr
```

<210> SEQ ID NO 340
<211> LENGTH: 41
<212> TYPE: PRT
<213> ORGANISM: Human Pegivirus 2

<400> SEQUENCE: 340

Gly Tyr Gly Pro Ile Leu Leu Ala Gly Ala Ala Leu Ala Ala Ser Phe
1               5                   10                  15

Ala Phe Ala Gly Ala Thr Gly Ala Leu Val Pro Ser Ala Val Trp Ser
                20                  25                  30

Val Asp Asn Gly Leu Ala Gly Val Thr
                35                  40

<210> SEQ ID NO 341
<211> LENGTH: 262
<212> TYPE: PRT
<213> ORGANISM: Human Pegivirus 2
<220> FEATURE:
<221> NAME/KEY: MISC_FEATURE
<222> LOCATION: (191)..(193)
<223> OTHER INFORMATION: Xaa = any amino acid

<400> SEQUENCE: 341

Arg Pro Asp Ala Thr Asp Glu Thr Ala Ala Tyr Ala Gln Arg Leu Tyr
1               5                   10                  15

Gln Ala Cys Ala Asp Ser Gly Leu Phe Ala Ser Leu Gln Gly Thr Ala
                20                  25                  30

Ser Ala Ala Leu Gly Lys Leu Ala Asp Ala Ser Arg Gly Ala Ser Gln
                35                  40                  45

Tyr Leu Ala Ala Pro Pro Ser Pro Ala Pro Leu Val Gln Val Leu
    50                  55                  60

His Phe Leu Glu Thr Asn Phe Ser Ser Ile Ala Ser Phe Gly Leu Leu
65                  70                  75                  80

Cys Ala Gly Cys Gln Ala Gly Glu Cys Phe Thr Ala Leu Ala Gly Leu
                85                  90                  95

Val Ser Gly Ala Thr Ala Gly Leu Gly Gly Ala His Lys Trp Leu Leu
                100                 105                 110

Ala Ile Ala Gly Thr Trp Leu Val Ser Leu Gln Thr Gly Pro Arg Gly
                115                 120                 125

Gly Met Val Ala Gly Leu Ser Val Leu Ala Gly Cys Cys Ile Gly Ser
130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Val Asp Leu Leu Pro Ala Ile Phe Ser Xaa Xaa
                180                 185                 190

Xaa Gly Ile Ala Gly Ile Val Leu Val Phe Ile Leu Ser Asn Ser Ser
                195                 200                 205

Val Thr Thr Trp Ala Asn Arg Leu Leu Ser Met Cys Ala Lys Gln Thr
                210                 215                 220

Ile Cys Asp Asn Tyr Phe Leu Thr Glu Lys Phe Gly His Gln Leu Ser
225                 230                 235                 240

Lys Leu Ser Leu Trp Arg Ala Val Tyr His Trp Ala Gln Ala Arg Glu
                245                 250                 255

Gly Tyr Thr Gln Cys Gly
          260

<210> SEQ ID NO 342
<211> LENGTH: 458
<212> TYPE: PRT
<213> ORGANISM: Human Pegivirus 2

<400> SEQUENCE: 342

Val Val Ser Gly Ile Trp Ser Phe Val Leu Cys Ile Leu Arg Ala Val
1               5                   10                  15

Trp Asp Trp Ala Ala Lys His Val Pro Arg Phe Arg Val Pro Met Ile
            20                  25                  30

Gly Cys Ser Pro Ala Trp Cys Gly Arg Trp Leu Gly Thr Gly Thr Leu
        35                  40                  45

Leu Thr Thr Cys Gly Cys Gly Glu Arg Val Ser Leu Gln Cys Leu Cys
    50                  55                  60

Ser Thr Ser Asp Pro Thr Leu Ser Val Gly Arg Trp Cys Arg Cys Ser
65                  70                  75                  80

Trp Ser Val Gly Phe Pro Phe Asn Pro Thr Thr Thr Ala Thr Gly Asn
                85                  90                  95

Leu Arg Pro Asp Ile Ser Asp Ala Thr Lys Leu Gly Phe Arg Tyr Gly
            100                 105                 110

Ile Ala Glu Ile Val Glu Leu Glu Arg Arg Gly Asp Lys Trp His Val
        115                 120                 125

Cys Ala Ala Ser Cys Cys Leu Asp Arg Ala Ser Val Ala Ser Ala Val
    130                 135                 140

Lys Ala Pro Pro Val Thr Ala Asn Gly Ile Pro Ile Gly Thr Phe Ser
145                 150                 155                 160

Pro Pro Gln Thr Tyr Ser Leu Ser Leu Cys Ser Phe Asp Ser Val Cys
                165                 170                 175

Met Ser Ser Asn Leu Cys Asn Pro Ala Lys Thr Leu Ser Val Cys Ser
            180                 185                 190

Gln Glu Ala Val Glu Leu Leu Glu Glu Thr Val Asp Lys Ala Gln Val
        195                 200                 205

Met Met Cys Gln Asn Leu Glu Ala Arg Arg Arg Ala Glu Tyr Asp Ala
    210                 215                 220

Trp Gln Val Arg Gln Ala Val Gly Asp Glu Tyr Thr Arg Leu Ala Asp
225                 230                 235                 240

Glu Asp Val Asp Ala Thr Thr Ser Val Lys Pro Pro Val Ala Arg Ala
                245                 250                 255

Ala Val Gly Ser Ser Thr Leu Asp Asp Val Ser Val Leu Thr Val Leu
            260                 265                 270

Arg Glu Leu Gly Asp Gln Cys Gln Asn Ala Ile Lys Phe Val Val Gln
        275                 280                 285

Ala Ala Ser Arg Phe Val Pro Pro Val Pro Lys Pro Arg Thr Arg Val
    290                 295                 300

Ser Gly Val Leu Glu Arg Val Arg Met Cys Met Arg Thr Pro Pro Ile
305                 310                 315                 320

Lys Phe Glu Ala Thr Ala Val Pro Ile His Asn Ile Ile Pro Glu Val
                325                 330                 335

Cys His Ile Val Leu Arg Cys Thr Gly Cys Asn Asp Gln Ala Leu Thr
            340                 345                 350

Val Pro Tyr Gly Thr Cys Thr Gln Thr Leu Ile Lys His Leu Thr Asn
        355                 360                 365

```
Lys His Ser His Tyr Ile Pro Lys Gln Lys Ile Glu Glu Asp Thr Glu
    370                 375                 380

Val Thr Val Ile Cys Ala Val Pro Thr Thr Arg Ala Ser Lys Leu Ile
385                 390                 395                 400

Thr Phe Arg Ala Gly Asp Arg Ser Val Ser Cys Cys His Pro Leu Gln
                405                 410                 415

Thr Pro Val Arg Thr Leu Leu Lys Tyr Gly Leu Pro Ile Gly Lys
            420                 425                 430

Trp Ser Asp Cys Asn Gly Pro Leu Gly Asp Asp Ala Arg Val Cys Asp
            435                 440                 445

Ile Asn Gly Val Thr Thr Tyr Glu Pro Cys
        450                 455

<210> SEQ ID NO 343
<211> LENGTH: 567
<212> TYPE: PRT
<213> ORGANISM: Human Pegivirus 2
<220> FEATURE:
<221> NAME/KEY: MISC_FEATURE
<222> LOCATION: (89)..(89)
<223> OTHER INFORMATION: Xaa = any amino acid
<220> FEATURE:
<221> NAME/KEY: MISC_FEATURE
<222> LOCATION: (495)..(495)
<223> OTHER INFORMATION: Xaa = any amino acid
<220> FEATURE:
<221> NAME/KEY: MISC_FEATURE
<222> LOCATION: (539)..(539)
<223> OTHER INFORMATION: Xaa = any amino acid

<400> SEQUENCE: 343

Met Gln Ser Tyr Ser Trp Phe Arg Pro Ile Val Ala Pro Thr Thr Pro
1               5                   10                  15

Pro Leu Pro Ala Thr Arg Ser Val Ala Gly Ile Leu Arg Ala Asp Thr
            20                  25                  30

Ser Arg Val Tyr Thr Thr Thr Ala Val Asp Val Ser Glu Arg Gln Ala
        35                  40                  45

Lys Val Thr Ile Asp Gln Thr Ser Ala Lys Val Asp Gln Cys Phe Arg
    50                  55                  60

Asp Tyr Asn Cys Cys Leu Ala Lys Ala Lys Thr Phe Lys Gln Ser
65                  70                  75                  80

Gly Met Ser Tyr Glu Asp Ala Val Xaa Lys Met Arg Ala Asn Thr Thr
                85                  90                  95

Arg Asp His Asn Asn Gly Thr Thr Tyr Ser Asp Leu Val Ser Gly Arg
            100                 105                 110

Ala Lys Pro Val Val Gln Lys Ile Val Asp Gln Met Arg Ala Gly Val
        115                 120                 125

Tyr Asp Ala Pro Met Arg Ile Ile Pro Lys Pro Glu Val Phe Pro Arg
    130                 135                 140

Asp Lys Ser Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His
            180                 185                 190

Glu Arg Ala Arg Leu Leu Glu Gln Trp Trp Asn Arg Ala Thr Glu Pro
        195                 200                 205

Gln Ala Ile Ala Val Asp Ala Ile Cys Phe Asp Ser Thr Ile Thr Ala
```

```
                    210                 215                 220
Glu Asp Met Asp Arg Glu Ala Asn Ile Met Ala Ala His Ser Asp
225                 230                 235                 240

Pro Glu Gly Val His Gly Leu Tyr Lys Tyr Tyr Lys Arg Ser Pro Met
                245                 250                 255

Cys Asp Ile Thr Gly Lys Val Val Gly Val Arg Cys Cys Arg Ala Ser
                260                 265                 270

Gly Thr Leu Thr Thr Ser Ser Gly Asn Thr Leu Thr Cys Tyr Leu Lys
                275                 280                 285

Val Arg Ala Ala Cys Thr Arg Ala Gly Ile Lys Pro Ile Gly Leu Leu
            290                 295                 300

Ile His Gly Asp Asp Thr Leu Ile Val Thr Glu Arg Cys Ala Gln Glu
305                 310                 315                 320

Thr Leu Asp Glu Phe Ser Ser Ala Leu Asp Asp Tyr Gly Phe Pro His
                325                 330                 335

Thr Leu Gln Val Ser Gly Asp Leu Ser Ser Val Glu Cys Cys Ser Ala
                340                 345                 350

Arg Val Asp Ser Val Cys Leu Arg Gly Gly Met Arg Arg Met Leu Val
            355                 360                 365

Pro Gln Ala Arg Arg Ala Ile Ala Arg Val Leu Gly Glu Lys Gly Asp
        370                 375                 380

Pro Leu Gly Val Ile Ser Ser Tyr Ile Val Met Tyr Pro Thr Ala Ala
385                 390                 395                 400

Val Thr Val Tyr Val Leu Leu Pro Leu Leu Cys Met Leu Ile Arg Asn
                405                 410                 415

Glu Pro Ser Gln Thr Gly Thr Ile Val Thr Leu Thr Val His Gly Asn
                420                 425                 430

Ser Val Ser Val Pro Val Trp Leu Leu Pro Thr Ile Ile Val Asn Leu
            435                 440                 445

His Gly Arg Asp Ala Leu Gln Val Val Arg His Ser Ala Ala Ser Met
        450                 455                 460

Ala Glu Leu Ser Ser Ala Leu Ala Phe Phe Gly Met Arg Gly Leu Asn
465                 470                 475                 480

Cys Trp Arg Arg Arg Arg Ala Ile Arg Thr Asp Met Ile Xaa Leu
                485                 490                 495

Gly Gly Trp Ile Ala Asn Phe Ala Gln Met Leu Leu Trp Ser Pro Glu
            500                 505                 510

Val Arg Thr Pro Gln Pro Glu Pro Lys Gly Leu Cys Leu Leu Pro Pro
        515                 520                 525

Glu Leu Trp Glu Arg Pro Tyr Glu Asn Leu Xaa Leu Ser Thr Val Asp
        530                 535                 540

Arg Asn Arg Gly Ala Ser Arg Leu Arg Phe Trp Leu Val Ala Ser Ala
545                 550                 555                 560

Ile Leu Ala Leu Leu Cys Leu
                565

<210> SEQ ID NO 344
<211> LENGTH: 79
<212> TYPE: PRT
<213> ORGANISM: Human Pegivirus 2

<400> SEQUENCE: 344

Met Gly Cys Ser Thr Asp Gln Thr Ile Cys Ser Pro Val Val Gly Ala
1               5                   10                  15
```

Asp Tyr Asn Thr Ser Ser Gly Cys Arg Ala Leu Asn Gly Ser Tyr His
                20                  25                  30

Cys Gly Gly Gly Ser Cys Arg Ser Pro Ser Arg Val Gln Val Ala Arg
            35                  40                  45

Arg Val Leu Gln Leu Cys Ala Phe Leu Ala Leu Ile Gly Ser Gly Met
    50                  55                  60

Cys Ser Ile Arg Ser Lys Thr Glu Gly Arg Ile Glu Ser Gly Gln
65                  70                  75

<210> SEQ ID NO 345
<211> LENGTH: 191
<212> TYPE: PRT
<213> ORGANISM: Human Pegivirus 2

<400> SEQUENCE: 345

Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
                20                  25                  30

Trp Cys Val Thr Arg Pro Gly Cys Leu Val Cys Thr Gly Asn Ala Thr
            35                  40                  45

His Pro Ile Cys Trp Asp Tyr Leu Gly Ser Gly Val Ser Arg Arg Pro
    50                  55                  60

Ala Arg Arg Met Gly Glu Gly Ala Glu Ala Leu Leu Arg Leu Ile Gly
65                  70                  75                  80

Ile Ala Gly Trp Leu Gly Leu Leu Ala Glu Ser Leu Gly Met Ser Glu
                85                  90                  95

Val Tyr Ala Ala Ile Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Ile Leu Gln Leu Pro Gly Leu Leu Trp Gln Met Phe Val Ser Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
            180                 185                 190

<210> SEQ ID NO 346
<211> LENGTH: 354
<212> TYPE: PRT
<213> ORGANISM: Human Pegivirus 2

<400> SEQUENCE: 346

Tyr Lys His Gln Ser Glu Ser Tyr Leu Lys Tyr Cys Thr Ile Thr Asn
1               5                   10                  15

Thr Ser Thr Ser Met Asn Cys Asp Cys Pro Phe Gly Thr Phe Thr Arg
                20                  25                  30

Asn Thr Glu Ser Arg Phe Ser Ile Pro Arg Phe Cys Pro Val Lys Ile
            35                  40                  45

Asn Ser Ser Thr Phe Ile Cys Ser Trp Gly Ser Trp Trp Phe Ala
    50                  55                  60

Glu Asn Ile Thr Arg Pro Tyr Thr Asp Val Gly Met Pro Pro Ala Pro
65                  70                  75                  80

```
Ile Ser Ala Leu Cys Tyr Ile Tyr Ser Asn Asn Asp Pro Pro Trp
                85                  90                  95

Tyr His Asn Thr Thr Ile Ile Pro Gln Asn Cys Arg Asn Ser Thr Val
            100                 105                 110

Asp Pro Thr Thr Ala Pro Cys Arg Asp Lys Trp Gly Asn Ala Thr Ala
            115                 120                 125

Cys Ile Leu Asp Arg Arg Ser Arg Phe Cys Gly Asp Cys Tyr Gly Gly
130                 135                 140

Cys Phe Tyr Thr Asn Gly Ser His Asp Arg Ser Trp Asp Arg Cys Gly
145                 150                 155                 160

Ile Gly Tyr Arg Asp Gly Leu Ile Glu Phe Val Gln Leu Gly Gln Ile
            165                 170                 175

Arg Pro Asn Ile Ser Asn Thr Thr Ile Glu Leu Leu Ala Gly Ala Ser
            180                 185                 190

Leu Val Ile Ala Ser Gly Leu Arg Pro Gly Phe Gly Cys Ser Arg Ala
            195                 200                 205

His Gly Val Val His Cys Tyr Arg Cys Pro Ser Tyr Arg Asp Leu Glu
            210                 215                 220

Gln Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
            245                 250                 255

Met Ser Asn Asn Pro Leu Ser Leu Leu Gln Thr Phe Val Glu Asp Ile
            260                 265                 270

Phe Leu Ala Pro Phe Cys Asn Pro Thr Pro Gly Arg Val Arg Val Cys
275                 280                 285

Asn Asn Thr Ala Phe Tyr Pro Arg Gly Gly Phe Val Gln Leu Ile
            290                 295                 300

Gly Asp Val Gln Val Leu Thr Pro Asn Thr Ala Ser Leu His Ser Leu
305                 310                 315                 320

Leu Thr Leu Ile Ser Leu Ile Leu Leu Val Cys Val Val Ser Gly Ala
            325                 330                 335

Arg Phe Val Pro Leu Ile Ile Ile Phe Phe Trp Ser Ala Arg His Val
            340                 345                 350

Tyr Ala

<210> SEQ ID NO 347
<211> LENGTH: 237
<212> TYPE: PRT
<213> ORGANISM: Human Pegivirus 2

<400> SEQUENCE: 347

Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
            20                  25                  30

Val Ala Thr Arg Ile Ser Ser Cys Gly His Ala Val Pro Pro Pro Asp
            35                  40                  45

Arg Gly Trp Glu Val Pro Ala Ala Met Ser Trp Val Ile Ser Arg Thr
50                  55                  60

Thr Gly Leu Thr Phe Asp Val Phe Ser Phe Ile Gln Tyr Leu Pro Thr
65                  70                  75                  80

Val Pro Gly Asn Asn Thr Asn Ile Ile Tyr Cys Gly Glu Pro Thr Phe
            85                  90                  95
```

```
Leu Gly Asp Ile Thr Gly Ile Tyr Trp Pro Tyr Phe Leu Pro Gly Ala
            100                 105                 110

Ile Leu Leu Tyr Leu Thr Pro Phe Leu Gly Leu Arg Leu Met Leu Ala
        115                 120                 125

Gly Phe Asn Ile Asp Gly Leu Phe Pro Ile Arg His Ala Thr Ala Ala
    130                 135                 140

Leu Arg Phe Ser Thr Ser Arg Val Thr Leu Cys Val Val Ala Phe
145                 150                 155                 160

Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
            180                 185                 190

His Glu Thr Val Leu Tyr Ile Leu Cys Leu Leu Tyr Leu Gln Val
        195                 200                 205

Ser Pro Arg Ala Gly Leu Ala Ala Met Val Ala Ile Lys Leu Ser Arg
    210                 215                 220

Gly Leu Leu Phe Ala Val Val Leu Ala His Gly Val Cys
225                 230                 235

<210> SEQ ID NO 348
<211> LENGTH: 240
<212> TYPE: PRT
<213> ORGANISM: Human Pegivirus 2

<400> SEQUENCE: 348

Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
            20                  25                  30

Ser Phe Trp Cys Ala Val Phe Ala Phe Thr Ser Pro Leu Gly Arg His
        35                  40                  45

Tyr Lys Ile Gln Ile Tyr Arg Tyr Trp Ala Gln Val Tyr Ala Arg Leu
    50                  55                  60

Val Leu Ala Val Gly Cys Gly Pro Leu Gly Arg Glu Phe His Phe Arg
65                  70                  75                  80

Ala Ser Val Gly Val Leu Trp Cys Gly Ala Cys Met Leu Trp Pro Arg
                85                  90                  95

Glu Cys Ser Glu Ile Ser Leu Val Phe Ile Leu Cys Ala Leu Thr Val
            100                 105                 110

Asp Thr Ile Asp Thr Trp Leu Val Ala Cys Leu Ser Ala Gly Pro Ser
        115                 120                 125

Ala Arg Thr Leu Ala Ile Leu Ala Asp Asp Met Ala Arg Ile Gly Asp
    130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Leu Gly Gly Cys Leu Glu Pro Val Val Leu Glu Glu Pro
            180                 185                 190

Thr Phe Thr Glu Ile Val Asp Asp Thr Met Ser Leu Val Cys Gly Gln
        195                 200                 205

Leu Leu Gly Gly Lys Pro Val Val Ala Arg Cys Gly Thr Arg Val Leu
    210                 215                 220

Val Gly His Leu Asn Pro Glu Asp Leu Pro Pro Gly Phe Gln Leu Ser
225                 230                 235                 240
```

<210> SEQ ID NO 349
<211> LENGTH: 628
<212> TYPE: PRT
<213> ORGANISM: Human Pegivirus 2

<400> SEQUENCE: 349

```
Ala Pro Val Val Ile Thr Arg Pro Ser Ile Gly Thr Trp Ser Phe Leu
1               5                   10                  15

Lys Ala Thr Leu Thr Gly Arg Ala Glu Thr Pro Gly Ser Gly Gln Ile
            20                  25                  30

Val Val Leu Ser Ser Leu Thr Gly Arg Ser Met Gly Thr Ala Val Asn
        35                  40                  45

Gly Thr Leu Tyr Ala Thr Gly His Gly Ala Gly Ala Arg Gly Leu Ala
    50                  55                  60

Thr Cys Ala Gly Leu Arg Thr Pro Leu Tyr Thr Ala Leu Ser Asp Asp
65                  70                  75                  80

Val Val Ala Tyr Ser Cys Leu Pro Gly Met Ser Ser Leu Asp Pro Cys
                85                  90                  95

Cys Cys Ser Pro Ser Arg Val Trp Val Met Asn Asn Asn Gly Gly Leu
            100                 105                 110

Val Cys Gly Arg Val Glu Asn Asp Asp Val Cys Leu Asp Cys Pro Thr
        115                 120                 125

His Ile Asp Gln Leu Arg Gly Ala Ser Gly Ser Pro Val Leu Cys Asp
    130                 135                 140

His Gly His Ala Tyr Ala Leu Met Leu Gly Gly Tyr Ser Thr Ser Gly
145                 150                 155                 160

Ile Cys Ala Arg Val Arg Thr Val Arg Pro Trp His Asn Ala Tyr Ser
                165                 170                 175

Ser Ser Gly Gly Gln Gly Gly Met Gln Ala Pro Ala Val Thr Pro Thr
            180                 185                 190

Tyr Ser Glu Ile Thr Tyr Tyr Ala Pro Thr Gly Ser Gly Lys Ser Thr
        195                 200                 205

Lys Tyr Pro Val Asp Leu Val Lys Gln Gly His Lys Val Leu Val Leu
    210                 215                 220

Leu Pro Ser Val Ala Val Lys Ser Met Ala Pro Tyr Ile Lys Glu
225                 230                 235                 240

Thr Tyr Lys Ile Arg Pro Glu Ile Arg Ala Gly Thr Gly Pro Asp Gly
                245                 250                 255

Val Thr Val Ile Thr Gly Glu Asn Leu Ala Tyr Met Thr Tyr Gly Arg
            260                 265                 270

Phe Leu Val Asp Pro Glu Thr Asn Leu Arg Gly Tyr Ala Val Val Ile
        275                 280                 285

Cys Asp Glu Cys His Asp Thr Ser Ser Thr Thr Leu Leu Gly Ile Gly
    290                 295                 300

Ala Val Arg Met Tyr Ala Glu Lys Ala Gly Val Lys Thr Val Val Phe
305                 310                 315                 320

Ala Thr Ala Thr Pro Ala Gly Ile Gln Val Gln Ser His Ser Asn Ile
                325                 330                 335

Asp Glu Tyr Leu Leu Thr Asp Thr Gly Asp Val Glu Phe Tyr Gly Ala
            340                 345                 350

Lys Ile Lys Met Asp Asn Ile Arg Thr Gly Arg His Val Ile Phe Cys
        355                 360                 365

His Ser Lys Ala Arg Cys Ala Glu Leu Thr Gln Gln Leu Ser Gly Leu
```

```
                 370                 375                 380
Gly Ile Arg Ala Val Ser Phe Trp Arg Gly Cys Asp Ile Lys Thr Ile
385                 390                 395                 400

Pro Ala Ser Asp Ser Ile Val Val Ala Thr Asp Ala Leu Ser Thr
                405                 410                 415

Gly Tyr Thr Gly Asn Phe Asp Ser Val Ile Asp Cys Gly Cys Cys Val
                420                 425                 430

Glu Gln Thr Val Thr Ile Asp Met Asp Pro Thr Phe Ser Ile Ser Ala
                435                 440                 445

Arg Val Val Pro Cys Thr Ala Ala Leu Arg Met Gln Arg Arg Gly Arg
                450                 455                 460

Thr Gly Arg Gly Arg Gly Ala Tyr Tyr Thr Thr Ser Pro Gly Ala
465                 470                 475                 480

Ala Pro Cys Val Ser Val Pro Asp Ala Asn Val Trp Gln Ala Val Glu
                485                 490                 495

Ser Ala Met Val Phe Tyr Asp Trp Ser Ala Thr Arg Ile Gln Gln Cys
                500                 505                 510

Leu Ala Ala Tyr His Asp Leu Gly Cys Thr Pro Arg Ile Ser Cys Asp
                515                 520                 525

Pro His Thr Pro Val Arg Val Met Asp Thr Leu Arg Ala Tyr Leu Arg
                530                 535                 540

Arg Pro Glu Val Thr Thr Ala Ala Leu Ala Gly Glu Gln Trp Pro Leu
545                 550                 555                 560

Leu Tyr Gly Ala Gln Leu Cys Ile Cys Lys Glu Thr Glu Ala His Gly
                565                 570                 575

Pro Asp Asp Ser Ile Lys Trp Lys Cys Leu Leu Asn Asn Ser Asn Lys
                580                 585                 590

Thr Pro Leu Leu Tyr Ala Leu Asp Asn Pro Thr Leu Glu Phe Thr Thr
                595                 600                 605

Gln His Asp Leu Thr Arg Arg Ile Ala Gly Ala Leu Ser Ser Thr Val
                610                 615                 620

Phe Val Glu Thr
625

<210> SEQ ID NO 350
<211> LENGTH: 41
<212> TYPE: PRT
<213> ORGANISM: Human Pegivirus 2

<400> SEQUENCE: 350

Gly Tyr Gly Pro Ile Leu Leu Ala Gly Ala Ala Leu Ala Ala Ser Phe
1               5                   10                  15

Ala Phe Ala Gly Ala Thr Gly Ala Leu Val Pro Ser Ala Val Trp Ser
                20                  25                  30

Val Glu Val Arg Pro Ala Gly Val Thr
        35                  40

<210> SEQ ID NO 351
<211> LENGTH: 262
<212> TYPE: PRT
<213> ORGANISM: Human Pegivirus 2

<400> SEQUENCE: 351

Arg Pro Asp Ala Thr Asp Glu Thr Ala Ala Tyr Ala Gln Arg Leu Tyr
1               5                   10                  15

Gln Ala Cys Ala Asp Ser Gly Ile Phe Ala Ser Leu Gln Gly Thr Ala
```

```
            20                  25                  30
Ser Ala Ala Leu Gly Lys Leu Ala Asp Ala Ser Arg Gly Ala Ser Gln
        35                  40                  45

Tyr Leu Ala Ala Ala Pro Pro Ser Pro Ala Pro Leu Val Gln Val Leu
 50                  55                  60

Gln Phe Leu Glu Thr Asn Phe Ser Ser Ile Ala Ser Phe Gly Leu Leu
 65                  70                  75                  80

Cys Ala Gly Cys Gln Ala Gly Glu Cys Phe Thr Ala Leu Ala Gly Leu
                 85                  90                  95

Val Ser Gly Ala Thr Ala Gly Leu Gly Gly Ala His Lys Trp Leu Leu
            100                 105                 110

Ala Ile Ala Gly Thr Trp Leu Val Ser Leu Gln Thr Gly Ser Arg Gly
            115                 120                 125

Gly Met Val Ala Gly Leu Ser Ile Leu Ala Gly Cys Cys Ile Gly Ser
            130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Val Asp Leu Leu Pro Ala Leu Phe Ser Pro Gly
            180                 185                 190

Ala Gly Ile Ala Gly Ile Val Leu Val Phe Ile Leu Ser Asn Ser Ser
            195                 200                 205

Val Thr Thr Trp Ala Asn Arg Leu Leu Ser Met Cys Ala Lys Gln Thr
            210                 215                 220

Ile Cys Glu Asn Tyr Phe Leu Ser Glu Arg Phe Gly Gln Gln Leu Ser
225                 230                 235                 240

Lys Leu Ser Leu Trp Arg Ser Val Tyr His Trp Ala Gln Ala Arg Glu
                245                 250                 255

Gly Tyr Thr Gln Cys Gly
            260

<210> SEQ ID NO 352
<211> LENGTH: 458
<212> TYPE: PRT
<213> ORGANISM: Human Pegivirus 2

<400> SEQUENCE: 352

Val Ile Ser Gly Ile Trp Ser Phe Ala Leu Cys Ile Leu Arg Ala Val
 1               5                  10                  15

Trp Asp Trp Ala Ala Lys His Val Pro Arg Phe Arg Val Pro Met Ile
                 20                  25                  30

Gly Cys Ser Pro Ala Trp Cys Gly Arg Trp Leu Gly Thr Gly Thr Leu
            35                  40                  45

Leu Thr Thr Cys Ala Cys Gly Glu Arg Val Ser Leu Gln Cys Leu Cys
 50                  55                  60

Ser Thr Ser Asp Pro Gln Leu Ser Val Gly Arg Trp Cys Arg Cys Ser
 65                  70                  75                  80

Trp Ser Val Gly Phe Pro Phe Asn Pro Thr Thr Thr Gly Thr Gly Thr
                 85                  90                  95

Leu Arg Pro Asp Ile Ser Asp Ala Asn Lys Leu Gly Phe Arg Tyr Gly
            100                 105                 110

Val Ala Asp Ile Val Glu Leu Glu Arg Arg Gly Asp Lys Trp His Val
            115                 120                 125
```

```
Cys Ala Ala Ser Cys Cys Leu Asp Arg Ala Ser Val Ala Ser Ala Val
            130                 135                 140

Lys Ala Pro Pro Val Thr Ala Asn Gly Ile Pro Ile Asn Ser Phe Ser
145                 150                 155                 160

Pro Pro Gln Thr Tyr Cys Leu Ser Leu Cys Ser Phe Asp Thr Val Cys
                165                 170                 175

Met Ser Thr Asn Leu Cys Asn Pro Ala Lys Thr Leu Ser Val Cys Gln
            180                 185                 190

Glu Glu Ala Val Glu Leu Leu Glu Thr Val Asp Thr Ala Gln Val
            195                 200                 205

Val Met Ser Gln Asn Leu Ala Ala Arg Arg Ala Glu Tyr Asp Ala
    210                 215                 220

Trp Gln Val Arg Gln Ala Val Gly Asp Glu Tyr Thr Arg Leu Ala Asp
225                 230                 235                 240

Glu Asp Val Asp Met Thr Ala Ser Val Lys Pro Val Ala Arg Ala
                245                 250                 255

Ala Val Gly Ser Ser Thr Leu Asp Asp Val Ser Val Leu Thr Val Leu
            260                 265                 270

Arg Glu Leu Gly Asp Gln Cys Gln Asn Ala Ile Lys Phe Val Val Gln
    275                 280                 285

Ala Ala Ser Arg Phe Val Pro Pro Val Pro Lys Pro Arg Thr Arg Val
    290                 295                 300

Ser Gly Val Leu Glu Arg Val Arg Met Cys Met Arg Thr Pro Pro Ile
305                 310                 315                 320

Lys Phe Glu Ala Thr Ala Val Pro Ile His Asn Ile Ile Pro Glu Glu
                325                 330                 335

Cys His Ile Val Leu Arg Cys Thr Gly Cys Cys Asp Gln Ala Leu Thr
            340                 345                 350

Val Pro Tyr Gly Thr Cys Ser Leu Thr Leu Thr Lys Tyr Leu Thr Asn
    355                 360                 365

Lys His Ser His Tyr Ile Pro Lys Glu Lys Ile Glu Glu Asp Thr Glu
    370                 375                 380

Ile Ala Val Ile Cys Ala Val Pro Thr Lys Arg Ala Ser Lys Leu Ile
385                 390                 395                 400

Thr Phe Arg Ala Gly Asp Arg Ser Val Ser Cys Cys His Pro Leu Gln
                405                 410                 415

Thr Pro Ile Arg Ala Leu Leu Gln Lys Tyr Gly Leu Pro Ile Gly Lys
            420                 425                 430

Trp Ser Asp Cys Asn Gly Pro Leu Gly Asp Asp Ala Arg Val Cys Asp
    435                 440                 445

Val Asn Gly Val Thr Thr Tyr Glu Pro Cys
    450                 455

<210> SEQ ID NO 353
<211> LENGTH: 567
<212> TYPE: PRT
<213> ORGANISM: Human Pegivirus 2

<400> SEQUENCE: 353

Met Gln Ser Tyr Asn Trp Phe Arg Ser Ile Val Ala Pro Thr Thr Pro
1               5                   10                  15

Pro Leu Pro Ala Thr Arg Ser Val Ala Gly Ile Leu Arg Ala Asp Thr
            20                  25                  30

Ser Arg Val Tyr Thr Thr Thr Ala Val Asp Val Ser Glu Arg Gln Ala
        35                  40                  45
```

-continued

```
Lys Val Thr Ile Asp Gln Lys Ser Ala Lys Val Asp Gln Cys Leu Arg
 50                  55                  60
Asp Thr Tyr Asn Cys Cys Leu Ala Lys Ala Lys Thr Phe Arg Gln Ser
 65                  70                  75                  80
Gly Met Ser Tyr Glu Asp Ala Val Ser Lys Met Arg Ala Asn Thr Thr
                 85                  90                  95
Arg Asp His Asn Asn Gly Ile Thr Tyr Thr Asp Leu Val Ser Gly Arg
                100                 105                 110
Ala Lys Pro Val Val Gln Lys Ile Val Asp Gln Met Arg Ala Gly Val
                115                 120                 125
Tyr Asp Ala Pro Met Arg Ile Ile Pro Lys Pro Glu Val Phe Pro Arg
130                 135                 140
Asp Lys Ser Thr Arg Lys Pro Pro Arg Phe Ile Val Phe Pro Gly Cys
145                 150                 155                 160
Ala Ala Arg Val Ala Glu Lys Met Ile Leu Gly Asp Pro Gly Ala Ile
                165                 170                 175
Thr Lys His Val Leu Gly Asp Ala Tyr Gly Phe Ala Thr Pro Pro His
                180                 185                 190
Glu Arg Ala Arg Leu Leu Glu Gln Trp Trp Asn Arg Ala Thr Glu Pro
                195                 200                 205
Gln Ala Ile Ala Val Asp Ala Val Cys Phe Asp Ser Thr Ile Thr Ala
210                 215                 220
Glu Asp Met Asp Arg Glu Ala Asn Ile Val Ala Ala His Thr Asp
225                 230                 235                 240
Pro Glu Gly Val His Gly Leu Tyr Asn Tyr Tyr Lys Arg Ser Pro Met
                245                 250                 255
Cys Asp Ile Thr Gly Lys Val Gly Val Arg Ser Cys Arg Ala Ser
                260                 265                 270
Gly Thr Leu Thr Thr Ser Ser Gly Asn Thr Leu Thr Cys Tyr Leu Lys
                275                 280                 285
Val Arg Ala Ala Cys Thr Arg Ala Gly Ile Lys Pro Ile Gly Leu Leu
290                 295                 300
Ile His Gly Asp Asp Thr Leu Ile Ile Thr Glu Arg Cys Ala Gln Glu
305                 310                 315                 320
Thr Leu Asp Glu Phe Ser Asn Ala Leu Asp Asp Tyr Gly Phe Thr His
                325                 330                 335
Thr Met Gln Val Ser Gly Asp Leu Ser Ser Ile Glu Cys Cys Ser Ala
                340                 345                 350
Arg Val Asp Ser Val Cys Leu Arg Gly Gly Met Arg Met Leu Val
                355                 360                 365
Pro Gln Ala Arg Arg Ala Ile Ala Arg Val Leu Gly Glu Lys Gly Asp
                370                 375                 380
Pro Leu Gly Val Ile Ser Ser Tyr Ile Val Met Tyr Pro Thr Ala Ala
385                 390                 395                 400
Val Thr Val Tyr Val Leu Met Pro Leu Leu Cys Met Leu Ile Arg Asn
                405                 410                 415
Glu Pro Ser Gln Thr Gly Thr Leu Val Thr Leu Thr Val His Gly Asn
                420                 425                 430
Ser Val Ser Val Pro Val Trp Leu Leu Pro Thr Ile Ile Ala Asn Leu
                435                 440                 445
His Gly Arg Asp Ala Leu Gln Val Val Arg His Ser Ala Ala Ser Met
                450                 455                 460
```

```
Ala Glu Leu Ser Ser Ala Leu Ala Phe Phe Gly Met Arg Gly Leu Asn
465                 470                 475                 480

Cys Trp Arg Arg Arg Arg Ala Ile Arg Thr Asp Met Ile Lys Leu
            485                 490                 495

Gly Gly Trp Asn Ala Asn Phe Ala Gln Met Leu Leu Trp Ser Pro Glu
                500                 505                 510

Val Arg Thr Pro Gln Pro Glu Pro Lys Gly Met Cys Leu Leu Pro Pro
            515                 520                 525

Glu Leu Trp Glu Arg Pro Tyr Glu Asn Leu His Leu Ser Thr Ile Asp
        530                 535                 540

Arg Asn Arg Gly Ala Ser Arg Leu Arg Phe Trp Leu Val Ala Ser Ala
545                 550                 555                 560

Ile Leu Ala Leu Leu Cys Leu
                565

<210> SEQ ID NO 354
<211> LENGTH: 9718
<212> TYPE: DNA
<213> ORGANISM: Human Pegivirus 2
<220> FEATURE:
<221> NAME/KEY: misc_feature
<222> LOCATION: (16)..(19)
<223> OTHER INFORMATION: N = A, C, T or G
<220> FEATURE:
<221> NAME/KEY: misc_feature
<222> LOCATION: (35)..(135)
<223> OTHER INFORMATION: N = A, C, T or G
<220> FEATURE:
<221> NAME/KEY: misc_feature
<222> LOCATION: (157)..(264)
<223> OTHER INFORMATION: N = A, C, T or G
<220> FEATURE:
<221> NAME/KEY: misc_feature
<222> LOCATION: (280)..(319)
<223> OTHER INFORMATION: N = A, C, T or G
<220> FEATURE:
<221> NAME/KEY: misc_feature
<222> LOCATION: (335)..(340)
<223> OTHER INFORMATION: N = A, C, T or G
<220> FEATURE:
<221> NAME/KEY: misc_feature
<222> LOCATION: (359)..(460)
<223> OTHER INFORMATION: N = A, C, T or G
<220> FEATURE:
<221> NAME/KEY: misc_feature
<222> LOCATION: (483)..(516)
<223> OTHER INFORMATION: N = A, C, T or G
<220> FEATURE:
<221> NAME/KEY: misc_feature
<222> LOCATION: (559)..(625)
<223> OTHER INFORMATION: N = A, C, T or G
<220> FEATURE:
<221> NAME/KEY: misc_feature
<222> LOCATION: (646)..(671)
<223> OTHER INFORMATION: N = A, C, T or G
<220> FEATURE:
<221> NAME/KEY: misc_feature
<222> LOCATION: (1336)..(1577)
<223> OTHER INFORMATION: N = A, C, T or G
<220> FEATURE:
<221> NAME/KEY: misc_feature
<222> LOCATION: (1605)..(1629)
<223> OTHER INFORMATION: N = A, C, T or G
<220> FEATURE:
<221> NAME/KEY: misc_feature
<222> LOCATION: (1790)..(1815)
<223> OTHER INFORMATION: N = A, C, T or G
<220> FEATURE:
<221> NAME/KEY: misc_feature
<222> LOCATION: (1996)..(2001)
<223> OTHER INFORMATION: N = A, C, T or G
<220> FEATURE:
```

-continued

```
<221> NAME/KEY: misc_feature
<222> LOCATION: (2067)..(2103)
<223> OTHER INFORMATION: N = A, C, T or G
<220> FEATURE:
<221> NAME/KEY: misc_feature
<222> LOCATION: (2633)..(2641)
<223> OTHER INFORMATION: N = A, C, T or G
<220> FEATURE:
<221> NAME/KEY: misc_feature
<222> LOCATION: (2669)..(2670)
<223> OTHER INFORMATION: N = A, C, T or G
<220> FEATURE:
<221> NAME/KEY: misc_feature
<222> LOCATION: (2706)..(2716)
<223> OTHER INFORMATION: N = A, C, T or G
<220> FEATURE:
<221> NAME/KEY: misc_feature
<222> LOCATION: (2733)..(2907)
<223> OTHER INFORMATION: N = A, C, T or G
<220> FEATURE:
<221> NAME/KEY: misc_feature
<222> LOCATION: (2927)..(2965)
<223> OTHER INFORMATION: N = A, C, T or G
<220> FEATURE:
<221> NAME/KEY: misc_feature
<222> LOCATION: (2981)..(3059)
<223> OTHER INFORMATION: N = A, C, T or G
<220> FEATURE:
<221> NAME/KEY: misc_feature
<222> LOCATION: (3171)..(3386)
<223> OTHER INFORMATION: N = A, C, T or G
<220> FEATURE:
<221> NAME/KEY: misc_feature
<222> LOCATION: (3402)..(3425)
<223> OTHER INFORMATION: N = A, C, T or G
<220> FEATURE:
<221> NAME/KEY: misc_feature
<222> LOCATION: (3450)..(3524)
<223> OTHER INFORMATION: N = A, C, T or G
<220> FEATURE:
<221> NAME/KEY: misc_feature
<222> LOCATION: (3450)..(3580)
<223> OTHER INFORMATION: N = A, C, T or G
<220> FEATURE:
<221> NAME/KEY: misc_feature
<222> LOCATION: (3608)..(3679)
<223> OTHER INFORMATION: N = A, C, T or G
<220> FEATURE:
<221> NAME/KEY: misc_feature
<222> LOCATION: (3699)..(3713)
<223> OTHER INFORMATION: N = A, C, T or G
<220> FEATURE:
<221> NAME/KEY: misc_feature
<222> LOCATION: (3732)..(3813)
<223> OTHER INFORMATION: N = A, C, T or G
<220> FEATURE:
<221> NAME/KEY: misc_feature
<222> LOCATION: (3834)..(3862)
<223> OTHER INFORMATION: N = A, C, T or G
<220> FEATURE:
<221> NAME/KEY: misc_feature
<222> LOCATION: (3900)..(3967)
<223> OTHER INFORMATION: N = A, C, T or G
<220> FEATURE:
<221> NAME/KEY: misc_feature
<222> LOCATION: (3992)..(4178)
<223> OTHER INFORMATION: N = A, C, T or G
<220> FEATURE:
<221> NAME/KEY: misc_feature
<222> LOCATION: (4206)..(4240)
<223> OTHER INFORMATION: N = A, C, T or G
<220> FEATURE:
<221> NAME/KEY: misc_feature
<222> LOCATION: (4257)..(4359)
<223> OTHER INFORMATION: N = A, C, T or G
<220> FEATURE:
<221> NAME/KEY: misc_feature
<222> LOCATION: (4378)..(4386)
<223> OTHER INFORMATION: N = A, C, T or G
```

```
<220> FEATURE:
<221> NAME/KEY: misc_feature
<222> LOCATION: (4595)..(4748)
<223> OTHER INFORMATION: N = A, C, T or G
<220> FEATURE:
<221> NAME/KEY: misc_feature
<222> LOCATION: (4812)..(4890)
<223> OTHER INFORMATION: N = A, C, T or G
<220> FEATURE:
<221> NAME/KEY: misc_feature
<222> LOCATION: (4916)..(4974)
<223> OTHER INFORMATION: N = A, C, T or G
<220> FEATURE:
<221> NAME/KEY: misc_feature
<222> LOCATION: (5393)..(5411)
<223> OTHER INFORMATION: N = A, C, T or G
<220> FEATURE:
<221> NAME/KEY: misc_feature
<222> LOCATION: (5458)..(5463)
<223> OTHER INFORMATION: N = A, C, T or G
<220> FEATURE:
<221> NAME/KEY: misc_feature
<222> LOCATION: (5490)..(5535)
<223> OTHER INFORMATION: N = A, C, T or G
<220> FEATURE:
<221> NAME/KEY: misc_feature
<222> LOCATION: (5551)..(5614)
<223> OTHER INFORMATION: N = A, C, T or G
<220> FEATURE:
<221> NAME/KEY: misc_feature
<222> LOCATION: (5630)..(5786)
<223> OTHER INFORMATION: N = A, C, T or G
<220> FEATURE:
<221> NAME/KEY: misc_feature
<222> LOCATION: (5852)..(5855)
<223> OTHER INFORMATION: N = A, C, T or G
<220> FEATURE:
<221> NAME/KEY: misc_feature
<222> LOCATION: (5883)..(5884)
<223> OTHER INFORMATION: N = A, C, T or G
<220> FEATURE:
<221> NAME/KEY: misc_feature
<222> LOCATION: (6034)..(6086)
<223> OTHER INFORMATION: N = A, C, T or G
<220> FEATURE:
<221> NAME/KEY: misc_feature
<222> LOCATION: (6121)..(6121)
<223> OTHER INFORMATION: N = A, C, T or G
<220> FEATURE:
<221> NAME/KEY: misc_feature
<222> LOCATION: (6137)..(6184)
<223> OTHER INFORMATION: N = A, C, T or G
<220> FEATURE:
<221> NAME/KEY: misc_feature
<222> LOCATION: (6137)..(6327)
<223> OTHER INFORMATION: N = A, C, T or G
<220> FEATURE:
<221> NAME/KEY: misc_feature
<222> LOCATION: (6343)..(6386)
<223> OTHER INFORMATION: N = A, C, T or G
<220> FEATURE:
<221> NAME/KEY: misc_feature
<222> LOCATION: (6627)..(6637)
<223> OTHER INFORMATION: N = A, C, T or G
<220> FEATURE:
<221> NAME/KEY: misc_feature
<222> LOCATION: (6659)..(6662)
<223> OTHER INFORMATION: N = A, C, T or G
<220> FEATURE:
<221> NAME/KEY: misc_feature
<222> LOCATION: (6869)..(6903)
<223> OTHER INFORMATION: N = A, C, T or G
<220> FEATURE:
<221> NAME/KEY: misc_feature
<222> LOCATION: (6939)..(6952)
<223> OTHER INFORMATION: N = A, C, T or G
<220> FEATURE:
<221> NAME/KEY: misc_feature
<222> LOCATION: (6971)..(7009)
```

```
<223> OTHER INFORMATION: N = A, C, T or G
<220> FEATURE:
<221> NAME/KEY: misc_feature
<222> LOCATION: (7150)..(7246)
<223> OTHER INFORMATION: N = A, C, T or G
<220> FEATURE:
<221> NAME/KEY: misc_feature
<222> LOCATION: (7462)..(7470)
<223> OTHER INFORMATION: N = A, C, T or G
<220> FEATURE:
<221> NAME/KEY: misc_feature
<222> LOCATION: (7911)..(7968)
<223> OTHER INFORMATION: N = A, C, T or G
<220> FEATURE:
<221> NAME/KEY: misc_feature
<222> LOCATION: (7987)..(8114)
<223> OTHER INFORMATION: N = A, C, T or G
<220> FEATURE:
<221> NAME/KEY: misc_feature
<222> LOCATION: (8139)..(8175)
<223> OTHER INFORMATION: N = A, C, T or G
<220> FEATURE:
<221> NAME/KEY: misc_feature
<222> LOCATION: (8198)..(8386)
<223> OTHER INFORMATION: N = A, C, T or G
<220> FEATURE:
<221> NAME/KEY: misc_feature
<222> LOCATION: (8413)..(8442)
<223> OTHER INFORMATION: N = A, C, T or G
<220> FEATURE:
<221> NAME/KEY: misc_feature
<222> LOCATION: (8483)..(8487)
<223> OTHER INFORMATION: N = A, C, T or G
<220> FEATURE:
<221> NAME/KEY: misc_feature
<222> LOCATION: (8506)..(8513)
<223> OTHER INFORMATION: N = A, C, T or G
<220> FEATURE:
<221> NAME/KEY: misc_feature
<222> LOCATION: (8529)..(8732)
<223> OTHER INFORMATION: N = A, C, T or G
<220> FEATURE:
<221> NAME/KEY: misc_feature
<222> LOCATION: (8748)..(8799)
<223> OTHER INFORMATION: N = A, C, T or G
<220> FEATURE:
<221> NAME/KEY: misc_feature
<222> LOCATION: (8977)..(9017)
<223> OTHER INFORMATION: N = A, C, T or G
<220> FEATURE:
<221> NAME/KEY: misc_feature
<222> LOCATION: (9052)..(9383)
<223> OTHER INFORMATION: N = A, C, T or G
<220> FEATURE:
<221> NAME/KEY: misc_feature
<222> LOCATION: (9402)..(9476)
<223> OTHER INFORMATION: N = A, C, T or G
<220> FEATURE:
<221> NAME/KEY: misc_feature
<222> LOCATION: (9530)..(9718)
<223> OTHER INFORMATION: N = A, C, T or G

<400> SEQUENCE: 354
gtgtttgaca atgccnnnng ggatcatgtc actgnnnnnn nnnnnnnnnn       60
nnnnnnnnnn nnnnnnnnnn nnnnnnnnnn nnnnnnnnnn nnnnnnnnnn nnnnnnnnnn   120
nnnnnnnnnn nnnnngcaga caggatggg tccctgnnnn nnnnnnnnnn nnnnnnnnnn   180
nnnnnnnnnn nnnnnnnggt ggcggcgggc ccnnnnnnnn nnnnnnnnnn nnnnnnnnnn   240
nnnnnnnnnn nnnnnnnnnn nnnnatttgt tctccagtcn nnnnnnnnnn nnnnnnnnnn   300
nnnnnnnnnn nnnnnnnnnt aaatgggagc taccnnnnnn gtggtggctc ttgcctgtnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn gcattgagtc agggcaaact   480
```

-continued

```
atnnnnnnnn nnnnnnnnnn nnnnnnnnnn nnnnntttt ctccttcatt tcaactttgg    540
tgaatctgat attatgtgnn nnnnnnnnnn nnnnnnnnnn nnnnnnnnnn nnnnnnnnnn    600
nnnnnnnnnn nnnnnnnnnn nnnnnatctg ctgggactat cttggnnnnn nnnnnnnnnn    660
nnnnnnnnnn ngttgaatgg gtgagggagg aagcaatgtc ttcgcttgat cggcattgca    720
ggttggcttg gactgtgtga gtctcttggt atgtctgaga tctacgcagc tattctttgc    780
tttggattta ttgcttggta tggctggggt atacctaaaa cattggtgtg cacagtctgc    840
cctgcagtga acatttcccc ctatagcttc ttatctccag atactatcgc atttggtacg    900
tggatactac aactacctga tcttttgtgg caaatgattg tcagattccc tatactttac    960
agtacttgga ttctttggtt gttgctcagc ggcaagactg ttgctgtgat agcgatcctt   1020
ttggctagtc ctacggttat ggcatacaac tcaatctgaa agctaacctc aaatatgaac   1080
cataaccaat actatcaact gctatgaact gtgactgccc ctttggaact ttcactcgca   1140
atactgagtc tggtttctca atatccatag attctgtcct gttaaaatca atagctctca   1200
tttatttgtt catgggggtc gtggtggtgg tttgctgcac agatcacccg tccatactac   1260
gggacgttct caccccgcca gcaccgattt ccgctttgtg ctatatctat tcaagcaatg   1320
acccaccttc ttggtnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nttctatact aatggtagtn   1500
nnnnnnnnnn nnnnnnnnnn nnnnnnnnnn nnnnnnnnnn nnnnnnnnnn nnnnnnnnnn   1560
nnnnnnnnnn nnnnnnncct aacatctcga atactacctt tcgannnnnn nnnnnnnnnn   1620
nnnnnnnnna tcgcatccgg tcttcgggct gggtatggtt gcagccgagc gcacggcgtg   1680
gtgcactgct ttaagtgtcc ttcataccgt gacctgtgaa tccatttggt cctgggcttg   1740
ggaaatgggt gccattgcct ggcgagcctg tcccggagtt gtgtattaan nnnnnnnnnn   1800
nnnnnnnnnn nnnnnggtgt ctaacaatgc tttcagcttg ttgcagacct tcgttgagga   1860
cattttccta gcacccttt  gcaacccgac gcctgggcgt gtacgtgtgt gtaacaacac   1920
tgctttctat ccgagaggag gcggttttgt gcagctcatc ggagacgtcc aggtgctaac   1980
ccctaacact gcatcnnnnn nctctgtgct gactttgata tcgtctaact cttgtgtggt   2040
gtgtgttgtt tgtgtgtgcg cattgtnnnn nnnnnnnnnn nnnnnnnnnn nnnnnnnnnn   2100
nnngtatatt cttttttttt attaatttgt tattgggctg tttgcaacga tgcgttctgt   2160
ttcacatctg gcacttgtgc tacctcaatg acgtcttgtg tctgccggtt gcgacgcgta   2220
tatcgtcctg tggccatgct gtgccacctc ccgaccgtgg ttgggaggtg cctgcggcaa   2280
tgtcatgggc gatttcgcgg actactggtt tgacgttcga tgtcttttcc tttgtccagt   2340
atcttcctac tgtgcctggc aacaataccg atatcattta ctgtggtgaa ccaaccttct   2400
ttggggacat cacgggcatc tattggcctt acttcttgcc tggcgtgcta ctgttgtact   2460
tgactccttt cttgggctta aggttaatgc ttgctggctt caatatagat ggcttgtttc   2520
ccatacggca tgccacggct gcactgaggt tctcgacttc acgtgtgacc ttgtgtgtcg   2580
tactcgcctt cctaatctat atattatctc atcctgtcaa tgctgcactc aannnnnnnn   2640
ncttgagcat ctgcaaattt agagatgann ttatcttttg ataccttata tgagactgtt   2700
cttatnnnnn nnnnnnattg ctctacctcc agnnnnnnnn nnnnnnnnnn nnnnnnnnnn   2760
nnnnnnnnnn nnnnnnnnnn nnnnnnnnnn nnnnnnnnnn nnnnnnnnnn nnnnnnnnnn   2820
```

```
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnncca tgtgtcttct cttttnnnn nnnnnnnnnn      2940
nnnnnnnnnn nnnnnnnnnn nnnnnactat aagattcaga nnnnnnnnnn nnnnnnnnnn     3000
nnnnnnnnnn nnnnnnnnnn nnnnnnnnnn nnnnnnnnnn nnnnnnnnnn nnnnnnnnnc     3060
cgctgaagtg tgggcgtgct tggagagtag cttgcatgct ctggcacgtg agtgctctga     3120
aatcagcctg tgtcttcatt ctgtgtgctc tgacatagac accatagaca catnnnnnnn     3180
nnnnnnnnnn nnnnnnnnnn nnnnnnnnnn nnnnnnnnnn nnnnnnnnnn nnnnnnnnnn     3240
nnnnnnnnnn nnnnnnnnnn nnnnnnnnnn nnnnnnnnnn nnnnnnnnnn caccaggcac     3300
atacatatac acaccacatg ggccaagnnn nnnnnnnnnn nnnnnnnnnn nnnnnnnnnn     3360
nnnnnnnnnn nnnnnnnnnn nnnnnnttgg aggagcccac cnnnnnnnnn nnnnnnnnnn     3420
nnnnntgtgt ttgagtgtgt ggacaattgn nnnnnnnnnn nnnnnnnnnn nnnnnnnnnn     3480
nnnnnnnnnn nnnnnnnnnn nnnntcaacc ctgaagatcn nnnncctggt ttccagctgn     3540
nnnnnnnnnn nnnnnnnnnn nnnnnnnnnn nnnnnnnnnn gtccttcctt aaggctgaca     3600
tctaacannn nnnnnnnnnn nnnnnnnnnn nnnnnnnnnn nnnnnnnnnn nnnnnnnnnn     3660
nnnnnnnnnn nnnnnnnnng cagtgaatgg cacacatgnn nnnnnnnnnn nnnggcgccg     3720
gcgcgcgcgg cnnnnnnnnn nnnnnnnnnn nnnnnnnnnn nnnnnnnnnn nnnnnnnnnn     3780
nnnnnnnnnn nnnnnnnnnn nnnnnnnnnn nnntgagttc cctagacccc tgcnnnnnnn     3840
nnnnnnnnnn nnnnnnnnnn nngaataaga cagtgagaat tggtgtgtgg cagagggagn     3900
nnnnnnnnnn nnnnnnnnnn nnnnnnnnnn nnnnnnnnnn nnnnnnnnnn nnnnnnnnnn     3960
nnnnnnnttt gtgtgatcac ggctcactgc annnnnnnnn nnnnnnnnnn nnnnnnnnnn     4020
nnnnnnnnnn nnnnnnnnnn nnnnnnnnnn nnnnnnnnnn nnnnnnnnnn nnnnnnnnnn     4080
nnnnnnnnnn nnnnnnnnnn nnnnnnnnnn nnnnnnnnnn nnnnnnnnnn nnnnnnnnnn     4140
nnnnnnnnnn nctggttctg gtaagtcaac aaannnnnca gtggacctag tcaaacaggg     4200
acacannnnn nnnnnnnnnn nnnnnnnnnn nnnnnnnnnn aaaagtatgg cccctnnnn     4260
nnnnnnnnnn nnnnnnnnnn nnnnnnnnnn nnnngctggc acaggtcctn nnnnnnnnnn     4320
nnnnnnnnnn nnnnnnnnnn nnnnnnnnnn nnnnnnnnnc cgcttccttg tggagccnnn     4380
nnnnnntcgg cggggttcg ctgtagtcat ttgcgtcgag tgccatgaac acatcactcc      4440
accacgcgac tcggcggcgg ctcagtgcgc atgtatggag aaagctggag tgaagtccgt     4500
tgtatttgcg acagacactt ctgctggcat tcaagtacag tcacattctc aacattgatg     4560
aatatctatt gactgataca ggcgacgtgg aattnnnnnn nnnnnnnnnn nnnnnnnnnn     4620
nnnnnnnnnn nnnnnnnnnn nnnnnnnnnn nnnnnnnnnn nnnnnnnnnn nnnnnnnnnn     4680
nnnagcagct ctccggcctt ggacagtcgt gcagtgagtt ttnnnnnnnn nnnnnnnnnn     4740
nnnnnnnntc ccgcctcaga cacacatgtt gtggtggcaa ctgcatgaat ttccacgcta     4800
cacaggaaac tnnnnnnnnn nnnnnnnnnn nnnnnnnnnn nnnnnnnnnn nnnnnnnnnn     4860
nnnnnnnnnn nnnnnnnnnn nnnnnnnnnn ccaagatggt gccatgtact gcagcnnnnn     4920
nnnnnnnnnn nnnnnnnnnn nnnnnnnnnn nnnnnnnnnn nnnnnnnnnn nnnnctactc     4980
caggagcagc accctgcgtc ggcgttcccg acgccaacgt ctggcaagca gtggagtcag     5040
ccatggtctt ttatgattgg agtgctgcca ggatacagca gtgtctggcg gcataccatg     5100
atttagggtg tacaccacgc atcagctgtg acccacacac tccagtgcgg gtgatggaca     5160
cactgagggc gtatctgcgc aggcccgagg tgacgactgc agctctcgca ggagagcagt     5220
```

```
ggccgctgct ttacggtgtg cagctgtgca tctgcaaaga gaccgaggcc cacggtccag    5280
acgatggtat caagtggaag tgcttactca acaacagtaa taaaacaccc ctgttgtacg    5340
ccttagacaa tcctcacact ggaattcaca ctcaacatga cttgactcga ccnnnnnnnn    5400
nnnnnnnnnn ngagagcagt gttcgtggag agaggcaacg gccccatcct ccttgctnnn    5460
nnngctttgg ctgcctccat cgcctttgcn nnnnnnnnnn nnnnnnnnnn nnnnnnnnnn    5520
nnnnnnnnnn nnnnngtcag gcctgctggc nnnnnnnnnn nnnnnnnnnn nnnnnnnnnn    5580
nnnnnnnnnn nnnnnnnnnn nnnnnnnnnn nnnncagatt caggaatttn nnnnnnnnnn    5640
nnnnnnnnnn nnnnnnnggt gctgggcaaa ctggcnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnncgga cctgctctgt caccctggct gccaggctgg    5820
cgggggcatt ctggcttttc tgtagctggt gnnnngtgac tccagccctg cttgggggg    5880 tgnncataag tggttgttag ctattgcagg aacttggcta gttagcttgc agactgggcc    5940
ccgtggcggc atggttgcgg gcctctcagt tctagcaggc tgttgcatcg gtagtgtcac    6000
cgggcttgac ttcctgtttg ggtgccttac aggnnnnnnn nnnnnnnnnn nnnnnnnnnn    6060
nnnnnnnnnn nnnnnnnnnn nnnnnncagt agatatctac tcactctggt agatctctac    6120
ntgctctttt ctccccnnnn nnnnnnnnnn nnnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn nnnnnngtg agggatacac acnnnnnnnn nnnnnnnnnn    6360
nnnnnnnnnn nnnnnnnnnn nnnnnnctac gtgctgtgtg ggattgggcg gctcaaacat    6420
gtgccacggt tccgtgtgcc tatgattggc tgctcacctg cgtggtgcgg gcgctggctt    6480
ggtactggca ccttgttgac cacctgtggg tgtggagaac gtgtatccct tcagtgcctt    6540
tgctcaacat ctgacccaca ctcagtgtgg gccgttggtg ttggtgtagt tggagtgttg    6600
ggttccattc aacacgacga cgacagnnnn nnnnnnntta cggccggaca tcgtgacgnn    6660
nncaaattgg gtttccggtt tggtttcgcc gaattcgtgg atttagagcg ccggggaaac    6720
aaatggcatg tctgtgcagc atcatgttgc ttggaccggg ccagcgttgc atccgctgtg    6780
aaggccccac cggtcacggc cgatggcata cctatcagta cctttctcc accacaaact    6840 tattcccaat ctctctgttc ctttgaacnn nnnnnnnnnn nnnnnnnnnn nnnnnnnnnn    6900
nnnagaccct gagtgtgtgc caagagatgc tgtctgagnn nnnnnnnnnn nnagttgaca    6960
cagcacatgt nnnnnnnnnn nnnnnnnnnn nnnnnnnnnn nnnnnnnnng tttgaagcat    7020
ggcaagttcg cgaagcaatt cgcgacgagt cacgcgtttt ggcagacgag gatgttgacg    7080
cgacaacgtc ggtgaaaccc ccggtggcca gggctgctgt gggtagctcg acgttggatg    7140
atgttagcgn nnnnnnnnnn nnnnnnnnnn nnnnnnnnnn nnnnnnnnnn nnnnnnnnnn    7200
nnnnnnnnnn nnnnnnnnnn nnnnnnnnnn nnnnnnnnnn nnnnnnnnnn nnnnnacgc    7260 cgggtgtgtt ggagcgcgtg cgcatgtgca tgcgcaccca cactcaagtt tgaggccatc    7320
ccagtaccaa ttcatagtat aatcccaaaa gagtgtcaca ttgtgctacg ctgtaccggc    7380
tgtaatgacc aggccttgac tgttccgtac ggcacctgca ctcagacttt agccaaacat    7440
ctgactaaca aacacaacac tnnnnnnnnn aagaagata gaagaagaaa caaataagg    7500 ctgtcatttg cgctgtacca acaaagcgcg caaccaaact catcactttc agagcaggtg    7560
```

```
accgatcagt ctcatgttgt caccccttgc aaactcctgt tagggccctg cttgaaaagt    7620
acgggttacc tatcgggaag tggtccgact gcaacggccc gcttggtgac gatgcccgag    7680
tctgtgacgt caatggagta acaacttatg aaccatgcat ggagtcctac agttggttcc    7740
gaccaattgt ggcaccaaca accccacctt tacctgcaac ccggagtgtg ctggcatttt    7800
tacgcgcaga cacatcgcgc gtttacatca aacggcggt tgacgtcccc gagcggcagg    7860
ctaaggtcac aatcgatcaa acatcagcca aggtggatca gtgtttccga nnnnnnnnnn    7920
nnnnnnnnnn nnnnnnnnnn nnnnnnnnnn nnnnnnnnnn nnnnnnnnat gggatgctgt    7980
gtcaaannnn nnnnnnnnnn nnnnnnnnnn nnnnnnnnnn nnnnnnnnnn nnnnnnnnnn    8040
nnnnnnnnnn nnnnnnnnnn nnnnnnnnnn nnnnnnnnnn nnnnnnnnnn nnnnnnnnnn    8100
nnnnnnnnnn nnnntgccag tactccaaaa cctgaagtnn nnnnnnnnnn nnnnnnnnnn    8160
nnnnnnnnnn nnnnttctc gttttccctg ggtgtgcnnn nnnnnnnnnn nnnnnnnnnn    8220
nnnnnnnnnn nnnnnnnnnn nnnnnnnnnn nnnnnnnnnn nnnnnnnnnn nnnnnnnnnn    8280
nnnnnnnnnn nnnnnnnnnn nnnnnactgg ctaacaatgg tggaaccnnn nnnnnnnnnn    8340
nnnnnnnnnn nnnnnnnnnn nnnnnnnnnn nnnnnnnnnn nnnnnnttac aggaaaggaa    8400
gccccatgtg tgnnnnnnnn nnnnnnnnnn nnnnnnnnnn nngctgtcga gcctcagcgt    8460
cagttacaga ccagagagtc gcnnnnnngct tacttgctac cttaannnnn nnncagcttg    8520
cacgcgcgnn nnnnttagac tcaattggct tactaaatta aaggagatgg ctccctcatc    8580
gtgagagaaa gttgagctaa ggaaaaattg atgagttcag caacagcact tgatgnnnnn    8640
nnnnnnnnnn nnnnnntgtc aggtgtctgg ggaccnnnnn nnnnnnnnnn nnnnnnnnnn    8700
nnnnnnnnnn nnnnnnnnnn nnnnnnnnnn nntgcgtcgc atgctcgnnn nnnnnnnnnn    8760
nnnnnnnnnn nnnnnnnnnn nnnnnnnnnn nnnnnnnnna ctgggtacca tcggtagcta    8820
tgttgtcatg tatcccactg cggccgtgac tgtctacgtg ctattgcccc tgttgtgcat    8880
gctcatacga aatgagccat cacagacggg gacacttgtg acgctgacgg tccacggtaa    8940
cagtgtgagc gtgccagtgt ggctgcttcc aaccatnnnn nnnnnnnnnn nnnnnnnnnn    9000
nnnnnnnnnn nnnnnngtc atagttgcag ctgactccat ggcggaactg tnnnnnnnnn    9060
nnnnnnnnnn nnnnnnnnnn nnnnnnnnnn nnnnnnnnnn nnnnnnnnnn nnnnnnnnnn    9120
nnnnnnnnnn nnnnnnnnnn nnnnnnnnnn nnnnnnnnnn nnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnnnnnnnnn    9360
nnnnnnnnnn nnnnnnnnnn nnnaggagga ggtgaagtca gnnnnnnnnn nnnnnnnnnn    9420
nnnnnnnnnn nnnnnnnnnn nnnnnnnnng agttgggcaa ggtannnnnn nnnnnntgag    9480
accccgcccc cccagatcta caccagagag cacgggcaag gcagctaggn nnnnnnnnnn    9540
nnnnnnnnnn nnnnnnnnnn nnnnnnnnnn nnnnnnnnnn nnnnnnnnnn nnnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnnnnnnnnn nnnnnnnnnn nnnnnnnn     9718
```

<210> SEQ ID NO 355
<211> LENGTH: 9353
<212> TYPE: DNA
<213> ORGANISM: Human Pegivirus 2
<220> FEATURE:
<221> NAME/KEY: misc_feature

```
<222> LOCATION: (1)..(233)
<223> OTHER INFORMATION: N = A, C, T, or G
<220> FEATURE:
<221> NAME/KEY: misc_feature
<222> LOCATION: (249)..(484)
<223> OTHER INFORMATION: N = A, C, T, or G
<220> FEATURE:
<221> NAME/KEY: misc_feature
<222> LOCATION: (500)..(696)
<223> OTHER INFORMATION: N = A, C, T, or G
<220> FEATURE:
<221> NAME/KEY: misc_feature
<222> LOCATION: (936)..(1172)
<223> OTHER INFORMATION: N = A, C, T, or G
<220> FEATURE:
<221> NAME/KEY: misc_feature
<222> LOCATION: (1250)..(1409)
<223> OTHER INFORMATION: N = A, C, T, or G
<220> FEATURE:
<221> NAME/KEY: misc_feature
<222> LOCATION: (1250)..(1803)
<223> OTHER INFORMATION: N = A, C, T, or G
<220> FEATURE:
<221> NAME/KEY: misc_feature
<222> LOCATION: (1819)..(1956)
<223> OTHER INFORMATION: N = A, C, T, or G
<220> FEATURE:
<221> NAME/KEY: misc_feature
<222> LOCATION: (2003)..(2079)
<223> OTHER INFORMATION: N = A, C, T, or G
<220> FEATURE:
<221> NAME/KEY: misc_feature
<222> LOCATION: (2221)..(2290)
<223> OTHER INFORMATION: N = A, C, T, or G
<220> FEATURE:
<221> NAME/KEY: misc_feature
<222> LOCATION: (2319)..(3339)
<223> OTHER INFORMATION: N = A, C, T, or G
<220> FEATURE:
<221> NAME/KEY: misc_feature
<222> LOCATION: (3358)..(4492)
<223> OTHER INFORMATION: N = A, C, T, or G
<220> FEATURE:
<221> NAME/KEY: misc_feature
<222> LOCATION: (4509)..(4587)
<223> OTHER INFORMATION: N = A, C, T, or G
<220> FEATURE:
<221> NAME/KEY: misc_feature
<222> LOCATION: (4613)..(4707)
<223> OTHER INFORMATION: N = A, C, T, or G
<220> FEATURE:
<221> NAME/KEY: misc_feature
<222> LOCATION: (4723)..(4755)
<223> OTHER INFORMATION: N = A, C, T, or G
<220> FEATURE:
<221> NAME/KEY: misc_feature
<222> LOCATION: (4781)..(5066)
<223> OTHER INFORMATION: N = A, C, T, or G
<220> FEATURE:
<221> NAME/KEY: misc_feature
<222> LOCATION: (5083)..(6122)
<223> OTHER INFORMATION: N = A, C, T, or G
<220> FEATURE:
<221> NAME/KEY: misc_feature
<222> LOCATION: (6153)..(6414)
<223> OTHER INFORMATION: N = A, C, T, or G
<220> FEATURE:
<221> NAME/KEY: misc_feature
<222> LOCATION: (6440)..(6573)
<223> OTHER INFORMATION: N = A, C, T, or G
<220> FEATURE:
<221> NAME/KEY: misc_feature
<222> LOCATION: (6592)..(6593)
<223> OTHER INFORMATION: N = A, C, T, or G
<220> FEATURE:
<221> NAME/KEY: misc_feature
<222> LOCATION: (6613)..(7289)
<223> OTHER INFORMATION: N = A, C, T, or G
<220> FEATURE:
```

```
<221> NAME/KEY: misc_feature
<222> LOCATION: (7305)..(7309)
<223> OTHER INFORMATION: N = A, C, T, or G
<220> FEATURE:
<221> NAME/KEY: misc_feature
<222> LOCATION: (7340)..(7882)
<223> OTHER INFORMATION: N = A, C, T, or G
<220> FEATURE:
<221> NAME/KEY: misc_feature
<222> LOCATION: (7907)..(9353)
<223> OTHER INFORMATION: N = A, C, T, or G

<400> SEQUENCE: 355
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnatttgtt     240
ctccagtcnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnttttgc tttcttttcn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnggct cgggctgtta gctgagactc     720
ttggtatgtc cgagatctat gcagctgttc tttgcttcgg atttattgct tggtatggct     780
ggggtatacc taaaacgttg gtgtgcacag tctgccctgc agtgaacatt tctccctata     840
gcttcttatc tccagatact atcgcatttg gtacgtggat actacaacta cctggtcttt     900
tgtggcaaat gtttgtcagc tttcctatac tttacnnnnn nnnnnnnnnn nnnnnnnnnn     960
nnnnnnnnnn nnnnnnnnnn nnnnnnnnnn nntgaaccat aaccaatact nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnacatttat ctgttcatgg gggtcgtggt    1200
ggtggtttgc tgagaacatc acacgtccat actcggacgt tggcatgccn nnnnnnnnnn    1260
nnnnnnnnnn nngctatatc tattctaann nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnntgagctt gctacagann nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnacac tgcatcttta ctatagcttt    1980
```

```
gcactggact ttgaatttgc ttnnnnnnnn nnnnnnnnnn nnnnnnnnnn nnnnnnnnnn    2040
nnnnnnnnnn nnnnnnnnnn nnnnnnnnnn nnnnnnnnna tatgcttcct gttatttaag    2100
ctgtgattgg gctgtttgta atgatgcgtt ctgtttcacg tctggcactt gtgctacctt    2160
caatgacgtc ttgtgtctgc cggttgcggc gcgcatatcg tcctgtggcc atgctgtgcc    2220
nnnnnnnnnn nnnnnnnnnn nnnnnnnnnn nnnnnnnnnn nnnnnnnnnn nnnnnnnnnn    2280
nnnnnnnnnn ttagatgtct tttccttcaa ttcagctann nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnntttg atcagtgctc    2700
tacctccagg ttcnnnnngt gcgggcttgg ccgnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn tcttggttgg tggagtnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnng cggttgcttg gaacaagnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnntggttct ggtaagtcaa    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnnnnnnnn nnnnnnnnnn nnnnnnnnnn    4260
nnnnnnnnnn nnnnnnnnnn nnnnnnnnnn nnnnnnnnnn nnnnnnnnnn nnnnnnnnnn    4320
```

```
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nntgctggca    4500
ttcaagtann nnnnnnnnnn nnnnnnnnnn nnnnnnnnnn nnnnnnnnnn nnnnnnnnnn    4560
nnnnnnnnnn nnnnnnnnnn nnnnnnnaca acatcagaac tggtaggtca tgnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnatc aaaaccattc ccnnnnnnnn nnnnnnnnnn    4740
nnnnnnnnnn nnnnngcatt tcaccgctac acaggaaact nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnntgat ttggggtgca cannnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnnnnnnnn nnnnnnnnnn nnnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnn nnnnnnnnnn nnnnnnnnnn nnnnnnnnnn nnnnnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nntgtttcct taagcaattc aagtgtaacc acnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnngcggtg    6420
gtgcgggcgc tgcgcctggn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnncgatacg acaggcactg gnnccttacg    6600
gccggacacg tgannnnnnn nnnnnnnnnn nnnnnnnnnn nnnnnnnnnn nnnnnnnnnn    6660
nnnnnnnnnn nnnnnnnnnn nnnnnnnnnn nnnnnnnnnn nnnnnnnnnn nnnnnnnnnn    6720
```

```
nnnnnnnnnn nnnnnnnnnn nnnnnnnnnn nnnnnnnnnn nnnnnnnnnn nnnnnnnnnn      6780
nnnnnnnnnn nnnnnnnnnn nnnnnnnnnn nnnnnnnnnn nnnnnnnnnn nnnnnnnnnn      6840
nnnnnnnnnn nnnnnnnnnn nnnnnnnnnn nnnnnnnnnn nnnnnnnnnn nnnnnnnnnn      6900
nnnnnnnnnn nnnnnnnnnn nnnnnnnnnn nnnnnnnnnn nnnnnnnnnn nnnnnnnnnn      6960
nnnnnnnnnn nnnnnnnnnn nnnnnnnnnn nnnnnnnnnn nnnnnnnnnn nnnnnnnnnn      7020
nnnnnnnnnn nnnnnnnnnn nnnnnnnnnn nnnnnnnnnn nnnnnnnnnn nnnnnnnnnn      7080
nnnnnnnnnn nnnnnnnnnn nnnnnnnnnn nnnnnnnnnn nnnnnnnnnn nnnnnnnnnn      7140
nnnnnnnnnn nnnnnnnnnn nnnnnnnnnn nnnnnnnnnn nnnnnnnnnn nnnnnnnnnn      7200
nnnnnnnnnn nnnnnnnnnn nnnnnnnnnn nnnnnnnnnn nnnnnnnnnn nnnnnnnnnn      7260
nnnnnnnnnn nnnnnnnnnn nnnnnnnnna ttcataatat aatcnnnnna gagtgtcata      7320
ttgtgctacg ctgtaccggn nnnnnnnnnn nnnnnnnnnn nnnnnnnnnn nnnnnnnnnn      7380
nnnnnnnnnn nnnnnnnnnn nnnnnnnnnn nnnnnnnnnn nnnnnnnnnn nnnnnnnnnn      7440
nnnnnnnnnn nnnnnnnnnn nnnnnnnnnn nnnnnnnnnn nnnnnnnnnn nnnnnnnnnn      7500
nnnnnnnnnn nnnnnnnnnn nnnnnnnnnn nnnnnnnnnn nnnnnnnnnn nnnnnnnnnn      7560
nnnnnnnnnn nnnnnnnnnn nnnnnnnnnn nnnnnnnnnn nnnnnnnnnn nnnnnnnnnn      7620
nnnnnnnnnn nnnnnnnnnn nnnnnnnnnn nnnnnnnnnn nnnnnnnnnn nnnnnnnnnn      7680
nnnnnnnnnn nnnnnnnnnn nnnnnnnnnn nnnnnnnnnn nnnnnnnnnn nnnnnnnnnn      7740
nnnnnnnnnn nnnnnnnnnn nnnnnnnnnn nnnnnnnnnn nnnnnnnnnn nnnnnnnnnn      7800
nnnnnnnnnn nnnnnnnnnn nnnnnnnnnn nnnnnnnnnn nnnnnnnnnn nnnnnnnnnn      7860
nnnnnnnnnn nnnnnnnnnn nnttctgcct tgccaaggca gaagacnnnn nnnnnnnnnn      7920
nnnnnnnnnn nnnnnnnnnn nnnnnnnnnn nnnnnnnnnn nnnnnnnnnn nnnnnnnnnn      7980
nnnnnnnnnn nnnnnnnnnn nnnnnnnnnn nnnnnnnnnn nnnnnnnnnn nnnnnnnnnn      8040
nnnnnnnnnn nnnnnnnnnn nnnnnnnnnn nnnnnnnnnn nnnnnnnnnn nnnnnnnnnn      8100
nnnnnnnnnn nnnnnnnnnn nnnnnnnnnn nnnnnnnnnn nnnnnnnnnn nnnnnnnnnn      8160
nnnnnnnnnn nnnnnnnnnn nnnnnnnnnn nnnnnnnnnn nnnnnnnnnn nnnnnnnnnn      8220
nnnnnnnnnn nnnnnnnnnn nnnnnnnnnn nnnnnnnnnn nnnnnnnnnn nnnnnnnnnn      8280
nnnnnnnnnn nnnnnnnnnn nnnnnnnnnn nnnnnnnnnn nnnnnnnnnn nnnnnnnnnn      8340
nnnnnnnnnn nnnnnnnnnn nnnnnnnnnn nnnnnnnnnn nnnnnnnnnn nnnnnnnnnn      8400
nnnnnnnnnn nnnnnnnnnn nnnnnnnnnn nnnnnnnnnn nnnnnnnnnn nnnnnnnnnn      8460
nnnnnnnnnn nnnnnnnnnn nnnnnnnnnn nnnnnnnnnn nnnnnnnnnn nnnnnnnnnn      8520
nnnnnnnnnn nnnnnnnnnn nnnnnnnnnn nnnnnnnnnn nnnnnnnnnn nnnnnnnnnn      8580
nnnnnnnnnn nnnnnnnnnn nnnnnnnnnn nnnnnnnnnn nnnnnnnnnn nnnnnnnnnn      8640
nnnnnnnnnn nnnnnnnnnn nnnnnnnnnn nnnnnnnnnn nnnnnnnnnn nnnnnnnnnn      8700
nnnnnnnnnn nnnnnnnnnn nnnnnnnnnn nnnnnnnnnn nnnnnnnnnn nnnnnnnnnn      8760
nnnnnnnnnn nnnnnnnnnn nnnnnnnnnn nnnnnnnnnn nnnnnnnnnn nnnnnnnnnn      8820
nnnnnnnnnn nnnnnnnnnn nnnnnnnnnn nnnnnnnnnn nnnnnnnnnn nnnnnnnnnn      8880
nnnnnnnnnn nnnnnnnnnn nnnnnnnnnn nnnnnnnnnn nnnnnnnnnn nnnnnnnnnn      8940
nnnnnnnnnn nnnnnnnnnn nnnnnnnnnn nnnnnnnnnn nnnnnnnnnn nnnnnnnnnn      9000
nnnnnnnnnn nnnnnnnnnn nnnnnnnnnn nnnnnnnnnn nnnnnnnnnn nnnnnnnnnn      9060
```

-continued

```
nnnnnnnnnn nnnnnnnnnn nnnnnnnnnn nnnnnnnnnn nnnnnnnnnn nnnnnnnnnn    9120
nnnnnnnnnn nnnnnnnnnn nnnnnnnnnn nnnnnnnnnn nnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnn           9353

<210> SEQ ID NO 356
<211> LENGTH: 9818
<212> TYPE: DNA
<213> ORGANISM: Human Pegivirus 2
<220> FEATURE:
<221> NAME/KEY: misc_feature
<222> LOCATION: (35)..(135)
<223> OTHER INFORMATION: N = A, C, T or G
<220> FEATURE:
<221> NAME/KEY: misc_feature
<222> LOCATION: (155)..(195)
<223> OTHER INFORMATION: N = A, C, T or G
<220> FEATURE:
<221> NAME/KEY: misc_feature
<222> LOCATION: (211)..(317)
<223> OTHER INFORMATION: N = A, C, T or G
<220> FEATURE:
<221> NAME/KEY: misc_feature
<222> LOCATION: (333)..(338)
<223> OTHER INFORMATION: N = A, C, T or G
<220> FEATURE:
<221> NAME/KEY: misc_feature
<222> LOCATION: (357)..(458)
<223> OTHER INFORMATION: N = A, C, T or G
<220> FEATURE:
<221> NAME/KEY: misc_feature
<222> LOCATION: (480)..(513)
<223> OTHER INFORMATION: N = A, C, T or G
<220> FEATURE:
<221> NAME/KEY: misc_feature
<222> LOCATION: (559)..(625)
<223> OTHER INFORMATION: N = A, C, T or G
<220> FEATURE:
<221> NAME/KEY: misc_feature
<222> LOCATION: (646)..(671)
<223> OTHER INFORMATION: N = A, C, T or G
<220> FEATURE:
<221> NAME/KEY: misc_feature
<222> LOCATION: (730)..(730)
<223> OTHER INFORMATION: N = A, C, T or G
<220> FEATURE:
<221> NAME/KEY: misc_feature
<222> LOCATION: (733)..(733)
<223> OTHER INFORMATION: N = A, C, T or G
<220> FEATURE:
<221> NAME/KEY: misc_feature
<222> LOCATION: (760)..(760)
<223> OTHER INFORMATION: N = A, C, T or G
<220> FEATURE:
<221> NAME/KEY: misc_feature
<222> LOCATION: (1084)..(1084)
<223> OTHER INFORMATION: N = A, C, T or G
<220> FEATURE:
<221> NAME/KEY: misc_feature
<222> LOCATION: (1165)..(1165)
<223> OTHER INFORMATION: N = A, C, T or G
<220> FEATURE:
<221> NAME/KEY: misc_feature
<222> LOCATION: (1210)..(1210)
<223> OTHER INFORMATION: N = A, C, T or G
<220> FEATURE:
<221> NAME/KEY: misc_feature
<222> LOCATION: (1243)..(1243)
<223> OTHER INFORMATION: N = A, C, T or G
<220> FEATURE:
<221> NAME/KEY: misc_feature
<222> LOCATION: (1315)..(1315)
<223> OTHER INFORMATION: N = A, C, T or G
```

-continued

```
<220> FEATURE:
<221> NAME/KEY: misc_feature
<222> LOCATION: (1338)..(1483)
<223> OTHER INFORMATION: N = A, C, T or G
<220> FEATURE:
<221> NAME/KEY: misc_feature
<222> LOCATION: (1502)..(1579)
<223> OTHER INFORMATION: N = A, C, T or G
<220> FEATURE:
<221> NAME/KEY: misc_feature
<222> LOCATION: (1606)..(1630)
<223> OTHER INFORMATION: N = A, C, T or G
<220> FEATURE:
<221> NAME/KEY: misc_feature
<222> LOCATION: (1722)..(1722)
<223> OTHER INFORMATION: N = A, C, T or G
<220> FEATURE:
<221> NAME/KEY: misc_feature
<222> LOCATION: (1789)..(1817)
<223> OTHER INFORMATION: N = A, C, T or G
<220> FEATURE:
<221> NAME/KEY: misc_feature
<222> LOCATION: (2006)..(2006)
<223> OTHER INFORMATION: N = A, C, T or G
<220> FEATURE:
<221> NAME/KEY: misc_feature
<222> LOCATION: (2065)..(2101)
<223> OTHER INFORMATION: N = A, C, T or G
<220> FEATURE:
<221> NAME/KEY: misc_feature
<222> LOCATION: (2213)..(2213)
<223> OTHER INFORMATION: N = A, C, T or G
<220> FEATURE:
<221> NAME/KEY: misc_feature
<222> LOCATION: (2335)..(2335)
<223> OTHER INFORMATION: N = A, C, T or G
<220> FEATURE:
<221> NAME/KEY: misc_feature
<222> LOCATION: (2447)..(2447)
<223> OTHER INFORMATION: N = A, C, T or G
<220> FEATURE:
<221> NAME/KEY: misc_feature
<222> LOCATION: (2449)..(2449)
<223> OTHER INFORMATION: N = A, C, T or G
<220> FEATURE:
<221> NAME/KEY: misc_feature
<222> LOCATION: (2560)..(2560)
<223> OTHER INFORMATION: N = A, C, T or G
<220> FEATURE:
<221> NAME/KEY: misc_feature
<222> LOCATION: (2582)..(2582)
<223> OTHER INFORMATION: N = A, C, T or G
<220> FEATURE:
<221> NAME/KEY: misc_feature
<222> LOCATION: (2632)..(2640)
<223> OTHER INFORMATION: N = A, C, T or G
<220> FEATURE:
<221> NAME/KEY: misc_feature
<222> LOCATION: (2667)..(2668)
<223> OTHER INFORMATION: N = A, C, T or G
<220> FEATURE:
<221> NAME/KEY: misc_feature
<222> LOCATION: (2705)..(2708)
<223> OTHER INFORMATION: N = A, C, T or G
<220> FEATURE:
<221> NAME/KEY: misc_feature
<222> LOCATION: (2737)..(2741)
<223> OTHER INFORMATION: N = A, C, T or G
<220> FEATURE:
<221> NAME/KEY: misc_feature
<222> LOCATION: (2757)..(2863)
<223> OTHER INFORMATION: N = A, C, T or G
<220> FEATURE:
<221> NAME/KEY: misc_feature
<222> LOCATION: (2880)..(2906)
<223> OTHER INFORMATION: N = A, C, T or G
<220> FEATURE:
<221> NAME/KEY: misc_feature
<222> LOCATION: (2925)..(2963)
```

```
<223> OTHER INFORMATION: N = A, C, T or G
<220> FEATURE:
<221> NAME/KEY: misc_feature
<222> LOCATION: (2979)..(2987)
<223> OTHER INFORMATION: N = A, C, T or G
<220> FEATURE:
<221> NAME/KEY: misc_feature
<222> LOCATION: (2979)..(3057)
<223> OTHER INFORMATION: N = A, C, T or G
<220> FEATURE:
<221> NAME/KEY: misc_feature
<222> LOCATION: (3079)..(3079)
<223> OTHER INFORMATION: N = A, C, T or G
<220> FEATURE:
<221> NAME/KEY: misc_feature
<222> LOCATION: (3174)..(3290)
<223> OTHER INFORMATION: N = A, C, T or G
<220> FEATURE:
<221> NAME/KEY: misc_feature
<222> LOCATION: (3295)..(3295)
<223> OTHER INFORMATION: N = A, C, T or G
<220> FEATURE:
<221> NAME/KEY: misc_feature
<222> LOCATION: (3327)..(3362)
<223> OTHER INFORMATION: N = A, C, T or G
<220> FEATURE:
<221> NAME/KEY: misc_feature
<222> LOCATION: (3381)..(3385)
<223> OTHER INFORMATION: N = A, C, T or G
<220> FEATURE:
<221> NAME/KEY: misc_feature
<222> LOCATION: (3401)..(3425)
<223> OTHER INFORMATION: N = A, C, T or G
<220> FEATURE:
<221> NAME/KEY: misc_feature
<222> LOCATION: (3449)..(3503)
<223> OTHER INFORMATION: N = A, C, T or G
<220> FEATURE:
<221> NAME/KEY: misc_feature
<222> LOCATION: (3519)..(3523)
<223> OTHER INFORMATION: N = A, C, T or G
<220> FEATURE:
<221> NAME/KEY: misc_feature
<222> LOCATION: (3539)..(3579)
<223> OTHER INFORMATION: N = A, C, T or G
<220> FEATURE:
<221> NAME/KEY: misc_feature
<222> LOCATION: (3605)..(3676)
<223> OTHER INFORMATION: N = A, C, T or G
<220> FEATURE:
<221> NAME/KEY: misc_feature
<222> LOCATION: (3695)..(3709)
<223> OTHER INFORMATION: N = A, C, T or G
<220> FEATURE:
<221> NAME/KEY: misc_feature
<222> LOCATION: (3728)..(3809)
<223> OTHER INFORMATION: N = A, C, T or G
<220> FEATURE:
<221> NAME/KEY: misc_feature
<222> LOCATION: (3830)..(3858)
<223> OTHER INFORMATION: N = A, C, T or G
<220> FEATURE:
<221> NAME/KEY: misc_feature
<222> LOCATION: (3896)..(3963)
<223> OTHER INFORMATION: N = A, C, T or G
<220> FEATURE:
<221> NAME/KEY: misc_feature
<222> LOCATION: (3986)..(4145)
<223> OTHER INFORMATION: N = A, C, T or G
<220> FEATURE:
<221> NAME/KEY: misc_feature
<222> LOCATION: (4168)..(4172)
<223> OTHER INFORMATION: N = A, C, T or G
<220> FEATURE:
<221> NAME/KEY: misc_feature
<222> LOCATION: (4200)..(4234)
<223> OTHER INFORMATION: N = A, C, T or G
<220> FEATURE:
<221> NAME/KEY: misc_feature
```

```
<222> LOCATION: (4251)..(4288)
<223> OTHER INFORMATION: N = A, C, T or G
<220> FEATURE:
<221> NAME/KEY: misc_feature
<222> LOCATION: (4304)..(4353)
<223> OTHER INFORMATION: N = A, C, T or G
<220> FEATURE:
<221> NAME/KEY: misc_feature
<222> LOCATION: (4372)..(4380)
<223> OTHER INFORMATION: N = A, C, T or G
<220> FEATURE:
<221> NAME/KEY: misc_feature
<222> LOCATION: (4390)..(4390)
<223> OTHER INFORMATION: N = A, C, T or G
<220> FEATURE:
<221> NAME/KEY: misc_feature
<222> LOCATION: (4471)..(4471)
<223> OTHER INFORMATION: N = A, C, T or G
<220> FEATURE:
<221> NAME/KEY: misc_feature
<222> LOCATION: (4588)..(4610)
<223> OTHER INFORMATION: N = A, C, T or G
<220> FEATURE:
<221> NAME/KEY: misc_feature
<222> LOCATION: (4635)..(4676)
<223> OTHER INFORMATION: N = A, C, T or G
<220> FEATURE:
<221> NAME/KEY: misc_feature
<222> LOCATION: (4715)..(4729)
<223> OTHER INFORMATION: N = A, C, T or G
<220> FEATURE:
<221> NAME/KEY: misc_feature
<222> LOCATION: (4756)..(4756)
<223> OTHER INFORMATION: N = A, C, T or G
<220> FEATURE:
<221> NAME/KEY: misc_feature
<222> LOCATION: (4782)..(4783)
<223> OTHER INFORMATION: N = A, C, T or G
<220> FEATURE:
<221> NAME/KEY: misc_feature
<222> LOCATION: (4785)..(4785)
<223> OTHER INFORMATION: N = A, C, T or G
<220> FEATURE:
<221> NAME/KEY: misc_feature
<222> LOCATION: (4791)..(4791)
<223> OTHER INFORMATION: N = A, C, T or G
<220> FEATURE:
<221> NAME/KEY: misc_feature
<222> LOCATION: (4806)..(4884)
<223> OTHER INFORMATION: N = A, C, T or G
<220> FEATURE:
<221> NAME/KEY: misc_feature
<222> LOCATION: (4909)..(4967)
<223> OTHER INFORMATION: N = A, C, T or G
<220> FEATURE:
<221> NAME/KEY: misc_feature
<222> LOCATION: (5098)..(5098)
<223> OTHER INFORMATION: N = A, C, T or G
<220> FEATURE:
<221> NAME/KEY: misc_feature
<222> LOCATION: (5362)..(5362)
<223> OTHER INFORMATION: N = A, C, T or G
<220> FEATURE:
<221> NAME/KEY: misc_feature
<222> LOCATION: (5385)..(5403)
<223> OTHER INFORMATION: N = A, C, T or G
<220> FEATURE:
<221> NAME/KEY: misc_feature
<222> LOCATION: (5450)..(5455)
<223> OTHER INFORMATION: N = A, C, T or G
<220> FEATURE:
<221> NAME/KEY: misc_feature
<222> LOCATION: (5482)..(5527)
<223> OTHER INFORMATION: N = A, C, T or G
<220> FEATURE:
<221> NAME/KEY: misc_feature
<222> LOCATION: (5543)..(5606)
<223> OTHER INFORMATION: N = A, C, T or G
<220> FEATURE:
```

```
<221> NAME/KEY: misc_feature
<222> LOCATION: (5600)..(5649)
<223> OTHER INFORMATION: N = A, C, T or G
<220> FEATURE:
<221> NAME/KEY: misc_feature
<222> LOCATION: (5668)..(5778)
<223> OTHER INFORMATION: N = A, C, T or G
<220> FEATURE:
<221> NAME/KEY: misc_feature
<222> LOCATION: (5830)..(5830)
<223> OTHER INFORMATION: N = A, C, T or G
<220> FEATURE:
<221> NAME/KEY: misc_feature
<222> LOCATION: (5840)..(5843)
<223> OTHER INFORMATION: N = A, C, T or G
<220> FEATURE:
<221> NAME/KEY: misc_feature
<222> LOCATION: (5868)..(5869)
<223> OTHER INFORMATION: N = A, C, T or G
<220> FEATURE:
<221> NAME/KEY: misc_feature
<222> LOCATION: (6019)..(6071)
<223> OTHER INFORMATION: N = A, C, T or G
<220> FEATURE:
<221> NAME/KEY: misc_feature
<222> LOCATION: (6101)..(6101)
<223> OTHER INFORMATION: N = A, C, T or G
<220> FEATURE:
<221> NAME/KEY: misc_feature
<222> LOCATION: (6105)..(6105)
<223> OTHER INFORMATION: N = A, C, T or G
<220> FEATURE:
<221> NAME/KEY: misc_feature
<222> LOCATION: (6121)..(6147)
<223> OTHER INFORMATION: N = A, C, T or G
<220> FEATURE:
<221> NAME/KEY: misc_feature
<222> LOCATION: (6157)..(6157)
<223> OTHER INFORMATION: N = A, C, T or G
<220> FEATURE:
<221> NAME/KEY: misc_feature
<222> LOCATION: (6181)..(6311)
<223> OTHER INFORMATION: N = A, C, T or G
<220> FEATURE:
<221> NAME/KEY: misc_feature
<222> LOCATION: (6327)..(6370)
<223> OTHER INFORMATION: N = A, C, T or G
<220> FEATURE:
<221> NAME/KEY: misc_feature
<222> LOCATION: (6543)..(6543)
<223> OTHER INFORMATION: N = A, C, T or G
<220> FEATURE:
<221> NAME/KEY: misc_feature
<222> LOCATION: (6619)..(6620)
<223> OTHER INFORMATION: N = A, C, T or G
<220> FEATURE:
<221> NAME/KEY: misc_feature
<222> LOCATION: (6638)..(6638)
<223> OTHER INFORMATION: N = A, C, T or G
<220> FEATURE:
<221> NAME/KEY: misc_feature
<222> LOCATION: (6645)..(6648)
<223> OTHER INFORMATION: N = A, C, T or G
<220> FEATURE:
<221> NAME/KEY: misc_feature
<222> LOCATION: (6679)..(6679)
<223> OTHER INFORMATION: N = A, C, T or G
<220> FEATURE:
<221> NAME/KEY: misc_feature
<222> LOCATION: (6831)..(6831)
<223> OTHER INFORMATION: N = A, C, T or G
<220> FEATURE:
<221> NAME/KEY: misc_feature
<222> LOCATION: (6856)..(6890)
<223> OTHER INFORMATION: N = A, C, T or G
<220> FEATURE:
<221> NAME/KEY: misc_feature
<222> LOCATION: (6926)..(6939)
<223> OTHER INFORMATION: N = A, C, T or G
```

```
<220> FEATURE:
<221> NAME/KEY: misc_feature
<222> LOCATION: (6958)..(6996)
<223> OTHER INFORMATION: N = A, C, T or G
<220> FEATURE:
<221> NAME/KEY: misc_feature
<222> LOCATION: (7137)..(7233)
<223> OTHER INFORMATION: N = A, C, T or G
<220> FEATURE:
<221> NAME/KEY: misc_feature
<222> LOCATION: (7288)..(7288)
<223> OTHER INFORMATION: N = A, C, T or G
<220> FEATURE:
<221> NAME/KEY: misc_feature
<222> LOCATION: (7348)..(7348)
<223> OTHER INFORMATION: N = A, C, T or G
<220> FEATURE:
<221> NAME/KEY: misc_feature
<222> LOCATION: (7452)..(7463)
<223> OTHER INFORMATION: N = A, C, T or G
<220> FEATURE:
<221> NAME/KEY: misc_feature
<222> LOCATION: (7901)..(7912)
<223> OTHER INFORMATION: N = A, C, T or G
<220> FEATURE:
<221> NAME/KEY: misc_feature
<222> LOCATION: (7937)..(7958)
<223> OTHER INFORMATION: N = A, C, T or G
<220> FEATURE:
<221> NAME/KEY: misc_feature
<222> LOCATION: (7978)..(8105)
<223> OTHER INFORMATION: N = A, C, T or G
<220> FEATURE:
<221> NAME/KEY: misc_feature
<222> LOCATION: (8131)..(8167)
<223> OTHER INFORMATION: N = A, C, T or G
<220> FEATURE:
<221> NAME/KEY: misc_feature
<222> LOCATION: (8191)..(8298)
<223> OTHER INFORMATION: N = A, C, T or G
<220> FEATURE:
<221> NAME/KEY: misc_feature
<222> LOCATION: (8319)..(8349)
<223> OTHER INFORMATION: N = A, C, T or G
<220> FEATURE:
<221> NAME/KEY: misc_feature
<222> LOCATION: (8373)..(8457)
<223> OTHER INFORMATION: N = A, C, T or G
<220> FEATURE:
<221> NAME/KEY: misc_feature
<222> LOCATION: (8481)..(8510)
<223> OTHER INFORMATION: N = A, C, T or G
<220> FEATURE:
<221> NAME/KEY: misc_feature
<222> LOCATION: (8527)..(8531)
<223> OTHER INFORMATION: N = A, C, T or G
<220> FEATURE:
<221> NAME/KEY: misc_feature
<222> LOCATION: (8537)..(8539)
<223> OTHER INFORMATION: N = A, C, T or G
<220> FEATURE:
<221> NAME/KEY: misc_feature
<222> LOCATION: (8542)..(8544)
<223> OTHER INFORMATION: N = A, C, T or G
<220> FEATURE:
<221> NAME/KEY: misc_feature
<222> LOCATION: (8551)..(8555)
<223> OTHER INFORMATION: N = A, C, T or G
<220> FEATURE:
<221> NAME/KEY: misc_feature
<222> LOCATION: (8574)..(8581)
<223> OTHER INFORMATION: N = A, C, T or G
<220> FEATURE:
<221> NAME/KEY: misc_feature
<222> LOCATION: (8597)..(8602)
<223> OTHER INFORMATION: N = A, C, T or G
<220> FEATURE:
<221> NAME/KEY: misc_feature
<222> LOCATION: (8702)..(8722)
```

<223> OTHER INFORMATION: N = A, C, T or G
<220> FEATURE:
<221> NAME/KEY: misc_feature
<222> LOCATION: (8741)..(8797)
<223> OTHER INFORMATION: N = A, C, T or G
<220> FEATURE:
<221> NAME/KEY: misc_feature
<222> LOCATION: (8813)..(8864)
<223> OTHER INFORMATION: N = A, C, T or G
<220> FEATURE:
<221> NAME/KEY: misc_feature
<222> LOCATION: (9042)..(9082)
<223> OTHER INFORMATION: N = A, C, T or G
<220> FEATURE:
<221> NAME/KEY: misc_feature
<222> LOCATION: (9113)..(9818)
<223> OTHER INFORMATION: N = A, C, T or G

<400> SEQUENCE: 356

```
gtgtttgaca atgccatgag ggatcatgac actgnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnngcaaa gggatgggtc cctgnnnnnn nnnnnnnnnn nnnnnnnnnn     180
nnnnnnnnnn nnnnnggtgg cggcgggccc nnnnnnnnnn nnnnnnnnnn nnnnnnnnnn     240
nnnnnnnnnn nnnnnnnnnn nnatttgttc tccagtcnnn nnnnnnnnnn nnnnnnnnnn     300
nnnnnnnnnn nnnnnnntaa atgggagcta ccnnnnnngt ggtggctctt gccggtnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnngc  attgagtcag ggcaaatatn     480
nnnnnnnnnn nnnnnnnnnn nnnnnnnnnn nnntttgct  ttcttttcta actgttgcaa     540
tcaatctgat attatgtgnn nnnnnnnnnn nnnnnnnnnn nnnnnnnnnn nnnnnnnnnn     600
nnnnnnnnnn nnnnnnnnnn nnnnatctg  ctgggactat cttggnnnnn nnnnnnnnnn     660
nnnnnnnnnn ngtcgaatgg gtgagggagc tgaagcgctt cttcgcttga tcggcattgc     720
aggttggctn ggnctgttag ctgagtctct tggtatgtcn gagatctatg cagctattct     780
ttgctttgga tttattgctt ggtatggctg gggtataacct aaaacattgg tgtgcacagt     840
ctgccctgca gtgaacattt ctccctatag cttcttatct ccagatacta tcgcatttgg     900
tacgtggata ctacaactac ctggtctttt gtggcaaatg tttgtcagct tccctatact     960
ttacagtact tggattcttt ggttgttgct cagcggcaag actgttgctg tgatagcgat    1020
ccttttggct agtcctacgg ttatggcata caagcatcaa tctgaaagct acctcaaata    1080
ctgnaccata accaatactt caactgctat gaactgtgac tgcccctttg aactttcac     1140
tcgcaatact gagtctggtt tctcnatacc tagattctgt cctgttaaaa tcaatagctc    1200
tacatttatn tgttcatggg ggtcgtggtg gtggtttgct ganaacatca cacgtccata    1260
ctcggacgtt ggcatgccgc cagcaccgat ttccgctttg tgctatatct attcnaacaa    1320
tgacccacct tcttggtnnn nnnnnnnnn nnnnnnnnnn nnnnnnnnnn nnnnnnnnnn     1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnttctata ctaatggtag    1500
tnnnnnnnnn nnnnnnnnnn nnnnnnnnnn nnnnnnnnnn nnnnnnnnnn nnnnnnnnnn    1560
nnnnnnnnnn nnnnnnnnnc ctaacatctc gaatacgacc attgannnnn nnnnnnnnn     1620
nnnnnnnnnn atcgcatccg gtcttcgggc tgggtatggt tgcagccgag cgcacggcgt    1680
ggtgcactgc tttaagtgtc cttcataccg tgaccttgaa cngttggtc  ctgggcttgg    1740
gaaatgggtg ccattgcctg gcgagcctgt cccggagttg tgtattaann nnnnnnnnnn    1800
```

```
nnnnnnnnnn nnnnggntgt ctaataatcc tttgagcttg ctacagacct tcgttgagga    1860
cattttccta gcgccttttt gcaatccgac gcctggccgt gtacgtgtgt gtaacaatac    1920
tgctttctat ccgagaggag gcggctttgt gcagctcatc ggagacgtcc aggtgctaac    1980
ccctaacact gcatctttac actctntgct gactttgata tcgcttatct tgttggtgtg    2040
tgttgtttct ggtgcgcgat tcgtnnnnnn nnnnnnnnnn nnnnnnnnnn nnnnnnnnnn    2100
ngtatatgct tcttgttact taagctgtga ttgggctgtt tgcaacgatg cgttctgttt    2160
cacatctggc acttgtgcta ccttcaatga cgtcttgtgt ctgccggttg cgncgcgcat    2220
atcgtcctgt ggccatgctg tgccacctcc cgaccgtggt tgggaggtgc ctgcggcgat    2280
gtcatgggcg atttcgcgga ctactggctt gacgttcgat gtcttttcct tcatncagta    2340
ccttcctact gtgcctggca acaataccga tatcatttac tgtggtgaac caaccttctt    2400
cggggacatc acgggcatct attggcctta cttttttgcct ggcgtgntnc tcttgtactt    2460
gactcccttc ctgggtttaa ggttaatgct tgccggcttc aatatagatg gcttgtttcc    2520
catacggcat gccacggctg cactgaggtt ctcgacttcn cgtgtgacct tgtgtgtcgt    2580
anttgctttc ctaatctata tattatctca tcctgttaat gctgcgctca annnnnnnnn    2640
cttagcatct gcaaatttag agatgannnn atcttttgat acctatcatg agactgttct    2700
ttatnnnntt tgtctattgc tctacctcca ggtgtcnnnn ngtgcgggct tggccgnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnntcttggt tggtggagtn    2880
nnnnnnnnnn nnnnnnnnnn nnnnnncctg tgtcttctct ttttnnnnnn nnnnnnnnnn    2940
nnnnnnnnnn nnnnnnnnnn nnnactataa gattcagann nnnnnnnnnn nnnnnnnnnn    3000
nnnnnnnnnn nnnnnnnnnn nnnnnnnnnn nnnnnnnnnn nnnnnnnnnn nnnnnnnccg    3060
tgcaagtgtg ggcgtgctnt ggtgtggagc ttgcatgctc tggccccgtg agtgctctga    3120
aatcagcctg gtcttcattc tgtgtgctct gacagtggac accatagaca catnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn cacgnggcac    3300
atacatatac aaccacatgg gccaagnnnn nnnnnnnnnn nnnnnnnnnn nnnnnnnnnn    3360
nngcggttgc ttggaaccag nnnnnttgga ggagcccacc nnnnnnnnnn nnnnnnnnnn    3420
nnnnntgagt ttggtgtgtg gacaattgnn nnnnnnnnnn nnnnnnnnnn nnnnnnnnnn    3480
nnnnnnnnnn nnnnnnnnnn nnntcaaccc tgaagatcnn nnncctggtt tccagctgnn    3540
nnnnnnnnnn nnnnnnnnnn nnnnnnnnnn nnnnnnnnng tccttcctta aggcgacact    3600
cacannnnnn nnnnnnnnnn nnnnnnnnnn nnnnnnnnnn nnnnnnnnnn nnnnnnnnnn    3660
nnnnnnnnnn nnnnnngcag tgaatggcac actgnnnnnn nnnnnnnnng gtgccggcgc    3720
gcgcggcnnn nnnnnnnnnn nnnnnnnnnn nnnnnnnnnn nnnnnnnnnn nnnnnnnnnn    3780
nnnnnnnnnn nnnnnnnnnn nnnnnnnnnt gagttcccta gacccctgcn nnnnnnnnnn    3840
nnnnnnnnnn nnnnnnnnga ataacaacgg agggttggtg tgtggcagag tggagnnnnn    3900
nnnnnnnnnn nnnnnnnnnn nnnnnnnnnn nnnnnnnnnn nnnnnnnnnn nnnnnnnnnn    3960
nnntttgtgt gatcacggtc atgcannnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
```

```
nnnnnctggt tctggtaagt caacaaannn nncagtggac ctagtcaaac agggacacan    4200
nnnnnnnnnn nnnnnnnnnn nnnnnnnnnn nnnnaaaagt atggccccct tnnnnnnnnn    4260
nnnnnnnnnn nnnnnnnnnn nnnnnnnngc tggcacaggt cctnnnnnnn nnnnnnnnnn    4320
nnnnnnnnnn nnnnnnnnnn nnnnnnnnnn nnnccgcttc cttgtggatc cnnnnnnnnn    4380
tctgcgggn tacgctgtag tcatttgcga cgagtgccat gacacatcat ccaccacgct    4440
actcggcatc ggcgcagtgc gcatgtatgc ngagaaagct ggagtgaaga ccgttgtatt    4500
cgccacagcc actcctgctg gcattcaagt acagtcacat tccaacattg atgaatatct    4560
attgactgat acaggcgacg tggaattnnn nnnnnnnnnn nnnnnnnnnn acaacatcag    4620
aactggtaga catgnnnnnn nnnnnnnnnn nnnnnnnnnn nnnnnnnnnn nnnnnnagca    4680
gctctccggc cttggcattc gtgcagtgag ttttnnnnnn nnnnnnnnna tcaaaaccat    4740
tcccgcctca gactcnattg ttgtggtggc aactgatgca tnntncaccg nctacacagg    4800
aaactnnnnn nnnnnnnnnn nnnnnnnnnn nnnnnnnnnn nnnnnnnnnn nnnnnnnnnn    4860
nnnnnnnnnn nnnnnnnnnn nnnnccgagt ggtgccatgt actgctgcnn nnnnnnnnn    4920
nnnnnnnnnn nnnnnnnnnn nnnnnnnnnn nnnnnnnnnn nnnnnncta ctccaggagc    4980
agcaccctgc gtcagcgttc ccgatgctaa cgtctggcaa gcagtggagt cagccatggt    5040
cttttatgat tggagtgctg ccaggataca gcagtgcctg gcggcatacc atgatttngg    5100
gtgcacacca cgcatcagct gtgacccaca cactccagtg cgggtgatgg acacactgag    5160
ggcgtatctg cgcagacctg aggtgacgac tgcagctctc gcaggagagc agtggccgct    5220
gctttacggt gtgcagttgt gcatctgcaa agagaccgag gcccacggtc cagacgatgg    5280
catcaagtgg aagtgcttac tcaacaacag taacaaaaca ccctgttgt atgccttaga    5340
caatcctaca ctggaattca cnacccaaca tgacttgact cgccnnnnnn nnnnnnnnnn    5400
nnngagcaca gtgttcgtgg agacaggcta cggccccatc ctccttgctn nnnngctttt    5460
ggctgcctcc ttcgcctttg cnnnnnnnnn nnnnnnnnnn nnnnnnnnnn nnnnnnnnnn    5520
nnnnnnngtc aggcctgctg gcnnnnnnnn nnnnnnnnnn nnnnnnnnnn nnnnnnnnnn    5580
nnnnnnnnnn nnnnnnnnnn nnnnnncaga ttcaggaatt tnnnnnnnnn nnnnnnnnnn    5640
nnnnnnnnng gcgctgggca aactggcnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnncg gcctgctctg tgctggctgc caggctggcg agtgcttcac    5820
tgcgcttgcn gggttggtgn nnngtgctac agctggcttg gggggtgnnc ataagtggtt    5880
gttagctatt gcaggaactt ggctagttag cttgcagact gggcccgtg gcggcatggt    5940
tgcgggcctc tcagttctag caggctgttg catcggtagt gtcaccgggc ttgacttcct    6000
gtttgggtgc cttacaggnn nnnnnnnnnn nnnnnnnnnn nnnnnnnnnn nnnnnnnnnn    6060
nnnnnnnnnn ncagctgata tgaccactct ggtagatctc ntacntgctc ttttctcccc    6120
nnnnnnnnnn nnnnnnnnnn nnnnnntgt cttcatntta agcaattcaa gtgtaaccac    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn ngtgagggat acacacnnnn nnnnnnnnnn nnnnnnnnnn nnnnnnnnnn    6360
nnnnnnnnnn ctacgtgctg tgtgggattg ggcggccaaa catgtgccac ggttccgtgt    6420
gcctatgatt ggctgctcac ctgcgtggtg cgggcgctgg cttggtactg gcaccttgtt    6480
gaccacctgt gggtgtggag aacgtgtatc ccttcagtgc ctttgctcaa catctgaccc    6540
```

```
acnactcagt gtgggccgtt ggtgttggtg tagttggagt gttgggttcc cattcaaccc    6600
gacgacgaca ggcactggnn ccttacggcc ggacatcngt gacgnnnnca aattgggttt    6660
ccggtatggt gtcgccgana tcgtggagct agagcggcgg ggcaacaaat ggcatgtctg    6720
tgcagcatca tgttgcttgg accgggccag cgttgcatcc gctgtgaagg ccccaccggt    6780
cacggccgat ggcataccta tcagtacctt ttctccacca caaacttatt ncctatctct    6840
ctgttccttt gatacnnnnn nnnnnnnnnn nnnnnnnnnn nnnnnnnnnn agaccctgag    6900
tgtgtgccaa gaggaggcgg ttgagnnnnn nnnnnnnnna gttgacacag cacaagtnnn    6960
nnnnnnnnnn nnnnnnnnnn nnnnnnnnnn nnnnngttt gatgcatggc aagttcgcga    7020
agcaattcgc gacgagtaca cgcgtttggc agacgaggat gttgacgcga caacgtcggt    7080 gaaaccccg gtgccaggg ctgctgtggg tagctcgacg ttggatgatg ttagcgnnnn    7140
nnnnnnnnnn nnnnnnnnnn nnnnnnnnnn nnnnnnnnnn nnnnnnnnnn nnnnnnnnnn    7200
nnnnnnnnnn nnnnnnnnnn nnnnnnnnnn nnnacgcacg cgtgtctcgg gtgtgttgga    7260
gcgcgtgcgc atgtgcatgc gcacgccncc aatcaagttt gaggccaccg cagtaccaat    7320
tcataatata atcccagaag agtgtcanat tgtgctacgc tgtaccggct gtaatgacca    7380
ggccttgact gttccgtacg gcacttgcac tcagacttta accaaacatt tgactaacaa    7440
acacagtcac tnnnnnnnnn aanagaagat agaagaagac acagaaatag ctgtcatttg    7500
cgccgtacca acaaagcgcg caagcaaact catcactttc agagcaggtg accgatcagt    7560
ctcatgttgt cacccccttgc aaactcctat tagggccctg cttcaaaagt acgggttacc    7620
tatcgggaag tggtccgact gcaacgggcc ccttggtgac gatgcccgag tctgtgacgt    7680
caatggagta acaacttatg aaccatgcat gcaatcctac agttggttcc gaccgattgt    7740
ggcaccaaca accccacctt tacctgcaac ccggagcgtg gctggcattt tacgcgcaga    7800
cacatcgcgc gtttacacca caacggcggt tgacgtctcc gagcggcagg ctaaggtcac    7860
aattgatcaa acatcagcca aggtggatca gtgtttccga nnnnnnnnnn nntgctgcct    7920
tgccaaggca aagaccnnnn nnnnnnnnnn nnnnnnnat gaggatgctg tgtcaaannn    7980
nnnnnnnnnn nnnnnnnnnn nnnnnnnnnn nnnnnnnnnn nnnnnnnnnn nnnnnnnnnn    8040
nnnnnnnnnn nnnnnnnnnn nnnnnnnnnn nnnnnnnnnn nnnnnnnnnn nnnnnnnnnn    8100
nnnnntgcgc attattccaa aacctgaagt nnnnnnnnnn nnnnnnnnnn nnnnnnnnnn    8160
nnnnnnnttc atcgttttcc ctgggtgtgc nnnnnnnnnn nnnnnnnnnn nnnnnnnnnn    8220
nnnnnnnnnn nnnnnnnnnn nnnnnnnnnn nnnnnnnnnn nnnnnnnnnn nnnnnnnnnn    8280
nnnnnnnnnn nnnnnnnnac tggaacaatg gtggaaccnn nnnnnnnnnn nnnnnnnnnn    8340
nnnnnnnnnt gcagtctgct ttgatagcac cannnnnnnn nnnnnnnnnn nnnnnnnnnn    8400
nnnnnnnnnn nnnnnnnnnn nnnnnnnnnn nnnnnnnnnn nnnnnnnnnn nnnnnnntta    8460
caaaagaagc cccatgtgtg nnnnnnnnnn nnnnnnnnnn nnnnnngtn gctgtcgagc    8520 ctcaggnncn nttacannnc annnagtggc nnnnngctta cttgctacct taannnnnnn    8580
ncagcttgca cgcgcgnnnn nnttaaacca attggcttac taattcatgg agatgacacc    8640
ctcatcgtca cagaacgttg cgctcaggaa actctcgatg agttcagcaa cgcacttgat    8700
gnnnnnnnnn nnnnnnnnnn nntgcaggtg tctggggacc nnnnnnnnnn nnnnnnnnnn    8760
nnnnnnnnnn nnnnnnnnnn nnnnnnnnnn nnnnnntgc gtcgcatgct cgnnnnnnnn    8820
nnnnnnnnnn nnnnnnnnnn nnnnnnnnnn nnnnnnnnnn nnnnactggg taccatcggt    8880
```

```
agctatgttg tcatgtatcc cactgcggcc gtgactgtct acgtgctatt gcccctgttg    8940
tgcatgctca tacgaaatga gccatcacag acggggacac ttgtgacgct gacggtccac    9000
ggtaacagtg tgagcgtgcc agtgtggctg cttccaacca tnnnnnnnnn nnnnnnnnnn    9060
nnnnnnnnnn nnnnnnnnnn nngtcacagt gcagcttcca tggcggaact gtnnnnnnnn    9120
nnnnnnnnnn nnnnnnnnnn nnnnnnnnnn nnnnnnnnnn nnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnnnnnnnnn    9360
nnnnnnnnnn nnnnnnnnnn nnnnnnnnnn nnnnnnnnnn nnnnnnnnnn nnnnnnnnnn    9420
nnnnnnnnnn nnnnnnnnnn nnnnnnnnnn nnnnnnnnnn nnnnnnnnnn nnnnnnnnnn    9480
nnnnnnnnnn nnnnnnnnnn nnnnnnnnnn nnnnnnnnnn nnnnnnnnnn nnnnnnnnnn    9540
nnnnnnnnnn nnnnnnnnnn nnnnnnnnnn nnnnnnnnnn nnnnnnnnng gnnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnnnnnnnnn nnnnnnnnnn nnnnnnnnnn    9720
nnnnnnnnnn nnnnnnnnnn nnnnnnnnnn nnnnnnnnnn nnnnnnnnnn nnnnnnnnnn    9780
nnnnnnnnnn nnnnnnnnnn nnnnnnnnnn nnnnnnnn                            9818
```

<210> SEQ ID NO 357
<211> LENGTH: 23
<212> TYPE: DNA
<213> ORGANISM: Artificial sequence
<220> FEATURE:
<223> OTHER INFORMATION: Synthetic

<400> SEQUENCE: 357
tgatcaagty gggcgggtgg aat                                             23

<210> SEQ ID NO 358
<211> LENGTH: 21
<212> TYPE: DNA
<213> ORGANISM: Artificial sequence
<220> FEATURE:
<223> OTHER INFORMATION: Synthetic

<400> SEQUENCE: 358
gaacaccaca rcccgaacca a                                               21

<210> SEQ ID NO 359
<211> LENGTH: 26
<212> TYPE: DNA
<213> ORGANISM: Artificial sequence
<220> FEATURE:
<223> OTHER INFORMATION: Synthetic

<400> SEQUENCE: 359
cgtccgtacg aaaatttgca cttgag                                          26

<210> SEQ ID NO 360
<211> LENGTH: 26
<212> TYPE: DNA
<213> ORGANISM: Artificial sequence
<220> FEATURE:
<223> OTHER INFORMATION: Synthetic

<400> SEQUENCE: 360
cgcaatcgtg gtgctagtcg cttacg                                          26

<210> SEQ ID NO 361
<211> LENGTH: 24
<212> TYPE: DNA
<213> ORGANISM: Artificial sequence
<220> FEATURE:
<223> OTHER INFORMATION: Synthetic

<400> SEQUENCE: 361
gctagtgcta tactcgctct gctt                                      24

<210> SEQ ID NO 362
<211> LENGTH: 19
<212> TYPE: DNA
<213> ORGANISM: Artificial sequence
<220> FEATURE:
<223> OTHER INFORMATION: Synthetic

<400> SEQUENCE: 362
tgatagggtg gcggcgggc                                            19

<210> SEQ ID NO 363
<211> LENGTH: 18
<212> TYPE: DNA
<213> ORGANISM: Artificial sequence
<220> FEATURE:
<223> OTHER INFORMATION: Synthetic

<400> SEQUENCE: 363
atacctcctc gggctgcc                                             18

<210> SEQ ID NO 364
<211> LENGTH: 21
<212> TYPE: DNA
<213> ORGANISM: Artificial sequence
<220> FEATURE:
<223> OTHER INFORMATION: Synthetic

<400> SEQUENCE: 364
atgggagcta ccactgcggt g                                         21

<210> SEQ ID NO 365
<211> LENGTH: 23
<212> TYPE: DNA
<213> ORGANISM: Artificial sequence
<220> FEATURE:
<223> OTHER INFORMATION: Synthetic

<400> SEQUENCE: 365
gccggtcacc aagtcgtrtg cag                                       23

<210> SEQ ID NO 366
<211> LENGTH: 24
<212> TYPE: DNA
<213> ORGANISM: Artificial sequence
<220> FEATURE:
<223> OTHER INFORMATION: Synthetic

<400> SEQUENCE: 366
ggtatgtgtt csatccggtc caaa                                      24

<210> SEQ ID NO 367
<211> LENGTH: 24
<212> TYPE: DNA
<213> ORGANISM: Artificial sequence
<220> FEATURE:

<223> OTHER INFORMATION: Synthetic

<400> SEQUENCE: 367
atccttctgg ctagtcctac ggtt                                    24

<210> SEQ ID NO 368
<211> LENGTH: 23
<212> TYPE: DNA
<213> ORGANISM: Artificial sequence
<220> FEATURE:
<223> OTHER INFORMATION: Synthetic

<400> SEQUENCE: 368
tttatttgtt catggggtc gtg                                      23

<210> SEQ ID NO 369
<211> LENGTH: 23
<212> TYPE: DNA
<213> ORGANISM: Artificial sequence
<220> FEATURE:
<223> OTHER INFORMATION: Synthetic

<400> SEQUENCE: 369
gaaaacatca cgcgtccata cac                                     23

<210> SEQ ID NO 370
<211> LENGTH: 19
<212> TYPE: DNA
<213> ORGANISM: Artificial sequence
<220> FEATURE:
<223> OTHER INFORMATION: Synthetic

<400> SEQUENCE: 370
caccagcacc gatttccgc                                          19

<210> SEQ ID NO 371
<211> LENGTH: 19
<212> TYPE: DNA
<213> ORGANISM: Artificial sequence
<220> FEATURE:
<223> OTHER INFORMATION: Synthetic

<400> SEQUENCE: 371
ttgtattctt gaccgccgg                                          19

<210> SEQ ID NO 372
<211> LENGTH: 19
<212> TYPE: DNA
<213> ORGANISM: Artificial sequence
<220> FEATURE:
<223> OTHER INFORMATION: Synthetic

<400> SEQUENCE: 372
gtaatccgac gcctggccg                                          19

<210> SEQ ID NO 373
<211> LENGTH: 18
<212> TYPE: DNA
<213> ORGANISM: Artificial sequence
<220> FEATURE:
<223> OTHER INFORMATION: Synthetic

<400> SEQUENCE: 373
tgtgtctgcc ggttgcga                                           18

```
<210> SEQ ID NO 374
<211> LENGTH: 23
<212> TYPE: DNA
<213> ORGANISM: Artificial sequence
<220> FEATURE:
<223> OTHER INFORMATION: Synthetic

<400> SEQUENCE: 374
tctcaccctg ttaatgctgc gct                                      23

<210> SEQ ID NO 375
<211> LENGTH: 24
<212> TYPE: DNA
<213> ORGANISM: Artificial sequence
<220> FEATURE:
<223> OTHER INFORMATION: Synthetic

<400> SEQUENCE: 375
ctgtcggttg tggtcctctc ggtc                                     24

<210> SEQ ID NO 376
<211> LENGTH: 23
<212> TYPE: DNA
<213> ORGANISM: Artificial sequence
<220> FEATURE:
<223> OTHER INFORMATION: Synthetic

<400> SEQUENCE: 376
aagtctcgga acgggtggcg caa                                      23

<210> SEQ ID NO 377
<211> LENGTH: 20
<212> TYPE: DNA
<213> ORGANISM: Artificial sequence
<220> FEATURE:
<223> OTHER INFORMATION: Synthetic

<400> SEQUENCE: 377
tggacaattg cttggaggta                                          20

<210> SEQ ID NO 378
<211> LENGTH: 20
<212> TYPE: DNA
<213> ORGANISM: Artificial sequence
<220> FEATURE:
<223> OTHER INFORMATION: Synthetic

<400> SEQUENCE: 378
tccttcctta aggcgacact                                          20

<210> SEQ ID NO 379
<211> LENGTH: 20
<212> TYPE: DNA
<213> ORGANISM: Artificial sequence
<220> FEATURE:
<223> OTHER INFORMATION: Synthetic

<400> SEQUENCE: 379
atcgtggtgt tgtcttccct                                          20

<210> SEQ ID NO 380
<211> LENGTH: 19
<212> TYPE: DNA
<213> ORGANISM: Artificial sequence
<220> FEATURE:
<223> OTHER INFORMATION: Synthetic
```

```
<400> SEQUENCE: 380
cactgtatgc gaccggcca                                               19

<210> SEQ ID NO 381
<211> LENGTH: 24
<212> TYPE: DNA
<213> ORGANISM: Artificial sequence
<220> FEATURE:
<223> OTHER INFORMATION: Synthetic

<400> SEQUENCE: 381
tagacccctg ctgctgttcg ccga                                         24

<210> SEQ ID NO 382
<211> LENGTH: 20
<212> TYPE: DNA
<213> ORGANISM: Artificial sequence
<220> FEATURE:
<223> OTHER INFORMATION: Synthetic

<400> SEQUENCE: 382
ctgtcccacg cacatagatc                                              20

<210> SEQ ID NO 383
<211> LENGTH: 20
<212> TYPE: DNA
<213> ORGANISM: Artificial sequence
<220> FEATURE:
<223> OTHER INFORMATION: Synthetic

<400> SEQUENCE: 383
tttgtgtgat cacggtcatg                                              20

<210> SEQ ID NO 384
<211> LENGTH: 21
<212> TYPE: DNA
<213> ORGANISM: Artificial sequence
<220> FEATURE:
<223> OTHER INFORMATION: Synthetic

<400> SEQUENCE: 384
ccaagtgtgg ctgtagtcaa a                                            21

<210> SEQ ID NO 385
<211> LENGTH: 24
<212> TYPE: DNA
<213> ORGANISM: Artificial sequence
<220> FEATURE:
<223> OTHER INFORMATION: Synthetic

<400> SEQUENCE: 385
gacgaatctg cggggctatg ctgt                                         24

<210> SEQ ID NO 386
<211> LENGTH: 20
<212> TYPE: DNA
<213> ORGANISM: Artificial sequence
<220> FEATURE:
<223> OTHER INFORMATION: Synthetic

<400> SEQUENCE: 386
gctactcggc attggcgcag                                              20

<210> SEQ ID NO 387
<211> LENGTH: 20
```

```
<212> TYPE: DNA
<213> ORGANISM: Artificial sequence
<220> FEATURE:
<223> OTHER INFORMATION: Synthetic

<400> SEQUENCE: 387
aaagctggag tgaagaccgt                                                    20

<210> SEQ ID NO 388
<211> LENGTH: 23
<212> TYPE: DNA
<213> ORGANISM: Artificial sequence
<220> FEATURE:
<223> OTHER INFORMATION: Synthetic

<400> SEQUENCE: 388
aacaacagta acaaaacacc cct                                                23

<210> SEQ ID NO 389
<211> LENGTH: 21
<212> TYPE: DNA
<213> ORGANISM: Artificial sequence
<220> FEATURE:
<223> OTHER INFORMATION: Synthetic

<400> SEQUENCE: 389
cttcctgttt gggtgcctta c                                                  21

<210> SEQ ID NO 390
<211> LENGTH: 24
<212> TYPE: DNA
<213> ORGANISM: Artificial sequence
<220> FEATURE:
<223> OTHER INFORMATION: Synthetic

<400> SEQUENCE: 390
ttacaggttg ggaagccgtg gtcg                                               24

<210> SEQ ID NO 391
<211> LENGTH: 24
<212> TYPE: DNA
<213> ORGANISM: Artificial sequence
<220> FEATURE:
<223> OTHER INFORMATION: Synthetic

<400> SEQUENCE: 391
ttacaggttg ggaggccgtg gtyg                                               24

<210> SEQ ID NO 392
<211> LENGTH: 24
<212> TYPE: DNA
<213> ORGANISM: Artificial sequence
<220> FEATURE:
<223> OTHER INFORMATION: Synthetic

<400> SEQUENCE: 392
ttacgggttg ggaagccgtg gtcg                                               24

<210> SEQ ID NO 393
<211> LENGTH: 21
<212> TYPE: DNA
<213> ORGANISM: Artificial sequence
<220> FEATURE:
<223> OTHER INFORMATION: Synthetic

<400> SEQUENCE: 393
```
wtcgtggaky tagagcgscg g                                        21

<210> SEQ ID NO 394
<211> LENGTH: 24
<212> TYPE: DNA
<213> ORGANISM: Artificial sequence
<220> FEATURE:
<223> OTHER INFORMATION: Synthetic

<400> SEQUENCE: 394
gtagttcagg cggcttcacg gttt                                     24

<210> SEQ ID NO 395
<211> LENGTH: 23
<212> TYPE: DNA
<213> ORGANISM: Artificial sequence
<220> FEATURE:
<223> OTHER INFORMATION: Synthetic

<400> SEQUENCE: 395
agtttgaggc caccgcagta cca                                      23

<210> SEQ ID NO 396
<211> LENGTH: 21
<212> TYPE: DNA
<213> ORGANISM: Artificial sequence
<220> FEATURE:
<223> OTHER INFORMATION: Synthetic

<400> SEQUENCE: 396
ttgaygtcyc cgagcggcag g                                        21

<210> SEQ ID NO 397
<211> LENGTH: 23
<212> TYPE: DNA
<213> ORGANISM: Artificial sequence
<220> FEATURE:
<223> OTHER INFORMATION: Synthetic

<400> SEQUENCE: 397
gttgtcgggg tgcgtagctg tcg                                      23

<210> SEQ ID NO 398
<211> LENGTH: 18
<212> TYPE: DNA
<213> ORGANISM: Artificial sequence
<220> FEATURE:
<223> OTHER INFORMATION: Synthetic

<400> SEQUENCE: 398
ctcaaggttc gcgcagct                                            18

<210> SEQ ID NO 399
<211> LENGTH: 24
<212> TYPE: DNA
<213> ORGANISM: Artificial sequence
<220> FEATURE:
<223> OTHER INFORMATION: Synthetic

<400> SEQUENCE: 399
aggatgctgt gtcaaagatg cgcg                                     24

<210> SEQ ID NO 400
<211> LENGTH: 24
<212> TYPE: DNA
<213> ORGANISM: Artificial sequence

```
<220> FEATURE:
<223> OTHER INFORMATION: Synthetic

<400> SEQUENCE: 400
tatcctactg cggctgtgac tgtc                                          24

<210> SEQ ID NO 401
<211> LENGTH: 21
<212> TYPE: DNA
<213> ORGANISM: Artificial sequence
<220> FEATURE:
<223> OTHER INFORMATION: Synthetic

<400> SEQUENCE: 401
cctcagcgtt ggccttcttt g                                             21

<210> SEQ ID NO 402
<211> LENGTH: 19
<212> TYPE: DNA
<213> ORGANISM: Artificial sequence
<220> FEATURE:
<223> OTHER INFORMATION: Synthetic

<400> SEQUENCE: 402
cctatccgag ttgggcaag                                                19

<210> SEQ ID NO 403
<211> LENGTH: 24
<212> TYPE: DNA
<213> ORGANISM: Artificial sequence
<220> FEATURE:
<223> OTHER INFORMATION: Synthetic

<400> SEQUENCE: 403
gtaagaacac cacagcccga acca                                          24

<210> SEQ ID NO 404
<211> LENGTH: 25
<212> TYPE: DNA
<213> ORGANISM: Artificial sequence
<220> FEATURE:
<223> OTHER INFORMATION: Synthetic

<400> SEQUENCE: 404
accacttaat ggtcgtaact cgacc                                         25

<210> SEQ ID NO 405
<211> LENGTH: 19
<212> TYPE: DNA
<213> ORGANISM: Artificial sequence
<220> FEATURE:
<223> OTHER INFORMATION: Synthetic

<400> SEQUENCE: 405
gtcaacggcc cctttcatt                                                19

<210> SEQ ID NO 406
<211> LENGTH: 1044
<212> TYPE: DNA
<213> ORGANISM: Artificial sequence
<220> FEATURE:
<223> OTHER INFORMATION: Synthetic

<400> SEQUENCE: 406
atgagagttc ctgcacaatt attaggatta ttattattat ggtttcctgg atctaggtgc   60
```

| | |
|---|---|
| tacaagcacc agagcgagag ctacctgaag tattgtacaa ttacaaatac atctacaagc | 120 |
| atgaactgcg attgcccttt tggcaccttc accaggaata cagagtctag attttctatt | 180 |
| cctagatttt gtccagtgaa gatcaatagc agcaccttca tctgctcttg gggatcttgg | 240 |
| tggtggtttg ctgaaaatat tacaagacct tatacagatg tgggaatgcc tccagctcca | 300 |
| atttctgctc tgtgttacat ctcagcaat aatgatcctc ctccttggta tcataatacc | 360 |
| accatcattc ctcagaactg cagaaatagc accgttgatc ctacaacagc tccttgtaga | 420 |
| gataaatggg gaaatgctac agcttgtatt cttgacagaa gaagcagatt ttgcggcgat | 480 |
| tgttatggag gatgcttta cacaaatgga agccatgata gatcttggga tagatgtgga | 540 |
| atcggctaca gagatggact gattgaattt gttcagttag gccagattag acccaatatc | 600 |
| agcaatacaa ccatcgaact gcttgctgga gcttctttag ttattgcttc tggattaaga | 660 |
| cctggatttg gatgttctag agctcatgga gttgtgcact gctatagatg tccttcttac | 720 |
| agagatttag agcaatttgg acctggactt ggaaaatggg tgcctttacc tggagaacct | 780 |
| gttcctgaat tatgtattaa tcctcaatgg gctagaagag gattcagaat gagcaataac | 840 |
| cctctgtctc tgctgcagac atttgttgaa gatatctttc ttgccccttt ctgtaatcct | 900 |
| acacctggaa gagttagagt gtgcaacaat acagcctttt atcctagagg aggaggattt | 960 |
| gttcaactta ttggcgatgt tcaggttctg accctaata caggatctgg atctggacat | 1020 |
| catcatcatc atcatcatca ctaa | 1044 |

<210> SEQ ID NO 407
<211> LENGTH: 249
<212> TYPE: DNA
<213> ORGANISM: Artificial sequence
<220> FEATURE:
<223> OTHER INFORMATION: Synthetic

<400> SEQUENCE: 407

| | |
|---|---|
| atggcccttg ttcccagcgc tgtgtggagt gttgaagtcc gccccgcagg cgtgacgcgc | 60 |
| cctgatgcca ccgatgaaac cgctgcgtac gctcaacgct tgtatcaggc ctgcgccgat | 120 |
| tcaggtatct ttgcgtcact tcaaggaacc gcgagtgcgg cgttgggcaa gctggcggat | 180 |
| gcctcgcgtg gcgcgagtca ataccctggca gccgccccac catcacctgc cccactggtg | 240 |
| caggtatta | 249 |

<210> SEQ ID NO 408
<211> LENGTH: 20
<212> TYPE: DNA
<213> ORGANISM: Artificial sequence
<220> FEATURE:
<223> OTHER INFORMATION: Synthetic

<400> SEQUENCE: 408

| | |
|---|---|
| tgttggccct accggtgtta | 20 |

<210> SEQ ID NO 409
<211> LENGTH: 18
<212> TYPE: DNA
<213> ORGANISM: Artificial sequence
<220> FEATURE:
<223> OTHER INFORMATION: Synthetic

<400> SEQUENCE: 409

| | |
|---|---|
| ccgtacgtgg gcgtcgtt | 18 |

```
<210> SEQ ID NO 410
<211> LENGTH: 24
<212> TYPE: DNA
<213> ORGANISM: Artificial sequence
<220> FEATURE:
<223> OTHER INFORMATION: Synthetic

<400> SEQUENCE: 410
ctcgtcgtta aaccgagccc gtca                                              24

<210> SEQ ID NO 411
<211> LENGTH: 24
<212> TYPE: DNA
<213> ORGANISM: Artificial sequence
<220> FEATURE:
<223> OTHER INFORMATION: Synthetic

<400> SEQUENCE: 411
ctcgtcgtta aaccgagacc gtca                                              24

<210> SEQ ID NO 412
<211> LENGTH: 24
<212> TYPE: DNA
<213> ORGANISM: Artificial sequence
<220> FEATURE:
<223> OTHER INFORMATION: Synthetic

<400> SEQUENCE: 412
cacgccgtta aaccgagacc gtta                                              24

<210> SEQ ID NO 413
<211> LENGTH: 22
<212> TYPE: DNA
<213> ORGANISM: Artificial sequence
<220> FEATURE:
<223> OTHER INFORMATION: Synthetic

<400> SEQUENCE: 413
gtgggacacc tcaaccctga ag                                                22

<210> SEQ ID NO 414
<211> LENGTH: 24
<212> TYPE: DNA
<213> ORGANISM: Artificial sequence
<220> FEATURE:
<223> OTHER INFORMATION: Synthetic

<400> SEQUENCE: 414
gggaagacaa caccacgatc tggc                                              24

<210> SEQ ID NO 415
<211> LENGTH: 23
<212> TYPE: DNA
<213> ORGANISM: Artificial sequence
<220> FEATURE:
<223> OTHER INFORMATION: Synthetic

<400> SEQUENCE: 415
cctggtttcc agctgagtgc tcc                                               23

<210> SEQ ID NO 416
<211> LENGTH: 21
<212> TYPE: DNA
<213> ORGANISM: Artificial sequence
<220> FEATURE:
<223> OTHER INFORMATION: Synthetic
```

<400> SEQUENCE: 416
cgctgatcgt gcaaagggat g                                                      21

<210> SEQ ID NO 417
<211> LENGTH: 21
<212> TYPE: DNA
<213> ORGANISM: Artificial sequence
<220> FEATURE:
<223> OTHER INFORMATION: Synthetic

<400> SEQUENCE: 417
gctccacgga cgtcacactg g                                                      21

<210> SEQ ID NO 418
<211> LENGTH: 22
<212> TYPE: DNA
<213> ORGANISM: Artificial sequence
<220> FEATURE:
<223> OTHER INFORMATION: Synthetic

<400> SEQUENCE: 418
gcaccactcc gtacagcctg at                                                     22

<210> SEQ ID NO 419
<211> LENGTH: 9864
<212> TYPE: DNA
<213> ORGANISM: Human Pegivirus 2
<220> FEATURE:
<221> NAME/KEY: misc_feature
<222> LOCATION: (9595)..(9635)
<223> OTHER INFORMATION: N = A, C, T, or G
<220> FEATURE:
<221> NAME/KEY: misc_feature
<222> LOCATION: (9851)..(9864)
<223> OTHER INFORMATION: N = A, C, T, or G

<400> SEQUENCE: 419
aactgttgtt gtagcaatgc gcatattgct acttcggtac gcctaattgg taggcgcccg      60
gccgaccggc cccgcaaggg cctagtagga cgtgtgacaa tgccatgagg gattatgaca     120
ctggggtgag cggaggcagc accgaagtcg ggtgaactcg actcccagtg cgaccacctg     180
gcttggtcgt tcatggaggg catgcccacg ggaacgctga tcgtgcaaag ggatgggtcc     240
ctgcactggt gccatgcgcg gcaccactcc gtacagcctg ataggggtggc ggcgggcccc     300 cccagtgtga cgtccgtgga gcgcaacatg gggtgttcaa ctgatcaaac catttgttct     360
ccagtcgtgg gggccgacta taatacctcc tcgggctgcc gggccttaaa tgggagctac     420
cactgcggtg gtggctcttg ccggtcacca agtcgtgtgc aggttgcgag acgagtcttg     480
cagctgagcg cattccttgc gttgatcgga tccggtatgt gttcgatccg gtccaaaact     540
gaagggcgca ttgagtcggg gcaaatattg cagtctcagc gcgcatgttg gactggtgag     600
ggttttgctt tcttttctaa ctgttgcaat caatctgata tcatgtggtg tttgcaccgt     660
tggtgtgtga caagacctgg ctgtttagtg tgcacgggca atgccactca tcctgtctgc     720
tgggactatc ttgggtccgg tgtaagccgg cggcctgcgc gtcgaatggg tgagggagct     780
gaagcgcttc ttcgcttgat cggcattgca gttggctcg gctgctagc tgaggctctt     840 ggtatgtccg aactctacgc agctattctt tgctttggat ttattgcttg gtatggttgg     900
ggtataccta aaacattggt gtgcacagtc tgccctgcag taaacatttc tccctatagc     960
ttcttatctc cagacactat cgcatttggt acgtggatac tacaactacc tggtcttttg    1020
tggcaaatgt ttgtcagctt tcctatactt tacagcactt ggattctttg gttgttgctc    1080

```
agcggcaaaa ctgttgctgt gatagcaatt cttttggcga gtcctacggt tatggcatac    1140
aagcatcaat ctgacagcta cctcaaatac tgtaccataa ccaatgcttc aactgctatg    1200
aactgtgact gccccctttgg aacctttact cgcaatactg agtctcgttt ctctatacct   1260
agattctgtc ctgttaaaat taatagctct acatttatct gctcatgggg gtcgtggtgg    1320
tggtttgctg agaacatcac gcgtccatac tcggacgttg gcatgccacc ggcaccgatt    1380
tctgctttgt gctatatcta ttcaaacaat gaccctcctc cttggtacca taatacaact    1440
atcataccte agaactgtcg caactccacg gctgatccca ccacagcccc atgccgtgac    1500
aagtggggca acgcaactgc ttgtattctt gaccgccggt cgcggttctg cggggactgc    1560
tatggcggct gcttctatac taatggtagt catgatcgat cctgggatcg atgcgggatt    1620
ggttaccgtg atggactcat agagttcgtg cagctcggtc agattcgacc caacatctcg    1680
aatacgacca ttgagctcct cgctggcgcc tcgctagtga ttgcatccgg tcttcgggct    1740
gggtacggtt gcagccgagc gcatggcgtg gtgcactgct ataagtgtcc ttataccgt    1800
gaccttgaac aatttggtcc cgggctcggg aaatgggtgc cattgcctgg cgagcctgtc    1860
ccggagttgt gtattaaccc ccagtgggcg aggcgcggct tccgggtgtc taacaatcct    1920
ttgcacttga tacagacctt tgttgaggac atcttcctag cacctttttg cagtccgacg    1980
cctggccgtg tacgtgtgtg taacaatact gcttttctatc cgacaggagg tggttttgtg    2040
cagctcatcg gagacgtcca ggtgctaacc cctaacactg catctttaca ctctctgctg    2100
actttaatat cccttatctt gctagtgtgt gttgtttctg gcgcgcggtt catcccatta    2160
atcatcatat ttttctggag cgtgcgccac gtatatgctt cttgttactt aagctgtgat    2220
tgggctgttt gcaacgatgc gttctgtttc acatctggca cttgtgctac cttcaatgac    2280
gtcttgtgtc tgccggttgc ggcgcgcata tcgtcctgtg gccacgctgt gccacctccc    2340
gaccgtggtt gggaggtgcc tgcggcgatg tcatgggcga tttcgcggac tactggtttg    2400
acgttcgatg tcttctcctt tattcagtat ttccctacag tgcctggcaa caacaccgat    2460
atcatttact gtggtgaacc aaccttcttc ggggacatca caggcatcta ttggccttac    2520
ttttttgcctg gcttgttgct cttgtacttg actcctctac tgggttttag gttaatgctt    2580
gccggcttca atatagatgg cttgtttccc atacggcatg ccacggctgc gctgaggttc    2640
tcgacctcac gtgcgaccat gtgtgtcgta tctgctttcc taatctatat attatctcat    2700
cctgttaatg ctgcgctcaa tagaatgttc ctagcatctg caaacttaga gatgatctta    2760
tcttttgata cctatcatga gactatcctt tacatcgctt gtctattgct ctacctccag    2820
gtgtcgcccc gcgcgggctt ggccgctatg gtggccatca agctgtctcg aggcctgcta    2880
ttcgctgtgt gttggcgcca cggcgtgtgc gacctgggc gggtatttgg tcttgaggtt    2940
tgcgcggaca tctcatggtt ggtggagttt actggcaact gcacttggta catgtcctgt    3000
gtcttctctt tttggtgcgc agtgtttgcc ttcaccagtc cacttggacg acactataag    3060
cttcagatct accggtactg ggcgcaggtc tatgccagac tcatccttgc tgtcggttgt    3120
ggtcctctcg gacgagagtt ccatttccgt gcaagcgtgg gtgtgctttg gtgtggtgct    3180
tgcatgctct ggccccgtga gtgctctgaa atcagcttgg tcttcattct gtgtgctctg    3240
acagtggaca ccatagacac atggttagta gcgtgcttgt ccgcagggcc gagtgcgcga    3300
acccttgcaa cactggccga tgacatgcg cgctttggtg accaccgggc gttgcgcgcc    3360
gtgttgcgtt gctttggatc acgtggcaca tacatataca accacatggg ccaggtctca    3420
```

```
gaacgggtgg cgcaagcagt cagggatttc ggcggttgct tggaaccagt cgtgttggag    3480
gagcccacct ttactgaggt cgtggatgac acaatgaatt tagtgtgtgg acaattgctt    3540
ggaggtaagc ctgtggtggc ccgctgcggc acgcgtgtct tggtgggaca cctcaaccct    3600
gaagatctgc cacctggttt ccagctgagt gctccggtca ttatcaccaa accaagcatt    3660
ggtacgtggt ccttccttaa ggcgacactc acagggcgtg ctgaaacacc gggatccggc    3720
cagatcgtgt tgttgtcttc cctgacaggt cggtcaatgg gtactgcagt gagtggcaca    3780
ctgtatgcga ccggccatgg tgctggtgcg cgcggcctag ccacgtgcgc cggtttgagg    3840
acgccacttt acacggcatt atctgatgat gtcgtggcct actcttgcct cccgggcatg    3900
agttccctag agccctgccg ctgtgcgccg agccgggttt gggtgatgaa caacaatgga    3960
gggttggtgt gtggcagagt ggagaatgag acgtctgtt tggactgtcc cacgcacata    4020
gatcaactgc ggggtgcttc gggatcgccg gtcttgtgtg atcacggtca tgcatacgcg    4080
ctgatgctcg gtggttactc taccagtggt atttgtgcgc gtgtccggat agtccggcca    4140
tggcagaacg cctattcctc ctcagggggg caaggcggga tgcaggcgcc agctgtgaca    4200
ccaacatact ctgaaatcac ctactatgcc cctactggtt ctggtaagtc aacaaaatat    4260
ccagtggacc tggtcaaaca gggacacaaa gtattggtcc ttataccaag tgtggctgtc    4320
gtcaaaagca tggccccta cattaaggag acatataaga ttagacctga aattagagct    4380
ggcacaggcc ctgacggtgt gacggtcatc actggtgaga acttggcgta catgacctat    4440
ggccgcttcc ttgtggatcc ggagacgaat ctgcagggtt atgccgtagt catttgcgac    4500
gagtgccacg acacatcatc caccacgcta ctcggcattg gcgcagtgcg catgtatgcc    4560
gagaaagctg gagtgaggac cgttgtattc gccacagcca ctcctgctgg cattcaagta    4620
cagccacacc ccaacattga tgaatattta ttgactaatg aaggcgacgt ggacttctac    4680
ggcgccaaaa tcaaattgga caacatcaga actggtagac atgttatctt ttgtcactcg    4740
aaggccaggt gcgcggaact aacgcagcag ctctccggcc ttggcgttca tgcagtgagt    4800
ttttggcgcg gctgtgacat caaaaccatt cccgcctcag gctctattgt tgtagtggca    4860
actgatgcat tgtccacagg cttcacagga aattttgatt cggtcatcga ctgcgggtgt    4920
tgcgtagagc aaactgtgac aattgacatg gaccccacgt tctccatctc ggcccgagtg    4980
gtgccatgta ctgctgcatt gcgtatgcag cggcgcggac gcaccggtcg tggcagaagg    5040
ggagcgtact acacaaccac tccaggagca gcaccctgcg tcagcgttcc cgatgctaac    5100
gtctggcaag cagcggagag cgccatggtc ttttatgatt ggaatgctgc taggatacag    5160
cagtgcctgg cggcatacca tgacttaggg tgcacaccac gcatcggttg tgacccacac    5220
actccagtgc gggtgatgga cacactgagg gcgtacctgc gcagacctga ggtgacgact    5280
gcagctctcg cgggagagca gtggccgctg ctttatggtg tgcagttgtg catctgcaaa    5340
gagaccgagg cccacggtcc agatgatggc atcaagtgga gtgcttact caacaatact    5400 aataaaacac ccctgttgta tgccttagac aatcctacac tggaattcac tacccaacat    5460
gacttgactc gccgtatagc cggcgcttta tcgagcacag tgttcgtgga agcaggctac    5520
ggccccatcc tccttgctgg cgccgctttg gcagcctcct tcgcctttgc gggcgccact    5580
ggagctttag tgccgtcggc cgtttggagc gttgacaacg gcctgctgg cgtgacccgt    5640 cccgacgcga cagacgagac tgcggcctac gcgcagcgct tgtaccaagc ctgcgcagat    5700
tcaggaattc tcgccagctt gcagggcaca gcgtgtgcgg cgctgagcaa actggccgat    5760
gccagtaggg gtgctagtca atatctggca gccgcgcctc cttcgcccgc ccccctggtg    5820
```

```
caggtgctgc agttcctcga gactaacttt agctccattg catccttcgg tctgctctgt   5880
gctggttgtc aggctggcga gtgcttcacc gcacttgccg ggttggtgtc cggcgctaca   5940
gcaggcttgg gaggtgccca taagtggttg ttggctattg caggaacttg gctggttagc   6000
ctgcagaccg ggccccgtgg cggcatggtt gcgggcctct cggttctagc aggctgttgc   6060
atcggcagtg tcaccgggct tgacttcctg tttgggtgcc ttacggggttg ggaggccgtg   6120
gtcggtgctg cggttgcgac acagaaaatc ttgtctggtt cggctgacat gaccactctg   6180
gtagatctct tacctgctat cttctctcct ggtgccggca tagccggcgt cgtgctcgtc   6240
tttattctaa gcaactcaag tgtaaccacg tgggctaatc ggctattgtc catgtgtgca   6300
aaacaaacca tttgtgaaaa ttacttcttg actgagagat ttggccaaca attaagcaaa   6360
cttccctgt ggcgcgctgt gtaccattgg gcacaggcgc gcgagggata cacacagtgc     6420
ggtgtggtcg gcgggatctg gagctttgcc ttgtgcgtcc tgcgagctgt gtgggattgg   6480
gcggctaggc atgtgccacg gttccgtgtg cccatgattg gctgctcacc tgcatggtgc   6540
gggcgctggc ttggtaccgg caccttgttg accacctgtg ggtgtggaga acgtgtgtcc   6600
cttcagtgcc tttgctcgac gtctgaccca acactcagtg tgggccgttg gtgtcggtgc   6660
agttggagtg ttgggttccc attcaacccg actacgacag ccaccggcac tttacggccg   6720
gacattagcg acgccactaa attgggtttc cggtatggtg ttgctgagat tgtgagcta    6780
gagtggcggg acaacaaatg gcacgtctgc gcagcatcat gttgcgtgga ccgagctagt   6840
gttgcatctg ccgtgaaggc cccaccggtc acagccaatg gcatacctat cagtactttt   6900
tctccaccag aaacttacaa actctctctc tgttcttttg attcagtctg catgtctaac   6960
tcaagtaacc cagctaagac cctgagtgtg tgctcacagg aggctgttga gctgctggaa   7020
gaaacagttg atacagcaca agcagtgatg tgtaagaatc tggaggcgcg aagacgcgct   7080
gaatatgatg catggcaggt tcgtcaagca gttggcgacg agtacacgcg cttggctgac   7140
gaggatgttg acacaacagc gtcggtgaaa ccccccggtgg ccagggctgc tgtgggtagc   7200
tcaacgttgg atgatgttaa cgtgctgact gtcttgcgcg agctcggtga ccaatgccaa   7260
aatgctatca aatttgtagt ccaggcggct tcacggtttt ttccaccagt gcccaggccg   7320
cgcacgcgtg tctcgggtgt gttggagcgc gtgcgcatgt gcatgcgcac gccaccaatc   7380
aagtttgagg ccaccgcagt accaattcat aacataatcc cagaagagtg tcacattgtg   7440
ctacgctgta ccggctgtag tgaccaggcc ttgactgttc cgtacggcac ttgcactcag   7500
actttaacca aacatttgac taacaaacac agccattaca ttccaaaaca gaagatagaa   7560
gaagacacag aagtaactgt tatctgcgcc gtaccaacaa cgcgcgcatc taaactcatc   7620
actttcagag caggtgatcg atcagtctct tgttgtcacc ccttacaaac tcctattagg   7680
gccctgcttc taaagtacgg gttacctatc gggaagtggt ctgactgcaa cggccccctt   7740
ggtgacgacg cccgagtctg tgacgtcaat ggagtaacaa cttatgaacc atgcatgcaa   7800
tcctacagtt ggttccgacc gattgtggca ccaacaaccc cacctttgcc tgcaacccgg   7860
agcgtggctg gcattttacg cgcagacaca tcgcgcgttt acaccacaac ggcggttgac   7920
gtctccgaga ggcaggctaa ggtcacaatc gatcaaacat cagccaaggt ggatcagtgt   7980
ttccgagaca cctacaattg ttgccttgct aaggcaaaga ccttcaaaca atctggcatg   8040
tcatatgagg atgctgtgtc aaagatgcgc gcaaacacca cgcgtgatca taaccatggc   8100
actacttatt cagatttggt ctctggacgc gcaaaacctg tcgttcagaa aattgtaaat   8160
```

-continued

```
caaatgcgcg ctggagtgta cgacgctcca atgcgcatta tcccaaaacc tgaggtgttc     8220
cctcgagaca aggaaacacg gaagccacca cggttcattg ttttccctgg gtgcgccgca     8280
cgagtcgcgg agaaaatgat cctgggcgat cctggtgcga taaccaagca cgtgctaggt     8340
gatgcctacg ggtttgccac tccgccccac gagcgcgcgc gcctgttgga caatggtgg     8400 aaccgcgcaa cagagccaca agctatcgcg gttgatgcga tctgctttga tagcactatc     8460
acggcagagg acatggatcg tgaagccaac atcgtggctg cagcgcatgc ggaccctgaa     8520
ggtgttcacg gcctatacaa ttattacaaa agaagcccca tgtgtgacat cacaggaaat     8580
attgtcgggg tgcgttgctg ccgagcctca ggtacgctta caacaagcag tgcaacacg     8640 cttacttgct acctcaaggt tcgcgcggct tgcacgcggg ccggcattaa accaattggc     8700
ttactaattc atggagatga caccctcatt atcacagaac gttgcgctca gaaactctc     8760 gatgagttca gcagggcact tgatgactat gggttccccc acaccttcca ggcgtctggg     8820
gacctctcgt ctatcgagtg ctgcagcgca cacgtggaca gtgtttgcct ccggggaggt     8880
atgcgtcgca tgctcgtgcc acaagctcga cgtgcgattg cacgcgttct cggggaaaag     8940
ggcgatccac tgggtgtcat cagcagctat attgtcatgt atcctactgc ggccgtgact     9000
gtctatgtgc tattgcctct gttgtgcatg ctcattcgaa atgagccatc gcagacgggg     9060
acatttgtga cgttgacggt ccacggcaac agtgtgagcg tgccagtgtg gctgcttcca     9120
accatcattg taaatttaca tggtcgtgac gcactacaag tagtccgtca cactgcagct     9180
tccatggcgg agctgtcctc agcgttggcc ttctttggca tgagagggtt gaactgctgg     9240
aggcggagac gccgtgccat cagggctgat atgatcaagt tgggcgggtg gaatgcgaac     9300
ttcgcgcaga tgttactgtg gtcaccggag gtgagaacac cacagcccga accaaagggc     9360
atgtgtctct taccaccgga actatgggag cgtccgtacg aaaatttgca tttgagcacg     9420
atcgaccgca atcgtggtgc tagtcgctta cggttttggt tggttgctag tgctatactc     9480
gctctgcttt gcttgtaaat cctaaatcaa tgtagtacca ggactacaag gcaggaggtg     9540
aagtcagctg tacccacggc tggctgaaac cggggcttga cgacccccc tatcnnnnn     9600 nnnnnnnnnn nnnnnnnnnn nnnnnnnnnn nnnnccccc atgtcgcgcg taagcgcacg     9660
ggcaaggcag ctaggctgag agtctgggca actctcccgt accccacccg aggctacgcc     9720
tcgtcctggc gaggaccgta acatacgtc gtcagcgtgg tgacctgacg tatcttgtta     9780
accacttaat ggtcgtaact cgaccccgt gctggggatc taagcgcggc accgcgatga     9840
gaagggtcaa nnnnnnnnnn nnnn                                           9864
```

<210> SEQ ID NO 420
<211> LENGTH: 79
<212> TYPE: PRT
<213> ORGANISM: Human Pegivirus 2

<400> SEQUENCE: 420

```
Met Gly Cys Ser Thr Asp Gln Thr Ile Cys Ser Pro Val Val Gly Ala
1               5                   10                  15

Asp Tyr Asn Thr Ser Ser Gly Cys Arg Ala Leu Asn Gly Ser Tyr His
            20                  25                  30

Cys Gly Gly Gly Ser Cys Arg Ser Pro Ser Arg Val Gln Val Ala Arg
        35                  40                  45

Arg Val Leu Gln Leu Ser Ala Phe Leu Ala Leu Ile Gly Ser Gly Met
    50                  55                  60

Cys Ser Ile Arg Ser Lys Thr Glu Gly Arg Ile Glu Ser Gly Gln
```

```
                65                  70                  75

<210> SEQ ID NO 421
<211> LENGTH: 191
<212> TYPE: PRT
<213> ORGANISM: Human Pegivirus 2

<400> SEQUENCE: 421

Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
            20                  25                  30

Trp Cys Val Thr Arg Pro Gly Cys Leu Val Cys Thr Gly Asn Ala Thr
        35                  40                  45

His Pro Val Cys Trp Asp Tyr Leu Gly Ser Gly Val Ser Arg Arg Pro
    50                  55                  60

Ala Arg Arg Met Gly Glu Gly Ala Glu Ala Leu Leu Arg Leu Ile Gly
65                  70                  75                  80

Ile Ala Gly Trp Leu Gly Leu Leu Ala Glu Ala Leu Gly Met Ser Glu
                85                  90                  95

Leu Tyr Ala Ala Ile Leu Cys Phe Gly Phe Ile Ala Trp Tyr Gly Trp
            100                 105                 110

Gly Ile Pro Lys Thr Leu Val Cys Thr Val Cys Pro Ala Val Asn Ile
        115                 120                 125

Ser Pro Tyr Ser Phe Leu Ser Pro Asp Thr Ile Ala Phe Gly Thr Trp
    130                 135                 140

Ile Leu Gln Leu Pro Gly Leu Leu Trp Gln Met Phe Val Ser Phe Pro
145                 150                 155                 160

Ile Leu Tyr Ser Thr Trp Ile Leu Trp Leu Leu Leu Ser Gly Lys Thr
                165                 170                 175

Val Ala Val Ile Ala Ile Leu Leu Ala Ser Pro Thr Val Met Ala
            180                 185                 190

<210> SEQ ID NO 422
<211> LENGTH: 354
<212> TYPE: PRT
<213> ORGANISM: Human Pegivirus 2

<400> SEQUENCE: 422

Tyr Lys His Gln Ser Asp Ser Tyr Leu Lys Tyr Cys Thr Ile Thr Asn
1               5                   10                  15

Ala Ser Thr Ala Met Asn Cys Asp Cys Pro Phe Gly Thr Phe Thr Arg
            20                  25                  30

Asn Thr Glu Ser Arg Phe Ser Ile Pro Arg Phe Cys Pro Val Lys Ile
        35                  40                  45

Asn Ser Ser Thr Phe Ile Cys Ser Trp Gly Ser Trp Trp Trp Phe Ala
    50                  55                  60

Glu Asn Ile Thr Arg Pro Tyr Ser Asp Val Gly Met Pro Pro Ala Pro
65                  70                  75                  80

Ile Ser Ala Leu Cys Tyr Ile Tyr Ser Asn Asn Asp Pro Pro Pro Trp
                85                  90                  95

Tyr His Asn Thr Thr Ile Ile Pro Gln Asn Cys Arg Asn Ser Thr Ala
            100                 105                 110

Asp Pro Thr Thr Ala Pro Cys Arg Asp Lys Trp Gly Asn Ala Thr Ala
        115                 120                 125

Cys Ile Leu Asp Arg Arg Ser Arg Phe Cys Gly Asp Cys Tyr Gly Gly
```

```
            130                 135                 140
Cys Phe Tyr Thr Asn Gly Ser His Asp Arg Ser Trp Asp Arg Cys Gly
145                 150                 155                 160

Ile Gly Tyr Arg Asp Gly Leu Ile Glu Phe Val Gln Leu Gly Gln Ile
                165                 170                 175

Arg Pro Asn Ile Ser Asn Thr Thr Ile Glu Leu Leu Ala Gly Ala Ser
            180                 185                 190

Leu Val Ile Ala Ser Gly Leu Arg Ala Gly Tyr Gly Cys Ser Arg Ala
                195                 200                 205

His Gly Val Val His Cys Tyr Lys Cys Pro Ser Tyr Arg Asp Leu Glu
            210                 215                 220

Gln Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
                245                 250                 255

Val Ser Asn Asn Pro Leu His Leu Ile Gln Thr Phe Val Glu Asp Ile
            260                 265                 270

Phe Leu Ala Pro Phe Cys Ser Pro Thr Pro Gly Arg Val Arg Val Cys
                275                 280                 285

Asn Asn Thr Ala Phe Tyr Pro Thr Gly Gly Phe Val Gln Leu Ile
            290                 295                 300

Gly Asp Val Gln Val Leu Thr Pro Asn Thr Ala Ser Leu His Ser Leu
305                 310                 315                 320

Leu Thr Leu Ile Ser Leu Ile Leu Leu Val Cys Val Val Ser Gly Ala
                325                 330                 335

Arg Phe Ile Pro Leu Ile Ile Ile Phe Phe Trp Ser Val Arg His Val
                340                 345                 350

Tyr Ala

<210> SEQ ID NO 423
<211> LENGTH: 237
<212> TYPE: PRT
<213> ORGANISM: Human Pegivirus 2

<400> SEQUENCE: 423

Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
                20                  25                  30

Val Ala Ala Arg Ile Ser Ser Cys Gly His Ala Val Pro Pro Pro Asp
            35                  40                  45

Arg Gly Trp Glu Val Pro Ala Ala Met Ser Trp Ala Ile Ser Arg Thr
50                  55                  60

Thr Gly Leu Thr Phe Asp Val Phe Ser Phe Ile Gln Tyr Phe Pro Thr
65                  70                  75                  80

Val Pro Gly Asn Asn Thr Asp Ile Ile Tyr Cys Gly Glu Pro Thr Phe
                85                  90                  95

Phe Gly Asp Ile Thr Gly Ile Tyr Trp Pro Tyr Phe Leu Pro Gly Leu
                100                 105                 110

Leu Leu Leu Tyr Leu Thr Pro Leu Leu Gly Phe Arg Leu Met Leu Ala
            115                 120                 125

Gly Phe Asn Ile Asp Gly Leu Phe Pro Ile Arg His Ala Thr Ala Ala
            130                 135                 140

Leu Arg Phe Ser Thr Ser Arg Ala Thr Met Cys Val Val Ser Ala Phe
```

```
            145                 150                 155                 160
Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
                180                 185                 190

His Glu Thr Ile Leu Tyr Ile Ala Cys Leu Leu Tyr Leu Gln Val
                195                 200                 205

Ser Pro Arg Ala Gly Leu Ala Ala Met Val Ala Ile Lys Leu Ser Arg
            210                 215                 220

Gly Leu Leu Phe Ala Val Val Leu Ala His Gly Val Cys
225                 230                 235
```

<210> SEQ ID NO 424
<211> LENGTH: 240
<212> TYPE: PRT
<213> ORGANISM: Human Pegivirus 2

<400> SEQUENCE: 424

```
Arg Pro Gly Arg Val Phe Gly Leu Glu Val Cys Ala Asp Ile Ser Trp
1               5                   10                  15

Leu Val Glu Phe Thr Gly Asn Cys Thr Trp Tyr Met Ser Cys Val Phe
                20                  25                  30

Ser Phe Trp Cys Ala Val Phe Ala Phe Thr Ser Pro Leu Gly Arg His
            35                  40                  45

Tyr Lys Leu Gln Ile Tyr Arg Tyr Trp Ala Gln Val Tyr Ala Arg Leu
    50                  55                  60

Ile Leu Ala Val Gly Cys Gly Pro Leu Gly Arg Glu Phe His Phe Arg
65                  70                  75                  80

Ala Ser Val Gly Val Leu Trp Cys Gly Ala Cys Met Leu Trp Pro Arg
                85                  90                  95

Glu Cys Ser Glu Ile Ser Leu Val Phe Ile Leu Cys Ala Leu Thr Val
                100                 105                 110

Asp Thr Ile Asp Thr Trp Leu Val Ala Cys Leu Ser Ala Gly Pro Ser
            115                 120                 125

Ala Arg Thr Leu Ala Thr Leu Ala Asp Asp Met Ala Arg Phe Gly Asp
    130                 135                 140

His Arg Ala Leu Arg Ala Val Leu Arg Cys Phe Gly Ser Arg Gly Thr
145                 150                 155                 160

Tyr Ile Tyr Asn His Met Gly Gln Val Ser Glu Arg Val Ala Gln Ala
                165                 170                 175

Val Arg Asp Phe Gly Gly Cys Leu Glu Pro Val Val Leu Glu Glu Pro
            180                 185                 190

Thr Phe Thr Glu Val Val Asp Asp Thr Met Asn Leu Val Cys Gly Gln
    195                 200                 205

Leu Leu Gly Gly Lys Pro Val Val Ala Arg Cys Gly Thr Arg Val Leu
    210                 215                 220

Val Gly His Leu Asn Pro Glu Asp Leu Pro Pro Gly Phe Gln Leu Ser
225                 230                 235                 240
```

<210> SEQ ID NO 425
<211> LENGTH: 628
<212> TYPE: PRT
<213> ORGANISM: Human Pegivirus 2

<400> SEQUENCE: 425

Ala Pro Val Ile Ile Thr Lys Pro Ser Ile Gly Thr Trp Ser Phe Leu

-continued

```
1               5                    10                   15
Lys Ala Thr Leu Thr Gly Arg Ala Glu Thr Pro Gly Ser Gly Gln Ile
                20                  25                  30
Val Val Leu Ser Ser Leu Thr Gly Arg Ser Met Gly Thr Ala Val Ser
                35                  40                  45
Gly Thr Leu Tyr Ala Thr Gly His Gly Ala Gly Arg Gly Leu Ala
        50                  55                  60
Thr Cys Ala Gly Leu Arg Thr Pro Leu Tyr Thr Ala Leu Ser Asp Asp
65                  70                  75                  80
Val Val Ala Tyr Ser Cys Leu Pro Gly Met Ser Ser Leu Glu Pro Cys
                85                  90                  95
Arg Cys Ala Pro Ser Arg Val Trp Val Met Asn Asn Asn Gly Gly Leu
                100                 105                 110
Val Cys Gly Arg Val Glu Asn Glu Asp Val Cys Leu Asp Cys Pro Thr
                115                 120                 125
His Ile Asp Gln Leu Arg Gly Ala Ser Gly Ser Pro Val Leu Cys Asp
        130                 135                 140
His Gly His Ala Tyr Ala Leu Met Leu Gly Gly Tyr Ser Thr Ser Gly
145                 150                 155                 160
Ile Cys Ala Arg Val Arg Ile Val Arg Pro Trp Gln Asn Ala Tyr Ser
                165                 170                 175
Ser Ser Gly Gly Gln Gly Gly Met Gln Ala Pro Ala Val Thr Pro Thr
                180                 185                 190
Tyr Ser Glu Ile Thr Tyr Tyr Ala Pro Thr Gly Ser Gly Lys Ser Thr
                195                 200                 205
Lys Tyr Pro Val Asp Leu Val Lys Gln Gly His Lys Val Leu Val Leu
                210                 215                 220
Ile Pro Ser Val Ala Val Lys Ser Met Ala Pro Tyr Ile Lys Glu
225                 230                 235                 240
Thr Tyr Lys Ile Arg Pro Glu Ile Arg Ala Gly Thr Gly Pro Asp Gly
                245                 250                 255
Val Thr Val Ile Thr Gly Glu Asn Leu Ala Tyr Met Thr Tyr Gly Arg
                260                 265                 270
Phe Leu Val Asp Pro Glu Thr Asn Leu Gln Gly Tyr Ala Val Val Ile
                275                 280                 285
Cys Asp Glu Cys His Asp Thr Ser Ser Thr Leu Leu Gly Ile Gly
                290                 295                 300
Ala Val Arg Met Tyr Ala Glu Lys Ala Gly Val Arg Thr Val Val Phe
305                 310                 315                 320
Ala Thr Ala Thr Pro Ala Gly Ile Gln Val Gln Pro His Pro Asn Ile
                325                 330                 335
Asp Glu Tyr Leu Leu Thr Asn Glu Gly Asp Val Asp Phe Tyr Gly Ala
                340                 345                 350
Lys Ile Lys Leu Asp Asn Ile Arg Thr Gly Arg His Val Ile Phe Cys
                355                 360                 365
His Ser Lys Ala Arg Cys Ala Glu Leu Thr Gln Gln Leu Ser Gly Leu
        370                 375                 380
Gly Val His Ala Val Ser Phe Trp Arg Gly Cys Asp Ile Lys Thr Ile
385                 390                 395                 400
Pro Ala Ser Gly Ser Ile Val Val Ala Thr Asp Ala Leu Ser Thr
                405                 410                 415
Gly Phe Thr Gly Asn Phe Asp Ser Val Ile Asp Cys Gly Cys Cys Val
                420                 425                 430
```

```
Glu Gln Thr Val Thr Ile Asp Met Asp Pro Thr Phe Ser Ile Ser Ala
            435                 440                 445

Arg Val Val Pro Cys Thr Ala Ala Leu Arg Met Gln Arg Arg Gly Arg
        450                 455                 460

Thr Gly Arg Gly Arg Gly Ala Tyr Tyr Thr Thr Thr Pro Gly Ala
465                 470                 475                 480

Ala Pro Cys Val Ser Val Pro Asp Ala Asn Val Trp Gln Ala Ala Glu
                485                 490                 495

Ser Ala Met Val Phe Tyr Asp Trp Asn Ala Ala Arg Ile Gln Gln Cys
            500                 505                 510

Leu Ala Ala Tyr His Asp Leu Gly Cys Thr Pro Arg Ile Gly Cys Asp
        515                 520                 525

Pro His Thr Pro Val Arg Val Met Asp Thr Leu Arg Ala Tyr Leu Arg
    530                 535                 540

Arg Pro Glu Val Thr Thr Ala Ala Leu Ala Gly Glu Gln Trp Pro Leu
545                 550                 555                 560

Leu Tyr Gly Val Gln Leu Cys Ile Cys Lys Glu Thr Glu Ala His Gly
                565                 570                 575

Pro Asp Asp Gly Ile Lys Trp Lys Cys Leu Leu Asn Asn Thr Asn Lys
            580                 585                 590

Thr Pro Leu Leu Tyr Ala Leu Asp Asn Pro Thr Leu Glu Phe Thr Thr
        595                 600                 605

Gln His Asp Leu Thr Arg Arg Ile Ala Gly Ala Leu Ser Ser Thr Val
    610                 615                 620

Phe Val Glu Ala
625

<210> SEQ ID NO 426
<211> LENGTH: 41
<212> TYPE: PRT
<213> ORGANISM: Human Pegivirus 2

<400> SEQUENCE: 426

Gly Tyr Gly Pro Ile Leu Leu Ala Gly Ala Leu Ala Ala Ser Phe
1               5                   10                  15

Ala Phe Ala Gly Ala Thr Gly Ala Leu Val Pro Ser Ala Val Trp Ser
            20                  25                  30

Val Asp Asn Gly Pro Ala Gly Val Thr
            35                  40

<210> SEQ ID NO 427
<211> LENGTH: 262
<212> TYPE: PRT
<213> ORGANISM: Human Pegivirus 2

<400> SEQUENCE: 427

Arg Pro Asp Ala Thr Asp Glu Thr Ala Ala Tyr Ala Gln Arg Leu Tyr
1               5                   10                  15

Gln Ala Cys Ala Asp Ser Gly Ile Leu Ala Ser Leu Gln Gly Thr Ala
            20                  25                  30

Cys Ala Ala Leu Ser Lys Leu Ala Asp Ala Ser Arg Gly Ala Ser Gln
        35                  40                  45

Tyr Leu Ala Ala Ala Pro Pro Ser Pro Ala Pro Leu Val Gln Val Leu
    50                  55                  60

Gln Phe Leu Glu Thr Asn Phe Ser Ser Ile Ala Ser Phe Gly Leu Leu
65                  70                  75                  80
```

```
Cys Ala Gly Cys Gln Ala Gly Glu Cys Phe Thr Ala Leu Ala Gly Leu
                85                  90                  95

Val Ser Gly Ala Thr Ala Gly Leu Gly Gly Ala His Lys Trp Leu Leu
            100                 105                 110

Ala Ile Ala Gly Thr Trp Leu Val Ser Leu Gln Thr Gly Pro Arg Gly
            115                 120                 125

Gly Met Val Ala Gly Leu Ser Val Leu Ala Gly Cys Cys Ile Gly Ser
130                 135                 140

Val Thr Gly Leu Asp Phe Leu Phe Gly Cys Leu Thr Gly Trp Glu Ala
145                 150                 155                 160

Val Val Gly Ala Ala Val Ala Thr Gln Lys Ile Leu Ser Gly Ser Ala
                165                 170                 175

Asp Met Thr Thr Leu Val Asp Leu Leu Pro Ala Ile Phe Ser Pro Gly
            180                 185                 190

Ala Gly Ile Ala Gly Val Val Leu Val Phe Ile Leu Ser Asn Ser Ser
            195                 200                 205

Val Thr Thr Trp Ala Asn Arg Leu Leu Ser Met Cys Ala Lys Gln Thr
210                 215                 220

Ile Cys Glu Asn Tyr Phe Leu Thr Glu Arg Phe Gly Gln Gln Leu Ser
225                 230                 235                 240

Lys Leu Ser Leu Trp Arg Ala Val Tyr His Trp Ala Gln Ala Arg Glu
                245                 250                 255

Gly Tyr Thr Gln Cys Gly
                260

<210> SEQ ID NO 428
<211> LENGTH: 457
<212> TYPE: PRT
<213> ORGANISM: Human Pegivirus 2

<400> SEQUENCE: 428

Val Val Gly Gly Ile Trp Ser Phe Ala Leu Cys Val Leu Arg Ala Val
1               5                   10                  15

Trp Asp Trp Ala Ala Arg His Val Pro Arg Phe Arg Val Pro Met Ile
            20                  25                  30

Gly Cys Ser Pro Ala Trp Cys Gly Arg Trp Leu Gly Thr Gly Thr Leu
            35                  40                  45

Leu Thr Thr Cys Gly Cys Gly Glu Arg Val Ser Leu Gln Cys Leu Cys
        50                  55                  60

Ser Thr Ser Asp Pro Thr Leu Ser Val Gly Arg Trp Cys Arg Cys Ser
65                  70                  75                  80

Trp Ser Val Gly Phe Pro Phe Asn Pro Thr Thr Thr Ala Thr Gly Thr
                85                  90                  95

Leu Arg Pro Asp Ile Ser Asp Ala Thr Lys Leu Gly Phe Arg Tyr Gly
            100                 105                 110

Val Ala Glu Ile Val Glu Leu Glu Trp Arg Asp Asn Lys Trp His Val
            115                 120                 125

Cys Ala Ala Ser Cys Cys Val Asp Arg Ala Ser Val Ala Ser Ala Val
130                 135                 140

Lys Ala Pro Pro Val Thr Ala Asn Gly Ile Pro Ile Ser Thr Phe Ser
145                 150                 155                 160

Pro Pro Glu Thr Tyr Lys Leu Ser Leu Cys Ser Phe Asp Ser Val Cys
                165                 170                 175

Met Ser Asn Ser Ser Asn Pro Ala Lys Thr Leu Ser Val Cys Ser Gln
```

```
                180             185             190
Glu Ala Val Glu Leu Leu Glu Glu Thr Val Asp Thr Ala Gln Ala Val
            195                 200                 205
Met Cys Lys Asn Leu Glu Ala Arg Arg Arg Ala Glu Tyr Asp Ala Trp
            210                 215                 220
Gln Val Arg Gln Ala Val Gly Asp Glu Tyr Thr Arg Leu Ala Asp Glu
225                 230                 235                 240
Asp Val Asp Thr Thr Ala Ser Val Lys Pro Val Ala Arg Ala Ala
            245                 250                 255
Val Gly Ser Ser Thr Leu Asp Asp Val Asn Val Leu Thr Val Leu Arg
            260                 265                 270
Glu Leu Gly Asp Gln Cys Gln Asn Ala Ile Lys Phe Val Gln Ala
            275                 280                 285
Ala Ser Arg Phe Val Pro Pro Val Pro Arg Pro Arg Thr Arg Val Ser
            290                 295                 300
Gly Val Leu Glu Arg Val Arg Met Cys Met Arg Thr Pro Pro Ile Lys
305                 310                 315                 320
Phe Glu Ala Thr Ala Val Pro Ile His Asn Ile Ile Pro Glu Glu Cys
            325                 330                 335
His Ile Val Leu Arg Cys Thr Gly Cys Ser Asp Gln Ala Leu Thr Val
            340                 345                 350
Pro Tyr Gly Thr Cys Thr Gln Thr Leu Thr Lys His Leu Thr Asn Lys
            355                 360                 365
His Ser His Tyr Ile Pro Lys Gln Lys Ile Glu Glu Asp Thr Glu Val
            370                 375                 380
Thr Val Ile Cys Ala Val Pro Thr Thr Arg Ala Ser Lys Leu Ile Thr
385                 390                 395                 400
Phe Arg Ala Gly Asp Arg Ser Val Ser Cys Cys His Pro Leu Gln Thr
            405                 410                 415
Pro Ile Arg Ala Leu Leu Leu Lys Tyr Gly Leu Pro Ile Gly Lys Trp
            420                 425                 430
Ser Asp Cys Asn Gly Pro Leu Gly Asp Asp Ala Arg Val Cys Asp Val
            435                 440                 445
Asn Gly Val Thr Thr Tyr Glu Pro Cys
            450                 455
```

<210> SEQ ID NO 429
<211> LENGTH: 567
<212> TYPE: PRT
<213> ORGANISM: Human Pegivirus 2

<400> SEQUENCE: 429

```
Met Gln Ser Tyr Ser Trp Phe Arg Pro Ile Val Ala Pro Thr Thr Pro
1               5                   10                  15
Pro Leu Pro Ala Thr Arg Ser Val Ala Gly Ile Leu Arg Ala Asp Thr
            20                  25                  30
Ser Arg Val Tyr Thr Thr Thr Ala Val Asp Val Ser Glu Arg Gln Ala
            35                  40                  45
Lys Val Thr Ile Asp Gln Thr Ser Ala Lys Val Asp Gln Cys Phe Arg
    50                  55                  60
Asp Thr Tyr Asn Cys Cys Leu Ala Lys Ala Lys Thr Phe Lys Gln Ser
65                  70                  75                  80
Gly Met Ser Tyr Glu Asp Ala Val Ser Lys Met Arg Ala Asn Thr Thr
                85                  90                  95
```

```
Arg Asp His Asn His Gly Thr Thr Tyr Ser Asp Leu Val Ser Gly Arg
            100                 105                 110

Ala Lys Pro Val Val Gln Lys Ile Val Asn Gln Met Arg Ala Gly Val
        115                 120                 125

Tyr Asp Ala Pro Met Arg Ile Ile Pro Lys Pro Glu Val Phe Pro Arg
    130                 135                 140

Asp Lys Glu Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His
            180                 185                 190

Glu Arg Ala Arg Leu Leu Glu Gln Trp Trp Asn Arg Ala Thr Glu Pro
        195                 200                 205

Gln Ala Ile Ala Val Asp Ala Ile Cys Phe Asp Ser Thr Ile Thr Ala
    210                 215                 220

Glu Asp Met Asp Arg Glu Ala Asn Ile Val Ala Ala His Ala Asp
225                 230                 235                 240

Pro Glu Gly Val His Gly Leu Tyr Asn Tyr Tyr Lys Arg Ser Pro Met
                245                 250                 255

Cys Asp Ile Thr Gly Asn Ile Val Gly Val Arg Cys Cys Arg Ala Ser
            260                 265                 270

Gly Thr Leu Thr Thr Ser Ser Gly Asn Thr Leu Thr Cys Tyr Leu Lys
        275                 280                 285

Val Arg Ala Ala Cys Thr Arg Ala Gly Ile Lys Pro Ile Gly Leu Leu
    290                 295                 300

Ile His Gly Asp Asp Thr Leu Ile Ile Thr Glu Arg Cys Ala Gln Glu
305                 310                 315                 320

Thr Leu Asp Glu Phe Ser Arg Ala Leu Asp Asp Tyr Gly Phe Pro His
                325                 330                 335

Thr Phe Gln Ala Ser Gly Asp Leu Ser Ser Ile Glu Cys Cys Ser Ala
            340                 345                 350

His Val Asp Ser Val Cys Leu Arg Gly Gly Met Arg Arg Met Leu Val
        355                 360                 365

Pro Gln Ala Arg Arg Ala Ile Ala Arg Val Leu Gly Glu Lys Gly Asp
    370                 375                 380

Pro Leu Gly Val Ile Ser Ser Tyr Ile Val Met Tyr Pro Thr Ala Ala
385                 390                 395                 400

Val Thr Val Tyr Val Leu Leu Pro Leu Leu Cys Met Leu Ile Arg Asn
                405                 410                 415

Glu Pro Ser Gln Thr Gly Thr Phe Val Thr Leu Thr Val His Gly Asn
            420                 425                 430

Ser Val Ser Val Pro Val Trp Leu Leu Pro Thr Ile Ile Val Asn Leu
        435                 440                 445

His Gly Arg Asp Ala Leu Gln Val Val Arg His Thr Ala Ala Ser Met
    450                 455                 460

Ala Glu Leu Ser Ser Ala Leu Ala Phe Phe Gly Met Arg Gly Leu Asn
465                 470                 475                 480

Cys Trp Arg Arg Arg Arg Ala Ile Arg Ala Asp Met Ile Lys Leu
                485                 490                 495

Gly Gly Trp Asn Ala Asn Phe Ala Gln Met Leu Leu Trp Ser Pro Glu
            500                 505                 510

Val Arg Thr Pro Gln Pro Glu Pro Lys Gly Met Cys Leu Leu Pro Pro
```

```
          515                 520                 525
Glu Leu Trp Glu Arg Pro Tyr Glu Asn Leu His Leu Ser Thr Ile Asp
     530                 535                 540

Arg Asn Arg Gly Ala Ser Arg Leu Arg Phe Trp Leu Val Ala Ser Ala
545                 550                 555                 560

Ile Leu Ala Leu Leu Cys Leu
             565

<210> SEQ ID NO 430
<211> LENGTH: 9867
<212> TYPE: DNA
<213> ORGANISM: Human Pegivirus 2
<220> FEATURE:
<221> NAME/KEY: misc_feature
<222> LOCATION: (1)..(15)
<223> OTHER INFORMATION: N = A, C, T, or G
<220> FEATURE:
<221> NAME/KEY: misc_feature
<222> LOCATION: (3260)..(3360)
<223> OTHER INFORMATION: N = A, C, T, or G
<220> FEATURE:
<221> NAME/KEY: misc_feature
<222> LOCATION: (9542)..(9636)
<223> OTHER INFORMATION: N = A, C, T, or G
<220> FEATURE:
<221> NAME/KEY: misc_feature
<222> LOCATION: (9857)..(9867)
<223> OTHER INFORMATION: N = A, C, T, or G

<400> SEQUENCE: 430
nnnnnnnnnn nnnnnaatgc gcatattgct acttcggtac gcctaattgg taggcgcccg      60
gccgaccggc cccgcaaggg cctagtagga cgtgtgacaa tgccatgagg gatcatgaca     120
ctggggtgag cggaggcagc accgaagtcg ggtgaactcg actcccagtg cgaccacctg     180
gcttggtcgt tcatggaggg catgcccacg ggaacgctga tcgtgcaaag ggatgggtcc     240
ctgcactggt gccatgcgcg gcaccactcc gtacagcctg ataggggtggc ggcgggcccc     300 cccagtgtga cgtccgtgga gcgcaacatg gggtgttcaa ctgatcaaac catttgttct     360
ccagtcgtgg gggccgacta taatacctcc tcgggctgcc gggccttaaa tgggagctac     420
cactgcggtg gtggctcttg ccggtcacca agtcgtgtgc aggtcgcggg acgagtcttg     480
cggctgtgcg cattccttgc gttgatcgga tccggtatgt gttcgatccg gtccaaaact     540
gaagggcgca ttgagtcagg gcaaatattg cagtctcagc gcgcatgttg gactggtgag     600
ggtttcgctt tcttttctaa ctgttgcaat caatctgata ttatgtggtg tttgcaccgt     660
tggtgtgtga caagacctgg ctgtttagtg tgcacgggca atgccactca tcctatctgc     720
tgggactatc ttgggtccgg tgtaagtcgg cggcctgcac gtcgaatggg tgagggagct     780
gaagtgcttc ttcgcttgat cggcattgca ggttggctcg gctgttagc tgagactctt     840 ggtatgtccg aattctatgc agctattcta tgctttggat ttattgcttg gtatggctgg     900
ggtataccta aaacattggt gtgcacggtc tgccctgcag tgaacatttc tccctatagc     960
ttcttatctc cagatactat cgcatttggt acgtggatac tacaactacc tggtcttttg    1020
tggcaaatgt tgtcaacttt cctatactt tacagcactt ggattctttg gttgttgctc    1080
agcggcaaga ctgttgctgt gatagcaatc cttttggcta gtcctacggt tatggcatac    1140
aagcatcaat ctgaaagcta cctcaaatac gtaccataa ccaatgcttc aactgctatg    1200
aattgtgact gccccttggg aacctttact cgtaatactg agtctcgttt ctctatacct    1260
agattctgtc ctgttaaaat tgacagctct acatttatct gctcgtgggg gtcgtggtgg    1320
```

```
tggtttgctg agaacatcac gcgtccatac tcggacgttg gcatgccgcc agcaccgatc    1380
tccgctttgt gctatatcta tgcaaacaat gacccacctc cttggtatca taacacaact    1440 atcataccte agaactgtcg caactcctcg gctgatccta ccactgctcc atgccgtgac    1500
aagtggggca atgcaactgc ttgtattctt gaccgccggt cgcggttctg cggggactgc    1560 tatgcggtt gttttctatac taatggcact cacgatcgat cctgggatcg atgcgggatt    1620
ggttaccgtg atggactcat agagtttgtg cagcttggtc agattcgacc caacatctcg    1680
aatacgacca ttgaactcct cgctggcgcc tcgcttgtga tcgcatccgg tcttcggcct    1740
ggctacggtt gcagccgtgc gcatggcgtg gtgcactgct ataggtgtcc ttcatatcgt    1800
gaccttgaac agtttggtcc cgggctcggg aaatgggtgc cactgcctgg cgagcctgtc    1860
ccggagttgt gtattaaccc tcagtgggcg agacgcggct tccgggtatc taacaaccct    1920
ttaagcttgc tgcagacctt cgttgaggac attttcctag cacctttttg caacccgacg    1980
cctggccgtg tacgtgtgtg taacaatact gctttctatc cgaagggagg cggctttgtg    2040
cagctcatcg gagacgtcca ggtgttaacc cctaacactg catctttaca ctctctgctg    2100
actttaatat ccettatttt gttagtgtgt gttgtttctg gcgcgcgatt cgtcccattg    2160
tttatcatat ttttctggag cgtgcgtcac gtatatgctt cttgttactt aagctgtgat    2220
tgggctgttt gcaacgatgc gttctgtttc acatctggca cttgtgctac tttcaatgac    2280
gtcttgtgtc tgccggttgc gacgcgcgta tcgtcctgcg gcatgctgt accacctccc    2340 gaccgtggtt gggaggtgcc tgcggcgatg tcatgggcga tctcacgaac tactggcttg    2400
acgttcgatg tcttttcctt catccagtac tttcctactg tgcctggcaa caacactgat    2460
atcatttact gtggtgaccc aactttcttc ggggacatca cgggcatcta ttggccttac    2520
tttttgcctg gcatgttgct cttgtacttg actcctttcc tgggtttaag gttaatgctt    2580
gctggcttca atatagatgg cttgtttccc atacggcacg ccacggctgc actgaggttc    2640
tcgacttcgc gtgtgacctt gagtgtcgta cttgctttct taatctatat actatctcac    2700
cctgttaatg ctgcgctcaa tagaatgttc ctagcatctg caaatttaga gatgatctta    2760
tcctttgaca cctatcatga gactattctt tacattcttt gcctgttgct ctacctccag    2820
gtgtcgcccc gcgctgggct ggccgctatg gtggccgtca gctatctcg aggcctgtta    2880 ttcgccgtgg tgttggcgca cggagtgtgc cgacccgggc gggtatttgg tcttgaggtc    2940
tgcgcggaca tcacttggtt ggtggagttt actggcaact gcacttggta catgtcctgt    3000
gttttctcat tttggtgcgc agtgttcgcc ttcaccagtc cacttggacg acggtataag    3060
cttcagatct accggtactg ggcgcaggtc tatgccagaa tcatcctcgc tgtcggttgt    3120
ggtcctctcg gacgggagtt ccatttccgt gcaggcgtgg gtgcgttttg gtgtggtgct    3180
tgcatgctct ggccccgtga gtgctctgaa atcagcttgg tcttcattct gtgtgctctg    3240
acgatggaca ccatagacan nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
gtgttgcgtt gctttggatc acgtggcaca tacatataca accacatggg ccaggtctca    3420
gaacgggtgg cgcaagcagt cagggatttc ggcggttgct tggaaccagt cgtgttggag    3480
gagcccacct ttactgaggt cgtggatgat acaatgagtc tagtgtgtgg acaattgctt    3540
ggaggtaaac ctgtggtggc ccgctgcggc acgcgtgtct tggtgggaca cctcaaccct    3600
gaagacttgc cacctggttt ccagctgagt gctccggtgg ttatcaccaa accaagcatt    3660
ggtacgtggt ccttccttaa ggcgacactc acagggcgtg ctgagacacc gggatccggc    3720
```

```
cagatcgtgg tgttgtcttc cctgacaggt cggtcaatgg gtaccgcagt gaatggcaca   3780
ctgtatgcga ccggccatgg tgctggtgcg cgcggcctag ccacgtgcgc tggcttgagg   3840
acgccacttt acacggcact atcagatgat gtcgtggcct actcttgcct tccgggcatg   3900
agttccctgg agccctgctg ctgttcgccg agccgggttt gggtgatgaa caacaatgga   3960
gggttggtgt gtggcagagt ggagaaggac gacgtctgtt tggactgtcc cacgcacata   4020
gatcagctgc ggggtgcctc ggggtcaccg gttttgtgtg atcacggtca cgcatacgcg   4080
ttgatgctcg gtggctactc taccagcggt atttgtgcgc gtgtccggat agtccggcca   4140
tggcagaacg cctattcctc ctcagggggg caaggcggaa tgcaggcgcc agctgtgaca   4200
ccaacatact ctgaaatcac ctactatgcc cctactggtt ctggtaagtc aacaaaatat   4260
ccagtggacc tagtcaaaca gggacacaag gtcttggttc ttataccaag cgtggctgtc   4320
gtcaaaagca tggccccttA cattaaggag acatataaga ttagacctga aattagagct   4380 ggcacaggge ctgacggtgt gacggtcatc actggtgaga acttggcgta catgacctat   4440
ggccgtttcc tcgtggatcc ggagacgaat ctgcggggtt atgccgtagt catttgcgac   4500
gagtgtcacg atacatcatc caccacgcta ctcggcattg gcgcagtgcg catgtatgcc   4560
gagcaagctg gagtgaagac cgttgtattc gccacagcca ctcctgctgg tatccaagta   4620
cagccacatc caaacattga tgaatattta ttgactgaca caggcgacgt ggatttctac   4680
ggcgccaaaa tcaaattgga caacattaga actggtagac atgttatctt ttgtcactcg   4740
aaagccaagt gtgcggaact aacgcagcag ctctccggcc ttggtgttcg tgcagtgagt   4800
ttttggcgcg gctgtgacat caaaaccatt cccgcctcag actctattgt tgtggtggca   4860
actgatgcat tgtccacagg ctacacagga aattttgatt cggtcattga ctgcgggtgt   4920
tgcgtagagc aaactgtgac aattgacatg gaccccacgt tctccatctc ggcccgagta   4980
gtgccatgca ctgctgcatt gcgaatgcag cggcgcggac gcaccggtcg tggcagaagg   5040
ggagcgtact acacaaccac tccaggagca gcaccctgcg tcaacgttcc cgatgctaac   5100
gtctggcaag cagtggagtc agccatggtc ttctatgatt ggaatgctgc caggatacag   5160
cagtgtctgg cggcatacca tgatttaggg tgtacaccac gcatcagttg tgacccacac   5220
actccagtgc gggtgatgga cacactgagg gcgtacctgc gcagacctga ggtgacgact   5280
gcggctctcg caggagagca gtggccgctg ctatacggtg tgcagttgtg catctgcaaa   5340
gagaccgagg cccacggtcc agatgatggc atcaagtgga atgtttact caataacaac   5400 aataaaacac cctgttgta tgccttagac aatcctacac tggaattcac tacccaacat   5460
gacttgactc gccgtatagc cggcgctcta tcgagcacag tgttcgtgga gacaggctat   5520
ggccccatcc tcctcgctgg cgccgctttg gctgcctcct tcgcctttgc gggcgccact   5580
ggagctttag tgccgtcggc cgtttggagt gttgacaacg gcctactgg cgtgacccgt   5640 cccgacgcga cagacgagac cgtggcctac gcgcagcgct tgtaccacgc tgcgcagat   5700 tcaggaattc tcgccagctt gcagggcacg gcgtgtgcgg cactgagtaa actggccgat   5760
gccagtaggg gtgctagtca atatctggca accgcgcctc cttcgcccgc cccctggta   5820 caggtgctgc agttcctcga gaccaacttt agctccattg catcttcgg tctgctctgt   5880 gctggttgtc aggctggtga gtgcttcact gcgcttgccg ggttggtgtc cggtgctaca   5940
gctggcttgg gaggtgccca taagtggttg ttagctattg caggaacttg gctagttagc   6000
ctgcagaccg ggccccgtgg cggcatggtt gcgggtctct cggttctagc gggctgttgc   6060
```

```
atcggcggtg tcaccgggct tgacttcctg tttgggtgcc ttacaggttg ggaggccgtg      6120
gtcggtgctg ccgttgcgac acagaagatc ttgtctggtt cggctgatat gaccactctg      6180
gtagatctct tacctgctct cttttcccct ggtgctggca tagctggcat cgtgcttgtc      6240
tttattctaa gcaacacaag tgtaaccgca tgggccaatc ggctattgtc catgtgtgca      6300
aaacaaacca tttgtgaaaa ctacttctta actgagaaat ttggccaaca attaagcaaa      6360 cttttccttgt ggcgtgctgt gtaccattgg gcgcaggcac atgaggggta cacacagtgc      6420
ggtgtggttg gcgggatctg gagctttgtc ctgtgcattc tacgcgctgc gtgggattgg      6480
gcggccaagc atgtgccacg gttccgtgtg cctatgattg ctgctcacc tgcgtggtgc       6540 gggcgctggc ttggtactgg caccttgttg accacctgtg ggtgtggaga acgtgtatcc      6600
cttcaatgcc tttgttcaac atctgaccca atactcagtg tgggccgttg gtgccggtgt      6660
agttggagtg ttgggtttcc attcaacccg accacgacag ccaccggcac tttacggccg      6720
gacatcggcg acgccaccag attgggtttc cggtatggca tcgccgagat cgtggagcta      6780
gaacggcggg gcgacaaatg gcatgtctgt gcagcatctt gttgcttgga ccgagctagc      6840
gttgcatccg ctgtgaaggc ccctccggtc acggctaatg gcatacctat cagtcctttc      6900
tctccaccac aaacttacaa actctctctc tgctcttttg attcagtttg catgtctatc      6960
aactcatgta atccatctaa gatcctgagt gtgtgctcac aggaagccgt tgagctgctg      7020
gaagaaacag tcgacacggc acaaacaatg atgtgtaaaa atctggaggc gcgaagacgc      7080
gccgaatttg acgcatggca agtccgccaa gcagttggcg acgagtacac acgcttggca      7140
gatgaggatg tcgacacgat aacgtcggtg aaaccccccgg tggccagggc tgctgtgggt      7200
agctcaacgt tggatgatgt tggcgtgctg actgtcttgc gcgagctcgg cgaccaatgc      7260
caaaatgcta tcaaatttgt agttgaagcg gcctcacggt ttgttccacc agtgcccaag      7320
ccgcgcacgc gtgtctcggg tgtgctggag cgtgtgcgca tgtgcatgcg cacgccacca      7380
atgaagtttg aggccgccgc agtaccaatc cacaacataa tcccagaaaa atgtcacatt      7440
gtgctacgct gtaccggctg tagtgaccag gccttgactg ttccgtacgg cacttgcact      7500
cagactttaa gcagccattt gactaacaaa cacagtcact acattccaaa acagaagata      7560
gaagaagaca cagaagtaac tgtcatttgc gccgtaccaa caaagcgcgc aagcaaactc      7620
attactttca gagtaggtga tcgatcagtc tcatgttgtc accccttgca aactcctgtt      7680
agggccctgc ttctaaagta cgggttgcct atcgggaagt ggtccgactg caacggccca      7740
cttggtgacg acgctcgagt ctgtgacgtc aatggagtga caacttatga accatgcatg      7800
caatcctaca gttggtttcg accgattgtg gcaccaacaa ccccaccttt gcctgtaacc      7860
cggagcgtgg ctggcatttt acgcgcagac acatcgcgcg tttacaccac aacagcggtt      7920
gatgtctccg agcggcaggc taaggtcaca attgatcaaa agtcagccaa ggtggatcag      7980
tgtttccgag acacatacaa ctgttgcctt gctaaggcaa agaccttcag acaatctggc      8040
atgtcatatg aggatgctgt gtcaaagatg cgcgcaaaca ccacgcgtga tcataacact      8100
ggcatcactt atacagattt ggtctctgga cgcgcaaaac ctgctgttca gaaaattgta      8160
gatcaaatgc gctctggagt gtacgacgct ccaatgcgca ttatcccaaa gcctgaagtg      8220
tttcctcgag acaagtcaac acggaagcca ccacggttca tcgttttccc tgggtgcgcc      8280
gcacgagtcg cggagaaaat gatcctgggc gatcctggtg cgataaccaa gcacgtgctg      8340
ggtgatgcct acgggtttgc cactccgcgc catgagcgtg cgcgcctatt ggaacaatgg      8400
tggaaccgcg cgacggagcc acaggctatc gcggttgatg cgatctgctt tgatagcacc      8460
```

```
atcacggcgg aggacatgga tcgcgaggcc cacatcgtgg ctgcagcgca cgcggaccca    8520
gaaggtgttc atggcctata caattattac aaaagaagcc ccatgtgtga catcacagga    8580
aaagttgtcg gggtgcgttg ctgtcgagcc tcaggtacgc ttacaacaag cagtggcaac    8640
acgcttactt gctacctcaa ggttcgcgcg gcttgcacgc gcgccggcat taaaccaatt    8700
ggcttactaa ttcatggaga tgacaccctc attatcacgg aacgttgcac tcaagaaact    8760
ctcgatgagt tcagcaacgc acttgatgac tacgggtttc ctcacacctt ccaggtgtct    8820
ggggacctct cgtctatcga gtgctgtagt gcacgtgtgg acagcgtttg cctccgagga    8880
ggtatgcgtc gcatgcttgt gccacaagct cgacgtgcga tcgcacgcgt tctcggagaa    8940
aagggtgatc cactgggtgt tatcagcagc tatattgtca tgtaccctac tgcagccgtg    9000
actgtctacg tactactgcc cctgttgtgc atgctcattc ggaatgagcc atcgcagacg    9060
gggacattgg tgacgctgac ggtccacggt aacagtgtga gcgtgccagt gtggctgctt    9120
ccaaccatca ttgcaaattt acatggccgt gacgcactac aggtggtccg ccacagtgca    9180
gcttccatgg cggaactgtc gtcagcgttg gccttctttg gcatgagagg gttgaactgc    9240
tggcggcgga cgccgtgc catcaggact gacatgatca aattgggcgg gtggaatgcg    9300
aatttcgcgc agatgttact gtggtcaccg gaggtaagaa caccacagcc cgaaccaaag    9360
ggcatgtgtc ttttgccacc ggaactatgg gagcgtccgt acgaaaattt gcacttgagc    9420
acgatcgacc gcgaccgtgg tgctagtcgc ttacggtttt ggttggttgc tagtgctgta    9480
ctcgctctgc tttgcttgta atcctaaat caatgtagta ccaggactac aaggcaggag    9540
gnnnnnnnnn nnnnnnnnnn nnnnnnnnnn nnnnnnnnnn nnnnnnnnnn nnnnnnnnnn    9600
nnnnnnnnnn nnnnnnnnnn nnnnnnnnnn nnnnncccc cccatgtcgc gcgtaagcgc    9660
acgggcaagg cagctaggct gagagtctgg gcaactctcc cgtaccccac ccgaggctac    9720
gcctcgtcct ggcgaggacc gtaaacatac gtcgtcagcg tggtgacctg acgtatcttg    9780
ttaaccactt aatggtcgta actcgacccc cgtgccgggg atctaagcgc ggcaccgcga    9840 tgagggggt caacggnnnn nnnnnnn                                        9867
```

<210> SEQ ID NO 431
<211> LENGTH: 79
<212> TYPE: PRT
<213> ORGANISM: Human Pegivirus 2

<400> SEQUENCE: 431

Met Gly Cys Ser Thr Asp Gln Thr Ile Cys Ser Pro Val Val Gly Ala
1               5                   10                  15

Asp Tyr Asn Thr Ser Ser Gly Cys Arg Ala Leu Asn Gly Ser Tyr His
            20                  25                  30

Cys Gly Gly Gly Ser Cys Arg Ser Pro Ser Arg Val Gln Val Ala Gly
        35                  40                  45

Arg Val Leu Arg Leu Cys Ala Phe Leu Ala Leu Ile Gly Ser Gly Met
    50                  55                  60

Cys Ser Ile Arg Ser Lys Thr Glu Gly Arg Ile Glu Ser Gly Gln
65                  70                  75

<210> SEQ ID NO 432
<211> LENGTH: 191
<212> TYPE: PRT
<213> ORGANISM: Human Pegivirus 2

<400> SEQUENCE: 432

```
Ile Leu Gln Ser Gln Arg Ala Cys Trp Thr Gly Glu Gly Phe Ala Phe
1               5                   10                  15

Phe Ser Asn Cys Cys Asn Gln Ser Asp Ile Met Trp Cys Leu His Arg
            20                  25                  30

Trp Cys Val Thr Arg Pro Gly Cys Leu Val Cys Thr Gly Asn Ala Thr
            35                  40                  45

His Pro Ile Cys Trp Asp Tyr Leu Gly Ser Gly Val Ser Arg Arg Pro
        50                  55                  60

Ala Arg Arg Met Gly Glu Gly Ala Glu Val Leu Leu Arg Leu Ile Gly
65                  70                  75                  80

Ile Ala Gly Trp Leu Gly Leu Leu Ala Glu Thr Leu Gly Met Ser Glu
                85                  90                  95

Phe Tyr Ala Ala Ile Leu Cys Phe Gly Phe Ile Ala Trp Tyr Gly Trp
                    100                 105                 110

Gly Ile Pro Lys Thr Leu Val Cys Thr Val Cys Pro Ala Val Asn Ile
                115                 120                 125

Ser Pro Tyr Ser Phe Leu Ser Pro Asp Thr Ile Ala Phe Gly Thr Trp
            130                 135                 140

Ile Leu Gln Leu Pro Gly Leu Leu Trp Gln Met Phe Val Asn Phe Pro
145                 150                 155                 160

Ile Leu Tyr Ser Thr Trp Ile Leu Trp Leu Leu Ser Gly Lys Thr
                165                 170                 175

Val Ala Val Ile Ala Ile Leu Leu Ala Ser Pro Thr Val Met Ala
                180                 185                 190

<210> SEQ ID NO 433
<211> LENGTH: 354
<212> TYPE: PRT
<213> ORGANISM: Human Pegivirus 2

<400> SEQUENCE: 433

Tyr Lys His Gln Ser Glu Ser Tyr Leu Lys Tyr Cys Thr Ile Thr Asn
1               5                   10                  15

Ala Ser Thr Ala Met Asn Cys Asp Cys Pro Phe Gly Thr Phe Thr Arg
            20                  25                  30

Asn Thr Glu Ser Arg Phe Ser Ile Pro Arg Phe Cys Pro Val Lys Ile
            35                  40                  45

Asp Ser Ser Thr Phe Ile Cys Ser Trp Gly Ser Trp Trp Phe Ala
        50                  55                  60

Glu Asn Ile Thr Arg Pro Tyr Ser Asp Val Gly Met Pro Pro Ala Pro
65                  70                  75                  80

Ile Ser Ala Leu Cys Tyr Ile Tyr Ala Asn Asn Asp Pro Pro Trp
                85                  90                  95

Tyr His Asn Thr Thr Ile Ile Pro Gln Asn Cys Arg Asn Ser Ser Ala
                100                 105                 110

Asp Pro Thr Thr Ala Pro Cys Arg Asp Lys Trp Gly Asn Ala Thr Ala
            115                 120                 125

Cys Ile Leu Asp Arg Arg Ser Arg Phe Cys Gly Asp Cys Tyr Gly Gly
130                 135                 140

Cys Phe Tyr Thr Asn Gly Thr His Asp Arg Ser Trp Asp Arg Cys Gly
145                 150                 155                 160

Ile Gly Tyr Arg Asp Gly Leu Ile Glu Phe Val Gln Leu Gly Gln Ile
                165                 170                 175

Arg Pro Asn Ile Ser Asn Thr Thr Ile Glu Leu Leu Ala Gly Ala Ser
```

```
                180                 185                 190
Leu Val Ile Ala Ser Gly Leu Arg Pro Gly Tyr Gly Cys Ser Arg Ala
            195                 200                 205

His Gly Val Val His Cys Tyr Arg Cys Pro Ser Tyr Arg Asp Leu Glu
        210                 215                 220

Gln Phe Gly Pro Gly Leu Gly Lys Trp Val Pro Leu Pro Gly Glu Pro
225                 230                 235                 240

Val Pro Glu Leu Cys Ile Asn Pro Gln Trp Ala Arg Arg Gly Phe Arg
            245                 250                 255

Val Ser Asn Asn Pro Leu Ser Leu Leu Gln Thr Phe Val Glu Asp Ile
            260                 265                 270

Phe Leu Ala Pro Phe Cys Asn Pro Thr Pro Gly Arg Val Arg Val Cys
            275                 280                 285

Asn Asn Thr Ala Phe Tyr Pro Lys Gly Gly Phe Val Gln Leu Ile
            290                 295                 300

Gly Asp Val Gln Val Leu Thr Pro Asn Thr Ala Ser Leu His Ser Leu
305                 310                 315                 320

Leu Thr Leu Ile Ser Leu Ile Leu Leu Val Cys Val Val Ser Gly Ala
                325                 330                 335

Arg Phe Val Pro Leu Phe Ile Ile Phe Phe Trp Ser Val Arg His Val
            340                 345                 350

Tyr Ala

<210> SEQ ID NO 434
<211> LENGTH: 237
<212> TYPE: PRT
<213> ORGANISM: Human Pegivirus 2

<400> SEQUENCE: 434

Ser Cys Tyr Leu Ser Cys Asp Trp Ala Val Cys Asn Asp Ala Phe Cys
1               5                   10                  15

Phe Thr Ser Gly Thr Cys Ala Thr Phe Asn Asp Val Leu Cys Leu Pro
                20                  25                  30

Val Ala Thr Arg Val Ser Ser Cys Gly His Ala Val Pro Pro Pro Asp
            35                  40                  45

Arg Gly Trp Glu Val Pro Ala Ala Met Ser Trp Ala Ile Ser Arg Thr
        50                  55                  60

Thr Gly Leu Thr Phe Asp Val Phe Ser Phe Ile Gln Tyr Phe Pro Thr
65                  70                  75                  80

Val Pro Gly Asn Asn Thr Asp Ile Ile Tyr Cys Gly Asp Pro Thr Phe
                85                  90                  95

Phe Gly Asp Ile Thr Gly Ile Tyr Trp Pro Tyr Phe Leu Pro Gly Met
            100                 105                 110

Leu Leu Leu Tyr Leu Thr Pro Phe Leu Gly Leu Arg Leu Met Leu Ala
        115                 120                 125

Gly Phe Asn Ile Asp Gly Leu Phe Pro Ile Arg His Ala Thr Ala Ala
    130                 135                 140

Leu Arg Phe Ser Thr Ser Arg Val Thr Leu Ser Val Val Leu Ala Phe
145                 150                 155                 160

Leu Ile Tyr Ile Leu Ser His Pro Val Asn Ala Ala Leu Asn Arg Met
                165                 170                 175

Phe Leu Ala Ser Ala Asn Leu Glu Met Ile Leu Ser Phe Asp Thr Tyr
            180                 185                 190

His Glu Thr Ile Leu Tyr Ile Leu Cys Leu Leu Leu Tyr Leu Gln Val
```

```
                195             200             205
Ser Pro Arg Ala Gly Leu Ala Ala Met Val Ala Val Lys Leu Ser Arg
    210             215             220
Gly Leu Leu Phe Ala Val Val Leu Ala His Gly Val Cys
225             230             235

<210> SEQ ID NO 435
<211> LENGTH: 240
<212> TYPE: PRT
<213> ORGANISM: Human Pegivirus 2
<220> FEATURE:
<221> NAME/KEY: MISC_FEATURE
<222> LOCATION: (117)..(150)
<223> OTHER INFORMATION: Xaa = any amino acid

<400> SEQUENCE: 435

Arg Pro Gly Arg Val Phe Gly Leu Glu Val Cys Ala Asp Ile Thr Trp
1               5                   10                  15
Leu Val Glu Phe Thr Gly Asn Cys Thr Trp Tyr Met Ser Cys Val Phe
            20                  25                  30
Ser Phe Trp Cys Ala Val Phe Ala Phe Thr Ser Pro Leu Gly Arg Arg
        35                  40                  45
Tyr Lys Leu Gln Ile Tyr Arg Tyr Trp Ala Gln Val Tyr Ala Arg Ile
    50                  55                  60
Ile Leu Ala Val Gly Cys Gly Pro Leu Gly Arg Glu Phe His Phe Arg
65                  70                  75                  80
Ala Gly Val Gly Ala Phe Trp Cys Gly Ala Cys Met Leu Trp Pro Arg
                85                  90                  95
Glu Cys Ser Glu Ile Ser Leu Val Phe Ile Leu Cys Ala Leu Thr Met
            100                 105                 110
Asp Thr Ile Asp Xaa Xaa Xaa Xaa Xaa Xaa Xaa Xaa Xaa Xaa Xaa Xaa
        115                 120                 125
Xaa Xaa Xaa Xaa Xaa Xaa Xaa Xaa Xaa Xaa Xaa Xaa Xaa Xaa Xaa Xaa
    130                 135                 140
Xaa Xaa Xaa Xaa Xaa Xaa Val Leu Arg Cys Phe Gly Ser Arg Gly Thr
145                 150                 155                 160
Tyr Ile Tyr Asn His Met Gly Gln Val Ser Glu Arg Val Ala Gln Ala
                165                 170                 175
Val Arg Asp Phe Gly Cys Leu Glu Pro Val Val Leu Glu Glu Pro
            180                 185                 190
Thr Phe Thr Glu Val Val Asp Asp Thr Met Ser Leu Val Cys Gly Gln
        195                 200                 205
Leu Leu Gly Gly Lys Pro Val Val Ala Arg Cys Gly Thr Arg Val Leu
    210                 215                 220
Val Gly His Leu Asn Pro Glu Asp Leu Pro Pro Gly Phe Gln Leu Ser
225                 230                 235                 240

<210> SEQ ID NO 436
<211> LENGTH: 628
<212> TYPE: PRT
<213> ORGANISM: Human Pegivirus 2

<400> SEQUENCE: 436

Ala Pro Val Val Ile Thr Lys Pro Ser Ile Gly Thr Trp Ser Phe Leu
1               5                   10                  15
Lys Ala Thr Leu Thr Gly Arg Ala Glu Thr Pro Gly Ser Gly Gln Ile
            20                  25                  30
```

-continued

```
Val Val Leu Ser Ser Leu Thr Gly Arg Ser Met Gly Thr Ala Val Asn
             35                  40                  45

Gly Thr Leu Tyr Ala Thr Gly His Gly Ala Gly Ala Arg Gly Leu Ala
 50                  55                  60

Thr Cys Ala Gly Leu Arg Thr Pro Leu Tyr Thr Ala Leu Ser Asp Asp
 65                  70                  75                  80

Val Val Ala Tyr Ser Cys Leu Pro Gly Met Ser Ser Leu Glu Pro Cys
                 85                  90                  95

Cys Cys Ser Pro Ser Arg Val Trp Met Asn Asn Asn Gly Gly Leu
                100                 105                 110

Val Cys Gly Arg Val Glu Lys Asp Asp Val Cys Leu Asp Cys Pro Thr
            115                 120                 125

His Ile Asp Gln Leu Arg Gly Ala Ser Gly Ser Pro Val Leu Cys Asp
130                 135                 140

His Gly His Ala Tyr Ala Leu Met Leu Gly Gly Tyr Ser Thr Ser Gly
145                 150                 155                 160

Ile Cys Ala Arg Val Arg Ile Val Arg Pro Trp Gln Asn Ala Tyr Ser
                165                 170                 175

Ser Ser Gly Gly Gln Gly Gly Met Gln Ala Pro Ala Val Thr Pro Thr
            180                 185                 190

Tyr Ser Glu Ile Thr Tyr Tyr Ala Pro Thr Gly Ser Gly Lys Ser Thr
        195                 200                 205

Lys Tyr Pro Val Asp Leu Val Lys Gln Gly His Lys Val Leu Val Leu
    210                 215                 220

Ile Pro Ser Val Ala Val Val Lys Ser Met Ala Pro Tyr Ile Lys Glu
225                 230                 235                 240

Thr Tyr Lys Ile Arg Pro Glu Ile Arg Ala Gly Thr Gly Pro Asp Gly
                245                 250                 255

Val Thr Val Ile Thr Gly Glu Asn Leu Ala Tyr Met Thr Tyr Gly Arg
            260                 265                 270

Phe Leu Val Asp Pro Glu Thr Asn Leu Arg Gly Tyr Ala Val Val Ile
        275                 280                 285

Cys Asp Glu Cys His Asp Thr Ser Ser Thr Thr Leu Leu Gly Ile Gly
    290                 295                 300

Ala Val Arg Met Tyr Ala Glu Gln Ala Gly Val Lys Thr Val Val Phe
305                 310                 315                 320

Ala Thr Ala Thr Pro Ala Gly Ile Gln Val Gln Pro His Pro Asn Ile
                325                 330                 335

Asp Glu Tyr Leu Leu Thr Asp Thr Gly Asp Val Asp Phe Tyr Gly Ala
            340                 345                 350

Lys Ile Lys Leu Asp Asn Ile Arg Thr Gly Arg His Val Ile Phe Cys
        355                 360                 365

His Ser Lys Ala Lys Cys Ala Glu Leu Thr Gln Gln Leu Ser Gly Leu
    370                 375                 380

Gly Val Arg Ala Val Ser Phe Trp Arg Gly Cys Asp Ile Lys Thr Ile
385                 390                 395                 400

Pro Ala Ser Asp Ser Ile Val Val Ala Thr Asp Ala Leu Ser Thr
                405                 410                 415

Gly Tyr Thr Gly Asn Phe Asp Ser Val Ile Asp Cys Gly Cys Cys Val
            420                 425                 430

Glu Gln Thr Val Thr Ile Asp Met Asp Pro Thr Phe Ser Ile Ser Ala
        435                 440                 445

Arg Val Val Pro Cys Thr Ala Ala Leu Arg Met Gln Arg Arg Gly Arg
```

```
            450                 455                 460
Thr Gly Arg Gly Arg Arg Gly Ala Tyr Tyr Thr Thr Thr Pro Gly Ala
465                     470                 475                 480

Ala Pro Cys Val Asn Val Pro Asp Ala Asn Val Trp Gln Ala Val Glu
                485                 490                 495

Ser Ala Met Val Phe Tyr Asp Trp Asn Ala Ala Arg Ile Gln Gln Cys
            500                 505                 510

Leu Ala Ala Tyr His Asp Leu Gly Cys Thr Pro Arg Ile Ser Cys Asp
            515                 520                 525

Pro His Thr Pro Val Arg Val Met Asp Thr Leu Arg Ala Tyr Leu Arg
        530                 535                 540

Arg Pro Glu Val Thr Thr Ala Ala Leu Ala Gly Glu Gln Trp Pro Leu
545                 550                 555                 560

Leu Tyr Gly Val Gln Leu Cys Ile Cys Lys Glu Thr Glu Ala His Gly
                565                 570                 575

Pro Asp Asp Gly Ile Lys Trp Lys Cys Leu Leu Asn Asn Asn Asn Lys
                580                 585                 590

Thr Pro Leu Leu Tyr Ala Leu Asp Asn Pro Thr Leu Glu Phe Thr Thr
                595                 600                 605

Gln His Asp Leu Thr Arg Arg Ile Ala Gly Ala Leu Ser Ser Thr Val
        610                 615                 620

Phe Val Glu Thr
625

<210> SEQ ID NO 437
<211> LENGTH: 41
<212> TYPE: PRT
<213> ORGANISM: Human Pegivirus 2

<400> SEQUENCE: 437

Gly Tyr Gly Pro Ile Leu Leu Ala Gly Ala Leu Ala Ala Ser Phe
1               5                   10                  15

Ala Phe Ala Gly Ala Thr Gly Ala Leu Val Pro Ser Ala Val Trp Ser
                20                  25                  30

Val Asp Asn Gly Pro Thr Gly Val Thr
            35                  40

<210> SEQ ID NO 438
<211> LENGTH: 262
<212> TYPE: PRT
<213> ORGANISM: Human Pegivirus 2

<400> SEQUENCE: 438

Arg Pro Asp Ala Thr Asp Glu Thr Val Ala Tyr Ala Gln Arg Leu Tyr
1               5                   10                  15

His Ala Cys Ala Asp Ser Gly Ile Leu Ala Ser Leu Gln Gly Thr Ala
                20                  25                  30

Cys Ala Ala Leu Ser Lys Leu Ala Asp Ala Ser Arg Gly Ala Ser Gln
            35                  40                  45

Tyr Leu Ala Thr Ala Pro Pro Ser Pro Ala Pro Leu Val Gln Val Leu
50                  55                  60

Gln Phe Leu Glu Thr Asn Phe Ser Ser Ile Ala Ser Phe Gly Leu Leu
65                  70                  75                  80

Cys Ala Gly Cys Gln Ala Gly Glu Cys Phe Thr Ala Leu Ala Gly Leu
                85                  90                  95

Val Ser Gly Ala Thr Ala Gly Leu Gly Gly Ala His Lys Trp Leu Leu
```

```
                100                 105                 110
Ala Ile Ala Gly Thr Trp Leu Val Ser Leu Gln Thr Gly Pro Arg Gly
            115                 120                 125
Gly Met Val Ala Gly Leu Ser Val Leu Ala Gly Cys Cys Ile Gly Gly
            130                 135                 140
Val Thr Gly Leu Asp Phe Leu Phe Gly Cys Leu Thr Gly Trp Glu Ala
145                 150                 155                 160
Val Val Gly Ala Ala Val Ala Thr Gln Lys Ile Leu Ser Gly Ser Ala
                165                 170                 175
Asp Met Thr Thr Leu Val Asp Leu Leu Pro Ala Leu Phe Ser Pro Gly
            180                 185                 190
Ala Gly Ile Ala Gly Ile Val Leu Val Phe Ile Leu Ser Asn Thr Ser
            195                 200                 205
Val Thr Ala Trp Ala Asn Arg Leu Leu Ser Met Cys Ala Lys Gln Thr
            210                 215                 220
Ile Cys Glu Asn Tyr Phe Leu Thr Glu Lys Phe Gly Gln Gln Leu Ser
225                 230                 235                 240
Lys Leu Ser Leu Trp Arg Ala Val Tyr His Trp Ala Gln Ala His Glu
                245                 250                 255
Gly Tyr Thr Gln Cys Gly
            260

<210> SEQ ID NO 439
<211> LENGTH: 458
<212> TYPE: PRT
<213> ORGANISM: Human Pegivirus 2

<400> SEQUENCE: 439

Val Val Gly Gly Ile Trp Ser Phe Val Leu Cys Ile Leu Arg Ala Ala
1               5                   10                  15
Trp Asp Trp Ala Ala Lys His Val Pro Arg Phe Arg Val Pro Met Ile
            20                  25                  30
Gly Cys Ser Pro Ala Trp Cys Gly Arg Trp Leu Gly Thr Gly Thr Leu
        35                  40                  45
Leu Thr Thr Cys Gly Cys Gly Glu Arg Val Ser Leu Gln Cys Leu Cys
    50                  55                  60
Ser Thr Ser Asp Pro Ile Leu Ser Val Gly Arg Trp Cys Arg Cys Ser
65                  70                  75                  80
Trp Ser Val Gly Phe Pro Phe Asn Pro Thr Thr Ala Thr Gly Thr
            85                  90                  95
Leu Arg Pro Asp Ile Gly Asp Ala Thr Arg Leu Gly Phe Arg Tyr Gly
            100                 105                 110
Ile Ala Glu Ile Val Glu Leu Glu Arg Arg Gly Asp Lys Trp His Val
            115                 120                 125
Cys Ala Ala Ser Cys Cys Leu Asp Arg Ala Ser Val Ala Ser Ala Val
            130                 135                 140
Lys Ala Pro Pro Val Thr Ala Asn Gly Ile Pro Ile Ser Pro Phe Ser
145                 150                 155                 160
Pro Pro Gln Thr Tyr Lys Leu Ser Leu Cys Ser Phe Asp Ser Val Cys
                165                 170                 175
Met Ser Ile Asn Ser Cys Asn Pro Ser Lys Ile Leu Ser Val Cys Ser
            180                 185                 190
Gln Glu Ala Val Glu Leu Leu Glu Glu Thr Val Asp Thr Ala Gln Thr
            195                 200                 205
```

```
Met Met Cys Lys Asn Leu Glu Ala Arg Arg Ala Glu Phe Asp Ala
    210                 215                 220

Trp Gln Val Arg Gln Ala Val Gly Asp Glu Tyr Thr Arg Leu Ala Asp
225                 230                 235                 240

Glu Asp Val Asp Thr Ile Thr Ser Val Lys Pro Pro Val Ala Arg Ala
                245                 250                 255

Ala Val Gly Ser Ser Thr Leu Asp Asp Val Gly Val Leu Thr Val Leu
                260                 265                 270

Arg Glu Leu Gly Asp Gln Cys Gln Asn Ala Ile Lys Phe Val Val Glu
                275                 280                 285

Ala Ala Ser Arg Phe Val Pro Pro Val Pro Lys Pro Arg Thr Arg Val
            290                 295                 300

Ser Gly Val Leu Glu Arg Val Arg Met Cys Met Arg Thr Pro Pro Met
305                 310                 315                 320

Lys Phe Glu Ala Ala Ala Val Pro Ile His Asn Ile Ile Pro Glu Lys
                325                 330                 335

Cys His Ile Val Leu Arg Cys Thr Gly Cys Ser Asp Gln Ala Leu Thr
                340                 345                 350

Val Pro Tyr Gly Thr Cys Thr Gln Thr Leu Ser Ser His Leu Thr Asn
            355                 360                 365

Lys His Ser His Tyr Ile Pro Lys Gln Lys Ile Glu Glu Asp Thr Glu
        370                 375                 380

Val Thr Val Ile Cys Ala Val Pro Thr Lys Arg Ala Ser Lys Leu Ile
385                 390                 395                 400

Thr Phe Arg Val Gly Asp Arg Ser Val Ser Cys Cys His Pro Leu Gln
                405                 410                 415

Thr Pro Val Arg Ala Leu Leu Leu Lys Tyr Gly Leu Pro Ile Gly Lys
            420                 425                 430

Trp Ser Asp Cys Asn Gly Pro Leu Gly Asp Asp Ala Arg Val Cys Asp
        435                 440                 445

Val Asn Gly Val Thr Thr Tyr Glu Pro Cys
    450                 455

<210> SEQ ID NO 440
<211> LENGTH: 567
<212> TYPE: PRT
<213> ORGANISM: Human Pegivirus 2

<400> SEQUENCE: 440

Met Gln Ser Tyr Ser Trp Phe Arg Pro Ile Val Ala Pro Thr Thr Pro
1               5                   10                  15

Pro Leu Pro Val Thr Arg Ser Val Ala Gly Ile Leu Arg Ala Asp Thr
                20                  25                  30

Ser Arg Val Tyr Thr Thr Thr Ala Val Asp Val Ser Glu Arg Gln Ala
            35                  40                  45

Lys Val Thr Ile Asp Gln Lys Ser Ala Lys Val Asp Gln Cys Phe Arg
        50                  55                  60

Asp Thr Tyr Asn Cys Cys Leu Ala Lys Ala Lys Thr Phe Arg Gln Ser
65                  70                  75                  80

Gly Met Ser Tyr Glu Asp Ala Val Ser Lys Met Arg Ala Asn Thr Thr
                85                  90                  95

Arg Asp His Asn Thr Gly Ile Thr Tyr Thr Asp Leu Val Ser Gly Arg
            100                 105                 110

Ala Lys Pro Ala Val Gln Lys Ile Val Asp Gln Met Arg Ser Gly Val
        115                 120                 125
```

-continued

```
Tyr Asp Ala Pro Met Arg Ile Ile Pro Lys Pro Glu Val Phe Pro Arg
            130                 135                 140

Asp Lys Ser Thr Arg Lys Pro Pro Arg Phe Ile Val Phe Pro Gly Cys
145                 150                 155                 160

Ala Ala Arg Val Ala Glu Lys Met Ile Leu Gly Asp Pro Gly Ala Ile
                165                 170                 175

Thr Lys His Val Leu Gly Asp Ala Tyr Gly Phe Ala Thr Pro Pro His
            180                 185                 190

Glu Arg Ala Arg Leu Leu Glu Gln Trp Trp Asn Arg Ala Thr Glu Pro
            195                 200                 205

Gln Ala Ile Ala Val Asp Ala Ile Cys Phe Asp Ser Thr Ile Thr Ala
210                 215                 220

Glu Asp Met Asp Arg Glu Ala His Ile Val Ala Ala His Ala Asp
225                 230                 235                 240

Pro Glu Gly Val His Gly Leu Tyr Asn Tyr Tyr Lys Arg Ser Pro Met
                245                 250                 255

Cys Asp Ile Thr Gly Lys Val Val Gly Val Arg Cys Cys Arg Ala Ser
                260                 265                 270

Gly Thr Leu Thr Thr Ser Ser Gly Asn Thr Leu Thr Cys Tyr Leu Lys
            275                 280                 285

Val Arg Ala Ala Cys Thr Arg Ala Gly Ile Lys Pro Ile Gly Leu Leu
            290                 295                 300

Ile His Gly Asp Asp Thr Leu Ile Ile Thr Glu Arg Cys Thr Gln Glu
305                 310                 315                 320

Thr Leu Asp Glu Phe Ser Asn Ala Leu Asp Asp Tyr Gly Phe Pro His
                325                 330                 335

Thr Phe Gln Val Ser Gly Asp Leu Ser Ser Ile Glu Cys Cys Ser Ala
            340                 345                 350

Arg Val Asp Ser Val Cys Leu Arg Gly Gly Met Arg Arg Met Leu Val
            355                 360                 365

Pro Gln Ala Arg Arg Ala Ile Ala Arg Val Leu Gly Glu Lys Gly Asp
370                 375                 380

Pro Leu Gly Val Ile Ser Ser Tyr Ile Val Met Tyr Pro Thr Ala Ala
385                 390                 395                 400

Val Thr Val Tyr Val Leu Leu Pro Leu Leu Cys Met Leu Ile Arg Asn
                405                 410                 415

Glu Pro Ser Gln Thr Gly Thr Leu Val Thr Leu Thr Val His Gly Asn
                420                 425                 430

Ser Val Ser Val Pro Val Trp Leu Leu Pro Thr Ile Ile Ala Asn Leu
            435                 440                 445

His Gly Arg Asp Ala Leu Gln Val Val Arg His Ser Ala Ala Ser Met
450                 455                 460

Ala Glu Leu Ser Ser Ala Leu Ala Phe Phe Gly Met Arg Gly Leu Asn
465                 470                 475                 480

Cys Trp Arg Arg Arg Arg Ala Ile Arg Thr Asp Met Ile Lys Leu
                485                 490                 495

Gly Gly Trp Asn Ala Asn Phe Ala Gln Met Leu Leu Trp Ser Pro Glu
            500                 505                 510

Val Arg Thr Pro Gln Pro Glu Pro Lys Gly Met Cys Leu Leu Pro Pro
            515                 520                 525

Glu Leu Trp Glu Arg Pro Tyr Glu Asn Leu His Leu Ser Thr Ile Asp
530                 535                 540
```

```
Arg Asp Arg Gly Ala Ser Arg Leu Arg Phe Trp Leu Val Ala Ser Ala
545                 550                 555                 560
Val Leu Ala Leu Leu Cys Leu
                565
```

COMPOSITIONS AND METHODS FOR DETECTING HUMAN PEGIVIRUS 2 (HPGV-2)

The present application is a divisional of U.S. application Ser. No. 15/642,992, filed Jul. 6, 2017, which is a continuation of U.S. application Ser. No. 14/752,262, filed Jun. 26, 2015, now U.S. Pat. No. 9,777,340, issued Oct. 3, 2017, which claims priority to U.S. Provisional application Ser. No. 62/018,282, filed Jun. 27, 2014, and U.S. Provisional application Ser. No. 62/107,782, filed Jan. 26, 2015, all of which are herein incorporated by reference in their entireties.

STATEMENT REGARDING FEDERALLY SPONSORED RESEARCH OR DEVELOPMENT

This invention was made with government support under Grant No. R01-HL105704 awarded by the National Institutes of Health. The Government has certain rights in the invention.

FIELD OF THE INVENTION

Provided herein are compositions, methods, and kits for detecting human *Pegivirus* 2 (HPgV-2). In certain embodiments, provided herein are HPgV-2 specific nucleic acid probes and primers, and methods for detecting HPgV-2 nucleic acid. In other embodiments, provided herein are HPgV-2 immunogenic compositions, methods of treating a subject with immunogenic portions of HPgV-2, and methods of detecting HPgV-2 specific subject antibodies in a sample.

BACKGROUND

Within the family Flaviviridae, viruses belonging to the genus *Hepacivirus* have been shown to cause hepatitis (Hepatitis C virus (HCV) and GB virus (GBV-B)). The newly defined genus *Pegivirus* contains viruses similar to Hepaciviruses in genome organization but distinct in tropism and associated pathogenicity (Stapleton et al., J Gen Virol 2011: 92: 233-246). All members of the family Flaviviridae contain a positive sense, single stranded RNA genome of about 10 kb, that encodes for a single long open reading frame (ORF) polyprotein of about 3,000 amino acids (Lindenbach et al., Flaviviridae: The Viruses and Their Replication. Chapter 33. In Fields Virology Fifth Edition, (Knipe et al., Eds.) Wolters Kluwer/Lippincott Williams and Williams, Philadelphia Pa. Pages 1101-1152). The polyprotein is cleaved into smaller functional structural and non-structural (NS) components by a combination of host and viral proteases. The viral structural proteins are encoded at the amino terminal portion of the genome and include envelope glycoproteins and a nucleocapsid. While HCV and GBV-B encode a nucleocapsid protein, HPgV-1 does not appear encode a nucleocapsid protein in the polyprotein. Phylogenetic analysis show distinct evolutionary lineages between the genera but conserved amino acid motifs involved in the enzymatic functions of the NS3 helicase and the NS5 RNA dependent RNA polymerase. The genome is organized with 5' and 3' untranslated regions (UTRs) that are highly conserved and that are involved both in translation and in replication of the genome.

The *Pegivirus* genus, is named for the persistent (pe) GB virus (g) infection that is not associated with a specific pathogenicity. In 1995-1996, the first human *pegivirus*, GVB-C(HPgV-1), was detected independently by two groups in sera from patients with non-A, non-B hepatitis. Although originally discovered in chronic hepatitis patients, HPgV-1 appears to be lymphotropic, and not hepatotropic, and has not been associated with hepatitis or any other clinical illness in follow-up clinical and experimental studies. Some studies, however, have suggested that co-infection with HPgV-1 may slow the progression of HIV disease (Heringlake S, J Infect Dis 1998; 177:1723-1726). Together the incidence rate of HCV and HPgV-1 is estimated to be between 2-5% of the world's population (Stapleton et al., J Gen Virol 2011: 92: 233-246).

Pegiviruses infect a wide range of mammals, not limited to chimpanzees, new world primates, bats, rodents, and horses. Recently there have been viral discovery reports indicating the novel hepaciviruses and pegiviruses have been identified in rodents and that bats may be a natural reservoir for these genera of the Flavivirdae (Quan et al., PNAS 110: 8194-8199. 2013: Drexler et al., PLoS Pathog 9 (6) e1003438. 2013: Kapoor et al., mBIo 4(2) e000216-13. 2013). The only pegiviruses previously known to infect humans is HPgV-1. There is considerable sequence divergence between *pegivirus* variants in the structural proteins and conservation within the nonstructural NS3 and NS5B genes (Kapoor A, mBio. 2013 March-April; 4(2): e00216-13). Sampling of bats from different continents shows several distinct bat-derived *pegivirus* lineages suggesting bats are a natural reservoir for pegiviruses (Quan P, Proc Natl Acad Sci USA. May 14, 2013; 110(20): 8194-8199). Characterization of HPgV-2 described in this patent shows the viral variant is distinct from the other human-tropic virus HPgV-1.

Recently, it has been proposed that Theiler's disease, the most common cause of acute hepatitis in horses, is likely to be caused by TDAV (Theiler's Disease Associated Virus), a newly described horse flavivirus, phylogenetically related to the GB viruses (Chandriana et al., PNAS 110 (15): E 1407-1415. 2013) and classified as a *pegivirus*. Thus, unlike the case for HPgV-1, where there has been no clear association with disease, TDAV appears to be causally related to hepatitis cases in horses.

SUMMARY OF THE INVENTION

Provided herein are compositions, methods, and kits for detecting a human virus which has been termed "human *Pegivirus* 2" (HPgV-2) based on certain homology to human *Pegivirus* 1. In certain embodiments, provided herein are HPgV-2 specific nucleic acid probes and primers, and methods for detecting HPgV-2 nucleic acid. In other embodiments, provided herein are HPgV-2 immunogenic compositions, methods of treating a subject with immunogenic HPgV-2 peptides, and methods of detecting HPgV-2 specific subject antibodies in a sample.

In some embodiments, provided herein are compositions comprising a synthetic nucleic acid molecule which comprises at least 12 (e.g., at least 12 . . . 15 . . . 25 . . . 35 . . . 45 . . . or 55) consecutive nucleotides from human *Pegivirus* 2 (HPgV-2), and/or the encoded peptides from such nucleic acids, such as from type UC0125.US (aka "index case"), ABT0070P.US, ABT0096P.US, ABT0029A, ABT0239AN, ABT0055A, ABT0030P.US, ABT0041P.US, ABT0188P.US, and/or ABT0128AUS.

In certain embodiments, provided herein are compositions comprising a synthetic nucleic acid molecule, wherein said synthetic nucleic acid molecule comprises a nucleotide sequence at least 12 nucleotides in length (e.g., at least 12 . . . 15 . . . 18 . . . 27 . . . 35 . . . etc.) that hybridizes under stringent conditions (e.g., highly stringent conditions) to region 1, region 2, region 3, or region 4 of a genomic sequence of human *Pegivirus* 2 (HPgV-2) or complement thereof, wherein the genomic sequence of HPgV-2 is shown in SEQ ID NO:1, 75, and 299-303, and wherein region 1 is nucleotides 1-1401 of SEQ ID NO:1 or 75, region 2 is nucleotides 1431-4777 of SEQ ID NO:1 or 75, region 3 is nucleotides 4818-8134 of SEQ ID NO:1 or 75, and region 4 is nucleotides 8167-9778 of SEQ ID NO:1 or 75.

In particular embodiments, the synthetic nucleic acid molecule is at least 15 nucleotides in length and no more than 75 nucleotides in length. In further embodiments, the synthetic nucleic acid molecule comprises a detectable label (e.g., fluorescent label, chemiluminescent, enzymatic, etc.). In further embodiments, the synthetic nucleic acid molecule comprises at least one modified base (e.g., for nuclease resistance, higher binding efficiency, etc.). In certain embodiments, all or nearly all of the nucleotides are modified. In particular embodiments, at least one modified base is selected from the group consisting of: phosphorothioate, boranophosphate, 4'-thio-ribose, locked nucleic acid, 2'-O-(2'-methoxyethyl), 2'-O-methyl, 2'-fluoro, 2'-deoxy-2'-fluoro-b-D-arabinonucleic acid, phosphonoacetate, 2'-3'-seco-RNA, Morpholino nucleic acid analog, Peptide nucleic acid analog, phosphorodithioate, phosphoramidate, methylphosphonate, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, 2-aminopurine, 5-amino-allyluracil, 5-hydroxymethylcytosine, 5-iodouracil, 5-nitroindole, 5-propynylcytosine, 5-propynyluracil, hypoxanthine, N3-methyluracil, N6,N6-dimethyladenine, purine, C-5-propynyl cytosine, C-5-propynyl uracil, and difluorotouyl.

In particular embodiments, the synthetic nucleic acid molecule comprises DNA (e.g., the entire or nearly the entire nucleic acid molecules is DNA). In further embodiments, the composition further comprises a hybridization and/or amplification buffer. In other embodiments, the synthetic nucleic acid molecule is linked to a heterologous nucleic acid sequence (e.g., an expression vector, a sequencing tag, a promoter, etc.).

In certain embodiments, the synthetic nucleic acid molecule hybridizes to a portion of the HPgV-2 genome selected from the group consisting of: the 5'UTR, the S gene, the E1 gene, the E2 gene, the X gene, and the NS2 gene. In particular embodiments, the 5' UTR is nucleotides 1-103 of SEQ ID NO:1, nucleotides 1-110 of SEQ ID NO:75, nucleotides 1-327 of SEQ ID NOs:299-301, 419, and 430, nucleotides 12-327 of SEQ ID NO:302, and nucleotides 24-327 of SEQ ID NO:303; said S gene is nucleotides 104-475 of SEQ ID NO:1, nucleotides 111-482 of SEQ ID NO:75, or nucleotides 328-564 of SEQ ID NOs: 299-303, 419, and 430; said E1 gene is nucleotides 476-1048 of SEQ ID NO:1, nucleotides 483-1055 of SEQ ID NO:75, or nucleotides 565-1137 of SEQ ID NOs:299-303; said E2 gene is nucleotides 1049-2110 of SEQ ID NO:1, nucleotides 1056-2117 of SEQ ID NO:75, or nucleotides 1138-2199 of SEQ ID NOs:299-303, 419, and 430; said X gene is nucleotides 2111-2821 of SEQ ID NO:1, nucleotides 2118-2828 of SEQ ID NO:75, or nucleotides 2200-2910 of SEQ ID NOs:299-303, 419, and 430; and said NS2 gene is nucleotides 2822-3541 of SEQ ID NO:1, nucleotides 2829-3548 of SEQ ID NO:75, or nucleotides 2911-3630 of SEQ ID NOs:299-303, 419, and 430. In certain embodiments, the nucleic acid molecule hybridizes to a portion of said HPgV-2 genome selected from the group consisting of: the NS3 gene, the NS4A gene, the NS4B gene, the NS5A gene, the NS5B gene, and the 3'UTR (e.g., as shown in any of the figures with such sequences). In some embodiments, the NS3 gene is nucleotides 3542-5425 of SEQ ID NO: 1, nucleotides 3549-5432 of SEQ ID NO:75, or nucleotides 3631-5514 of SEQ ID NOs:299-303, 419, and 430; said NS4A gene is nucleotides 5426-5548 of SEQ ID NO:1, nucleotides 5433-5555 of SEQ ID NO:75, or nucleotides 5515-5637 of SEQ ID NOs:299-303, 419, and 430; said NS4B gene is nucleotides 5549-6334 of SEQ ID NO:1, nucleotides 5556-6341 of SEQ ID NO:75, or nucleotides 5638-6423 of SEQ ID NOs:299-303, 419, and 430; said NS5A gene is nucleotides 6335-7708 of SEQ ID NO:1, nucleotides 6342-7715 of SEQ ID NO:75, or nucleotides 6424-7797 of SEQ ID NOs:299-303 and 430, or 6424-7794 of SEQ ID NO:419; said NS5B gene is nucleotides 7709-9409 of SEQ ID NO:1, nucleotides 7716-9416 of SEQ ID NO:75 or nucleotides 7798-9498 of SEQ ID NOs:299-303 and 430, or 7795-9495 of SEQ ID NO:419; and wherein at least a portion of said 3'UTR is nucleotides 9410-9778 of SEQ ID NO:1, nucleotides 9417-9431 of SEQ ID NO:75, or nucleotides 9499-9867 of SEQ ID NOs:299-303 and 430, or 9496-9864 of SEQ ID NO:419.

In certain embodiments, provided herein are compositions comprising a synthetic nucleic acid molecule, wherein the synthetic nucleic acid molecule comprises a nucleotide sequence at least 12 nucleotides in length (e.g., at least 12 . . . 15 . . . 25 . . . or 35 nucleotides in length) that: i) does not hybridize under stringent conditions (e.g., highly stringent conditions) to three regions of SEQ ID NO: 1 or 75 selected from 1402-1430, 4778-4817, and 8135-8166, and ii) does hybridize under stringent conditions (e.g., highly stringent conditions) to: a) a 5' untranslated region (5'UTR) of human *Pegivirus* 2 (HPgV-2) or complement thereof, wherein the 5'UTR has a nucleic acid sequence as shown in nucleotides 1-103 of SEQ ID NO:1 or nucleotides 1-110 of SEQ ID NO:75; b) a first nucleic acid sequence, or complement thereof, wherein the first nucleic acid sequence encodes a HPgV-2 S-protein with the amino acid sequence shown in SEQ ID NO:2, 76, 304, 314, 324, 334, or 344; c) a second nucleic acid sequence, or complement thereof, wherein the second nucleic acid sequence encodes a HPgV-2 E1 protein with the amino acid sequence shown in SEQ ID NO:3, 77, 305, 315, 325, 335, or 345; d) a third nucleic acid sequence, or complement thereof, wherein the third nucleic acid sequence encodes a HPgV-2 E2 protein with the amino acid sequence shown in SEQ ID NO:4, 78, 306, 316, 326, 336, or 346; e) a fourth nucleic acid sequence, or complement thereof, wherein the fourth nucleic acid sequence encodes a HPgV-2 X-protein with the amino acid sequence shown in SEQ ID NO:5, 79, 307, 317, 327, 337, or 347; f) a fifth nucleic acid sequence, or complement thereof, wherein the fifth nucleic acid sequence encodes a HPgV-2 NS2 protein with the amino acid sequence shown in SEQ ID NO:6, 80, 308, 318, 328, 338, or 348; g) a sixth nucleic acid sequence, or complement thereof, wherein the sixth nucleic acid sequence encodes a HPgV-2 NS3 protein with the amino acid sequence shown in SEQ ID NO:7, 81, 309, 319, 329, 339, or 349; h) a seventh nucleic acid sequence, or complement thereof, wherein the seventh nucleic acid sequence encodes a HPgV-2 NS4A protein with the amino acid sequence shown in SEQ ID NO:8, 82, 310, 320, 330, 340, or 350; i) a eighth nucleic acid sequence, or complement thereof, wherein the eighth nucleic acid sequence encodes a HPgV-2 NS4B protein with the amino acid sequence shown in SEQ ID NO:9, 83, 311, 321, 331, 341, or 351; j) a ninth nucleic acid sequence, or complement thereof, wherein the ninth nucleic acid sequence encodes a HPgV-2 NS5A protein with the amino acid sequence shown in SEQ ID NO: 10, 84, 312, 322, 332, 342, or 352; k) a tenth nucleic acid sequence, or complement thereof, wherein the tenth nucleic acid sequence encodes a HPgV-2 NS5B protein with the amino acid sequence shown in SEQ ID NO:11, 85, 313, 323, 333, 343, or 353; and 1) a 3' untranslated region (3'UTR) of Human *Pegivirus* 2 (HPgV-2) or complement thereof, wherein at least a portion of the 3'UTR has a nucleic acid sequence as shown in nucleotides 9410-9778 of SEQ ID NO:1, nucleotides 9417-9431 of SEQ ID NO:75, or nucleotides 9499-9867 of SEQ ID NOs:299-303

In certain embodiments, the synthetic nucleic acid molecule is at least 15 nucleotides in length and no more than 75 nucleotides in length. In further embodiments, the synthetic nucleic acid molecule comprises a detectable label. In other embodiments, the composition further comprises a hybridization and/or amplification buffer. In some embodiments, the synthetic nucleic acid molecule is linked to a heterologous nucleic acid sequence. In other embodiments, the heterologous nucleic acid sequence comprises an expression vector. In additional embodiments, the synthetic nucleic acid molecule comprises at least one modified base. In further embodiments, the synthetic nucleic acid molecules comprises DNA.

In particular embodiments, provided herein are compositions comprising a synthetic nucleic acid molecule, wherein said synthetic nucleic acid molecule comprises a nucleotide sequence that has at least 75% identity (e.g., at least 75% . . . 85% . . . 95% . . . 99% or 99.5%) to a portion of region 1, region 2, region 3, or region 4 of SEQ ID NO:1 or 75 or complement thereof, or to a portion of SEQ ID NOs:299-303 or 354-356, wherein said portion is at least 15 nucleotides in length (e.g., at least 15 . . . 25 . . . 37 . . . 48 . . . 57 . . . or 65 nucleotides in length), and wherein region 1 is nucleotides 1-1401 of SEQ ID NO: 1 or 75, region 2 is nucleotides 1431-4777 of SEQ ID NO: 1 or 75, region 3 is nucleotides 4818-8134 of SEQ ID NO:1 or 75, and region 4 is nucleotides 8167-9778 of SEQ ID NO: 1 or 75. In certain embodiments, the portion is at least 15 nucleotides in length, but not more than 75 nucleotides in length. In other embodiments, the synthetic nucleic acid molecule comprises a detectable label. In additional embodiments, the composition further comprises a hybridization and/or amplification buffer. In other embodiments, the synthetic nucleic acid molecule is linked to a heterologous nucleic acid sequence. In certain embodiments, the heterologous nucleic acid sequence comprises an expression vector.

In some embodiments, provided herein are compositions comprising a substantially purified recombinant peptide, wherein the recombinant peptide comprises an amino acid sequence that has at least 75% identity (e.g., at least 75% . . . 85% . . . 95% or 99% identity) to a portion of any one of SEQ ID NOs:2-11, 76-85, 304-353, 420-429, or 431-440, wherein the portion is at least 10 amino acids in length (e.g., at least 10 . . . 15 . . . 25 . . . or 35 amino acids in length). In particular embodiments, the recombinant peptide is conjugated to a label (e.g., detectable label or a hapten). In other embodiments, the peptides are glycosylated (e.g., an E2 glycosylated peptide). In further embodiments, the compositions further comprise a physiologically tolerable buffer suitable for injection into a mammal.

In some embodiments, described herein are methods for detecting human *Pegivirus* 2 (HPgV-2) nucleic acid comprising: a) contacting a sample suspected of containing HPgV-2 nucleic acid with a nucleic acid molecule, wherein the nucleic acid molecule comprises a nucleotide sequence at least 12 nucleotides in length (e.g., at least 12 . . . 18 . . . 25 . . . 35 . . . or more) that hybridizes under stringent conditions (e.g., highly stringent conditions) to SEQ ID NOs:299-303, or to region 1, region 2, region 3, or region 4 of a genomic sequence of human *Pegivirus* 2 (HPgV-2) or complement thereof, wherein the genomic sequence of HPgV-2 is shown in SEQ ID NO: 1 or 75, and wherein region 1 is nucleotides 1-1401 of SEQ ID NO:1 or 75, region 2 is nucleotides 1431-4777 of SEQ ID NO:1 or 75, region 3 is nucleotides 4818-8134 of SEQ ID NO:1 or 75, and region 4 is nucleotides 8167-9778 of SEQ ID NO:1 or 75; and b) detecting the presence or absence of hybridization of the nucleic acid molecule to the HPgV-2 nucleic acid, wherein detecting said presence of hybridization indicates the presence of the HPgV-2 nucleic acid in said sample.

In certain embodiments, the nucleotide sequence is at least 15 nucleotides in length and wherein the nucleic acid molecule is no more than 75 nucleotides in length (e.g., 15 . . . 25 . . . 39 . . . 54 . . . 68 . . . 75). In other embodiments, the nucleic acid molecule comprises a detectable label. In further embodiments, the nucleic acid molecule hybridizes to a portion of the HPgV-2 genome selected from the group consisting of: the 5'UTR, the S gene, the E1 gene, the E2 gene, the X gene, and the NS2 gene.

In additional embodiments, provided herein are methods for detecting human *Pegivirus* 2 (HPgV-2) nucleic acid comprising: a) contacting a sample suspected of containing HPgV-2 nucleic acid with a first primer such that HPgV-2 amplification products are produced, wherein the first primer comprises a nucleotide sequence at least 12 nucleotides in length that hybridizes under stringent conditions (e.g., highly stringent conditions) to SEQ ID NOs:299-303, or to region 1, region 2, region 3, or region 4 of a genomic sequence of human *Pegivirus* 2 (HPgV-2) or complement thereof, (or, if a second primer is employed, the first primer hybridizes under stringent conditions (e.g., highly stringent conditions) to any portion of SEQ ID NO: 1 or 75), wherein said genomic sequence of HPgV-2 is shown, for example, in SEQ ID NO: 1 or 75, and wherein region 1 is nucleotides 1-1401 of SEQ ID NO:1 or 75, region 2 is nucleotides 1431-4777 of SEQ ID NO:1 or 75, region 3 is nucleotides 4818-8134 of SEQ ID NO:1 or 75, and region 4 is nucleotides 8167-9778 of SEQ ID NO:1 or 75; and b) detecting said HPgV-2 amplification products, thereby detecting the presence of the HPgV-2 nucleic acid in said sample (e.g., detecting type UC0125.US, ABT0070P.US, ABT0096P.US, ABT0029A, ABT0239AN, ABT0030P.US, ABT0041P.US, ABT0188P.US, and/or ABT0128A.US).

In certain embodiments, the methods further comprise contacting the sample with a second primer that comprises a nucleotide sequence at least 12 nucleotides in length that hybridizes to SEQ ID NOs:1, 75, 299-303, 419, 430, or complement thereof. In some embodiments, the first and second primers together generate an amplicon that is between 50 and 400 base pairs in length. In certain embodiments, the amplified nucleic acid is sequenced (e.g., adapters are ligated onto the amplified nucleic acid and it is subjected to sequencing protocol).

In other embodiments, the detecting comprises sequencing the HPgV-2 amplification products. In additional embodiments, the first and/or second primer is at least 15 nucleotides in length and no more than 75 nucleotides in length. In certain embodiments, the first and/or second primer comprises a detectable label. In further embodiments, the first primer hybridizes to a portion of the HPgV-2 genome selected from the group consisting of: the 5'UTR, the S gene, the E1 gene, the E2 gene, the X gene, and the NS2 gene.

In certain embodiments, provided herein are methods for detecting human *Pegivirus* 2 (HPgV-2) in a sample comprising: a) contacting a sample suspected of containing human *Pegivirus* 2 (HPgV-2) with an antibody (e.g., biotin labeled antibody) that specifically binds a portion of the HPgV-2 to form a HPgV-2/antibody complex, wherein the antibody is a full antibody or an antigen binding portion of a full antibody (Fab fragment or Fc fragment); and b) detecting the presence of the HPgV-2/antibody complex, thereby detecting the presence of the HPgV-2.

In certain embodiment, the HPgV-2 comprises the amino acid sequences encoded by the nucleic acid sequence shown in SEQ ID NO:1, 75, 299-303, 419, or 430. In further embodiments, the portion of the HPgV-2 is part of a HPgV-2 protein selected from the group consisting of: the S protein, the E1 protein, the E2 protein, the X protein, the NS2 protein, the NS3 protein, the NS4A protein, the NS4B protein, the NS5A protein, and the NS5B protein. In some embodiments, the amino acid sequence of the S protein is as shown in SEQ ID NO:2, 76, 304, 314, 324, 334, 334, 420, or 431, or a variant having 90-99% amino acid sequence identity with SEQ ID NO:2, 76, 304, 314, 324, 334, 344, 420, or 431. In additional embodiments, the amino acid sequence of the E1 protein is as shown in SEQ ID NO:3, 77, 305, 315, 325, 335, 345, 421, or 432, or a variant having 90-99% amino acid sequence identity with SEQ ID NO:3, 77, 305, 315, 325, 335, 345, 421, or 432. In further embodiments, the amino acid sequence of the E2 protein is as shown in SEQ ID NO:4, 78, 306, 316, 326, 336, 346, 422, 433, or a variant having 90-99% amino acid sequence identity with SEQ ID NO:4, 78, 306, 316, 326, 336, 346, 422, or 433. In other embodiments, the amino acid sequence of the X protein is as shown in SEQ ID NO:5, 79, 307, 317, 327, 337, 347, 423, 434, or a variant having 90-99% amino acid sequence identity with SEQ ID NO:5, 79, 307, 317, 327, 337, 347, 423, or 434. In additional embodiments, the amino acid sequence of the NS2 protein is as shown in SEQ ID NO:6, 80, 308, 318, 328, 338, 348, 424, 435, or a variant having 90-99% amino acid sequence identity with SEQ ID NO:6, 80, 308, 318, 328, 338, 348, 424, or 435. In additional embodiments, the amino acid sequence of the NS3 protein is as shown in SEQ ID NO:7, 81, 309, 319, 329, 339, 349, 425, 436, or a variant having 90-99% amino acid sequence identity with SEQ ID NO:7, 81, 309, 319, 329, 339, 349, 425, or 436. In additional embodiments, the amino acid sequence of the NS4A protein is as shown in SEQ ID NO:8, 82, 310, 320, 330, 340, 350, 426, 437, or a variant having 90-99% amino acid sequence identity with SEQ ID NOs:8, 82, 310, 320, 330, 340, 350, 426, or 437. In some embodiments, the amino acid sequence of the NS4B protein is as shown in SEQ ID NO:9, 83, 311, 321, 331, 341, 351, 427, 438, or a variant having 90-99% amino acid sequence identity with SEQ ID NO:9, 83, 311, 321, 331, 341, 351, 427, or 438. In further embodiments, the amino acid sequence of the NS5A protein is as shown in SEQ ID NO:10, 84, 312, 322, 332, 342, 352, 428, 439, or a variant having 90-99% amino acid sequence identity with SEQ ID NO:10, 84, 312, 322, 332, 342, 352, 428, or 439. In additional embodiments, the amino acid sequence of the NS5B protein is as shown in SEQ ID NO:11, 85, 313, 323, 333, 343, 353, 429, 440, or a variant having 90-99% amino acid sequence identity with SEQ ID NO:11, 85, 313, 323, 333, 343, 353, 429, or 440. In some embodiments, the antibody is labeled. In certain embodiments, the antigen binding portion of a full antibody comprises a Fab fragment.

In some embodiments, provided herein are methods of detecting human *Pegivirus* 2 (HPgV-2) infection in a subject comprising: a) contacting a sample from a subject suspected of containing a patient antibody to HPgV-2 with a peptide (or antibody specific for the HPgV-2 antibody), wherein the peptide (or the antibody specific for the HPgV-2 antibody) specifically binds the patient antibody to form a complex; and b) detecting the presence of the complex, thereby detecting the presence of past or present HPgV-2 infection in the subject. In certain embodiments, the peptide comprises or consists of at least part of the peptides shown in SEQ ID NOs:86-99 or 100-218, 420-429, 431-440, or variants thereof with 1 or 2 conservative amino acid changes, or with 1 or 2 non-conservative amino acid changes, or with 4 or more amino acid changes. In certain embodiments, the peptide is glycosylated (e.g., an E2 glycosylated peptide).

In other embodiments, the peptide has at least 75% identity (e.g., at least 75% . . . 85% . . . 95% . . . or 99% identity) to a portion of any one of SEQ ID NOs:2-11, 76-85, 86-99, 100-218, 304-353, 420-429, or 431-440, and wherein the portion is at least 10 amino acids in length (e.g., at least 10 . . . 15 . . . 25 . . . 30 or 35 amino acids in length). In further embodiments, the peptide is labeled. In certain embodiments, the peptide is labeled and is free in solution to bind to the subject antibody to form a complex. In certain embodiments, this complex is then bound, via the label on the peptide to a solid support that has a moiety that binds the label (e.g., streptavidin-biotin binding). In particular embodiments, a secondary antibody is added that is able to bind to the patient antibody in the complex. In other embodiments, the peptide is labeled and free in solution to bind to: 1) antibodies free solution which could then bind to an unlabeled peptide or other antigen provided on the solid phase; 2) antibodies free in solution which could then bind to an unlabeled peptide also free in solid solution but containing a biotin molecule (or other moiety) which can then be complexed to a solid phase containing a biotin-binding molecule (e.g. streptavidin, neutravidin, antibodies to biotin, etc.); or 3) an antibody/peptide complex present on the solid phase.

In certain embodiments, provided herein are methods for detecting human *Pegivirus* 2 (HPgV-2) infection in a subject comprising: a) contacting a sample from a subject suspected of containing a patient antibody to HPgV-2 with a peptide and a solid support, wherein said peptide comprises a label, and wherein said solid support comprises moieties that bind said label; and b) incubating said sample under conditions such that: i) said peptide specifically binds said patient antibody to form a complex, and ii) said complex binds to said solid support via said label binding at least one of said moieties; c) washing said solid support; d) adding a detectably labeled secondary antibody capable of binding said patient antibody in said complex; e) washing said solid support; and f) detecting said the presence of said complex, thereby detecting the presence of past or present HPgV-2 infection in the subject. In certain embodiments, the label on said peptide comprises biotin. In further embodiments, the moieties on said solid support comprise avidin molecules. In other embodiments, the solid support comprises beads.

In certain embodiments, the peptide comprises at least a portion of the HPgV-2 selected from the group consisting of: the S protein, the E1 protein, the E2 protein, the X protein, the NS2 protein, the NS3 protein, the NS4A protein, the NS4B protein, the NS5A protein, and the NS5B protein. In some embodiments, the amino acid sequence of the S protein is as shown in SEQ ID NO:2, 76, 304, 314, 324, 334, or 334, or a variant having 90-99% amino acid sequence identity with SEQ ID NO:2, 76, 304, 314, 324, 334, or 344. In additional embodiments, the amino acid sequence of the E1 protein is as shown in SEQ ID NO:3, 77, 305, 315, 325, 335, or 345, or a variant having 90-99% amino acid sequence identity with SEQ ID NO:3, 77, 305, 315, 325, 335, or 345. In further embodiments, the amino acid sequence of the E2 protein is as shown in SEQ ID NO:4, 78, 306, 316, 326, 336, or 346, or a variant having 90-99% amino acid sequence identity with SEQ ID NO:4, 78, 306, 316, 326, 336, or 346. In other embodiments, the amino acid sequence of the X protein is as shown in SEQ ID NO:5, 79, 307, 317, 327, 337, or 347, or a variant having 90-99% amino acid sequence identity with SEQ ID NO:5, 79, 307, 317, 327, 337, or 347. In additional embodiments, the amino acid sequence of the NS2 protein is as shown in SEQ ID NO:6, 80, 308, 318, 328, 338, or 348, or a variant having 90-99% amino acid sequence identity with SEQ ID NO:6, 80, 308, 318, 328, 338, or 348. In additional embodiments, the amino acid sequence of the NS3 protein is as shown in SEQ ID NO:7, 81, 309, 319, 329, 339, or 349, or a variant having 90-99% amino acid sequence identity with SEQ ID NO:7, 81, 309, 319, 329, 339, or 349. In additional embodiments, the amino acid sequence of the NS4A protein is as shown in SEQ ID NO:8, 82, 310, 320, 330, 340, or 350, or a variant having 90-99% amino acid sequence identity with SEQ ID NOs:8, 82, 310, 320, 330, 340, or 350. In some embodiments, the amino acid sequence of the NS4B protein is as shown in SEQ ID NO:9, 83, 311, 321, 331, 341, or 351, or a variant having 90-99% amino acid sequence identity with SEQ ID NO:9, 83, 311, 321, 331, 341, or 351. In further embodiments, the amino acid sequence of the NS5A protein is as shown in SEQ ID NO:10, 84, 312, 322, 332, 342, or 352, or a variant having 90-99% amino acid sequence identity with SEQ ID NO:10, 84, 312, 322, 332, 342, or 352. In additional embodiments, the amino acid sequence of the NS5B protein is as shown in SEQ ID NO:11, 85, 313, 323, 333, 343, or 353, or a variant having 90-99% amino acid sequence identity with SEQ ID NO:11, 85, 313, 323, 333, 343, or 353. In some embodiments, the antibody is labeled. In certain embodiments, the antigen binding portion of a full antibody comprises a Fab fragment.

In certain embodiments, provided herein are methods of sequencing HPgV-2 nucleic acid comprising: a) treating a sample to generate isolated HPgV-2 RNA; b) contacting said isolated HPgV-2 RNA with random primers, or primers specific to a region of said HPgV-2 RNA, and amplifying such that a cDNA library is generated; c) contacting said cDNA library with sequencing adapters under conditions such that an adapter-conjugated library is generated; and d) sequencing said adapter-conjugated cDNA library to at least partially determine the nucleic acid sequence of said isolated HPgV-2 RNA.

In some embodiments, provided herein are methods for treating or preventing a human *Pegivirus* 2 (HPgV-2) infection in a subject comprising: administering to a subject a composition comprising attenuated or inactivated HPgV-2 particles, and/or an antigenic portion of the HPgV-2, thereby generating an immune response in the subject directed against the HPgV-2. In other embodiments, the immune response is sufficient to prevent or treat an infection by the HPgV-2. In some embodiments, the antigenic portion of the HPgV-2 comprises a peptide, wherein the peptide comprises at least a portion of the HPgV-2 selected from the group consisting of: the S protein, the E1 protein, the E2 protein, the X protein, the NS2 protein, the NS3 protein, the NS4A protein, the NS4B protein, the NS5A protein, and the NS5B protein.

In other embodiments, provided herein are immunogenic compositions suitable for administration to a subject comprising: a composition comprising attenuated or inactivated HPgV-2 particles, and/or an antigenic portion of the HPgV-2. In further embodiments, the antigenic portion of the HPgV-2 comprises a peptide, wherein the peptide wherein the peptide comprises at least a portion of the HPgV-2 selected from the group consisting of: the S protein, the E1 protein, the E2 protein, the X protein, the NS2 protein, the NS3 protein, the NS4A protein, the NS4B protein, the NS5A protein, and the NS5B protein.

In further embodiments, provided herein are kits or systems for detecting human *Pegivirus* 2 (HPgV-2) comprising at least one of the following components: a) a first composition comprising a first synthetic nucleic acid molecule, wherein the first synthetic nucleic acid molecule comprises a nucleotide sequence at least 12 nucleotides in length that hybridizes under stringent conditions to SEQ ID NOs:209-303, 419, 430, or to region 1, region 2, region 3, or region 4 of a genomic sequence of human *Pegivirus* 2 (HPgV-2) or complement thereof, wherein the genomic sequence of HPgV-2 is shown in SEQ ID NO:1 or 75, and wherein region 1 is nucleotides 1-1401 of SEQ ID NO:1 or 75, region 2 is nucleotides 1431-4777 of SEQ ID NO:1 or 75, region 3 is nucleotides 4818-8134 of SEQ ID NO:1 or 75, and region 4 is nucleotides 8167-9778 of SEQ ID NO:1 or 75; and b) a second composition comprising a second synthetic nucleic acid molecule, wherein the second synthetic nucleic acid molecule comprises a nucleotide sequence that has at least 75% identity to a portion of SEQ ID NOs:209-303, or to region 1, region 2, region 3, or region 4 of SEQ ID NO: 1 or 75 or complement thereof, wherein the portion is at least 15 nucleotides in length (e.g., at least 15 . . . 24 . . . 37 . . . etc.), and wherein region 1 is nucleotides 1-1401 of SEQ ID NO:1 or 75, region 2 is nucleotides 1431-4777 of SEQ ID NO:1 or 75, region 3 is nucleotides 4818-8134 of SEQ ID NO:1 or 75, and region 4 is nucleotides 8167-9778 of SEQ ID NO:1 or 75. In some embodiments, the kits and systems further comprise an additional component selected from the group consisting of: an amplification buffer; reagents for sequencing, reagents for PCR, written instructions for using the first or second synthetic nucleic acid molecule; a liquid container for holding the first and/or second composition; and a shipping container for holding the liquid container.

In certain embodiments, provided herein are kits and systems for detecting human *Pegivirus* 2 (HPgV-2) comprising a composition comprising a substantially purified recombinant peptide, wherein the recombinant peptide comprises an amino acid sequence that has at least 75% identity (e.g., at least 75% . . . 85% . . . 95% . . . 99% identity) to a portion of any one of SEQ ID NOs:2-11, 76-85, 86-99, 100-218, 304-353, 420-429, and 431-440, and wherein the portion is at least 10 amino acids in length (e.g., at least 10 . . . 15 . . . 25 or 35 amino acids in length). In other embodiments, the kits comprise an antibody (e.g., biotin labeled antibody) specific to a patient's HPgV-2 antibody. In some embodiments, the kits and systems further comprise an additional component selected from the group consisting of: an immunoassay buffer; immunoassay beads, chemiluminescent microparticles, a solid support (e.g., a solid support capable of binding biotin, such as an avidin labeled solid support), such as beads, with the recombinant peptide attached thereto, reagents for a sandwich assay, written instructions for using the composition to detect patient antibodies; a liquid container for holding the composition; and a shipping container for holding the liquid container.

In some embodiments, provided herein are methods of assaying for an anti-HPgV-2 compound comprising: a) contacting a sample containing a human *Pegivirus* 2 (HPgV-2) with a test compound; and b) determining whether the test compound inhibits HPgV-2 replication, wherein inhibition of HPgV-2 replication indicates that the test compound is an anti-HPgV-2 compound.

In certain embodiments, provided herein are compositions comprising a substantially purified recombinant peptide, wherein said recombinant peptide comprises at least one of the following: a) a first amino acid sequence that comprises at least 17 consecutive amino acids (e.g., at least 17 . . . 24 . . . 35 . . . or more) from the HPgV-2 NS3 protein; b) a second amino acid sequence that comprises at least 13 consecutive amino acids from the HPgV-2 NS5B protein (e.g., at least 13 . . . 17 . . . 25 . . . 35 or more); c) a third amino acid sequence that comprises at least 11 consecutive amino acids (e.g., at least 11 . . . 15 . . . 19 . . . 25 . . . 35 or more) from the HPgV-2 NS2 protein; d) a fourth amino acid sequence that comprises at least 8 consecutive amino acids (e.g., at least 8 . . . 11 . . . 15 . . . 23 . . . 35 or more) from the HPgV-2 NS4B protein; e) a fifth amino acid sequence that comprises at least 5 consecutive amino acids from the HPgV-2 NS4a protein (e.g., at least 5 . . . 10 . . . 18 . . . 25 . . . 35 or more); f) a sixth amino acid sequence that comprises at least 6 consecutive amino acids (e.g., at least 6 . . . 12 . . . 18 . . . 25 . . . 35 or more) from the HPgV-2 S protein; g) a seventh amino acid sequence that comprises at least 6 consecutive amino acids (e.g., at least 6 . . . 12 . . . 17 . . . 25 . . . 35 or more) from the HPgV-2 E1 protein; and h) an eighth amino acid sequence that comprises at least 8 consecutive amino acid (e.g., at least 8 . . . 14 . . . 25 . . . 35 or more) from the HPgV-2 X protein. In particular embodiments, the HPgV-2 NS3 protein is as shown in SEQ ID NOs: 7, 81, 309, 319, 329, 339, and 349. In other embodiments, the HPgV-2 NS5B protein is as shown in SEQ ID NOs: 11, 85, 313, 323, 333, 343, or 353. In additional embodiments, the HPgV-2 NS2 protein is as shown in SEQ ID NOs: 6, 80, 308, 318, 328, 338, or 348. In additional embodiments, the HPgV-2 NS4B protein is as shown in SEQ ID NOs: 9, 83, 311, 321, 331, 341, or 351. In further embodiments, the HPgV-2 NS4a protein is as shown in SEQ ID NOs: 8, 82, 310, 320, 330, 340, or 350. In other embodiments, the HPgV-2 S protein is as shown in SEQ ID NOs: 2, 76, 304, 314, 324, 334, or 344. In further embodiments, the HPgV-2 E1 protein is as shown in SEQ ID NOs: 3, 77, 305, 315, 325, 335, or 345. In additional embodiments, the HPgV-2 X protein is as shown in SEQ ID NOs: 5, 79, 307, 317, 327, 337, or 347.

In certain embodiments, the peptides and proteins described herein are expressed recombinantly in prokaryotic cells. In other embodiments, the peptides and proteins described herein (e.g., E1 and E1) are expressed recombinantly in mammalian cells.

In some embodiments, provided herein are methods (and corresponding kits with recited components) for detection of HPgV-2 antigen and HPgV-2 antibody in a test sample comprising: a) providing the following reagents: i) a solid phase capable of binding to biotin, ii) biotinylated anti-HPgV-2 antibody for the capture of an HPgV-2 antigen present said test sample; iii) a biotinylated HPgV-2 antigen for the capture of anti-HPgV-2 antibody in said test sample; and iv) a detectably labeled HPgV-2 antigen for binding to anti-HPgV-2 antibody captured by the biotinylated HPgV-2 antigen of (iii); and b) incubating the reagents of step (a) under conditions to produce a reaction mixture that: (i) the biotinylated anti-HPgV-2 antibody of (a)(ii) binds to said solid phase through said biotin and specifically binds to HPgV-2 antigen present in said test sample to produce an anti-HPgV-2 antibody-HPgV-2 antigen complex captured on said solid phase; (ii) the biotinylated antigen of (a)(iii) binds to said solid phase through said biotin and specifically binds to anti-HPgV-2 antibodies present in said test sample to produce an HPgV-2 antigen-anti-HPgV-2 antibody complex captured on said solid phase and said detectably labeled HPgV-2 antigen of (a)(iv) specifically binds to the anti-HPgV-2 antibody in said an HPgV-2 antigen-anti-HPgV-2 antibody complex captured on said solid phase; c) isolating solid phase that comprises attached captured antibody, and captured HPgV-2 antigen from unreacted test sample and reagents, d) contacting the isolated solid phase with a detectably labeled conjugate antibody that binds to said HPgV-2 antigen captured in the an anti-HPgV-2-antibody-HPgV-2 antigen complex of (b)(ii); and e) detecting the signal generated from the detectable label moieties upon triggering of said signal, wherein presence of said signal indicates presence of HPgV-2 in said test sample.

In certain embodiments, the methods (and corresponding kits) further comprise providing: (v) a second biotinylated HPgV-2 antigen for the capture of anti-HPgV-2 antibody in said test sample wherein said second HPgV-2 antigen is distinct from the HPgV-2 antigen in step (aiii); and (vi) a detectably labeled HPgV-2 antigen for binding to anti-HPgV-2 antibody captured by the biotinylated HPgV2 antigen of (v); and (b) (iii) the biotinylated antigen of (a)(v) binds to said solid phase through said biotin and specifically binds to anti-HPgV-2 antibodies present in said test sample to produce an HPgV-2 antigen-anti-HPgV-2 antibody complex captured on said solid phase and said detectably labeled HPgV-2 antigen of (a)(vi) specifically binds to the anti-HPgV-2 antibody in said an HPgV-2 antigen-anti-HPgV-2 antibody complex captured on said solid phase. In certain embodiments, the methods further comprises: (a) providing (vii) a third biotinylated HPgV-2 antigen for the capture of anti-HPgV-2 antibody in said test sample wherein said third HPgV-2 antigen is distinct from the HPgV-2 antigen in step 1(a)(iii) or step 2(a)(v); and (viii) a detectably labeled HPgV-2 antigen for binding to anti-HPgV-2 antibody captured by the biotinylated HPgV-2 antigen of (vii); and (b) (iv) the biotinylated antigen of (a)(vii) binds to said solid phase through said biotin and specifically binds to anti-HPgV-2 antibodies present in said test sample to produce an HPgV-2 antigen-anti-HPgV-2 antibody complex captured on said solid phase and said detectably labeled HPgV2 antigen of (a)(viii) specifically binds to the anti-HPgV-2 antibody in said an HPgV-2 antigen-anti-HPgV2 antibody complex captured on said solid phase.

In certain embodiments, provided herein are methods for the simultaneous detection of both HPgV-2 antigens and HPgV-2 antibodies in a test sample, wherein said combination assay comprises: a) protein; a first capture antigen comprising a peptide sequence of a first HPgV-2, b) a first detection antigen comprising a peptide sequence of a first HPgV-2 protein and further comprising a detectable label, c) a second capture antigen comprising an antigenic sequence from a second HPgV-2 protein, d) a second detection antigen comprising an antigenic sequence from a second HPgV-2 protein and further comprising a detectable label, e) a third capture antigen comprising an antigenic sequence from a third HPgV-2 protein, f) a third detection antigen comprising an antigenic sequence from a third HPgV-2 protein and further comprising a detectable label, g) a first capture antibody, h) a conjugate antibody comprising a detectable label, wherein said capture antibody and said conjugate antibody specifically bind a fourth HPgV-2 protein from said test sample, and said combination assay is performed by: (i) contacting said test sample with said capture antigen, said detection antigen, said capture antibody and said conjugate antibody under conditions to allow: a) formation of a sandwich complex between said first capture antigen and said detection antigen and first anti-HPgV-2 antibody present in said test sample; b) formation of a sandwich complex between said second capture antigen and said second detection antigen and an anti-HPgV-2 antibody against said second HPgV-2 protein present in said test sample; c) formation of a sandwich complex between said third capture antigen and said third detection antigen and an anti-HPgV-2 antibody against said third HPgV-2 protein present in said test sample; and d) formation of a complex between said capture antibody, said conjugate antibody and an HPgV-2 antigen present in said sample; and (ii) measuring a signal generated from said detectable labels as a result of formation of said complexes, thereby simultaneously detecting HPgV-2 antigens and HPgV-2 antibodies present in said sample.

In certain embodiments, the compositions and kits described anywhere herein further comprise at least one reagent selected from the group consisting of: microparticles (e.g., configured to bind a label on the peptide), Na Pyrophosphate (e.g., pH 6.3), NaCl (e.g., about 0.9 M), EDTA, Sucrose, Tergitol 15-S-40, BME, Tergitol 15-S-9, Azide (e.g., 0.08%), Korasilon Antifoam (e.g., 1 ppm), Bis-Tris buffer (e.g., pH 6.3), Sorbitol, Dextran, PVSA, BSA, Benzethonium chloride, Heparin sodium salt, Sodium fluoride, Triton X-100, Gentamycine, A56620, Glycine, Lauryl sulfobetaine, Palmityl sulfobetaine, Stearyl sulfobetaine, C16TAB, C18TAB, CHAPS, Saponin, Methyl Cellulose, Sodium Sulfite, Sodium azide, Urea, HCl, C12TAB, Palmityl sulfobetaine, Stearyl sulfobetaine, Maltose, Citric acid, 2-Diethylaminoethanthiol, NaHCO3/Na2CO3, Laurylsulfobetaine, CHAPS, NaOH, MES Buffer w/Triton X-405, NaCl, BSA, Nipasept, Quinolone, TRIS Buffer w/CKS protein, Yeast SOD, Triton X-405, Goat serum, EDTA, Quinolone, Antifoam, Dentran sulfate, Proclin, Gentamicin sulfate, labeled (e.g., acridinium labeled) anti-human IgG or IgM monoclonal antibody, streptavidin labeled microparticles, NFDM, SB3-14, PVSA (e.g., 0.8%), ACD, CPDA-1, CPD, CP2D, potassium oxalate, sodium EDTA, potassium EDTA sodium citrate, heparin, lithium heparin, sodium heparin, and sodium citrate.

In some embodiments, provided herein are methods of detecting both human *Pegivirus* 2 (HPgV-2) and human *Pegivirus* 1 (HPgV-1; aka GVC-C) infection in a subject comprising: a) contacting a sample from a subject suspected of containing a subject antibody to HPgV-2 and a subject antibody to HPgV-1, with a HPgV-2 derived peptide and a HPgV-1 derived peptide, wherein said peptides specifically bind said subject antibodies to form a complexes; and b) detecting the presence of said complexes, thereby detecting the presence of past or present HPgV-2 and HPgV-1 infection in said subject. In certain embodiments, provided herein are methods for detecting human *Pegivirus* 2 (HPgV-2) nucleic acid and human *Pegivirus* 1 (HPgV-1; aka GBV-C) nucleic acid comprising: a) contacting a sample suspected of containing HPgV-2 and HPgV-1 nucleic acid with: i) a first nucleic acid molecule at least 12 nucleotides in length that hybridizes under stringent conditions to a nucleic acid sequence of HPgV-2, and ii) a second nucleic acid molecule at least 12 nucleotides in length that hybridizes under stringent conditions to a nucleic acid sequence of HPgV-1, and b) detecting the presence or absence of hybridization of said first and second nucleic acid molecules to said HPgV-2 and HPgV-1 nucleic acid, wherein detecting said presence of hybridization indicates the presence of said HPgV-2 and HPgV-1 nucleic acid in said sample. In certain embodiments, the peptide and amino acid sequences for detecting HPgV-1 and HPgV-1 subject antibodies are found in U.S. Pat. No. 6,870,042 and Souza et al., J. Clin. Microbiol., 2006, 44(9):3105-3113.

In certain embodiments, provided herein are compositions comprising an anti-HPgV-2 antibody. Such antibody can be generated using any of the peptides described herein as an immunogen in a host animal (e.g., mouse, rabbit, etc.), such that polyclonal or monoclonal antibodies to HPgV-2 are generated.

DESCRIPTION OF THE FIGURES

FIGS. 1A-C provide a genomic nucleic acid sequence of an HPgV-2 isolate called UC0125.US, which is labeled SEQ ID NO:1. It is understood that the HPgV-2 genome is a positive strand RNA sequence. SEQ ID NO: 1 is shown with the uracils as thymine.

FIGS. 2A-C show the amino acid sequences and describes the nucleic acid sequences of HPgV-2 index case UC0125.US. FIG. 2A shows: 1) the amino acid sequence (SEQ ID NO:2) and describes the nucleic acid sequence (nucleotides 104-475 of SEQ ID NO: 1) of the S protein of HPgV-2; 2) the amino acid sequence (SEQ ID NO:3) and describes the nucleic acid sequences (nucleotides 476-1048 of SEQ ID NO:1) of the E1 protein of HPgV-2; 3) the amino acid sequence (SEQ ID NO:4) and describes the nucleic acid sequence (nucleotides 1049-2110 of SEQ ID NO: 1) of the E2 protein of HPgV-2; and 4) the amino acid sequence (SEQ ID NO:5) and describes the nucleic acid sequence (nucleotides 2111-2821 of SEQ ID NO:1) of the X protein of HPgV-2. FIG. 2B shows: 1) the amino acid sequence (SEQ ID NO:6) and describes the nucleic acid sequences (nucleotides 2822-3541 of SEQ ID NO:1) of the NS2 protein of HPgV-2; 2) the amino acid sequence (SEQ ID NO:7) and describes the nucleic acid sequence (nucleotides 3542-5425 of SEQ ID NO: 1) of the NS3 protein of HPgV-2; 3) the amino acid sequence (SEQ ID NO:8) and describes the nucleic acid sequence (nucleotides 5426-5548 of SEQ ID NO: 1) of the NS4A protein of HPgV-2; and 4) the amino acid sequence (SEQ ID NO:9) and describes the nucleic acid sequences (nucleotides 5549-6334 of SEQ ID NO:1) of the NS4B protein of HPgV-2. FIG. 2C shows: 1) the amino acid sequence (SEQ ID NO: 10) and describes the nucleic acid sequence (nucleotides 6335-7708 of SEQ ID NO: 1) of the NS5A protein of HPgV-2; 2) the amino acid sequence (SEQ ID NO: 11) and describes the nucleic acid sequence (nucleotides 7709-9409 of SEQ ID NO: 1) of the NS5B protein of HPgV-2; 3) the 5' UTR nucleic acid sequence (nucleotides 1-103 of SEQ ID NO: 1) of HPgV-2; and 4) the nucleic acid sequence (nucleotides 9410-9778 of SEQ ID NO: 1) of the 3' UTR of HPgV-2.

Figure 3A:
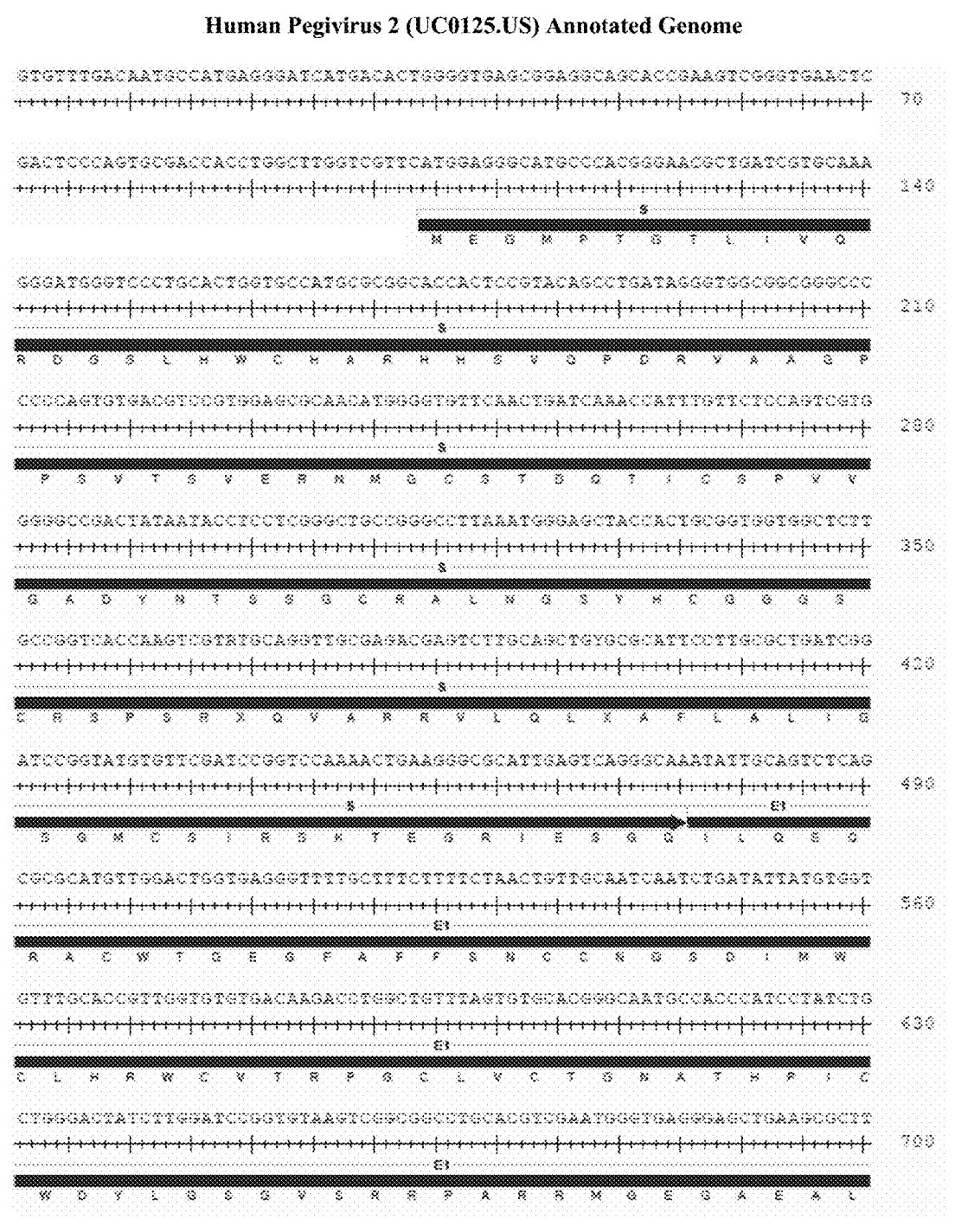
Figure 3B:
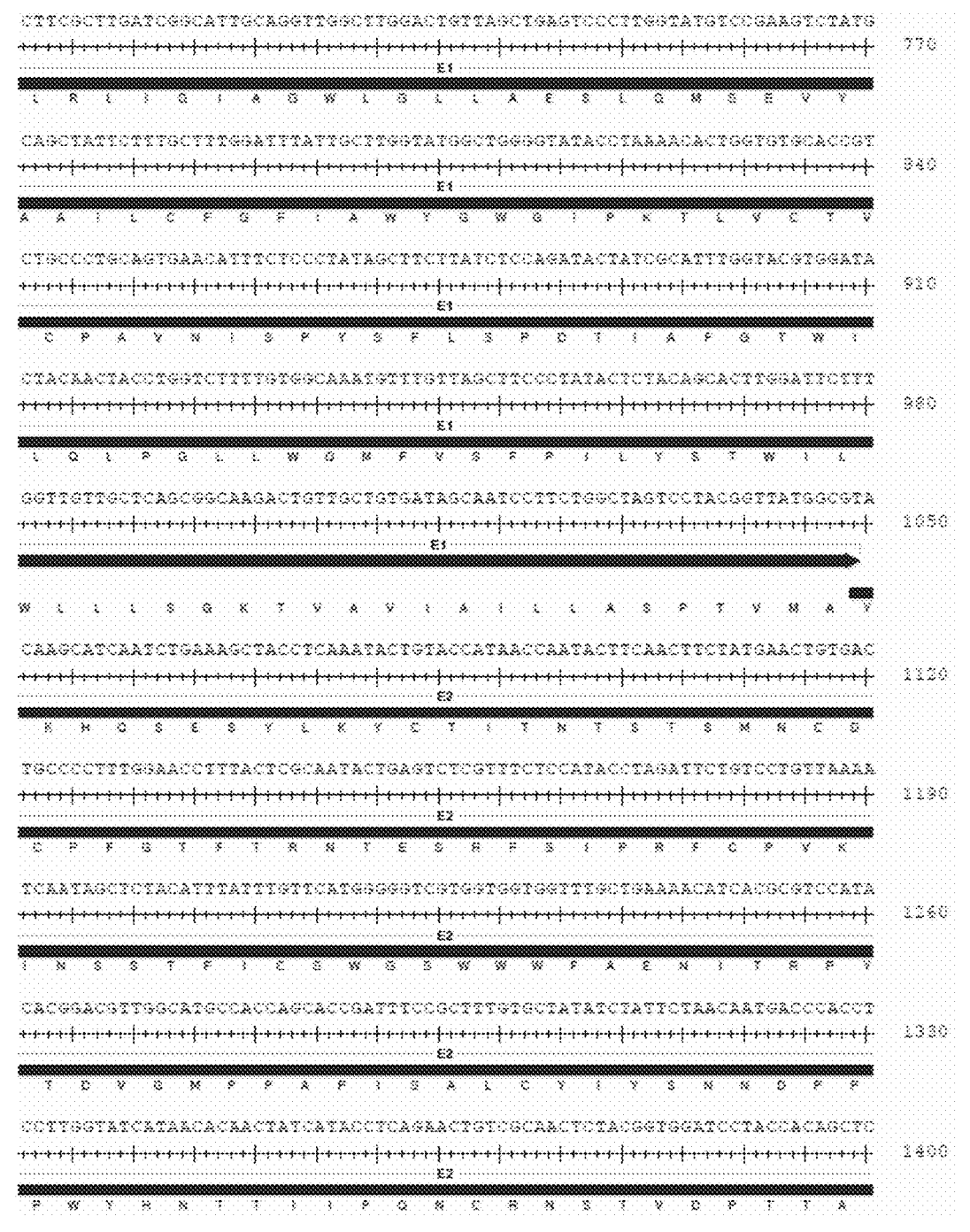
Figure 3C:
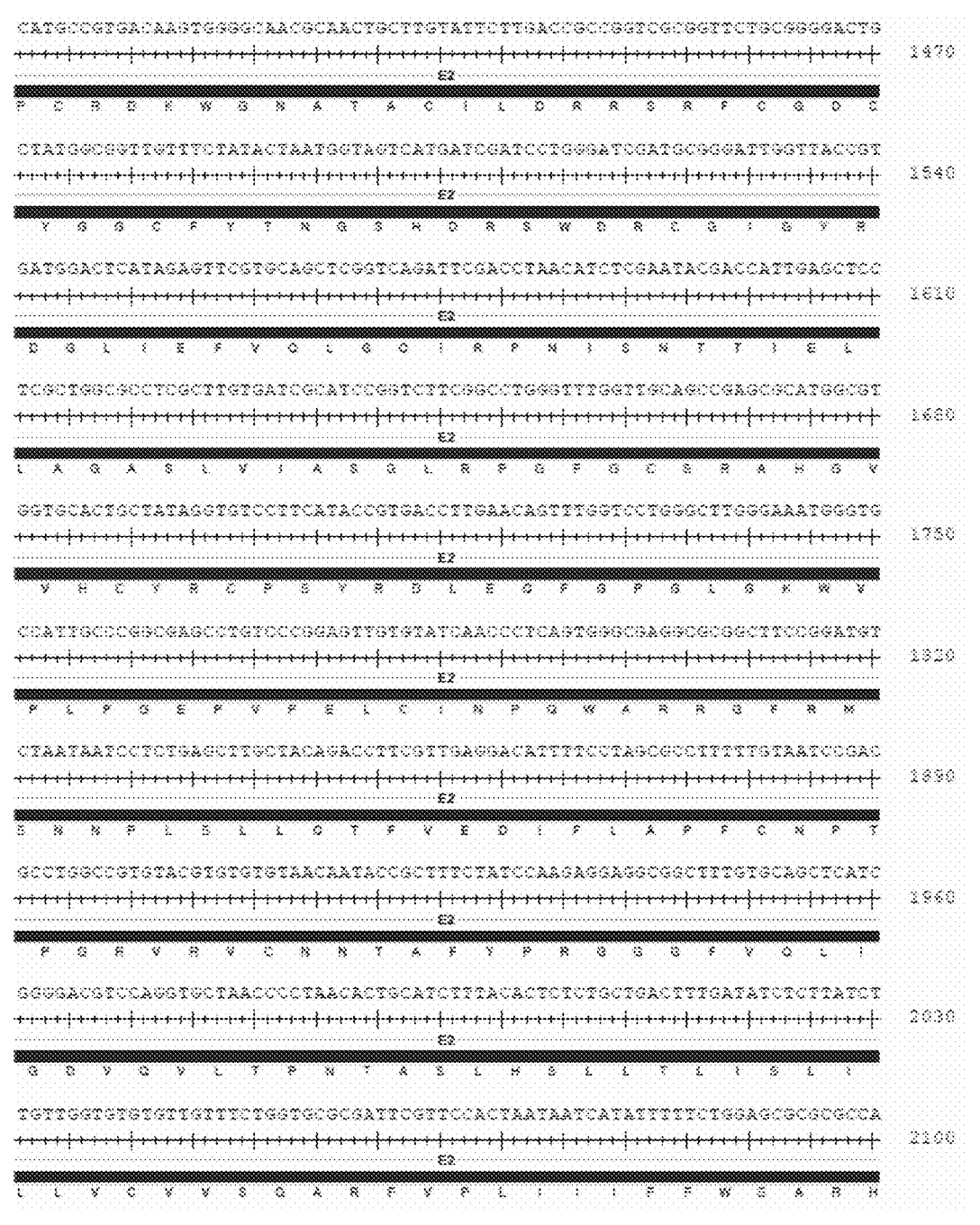
Figure 3D:
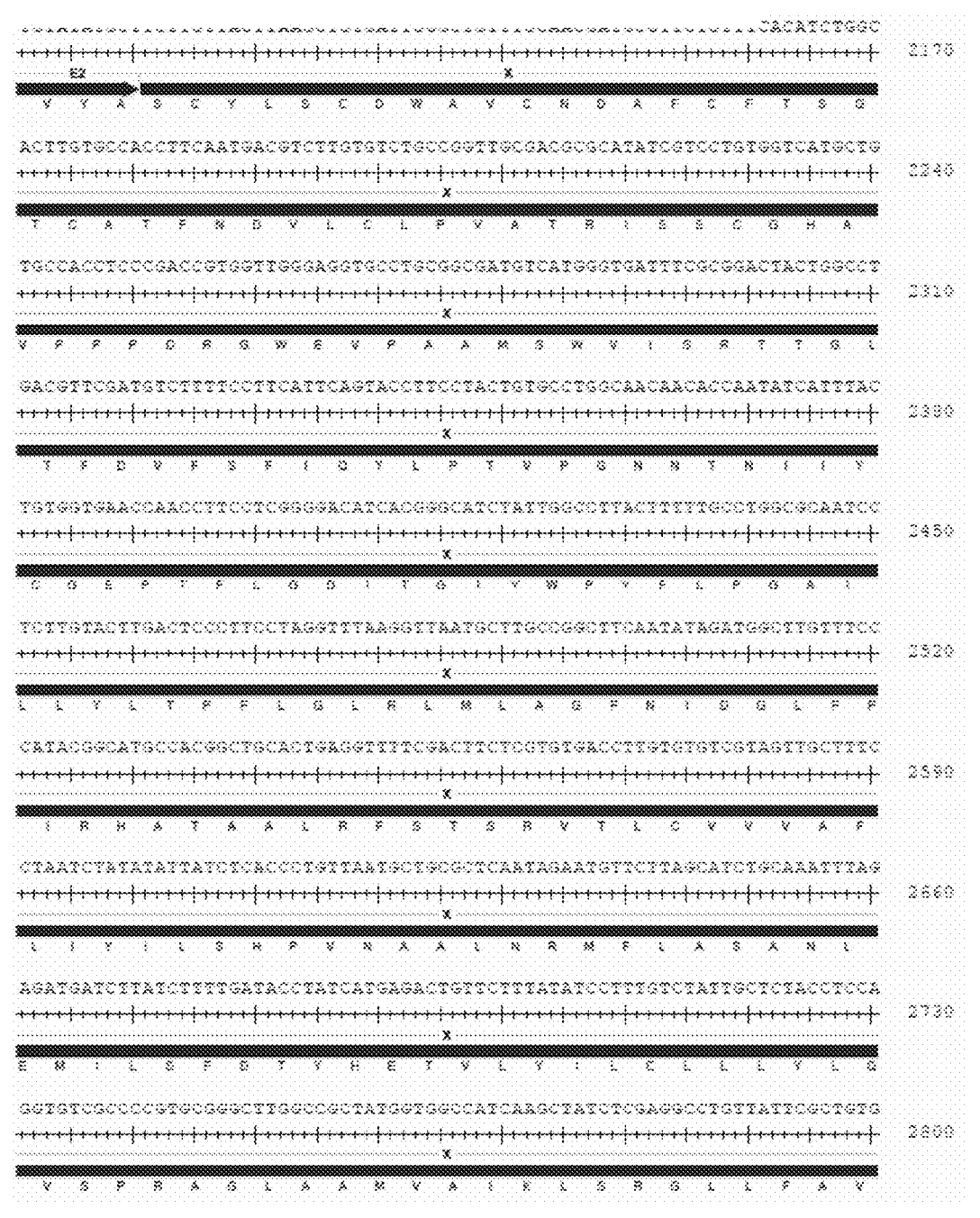
Figure 3E:
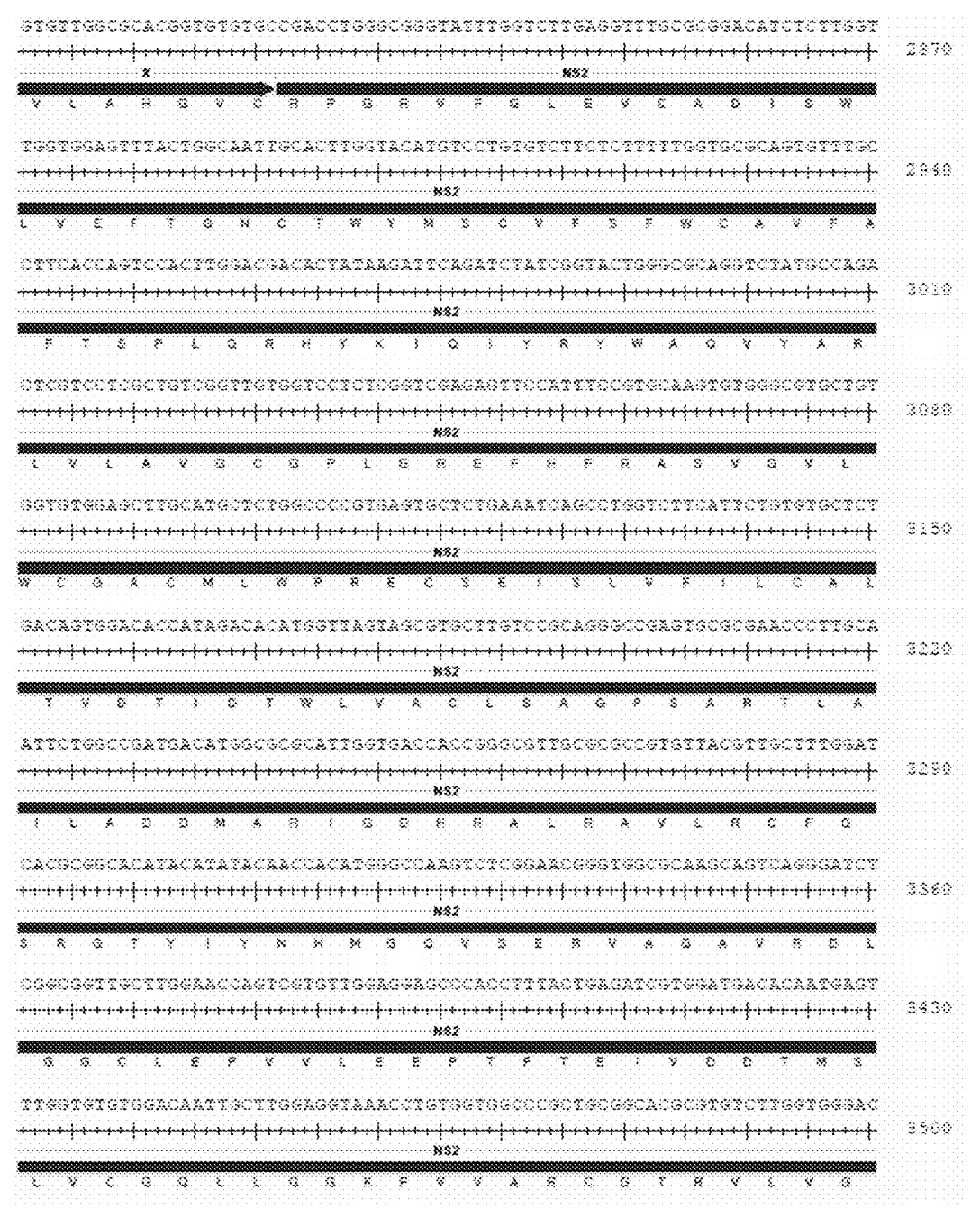
Figure 3F:
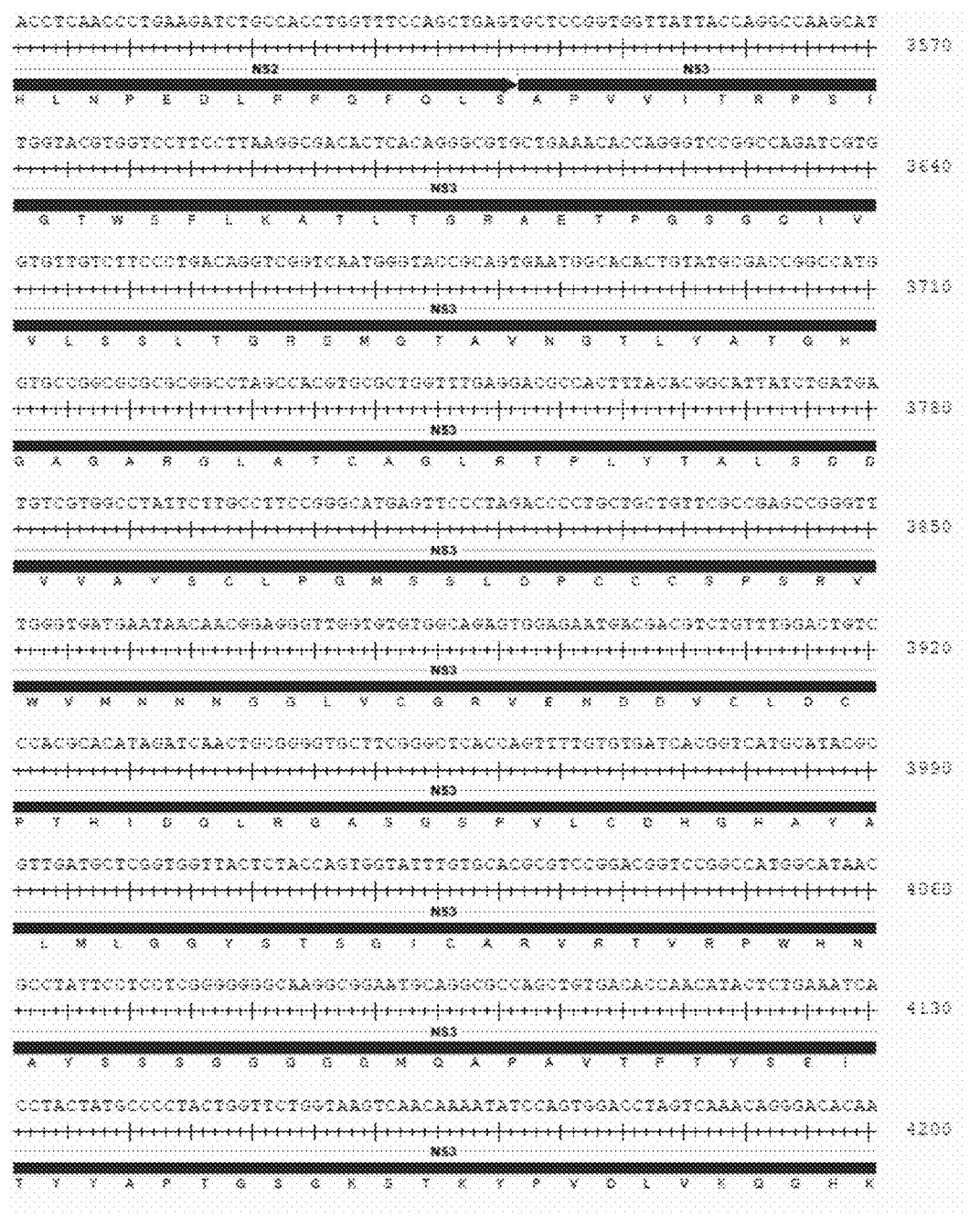
Figure 3G:
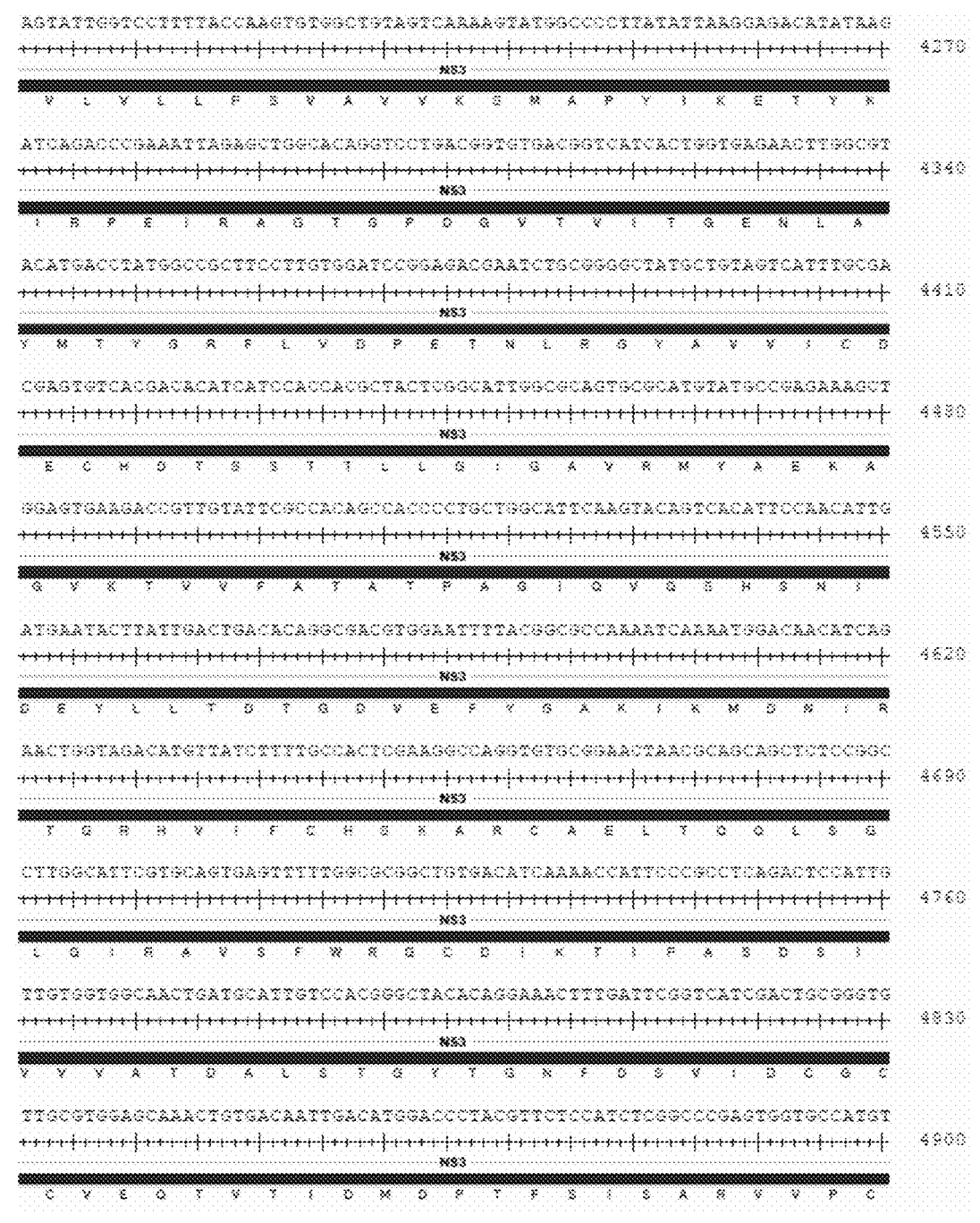
Figure 3H:
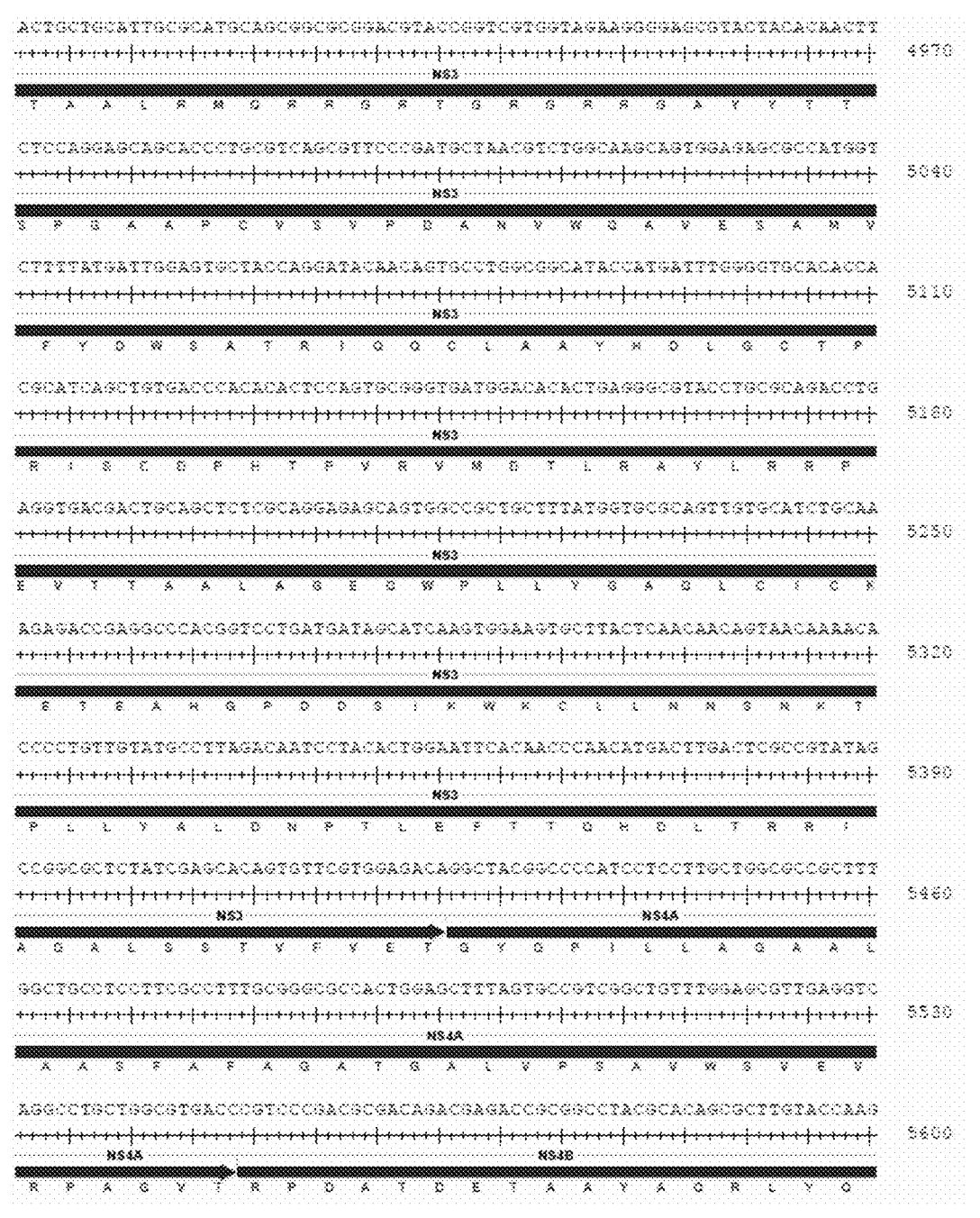
Figure 3I:
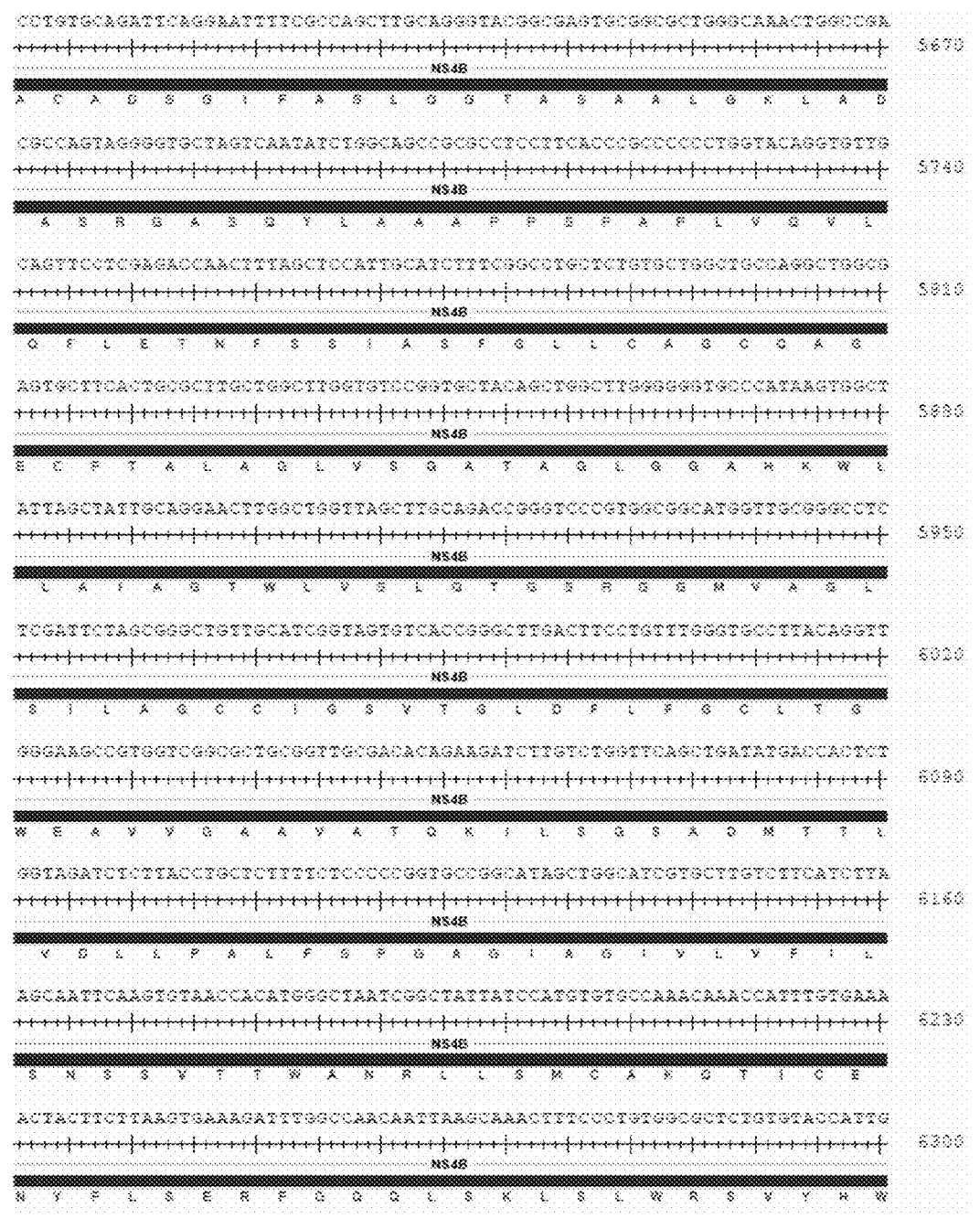
Figure 3J:
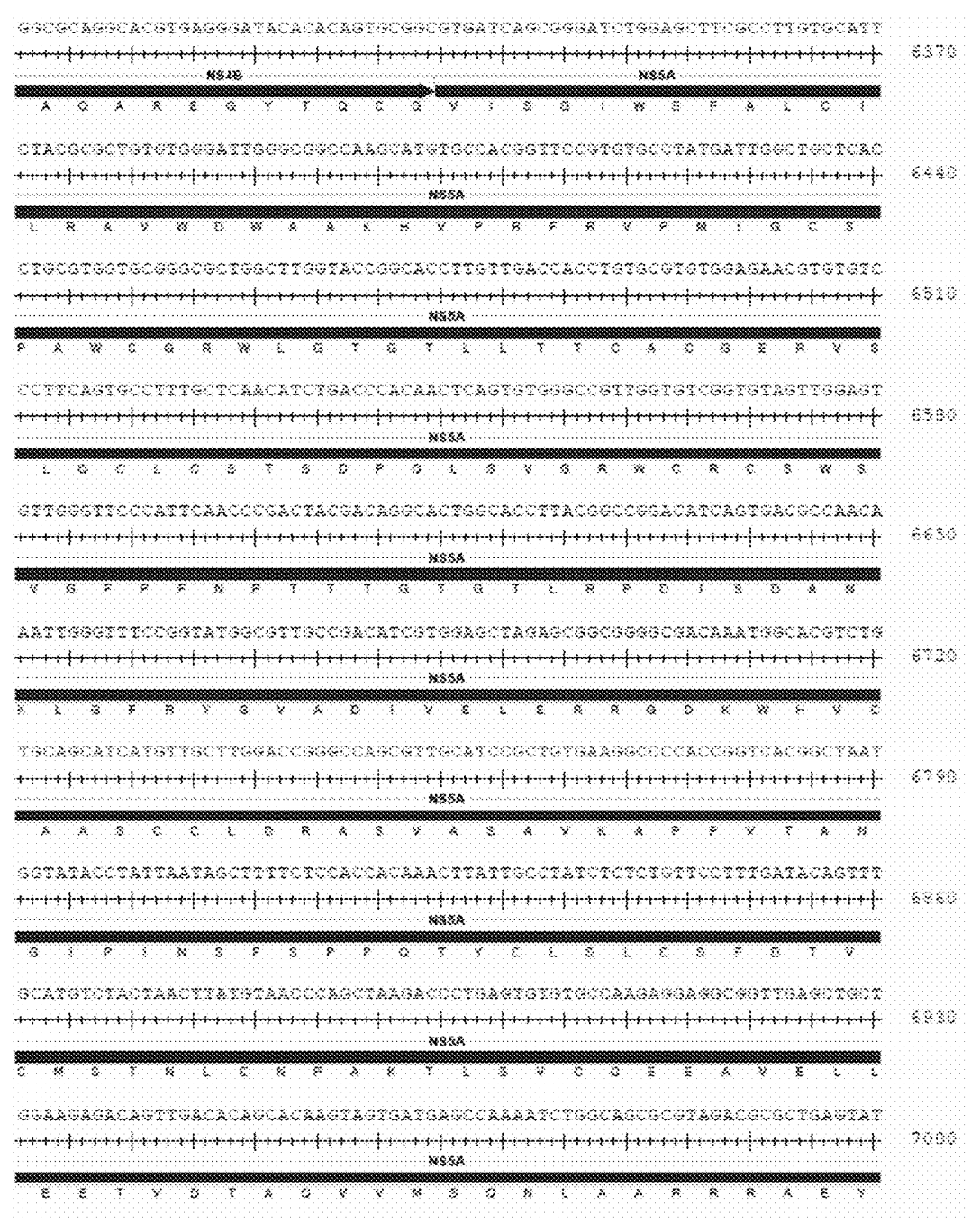
Figure 3K:
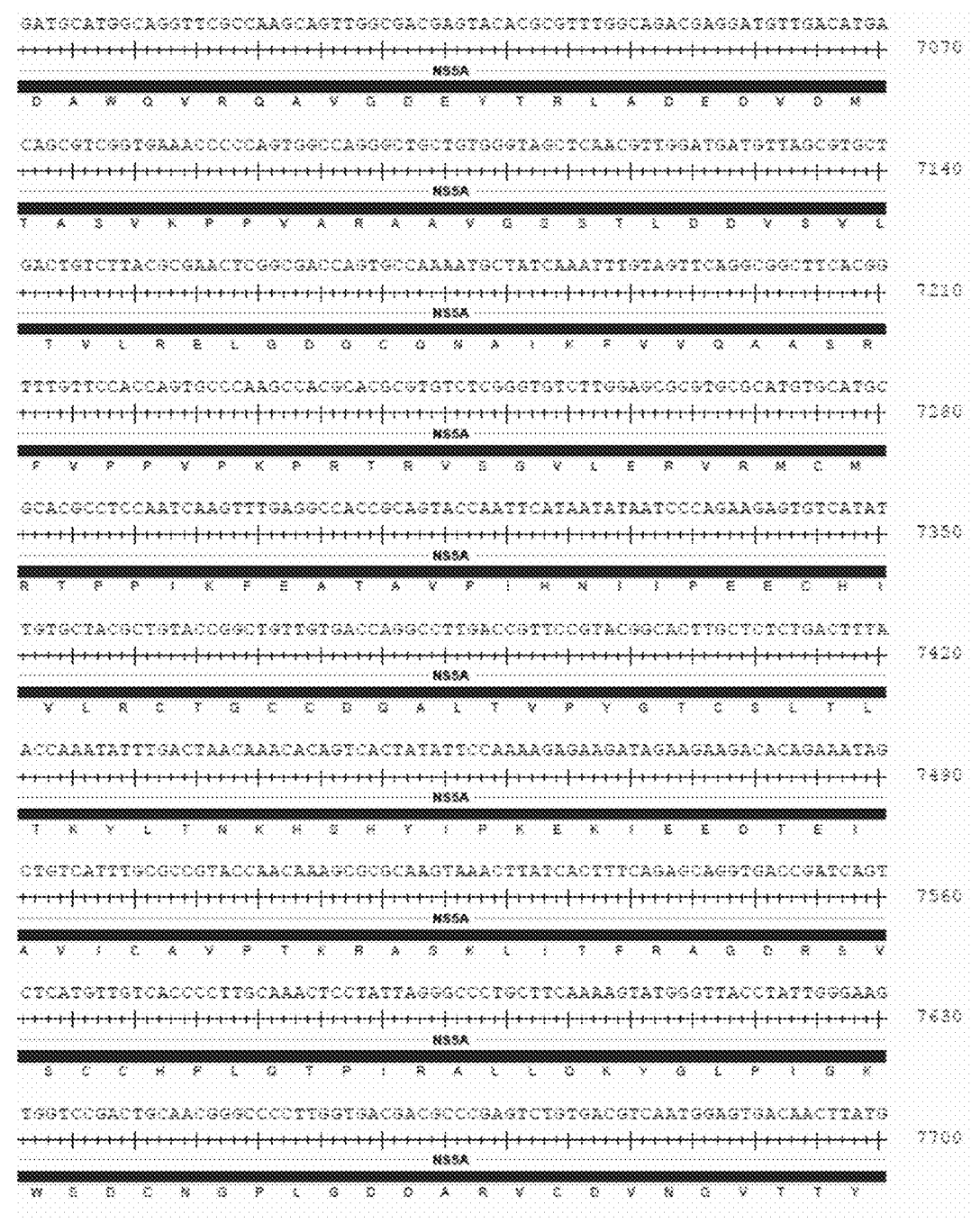
Figure 3L:
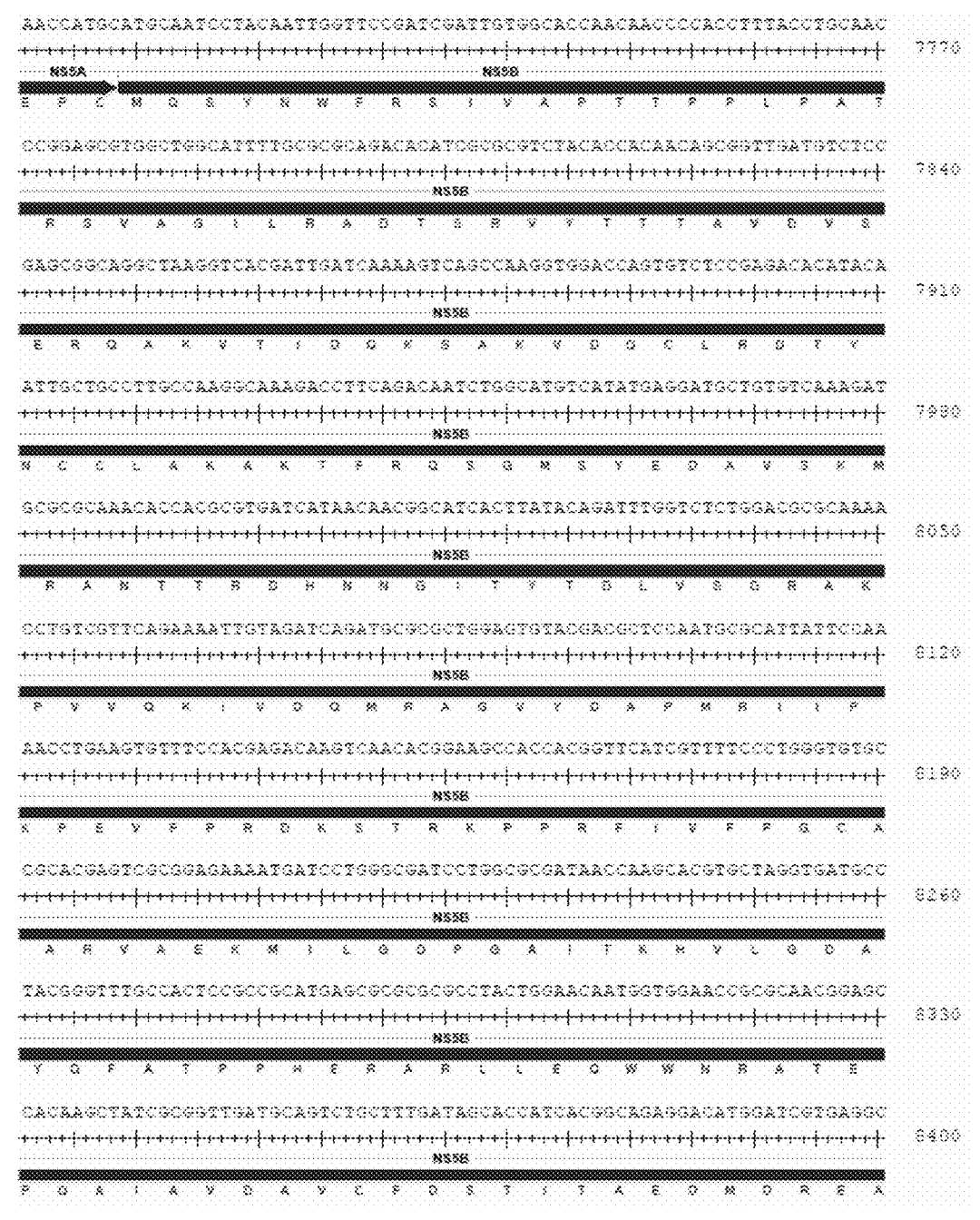
Figure 3M:
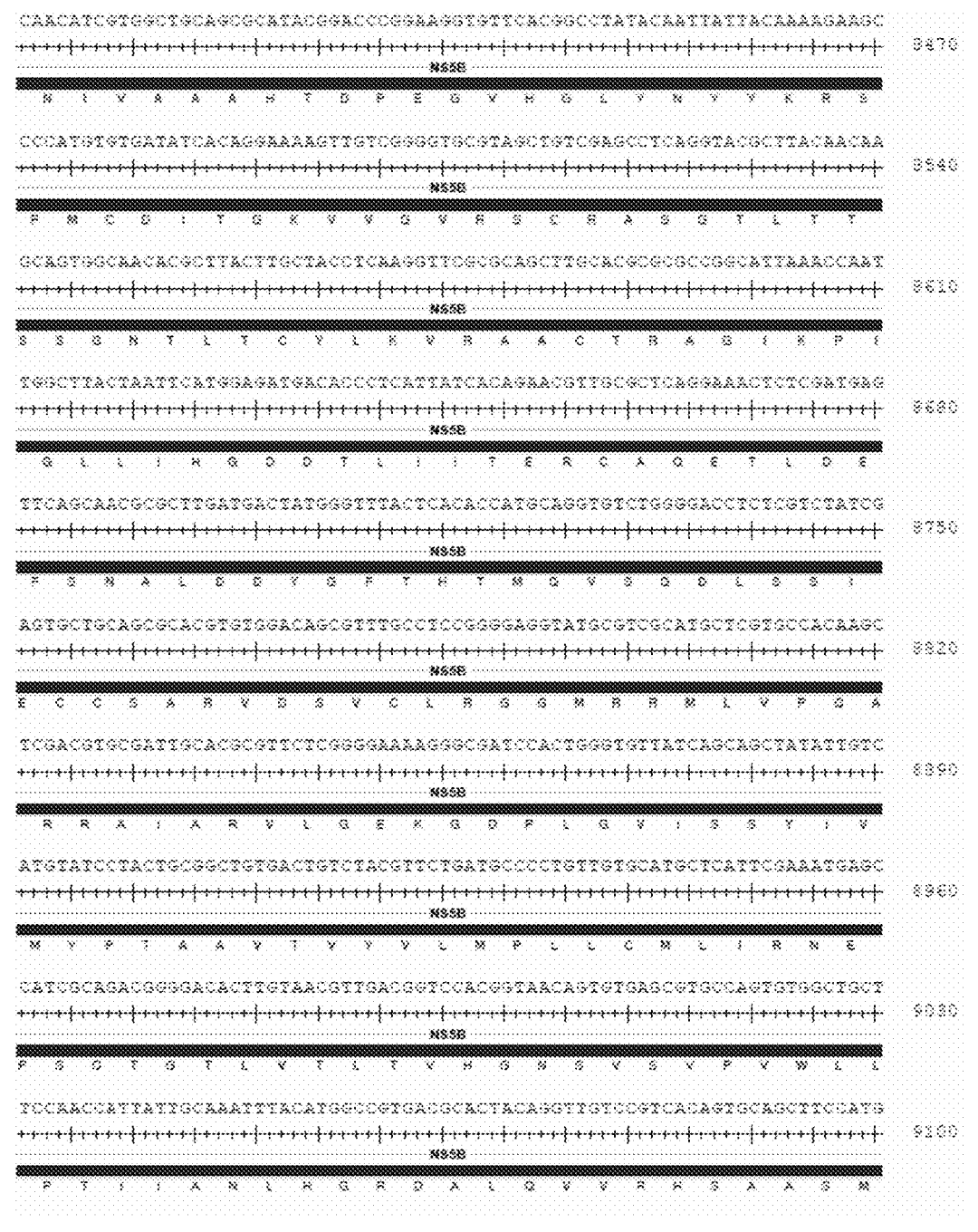
Figure 3N:
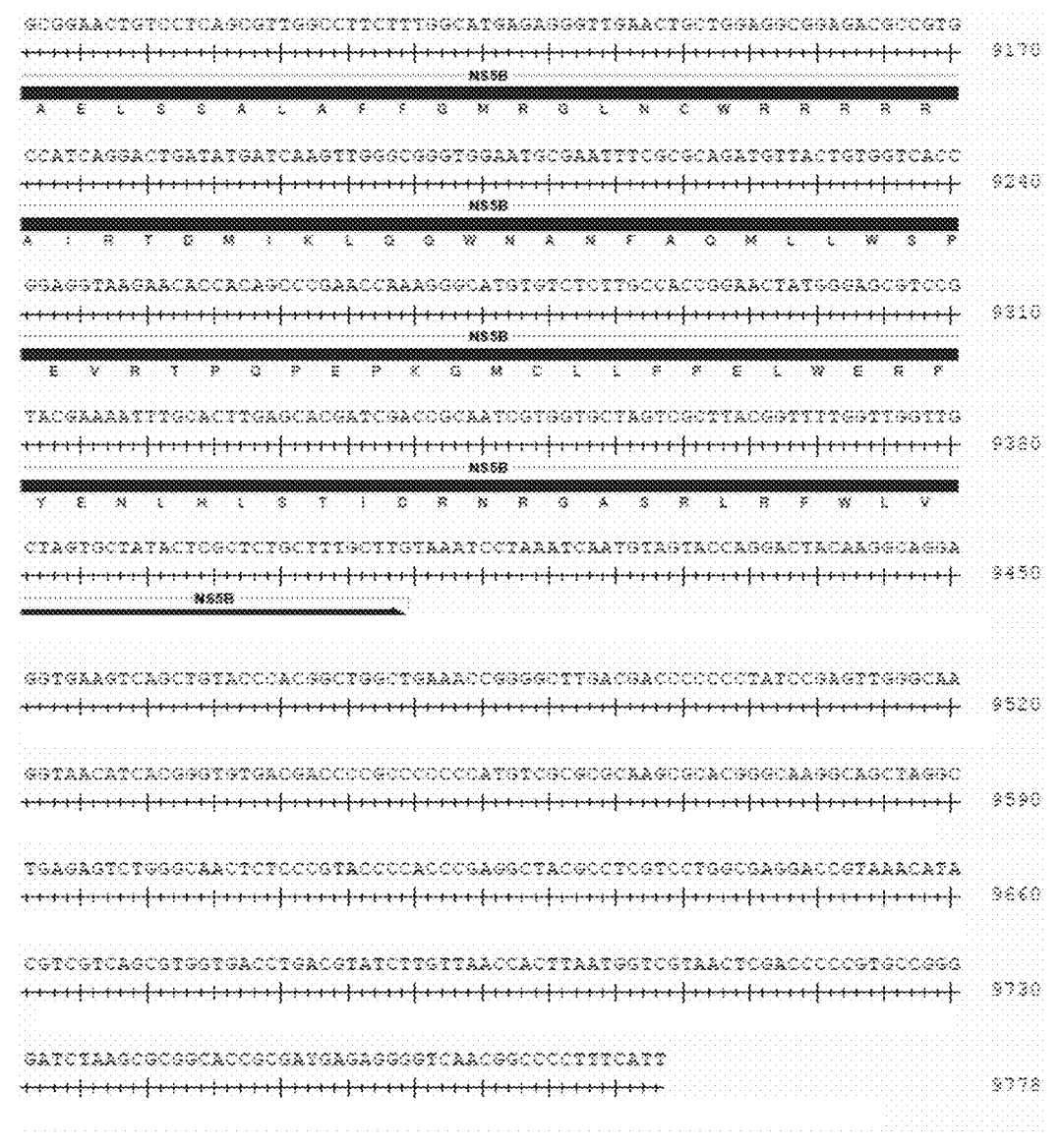

FIGS. 3A-N show an annotated version of the nucleic acid sequence of SEQ ID NO: 1 with the corresponding encoded amino acid sequence below.

FIG. 4 shows a cloned portion of the HPgV-2 genome representing nucleotides 3253-4512 of SEQ ID NO:1, along with seven sets of primers and probes (underlined) used for qPCR in Example 3.

FIG. 5A shows HPgV-2 primer/TaqMan probe sets (1-2-3-5-7; see FIG. 4 for sequences and positions) were used to detect 10-fold serial dilutions of the NS23Ex in vitro transcript and a 10-fold dilution of the HPgV-2 index case (UC0125.US) RNA (highlighted in bold). The lower right panel shows detection of 100 ng of NS23Ex and HPgV-2 RNA for each primer/probe set. FIG. 5B shows Ct values that were normalized to set 1_100 ng results and plotted on a log scale to estimate the amount of HPgV-2 RNA present in the index case. Negative controls included in the experiment were: 1) water, 2) pTRI (an irrelevant in vitro transcript), 3) CHU2725 (HIV+/GBV-C+ sample), and 4) N-505 (HIV+/GBV-C− sample) indicate there is no cross-reactivity with other infections (HIV, GBV-C).

FIG. 7A shows the results of a TaqMan qPCR assay using primer/probe set 3 (top panel) and primer/probe set 2 (bottom panel), which detected isolates ABT0070P.US and ABT0096P.US in an HCV(+) plasmapheresis donor plasma samples.

FIG. 7B shows results of an assay where RNA extracted from American Red Cross blood donor plasma (HCV RNA+/antibody+) samples were screened with TaqMan primer/probe sets 2 and 3 ABT0128A.US was detected, but only by set 2 (bold).

FIGS. 9A-C provide the genomic nucleic acid sequence of an HPgV-2 isolate called ABT0070P.US, which is labeled SEQ ID NO:75. It is understood that the HPgV-2 genome is a positive strand RNA sequence. SEQ ID NO:75 is shown with the uracils as thymine.

FIGS. 10A-C show the amino acid sequences of various proteins from HPgV-2 variant ABT0070P.US, as well as the corresponding nucleic acid coding sequences. FIG. 10A shows: 1) the amino acid sequence (SEQ ID NO:76) and describes the nucleic acid sequence (nucleotides 111-482 of SEQ ID NO:75) of the S protein of HPgV-2; 2) the amino acid sequence (SEQ ID NO:77) and describes the nucleic acid sequences (nucleotides 483-1055 of SEQ ID NO:75) of the E1 protein of HPgV-2; 3) the amino acid sequence (SEQ ID NO:78) and describes the nucleic acid sequence (nucleotides 1056-2117 of SEQ ID NO:75) of the E2 protein of HPgV-2; and 4) the amino acid sequence (SEQ ID NO:79) and describes the nucleic acid sequence (nucleotides 2118-2828 of SEQ ID NO:75) of the X protein of HPgV-2. FIG. 10B shows: 1) the amino acid sequence (SEQ ID NO:80) and describes the nucleic acid sequences (nucleotides 2829-3548 of SEQ ID NO:75) of the NS2 protein of HPgV-2; 2) the amino acid sequence (SEQ ID NO:81) and describes the nucleic acid sequence (nucleotides 3549-5432 of SEQ ID NO:75) of the NS3 protein of HPgV-2; 3) the amino acid sequence (SEQ ID NO:82) and describes the nucleic acid sequence (nucleotides 5433-5555 of SEQ ID NO:75) of the NS4A protein of HPgV-2; and 4) the amino acid sequence (SEQ ID NO:83) and describes the nucleic acid sequences (nucleotides 5556-6341 of SEQ ID NO:75) of the NS4B protein of HPgV-2. FIG. 10C shows: 1) the amino acid sequence (SEQ ID NO:84) and describes the nucleic acid sequence (nucleotides 6342-7715 of SEQ ID NO:75) of the NS5A protein of HPgV-2; 2) the amino acid sequence (SEQ ID NO:85) and describes the nucleic acid sequence (nucleotides 7716-9416 of SEQ ID NO:75) of the NS5B protein of HPgV-2; 3) describes the 5' UTR nucleic acid sequence (nucleotides 1-110 of SEQ ID NO:75) of HPgV-2; and 4) describes the nucleic acid sequence (nucleotides 9417-9431 of SEQ ID NO:75) of a portion of the 3' UTR of HPgV-2.

FIGS. 12A-C show phylogenetic trees of HPgV-2 (UC0125.US; SEQ ID 1) and ABT0070P.US (SEQ ID 75) along with 29 representative flaviviruses (GenBank accession numbers listed in Figure) constructed in Geneious using the Jukes-Cantor model and neighbor joining algorithm with 10,000 bootstrap replicates used to calculate branch supports. These tree topologies were then refined using a maximum likelihood Bayesian approach with MrBayes V3.2 software (1,000,000 sample trees, 10% of trees discarded as burn-in, convergence defined at an average standard deviation of <0.01). Each tree was rooted with dengue virus type 1 (DENV1) and yellow fever virus (YFV) as outgroups. Analysis was performed on entire (A) polyprotein sequences, as well as on (B) NS3 and (C) NS5B proteins individually.

FIGS. 13A-C provide the genomic nucleic acid sequence of an HPgV-2 consensus sequence, which is labeled SEQ ID NO:299. It is understood that the HPgV-2 genome is a positive strand RNA sequence. SEQ ID NO:299 is shown with the uracils as thymine.

FIGS. 14A-C show the amino acid sequences of various proteins from a HPgV-2 consensus sequence, as well as the corresponding nucleic acid coding sequences. FIG. 14A: 1) describes the 5'UTR sequence (nucleotides 1-327 of SEQ ID NO:299); 2) shows the amino acid sequence (SEQ ID NO:304) and describes the nucleic acid sequence (nucleotides 328-564 of SEQ ID NO:299) of the S protein of HPgV-2; 3) shows the amino acid sequence (SEQ ID NO:305) and describes the nucleic acid sequence (nucleotides 565-1137 of SEQ ID NO:299) of the E1 protein of HPgV-2; 4) shows the amino acid sequence (SEQ ID NO:306) and describes the nucleic acid sequence (nucleotides 1138-2199 of SEQ ID NO:299) of the E2 protein of HPgV-2; and 5) shows the amino acid sequence (SEQ ID NO:307) and describes the nucleic acid sequence (nucleotides 2200-2910 of SEQ ID NO:299) of the X protein of HPgV-2. FIG. 14B shows: 1) the amino acid sequence (SEQ ID NO:308) and describes the nucleic acid sequences (nucleotides 2911-3630 of SEQ ID NO:299) of the NS2 protein of HPgV-2; 2) the amino acid sequence (SEQ ID NO:309) and describes the nucleic acid sequence (nucleotides 3631-5514 of SEQ ID NO:299) of the NS3 protein of HPgV-2; 3) the amino acid sequence (SEQ ID NO:310) and describes the nucleic acid sequence (nucleotides 5515-5637 of SEQ ID NO:299) of the NS4A protein of HPgV-2; and 4) the amino acid sequence (SEQ ID NO:311) and describes the nucleic acid sequences (nucleotides 5638-6423 of SEQ ID NO:299) of the NS4B protein of HPgV-2. FIG. 14C shows: 1) the amino acid sequence (SEQ ID NO:312) and describes the nucleic acid sequence (nucleotides 6424-7797 of SEQ ID NO:299) of the NS5A protein of HPgV-2; 2) the amino acid sequence (SEQ ID NO:313) and describes the nucleic acid sequence (nucleotides 7798-9498 of SEQ ID NO:299) of the NS5B protein of HPgV-2; and 3) describes the nucleic acid sequence (nucleotides 9499-9867 of SEQ ID NO:299) of at least a portion of the 3' UTR of HPgV-2.

FIGS. 15A-C provide the genomic nucleic acid sequence of an HPgV-2 isolate called ABT0070P, which is labeled SEQ ID NO:300. It is understood that the HPgV-2 genome is a positive strand RNA sequence. SEQ ID NO:300 is shown with the uracils as thymine.

FIGS. 16A-C show the amino acid sequences of various proteins from an HPgV-2 isolate called ABT0070P, as well as the corresponding nucleic acid coding sequences. FIG. 16A: 1) describes the 5'UTR sequence (nucleotides 1-327 of SEQ ID NO:300); 2) shows the amino acid sequence (SEQ ID NO:314) and describes the nucleic acid sequence (nucleotides 328-564 of SEQ ID NO:300) of the S protein of HPgV-2; 3) shows the amino acid sequence (SEQ ID NO:315) and describes the nucleic acid sequence (nucleotides 565-1137 of SEQ ID NO:300) of the E1 protein of HPgV-2; 4) shows the amino acid sequence (SEQ ID NO:316) and describes the nucleic acid sequence (nucleotides 1138-2199 of SEQ ID NO:300) of the E2 protein of HPgV-2; and 5) shows the amino acid sequence (SEQ ID NO:317) and describes the nucleic acid sequence (nucleotides 2200-2910 of SEQ ID NO:300) of the X protein of HPgV-2. FIG. 16B shows: 1) the amino acid sequence (SEQ ID NO:318) and describes the nucleic acid sequences (nucleotides 2911-3630 of SEQ ID NO:300) of the NS2 protein of HPgV-2; 2) the amino acid sequence (SEQ ID NO:319) and describes the nucleic acid sequence (nucleotides 3631-5514 of SEQ ID NO:300) of the NS3 protein of HPgV-2; 3) the amino acid sequence (SEQ ID NO:320) and describes the nucleic acid sequence (nucleotides 5515-5637 of SEQ ID NO:300) of the NS4A protein of HPgV-2; and 4) the amino acid sequence (SEQ ID NO:321) and describes the nucleic acid sequences (nucleotides 5638-6423 of SEQ ID NO:300) of the NS4B protein of HPgV-2. FIG. 16C shows: 1) the amino acid sequence (SEQ ID NO:322) and describes the nucleic acid sequence (nucleotides 6424-7797 of SEQ ID NO:300) of the NS5A protein of HPgV-2; 2) the amino acid sequence (SEQ ID NO:323) and describes the nucleic acid sequence (nucleotides 7798-9498 of SEQ ID NO:300) of the NS5B protein of HPgV-2; and 3) describes the nucleic acid sequence (nucleotides 9499-9867 of SEQ ID NO:300) of at least a portion of the 3' UTR of HPgV-2.

FIG. 17A-C provides the genomic nucleic acid sequence of an HPgV-2 isolate called ABT0029A, which is labeled SEQ ID NO:301. It is understood that the HPgV-2 genome is a positive strand RNA sequence. SEQ ID NO:301 is shown with the uracils as thymine.

FIGS. 18A-C show the amino acid sequences of various proteins from an HPgV-2 isolate called ABT0029A, as well as the corresponding nucleic acid coding sequences. FIG. 18A: 1) describes the 5'UTR sequence (nucleotides 1-327 of SEQ ID NO:301); 2) shows the amino acid sequence (SEQ ID NO:324) and describes the nucleic acid sequence (nucleotides 328-564 of SEQ ID NO:301) of the S protein of HPgV-2; 3) shows the amino acid sequence (SEQ ID NO:325) and describes the nucleic acid sequence (nucleotides 565-1137 of SEQ ID NO:301) of the E1 protein of HPgV-2; 4) shows the amino acid sequence (SEQ ID NO:326) and describes the nucleic acid sequence (nucleotides 1138-2199 of SEQ ID NO:301) of the E2 protein of HPgV-2; and 5) shows the amino acid sequence (SEQ ID NO:327) and describes the nucleic acid sequence (nucleotides 2200-2910 of SEQ ID NO:301) of the X protein of HPgV-2. FIG. 18B shows: 1) the amino acid sequence (SEQ ID NO:328) and describes the nucleic acid sequences (nucleotides 2911-3630 of SEQ ID NO:301) of the NS2 protein of HPgV-2; 2) the amino acid sequence (SEQ ID NO:329) and describes the nucleic acid sequence (nucleotides 3631-5514 of SEQ ID NO:301) of the NS3 protein of HPgV-2; 3) the amino acid sequence (SEQ ID NO:330) and describes the nucleic acid sequence (nucleotides 5515-5637 of SEQ ID NO:301) of the NS4A protein of HPgV-2; and 4) the amino acid sequence (SEQ ID NO:331) and describes the nucleic acid sequences (nucleotides 5638-6423 of SEQ ID NO:301) of the NS4B protein of HPgV-2. FIG. 18C shows: 1) the amino acid sequence (SEQ ID NO:332) and describes the nucleic acid sequence (nucleotides 6424-7797 of SEQ ID NO:301) of the NS5A protein of HPgV-2; 2) the amino acid sequence (SEQ ID NO:333) and describes the nucleic acid sequence (nucleotides 7798-9498 of SEQ ID NO:301) of the NS5B protein of HPgV-2; and 3) describes the nucleic acid sequence (nucleotides 9499-9867 of SEQ ID NO:301) of at least a portion of the 3' UTR of HPgV-2.

FIGS. 19A-C provide the genomic nucleic acid sequence of an HPgV-2 isolate called ABT0239AN.US, which is labeled SEQ ID NO:302. It is understood that the HPgV-2 genome is a positive strand RNA sequence. SEQ ID NO:302 is shown with the uracils as thymine.

FIGS. 20A-C show the amino acid sequences of various proteins from an HPgV-2 isolate called ABT0239AN.US, as well as the corresponding nucleic acid coding sequences. FIG. 20A: 1) describes the 5'UTR sequence (nucleotides 1-327 of SEQ ID NO:302); 2) shows the amino acid sequence (SEQ ID NO:334) and describes the nucleic acid sequence (nucleotides 328-564 of SEQ ID NO:302) of the S protein of HPgV-2; 3) shows the amino acid sequence (SEQ ID NO:335) and describes the nucleic acid sequence (nucleotides 565-1137 of SEQ ID NO:302) of the E1 protein of HPgV-2; 4) shows the amino acid sequence (SEQ ID NO:336) and describes the nucleic acid sequence (nucleotides 1138-2199 of SEQ ID NO:302) of the E2 protein of HPgV-2; and 5) shows the amino acid sequence (SEQ ID NO:337) and describes the nucleic acid sequence (nucleotides 2200-2910 of SEQ ID NO:302) of the X protein of HPgV-2. FIG. 20B shows: 1) the amino acid sequence (SEQ ID NO:338) and describes the nucleic acid sequences (nucleotides 2911-3630 of SEQ ID NO:302) of the NS2 protein of HPgV-2; 2) the amino acid sequence (SEQ ID NO:339) and describes the nucleic acid sequence (nucleotides 3631-5514 of SEQ ID NO:302) of the NS3 protein of HPgV-2; 3) the amino acid sequence (SEQ ID NO:340) and describes the nucleic acid sequence (nucleotides 5515-5637 of SEQ ID NO:302) of the NS4A protein of HPgV-2; and 4) the amino acid sequence (SEQ ID NO:341) and describes the nucleic acid sequences (nucleotides 5638-6423 of SEQ ID NO:302) of the NS4B protein of HPgV-2. FIG. 20C shows: 1) the amino acid sequence (SEQ ID NO:342) and describes the nucleic acid sequence (nucleotides 6424-7797 of SEQ ID NO:302) of the NS5A protein of HPgV-2; 2) the amino acid sequence (SEQ ID NO:343) and describes the nucleic acid sequence (nucleotides 7798-9498 of SEQ ID NO:302) of the NS5B protein of HPgV-2; and 3) describes the nucleic acid sequence (nucleotides 9499-9867 of SEQ ID NO:302) of at least a portion of the 3' UTR of HPgV-2.

FIG. 21A-C provide the genomic nucleic acid sequence of an HPgV-2 isolate called UC0125.US, which is labeled SEQ ID NO:303, and which is an extended version of UC0125 (SEQ ID NO:1) provided in FIG. 1 (e.g., 5' UTR was extended). It is understood that the HPgV-2 genome is a positive strand RNA sequence. SEQ ID NO:303 is shown with the uracils as thymine.

FIGS. 22A-C show the amino acid sequences of various proteins from an HPgV-2 isolate called UC0125.US, as well as the corresponding nucleic acid coding sequences. FIG. 22A: 1) describes the 5'UTR sequence (nucleotides 1-327 of SEQ ID NO:303); 2) shows the amino acid sequence (SEQ ID NO:344) and describes the nucleic acid sequence (nucleotides 328-564 of SEQ ID NO:303) of the S protein of HPgV-2; 3) shows the amino acid sequence (SEQ ID NO:345) and describes the nucleic acid sequence (nucleotides 565-1137 of SEQ ID NO:303) of the E1 protein of HPgV-2; 4) shows the amino acid sequence (SEQ ID NO:346) and describes the nucleic acid sequence (nucleotides 1138-2199 of SEQ ID NO:303) of the E2 protein of HPgV-2; and 5) shows the amino acid sequence (SEQ ID NO:347) and describes the nucleic acid sequence (nucleotides 2200-2910 of SEQ ID NO:303) of the X protein of HPgV-2. FIG. 22B shows: 1) the amino acid sequence (SEQ ID NO:348) and describes the nucleic acid sequences (nucleotides 2911-3630 of SEQ ID NO:303) of the NS2 protein of HPgV-2; 2) the amino acid sequence (SEQ ID NO:349) and describes the nucleic acid sequence (nucleotides 3631-5514 of SEQ ID NO:303) of the NS3 protein of HPgV-2; 3) the amino acid sequence (SEQ ID NO:350) and describes the nucleic acid sequence (nucleotides 5515-5637 of SEQ ID NO:303) of the NS4A protein of HPgV-2; and 4) the amino acid sequence (SEQ ID NO:351) and describes the nucleic acid sequences (nucleotides 5638-6423 of SEQ ID NO:303) of the NS4B protein of HPgV-2. FIG. 22C shows: 1) the amino acid sequence (SEQ ID NO:352) and describes the nucleic acid sequence (nucleotides 6424-7797 of SEQ ID NO:303) of the NS5A protein of HPgV-2; 2) the amino acid sequence (SEQ ID NO:353) and describes the nucleic acid sequence (nucleotides 7798-9498 of SEQ ID NO:303) of the NS5B protein of HPgV-2; and 3) describes the nucleic acid sequence (nucleotides 9499-9867 of SEQ ID NO:303) of at least a portion of the 3' UTR of HPgV-2.

FIGS. 29A-C provide the genomic nucleic acid sequence of an HPgV-2 isolate called ABT0030P.US, which is labeled SEQ ID NO:419. It is understood that the HPgV-2 genome is a positive strand RNA sequence. SEQ ID NO:419 is shown with the uracils as thymine.

FIGS. 30A-C show the amino acid sequences of various proteins from an HPgV-2 isolate called ABT0030P.US, as well as the corresponding nucleic acid coding sequences. FIG. 30A: 1) describes the 5'UTR sequence (nucleotides 1-327 of SEQ ID NO:419); 2) shows the amino acid sequence (SEQ ID NO:420) and describes the nucleic acid sequence (nucleotides 328-564 of SEQ ID NO:419) of the S protein of HPgV-2; 3) shows the amino acid sequence (SEQ ID NO:421) and describes the nucleic acid sequence (nucleotides 565-1137 of SEQ ID NO:419) of the E1 protein of HPgV-2; 4) shows the amino acid sequence (SEQ ID NO:422) and describes the nucleic acid sequence (nucleotides 1138-2199 of SEQ ID NO:419) of the E2 protein of HPgV-2; and 5) shows the amino acid sequence (SEQ ID NO:423) and describes the nucleic acid sequence (nucleotides 2200-2910 of SEQ ID NO:419) of the X protein of HPgV-2. FIG. 30B shows: 1) the amino acid sequence (SEQ ID NO:424) and describes the nucleic acid sequences (nucleotides 2911-3630 of SEQ ID NO:419) of the NS2 protein of HPgV-2; 2) the amino acid sequence (SEQ ID NO:425) and describes the nucleic acid sequence (nucleotides 3631-5514 of SEQ ID NO:419) of the NS3 protein of HPgV-2; 3) the amino acid sequence (SEQ ID NO:426) and describes the nucleic acid sequence (nucleotides 5515-5637 of SEQ ID NO:419) of the NS4A protein of HPgV-2; and 4) the amino acid sequence (SEQ ID NO:427) and describes the nucleic acid sequences (nucleotides 5638-6423 of SEQ ID NO:419) of the NS4B protein of HPgV-2. FIG. 30C shows: 1) the amino acid sequence (SEQ ID NO:428) and describes the nucleic acid sequence (nucleotides 6424-7794 of SEQ ID NO:419) of the NS5A protein of HPgV-2; 2) the amino acid sequence (SEQ ID NO:429) and describes the nucleic acid sequence (nucleotides 7795-9495 of SEQ ID NO:419) of the NS5B protein of HPgV-2; and 3) describes the nucleic acid sequence (nucleotides 9496-9864 of SEQ ID NO:419) of at least a portion of the 3' UTR of HPgV-2.

FIGS. 31A-C provide the genomic nucleic acid sequence of an HPgV-2 isolate called ABT0030P.US, which is labeled SEQ ID NO:430. It is understood that the HPgV-2 genome is a positive strand RNA sequence. SEQ ID NO:430 is shown with the uracils as thymine.

FIGS. 32A-C show the amino acid sequences of various proteins from an HPgV-2 isolate called ABT0041P.US, as well as the corresponding nucleic acid coding sequences. FIG. 32A: 1) describes the 5'UTR sequence (nucleotides 1-327 of SEQ ID NO:430); 2) shows the amino acid sequence (SEQ ID NO:431) and describes the nucleic acid sequence (nucleotides 328-564 of SEQ ID NO:430) of the S protein of HPgV-2; 3) shows the amino acid sequence (SEQ ID NO:432) and describes the nucleic acid sequence (nucleotides 565-1137 of SEQ ID NO:430) of the E1 protein of HPgV-2; 4) shows the amino acid sequence (SEQ ID NO:433) and describes the nucleic acid sequence (nucleotides 1138-2199 of SEQ ID NO:430) of the E2 protein of HPgV-2; and 5) shows the amino acid sequence (SEQ ID NO:434) and describes the nucleic acid sequence (nucleotides 2200-2910 of SEQ ID NO:430) of the X protein of HPgV-2. FIG. 32B shows: 1) the amino acid sequence (SEQ ID NO:435) and describes the nucleic acid sequences (nucleotides 2911-3630 of SEQ ID NO:430) of the NS2 protein of HPgV-2; 2) the amino acid sequence (SEQ ID NO:436) and describes the nucleic acid sequence (nucleotides 3631-5514 of SEQ ID NO:430) of the NS3 protein of HPgV-2; 3) the amino acid sequence (SEQ ID NO:437) and describes the nucleic acid sequence (nucleotides 5515-5637 of SEQ ID NO:430) of the NS4A protein of HPgV-2; and 4) the amino acid sequence (SEQ ID NO:438) and describes the nucleic acid sequences (nucleotides 5638-6423 of SEQ ID NO:430) of the NS4B protein of HPgV-2. FIG. 32C shows: 1) the amino acid sequence (SEQ ID NO:439) and describes the nucleic acid sequence (nucleotides 6424-7797 of SEQ ID NO:430) of the NS5A protein of HPgV-2; 2) the amino acid sequence (SEQ ID NO:440) and describes the nucleic acid sequence (nucleotides 7798-9498 of SEQ ID NO:430) of the NS5B protein of HPgV-2; and 3) describes the nucleic acid sequence (nucleotides 9499-9867 of SEQ ID NO:430) of at least a portion of the 3' UTR of HPgV-2.

DEFINITIONS

Figure 5A:
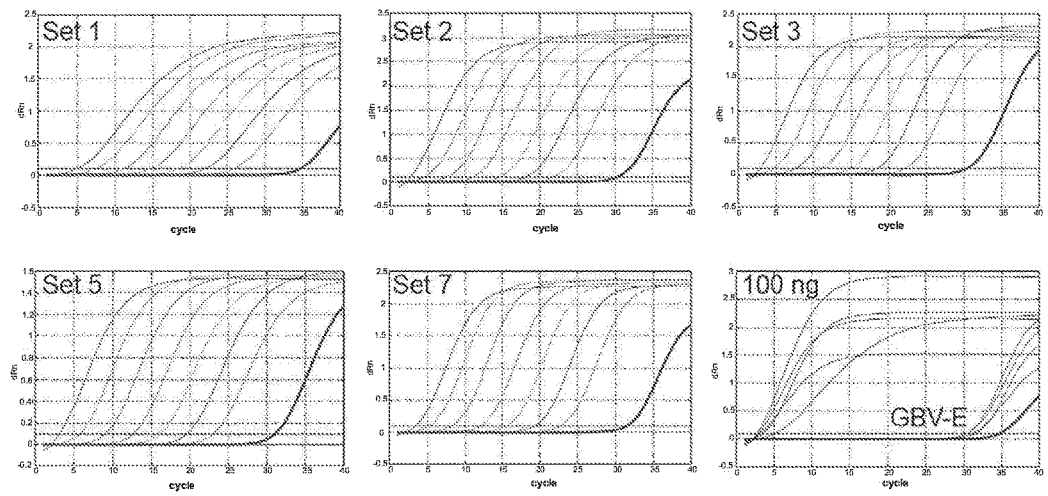
FIGS. 5A-B show the results of the qPCR TaqMan based detection assays in Example 3 below. In particular.

The terms "sample" and "specimen" are used in their broadest sense and encompass samples or specimens obtained from any source, including a human patient. In some embodiments of this invention, biological samples include tissue or cells, cerebrospinal fluid (CSF), serous fluid, urine, saliva, blood, and blood products such as plasma, serum and the like. However, these examples are not to be construed as limiting the types of samples that find use with the methods and compositions described herein. In some embodiments, the sample is a blood, serum, or plasma sample from a patient known to be infected with HCV and/or HIV.

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the terms "administration" and "administering" refer to the act of giving therapeutic treatment (e.g., a immunogenic composition) to a subject (e.g., a subject or in vivo, in vitro, or ex vivo cells, tissues, and organs). Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, 2-aminopurine, 5-amino-allyluracil, 5-hydroxymethylcytosine, 5-iodouracil, 5-nitroindole, 5-propynylcytosine, 5-propynyluracil, hypoxanthine, N3-methyluracil, N6,N6-dimethyladenine, purine, C-5-propynyl cytosine, C-5-propynyl uracil, and difluorotouyl.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene.

As used herein, the terms "gene expression" and "expression" refer to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refer to regulation that increases and/or enhances the production of gene expression products (e.g., RNA or protein), while "down-regulation" or "repression" refer to regulation that decrease production. Molecules (e.g., transcription factors) that are involved in up-regulation or down-regulation are often called "activators" and "repressors," respectively.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific viral RNA sequences encoding a specific protein, are generally found in the cell as a mixture with numerous other host mRNAs that encode a multitude of proteins. The isolated nucleic acid, oligonucleotide, or polynucleotide may be present in single-stranded or double-stranded form.

The term "synthetic" when used in reference to nucleic acid molecules (e.g., primers or probes of HPgV-2) refers to non-natural molecules made directly (e.g., in a laboratory) or indirectly (e.g., from expression in a cell of a construct made in a laboratory) by mankind.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (e.g., Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids.

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of Tm.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 degrees Celsius in a solution consisting of 5×SSPE (43.8 g/l NaCl, 6.9 g/l NaH2PO4.H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42 degrees Celsius when a probe of about 500 nucleotides in length is employed.

"Medium stringency conditions" when used in reference to nucleic acid hybridization comprise conditions equivalent to binding or hybridization at 42 degrees Celsiuis in a solution consisting of 5×SSPE (43.8 g/l NaCl, 6.9 g/l NaH2PO4.H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42 degrees C. when a probe of about 500 nucleotides in length is employed.

"Low stringency conditions" comprise conditions equivalent to binding or hybridization at 42 degrees Celsius in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42 degrees Celsius when a probe of about 500 nucleotides in length is employed.

The following terms are used to describe the sequence relationships between two or more polynucleotides: "reference sequence," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA sequence given in a sequence listing (e.g., SEQ ID NO: 1 or 75) or may comprise a gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.A.) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. In certain embodiments, provided herein are peptides that have substantial identity to at least a portion of the amino acid sequences shown in SEQ ID NOs:2-11 or 304-353.

The term "fragment" or "portion" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular nucleic acid sequences. It is contemplated that, in certain embodiments, a probe used in the present methods and compositions will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the methods and compositions be limited to any particular detection system or label.

As used herein, the term "recombinant nucleic acid molecule" as used herein refers to a nucleic molecule that is comprised of segments of nucleic acid joined together by means of molecular biological techniques.

As used herein, "peptide" refers to a linear polymer of amino acids joined by peptide bonds in a specific sequence. As used herein, "peptide" also encompasses polypeptide, oligopeptide and protein. A peptide may be, for example, a short amino acid stretch from the HPgV-2 virus (e.g., 25 amino acids), but may also be a long sequence, such as the amino acid sequence of the entire NS3 protein (e.g., SEQ ID NO:7).

The term "recombinant protein" or "recombinant polypeptide" as used herein refers to a protein molecule that is expressed from a recombinant nucleic acid molecule.

The term "antigenic determinant" or "epitope" as used herein refers to that portion of an antigen that makes contact with a particular antibody. When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein, a "solid support" is any surface or material to which a biological molecules, such as a HPgV-2 nucleic acid, protein, or antibody may be attached and employed in a biological assay. Examples of solid supports which may be utilized in the assays described herein are well-known in the art and included, but are not limited to, a magnetic particles, a beads, microparticle, a test tube, a microtiter plate, a cuvette, a membrane, a scaffolding molecule, a film, a filter paper, a disc and a chip.

DETAILED DESCRIPTION

Provided herein are compositions, methods, and kits for detecting human *Pegivirus* 2 (HPgV-2). In certain embodiments, provided herein are HPgV-2 specific nucleic acid probes and primers, and methods for detecting HPgV-2 nucleic acid. In other embodiments, provided herein are HPgV-2 immunogenic compositions, methods of treating a subject with immunogenic peptides to develop resistance to infection, and methods of detecting HPgV-2 subject antibodies in a sample.

I. Human *Pegivirus* 2

Complete genomic nucleic acid sequences of human *Pegivirus* 2 (HPgV-2), also called GBV-E, are shown in SEQ ID NOs:1 and 75 (FIGS. 1 and 8) and SEQ ID NOs:299-303. HPgV-2 is a positive single stranded RNA virus and encodes the following proteins: S protein (e.g., SEQ ID NO:2, 76, 304, 314, 324, 334, and 344), E1 protein (e.g., SEQ ID NO:3, 77, 305, 315, 325, 335, and 345), E2 protein (e.g., SEQ ID NO:4, 78, 306, 316, 326, 336, and 346), X protein (e.g., SEQ ID NO:5, 79, 307, 317, 327, 337, and 347), NS2 protein (e.g., SEQ ID NO:6, 80, 308, 318, 328, 338, and 348), NS3 protein (e.g., SEQ ID NO:7, 81, 309, 319, 329, 339, and 349), NS4A protein (e.g., SEQ ID NO:8, 82, 310, 320, 330, 340, and 350), NS4B protein (e.g., SEQ ID NO:9, 83, 311, 321, 331, 341, and 351), NS5A protein (e.g., SEQ ID NO:10, 84, 312, 322, 332, 342, and 352), and NS5B protein (e.g., SEQ ID NO:11, 85, 313, 323, 333, 343, and 353). Certain determined portions of the 5' UTR include nucleotides 1-103 of SEQ ID NO: 1, nucleotides 1-110 of SEQ ID NO:75, nucleotides 1-327 of SEQ ID NOs:299-301, nucleotides 12-327 of SEQ ID NO:302, and nucleotides 24-327 of SEQ ID NO:303; and exemplary certain determined portions of the 3' UTR include nucleotides 9410-9778 of SEQ ID NO:1, nucleotides 9417-9431 of SEQ ID NO:75, and nucleotides 9499-9867 of SEQ ID NOS:299-303. Based on sequence relatedness, the organization of the HPgV-2 genome is most similar to both the Pegiviruses and the Hepaciviruses, both currently classified as members of the Flaviviridae family. It has recently been proposed that HCV and GBV-B are to be included within the *Hepacivirus* genus of the Flaviviridae family and that GBV-A and GBV-C (HPgV-1) are to be included within the *Pegivirus* genus of the Flaviviridae family (Stapleton et al., J Gen Virol 2011: 92: 233-246).

All members of the Flaviviridae family of viruses have a positive sense, single stranded RNA genome of about 10 kb, that that contains a single long open reading frame (ORF) encoding a polyprotein of about 3,000 amino acids (Lindenbach et al., Flaviviridae: The Viruses and Their Replication. Chapter 33. In Fields Virology Fifth Edition, (Knipe et al., Eds.) Wolters Kluwer/Lippincott Williams and Williams, Philadelphia Pa. Pages 1101-1152). For Flaviviridae, the polyproteins are cleaved into smaller functional non-structural and structural components by a combination of host and viral proteases. The viral structural proteins are located at the amino terminal portion of the genome and include two envelope glycoproteins, E1 and E2 for both HCV and the GB viruses. While HCV and GBV-B contain a capsid protein, GBV-A and GBV-C (HPgV-1) lack a typical capsid-like protein. For all Flaviviruses, the non-structural proteins are located downstream of the structural proteins, and include an NS3 protein that contains an N-terminus serine protease and a C-terminal RNA helicase protein and an NS5 protein that is a multifunctional protein with methyltransferase and RNA-dependent RNA replication activities. The ORF is flanked at both the 5' end and the 3' by untranslated regions that are highly conserved and that are involved both in translation and in replication of the genome.

In certain embodiments, patient samples that are known to be HCV positive are tested for the presence of HPgV-2 (e.g., for patient antibodies or by PCR). In particular embodiments, HCV infected blood donors who are anti-HCV negative but HCV RNA positive are tested. Such samples are termed as "preseroconversion window period" samples. In other embodiments, samples are tested from HCV infected patients who are anti-HCV positive and HCV RNA positive. In certain embodiments, samples that are HIV positive are tested. In particular embodiments, high risk groups are tested for the presence of HPgV-2 infection. High risk groups include multiply transfused individuals, plasmapheresis donors (some of whom may be positive for HBV, HIV or HCV), intravenous drug users, and individuals with sexually transmitted diseases.

FIG. 10 shows an alignment of the genomes or partial genomes of HPgV-2 variants UC0125.US, ABT0070P.US, ABT0096P.US, and ABT0128A.US, along with a majority consensus sequence. The amino acid similarities between UC0125.US and ABT0070P.US are shown in Table 16 below:

TABLE 16

| protein | amino acids | mismatches | % identity |
|---|---|---|---|
| polyprotein | 3102 | 157 | 94.94 |
| S | 124 | 4 | 96.77 |
| E1 | 191 | 6 | 96.86 |
| E2 | 354 | 24 | 93.22 |
| X | 237 | 13 | 94.51 |
| NS2 | 240 | 8 | 96.67 |
| NS3 | 628 | 22 | 96.50 |
| NS4A | 41 | 3 | 92.68 |
| NS4B | 262 | 10 | 96.18 |
| NS5A | 458 | 43 | 90.61 |
| NS5B | 567 | 24 | 95.77 |
|  | 3102 | 157 |  |

II. Amplification

In some embodiments, provided herein are compositions and methods for the amplification of HPgV-2 nucleic acids (e.g. DNA, RNA, etc.). In some embodiments, amplification is performed on a bulk sample of nucleic acids. In some embodiments, amplification is performed on a single nucleic acid target molecule. In some embodiments, provided herein are compositions (e.g. primers, buffers, salts, nucleic acid targets, etc.) and methods for the amplification of nucleic acid (e.g. digital droplet amplification, PCR amplification, combinations thereof, etc.). In some embodiments, an amplification reaction is any reaction in which nucleic acid replication occurs repeatedly over time to form multiple copies of at least one segment of a template or target nucleic acid molecule (e.g., HPgV-2 nucleic acid). In some embodiments, amplification generates an exponential or linear increase in the number of copies of the template nucleic acid. Amplifications may produce in excess of a 1,000-fold increase in template copy-number and/or target-detection signal. Exemplary amplification reactions include, but are not limited to the polymerase chain reaction (PCR) or ligase chain reaction (LCR), each of which is driven by thermal cycling.

Amplification may be performed with any suitable reagents (e.g. template nucleic acid (e.g. DNA or RNA), primers, probes, buffers, replication catalyzing enzyme (e.g. DNA polymerase, RNA polymerase), nucleotides, salts (e.g. $MgCl_2$), etc. In some embodiments, an amplification mixture includes any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), etc.

In some embodiments, the systems, devices, and methods utilize nucleic acid amplification that relies on alternating cycles of heating and cooling (i.e., thermal cycling) to achieve successive rounds of replication (e.g., PCR). In some embodiments, PCR is used to amplify target nucleic acids (e.g. HPgV-2 nucleic acid). PCR may be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR may be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. Typical PCR methods produce an exponential increase in the amount of a product amplicon over successive cycles, although linear PCR methods also find use.

Any suitable PCR methodology, combination of PCR methodologies, or combination of amplification techniques may be utilized, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, etc.

In some embodiments, the systems, devices, and methods employ RT-PCR (reverse transcription-PCR). In some embodiments, the systems, devices, and methods employ real-time PCR. In some embodiments, the systems, devices, and methods employ endpoint PCR.

In some embodiments, the systems, devices, and methods utilize isothermal nucleic acid amplification methods. Any suitable isothermal amplification methodology or combination of amplification techniques may be utilized, such as transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification.

III. Nucleic Acid Detection

In some embodiments, provided herein are systems, devices, methods, and compositions to identify the presence of HPgV-2 nucleic acids (e.g. amplicons, labeled nucleic acids). In some embodiments, detection involves measurement or detection of a characteristic of a non-amplified nucleic acid, amplified nucleic acid, a component comprising amplified nucleic acid, or a byproduct of the amplification process, such as a physical, chemical, luminescence, or electrical aspect, which correlates with amplification (e.g. fluorescence, pH change, heat change, etc.).

In some embodiments, fluorescence detection methods are provided for detection of amplified HPgV-2 nucleic acid, and/or identification of amplified nucleic acids. In addition to the reagents already discussed, and those known to those of skill in the art of nucleic acid amplification and detection, various detection reagents, such as fluorescent and non-fluorescent dyes and probes are provided. For example, the protocols may employ reagents suitable for use in a TaqMan reaction, such as a TaqMan probe; reagents suitable for use in a SYBR Green fluorescence detection; reagents suitable for use in a molecular beacon reaction, such as molecular beacon probes; reagents suitable for use in a scorpion reaction, such as a scorpion probe; reagents suitable for use in a fluorescent DNA-binding dye-type reaction, such as a fluorescent probe; and/or reagents for use in a LightUp protocol, such as a LightUp probe. In some embodiments, provided herein are methods and compositions for detecting and/or quantifying a detectable signal (e.g. fluorescence) from amplified target nucleic acid. Thus, for example, methods may employ labeling (e.g. during amplification, post-amplification) amplified nucleic acids with a detectable label, exposing partitions to a light source at a wavelength selected to cause the detectable label to fluoresce, and detecting and/or measuring the resulting fluorescence. Fluorescence emitted from label can be tracked during amplification reaction to permit monitoring of the reaction (e.g., using a SYBR Green-type compound), or fluorescence can be measure post-amplification.

In some embodiments, detection of amplified nucleic acids employs one or more of fluorescent labeling, fluorescent intercalation dyes, FRET-based detection methods (U.S. Pat. No. 5,945,283; PCT Publication WO 97/22719; both of which are incorporated by reference in their entireties), quantitative PCR, real-time fluorogenic methods (U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety), molecular beacons (Piatek, A. S., et al., Nat. Biotechnol. 16:359-63 (1998); Tyagi, S. and Kramer, F. R., Nature Biotechnology 14:303-308 (1996); and Tyagi, S. et al., Nat. Biotechnol. 16:49-53 (1998); herein incorporated by reference in their entireties), Invader assays (Third Wave Technologies, (Madison, Wis.)) (Neri, B. P., et al., Advances in Nucleic Acid and Protein Analysis 3826:117-125, 2000; herein incorporated by reference in its entirety), nucleic acid sequence-based amplification (NASBA; (See, e.g., Compton, J. Nucleic Acid Sequence-based Amplification, Nature 350: 91-91, 1991; herein incorporated by reference in its entirety), Scorpion probes (Thelwell, et al. Nucleic Acids Research, 28:3752-3761, 2000; herein incorporated by reference in its entirety), partially double-stranded linear probes (Luk, K.-C., et al, J. Virological Methods 144:1-11, 2007; herein incorporated by reference in its entirety), capacitive DNA detection (See, e.g., Sohn, et al. (2000) Proc. Natl. Acad. Sci. U.S.A. 97:10687-10690; herein incorporated by reference in its entirety), etc.

IV. Nucleic Acid Analysis

Nucleic acid molecules (e.g., amplified HPgV-2 nucleic acid) may be analyzed by any number of techniques to determine the presence of, amount of, or identity of the molecule. Non-limiting examples include sequencing, mass determination, and base composition determination. The analysis may identify the sequence of all or a part of the amplified nucleic acid or one or more of its properties or characteristics to reveal the desired information. For example, in some embodiments, the presence of a polymorphism or of a particular HPgV-2 strain or isolate is determined. In some embodiments, the methylation status of a nucleic acid is determined.

Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack experimentally RNA is usually, although not necessarily, reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, and 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308 and 6,833,246; herein incorporated by reference in their entireties), Illumina Single base sequencing technology, the Lynx massively parallel signature sequencing technology (Brenner et al. (2000). Nat. Biotechnol. 18:630-634; U.S. Pat. Nos. 5,695,934 and 5,714,330; herein incorporated by reference in their entireties) and the Adessi PCR colony technology (Adessi et al. (2000). Nucleic Acid Res. 28, E87; WO 00018957; herein incorporated by reference in its entirety).

In some embodiments, chain terminator sequencing is utilized. Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., *Clinical Chem.*, 55: 641-658, 2009; MacLean et al., *Nature Rev. Microbiol.*, 7: 287-296; each herein incorporated by reference in their entirety). These techniques may be used to sequence portions of HPgV-2 nucleic acid. Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891 and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotiter plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1\times10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246, 7,115,400, and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 600 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148, and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined.

Another exemplary nucleic acid sequencing approach that may be adapted for use with the systems, devices, and methods was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Patent Publication No. 20090035777, entitled "HIGH THROUGHPUT NUCLEIC ACID SEQUENCING BY EXPANSION," that was filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-658, 2009; U.S. Pat. No. 7,329,492; U.S. patent application Ser. Nos. 11/671,956, and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al., U.S. Pat. No. 7,315,019, entitled "Arrays of optical confinements and uses thereof", issued Jan. 1, 2008 to Turner et al., U.S. Pat. No. 7,313,308, entitled "Optical analysis of molecules", issued Dec. 25, 2007 to Turner et al., U.S. Pat. No. 7,302,146, entitled "Apparatus and method for analysis of molecules", issued Nov. 27, 2007 to Turner et al., and U.S. Pat. No. 7,170,050, entitled "Apparatus and methods for optical analysis of molecules", issued Jan. 30, 2007 to Turner et al., U.S. Patent Publications Nos. 20080212960, entitled "Methods and systems for simultaneous real-time monitoring of optical signals from multiple sources", filed Oct. 26, 2007 by Lundquist et al., 20080206764, entitled "Flowcell system for single molecule detection", filed Oct. 26, 2007 by Williams et al., 20080199932, entitled "Active surface coupled polymerases", filed Oct. 26, 2007 by Hanzel et al., 20080199874, entitled "CONTROLLABLE STRAND SCISSION OF MINI CIRCLE DNA", filed Feb. 11, 2008 by Otto et al., 20080176769, entitled "Articles having localized molecules disposed thereon and methods of producing same", filed Oct. 26, 2007 by Rank et al., 20080176316, entitled "Mitigation of photodamage in analytical reactions", filed Oct. 31, 2007 by Eid et al., 20080176241, entitled "Mitigation of photodamage in analytical reactions", filed Oct. 31, 2007 by Eid et al., 20080165346, entitled "Methods and systems for simultaneous real-time monitoring of optical signals from multiple sources", filed Oct. 26, 2007 by Lundquist et al., 20080160531, entitled "Uniform surfaces for hybrid material substrates and methods for making and using same", filed Oct. 31, 2007 by Korlach, 20080157005, entitled "Methods and systems for simultaneous real-time monitoring of optical signals from multiple sources", filed Oct. 26, 2007 by Lundquist et al., 20080153100, entitled "Articles having localized molecules disposed thereon and methods of producing same", filed Oct. 31, 2007 by Rank et al., 20080153095, entitled "CHARGE SWITCH NUCLEOTIDES", filed Oct. 26, 2007 by Williams et al., 20080152281, entitled "Substrates, systems and methods for analyzing materials", filed Oct. 31, 2007 by Lundquist et al., 20080152280, entitled "Substrates, systems and methods for analyzing materials", filed Oct. 31, 2007 by Lundquist et al., 20080145278, entitled "Uniform surfaces for hybrid material substrates and methods for making and using same", filed Oct. 31, 2007 by Korlach, 20080128627, entitled "SUBSTRATES, SYSTEMS AND METHODS FOR ANALYZING MATERIALS", filed Aug. 31, 2007 by Lundquist et al., 20080108082, entitled "Polymerase enzymes and reagents for enhanced nucleic acid sequencing", filed Oct. 22, 2007 by Rank et al., 20080095488, entitled "SUBSTRATES FOR PERFORMING ANALYTICAL REACTIONS", filed Jun. 11, 2007 by Foquet et al., 20080080059, entitled "MODULAR OPTICAL COMPONENTS AND SYSTEMS INCORPORATING SAME", filed Sep. 27, 2007 by Dixon et al., 20080050747, entitled "Articles having localized molecules disposed thereon and methods of producing and using same", filed Aug. 14, 2007 by Korlach et al., 20080032301, entitled "Articles having localized molecules disposed thereon and methods of producing same", filed Mar. 29, 2007 by Rank et al., 20080030628, entitled "Methods and systems for simultaneous real-time monitoring of optical signals from multiple sources", filed Feb. 9, 2007 by Lundquist et al., 20080009007, entitled "CONTROLLED INITIATION OF PRIMER EXTENSION", filed Jun. 15, 2007 by Lyle et al., 20070238679, entitled "Articles having localized molecules disposed thereon and methods of producing same", filed Mar. 30, 2006 by Rank et al., 20070231804, entitled "Methods, systems and compositions for monitoring enzyme activity and applications thereof", filed Mar. 31, 2006 by Korlach et al., 20070206187, entitled "Methods and systems for simultaneous real-time monitoring of optical signals from multiple sources", filed Feb. 9, 2007 by Lundquist et al., 20070196846, entitled "Polymerases for nucleotide analogue incorporation", filed Dec. 21, 2006 by Hanzel et al., 20070188750, entitled "Methods and systems for simultaneous real-time monitoring of optical signals from multiple sources", filed Jul. 7, 2006 by Lundquist et al., 20070161017, entitled "MITIGATION OF PHOTODAMAGE IN ANALYTICAL REACTIONS", filed Dec. 1, 2006 by Eid et al., 20070141598, entitled "Nucleotide Compositions and Uses Thereof", filed Nov. 3, 2006 by Turner et al., 20070134128, entitled "Uniform surfaces for hybrid material substrate and methods for making and using same", filed Nov. 27, 2006 by Korlach, 20070128133, entitled "Mitigation of photodamage in analytical reactions", filed Dec. 2, 2005 by Eid et al., 20070077564, entitled "Reactive surfaces, substrates and methods of producing same", filed Sep. 30, 2005 by Roitman et al., 20070072196, entitled "Fluorescent nucleotide analogs and uses therefore", filed Sep. 29, 2005 by Xu et al., and 20070036511, entitled "Methods and systems for monitoring multiple optical signals from a single source", filed Aug. 11, 2005 by Lundquist et al., and Korlach et al. (2008) "Selective aluminum passivation for targeted immobilization of single DNA polymerase molecules in zero-mode waveguide nanostructures" Proc. Nat'l. Acad. Sci. U.S.A. 105(4): 11761181—all of which are herein incorporated by reference in their entireties.

In some embodiments, nucleic acids are analyzed by determination of their mass and/or base composition. For example, in some embodiments, nucleic acids are detected and characterized by the identification of a unique base composition signature (BCS) using mass spectrometry (e.g., Abbott PLEX-ID system, Abbot Ibis Biosciences, Abbott Park, Ill.,) described in U.S. Pat. Nos. 7,108,974, 8,017,743, and 8,017,322; each of which is herein incorporated by reference in its entirety. In some embodiments, a MassARRAY system (Sequenom, San Diego, Calif.) is used to detect or analyze sequences (See e.g., U.S. Pat. Nos. 6,043,031; 5,777,324; and 5,605,798; each of which is herein incorporated by reference).

In certain embodiments, the Ion Torrent sequencing technology is employed to sequence HPgV-2 nucleic acid. The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a fragment of the NGS fragment library to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

In certain embodiments, HPgV-2 nucleic acid, including polymorphisms or bases that identify particular types, strains, or isolates are detected a hybridization assay. In a hybridization assay, the presence of absence of a given sequence, SNP, or mutation is determined based on the ability of the nucleic acid from the sample to hybridize to a complementary nucleic acid molecule (e.g., a oligonucleotide probe). A variety of hybridization assays using a variety of technologies for hybridization and detection are available and known in the art.

V. HPgV-2 Peptides

In other embodiments, provided herein are HPgV-2 polynucleotide sequences that encode HPgV-2 polypeptide sequences. HPgV-2 polypeptides (e.g., SEQ ID NOs:2-11, 76-85, and 304-353) are described in FIGS. 2, 9, 14, 16, 18, 20, and 22. Other embodiments provide fragments, fusion proteins or functional equivalents of these HPgV-2 proteins. In still other embodiments, nucleic acid sequences corresponding to various HPgV-2 homologs and mutants may be used to generate recombinant DNA molecules that direct the expression of HPgV-2 homologs and mutants in appropriate host cells. In some embodiments, the polypeptide may be a purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture).

In certain embodiments, due to the inherent degeneracy of the genetic code, DNA sequences other than the polynucleotide sequences of SEQ ID NO:1, 75, or 299-303 which encode substantially the same or a functionally equivalent amino acid sequence, may be used to clone and express HPgV-2 peptides. In general, such polynucleotide sequences hybridize to SEQ ID NO:1, SEQ ID NO:75, or SEQ ID NOS:299-303, under conditions of high to medium stringency as described above. As will be understood by those of skill in the art, it may be advantageous to produce HPgV-2 encoding nucleotide sequences possessing non-naturally occurring codons. Therefore, in some preferred embodiments, codons preferred by a particular prokaryotic or eukaryotic host (Murray et al., Nucl. Acids Res., 17 [1989]) are selected, for example, to increase the rate of HPgV-2 expression or to produce recombinant RNA transcripts having desirable properties, such as a longer half-life, than transcripts produced from naturally occurring sequence.

In certain embodiments, the peptides comprises or consist of the peptides in Table 15 below, or variants thereof with 1, 2, 3, or 4 amino acid changes. Such peptides, for example, may be used as capture peptides and/or immunogens to generate antibodies.

TABLE 15

| Isolate/Peptide | Protein | Amino Acid Sequence | SEQ ID NO: |
|---|---|---|---|
| Peptide 1 | S | GGSCRSPSRVQVARRVLQLSAFLALIGSGMSSIRSKTEGRIESGQ | 100 |
| Peptide 1 | S | GGSCRSPSRVQVARRVLQLSAFL | 101 |
| Peptide 1 | S | SAFLALIGSGMSSIRSKTEGRIESGQ | 102 |
| Peptide 1 | S | ARRVLQLSAFLALIGSGMSS | 103 |
| UC0125.US | S | GGSCRSPSRVQVARRVLQLCAFLALIGSGMCSIRSKTEGRIESGQ | 104 |

TABLE 15-continued

| Isolate/Peptide | Protein | Amino Acid Sequence | SEQ ID NO: |
|---|---|---|---|
| UC0125.US | S | GGSCRSPSRVQVARRVLQLCAFL | 105 |
| UC0125.US | S | CAFLALIGSGMCSIRSKTEGRIESGQ | 106 |
| UC0125.US | S | ARRVLQLCAFLALIGSGMCS | 107 |
| ABT0070P.US | S | GGSCRSPSRVQVAGRVLRLCAFLALIGSGMCSIRSKNEGRIESGQ | 108 |
| ABT0070P.US | S | GGSCRSPSRVQVAGRVLRLCAFL | 109 |
| ABT0070P.US | S | MCSIRSKNEGRIESGQ | 110 |
| ABT0070P.US | S | VAGRVLRLCAFLALIGSGMC | 111 |
| Peptide 2 | S | RDGSLHWSHARHHSVQPDRVAAGPPSVTSVERNMGSSTDQT | 112 |
| Peptide 2 | S | RDGSLHWSHARHHSVQPDRVAAG | 113 |
| UC0125.US | S | RDGSLHWCHARHHSVQPDRVAAGPPSVTSVERNMGSSTDQT | 114 |
| UC0125.US | S | RDGSLHWCHARHHSVQPDRVAAG | 115 |
| UC0125.US | S | VAAGPPSVTSVERNMGSSTDQT | 116 |
| UC0125.US | S | RHHSVQPDRVAAGPPSVTSVE | 117 |
| Peptide 3 | E2 | SMNSDSPFGTFTRNTESRFSIPRFSPVKINS | 118 |
| Peptide 3 | E2 | SMNCDCPFGTFTRNTESRFSIPRFCPVKINS | 119 |
| UC0125.U5 | E2 | SMNSDSPFGTFTRNTESRF | 120 |
| UC0125.US | E2 | SMNCDCPFGTFTRNTESRF | 121 |
| UC0125.US | E2 | SRFSIPRFSPVKINS | 122 |
| UC0125.US | E2 | FGTFTRNTESRFSIPR | 123 |
| ABT0070P.US | E2 | AMNCDCPFGTFTRNTESGFTIPRFCPVKLNS | 124 |
| ABT0070P.US | E2 | AMNCDCPFGTFTRNTESGF | 125 |
| ABT0070P.US | E2 | SGFTIPRFCPVKLNS | 126 |
| ABT0070P.US | E2 | FGTFTRNTESGFTIPR | 127 |
| ABT0096P.US | | AMNCDCPFGTFTRNTESGFSISIDSVLLKSI | 128 |
| UC0125.US | NS3 | QAPAVTPTYSEITYYAPTGSGKSTKYPVDLVKQGHKVLVL | 129 |
| UC0125.US | NS3 | QAPAVTPTYSEITYYAPTGSGKST | 130 |
| UC0125.US | NS3 | GKSTKYPVDLVKQGHKVLVL | 131 |
| UC0125.US | NS3 | ITYYAPTGSGKSTKYPVDLVKQG | 132 |
| UC0125.US | NS3 | VKSMAPYIKETYKIRPEIRAGTGPDGVTVITG | 133 |
| UC0125.US | NS3 | VKSMAPYIKETYKIRPEI | 134 |
| UC0125.US | NS3 | PEIRAGTGPDGVTVITG | 135 |
| UC0125.US | NS3 | IKETYKIRPEIRAGTGPDG | 136 |
| ABT0070P.US | NS3 | VKSMAPYIKEKYKIRPEIRAGTGPDGVTVITG | 137 |
| ABT0070P.US | NS3 | VKSMAPYIKEKYKIRPEI | 138 |
| ABT0070P.US | NS3 | IKEKYKIRPEIRAGTGPDG | 139 |
| UC0125.US | NS3 | LVDPETNLRGYAVVICDECHDTSSTTLLGIGAVRMYAEKA | 140 |
| UC0125.US | NS3 | LVDPETNLRGYAVVICDECHDTSS | 141 |
| UC0125.US | NS3 | TNLRGYAVVICDECHDTSSTTLLGI | 142 |

TABLE 15-continued

| Isolate/Peptide | Protein | Amino Acid Sequence | SEQ ID NO: |
|---|---|---|---|
| UC0125.US | NS3 | DTSSTTLLGIGAVRMYAEKA | 143 |
| UC0125.US | NS3 | PETNLRGYAVVISDESHDTSS | 144 |
| UC0125.US | NS3 | PETNLRGYAVVISD | 145 |
| UC0125.US | NS3 | VISDESHDTSS | 146 |
| ABT0070P.US | NS3 | PETNLRGYAVVICDECHDTSS | 147 |
| ABT0070P.US | NS3 | PETNLRGYAVVICD | 148 |
| ABT0096P.US | NS3 | RRGFAVVICVECHEHIT | 149 |
| UC0125.US | NS3 | PCTAALRMQRRGRTGRGRRGAYYTTSPGAAPCVS | 150 |
| UC0125.US | NS3 | PCTAALRMQRRGRTGRGRRG | 151 |
| UC0125.US | NS3 | GRRGAYYTTSPGAAPCVS | 152 |
| UC0125.US | NS3 | RRGRTGRGRRGAYYTTSPG | 153 |
| ABT0070P.US | NS3 | PCTAALRMQRRGRTGRGRRGAYYTTTPGAAPCV | 154 |
| ABT0070P.US | NS3 | GRRGAYYTTTPGAAPCV | 155 |
| ABT0070P.US | NS3 | RRGRTGRGRRGAYYTTTPG | 156 |
| UC0125.US | NS4B | LSERFGQQLSKLSLWRSVYHWAQAREGYTQCG | 157 |
| UC0125.US | NS4B | LSERFGQQLSKLSLWRSV | 158 |
| UC0125.US | NS4B | RSVYHWAQAREGYTQCG | 159 |
| UC0125.US | NS4B | LSKLSLWRSVYHWAQAREG | 160 |
| ABT0070P.US | NS4B | LTEKFGQQLSKLSLWRSVYHWAQAREGYTQCG | 161 |
| ABT0070P.US | NS4B | LTEKFGQQLSKLSLWRSV | 162 |
| UC0125.US | NS5A | NPTTTGTGTLRPDISDANKLGFRYGVADIVELERRGDKWH | 163 |
| UC0125.US | NS5A | FNPTTTGTGTLRPDISDANKLGFR | 164 |
| UC0125.US | NS5A | GFRYGVADIVELERRGDKWH | 165 |
| UC0125.US | NS5A | RPDISDANKLGFRYGVADI | 166 |
| ABT0070P.US | NS5A | NPTTTATGTLRPDISDATKLGFRYGVAEIVELERRGNKWH | 167 |
| ABT0070P.US | NS5A | NPTTTATGTLRPDISDATKLGFR | 168 |
| ABT0070P.US | NS5A | GFRYGVAEIVELERRGNKWH | 169 |
| ABT0070P.US | NS5A | RPDISDATKLGFRYGVAEI | 170 |
| UC0125.US | NS5A | QNLAARRRAEYDAWQVRQAVGDEYTRLADEDVD | 171 |
| UC0125.US | NS5A | QNLAARRRAEYDAWQVRQAV | 172 |
| UC0125.US | NS5A | RQAVGDEYTRLADEDVD | 173 |
| UC0125.US | NS5A | RAEYDAWQVRQAVGDEYTR | 174 |
| ABT0070P.US | NS5A | QNLEARRRAEFDAWQVREAIRDEYTRLADEDVD | 175 |
| ABT0070P.US | NS5A | QNLEARRRAEFDAWQVREAI | 176 |
| ABT0070P.US | NS5A | REAIRDEYTRLADEDVD | 177 |
| ABT0070P.US | NS5A | RAEFDAWQVREAIRDEYTR | 178 |
| ABT0096P.US | NS5A | FEAWQVREAIRDEYTRLADEDVD | 179 |
| UC0125.US | NS5A | RFVPPVPKPRTRVSGVLERVRMCMRTPPIKF | 180 |
| UC0125.US | NS5A | RFVPPVPKPRTRVSGV | 181 |

TABLE 15-continued

| Isolate/Peptide | Protein | Amino Acid Sequence | SEQ ID NO: |
|---|---|---|---|
| UC0125.US | NS5A | SGVLERVRMCMRTPPIKF | 182 |
| UC0125.US | NS5A | KPRTRVSGVLERVRM | 183 |
| ABT0096P.US | NS5A | RTRVSGVLERVRMCM<u>T</u>T | 184 |
| UC0125.US | NS5B | NTTRDHNNGITYTDLVSGRAKP | 185 |
| UC0125.US | NS5B | NTTRDHNNGITYTD | 186 |
| UC0125.US | NS5B | YTDLVSGRAKP | 187 |
| ABT0070P.US | NS5B | NTTRDHNNGITY<u>S</u>DLVSGRAKP | 188 |
| ABT0070P.US | NS5B | NTTRDHNNGITY<u>S</u>D | 189 |
| ABT0070P.US | NS5B | Y<u>S</u>DLVSGRAKP | 190 |
| UC0125.US | NS5B | DAPMRIIPKPEVFPRDKSTRKPPRFIVFPGCAARV | 191 |
| UC0125.US | NS5B | DAPMRIIPKPEVFPRDKSTRKPPR | 192 |
| UC0125.US | NS5B | DKSTRKPPRFIVFPGCAARV | 193 |
| UC0125.US | NS5B | IPKPEVFPRDKSTRKPPRFI | 194 |
| ABT0070P.US | NS5B | DAPMRIIPKPEVFPRDK<u>T</u>TRKPPRFIVFPGCAARV | 195 |
| ABT0070P.US | NS5B | DAPMRIIPKPEVFPRDK<u>T</u>TRKPPR | 196 |
| ABT0070P.US | NS5B | DK<u>T</u>TRKPPRFIVFPGCAARV | 197 |
| ABT0070P.US | NS5B | IPKPEVFPRDK<u>T</u>TRKPPRFI | 198 |
| UC0125.US | NS5B | MPLLCMLIRNEPSQTGTLVT | 199 |
| UC0125.US | NS5B | MPLLCMLIRNEPSQT | 200 |
| UC0125.US | NS5B | MLIRNEPSQTGTLVT | 201 |
| ABT0070P.US | NS5B | <u>L</u>PLLCMLIRNEPSQTGTLVT | 202 |
| ABT0070P.US | NS5B | <u>L</u>PLLCMLIRNEPSQT | 203 |
| ABT0096P.US | NS5B | <u>L</u>PLLCMLIRNEPSQTGTLVT | 204 |
| UC0125.US | S | AEAAPKSGELDSQCDHLAWSFMEGMPTGTLIVQRDGSLH | 205 |
| UC0125.US | S | AEAAPKSGELDSQCDHLAWSFME | 206 |
| UC0125.US | S | FMEGMPTGTLIVQRDGSLH | 207 |
| UC0125.US | S | QCDHLAWSFMEGMPTGT | 208 |
| UC0125.US | NS4A-B | SVEVRPAGVTRPDATDETAAYAQRLYQACADSGIFASLQGTASAALGKLA | 209 |
| UC0125.US | NS4A-B | SVEVRPAGVTRPDATDETAAYAQRLYQACAD | 210 |
| UC0125.US | NS4A-B | ACADSGIFASLQGTASAALGKLA | 211 |
| UC0125.US | NS4A-B | VTRPDATDETAAYAQRLYQACADSGIFASLQG | 212 |
| ABT0070P.US | NS4A-B | SVE<u>NGL</u>AGVTRPDATDETAAYAQRLYQACADSGI<u>L</u>ASLQGTASAAL<u>SR</u>LA | 213 |
| ABT0070P.US | NS4A-B | SVE<u>NGL</u>AGVTRPDATDETAAYAQRLYQACAD | 214 |

TABLE 15-continued

| Isolate/Peptide | Protein | Amino Acid Sequence | SEQ ID NO: |
|---|---|---|---|
| ABT0070P.US | NS4A-B | ACADSGILASLQGTASAALSRLA | 215 |
| ABT0070P.US | NS4A-B | VTRPDATDETAAYAQRLYQACADSGILASLQG | 216 |

The polynucleotides described herein may be employed for producing HPgV-2 polypeptides by recombinant techniques. Thus, for example, the polynucleotide may be included in any one of a variety of expression vectors for expressing a polypeptide. In some embodiments, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments provided herein are recombinant constructs comprising one or more of the sequences as broadly described above (e.g., SEQ ID NO:1, 75, 299-303, or sub-portion thereof). In some embodiments, the constructs comprise a vector, such as a plasmid or viral vector, into which a sequence of the invention has been inserted, in a forward or reverse orientation. In still other embodiments, the heterologous structural sequence is assembled in appropriate phase with translation initiation and termination sequences. In certain embodiments, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE 9 (Qiagen), pBS, pD10, phagescript, psiX174, pbluescript SK, pBSKS, pNH8A, pNH16a, pNH18A, pNH46A (Stratagene); ptrc99a, pKK223 3, pKK233 3, pDR540, pRIT5 (Pharmacia); pET vectors (Novagen); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host.

In certain embodiments, the DNA sequence in the expression vector is operatively linked to an appropriate expression control sequence(s) (promoter) to direct mRNA synthesis. Useful promoters include, but are not limited to, the LTR or SV40 promoter, the E. coli lac or trp, the phage lambda PL and PR, T3 and T7 promoters, and the cytomegalovirus (CMV) immediate early, herpes simplex virus (HSV) thymidine kinase, and mouse metallothionein I promoters and other promoters known to control expression of gene in prokaryotic or eukaryotic cells or their viruses. In other embodiments, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In a further embodiment, provided herein are host cells containing the above described constructs. In some embodiments, the host cell is a higher eukaryotic cell (e.g., a mammalian or insect cell). In other embodiments, the host cell is a lower eukaryotic cell (e.g., a yeast cell). In still other embodiments, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS 7 lines of monkey kidney fibroblasts, (Gluzman, Cell 23:175 [1981]), C127, 3T3, 293, 293T, HeLa and BHK cell lines.

HPgV-2 proteins can be expressed in mammalian cells, yeast, bacteria, or other cells under the control of appropriate promoters. Cell free translation systems can also be employed to produce such proteins using RNAs derived from the DNA constructs described herein. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

The present disclosure also provides methods for recovering and purifying HPgV-2 proteins from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments, protein refolding steps can be used as necessary, in completing configuration of the mature protein. In still other embodiments, high performance liquid chromatography (HPLC) can be employed for final purification steps.

The present disclosure further provides polynucleotides having the coding sequence (e.g., portions of SEQ ID NOs:1, 75, or 299-303) fused in frame to a marker sequence which allows for purification polypeptides. A non-limiting example of a marker sequence is a hexahistidine tag which may be supplied by a vector, preferably a pQE 9 vector, which provides for purification of the polypeptide fused to the marker in the case of a bacterial host, or, for example, the marker sequence may be a hemagglutinin (HA) tag when a mammalian host (e.g., COS 7 cells) is used. The HA tag corresponds to an epitope derived from the influenza hemagglutinin protein (Wilson et al., Cell, 37:767 [1984]).

In certain embodiments, the HPgV-2 peptides (e.g., SEQ ID NOs: 86-218 and 304-353) are conservatively modified. Conservatively modified variants applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

VI. Antibody Generation and Immunoassays

In some embodiments, antibodies are used for the detection of HPgV-2 protein. The antibodies may be prepared using various immunogens. In one embodiment, the immunogen is a HPgV-2 peptide (e.g., as shown in SEQ ID NOs:2-11, 76-218, and 304-353), or portions thereof, to generate antibodies that recognize HPgV-2. Such antibodies include, but are not limited to polyclonal, monoclonal, chimeric, single chain, Fab fragments, and Fab expression libraries.

Various procedures known in the art may be used for the production of polyclonal antibodies directed against HPgV-2. For the production of antibody, various host animals can be immunized by injection with the peptide corresponding to an HPgV-2 epitope including but not limited to rabbits, mice, rats, sheep, goats, etc. In certain embodiments, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette Guerin) and *Corynebacterium parvum*).

For preparation of monoclonal antibodies directed toward HPgV-2, it is contemplated, in certain embodiments, that any technique that provides for the production of antibody molecules by continuous cell lines in culture will find use with the present disclosure (See e.g., Harlow and Lane, Antibodies: A Laboratory Manual, Cold Spring Harbor Laboratory Press, Cold Spring Harbor, N.Y.). These include but are not limited to the hybridoma technique originally developed by Kihler and Milstein (Kihler and Milstein, Nature 256:495 497 [1975]), as well as the trioma technique, the human B cell hybridoma technique (See e.g., Kozbor et al., Immunol. Tod., 4:72 [1983]), and the EBV hybridoma technique to produce human monoclonal antibodies (Cole et al., in Monoclonal Antibodies and Cancer Therapy, Alan R. Liss, Inc., pp. 77 96 [1985]).

In certain embodiments, monoclonal antibodies are produced in germ free animals utilizing technology such as that described in PCT/US90/02545. Furthermore, it is contemplated that human antibodies may be generated by human hybridomas (Cote et al., Proc. Natl. Acad. Sci. USA 80:2026 2030 [1983]) or by transforming human B cells with EBV virus in vitro (Cole et al., in Monoclonal Antibodies and Cancer Therapy, Alan R. Liss, pp. 77 96 [1985]).

In addition, it is contemplated that techniques described for the production of single chain antibodies (U.S. Pat. No. 4,946,778; herein incorporated by reference) will find use in producing HPgV-2 specific single chain antibodies. An additional embodiment of the invention utilizes the techniques described for the construction of Fab expression libraries (Huse et al., Science 246:1275 1281 [1989]) to allow rapid and easy identification of monoclonal Fab fragments with the desired specificity for HPgV-2.

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme linked immunosorbant assay), "sandwich" immunoassays, immunoradiometric assays, gel diffusion precipitation reactions, immunodiffusion assays, in situ immunoassays (e.g., using colloidal gold, enzyme or radio-isotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. As is well known in the art, the immunogenic peptide should generally be provided free of the carrier molecule used in any immunization protocol. For example, if the peptide was conjugated to KLH, it may be conjugated to BSA, or used directly, in a screening assay to detect HPgV-2 in a sample. The foregoing antibodies can be used to detect HPgV-2 in a biological sample from an individual (e.g., suspected of being infected with HPgV-2). The biological sample can be a biological fluid, such as, but not limited to, blood, serum, plasma, interstitial fluid, urine, cerebrospinal fluid, and the like, containing cells.

The biological samples can then be tested directly for the presence of HPgV-2 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of HPgV-2 detected by immunoblotting (Western blotting). Immunoblotting techniques are generally more effective with antibodies generated against a peptide corresponding to an epitope of a protein, and hence, are particularly suited to the methods and compositions disclosed herein.

In some embodiments, HPgV-2 is detected with an immunoassay such as: 1) a sandwich immunoassay (e.g., monoclonal, polyclonal and/or DVD-Ig sandwich immunoassays or any variation thereof (e.g., monoclonal/DVD-Ig or DVD-Ig/polyclonal), including chemiluminescence detection, radioisotope detection (e.g., radioimmunoassay (RIA)) and enzyme detection (e.g., enzyme immunoassay (EIA) or enzyme-linked immunosorbent assay (ELISA) (e.g., Quantikine ELISA assays, R&D Systems, Minneapolis, Minn.))), 2) a competitive inhibition immunoassay (e.g., forward and reverse), 3) a fluorescence polarization immunoassay (FPIA), 4) an enzyme multiplied immunoassay technique (EMIT), 5) a bioluminescence resonance energy transfer (BRET), 6) a homogeneous chemiluminescent assay, 7) a SELDI-based immunoassay, 8) chemiluminescent microparticle immunoassay (CMIA) and 9) a clinical chemistry colorimetric assay (e.g., IMA, creatinine for eGFR determination and LC-MS/MS). (See, e.g., Tietz Textbook of Clinical Chemistry and Molecular Diagnostics. 4th Edition, edited by C A Burtis, E R Ashwood and D E Bruns, Elsevier Saunders, St. Louis, Mo., 2006.).

Further, if an immunoassay is being utilized, any suitable detectable label as is known in the art can be used. For example, the detectable label can be a radioactive label (such as 3H, 125I, 35S, 14C, 32P, and 33P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous or heterogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543, 524 and 5,783,699 (each of which is incorporated herein by reference in its entirety for its teachings regarding same). Another preferred acridinium compound is an acridinium-9-carboxylate aryl ester. An example of an acridinium-9-carboxylate aryl ester is 10-methyl-9-(phenoxycarbonyl) acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Further details regarding acridinium-9-carboxylate aryl ester and its use are set forth in U.S. published application no. 2008-0248493. Chemiluminescent assays (e.g., using acridinium as described above or other chemiluminescent agents) can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. Upon the simultaneous or subsequent addition of at least one basic solution to the sample, a detectable signal, namely, a chemiluminescent signal, indicative of the presence of analyte is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of analyte in the sample can be quantified. Specifically, the amount of analyte in the sample is proportional to the intensity of the signal generated. The amount of analyte present can be quantified by comparing the amount of light generated to a standard curve for the analyte or by comparison to a reference standard. The standard curve can be generated using serial dilutions or solutions of known concentrations of analyte by mass spectroscopy, gravimetric methods, and other techniques known in the art. While the above is described with emphasis on use of an acridinium compound as the chemiluminescent agent, one of ordinary skill in the art can readily adapt this description for use of other chemiluminescent agents.

Immunoassays can generally be conducted using any format known in the art, such as, but not limited to, a sandwich format. Specifically, in one immunoassay format, at least two antibodies are employed to separate and quantify HPgV-2 or a fragment thereof in a sample. More specifically, the at least two antibodies bind to different epitopes on HPgV-2 (or a fragment thereof) forming an immune complex, which is referred to as a "sandwich." Generally, in the immunoassays, one or more antibodies can be used to capture the HPgV-2 (or a fragment thereof) in the test sample (i.e., these antibodies are frequently referred to as a "capture" antibody or "capture" antibodies) and one or more antibodies can be used to bind a detectable (namely, quantifiable) label to the sandwich (i.e., these antibodies are frequently referred to as the "detection antibody," the "detection antibodies," the "conjugate," or the "conjugates"). Thus, in the context of a sandwich immunoassay format, an antibody (or a fragment, a variant, or a fragment of a variant thereof) can be used as a capture antibody, a detection antibody, or both. For example, one DVD-Ig having a domain that can bind a first epitope on HPgV-2 (or a fragment thereof) can be used as a capture antibody and/or another DVD-Ig having a domain that can bind a second epitope on HPgV-2 (or a fragment thereof) can be used as a detection antibody. In this regard, a DVD-Ig having a first domain that can bind a first epitope on an analyte (or a fragment thereof) and a second domain that can bind a second epitope on an analyte (or a fragment thereof) can be used as a capture antibody and/or a detection antibody. Alternatively, one DVD-Ig having a first domain that can bind an epitope on a first analyte (or a fragment thereof) and a second domain that can bind an epitope on a second analyte (or a fragment thereof) can be used as a capture antibody and/or a detection antibody to detect, and optionally quantify, two or more analytes.

Generally speaking, in an immunoassay, a sample being tested for (for example, suspected of containing) HPgV-2 (or a fragment thereof) can be contacted with at least one capture antibody (or antibodies) and at least one detection antibody (which can be a second detection antibody or a third detection antibody or even a successively numbered antibody, e.g., as where the capture and/or detection antibody comprise multiple antibodies) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, described above, a sample suspected of containing HPgV-2 (or a fragment thereof) is first brought into contact with at least one first capture antibody under conditions that allow the formation of a first antibody/HPgV-2 complex. If more than one capture antibody is used, a first capture antibody/HPgV-2 complex comprising two or more capture antibodies is formed. In a sandwich assay, the antibodies, i.e., preferably, the at least one capture antibody, are used in molar excess amounts of the maximum amount of HPgV-2 (or a fragment thereof) expected in the test sample. For example, from about 5 µg to about 1 mg of antibody per mL of buffer (e.g., microparticle coating buffer) can be used.

In contrast, competitive inhibition immunoassays, which are often used to measure small analytes because binding by only one antibody is required, comprise sequential and classic formats. In a sequential competitive inhibition immunoassay, a capture antibody to an analyte of interest (e.g., HPgV-2 protein) is coated onto a well of a microtiter plate or other solid support. When the sample containing the analyte of interest is added to the well, the analyte of interest binds to the capture antibody. After washing, a known amount of labeled analyte (e.g., acridinium, biotin or horseradish peroxidase (HRP)) is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay, an antibody to an analyte of interest is coated onto a solid support (e.g., a well of a microtiter plate). However, unlike the sequential competitive inhibition immunoassay, the sample and the labeled analyte are added to the well at the same time. Any analyte in the sample competes with labeled analyte for binding to the capture antibody. After washing, the signal generated by the labeled analyte is measured and is inversely proportional to the amount of analyte in the sample.

The concentration of HPgV-2 or a fragment thereof in the test sample is determined by appropriate means, such as by use of a standard curve that has been generated using serial dilutions of analyte or a fragment thereof of known concentration. Other than using serial dilutions of analyte or a fragment thereof, the standard curve can be generated gravimetrically, by mass spectroscopy and by other techniques known in the art.

In a chemiluminescent microparticle assay employing the ARCHITECT analyzer, the conjugate diluent pH may be about 6.0+/−0.2, the microparticle coating buffer may be maintained at about room temperature (i.e., at from about 17 to about 27.degree. C.), the microparticle coating buffer pH may be about 6.5+/−0.2, and the microparticle diluent pH may be about 7.8+/−0.2. Solids preferably are less than about 0.2%, such as less than about 0.15%, less than about 0.14%, less than about 0.13%, less than about 0.12%, or less than about 0.11%, such as about 0.10%. Of course, these ranges or numbers may be altered in order to enhance such properties of the assay including, for example, reduction in background interference, increased sensitivity, increased specificity, etc.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

The present description is not limited by the type of immunoassay employed to detect patient antibodies in a sample. A number of exemplary formats are as follows. In an indirect assay, HPgV-2 peptide or protein is coated on solid phase (e.g., beads) and then contacted with a sample (e.g. 18 minutes), followed by a wash step. Then, in a second step, patient antibodies to HPgV-2 are detected by contacting the immune complex with labeled "second" antibody to detect human IgG (or IgM) bound to the solid phase (e.g. for 4 minutes). Another assay is a two step direct (sandwich) assay. In this assay, HPgV-2 peptide or protein is coated on solid phase (e.g., beads) and contacted with sample (e.g. for about 18 minutes) and then washed. In a second step, antibodies to HPgV-2 are detected with a labeled HPgV-2 peptide/protein that binds to human IgG (or IgM) bound to the solid phase containing the HPgV-2 protein (e.g. for 4 minutes). A one-step direct (sandwich) assay could also be employed. In such an assay, HPgV-2 peptide or protein is coated on solid phase and contacted with sample (e.g., for about 18 minutes) and with labeled HPgV-2 peptide/protein at the same time or about the same time (e.g., for 18 minutes). Another type of assay is a solution phase capture. In such an assay, the sample is contacted with both protein tagged HPgV-2 peptide or protein (e.g., biotin tag, FLAG-tag, HA-tag, etc.) and labeled HPgV-2 peptide or protein in the presence of a solid phase coated with an affinity molecule (e.g., streptavidin or protein tag antibody). If the patient antibodies are present in the sample, the tagged peptide or protein and labeled HPgV-2 peptides or proteins can bind to patient antibodies in a complex that can be captured by the associated protein tag to a solid phase support. In all of these assay formats, the solid phase is further processed to elicit a signal from labeled HPgV-2 associated with patient antibodies and with the solid phase.

In particular embodiments, the antigens and antibodies described herein are contemplated for use as immunodiagnostic reagents in combination immunoassays designed for the detection of multiple HPgV-2 components found in a test sample suspected of having been infected with HPgV-2. Immunodiagnostic reagents may used in a combination assay that detects both peptides and patient antibodies. For purposes of capture, the antigens and/or antibodies of which the immunodiagnostic reagent is comprised can be coated on a solid support such as for example, a microparticle, (e.g., magnetic particle), bead, test tube, microtiter plate, cuvette, membrane, scaffolding molecule, film, filter paper, disc or chip. In this regard, where the immunodiagnostic reagent comprises a combination of antigens (e.g., directed at different HPgV-2 proteins or different fragments of the same HPgV-2 protein), the antigens can be co-coated on the same solid support or can be on separate solid supports. Likewise, where the immunodiagnostic reagent comprises one or more antibodies that will be used to capture one or more antigens from the test sample, such-antibodies can be co-coated on the same solid support or can be on separate solid supports.

Notably, the immunodiagnostic reagent may include the antigens and antibodies labeled with a detectable label or labeled with a specific partner that allows capture or detection. For example, the labels may be a detectable label, such as a fluorophore, radioactive moiety, enzyme, biotin/avidin label, chromophore, chemiluminescent label, or the like. Still further the invention contemplates the preparation of HPgV-2 diagnostic kits comprising the immunodiagnostic reagents described herein and instructions for the use of the immunodiagnostic reagents in immunoassays for determining the presence of HPgV-2 in a test sample by detecting the presence of two or more HPgV-2 proteins and/or anti-HPgV-2 antibodies in such a sample. For example, the kit can comprise instructions for assaying the test sample for anti-HPgV-2 antibody (e.g., an anti Core antibody in the test sample) by immunoassay. While certain embodiments employ chemiluminescent microparticle immunoassay for assaying the test sample, it should be understood that the antigens and antibodies used in the immunoassays of the present invention may be used in any other immunoassay formats known to those of skill in the art for determining the presence of HPgV-2 in a test sample. The instructions can be in paper form or computer-readable form, such as a disk, CD, DVD, or the like. Alternatively or additionally, the kit can comprise a calibrator or control, e.g., purified, and optionally lyophilized, anti-HPgV-2 antibody or antigen, and/or at least one container (e.g., tube, microtiter plates or strips, which can be already coated with one or more of the capture components (antigens and/or antibodies) of the immunoassay) for conducting the assay, and/or a buffer, such as an assay buffer or awash buffer, either one of which can be provided as a concentrated solution, a substrate solution for the detectable label (e.g., an enzymatic label), or a stop solution. In certain embodiments, the kit comprises all components, i.e., reagents, standards, buffers, diluents, etc., which are necessary to perform the assay. In specific embodiments, the components are individually presented in the kit such that the immunoassay may be performed as a capture-on-the-fly type combination immunoassay in which the solid support is coated with an agent that allows binding of the capturing moiety (e.g., a-33-biotinylated antigen or a biotinylated antibody) and the kit further comprises each of the individual capture and detection antigen pairs and the biotinylated capture antibodies in one container and a second container provides the detection antibody conjugate. The instructions for conducting the assay also can include instructions for generating a standard curve or a reference standard for purposes of quantifying anti-HPgV-2 antibody.

Any antibodies, which are provided in the kit, such as anti-IgG antibodies and anti-IgM antibodies, can also incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates. In certain immunoassays, there are two containers provided. In the first container is provided at least a first, second and third pair of antigens, wherein the first antigen in each pair is a capture antigen from a given HPgV-2 protein that is biotinylated and the second antigen in each pair is a detection antigen from the same protein as the first antigen but is labeled with a detectable label (e.g., it is acridinylated) as well as one or more biotinylated antibodies designed for detecting one or more HPgV-2 antigens from a test sample; and in the second container is provided the antibody that forms the conjugation partner for detection of the antigen that is captured by the biotinylated antibodies from the first container. It is contemplated that where there are multiple biotinylated antibodies in the first container, the multiple antibodies that form the conjugation partners may be present in a single container or individual containers for each different antigen detecting conjugate antibody.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

In preferred embodiments, the detectable label is at least one acridinium compound. In such embodiments, the kit can comprise at least one acridinium-9carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. It should be understood that in the immunodiagnostic reagent the antigens for antibody detection may be detectably labeled, and any antibodies provided in kit for use along with such reagents also may be detectably labeled. If desired, the kit can contain a solid support phase, such as a magnetic particle, bead, test tube, microtiter plate, cuvette, membrane, scaffolding molecule, film, filter paper, disc or chip.

The present disclosure provides immunoassays and combination immunoassays method for determining the presence, amount or concentration of anti-HPgV-2 antibodies and HPgV-2 antigens in a test sample. Any suitable assay known in the art can be used in such methods. Examples of such assays include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA)(e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc.

In specific embodiments of the immunoassays, the recombinant antigens (e.g., core, NS3 and NS4 antigens) may be used as capture reagents (e.g., by using such antigens in which the amino- or carboxy-terminal of the antigen comprises a biotin tag) or as a detection (conjugate) reagents in which the antigens are either directly or indirectly labeled with acridinium. Indirect labeling may employ the use of acridinylated BSA covalently coupled to the free thiol of unpaired cysteine residues within a protein via SMCC-type linker. To facilitate such indirect labeling certain of the antigens used in the immunoassays of the present invention may readily be further modified to include additional cysteine residues at the C-terminus.

Typically, immunoassays are performed in 1-step or 2-step format. Solid phase reagents for capture of immune complexes formed in solution in the 1-step assay include anti-biotin monoclonal antibody, streptavidin or neutravidin to capture the biotinylated moiety (be it a biotinylated antigen for capture of an HPgV-2 antibody or a biotinylated antibody for the capture of an HPgV-2 protein/antigen in the test sample).

In a SELDI-based immunoassay, a capture reagent that specifically binds anti-HPgV-2-antibody or an HPgV-2 antigen is attached to the surface of a mass spectrometry probe, such as a pre-activated protein chip array. The anti-HPgV-2 antibody or the antigen is then specifically captured on the biochip, and the captured moiety is detected by mass spectrometry. Alternatively, the anti-HPgV-2 antibody can be eluted from the capture reagent and detected by traditional MALDI (matrix-assisted laser desorption/ionization) or by SELOI. A chemiluminescent microparticle immunoassay, in particular one employing the ARCHITECT® automated analyzer (Abbott Laboratories, Abbott Park), is an example of an immunoassay in which a combination of multiple antigens (e.g., antigens from two or more HPgV-2 proteins) as well as multiple anti-HPgV-2 antibodies may readily be employed. An agglutination assay, such as a passive hemaglutination assay, also can be used. In an agglutination assay an antigen antibody reaction is detected by agglutination or clumping. In a passive hemaglutination assay, erythrocytes are coated with the antigen and the coated erythrocytes are used in the agglutination assay. A second embodiment of the measurement of HPgV-2 neutralizing antibodies is the traditional virus neutralization test which employs cell lines susceptible to infection with HPgV-2, and measuring inhibition by one or more methods (e.g. immunofluorescence, plaque assay methods, etc.) (see, Temperton et al., Virol. J., 10:266-213, 2013, herein incorporated by reference).

Methods well-known in the art for collecting, handling and processing urine, blood, serum and plasma, and other body fluids, are used in the practice of the present disclosure, for instance, when the immunodiagnostic reagents comprise multiple antigens and/or in an anti-HPgV-2 antibody immunoassay kit. The test sample can comprise further moieties in addition to the polypeptide of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform).

The pretreatment reagent can be any reagent appropriate for use with the immunoassays and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TOx, AxSYM®, and ARCHITECT® analyzers (Abbott Laboratories, Abbott Park, Ill.), as described in the literature (see, e.g., Yatscoff et ai.,—37—Abbott TDx Monoclonal Antibody Assay Evaluated for Measuring Cyclosporine in WholeBlood, Clin. Chem. 36: 1969-1973 (1990), and Wallemacq et al., Evaluation of the New AxSYM Cyclosporine Assay: Comparison with TDx Monoclonal Whole Blood and EMITCyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., protein that can bind to anti-HPgV-2 antibody or an antigen that can bind to an anti-HPgV-2 antibody form the present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for anti-HPgV-2 antibody (i.e., an antigen) or the labeled specific binding partner for the HPgV-2 antigen (i.e., an antibody). The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 methylene glycol) is still present (or remains) in the test sample mixture during capture.

In a heterogeneous format, after the test sample is obtained from a subject, a first mixture is prepared. The mixture contains the test sample being assessed for anti-HPgV-2 antibodies and a first specific capture binding partner, wherein the first specific capture binding partner and any anti-HPgV-2 antibodies contained in the test sample form a first specific capture binding partner-anti-HPgV-2 antibody complex. The first specific capture binding partner may be any of a core antigen, an NS3 antigen or an NS3, or other HPgV-2 protein. Likewise, in certain embodiments, in the combination assays of the invention the mixture also contains a second and third specific capture binding partner and these second and third specific capture binding partners form second and third specific capture binding partner-anti-HPgV-2 antibody complexes with anti-HPgV-2 antibodies that are present in the test sample.

In addition the combination immunoassay may include at least one anti-HPgV-2 capture antibody that will form a specific complex with a fourth specific binding partner that is found in the test sample (i.e., an antigen or HPgV-2 protein that is found in the test sample) so as to form an anti-HPgV-2 antibody-four the specific binding partner complex with the fourth antigen that is present in the test sample.

In the combination immunoassays, the order in which the test sample and the various specific binding partners are added to form the mixture is not critical. In some embodiments, the first, second, and third specific capture binding partners (i.e., antigens) and the anti-HPgV-2 capture antibody are immobilized on a solid phase. In still other embodiments, none of these four components are immobilized but are instead all added at the same time to the test sample to effect capture onto the solid phase. The solid phase used in the combination immunoassay can be any solid phase known in the art, such as, but not limited to, a magnetic particle, a bead, a test tube, a microtiter plate, a cuvette, a membrane, a scaffolding molecule, a film, a filter paper, a disc and a chip.

After the immunocomplexes are formed between the first, second and third specific capture binding partners and their respective anti-HPgV-2 antibodies found in the test sample, and the first anti-HPgV-2 capture antibodies (e.g., anti-Core) and their respective HPgV-2 antigens or HPgV-2 proteins found in the test sample, any unbound antiHPgV-2 antibody or HPgV-2 antigen/protein is removed from the complex using any technique known in the art. For example, the unbound anti-HPgV-2 antibody or antigen can be removed by washing. Desirably, however, the first, second and third specific binding partners and the anti-HPgV-2 antibodies are present in excess of any anti-HPgV-2 antibody and antigens, respectively present in the test sample, such that all anti-HPgV-2 antibody and antigens that are present in the test sample become bound by the first, second, and third specific binding partner and anti-HPgV-2 capture antibodies respectively.

After any unbound anti-HPgV-2 antibody and antigen is removed, detection is achieved by addition of a first specific detection binding partner to the mixture to form a first specific capture binding partner-anti-HPgV-2 antibody-first specific detection binding partner complex. The first specific detection binding partner is preferably a combination of an anti-IgG antibody and an anti-IgM antibody. Moreover, also preferably, the first specific detection binding partner is labeled with or contains a detectable label. In specific embodiments, the first specific detection partner may instead or in addition be an antigen that binds the captured antibody. Likewise, in the combination assays of the invention the mixture also contains a second and third specific detection binding partner and these second and third specific detection binding partners form second or third specific capture binding partner-anti-HPgV-2 antibody second or third specific detection binding partner complexes with the captured anti-HPgV-2 antibodies that are present in the test sample. Again, the second and third specific detection binding partners may be a combination of an anti-IgG antibody and an anti-IgM antibody. In specific embodiments, the second and third specific detection partners may instead or in addition be an antigen that binds the captured antibody. Moreover, the second and third specific detection binding partners, be they anti IgM or IgG antibodies or antigens, are labeled with or contains a detectable label. In addition the combination immunoassay may include at least one anti-HPgV-2 conjugate antibody that will form a specific complex with the captured antigen or HPgV-2 protein that is found in the test sample so as to form an anti-HPgV-2 antibody-fourth specific binding partner-anti-HPgV-2 conjugate antibody complex with the fourth antigen that captured from the test sample.

Any suitable detectable label as is known in the art can be used as anyone or more of the detectable labels. For example, the detectable label can be a radioactive label (such as 3H, 125I, 35S, 14C, 32p, and 33p), an enzymatic label (such as horseradish peroxidase, alkaline peroxidase, glucose 6-phosphate dehydrogenase, and the like), a chemiluminescent label (such as acridinium esters, thioesters, orsulfonamides; luminol, isoluminol, phenanthridinium esters, and the like), a fluorescentlabel (such as fluorescein (e.g., 5-fluorescein, 6-carboxyfluorescein, 3'6-carboxyfluorescein, 5(6)-carboxyfluorescein, 6-hexachloro-fluorescein, 6-tetra-chlorofluorescein, fluorescein isothiocyanate, and the like)), rhodamine, phycobiliproteins, R-phycoerythrin, quantum dots (e.g., zinc sulfide-capped cadmiumselenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359, 093, and 5,352,803, which are hereby incorporated by reference in their entireties). An acridinium compound can be used as a detectable label in a homogeneous chemiluminescent assay (see, e.g., Adamczyk etal., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 39173921(2004); and Adamczyk et al., Org. Lett. 5: 3779-3782 (2003)).

An exemplary acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 56365639(1998); Adamczyk et al., Tetrahedron 55: 10899-10914 (1999); Adamczyk et aI., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 37793782(2003); and U.S. Pat. Nos. 5,468,646, 5,543,524 and 5,783,699 (each of which is incorporated herein by reference in its entirety for its teachings regarding same).

Another exemplary acridinium compound is an acridinium-9-carboxylatearyl ester. An example of an acridinium-9-carboxylate aryl ester of formula II is 10methyl-9-(phenoxycarbonyl) acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi etaI., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9carboxylatearyl ester is completed rapidly, i.e., in under 1 second, while the acridinium9-carboxamide chemiluminescent emission extends over 2 seconds. Acridinium-9carboxylatearyl ester, however, loses its chemiluminescent properties in the presence of protein. Therefore, its use requires the absence of protein during signal generation and detection. Methods for separating or removing proteins in the sample are well known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697, 835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N dimethylformamide (DMF) or aqueous sodium cholate.

Chemiluminescent assays can be performed, for example, in accordance with the methods described in Adamczyk et al., Anal. Chim. Acta 579(1): 61-67 (2006). While any suitable assay format can be used, a microplate chemiluminometer (Mithras LB940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

Hydrogen peroxide can be generated in situ in the mixture or provided or supplied to the mixture before, simultaneously with, or after the addition of an above described acridinium compound. Hydrogen peroxide can be generated in situ in a number of ways such as would be apparent to one skilled in the art. Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of anti-HPgV-2 antibody (where capture is with an antigen) or antigen (where capture is with an antibody) is generated. In certain embodiments, the basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of anti-HPgV-2 antibody and/or antigen in the sample can be quantified. Specifically, the amount of anti-HPgV-2 antibody and/or in the sample is proportional to the intensity of the signal generated. The amount of anti-HPgV-2 antibody and/or antigen present can be quantified by comparing the amount of light generated to a standard curve for anti-HPgV-2 antibody and/or antigen or by comparison to a reference standard. The standard curve can be generated using serial dilutions or solutions of known concentrations of anti-HPgV-2 antibody by mass spectroscopy, gravimetric methods, and other techniques known in the art.

Anti-HPgV-2 antibody and/or antigen immunoassays can be conducted using any suitable format known in the art. In certain embodiments, a sample being tested for (for example, suspected of containing) anti-HPgV-2 antibodies can be contacted with a capture antigen and at least one detection antibody (which can be a second detection antibody or a third detection antibody), such as labeled anti-IgG and anti-IgM antibodies, either simultaneously or sequentially and in any order. Similarly, the test for presence of an antigen can be contacted with a captured antibody which binds the antigen in the test sample and the bound antigen may then be detected by a detection antibody.

For example, the test sample can be first contacted with at least one capture antigen and then (sequentially) with at least one detection antibody. Alternatively, the test sample can be first contacted with at least one detection antibody and then (sequentially) with at least one capture antibody. In yet another alternative, the test sample can be contacted simultaneously with a capture antigen and a detection antibody.

In the sandwich assay format, in certain embodiments, a sample suspected of containing anti-HPgV-2 antibodies (or a fragment thereof) is first brought into contact with an at least one first capture antigen under conditions that allow the formation of a first capture antigen/antiHPgV-2 antibody complex. In the combination assay, the same is repeated or simultaneously conducted with a second, third or more capture antigens. If more than one capture antigen is used, multiple first capture antigen/anti-HPgV-2 antibody complexes are formed. In a sandwich assay, the antigen(s), in certain embodiments, the at least one capture antigen, is/are used in molar excess amounts of the maximum amount of anti-HPgV-2 antibodies expected in the test sample. For example, from about 5 ug to about 1 mg of antigen per mL of buffer (e.g., microparticle coating buffer) can be used.

Competitive inhibition immunoassays, which are often used to measure small analytes, comprise sequential and classic formats. In a sequential competitive inhibition immunoassay the one or more capture antigen(s) (i.e., a polypeptide, and a pair of polypeptides, as described herein) to an antibody of interest (i.e., an anti-HPgV-2 antibody) is/are coated onto a well of a microtiter plate. When the sample containing the antibody/antibodies of interest is added to the well, the antibody of interest binds to the capture antigen(s). After washing, a known amount of labeled (e.g., biotin or horseradish peroxidase (HRP)) antibody is added to the well. A substrate for an enzymatic label is necessary to generate a signal. An example of a suitable substrate for HRP is 3,3',5,5'-tetramethylbenzidine (TMB). After washing, the signal generated by the labeled antibody is measured and is inversely proportional to the amount of antibody in the sample. In a classic competitive inhibition immunoassay antigen for an antibody of interest is coated onto a well of a microtiter plate. However, unlike the sequential competitive inhibition immunoassay, the sample containing the antibody of interest (i.e., an anti-HPgV-2 antibody) and the labeled antibody are added to the well at the same. Any antibody in the sample competes with labeled antibody for binding to the capture antigen. After washing, the signal generated by the labeled analyte is measured and is inversely proportional to the amount of analyte in the sample.

Optionally, prior to contacting the test sample with the at least one capture antigen (for example, the first capture antigen), the at least one capture antigen can be bound to a solid support, which facilitates the separation of the first antigen/anti-HPgV-2 antibody complex from the test sample. The substrate to which the capture antigen is bound can be any suitable solid support or solid phase that facilitates separation of the capture antigen-anti-HPgV-2 antibody complex from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or heteropolymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates may be in the form of sheets having a thickness of about 0.01 to about 0.5 mm, or about 0.1 mm. While the pore size may vary quite a bit, preferably the pore size is from about 0.025 to about 15 microns, or from about 0.15 to about 15 microns. The surface of such substrates can be activated by chemical processes that cause covalent linkage of an antibody to the substrate. Irreversible binding, generally by adsorption through hydrophobic forces, of the antigen to the substrate results; alternatively, a chemical coupling agent or other means can be used to bind covalently the antigen to the substrate, provided that such binding does not interfere with the ability of the antigen to bind to anti-HPgV-2 antibodies.

Alternatively, the anti-HPgV-2 antibody from the test sample can be bound with microparticles, which have been previously coated with antigen. If desired, one or more capture reagents, such as a pair of polypeptides as described herein, each of which can be bound by an anti-HPgV-2 antibody, can be attached to solid phases indifferent physical or addressable locations (e.g., such as in a biochip configuration (see,—46—e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828). If the capture reagent is attached to a mass spectrometry probe as the solid support, the amount of anti-HPgV-2 antibodies bound to the probe can be detected by laser desorption ionization mass spectrometry. Alternatively, a single column can be packed with different beads, which are derivatized with the one or more capture reagents, thereby capturing the anti-HPgV-2 antibody in a single place (see, antibody derivatized, bead based technologies, e.g., the xMAP technology of Luminex (Austin, Tex.)).

After the test sample being assayed for anti-HPgV-2 antibodies is brought into contact with at least one capture antigen (for example, the first capture antigen), the mixture is incubated in order to allow for the formation of a first antigen (or multiple antigen)-anti-HPgV-2 antibody (or a fragment thereof) complex. The incubation can be carried out at a pH of from about 4.5 to about 10.0, at a temperature of from about 20 C. to about 45 0 C., and for a period from at least about one (1) minute to about eighteen (18) hours, or from about 1 to about 24 minutes, or for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After or simultaneously with formation of the (first or multiple) capture antigen/anti-HPgV-2 antibody complex, the complex is then contacted with at least one detection antibody (under conditions which allow for the formation of a (first or multiple) capture antigen/anti-HPgV-2 antibody/first antibody detection complex). The at least one detection antibody can be the second, third, fourth, etc. antibodies used in the immunoassay. If the capture antigen/anti-HPgV-2 antibody complex is contacted with more than one detection antibody, then a (first or multiple) capture antigen/anti-HPgV-2 antibody/(multiple) detection antibody complex is formed. As with the capture antigen (e.g., the first capture antigen), when the at least second (and subsequent) detection antibody is brought into contact with the capture antigen/anti-HPgV-2 antibody complex, a period of incubation under conditions similar to those described above is required for the formation of the (first or multiple) capture antigen/anti-HPgV-2 antibody/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antigen/ anti-HPgV-2 antibody/(second or multiple) detection antibody complex. Any detectable label known in the art can be used (see discussion above, including Polak and Van Noorden (1997) and Haugland (1996)).

The detectable label can be bound to the antibodies (or antigens which may comprise detectable labels) either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-1 O-(3-sulfopropyl) acridinium carboxamide) or SPSP-Acridinium Ester (i.e., N10-(3-sulfopropyl)-N-(3-sulfopropyl)-acridinium-9carboxamide).

The (first or multiple) capture antigen/anti-HPgV-2 antibody/(second or multiple) detection antibody complex can be, but does not have to be, separated from the remainder of the test sample prior to quantification of the label. For example, if the at least one capture antigen (e.g., the first capture antigen) is bound to a solid support, such as a well or a bead, separation can be accomplished by removing the fluid (of the test sample) from contact with the solid support. Alternatively, if the at least first capture antigen is bound to a solid support, it can be simultaneously contacted with the anti-HPgV-2 antibody-containing sample and the at least one second detection antibody (or the labeled detection antigen) to form a first (multiple) antigen/anti-HPgV-2 antibody/second (multiple) antibody (and/or labeled detection antigen) complex, followed by removal of the fluid (test sample) from contact with the solid support. If the at least one first capture antigen is not bound to a solid support, then the (first or multiple) capture antigen/anti-HPgV-2 antibody/ (second or multiple) detection antibody (and/or detection antigen for the—48—captured antibody) complex does not have to be removed from the test sample for quantification of the amount of the label.

After formation of the labeled capture antigen/anti-HPgV-2 antibody/detection antigen (and/or detection antibody) complex (e.g., the first capture antigen/anti-HPgV-2 antibody/first detection antigen complex optionally also with a second detection antibody), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCO camera, etc. Once the amount of the label in the complex has been quantified, the concentration of anti-HPgV-2 antibody or antigen in the test sample is determined by use of a standard curve that has been generated using serial dilutions of anti-HPgV-2 antibody or antigens of known concentration. Other than using serial dilutions of anti-HPgV-2 antibodies or HPgV-2 antigens, the standard curve can be generated gravimetrically, by mass spectroscopy and by other techniques known in the art.

In a chemiluminescent microparticle assay employing the ARCHITECT® analyzer, the conjugate diluent pH may be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 6.5+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

In certain embodiments, the present disclosure provides methods of determining the presence, amount, or concentration of anti-HPgV-2 antibodies or antigens in a test sample. In some embodiments, the methods comprise assaying the test sample for anti-HPgV-2 antibodies or antigens by an assay: (i) employing an immunodiagnostic reagent comprising at least an isolated or purified polypeptide comprising HPgV-2 antigens, and at least one detectable label, and comparing a signal generated by the detectable label as a direct or indirect indication of the presence, amount or concentration of anti-HPgV-2 antibodies in the test sample to a signal generated as a direct or indirect indication of the presence, amount or concentration of anti-HPgV-2 antibodies in a control or calibrator, which is optionally part of a series of calibrators in which each of the calibrators differs from the other calibrators in the series by the concentration of anti-HPgV-2 antibodies. The method can comprise the following steps: (i) contacting the test sample with the immunodiagnostic reagent comprising one of more recombinant HPgV-2 antigens so as to form first, second and third specific capture binding partner/anti-HPgV-2 antibody complexes with HPgV-2 antibodies that may be present in the test sample, (ii) contacting the first, second and third specific capture binding partner/first, second and third anti-HPgV-2 antibody complexes with at least one detectably labeled second specific binding partner for anti-HPgV-2 antibody (e.g., anti-IgG antibody and anti-IgM antibody or polypeptides as described herein) so as to form first specific binding partner/first, second and third anti-HPgV-2 antibody, respectively/second specific binding partner complexes, and (iii) determining the presence, amount or concentration of anti-HPgV-2 antibodies in the test sample by detecting or measuring the signal generated by the detectable label in the first specific binding partner/anti-HPgV-2 antibody/second specific binding partner complexes formed in (ii).

In certain embodiments, in addition to, or instead of, use of the anti-IgG and IgM antibodies, the second step comprises addition of first, second and third detection antigens that will specifically bind the anti-HPgV-2 antibodies that have been specifically captured by the first, second and third capture antigens, respectively so as to form first specific binding partner/anti-HPgV-2 antibody/second specific binding partner complexes, and the third step comprises: (iii) determining the presence, amount or concentration of anti-HPgV-2 antibodies in the test sample by detecting or measuring the signal generated by the detectable label in the first, second and third specific capture binding partner/first, second and third anti-HPgV-2 antibodies/first, second and third specific detection binding partner complexes formed in (ii).

In some embodiments, the methods can comprise the following steps: (i) contacting the test sample with the immunodiagnostic reagent comprising one of more recombinant antigens and simultaneously or sequentially, in either order, contacting the test sample with at least one detectably labeled second specific binding partner, which can compete with anti-HPgV-2 antibody for binding to the at least one pair of first specific binding partners and which comprises detectably labeled anti-HPgV-2 antibodies, wherein any anti-HPgV-2 antibody present in the test sample and the at least one detectably labeled second specific binding partner compete with each other to form first specific binding partner/anti-HPgV-2 antibody complexes and first specific binding partner/second specific binding partner complexes, respectively, and (ii) determining the presence, amount or concentration of anti-HPgV-2 antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HPgV-2 antibodies in the test sample. The recombinant antigens of which the immunodiagnostic reagent is comprised can be coated on microparticles. In this regard, the antigens of which the immunodiagnostic reagent is comprised can be co-coated on the same microparticles as additional HPgV-2 antigens. When the polypeptides of which the immunodiagnostic reagent is comprised are co-coated on the same microparticles (e.g., a microparticle suspension containing 4% solids (4% weight/volume microparticles or 4 g microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified antigen of the present invention is at least about 40 µg/mL and the concentration of the other isolated or purified polypeptide is at least about 80 µg/mL. If the test sample was obtained from a patient, the method may further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

In certain embodiments, provided here are methods of determining the presence, amount, and/or concentration of anti-HPgV-2 antibodies or HPgV-2 antigens or proteins in a test sample. In some embodiments, the methods comprise assaying the test sample by an assay: (i) employing: an immunodiagnostic reagent comprising at least one HPgV-2 antigen (and preferably two, three or more antigens) at least one detectable label (preferably each antigen being detectably labeled), and (ii) comparing a signal generated by the detectable label as a direct or indirect indication of the presence, amount or concentration of anti-HPgV-2 antibodies in the test sample to a signal generated as a direct or indirect indication of the presence, amount or concentration of anti-HPgV-2 antibodies in a control or calibrator, which is optionally part of a series of calibrators in which each of the calibrators differs from the other calibrators in the series by the concentration of anti-HPgV-2 antibodies. The method can comprise the following steps: (i) contacting the test sample with the immunodiagnostic reagent comprising at least one, two, three or more recombinant HPgV-2 antigens invention so as to form first specific capture binding partner/anti-HPgV-2 antibody complexes, (ii) contacting the first specific capture binding partner/anti-HPgV-2 antibody complexes with at least one detectably labeled second specific binding partner for anti-HPgV-2 antibody (e.g., anti-IgG antibody and anti-IgM antibody or labeled antigens that bind the anti-HPgV-2 antibodies) so as to form first specific binding partner/anti-HPgV-2antibody/second specific binding partner complexes, and (iii) determining the presence, amount or concentration of anti-HPgV-2 antibodies in the test sample by detecting or measuring the signal generated by the detectable label in the first specific binding partner/anti-HPgV-2 antibody/second specific binding partner complexes formed in (ii). Alternatively, the method can comprise the following steps: (i) contacting the test sample with the immunodiagnostic reagent comprising at least one, two, three or more different HPgV-2 antigens and simultaneously or sequentially, in either order, contacting the test sample with at least one detectably labeled second specific binding partner, which can compete with anti-HPgV-2 antibody for binding to the at least one pair of first specific binding partners and which comprises detectably labeled anti-HPgV-2 antibodies, wherein any anti-HPgV-2 antibody present in the test sample and the at least one second specific binding partner compete with each other to form first specific binding partner/anti-HPgV-2 antibody complexes and a first specific binding partner/second specific binding partner complexes, respectively, and (ii) determining the presence, amount or concentration of anti-HPgV-2 antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HPgV-2 antibodies in the test sample. The polypeptides of which the immunodiagnostic reagent is comprised can be coated on microparticles. In this regard, the polypeptides of which the immunodiagnostic reagent is comprised can be co-coated on the same microparticles. When the polypeptides of which the immunodiagnostic reagent is comprised are co-coated on the same microparticles (e.g., a microparticle suspension containing 4% solids (4% weight/volume microparticles or 4 g microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified polypeptide comprising the recombinant HPgV-2 antigen is at least about 40 µg/mL and the concentration of the other isolated or purified polypeptide is at least about 80 µg/mL. If the test sample was obtained from a patient, the method can further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

In certain embodiments, the kits (or components thereof), as well as the methods of determining the concentration of anti-HPgV-2 antibodies and/or HPgV-2 antigens in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

In particular embodiments, some of the differences between an automated or semi-automated system as compared to a non-automated system (e.g., ELISA) include the substrate to which the first specific binding partner (e.g., antigen) is attached (which can impact sandwich formation and analyte reactivity), and the length and timing of the capture, detection and/or any optional wash steps. Whereas a non-automated format such as an ELISA may, in certain embodiments, require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for-63-example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT®system, the following configuration is exemplary. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In certain embodiments, a sample suspected of containing anti-HPgV-2 antibody and/or HPgV-2 antigens is added to the holding chamber of the test cartridge and the cartridge is inserted into the I-STAT® reader. After the detection antibody or detectably labeled detection antigen has dissolved into the sample, a pump element within the cartridge forces the sample into a conduit containing the chip. Here it is oscillated to promote formation of the sandwich between the capture antigen (or capture antibody), anti-HPgV-2 antibody (or HPgV-2 antigen), and the labeled detection antibody (and/or detection antigen). In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of anti-HPgV-2 antibody or HPgV-2 antigen in the sample by means of an embedded algorithm and factory-determined calibration curve.

The methods and kits as described herein encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N morpholino) ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, and U.S. patent application Ser. No. 12/650,241, improved signal generation may be obtained, e.g., in an I-STAT® cartridge format, using a nucleic acid sequence linked to the signal antibody as a signal amplifier.

VII. HPgV-2 Immunogenic Compositions

In certain embodiments, provided herein are immunogenic composition compositions for treating or preventing HPgV-2 infection. In certain embodiments, provided herein are pharmaceutical compositions comprise one or more such immunogenic composition compounds (e.g., portion of proteins shown in SEQ ID NOs:2-11, 76-218, and 304-353) and a physiologically acceptable carrier. Immunogenic compositions may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, NT); AS-2 (Smith line Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Pharmaceutical compositions and immunogenic compositions within the scope of the present disclosure may also contain other compounds, which may be biologically active or inactive. For example, one or more immunogenic portions of other antigens may be present, either incorporated into a fusion polypeptide or as a separate compound, within the composition or immunogenic composition. Polypeptides may, but need not, be conjugated to other macromolecules as described, for example, within U.S. Pat. Nos. 4,372,945 and 4,474,757. Pharmaceutical compositions and immunogenic compositions may generally be used for prophylactic and therapeutic purposes.

Nucleic acid immunogenic compositions encoding a genome, structural protein or non-structural protein or a fragment thereof of HPgV-2 can also be used to elicit an immune response to treat or prevent HPgV-2 infection. Numerous gene delivery techniques are well known in the art, such as those described by Rolland (1998) Crit. Rev. Therap. Drug Carrier Systems 75: 143-198, and references cited therein. Appropriate nucleic acid expression systems contain the necessary DNA sequences for expression in the patient (such as a suitable promoter and terminating signal). In certain embodiments, the DNA may be introduced using a viral expression system (e.g., vaccinia, pox virus, retrovirus, or adenovirus), which may involve the use of a non-pathogenic (defective), replication competent virus. Suitable systems are disclosed, for example, in Fisher-Hoch et al. (1989) Proc. Natl. Acad. Sci. USA 55:317-321; Flexner et al. (1989) Ann. N. Y. Acad. Sci. 569:86-103; Flexner et al. (1990) Immunogenic composition 5: 17-21; U.S. Pat. Nos. 4,603,112, 4,769,330, 4,777,127 and 5,017,487; WO 89/01973.

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present disclosure (see, e.g., Remington's Pharmaceutical Sciences, 17th ed., 1989). Administration can be in any convenient manner, e.g., by injection, oral administration, inhalation, transdermal application, or rectal administration. Formulations suitable for oral administration can be composed of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

VIII. Compound Screening

In certain embodiments, the HPgV-2 virus, nucleic acids and proteins of the present disclosure are used to assay for antiviral compounds, including compounds that inhibit (1) viral interactions at the cell surface, e.g., viral transduction (e.g., block viral cell receptor binding or internalization); (2) viral replication and gene expression, e.g., viral replication (e.g., by inhibiting non-structural protein activity, origin activity, or primer binding), viral transcription (promoter or splicing inhibition, nonstructural protein inhibition), viral protein translation, protein processing (e.g., cleavage or phosphorylation); and (3) viral assembly and egress, e.g., viral packaging, and virus release. Assays to identify compounds with HPgV-2 modulating activity can be performed in vitro. Such assays can use full length HPgV-2 or a variant thereof, or a mutant thereof, or a fragment thereof. Purified recombinant or naturally occurring protein can be used in the in vitro methods of the invention. In addition to purified HPgV-2, the recombinant or naturally occurring protein can be part of a cellular lysate or a cell membrane. In certain embodiments, the binding assay is either solid state or soluble. In certain embodiments, the protein or membrane is bound to a solid support, either covalently or non-covalently. In particular embodiments, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In certain embodiments, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify HPgV-2-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the protein is washed, interference with binding, either of the potential modulator or of the known ligand or substrate, is determined. Often, either the potential modulator or the known ligand or substrate is labeled.

Many different chemical compounds can be used as a potential modulator or ligand in the screening assays of the invention. In certain embodiments, the assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), and Fluka Chemika-Biochemica Analytika (Buchs Switzerland). In certain embodiments, high throughput screening methods involve providing a combinatorial small organic molecule or peptide library containing a large number of potential therapeutic compounds (potential modulator or ligand compounds). Such libraries are then screened in one or more assays, as described herein, to identify those library members (particular chemical species or subclasses) that display a desired characteristic activity. The compounds thus identified can serve as lead compounds or can themselves be used as potential or actual therapeutics.

IX. Kits and Systems

In certain embodiments, provided herein are kits and systems comprising one or more reagents for use in a variety of diagnostic assays, including for example, immunoassays such as ELISA and "sandwich"-type immunoassays, as well as nucleic acid assay, e.g., PCR assays. Such kits and systems may preferably include at least a first peptide, or a first antibody or antigen binding fragment of the invention, a functional fragment thereof, or a cocktail thereof, or a first oligonucleotide or oligonucleotide pair, and means for signal generation. The kit's components may be pre-attached to a solid support, or may be applied to the surface of a solid support when the kit is used. The signal generating means may come pre-associated with an antibody or nucleic acid of the invention or may require combination with one or more components, e.g., buffers, nucleic acids, antibody-enzyme conjugates, enzyme substrates, or the like, prior to use. Kits and systems may also include additional reagents, e.g., blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit or system, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit or system will also typically include a means for containing the vial(s) in close confinement for commercial sale and/or convenient packaging and delivery (e.g., a box or other container).

In certain embodiments, the kits disclosed herein comprise at least one component for assaying the test sample for HPgV-2 (or a fragment thereof) and instructions for assaying the test sample for the HPgV-2 (or a fragment thereof). The at least one component for assaying the test sample for the HPgV-2 (or a fragment thereof) can include a composition comprising, for example, an antibody or antibodies against HPgV-2 (or a fragment, a variant, or a fragment of a variant thereof), which is optionally immobilized on a solid phase. In some embodiments, the kit can comprise at least one component for assaying the test sample for HPgV-2 by assay, e.g., chemiluminescent microparticle immunoassay, and instructions for assaying the test sample for an analyte by immunoassay, e.g., chemiluminescent microparticle immunoassay. For example, the kit can comprise at least one specific binding partner for HPgV-2 such as an anti-analyte, monoclonal/polyclonal antibody (or a fragment thereof that can bind to HPgV-2, a variant thereof that can bind to HPgV-2, or a fragment of a variant that can bind to HPgV-2), either of which can be detectably labeled. Alternatively or additionally, the kit can comprise detectably labeled HPgV-2 protein (or a fragment thereof that can bind to an anti-HPgV-2, monoclonal/polyclonal antibody or an anti-HPgV-2 DVD-Ig (or a fragment, a variant, or a fragment of a variant thereof)), which can compete with any HPgV-2 proteins in a test sample for binding to an anti-HPgV-2, monoclonal/polyclonal antibody (or a fragment thereof that can bind to HPgV-2, a variant thereof that can bind to HPgV-2, or a fragment of a variant that can bind to the HPgV-2) or an anti-HPgV-2 DVD-Ig (or a fragment, a variant, or a fragment of a variant thereof), either of which can be immobilized on a solid support. The kit can comprise one or more calibrators or controls, e.g., isolated or purified HPgV-2. The kit can comprise at least one container (e.g., tube, microtiter plates or strips, which can be already coated with a first specific binding partner, for example) for conducting the assay, and/or a buffer, such as an assay buffer or a wash buffer, either one of which can be provided as a concentrated solution, a substrate solution for the detectable label (e.g., an enzymatic label) or a stop solution. Preferably, the kit comprises all components, i.e., reagents, standards, buffers, diluents, etc. which are necessary to perform the assay. The instructions can be in paper form or computer-readable form such as a disk, CD, DVD or the like.

Any antibodies, such as an anti-biomarker antibody or an anti-HPgV-2 DVD-Ig, or tracer can incorporate a detectable label as described herein such as a fluorophore, a radioactive moiety, an enzyme, a biotin/avidin label, a chromophore, a chemiluminescent label or the like, or the kit can include reagents for carrying out detectable labeling. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the assay kit reagents, and the standardization of assays.

The kit can also optionally include other reagents required to conduct a diagnostic assay or facilitate quality control evaluations such as buffers, salts, enzymes, enzyme co-factors, enzyme substrates, detection reagents, and the like. Other components, such as buffers and solutions for the isolation and/or treatment of a test sample (e.g., pretreatment reagents) also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. Further, if the detectable label is at least one acridinium compound, the kit also can comprise a source of hydrogen peroxide, such as a buffer, a solution, and/or at least one basic solution. If desired, the kit can contain a solid phase, such as a magnetic particle, bead, test tube, microtiter plate, cuvette, membrane, scaffolding molecule, film, filter paper, disc or chip.

The kit (or components thereof), as well as the method of determining the presence, amount or concentration of HPgV-2 in a test sample by an assay, such as the assays described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT. Some of the differences between an automated or semi-automated system as compared to a non-automated system (e.g., ELISA) include the substrate to which the first specific binding partner (e.g., an anti-HPgV-2, monoclonal/polyclonal antibody (or a fragment thereof, a variant thereof, or a fragment of a variant thereof) or an anti-HPgV-2 DVD-Ig (or a fragment thereof, a variant thereof, or a fragment of a variant thereof) is attached; either way, sandwich formation and HPgV-2 reactivity can be impacted), and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT, Abbott Laboratories) may have a relatively shorter incubation time (e.g., approximately 18 minutes for ARCHITECT). Similarly, whereas a non-automated format, such as an ELISA, may incubate a detection antibody, such as the conjugate reagent, for a relatively longer incubation time (e.g., about 2 hours), an automated or semi-automated format (e.g., ARCHITECT) may have a relatively shorter incubation time (e.g., approximately 4 minutes for the ARCHITECT).

Other platforms available from Abbott Laboratories include, but are not limited to, AxSYM, IMx (see, e.g., U.S. Pat. No. 5,294,404, which is hereby incorporated by reference in its entirety), PRISM, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STATED, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an HPgV-2 assay to the I-STAT system, the following configuration may be employed. A microfabricated silicon chip is manufactured with a pair of gold amperometric working electrodes and a silver-silver chloride reference electrode. On one of the working electrodes, polystyrene beads (0.2 mm diameter) with immobilized anti-HPgV-2, monoclonal/polyclonal antibody (or a fragment thereof, a variant thereof, or a fragment of a variant thereof) or anti-HPgV-2 DVD-Ig (or a fragment thereof, a variant thereof, or a fragment of a variant thereof), are adhered to a polymer coating of patterned polyvinyl alcohol over the electrode. This chip is assembled into an I-STAT cartridge with a fluidics format suitable for immunoassay. On a portion of the wall of the sample-holding chamber of the cartridge, there is a layer comprising a specific binding partner for an analyte, such as an anti-HPgV-2, monoclonal/polyclonal antibody (or a fragment thereof, a variant thereof, or a fragment of a variant thereof that can bind the HPgV-2) or an anti-HPgV-2 DVD-Ig (or a fragment thereof, a variant thereof, or a fragment of a variant thereof that can bind the HPgV-2), either of which can be detectably labeled. Within the fluid pouch of the cartridge is an aqueous reagent that includes p-aminophenol phosphate.

In operation, a sample suspected of containing an HPgV-2 is added to the holding chamber of the test cartridge, and the cartridge is inserted into the I-STAT reader. After the specific binding partner for HPgV-2 has dissolved into the sample, a pump element within the cartridge forces the sample into a conduit containing the chip. Here it is oscillated to promote formation of the sandwich. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of HPgV-2 in the sample by means of an embedded algorithm and factory-determined calibration curve.

In certain embodiments, the methods and kits as described herein may include other reagents and methods for carrying out the assays. For instance, encompassed are various buffers such as are known in the art and/or which can be readily prepared or optimized to be employed, e.g., for washing, as a conjugate diluent, microparticle diluent, and/or as a calibrator diluent. An exemplary conjugate diluent is ARCHITECT conjugate diluent employed in certain kits (Abbott Laboratories, Abbott Park, Ill.) and containing 2-(N-morpholino) ethanesulfonic acid (MES), a salt, a protein blocker, an antimicrobial agent, and a detergent. An exemplary calibrator diluent is ARCHITECT human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-Stat cartridge format, using a nucleic acid sequence linked to the signal antibody as a signal amplifier.

EXAMPLES

Example 1

Discovery of a Novel Virus Tentatively Named HPgV-2

A cohort of 105 serum samples collected from patients in the United States with chronic hepatitis were pooled into groups of 6 samples each (50 µl×6=300 µl serum per pool)

and treated with a mix of DNases (Turbo DNase, Ambion, Foster City, Calif. and Baseline DNase, Epicentre, San Diego, Calif.) at room temperature for 2.5 hours, followed by bead-based extraction using Qiagen's EZ1 viral extraction kit according to the manufacturer's protocol. Extracted nucleic acid from individual pools were grouped into two pools (N=12 samples) then prepared for next-generation sequencing library construction and indexing using a modified TruSeq (Illumina, San Diego, Calif.) protocol as previously described (Grard, et al. 2012; PLoS Pathogens 8(9): e1002924). The libraries were sequenced by Elim Biopharmaceuticals (Elim Biopharmaceuticals, Hayward, Calif.) in 2 lanes using Illumina's HiSeq2000 instrument. A total of 255 million raw paired-end reads were generated. These reads were processed using a customized bioinformatics pipeline titled sequence-based ultra-rapid pathogen identification (SURPI) (Naccache et al. 2014; Genome Research in press). By protein alignment, 3 paired-end reads were identified with remote homology to simian pegivirus, GB virus A in a single pool consisting of 32.7 million raw reads. PCR using primers (SEQ IDs:219 and 220) targeting one of the paired-end reads followed by confirmatory Sanger sequencing was used to pinpoint the individual sample containing HPgV-2.

To recover additional sequences from the viral genome, libraries were prepared from the remaining pooled nucleic acids (N=6 samples) using two library methods: Illumina TruSeq and Rubicon Genomics ThruPLEX (Ann Arbor, Mich.). These libraries were indexed and sequenced using Illumina MiSeq, generating a total of 13.4 million raw paired-end reads. The genome of the novel pegivirus was then reconstructed using (1) identification of overlapping reads by BLASTn (nucleotide) alignment to existing contigs at an e-value cutoff of $1\times10^{-8}$, (2) identification of additional reads by BLASTx (translated nucleotide) alignment at an e-value cutoff of $1\times10^{-2}$ to the published sequence of GBV-A (now Pegivirus A, NC_001837) as a reference, and (3) iterative de novo assembly and reference-based assembly to existing contigs using the PRICE aligner (Ruby, et al., 2013; G3 3:865-880) and Geneious (Biomatters, Auckland, New Zealand), respectively. This resulted in the generation of six contiguous sequences (contigs) spanning ~60% of the estimated pegivirus genome. These contigs were verified and gaps were closed using bridging PCR (primers shown in Table 18) and confirmation of resulting amplicons by Sanger sequencing. To recover the 5' and 3' ends, we ran a Rapid Amplification of cDNA Ends (RACE) procedure according to the manufacturer's instructions (FirstChoice RLM-RACE Kit, Ambion, Foster City, Calif.). The 3' RACE protocol required the addition of a poly(A)-tail to the 3' terminus with poly-A polymerase (New England BioLabs, Ipswich, Mass.) prior to RACE. The final 9,778-nt pegivirus draft genome included 604 sequence reads from the Illumina HiSeq run and 2,571 reads from the Illumina MiSeq run, with 87.8% of the assembled genome confirmed by PCR and Sanger sequencing All confirmatory Sanger sequencing was performed by purifying amplicons on a 2% agarose gel, cloning them into plasmid vectors using TOPO TA (Invitrogen, Carlsbad, Calif.), and sending them to an outside company (Elim Biopharmaceuticals, Hayward, Calif.), for Sanger sequencing in both directions using vector primers M13F and M13R.

TABLE 18

| Sequence_Name | Sequence | Tm | SEQ ID NO: |
|---|---|---|---|
| HPgV-2_set_1F | GAG TCA CGC GGG GTG CTT | 60.9 | 219 |
| HPgV-2_set_1R | CTT AAT ATA AGG GGC CAT ACT TTT GA | 52.9 | 220 |
| HPgV-2_set_2F | TGG AAC CAG TCG TGT TGG AG | 60.5 | 221 |
| HPgV-2_set_2R | GAA CAG CAG CAG GGG TCT AG | 62.5 | 222 |
| HPgV-2_set_3F | CTA GAC CCC TGC TGC TGT TC | 62.5 | 223 |
| HPgV-2_set_3R | TGA CTA CAG CCA CAC TTG GT | 58.4 | 224 |
| HPgV-2_set_4F | ATA TGG GAG CTA CCA CTG CGG T | 64.2 | 225 |
| HPgV-2_set_4R | TAA CAG GAC AGA ATC TAG GTA TGG AG | 64.6 | 226 |
| HPgV-2_set_5F | TGT CTA TTG CTC TAC CTC CAG GTG | 65.2 | 227 |
| HPgV-2_set_5R | TTC CAA AGC AAC GTA ACA CGG CG | 64.6 | 228 |
| HPgV-2_set_6F | CGC CGT GTT ACG TTG CTT TGG AA | 64.6 | 229 |
| HPgV-2_set_6R | TTA CCA GAA CCA GTA GGG GCA TAG | 65.2 | 230 |
| HPgV-2_set_7F | ACA GTC ACA TTC CAA CAT TGA TGA ATA C | 64.4 | 231 |
| HPgV-2_set_7R | TGC TCC CCT TCT ACC ACG ACC | 65.3 | 232 |
| HPgV-2_set_8F | TAG GCG TGT GGT TTT CCG GTC T | 64.2 | 233 |
| HPgV-2_set_8R | CCA ATC CCA CAC AGC GCG TAG A | 65.8 | 234 |
| HPgV-2_set_9F | TCT ACG CGC TGT GTG GGA TTG G | 65.8 | 235 |
| HPgV-2_set_9R | GGG TCT CAA ACT TGA TTG GAG GC | 64.6 | 236 |
| HPgV-2_set_10F | CTA TGC CCC TAC TGG TTC TGG TAA | 65.2 | 237 |

TABLE 18-continued

| Sequence_Name | Sequence | Tm | SEQ ID NO: |
|---|---|---|---|
| HPgV-2_set_10R | GTA TTC ATC AAT GTT GGA ATG TGA CTG T | 64.4 | 238 |
| HPgV-2_set_11F | ACT TAT TGA CTG ACA CAG GCG ACG | 65.2 | 239 |
| HPgV-2_set_11R | TGC ATG CGC AAT GCA GCA GTA CAT | 65.2 | 240 |
| HPgV-2_set_12F | GTG CCC ATA AGT GGC TAT TAG CTA T | 64.1 | 241 |
| HPgV-2_set_12R | TGC TTA ATT GTT GGC CAA ATC TTT CAC | 63.7 | 242 |
| HPgV-2_set_13F | ACG ATT CCG TGT GCC TAT GAT TGG | 65.2 | 243 |
| HPgV-2_set_13R | CTG GGT TAC ATA AGT TAG TAG ACA TGC | 65.3 | 244 |
| HPgV-2_set_14F | TCT CCG CCT CCA GCA GTT CAA | 63.2 | 245 |
| HPgV-2_set_14R | AGC CGC AGT AGG ATA CAT GAC AAT A | 64.1 | 246 |
| HPgV-2_set_15F | TGT GAT ATC ACA GGA AAA GTT GTC GG | 64.6 | 247 |
| HPgV-2_set_15R | ACA GTC ACA GCC GCA GTA GGA TA | 64.6 | 248 |
| HPgV-2_set_16F | GAG AAA ATG ATC CTG GGC GAT CCT G | 67.4 | 249 |
| HPgV-2_set_16R | GCC GTG ATG GTG CTA TCA AAG CA | 64.6 | 250 |
| HPgV-2_set_17F | GGG ACA CCT CAA CCC TGA AG | 62.5 | 251 |
| HPgV-2_set_17R | TCA CTG CGG TAC CCA TTG AC | 60.5 | 252 |
| HPgV-2_set_18F | ATA TGG GAG CTA CCA CTG CGG T | 64.2 | 253 |
| HPgV-2_set_18R | GGT ACA GTA UT GAG GTA GCT TTC AG | 64.6 | 254 |
| HPgV-2_set_19F | CTT TTT GGT GCG CAG TGT TTG CCT | 65.2 | 255 |
| HPgV-2_set_19R | TGT CAG GGA AGA CAA CAC CAC GAT | 65.2 | 256 |
| HPgV-2_set_20F | ACA CTC ACA GGG CGT GCT GAA A | 64.2 | 257 |
| HPgV-2_set_20R | ACG CCA AGT TCT CAC CAG TGA TG | 64.6 | 258 |
| HPgV-2_set_21F | GTG TGG CTG TAG TCA AAA GTA TGG C | 65.8 | 259 |
| HPgV-2_set_21R | CAG CAG TAC ATG GCA CCA CTC G | 65.8 | 260 |
| HPgV-2_set_22F | TTC GGT CAT CGA CTG CGG GTG T | 65.8 | 261 |
| HPgV-2_set_22R | CCA GCC AAG TTC CTG CAA TAG CTA A | 65.8 | 262 |
| HPgV-2_set_23F | TTC ACT GCG CTT GCT GGC TTG G | 65.8 | 263 |
| HPgV-2_set_23R | CCG TAA GGT GCC AGT GCC TGT | 65.3 | 264 |
| HPgV-2_set_24F | AAG CAT CAA TCT GAA AGC TAC CTC AAA | 63.7 | 265 |
| HPgV-2_set_24R | TGA ATC TTA TAG TGT CGT CCA AGT G | 62.5 | 266 |
| HPgV-2_set_25F | CTGTGACTGCCCCTTTGGAA | 60.5 | 267 |
| HPgV-2_set_25R | CATGCCAACGTCCGTGTATG | 60.5 | 268 |
| HPgV-2_set_26F | AAC CCT TGC AAT TCT GGC CGA TGA | 65.2 | 269 |
| HPgV-2_set_26R | AGA TCC CTG ACT GCT TGC GCC A | 65.8 | 270 |
| HPgV-2_set_27F | CCC ACG GTC CTG ATG ATA GCA T | 64.2 | 271 |
| HPgV-2_set_27R | GCT AAC CAG CCA AGT TCC TGC AA | 64.6 | 272 |
| HPgV-2_set_28F | AAG TGA AAG ATT TGG CCA ACA ATT AAG CAA | 65.1 | 273 |
| HPgV-2_set_28R | CCA CGC AGG TGA GCA GCC AA | 64.6 | 274 |
| HPgV-2_set_29F | ACA ATT ATT ACA AAA GAA GCC CCA T | 59.2 | 275 |
| HPgV-2_set_29R | AGT CAC AGC CGC AGT AGG A | 59.5 | 276 |

TABLE 18-continued

| Sequence_Name | Sequence | Tm | SEQ ID NO: |
|---|---|---|---|
| HPgV-2_set_30F | TTG ACA TGA CAG CGT CGG TG | 60.5 | 277 |
| HPgV-2_set_30R | AGCGCGCATCTGATCTACAA | 58.5 | 278 |
| HPgV-2_set_31F | AAC AGC GGT TGA TGT CTC C | 57.5 | 279 |
| HPgV-2_set_31R | AAA GAT GCG CGC AAA CAC C | 57.5 | 280 |
| HPgV-2_set_32F | AGCGCGCATCTGATCTACAA | 58.5 | 281 |
| HPgV-2_set_32R | GCT AGT GCT ATA CTC GCT CTG CTT | 65.2 | 282 |
| HPgV-2_set_33F | ATG ATG CAT GGC AGG TTC GCC AA | 64.6 | 283 |
| HPgV-2_set_33R | GAT CAA TCG TGA CCT TAG CCT GC | 64.6 | 284 |
| HPgV-2_set_34F | AAC TCG GCG ACC AGT GCC AAA AT | 64.6 | 285 |
| HPgV-2_set_34R | TGT CTG CGC GCA AAA TGC CAG C | 65.8 | 286 |
| HPgV-2_set_35F | GGC AAA GAC CTT CAG ACA ATC TGG | 65.2 | 287 |
| HPgV-2_set_35R | CAC CCC GAC AAC TU TCC TGT GA | 64.5 | 288 |
| HPgV-2_set_36F | TTG ATC GTG CAA AGG GAT GGG TC | 64.6 | 289 |
| HPgV-2_set_36R | CTA ACA GTC CAA GCC AAC CTG CA | 64.5 | 290 |
| HPgV-2_set_37F | GCC ATG AGG GAT CAT GAC ACT G | 64.5 | 291 |
| HPgV-2_set_37R | TTT GCA CGA TCA GCG TTC CCG T | 65.2 | 292 |
| HPgV-2_set_38F | CTG TCC TGT TAC TCC ATA CCT AGA TT | 64.6 | 293 |
| HPgV-2_set_38R | CG ACA CCT GGA GGT AGA GCA A | 63.2 | 294 |
| HPgV-2_set_39F | CCT CCA ATC AAG TTT GAG ACC C | 62.1 | 295 |
| HPgV-2_set_39R | GTA CAC TCC AGC GCG CAT CT | 62.5 | 296 |
| HPgV-2_set_40F | ACC AAG TGT GGC TGT AGT CA | 58.4 | 297 |
| HPgV-2_set_40R | CCC CTG TTG TAT GCC TAG CC | 62.5 | 298 |

Example 2

Confirmation of the Novel Virus, HPgV-2

This example describes methods used to confirm the presence of HPgV-2 virus in biological samples.

A. Sample Pre-treatment and RNA Extraction

To independently verify and confirm the novel virus, plasma collected from the index patient (harboring UC0125.US) was evaluated at Abbott laboratories. The plasma sample (130 µl) containing HPgV-2 was thawed at room temperature. The sample was spun at 2650 g for 5 min at room temperature and the supernatant was transferred to a fresh tube. The sample was pre-treated with benzonase for 2 hrs at 37° C. to degrade free DNA and RNA. The 10× benzonase buffer was as follows: 200 mM Tris-Cl pH 7.5, and 100 mM NaCl, 20 mM MgCl$_2$. The benzonase reaction was as follows: 14 µl 10× benzonase buffer, 130 µl plasma, and 0.5 µl (250 U/µl benzonase: 892 U/ml final) (Sigma, E8263-25KU). The sample was then filtered with 0.22 µM spin filters (Millipore, UFC306V00) by spinning at 2650 g for 3 min.

The Qiagen Viral Mini extraction spin protocol was used for viral RNA purification. Alternatively, the Total Nucleic Acid prep can be used and samples processed on an Abbott m2000 according to manufacturer instructions (not described here). This protocol is suitable for purification of viral RNA from 140 µl plasma, serum, urine, cell culture media, or cell-free body fluids using a microcentrifuge. Larger starting volumes, up to 560 µl (in multiples of 140 µl), can be processed by increasing the initial volumes proportionally and loading the QIAamp Mini column multiple times, as described below in the protocol.

Before starting the purification protocol: i) equilibrate samples to room temperature (15-25° C.); ii) equilibrate Buffer AVE to room temperature for elution later; iii) check that Buffer AW1 and Buffer AW2 have been prepared according to the instructions; and iv) add carrier RNA reconstituted in Buffer AVE to Buffer AVL according to instructions.

The purification procedure is as follows. Step 1, pipet 560 µl of prepared Buffer AVL containing 2 µl of tRNA-MagMax carrier RNA into a 1.5 ml microcentrifuge tube. Step 2, add 140 µl plasma, serum, urine, cell-culture supernatant, or cell-free body fluid to the Buffer AVL-carrier RNA in the microcentrifuge tube. Mix by pulse-vortexing for 15 seconds. Step 3, incubate at room temperature (15-25° C.) for 10 min. Viral particle lysis is complete after lysis for 10 min at room temperature. Longer incubation times have no effect on the yield or quality of the purified RNA. Potentially infectious agents and RNases are inactivated in Buffer AVL.

Step 4, briefly centrifuge the tube to remove drops from the inside of the lid. Step 5, add 560 µl of ethanol (96-100%)

to the sample, and mix by pulse-vortexing for 15 seconds. After mixing, briefly centrifuge the tube to remove drops from inside the lid. Step 6, carefully apply 630 µl of the solution from step 5 to the QIAamp Mini column (in a 2 ml collection tube) without wetting the rim. Close the cap, and centrifuge at 6000×g (8000 rpm) for 1 minute. Place the QIAamp Mini column into a clean 2 ml collection tube, and discard the tube containing the filtrate. Close each spin column to avoid cross-contamination during centrifugation. If the solution has not completely passed through the membrane, centrifuge again at a higher speed until all of the solution has passed through.

Step 7, carefully open the QIAamp Mini column, and repeat step 6. If the sample volume was greater than 140 µl, repeat this step until all of the lysate has been loaded onto the spin column. Step 8, carefully open the QIAamp Mini column, and add 500 µl of Buffer AW1. Close the cap, and centrifuge at 6000×g (8000 rpm) for 1 min. Place the QIAamp Mini column in a clean 2 ml collection tube (provided), and discard the tube containing the filtrate. It is not necessary to increase the volume of Buffer AW1 even if the original sample volume was larger than 140 µl.

Step 9, carefully open the QIAamp Mini column, and add 500 µl of Buffer AW2. Close the cap and centrifuge at full speed (20,000×g; 14,000 rpm) for 3 min. Continue directly with step 11, or to eliminate any chance of possible Buffer AW2 carryover, perform step 10, and then continue with step 11. Step 10, optionally place the QIAamp Mini column in a new 2 ml collection tube, and discard the old collection tube with the filtrate. Centrifuge at full speed for 1 min.

Step 11, place the QIAamp Mini column in a clean 1.5 ml microcentrifuge tube. Discard the old collection tube containing the filtrate. Carefully open the QIAamp Mini column and add 60 µl of Buffer AVE equilibrated to room temperature. Close the cap, and incubate at room temperature for 1 min. Centrifuge at 6000×g (8000 rpm) for 1 min. A first elution with 60 µl of Buffer AVE was performed and aliquots of 8 µl or 5 µl were stored at −20° C. or −70° C. A second elution of 60 µl was performed and frozen in one tube.

Step 12, RNA stocks are concentrated with RNA Clean & Concentrator-5 columns (Zymo Research) by adding 2 volumes RNA Binding Buffer to each sample RNA, mixing, then adding an equal volume of ethanol (95-100%). Samples are transferred to the Zymo-Spin™ IC Column in a 2 ml collection tube, centrifuged for 30 seconds and the flow-through is discarded. 400 µl of RNA Prep Buffer is added to the column, centrifuged for 30 seconds and the flow through discarded, followed by 700 µl of RNA Wash Buffer, centrifuging for 30 seconds, and discarding of the flow-through. A final 400 µl volume of RNA Wash Buffer is added to the column and centrifuged for 2 minutes to ensure complete removal of the wash buffer, then the column is transferred carefully to an RNase-free tube. 7 µl of DNase/RNase-Free water is added directly to the column matrix and centrifuged for 30 seconds to elute the RNA.

B. Reverse Transcription cDNA was generated by random hexamer priming using SS RTIII (Invitrogen: 18080-051) with the HPgV-2 sample RNA as template. This was to allow detection by PCR using the primers listed in below (section C.) in Table 1.

The following volumes were employed: 7.6 µl sample RNA, 1 µl of random hexamer (50 ng/µl), 0.4 µl of oligo dT (50 µM), 1 µl dNTP mix (10 mM). This was heated at 65° C. for 5 min and returned to ice to add 10 µl of master mix. The mastermix was as follows: 2 µl 10 RT buffer, 4 µl 25 mM MgCl$_2$, 2 µl 0.1 M DTT, 1 µl RNAseOUT (40 U/µl), 1 µl Superscript III RT (200 U/µl). Incubate for 10 min at 25° C., then 80 min at 50° C. Terminate at 85° C. for 5 min then 4° C. Add 1 µl of RNAseH (Invitrogen, Y01220) to reactions and incubate for 20 min at 37° C. and then to 4° C. cDNA was aliquoted into 2×10 µl samples and frozen at −80 C.

C. HPgV-2 Primer Design and Testing

The following primers, in Table 1, were shown to work for amplifying portions of the recited region of HPgV-2.

TABLE 1

| Forward Primers | | | | |
|---|---|---|---|---|
| Region detected | Name of Primer | v35 coordinates | Sequence (5'→3') | SEQ ID NO: |
| S | 35F | 24 | TATTGCTACTTCGGTACGCCTAAT | 12 |
| S | 81F | 76 | AAGGGCCTAGTAGGACGTGTGACA | 13 |
| S | 1F | 119 | CACTGGG GTGAGCGGAG GCAGCAC | 14 |
| S | 15F | 133 | GAG GCAGCACCGA AGTCGGGTGA A | 15 |
| E1 | 307F | 702 | TGCCACCCATCCTATCTGCT | 16 |
| E1 | 487F | 882 | TATTGCTTGGTATGGCTGGGGTAT | 17 |
| E1 | 804F | 893 | ATGGCTGGGGTATACCTAARACA | 18 |
| E2 | 1147F | 1133 | TGGCGTACAAGCATCAATC | 19 |
| E2 | 1392F | 1374 | ACCGATTTCCGCTTTGTGCTAT | 20 |
| E2 | 1840F | 1819 | CCTGGGCTTGGGAAATGG | 21 |
| X | 2283F | 2372 | CATG GGTGATTTCG CGGACTACT | 22 |
| X | 2368F | 2487 | CCTCGGGGA CATCACGGGC ATCTA | 23 |
| X | 2584F | 2702 | CTGTTAATGCTGCGCTCAATAGAA | 24 |
| NS2 | 2801F | 2919 | GCGGGTATTTGGTCTTGAGGTTTG | 25 |

TABLE 1-continued

| Region detected | Name on Primer | v35 coordinates | Sequence (5'→3') | SEQ ID NO: |
|---|---|---|---|---|
| NS2 | 2978F | 3372 | TTTGGATCACGCGGCACATACATA | 26 |
| NS2 | 3028F | 3423 | ACGGGTGGCGCAAGCAGTCAGG | 27 |
| NS2 | NS23_F5 | 3478 | GAGGAGCCCACCTTTACTGA | 28 |
| NS3 | Primer Set 2 | 3601 | GAAGATCTGCCACCTGGTTT | 29 |
| NS3 | Primer Set 7 | 3668 | TCCTTCCTTAAGGCGACACT | 30 |
| NS3 | 3535F | 3929 | GAGCCGGGTTTGGGTGATGAATAA | 31 |
| NS3 | Primer Set 4 | 3940 | TGGGTGATGAATAACAACGG | 32 |
| NS3 | Primer Set 3 | 4005 | AATGACGACGTCTGTTTGGA | 33 |
| NS3 | 3681 | 4076 | ACGCGTTGATGCTCGGTGGTTACT | 34 |
| NS3 | Primer Set 15 | 4189 | CCAGCTGTGACACCAACATA | 35 |
| NS3 | Primer Set 1 | 4508 | AGTCATTTGCGACGAGTGTC | 36 |
| NS3 | 5353F | 5348 | GGC CCA CGG TCC TGA TGA TA | 37 |
| NS3 | 5353Fv2 | 5348 | GGCCCAYGGTCCAGACGATR | 38 |
| NS3 | 5353Fv128 | 5348 | GGCCCATGGTCCGGATGATG | 39 |
| NS3 | 5605Fv2 | 5600 | CCGTTTGGAGYGTTGAYAAC | 40 |
| NS4B | 5605F | 5600 | CTGTTTGGAGCGTTGAGGTC | 41 |
| NS5A | 6466F | 6555 | TACYGGCACCTTGTTGACCACCTG | 42 |
| NS5A | 6383F | 6778 | CTAGAGCGGCGGGGCGACAAA | 43 |
| NS5A | 6608F | 7003 | GAGGCGGTTGAGCTGCTGGAAGAG | 44 |
| NS5A | 7284F | 7279 | TAG TTC AGG CGG CTT CAC GGT TTG | 45 |
| NS5A | 7499F | 7588 | TGCGCCGT ACCAACAAAG | 46 |
| NS5A | 7661F | 7606 | TGT CAC CCC TTG CAA ACT CCT ATT | 47 |
| NS5B | 7783F | 8178 | AGTGTACGACGCTCCAATG | 48 |
| NS5B | 8285F | 8280 | GCA CGA GTC GCG GAG AAA ATG A | 49 |
| NS5B | 7886F | 8283 | ACG AGTCGCGGAG AAAATGA | 50 |
| NS5B | 8385F | 8380 | CGC GCC TAC TGG AAC AAT | 51 |
| NS5B | 8781F | 8776 | ACG CGC TTGATG ACT ATG GGT TTA | 52 |
| NS5B | 9080F | 9075 | TTG ACG TCA CAC GGT AAC AG | 53 |
| NS5B/3'UTR | 3raceo_9186F | 9275 | TGATCAAGTYGGGCGGGTGGAAT | 357 |
| NS5B/3'UTR | 3raceo2_9249F | 9338 | GAACACCACARCCCGAACCAA | 358 |
| NS5B/3'UTR | 9276F | 9394 | CGTCCGTACGAAAATTTGCACTTGAG | 359 |
| NS5B/3'UTR | 9312F | 9429 | CGCAATCGTGGTGCTAGTCGCTTACG | 360 |
| NS5B/3'UTR | 3racei_9380F | 9469 | GCTAGTGCTATACTCGCTCTGCTT | 361 |

| Reverse Primers | | | | |
|---|---|---|---|---|
| Region detected | Name on Primer | v35 coordinates | Antiparallel Sequence (5'→3') | SEQ ID NO: |
| S | 208R | 297 | TGATAGGGTG GCGGCGGGC | 362 |
| S | E5RACEin311R | 400 | ATACCTCCTC GGGCTGCC | 363 |
| S | E313R | 430 | ATGGGAGCTA CCACTGCGGT G | 364 |
| S | 345R | 462 | GCCGGTCACC AAGTCGTRTG CAG | 365 |
| S | E5RACEo448R | 537 | GGTATGTGTT CSATCCGGTC CAAA | 366 |

TABLE 1-continued

| | | | | |
|---|---|---|---|---|
| E2 | 1042R | 1131 | ATCCTTCT GGCTAGTCCT ACGGTT | 367 |
| E2 | 1227R | 1316 | TT TATTTGTTCA TGGGGGTCGTG | 368 |
| E2 | 957R | 1352 | GAAAACATCA CGCGTCCATA CAC | 369 |
| E2 | 990R | 1385 | CACCAGCACC GATTTCCGC | 370 |
| E2 | 1558R | 1539 | TTGTATTCTT GACCGCCGG | 371 |
| E2 | 2009R | 1993 | GTAATCCGAC GCCTGGCCG | 372 |
| X | 2331R | 2302 | TGTGTCTGCC GGTTGCGA | 373 |
| X | 2628R | 2717 | TCTCACCCTG TAATGCTGCG CT | 374 |
| NS2 | 3015R | 3133 | CTGTCGGTTG TGGTCCTCTC GGTC | 375 |
| NS2 | 3317R | 3435 | AAGTCTCGGA ACGGGTGGCG CAA | 376 |
| NS3 | Primer Set 5 | 3548 | TGGACAATTGCTTGGAGGTA | 377 |
| NS3 | 3553R | 3690 | TCCTTCCTTA AGGCGACACT | 378 |
| NS3 | 3607R | 3744 | ATCGTGGTGT TGTCTTCCCT | 379 |
| NS3 | 3402R | 3797 | CACTGTATGC GACCGGCCA | 380 |
| NS3 | 3536R | 3922 | TAGACCCCTG CTGCTGTTCG CCGA | 381 |
| NS3 | Primer Set 4 | 4025 | CTGTCCCACGCACATAGATC | 382 |
| NS3 | Primer Set 3 | 4073 | TTTGTGTGATCACGGTCATG | 383 |
| NS3 | Primer Set 15 | 4372 | CCAAGTGTGGCTGTAGTCAAA | 384 |
| NS3 | 4092R | 4487 | GACGAATCTG CGGGGCTATG CTGT | 385 |
| NS3 | 4151R | 4446 | GCTACTCGGC ATTGGCGCAG | 386 |
| NS3 | Primer Set 1 | 4584 | AAAGCTGGAGTGAAGACCGT | 387 |
| NS4 | 5325R | 5414 | AACAACAGTAACAA AACACCCCT | 388 |
| NS4B | 6109R | 6104 | CTTCCTGTTTGGGTGCCTTAC | 389 |
| NS4B | 6129R | 6124 | TTACAGGTTGGGAAGCCGTGGTCG | 390 |
| NS4B | 6129Rv2 | 6124 | TTACAGGTTG GGAGGCCGTG GTYG | 391 |
| NS4B | 6129Rv128 | 6124 | TTACGGGTTG GGAAGCCGTG GTCG | 392 |
| NS5A | 6701R | 6789 | WTCGTGGAKY TAGAGCGSCG G | 393 |
| NS5A | 6907R | 7293 | GTAGTTCAGG CGGCTTCACG GTTT | 394 |
| NS5A | 7012R | 7407 | AGTTTGAGGC CACCGCAGTA CCA | 395 |
| NS5B | 7850R | 7939 | TTGAYGTCYC CGAGCGGCAG G | 396 |
| NS5B | 8211R | 8606 | GTTGTCGGGG TGCGTAGCTG TCG | 397 |
| NS5B | 8278R | 8666 | CTCAAGGTTC GCGCAGCT | 398 |
| NS5B | 8080R | 8076 | AGGATGCTGTGTCAAAGATGCGCG | 399 |
| NS5B | 9012R | 9007 | TATCCTACTGCGGCTGTGACTGTC | 400 |
| NS5B | 9227R | 9222 | CCTCAGCGTTGGCCTTCTTTG | 401 |
| 3'UTR | 9616R | 9611 | CCTATCCGAGTTGGGCAAG | 402 |
| NS5B | 9363R | 9358 | GTAAGAACACCACAGCCCGAACCA | 403 |
| 3'UTR | 9690R | 9808 | ACCACTTAAT GGTCGTAACT CGACC | 404 |
| 3'UTR | 9749R | 9867(END) | GTCAACGGCC CCTTTCATT | 405 |

The forward and reverse primers listed in Table 1 form primer pairs in the order listed in the table. For example, the following are primer pairs based on SEQ ID NOs are provided: 12:362, 13:363, 14:364, 15:365, 16:366, 17:367, 18:368, 19:369, 20:370, 21:371, 22:372, 23:373, 24:374, 25:375, 26:376, 27:377, 28:378, 29:379, 30:380, 31:381, 32:382, 33:383, 34:384, 35:385, 36:386, 37:387, 38:388, 39:389, 40:390, 41:391, 42:392, 43:393, 44:394, 45:395, 46:396, 47:397, 48:398, 49:399, 50:400, 51:401, 52:402, 53:403, 357:404, and 358:405. Other combinations of these primers can be used to generate other primer pairs.

Results

The presence of HPgV-2 in the UC0125.US sample was initially confirmed using the following primer pairs found in NS3: 3841F & 4460R (SEQ IDs: 38 & 39), 3987F & 4398R (SEQ IDs: 40 & 41); in NS5A: 6689F & 7318R (SEQ IDs: 42 & 43), 6914F and 7213R (SEQ IDs: 44 & 45); in NS2-NS3: 3334F & 3708R (SEQ IDs: 34 & 35); and in E1-E2: 793F & 1263R (SEQ IDs: 14 & 15). Bands of the expected sizes were detected after one round of 40 cycle RT-PCR and sequenced by Sanger, providing conclusive evidence of the existence of the HPgV-2 virus.

D. Next Generation Sequencing Library Prep

A randomly primed library was prepared from the sample discussed above for next generating sequencing (NGS) using the Ovation® RNA-SeqV2 kit (NuGen, Part No. 7102) according to manufacturer recommendations. Use 5 µl of each RNA (pre-treated and extracted as above in (A) as starting material. The thermal cycler programs were as follows.

Program 1: First Strand Primer Annealing (For RNA inputs >1 ng) 65° C.—5 min, hold at 4° C.

Program 2: First Strand Synthesis 4° C.—1 min, 25° C.—10 min, 42° C.—10 min, 70° C.—15 min, hold at 4° C.

Second strand cDNA Synthesis

Program 3: Second Strand Synthesis 4° C.—1 min, 25° C.—10 min, 50° C.—30 min, 80° C.—20 min, hold at 4° C.

Program 4: SPIA® Amplification 4° C.—1 min, 47° C.—60 min, 80° C.—20 min, hold at 4° C.

First Strand cDNA Synthesis—Thaw the First Strand cDNA Synthesis reagents (blue) and nuclease-free Water (green). Spin A3 ver 1 briefly and place on ice. Vortex A1 ver 4 and A2 ver 3, spin and place on ice. Leave nuclease-free water at room temperature. mix 2 µl of A1 and 5 µl of total RNA sample (500 µg to 100 ng) in a 0.2 ml PCR tube. Place the tubes in a thermal cycler running Program 1 (65° C.—2 min, hold at 4° C. or 65° C.—5 min, hold at 4° C.). Once the thermal cycler reaches 4° C., remove tubes and place on ice. Prepare First Strand Master Mix. Be sure to pipet A3 enzyme slowly and rinse out tip at least five times into buffer.

Per sample combine 2.5 µl Buffer Mix A2+0.5 µl Enzyme Mix A3. Add 3 µl of First Strand Master Mix to each tube, mix by pipetting, spin and place on ice. Place the tubes in a thermal cycler running Program 2 (4° C.—1 min, 25° C.—10 min, 42° C.—10 min, 70° C.—15 min, hold at 4° C.). Once the thermal cycler reaches 4° C., remove tubes, spin and place on ice. Continue immediately with Second Strand cDNA Synthesis.

Second Strand cDNA Synthesis—Resuspend the Agencourt® RNAClean® XP beads provided with the Ovation RNA-Seq System V2 and leave at room temperature for use in the next step. Thaw the Second Strand cDNA Synthesis reagents (yellow). Spin B2 ver 2 briefly and place on ice. Vortex B1 ver 3, spin and place on ice. Prepare Second Strand Master Mix. Be sure to pipet B2 enzyme slowly.

Per sample combine: 9.7 µl Buffer Mix B1+0.3 µl Enzyme Mix B2. Mix well. Add 10 µl of Second Strand Master Mix to each reaction tube, mix by pipetting, spin and place on ice. Place the tubes in a thermal cycler running Program 3 (4° C.—1 min, 25° C.—10 min, 50° C.—30 min, 80° C.—20 min, hold at 4° C.). Once the thermal cycler reaches 4° C., remove tubes, spin and place on bench top. Continue immediately with Purification of cDNA.

Purification of cDNA—Ensure the RNAClean XP beads have reached room temperature. Mix the beads by inverting several times. At room temperature, add 32 µl of RNAClean XP beads to each reaction tube and mix by pipetting 10 times. Incubate at room temperature for 10 minutes. Transfer the tubes to the magnet and let stand for an additional 5 minutes. Remove only 45 µl of the binding buffer. Add 200 µl of freshly prepared 70% ethanol and let stand for 30 seconds. Remove the ethanol using a pipette. Repeat the ethanol wash 2 more times. Remove all excess ethanol after the final wash and let beads air dry for 15 to 20 minutes. Ensure the tubes have completely dried and no residual ethanol is left. Continue immediately with SPIA Amplification, with the cDNA bound to the dry beads.

SPIA Amplification—SPIA is an isothermal strand-displacement amplification process that uses a DNA/RNA chimeric SPIA primer, DNA polymerase and RNAse H to amplify DNA. Thaw the SPIA Amplification reagents (red). Invert C3 ver 7 to mix, spin and place on ice. Vortex C1 ver 9 and C2 ver 11, spin and place on ice. Prepare SPIA Master Mix. Per sample combine 20 µl Buffer Mix C2+10 µl Primer Mix C1+10 µl Enzyme Mix C3. Add 40 µl of SPIA Master Mix to each reaction tube and resuspend beads thoroughly by pipetting. Place on ice. Place the tubes in a thermal cycler running Program 4 (4° C.—1 min, 47° C.—60 min, 80° C.—20 min, hold at 4° C.). Once the thermal cycler reaches 4° C., remove tubes, spin and place on ice.

Remove beads with magnet and transfer to new tube; store SPIA cDNA at −20° C.

SPIA amplified cDNA for sample UC0125.US was then purified with AMP Pure magnetic beads (Beckman Coutler, A63880) (1.8× volume=72 µl of beads) and eluted in 30 µl of EB buffer. SPIA amplified cDNA for samples ABT0070P.US and ABT0096P.US were purified using the Qiagen MinElute protocol as follows: (note: this is the preferred method of purification): Add 300 µl of buffer ERC (Enzymatic reaction clean-up) to 40 µl of sample. Vortex 5 sec then load entire sample to column (stored at 4° C.). Spin at 14K rpm for 1 min. Discard flow through and add 700 µl of buffer PE (EtOH added) to column. Spin at 14K rpm for 1 min then discard flow through. Replace column in same collection tube and spin again at 14K rpm for 2 min. Discard collection tube and blot column tip to paper towel to remove any residual EtOH from PE buffer. Finally, add 25 µl of EB buffer to the center of column filter placed in fresh Eppendorf collection tube. Let stand for 1 min then spin at 11K rpm for 1 min. Store eluted library on ice or at −20° C.

E. Determine cDNA Yield and Size Range

Run 1-2 µl of each cDNA on an agarose gel to estimate library size. With Qiagen Viral Mini extractions they are generally 150-250 bp in length. Measure the concentrations on a Qubit Fluorometer using dsDNA_BR (broad range) reagents (Molecular Probes/Life Technologies). Alternatively, libraries can be evaluated on a BioAnalyzer 2200 TapeStation.

F. Confirmatory PCR

Perform confirmatory PCRs to evaluate the virus-specific content of libraries Select primers for regions/genes of interest (see Table 1 of Section C). Use 2 µl of Ovation cDNA as template in PCR reaction. Determine appropriate controls and use Applied Biosystems Taq reagents. To 2 µl of cDNA template, add 2.5 µl 10×PCR buffer with 15 mM $MgCl_2$, 0.5 µl dNTP mix, 0.5 µl 10 uM fwd primer, 0.5 µl 10 µM rev primer, 0.2 µl Taq DNA polymerase, and 18.8 µl water. Run for 30-50 cycles depending on expectations and resolve products on an agarose gel to determine library quality/content.

G. Nextera Tagmentation

Nextera XT was used to incorporate Illumina adaptors and indexes into libraries. When multiplexing samples, it is essential to select compatible barcodes to achieve color balance. The Illumina protocol described below and was adapted from the Nextera XT Sample Prep kit (Illumina, #15032350) and used in conjuction with the Nextera Index kit: ref #15032353. Reactions can be assembled in 96 well plates, however, the samples were done here in 0.2 ml PCR tubes.

Step 1. Preparation—Remove the ATM, TD, and input DNA from −15° to −25° C. storage and thaw on ice. Ensure that NT is at room temperature. Visually inspect NT to ensure there is no precipitate. If there is precipitate, vortex until all particulates are resuspended. After thawing, ensure all reagents are adequately mixed by gently inverting the tubes 3-5 times, followed by a brief spin in a microcentrifuge. Reagent volumes are aliquoted as described and placed on ice (except NT) until added to reactions: TD Buffer: (sample #+1)*10 µl, ATM: (sample #+1)*5 µl, NT: (sample #+1)*5 µl, NPM: (sample #+1)*15 µl, Index 2: (sample #+1)*5 µl, Index 1: (sample #+1)*5 µl.

Step 2. Tagmentation of Input DNA—Ensure the reaction is assembled in the order described for optimal kit performance. The reaction does not need to be assembled on ice. Label a new 96-well TCY plate NTA (Nextera XT Tagment Amplicon Plate) or 0.2 ml tubes. Dilute cDNA in water to 0.2 ng/µl. This is typically ~30-300× dilution of starting cDNA. 1 ng of input (5 µl of 0.2 ng/µl) is required for optimal results. Use ~2 µl of stock in the appropriate volume of water to most accurately reach the final concentration of 0.2 ng/µl. Add 10 µl of TD Buffer to each well to be used in this assay. Change tips between samples. Add 5 µl of input DNA at 0.2 ng/µl (1 ng total) to each sample well of the NTA plate/tube. Add 5 µl of ATM to the wells/tubes containing input DNA and TD Buffer. Change tips between samples. Gently pipette up and down 5 times to mix. Change tips between samples. Cover the NTA plate with Microseal 'B'. Centrifuge at 280×g at 20° C. for 1 minute. Place the NTA plate/tubes in a thermocycler and run the following program: 55° C. for 5 minutes; Hold at 10° C. Once the sample reaches 10° C. proceed immediately to Neutralize NTA.

Step 3. Neutralize NTA—Carefully remove the Microseal "B" seal and add 5 µl of NT Buffer to each well/tube of the NTA plate. Change tips between samples. Gently pipette up and down 5 times to mix. Change tips between samples. Cover the NTA plate with Microseal 'B'/close tube. Centrifuge at 280×g at 20° C. for 1 minute. Place the NTA plate/tubes at room temperature for 5 minutes. After the tagmentation step, set up cycling conditions as described below.

Step 4. Library amplification and barcode addition—Place the NTA plate in the TruSeq Index Plate Fixture/tubes on ice. Add 15 µl of NPM (Nextera PCR Mix) to each well of the NTA plate/tube containing index primers. Add 5 µl of index 2 primers (white caps) to each column of the NTA plate/tube. Changing tips between columns is important to avoid cross-contamination. Add 5 µl of index 1 primers (orange caps) to each row of the NTA plate/tube. Tips should be changed after each row to avoid index cross-contamination.

Cover the plate with Microseal 'A' and seal with a rubber roller/close tubes. Centrifuge at 280×g at 20° C. for 1 minute. Perform PCR using the following program on a thermal cycler: Ensure that the thermocycler lid is heated during the incubation; 72° C. for 3 minutes; 95° C. for 30 seconds; set for 16 cycles of: 95° C. for 10 seconds; 55° C. for 30 seconds; 72° C. for 30 seconds; and 72° C. for 5 minutes. Hold at 10° C.

Library Purification—Samples were then purified using 1.8×AMP-PURE XP beads (Beckman Coulter, A63880) and eluted in 40 µl of RSB buffer (Illumina provided).

H. Library Quantification and Visualization

Visualize samples (1 µl) on the BioAnalyzer 2200 TapeStation using the following reagents from Agilent: D1K Screen Tape: ref #00-S019-120707-02-000084D1K ladder: ref #52715 90-240 Sample Buffer: ref #52907 98-221 Add 3 µl of loading buffer to 1 µl of library sample. Cap tube strips and vortex then spin to collect. Remove caps and place in appropriate slot of TapeStation. Enter sample information and run electrophoresis. Adjust window limits for integration measurement of peak to determine concentration.

I. Prepare for MiSeq Run

The following procedure was followed to run HPgV-2-containing libraries on a MiSeq. Step 1. Thaw −20° C. reagent cartridge (e.g. 300 or 500 cycle V2 reagent kit; Illumina, 15033625) in water container filled to designated line. Put HT buffer on bench at RT. Let both thaw for 1 hr, invert cartridge several times then hit gently on bench to dislodge to any bubbles from the bottom. Put cartridge and HT1 buffer in refrigerator until ready to dilute/load sample. Place 4° C. reagent box at room temperature (buffer and flow cell). Shake/invert buffer and allow bubbles to dissipate for >1 hour. Wash flow cell with $ddH_2O$ thoroughly to remove salts thedry completely with a Kimwipe.

Step 2. Create a new sample sheet in Illumina Experiment Manager (IEM). Select MiSeq->small genome->resequencing workflow. Record experiment name, reagent IDs, sample IDs and barcode information.

Step 3. Combine libraries in equimolar amounts (or as desired) for multiplexing of sequencing library. Using concentrations (nM) determined on BioAnalyzer, calculate the dilutions to be made with water to bring each library to a 1.1 nM final concentration in 18 µl. Add 2 µl of 1N NaOH and denature for 5 min at room temperature.

Step 4. Dilute 1 nM library (20 µl) with 980 µl of HT1 for a final library concentration of 20 pM. Vortex and place on ice.

Step 5. Dilute a second time with HT1 buffer at 1:1 for a 10 µM library, adding in 1% PhiX control, vortex then place on ice. The library should contain 500 µl 20 pM library, 10 µl PhiX (diluted and denatured), and 490 µl of HT1 buffer.

Step 6. Denature the 10 pM library (+1% PhiX) by heat for 2 min at 96° C. then place on ice water bath for >5 min.

Step 7. Go to MiSeq Control Software and hit "Sequence" to set up the instrument. Follow instructions as provided and load experiment sample sheet.

Step 8. Dispense 600 µl of 10 pM library into reagent cartridge and hit "Start".

Results

The MiSeq run was completed and the data was aligned to the consensus genome sequence generated in Example 1. From a total of 16,306,796 reads assigned to the HPg-V2 sample barcode, 249,693 (1.53%) of these mapped to HPgV-2. Sequences aligned uniformly and without gaps, covering 98.4% of the genome with an average depth of 3314X±426 reads/nt. In the region of overlap, this independent NGS dataset had 99.73% identity (9290/9315) to the draft genome produced in Example 1, with every mismatch either conserved (e.g. A→G, C→T) or resolving an ambiguous base in the latter (e.g. R→A, G). 156 bp of the 3'end previously determined by 3'RACE was absent in this NGS run, however, the data was mined by de novo assembly to extend the 5' end by an additional 306 nucleotides, thereby adding to the putative core protein (S) and/or 5'UTR sequence. The combined data from Examples 1 and 2 yielded the 9778 bp genomic sequence (SEQ ID 1) found in FIG. 1. Subsequent NGS runs for additional strains of HPgV-2 extended the 5'UTR such that the total length of the genome is now 9867 nt.

Example 3

Generating an in Vitro HPgV-2 Template Control and qPCR Assay

This example describes methods of generating a HPgV-2 template positive control and qPCR assays carried out with this template. The NS2-NS3 region in HPgV-2 was selected to probe specimens by qPCR. Based on our NGS data, this region exhibited the least amount of sequence heterogeneity. The region we cloned is approximately 1260 bp long and was inserted into pGEM-11Zf(+) (Promega, Madison Wis.) to enable in vitro transcription of this HPgV-2 template. This cloned sequence represents bases 3224 to 4483 of SEQ ID NO: 1 and is shown in FIG. 4. As described further below, 5 sets of primers and probes were designed to detect the HPgV-2 RNA.

A. Linearize NS23EX Plasmid for Use as in Vitro Transcription Template.

Step 1—Resuspend the 4 µg of lyophilized plasmid in 20 µl of elution buffer (EB) to bring concentration to 200 ng/µl.

Step 2—Digest with restriction enzyme(s) XbaI and HindIII found at the end of the 1260 bp insert. The pGEM®-1 Zf(+) Vector can be used as a standard cloning vector and as a template for in vitro transcription and the production of ssDNA. The plasmid contains T7 and SP6 RNA polymerase promoters flanking a multiple cloning region within the alpha-peptide coding region of beta-galactosidase. The following reaction mixture was generated: 5 µl DNA (1 jag), 2 µl 10×M buffer, 2 µl 0.1% BSA, 1 µl XbaI, 1 µl HindIII, and 9 µl water. This was incubated at 37° C. for 2.25 hrs.

Step 3—Precipitate linearized plasmid DNA in a reaction mixture of: 20 µl DNA, 2 µl NH4 stop solution (Ambion), and 40 µl EtOH. Incubate at −20° C. for 15 min; spin at top speed for 15 minutes; wash with 80% EtOH and respin 5 min. Dry for 5 min and resuspend in 10 µl of EB to an estimated concentration of 100 ng/µl.

Step 4—Measure DNA concentration on a NanoDrop.

Step 5—Visualize plasmid digestion on agarose gel. Run uncut and cut vector side by side to compare.

B. In Vitro Transcribe NS23EX Insert

Follow the Ambion Megascript T7 kit (AM1334) protocol as recommended then purify RNA. Step 1: Assemble 20 µl in vitro transcription reactions. Template DNA input volumes were as follows: 6.3 µl of linearized NS23Ex_pGEM11Zf (1 µg)+1.7 µl water; 2.0 µl of control pTRI-Xef vector+6 µl of water. Incubate for 4 hr at 37° C. in a plate incubator (dry). Add 1 µl of DNAse and digest for 15 min at 37° C.

Step 2: Trizol purification—Resuspend reaction in 230 µl of water then add 750 µl of Trizol. Suspended pTRI pellet in 25 µl of water and NS23Ex pellet in 50 µl of water.

Step 3: Quantify RNA by Nanodrop and on the BioAnalyzer as described above using the R6K screen tape.

C. Reverse Transcription cDNA was generated using SS RTIII (Invitrogen: 18080-051) for random hexamer priming. The HPgV-2 RNA in vitro transcribed from NS23EX/pGEM11-Zf(+) plasmid and the pTRI-Xef control RNA from Ambion were used as templates. Reactions were assembled as follows: 2.0 µl RNA (~400 ng), (used the 1/10 dilution of NS23EX RNA; straight for pTRI), 5.6 µl water, 1 µl of random hexamer (50 ng/µl), 0.4 µl of oligo dT (50 µM), And 1 µl dNTP mix (10 mM). Heat at 65° C. for 5 min and return to ice to add 10 µl of master mix. Prepare the mastermix as follows: 2 µl 10 RT buffer, 4 µl 25 mM MgCl$_2$, 2 µl 0.1 M DTT, 1 µl RNAseOUT (40 U/µl), and 1 µl Superscript III RT (200 U/µl).

Incubate for 10 min at 25° C., then 20 min at 50° C. Terminate at 85° C. for 5 min then 4° C. Add 1 µl of RNAse H (Invitrogen, Y01220) to reactions and incubate for 20 min at 37° C. and then to 4° C. cDNA was aliquoted into 2×10 µl samples and frozen at −80° C.

E. HPgV-2 PCR

The following primers were used to confirm the HPgV-2 RNA. These primers were named with an older version of the HPgV-2 genome. Refer to their sequence ID numbers.

```
PCR 1_617 bp product
                                    (SEQ ID NO: 38)
GAGCCGGGTTTGGGTGATGAATAA            3841F (SEQ ID NO: 39)
CTGCGCCAATGCCGAGTAGC                4460R PCR 2_412 bp product
                                    (SEQ ID NO: 40)
ACGCGTTGATGCTCGGTGGTTACT            3987F (SEQ ID NO: 41)
ACAGCATAGCCCCGCAGATTCGTC            4398R
```

The following volumes of reagents were used for PCR. 2 µl of diluted cDNA as template (NS23EX, pTRI; add 1.5 µl of cDNA stock+8 µl of water); 2.5 µl 10×PCR buffer with 15 mM MgCl$_2$; 0.5 µl dNTP mix; 0.5 µl 10 µM forward primer; 0.5 µl 10 µM reverse primer; 0.2 µl Taq DNA polymerase; and 18.8 µl water. Use the following PCR conditions: 1 cycle @94° C.: 2 min; 35 cycles @94° C.: 20 sec, 55° C.: 30 sec, 72° C.: 40 sec; 1 cycle 72° C.: 7 min; 1 cycle 4° C.: hold. 5 µl of each sample was resolved on an ethidium bromide gel and photographed under UV light.

F. qPCR with 7 Primer Sets

The following was performed to establish a TaqMan-based qPCR assay for the detection of HPgV-2 RNA in patient specimens. In vitro transcribed RNA (NS23Ex=2000 ng/µl), start the first dilution at 1/100 (20 ng/µl)→load 5 µl for 100 ng total. Repeat 10 fold dilutions using 2 µl in 18 µl of water for a total of 6 dilutions. For pTRI (200 ng/µl), dilute at 1/10→load 5 µl for 100 ng total. For total RNA, Take 3 µl of each RNA and dilute it with 27 µl of water (1/10). Included in this experiment were UC0125.US, CHU2725 [an HIV(+)/GBV-C(+) sample], and N-505 [HIV (+)/GBV-C(−) sample] all extracted in the same manner.

Make dilutions of primers & probes at the concentrations listed and combine reactions as follows for qPCR on an ABI light-cycler (Abbott m2000rt):

12.5 µl 2×RT-PCR Buffer

1 µl Forward primer, 10 uM

1 μl Reverse primer, 10 uM
1 μl Taq man probe, 3 uM
1 μl 25×RT-PCR enzyme mix
5 μl RNA sample
3.5 μl Nuclease-free water
25 μl total 20 ul of master-mix per well The 7 sets of probes and primer pairs employed are shown in Table 2 below. The binding locations for these sequences are shown in FIG. 4.

TABLE 2

| Primer Set 5: Amplicon Size = 70 | | |
|---|---|---|
| NS23Ex_F5 | GAGGAGCCCACCTTTACTGA | (SEQ ID NO: 54) |
| NS23Ex_R5 | TACCTCCAAGCAATTGTCCA | (SEQ ID NO: 55) |
| NS23Ex_Prb5 | CACCAAACTCATTGTGTCATCCACGA | (SEQ ID NO: 56) |
| Primer Set 2: Amplicon Size = 89 | | |
| NS23Ex_F2 | GAAGATCTGCCACCTGGTTT | (SEQ ID NO: 57) |
| NS23Ex_R2 | AGTGTCGCCTTAAGGAAGGA | (SEQ ID NO: 58) |
| NS23Ex_Prb2 | CCACCGGAGCACTCAGCTGG | (SEQ ID NO: 59) |
| Primer Set 7: Amplicon Size = 74 | | |
| NS23Ex_F7 | TCCTTCCTTAAGGCGACACT | (SEQ ID NO: 60) |
| NS23Ex_R7 | AGGGAAGACAACACCACGAT | (SEQ ID NO: 61) |
| NS23Ex_Prb7 | AAACACCAGGGTCCGGCCAG | (SEQ ID NO: 62) |
| Primer Set 4: Amplicon Size = 85 | | |
| NS23Ex_F4 | TGGGTGATGAATAACAACGG | (SEQ ID NO: 63) |
| NS23Ex_R4 | GATCTATGTGCGTGGGACAG | (SEQ ID NO: 64) |
| NS23Ex_Prb4 | CCACTCTGCCACACACCAACCC | (SEQ ID NO: 65) |
| Primer Set 3: Amplicon Size = 88 | | |
| NS23Ex_F3 | AATGACGACGTCTGTTTGGA | (SEQ ID NO: 66) |
| NS23Ex_R3 | CATGACCGTGATCACACAAA | (SEQ ID NO: 67) |
| NS23Ex_Prb3 | CTGGTGAGCCCGAAGCACCC | (SEQ ID NO: 68) |
| Primer Set 15: Amplicon Size = 138 | | |
| NS23Ex_F15 | CCAGCTGTGACACCAACATA | (SEQ ID NO: 69) |
| NS23Ex_R15 | TTTGACTACAGCCACACTTGG | (SEQ ID NO: 70) |
| NS23Ex_Prb15 | CCAGTGGACCTAGTCAAACAGGGACA | (SEQ ID NO: 71) |
| Primer Set 1: Amplicon Size = 96 | | |
| NS23Ex_F1 | AGTCATTTGCGACGAGTGTC | (SEQ ID NO: 72) |
| NS23Ex_R1 | ACGGTCTTCACTCCAGCTTT | (SEQ ID NO: 73) |
| NS23Ex_Prb1 | TCGGCATACATGCGCACTGC | (SEQ ID NO: 74) |

G. qPCR Assay A—TaqMan Based Detection of HPgV2

TaqMan assays using probes and primer pairs 1, 2, 3, 5, and 7 were performed to detect 10-fold serial dilutions of the NS23Ex in vitro transcript and a 10-fold dilution of the UC0125.US RNA. Primers were ordered from a Applied Biosystems and HPLC purified. Probes have 5'6FAM and 3'TAMRA modifications. Ag Path-ID One StepRT-PCR Kit (Applied Biosystems, 438724) was used for buffer and enzyme mixes. Primer (10 μM) and probe (3 μM) concentrations were used as recommended.

Realtime qPCR cycling conditions were as shown below:

| Step | Stage | Reps | Temp | Time |
|---|---|---|---|---|
| Reverse transcription | 1 | 1 | 45° C. | 10 min |
| RT inact/initial denaturation | 2 | 1 | 95° C. | 10 min |
| Amplification | 3 | 40 (45) | 95° C. | 15 sec |
| | | | 60° C. | 45 sec |

Dispense 5 μl of sample (NS23Ex RNA dilutions, controls or sample RNA) to each well. The optional detection enhancer was not added. Dispense 20 μl of mastermix to each well. Spin to collect and seal.

Figure 5B:
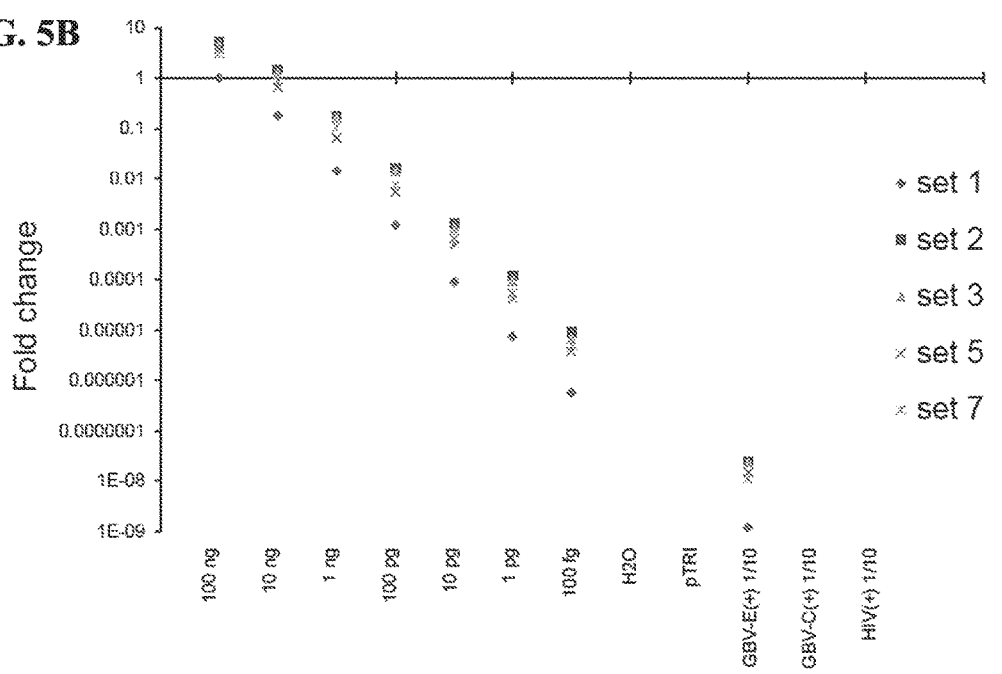

The results are shown in FIG. 5. FIG. 5A shows HPgV-2 primer/TaqMan probe sets (1-2-3-5-7; see FIG. 4 for sequences and positions) were used to detect 10-fold serial dilutions of the NS23Ex in vitro transcript and a 10-fold dilution of the HPgV-2 index case (UC0125.US) RNA (highlighted in bold). The lower right panel shows detection of 100 ng of NS23Ex and HPgV-2 RNA for each primer/probe set. FIG. 5B shows Ct values that were normalized to set 1_100 ng results and plotted on a log scale to estimate the amount of HPgV-2 RNA present in the index case. Negative controls included in the experiment were: 1) water, 2) pTRI (an irrelevant in vitro transcript), 3) CHU2725 (HIV+/GBV-C+ sample), and 4) N-505 (HIV+/GBV-C− sample) indicate there is no cross-reactivity with other infections (HIV, GBV-C). HCV purified virus (1000 plaque forming units) was tested at a later time and also shown to NOT cross-react with these primers (data not shown). The NS23Ex template was detected in a dose-dependent fashion by all primer/probe sets. None of the negative control RNAs were amplified by these primer, suggesting no cross-reactivity. The index case (UC0125.US) viral load is estimated at $1.5 \times 10^6$ copies/ml based on these results.

H. qPCR Assay B—SYBR Green qPCR

Figure 6:
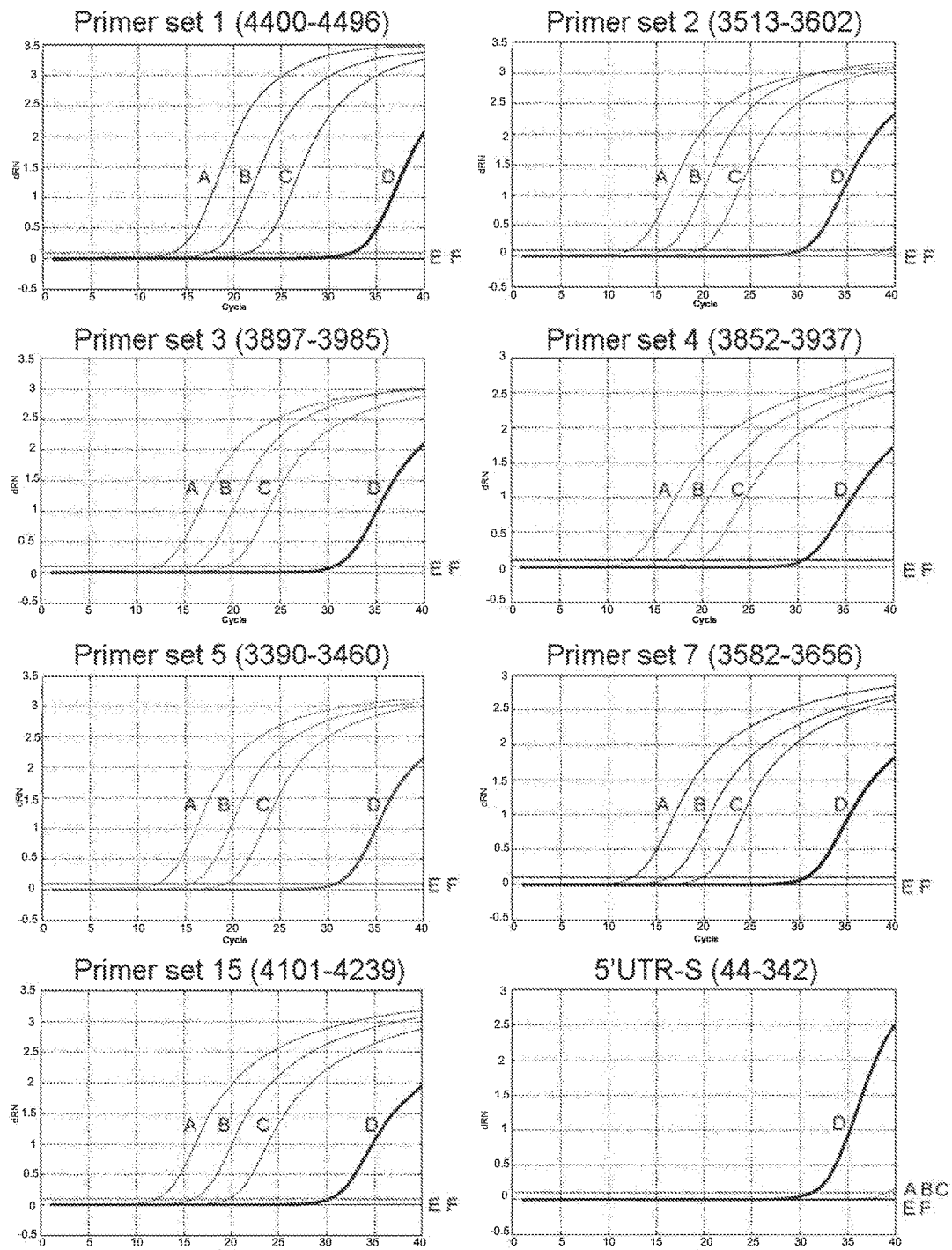
FIG. 6 shows the results of SYBR green qPCR assays that were conducted using probe and primer sets 1, 2, 3, 4, 5, 7, and 15 and 44F (SEQ ID NO:12) and 342R (SEQ ID NO: 13), which were used to detect 10-fold serial dilutions of cDNA made from the NS23Ex in vitro transcript (FIG. 6, curves A, B, C) and the HPgV-2 index (UC0125.US) case RNAs (FIG. 6, curve D). Negative controls (FIG. 6, curves E and F), N-505 (HIV(+)/GBV-C(−)) and water, were not amplified. Each graph is labeled with the primer set that was employed.

SYBR green qPCR assays were conducted using probe and primer sets 1, 2, 3, 4, 5, 7, and 15 and 44F (SEQ ID NO:12) and 342R (SEQ ID NO:13), which were used to detect 10-fold serial dilutions of cDNA made from the NS23Ex in vitro transcript (FIG. 6, curves A, B, C) and the HPgV-2 index case (UC0125.US) RNAs (FIG. 6, curve D). Negative controls (FIG. 6, curves E and F), N-505 (HIV(+)/GBV-C(−)) and water, were not amplified. The following samples were in each row: 1) NS23Ex 1:1000 cDNA; 2) NS23Ex 1:10,000 cDNA; 3) NS23Ex 1:100,000 cDNA; 4) GBV-E cDNA; 5) N505 cDNA; and 6) Water. The qPCR reactions were set up as follows: 2 μl cDNA (diluted at 1:5 from 20 μl SSRTIII reactions); 7.2 μl water; 0.4 μl Fwd primer (10 μM); 0.4 μl Rev primer (10 μM); and 10 μl SYBR green mix (Applied Biosystems).

The results are shown in FIG. 6. Each primer set showed a dose-dependent detection of the NS23Ex transcript and all detected UC0125.US cDNA at essentially the same Ct. None produced a signal for N505 or water.

I. qPCR Assay C

Primer/probe sets 2 and 3 were used in TaqMan qPCR assays and revealed three cases of HPgV-2 infection in donor plasma. RNA extracted from ProMedDx HCV(+) plasmapheresis donor plasma samples 48-96 was screened with TaqMan primer/probe sets 2 (top panel) and 3 (bottom panel) as described in FIG. 7A. Samples #70 and #96 (ABT0070P.US and ABT0096P.US) were detected by both sets. 10 ng and 10 fg of the NS23Ex in vitro transcript positive control are also shown. FIG. 7B shows results of an assay where RNA extracted from American Red Cross blood donor plasma [HCV RNA(+)/antibody(+)] samples were screened with TaqMan primer/probe sets 2 and 3 as above. Sample #128 (ABT0128A.US) was detected, but only by set 2 (bold). 10 ng and 10 fg of the NS23Ex in vitro transcript positive control are shown in green (probe 2) and purple (probe 3).

J. Tri-plex Mastermix qPCR Assay

Figure 28:
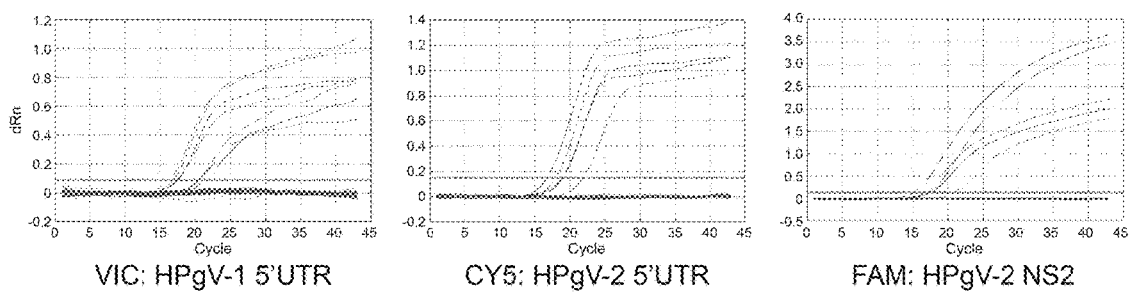
FIG. 28 shows the results of a newly designed Tri-plex mastermix for qPCR screening described in the Materials and Methods. A panel of 100 HIV positive specimens obtained from ProMedDx was extracted on the m2000sp and RNA was combined with the Tri-plex mastermix for thermocycling on the m2000rt. Six specimens were positive for the HPgV-1 (GBV-C) RNA through detection of it 5'UTR in the VIC channel. Four identical specimens were positive for HPgV-2 RNA and detected in the CY5 (5'UTR) and FAM (NS2) channels. These four specimens (PMDx30, 33, 35, 41) represent two bleeds from the same patients (e.g. 30=33, 35=41). Sanger sequencing confirmed the presence of HPgV-2 RNA and the identical nature of sequences from same patients.

A new qPCR assay was developed based off current HPgV-2 strain sequence alignments (see FIG. 23 alignment) to simultaneously screen for HPgV-2 and GBV-C (HPgV-1)-infected specimens. RNA was extracted from donor samples using the automated Abbott m2000sp system followed by qPCR on the m2000rt instrument. An example of results which led to the identification of strains ABT0030P.US and ABT0041P.US is shown in FIG. 28. Detection of HPgV1 was achieved by targeting the 5' UTR using FP 5'-TGTTGGCCCTACCGGTGTTA-3' (SEQ ID NO: 408) and RP 5'-CCGTACGTGGGCGTCGTT-3' (SEQ ID NO: 409) and three fluorescently labeled probes (5'-VIC-CTCGTCGTTAAACCGAGCCCGTCA-BHQ1-3'(SEQ ID NO: 410), 5'-VIC-CTCGTCGTTAAACCGAGACCGTCA-BHQ1-3'(SEQ ID NO: 411), 5'-VIC-CACGCCGTTAAAC-CGAGACCGTTA-BHQ1-3'(SEQ ID NO: 412)) to account for mismatched sequences. HPgV-2 primer/probe sequences are adapted from Keys, et al (Keys, J R. et al 2014 J Med Virol 86: 473-477) Detection of HPgV2 relied on amplification of the NS2-3 region (FP 5'-GTGGGACACCTCAAC-CCTGAAG-3'(SEQ ID NO: 413), RP 5'-GGGAAGA-CAACACCACGATCTGGC-3'(SEQ ID NO: 414), probe 5'-FAM-CCTGGTTTCCAGCTGAGTGCTCC-BHQ1-3' (SEQ ID NO: 415)) and the 5' UTR (FP 5'-CGCTGATCGT-GCAAAGGGATG-3'(SEQ ID NO: 416), RP 5'-GCTC-CACGGACGTCACACTGG-3'(SEQ ID NO: 417), probe 5'-Quasar670-GCACCACTCCGTACAGCCTGAT-BHQ2-3'(SEQ ID NO: 418)). All primers were synthesized by IDT (Coralville, Iowa) and probes synthesized at Abbott Molecular (Des Plaines, Ill.). Cycling conditions were the following: 50° C., 4 minutes (1×); 75° C., 5 minutes (1×); 60° C., 30 minutes (1×); 91° C., 30 seconds; 58° C., 45 seconds (6×); 91° C., 30 second; 60° C., 45 seconds (+2 sec/cycle) (4×); 91° C., 30 seconds; 60° C., 45 seconds (+2 sec/cycle) (43×-Read). Reverse transcription and DNA polymerase activity was performed using the enzyme, rTth (Roche). In FIG. 28, a total of 4 specimens among the HIV-positive set were reactive for HPgV-2 RNA (CY5 and FAM channels: 5'UTR and NS2, respectively), however, two of each were from the same donor. A total of six specimens were GBV-C positive (VIC channel: 5'UTR).

Example 4

Detection of Antibodies Directed Against HPgV-2 Peptide/Proteins

This example describes the selection and evaluation of potential antigenic peptides and recombinant proteins from the HPgV-2 genome. A series of peptides, shown in Table 3, ranging in length from 20 amino acid residues to 45 amino acids residues were designed taking into account the predicted surface exposure (hydrophillicity profile and surface probability) and antigenic index scores.

Briefly, HPgV-2 proteins (S, E1, E2, NS3, NS3, NS4A, NS4B, NSSA, and NSSB) were analyzed for predicted antigenic regions using DNASTAR Lasergene11 version 11.2.1 (29) Protean software (DNAStar, 3801 Regent Street Madison, Wis. 53705, USA). Potential antigenic regions were determined by a combination of hydropathy plot, antigenicity index, and predicted surface probability for each amino acid sequence. Hydropathy profiles for each open reading frame were generated and assessed for areas that had the potential to be exposed when in aqueous solution (hydrophilic). Surface probability determination refers to the bias a sequence has to being on the surface of the molecule. The Emini surface probability method was employed where the predicted probability of a given amino acid to be water solvent exposed is determined for a sequence of amino acids (Emini et al., J Virol. 1985 September: 55(3):836-9). Predicted antigenic regions would have the property of surface exposure. Antigenic index was determined using the Jameson-Wolf algorithm where surface accessibility of residues is combined with predicted backbone flexibility and secondary structure (Jameson B. A and Wolf H. Comput Appl Biosci (1988) 4 (1): 181-186). Peptides were designed to sequences found in HPgV-2 proteins (S, E1, E2, NS3, NS3, NS4A, NS4B, NS5A, and NS5B) with consideration of predicted surface exposure (hydrophilicity profile and surface probability) and antigenic index scores (Table 3).

Peptides (Table 3) were generated with an amino terminal biotinylation modification (Genscript USA Inc, Piscataway, N.J.). Peptides were biotinylated to allow for a strong covalent interaction with avidin and streptavidin coated microparticles which can be used to immobilize the peptides on a solid surface (e.g. microparticles), that are used for solid-phase based immunoassays.

TABLE 3

| Peptide # | Protein | Sequence | SEQ ID NO: |
|---|---|---|---|
| 1 | S | GGSCRSPSRVQVARRVLQLSAFLALIGSGMSSIRSKTEGRIESGQ | 86 |
| 2 | | RDGSLHWSHARHHSVQPDRVAAGPPSVTSVERNMGSSTDQT | 87 |
| 3 | E2 | SMNSDSPFGTFTRNTESRFSIPRFSPVKINS | 88 |
| 4 | NS3 | QAPAVTPTYSEITYYAPTGSGKSTKYPVDLVKQGHKVLVL | 89 |
| 5 | | VKSMAPYIKETYKIRPEIRAGTGPDGVTVITG | 90 |
| 6 | | PETNLRGYAVVISDESHDTSS | 91 |

TABLE 3-continued

| Peptide # | Protein | Sequence | SEQ ID NO: |
|---|---|---|---|
| 7 | | PCTAALRMQRRGRTGRGRRGAYYTTSPGAAPCVS | 92 |
| 8 | NS4B | LSERFGQQLSKLSLWRSVYHWAQAREGYTQCG | 93 |
| 9 | NS5A | NPTTTGTGTLRPDISDANKLGFRYGVADIVELERRGDKWH | 94 |
| 10 | | QNLAARRRAEYDAWQVRQAVGDEYTRLADEDVD | 95 |
| 11 | | RFVPPVPKPRTRVSGVLERVRMCMRTPPIKF | 96 |
| 12 | NS5B | NTTRDHNNGITYTDLVSGRAKP | 97 |
| 13 | | DAPMRIIPKPEVFPRDKSTRKPPRFIVFPGCAARV | 98 |
| 14 | | MPLLCMLIRNEPSQTGTLVT | 99 |
| 15 | S | AEAAPKSGELDSQCDHLAWSFMEGMPTGTLIVQRDGSLH | 217 |
| 16 | NS4A-B | SVEVRPAGVTRPDATDETAAYAQRLYQACADSGIFASLQGTASAALGKLA | 218 |

Populations to be Tested

Previous studies indicate that GBV-C, the human virus most closely related to HPgV-2, is frequently detected in HCV infected individuals and in commercial blood donors (e.g. paid plasmapheresis donors). It was postulated that HPgV-2 may likewise be found in higher prevalence rates in commercial donors than in the general population. Thus a population of samples from plasmapheresis donors was selected for study. Further, since the index case (UC0125.US)) was also HCV infected, it was reasoned that additional HPgV-2 cases might be detected among samples that are antibody positive for HCV. Thus, one of the first populations selected for study was plasmapheresis donors whose plasma were previously tested as positive both for antibodies to HCV and for HCV RNA.

Testing Procedures

Three pools of peptides were generated: Pool 1 contained the following peptides: P 1, 2, 4, 5, 7, 8; Pool 2 contained the following peptides: P 9, 10, 11, 13, 14; and Pool 3 contained the following peptides: P 3, 6, 12.

Figure 8:
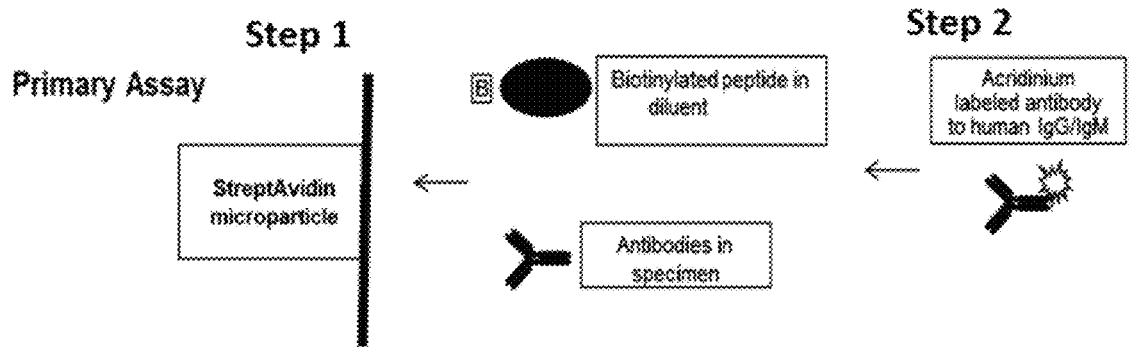
FIG. 8 provides a schematic of an exemplary solution phase capture assay that can be used to detect subject antibodies to HPgV-2 in a sample. Both sample and biotinylated peptide (s) are incubated together, followed by incubation with the streptavidin coated solid phase support. Immune complexes are captured on the solid phase support by the biotin linkage on the peptide (Step 1). Immune complexes are detected indirectly by using a chemiluminescent labeled human IgG (Step 2).

In the first step of the assay, a sample (e.g. human serum or plasma) is added to a reaction vessel along with a specimen diluent buffer (containing buffering salts and detergents) containing one of the pools of the biotinylated peptides (800 ng/ml each) and the solid phase coated with streptavidin (Dynabeads M-270 Streptavidin, Life Technologies 3175 Staley Road Grand Island, N.Y. 14072). This sample is incubated for 18 minutes. During this time, the solid phase captures both the biotinylated peptide and the antibody complexed to the peptide (immune complex). Following the 18 minute incubation step, unreacted sample is removed, and the second step of the assay is initiated by adding a signal generating conjugate to the reaction vessel. The conjugate (in this case, 16 ng/mL of mouse-anti-human IgG conjugated to a chemiluminescent enzyme (acridinium)) recognizes the human immunoglobulins that have bound to the peptide and are now affixed to the solid phase. After a washing step to remove unreacted material, the microparticles are washed, and then incubated with a substrate capable of triggering chemiluminescence. The amount of luminescence was then measured in relative light units (RLU) using a bioluminescence imager. The steps of this assay are shown in FIG. 8.

Each sample is tested using three pools of peptides as described above. Samples are considered to be reactive (or above the cutoff value) if the signal for a given sample is 10-fold or more fold higher than the signal obtained with a negative control sample. It is noted that the negative control sample is prepared by pooling a series of samples from individuals at low risk for viral infection and who have tested negative for several common viruses including HIV, HBV and HCV. A second type of control is used wherein the samples are reacted in a vessel that contains the diluents and streptavidin coated microparticles but does not contain any of the 14 peptides listed in Table 3. It is expected that sample results should be negative when peptides are not present. When samples are reactive in the absence of the peptides, the sample is considered to be non-specifically reactive with the solid phase containing streptavidin, and were not included in the various lists of antibody positive samples provided in the following tables.

Results:

A panel of samples from first-time plasmapheresis donors, testing positive for, both by an antibody test for HCV (Abbott Laboratories, Abbott Park Ill. 60064) and a HCV RNA test (Bayer Versant HCV RNA 3.0 assay (bDNA) was obtained from ProMedDx (Norton, Mass.). The samples were tested against the three pools of peptides as described above. A total of 19 of the 200 samples were reactive with one or more of the three peptide pools. One sample (S188) was reactive with all three peptides pools, while two samples (S 80 and S 96) were reactive with two peptides pools (Table 4).

TABLE 4

List of ProMedDx Samples that are antibody positive for HPgV-2 Peptide Pools

| ProMedDx Samples (anti-HCV positive, HCV RNA positive plasmapheresis donors) Sample ID | Peptide Pool 1 S/CO* | Peptide Pool 2 S/CO* | Peptide Pool 3 S/CO* |
|---|---|---|---|
| S 188 | 3.01 | 2.75 | 1.52 |
| S 80 | 2.05 | 12.16 | NR** |
| S 96 | NR | 9.93 | 1.42 |
| S 164 | 1.42 | NR | 5.25 |
| S 66 | 1.20 | NR | NR |

TABLE 4-continued

List of ProMedDx Samples that are antibody positive for HPgV-2 Peptide Pools

| ProMedDx Samples (anti-HCV positive, HCV RNA positive plasmapheresis donors) Sample ID | Peptide Pool 1 S/CO* | Peptide Pool 2 S/CO* | Peptide Pool 3 S/CO* |
|---|---|---|---|
| S 147 | 1.04 | NR | NR |
| S 182 | 2.07 | NR | NR |
| S 70 | NR | 7.61 | NR |
| S 27 | NR | 3.11 | NR |
| S 89 | NR | 2.75 | BR |
| S 192 | NR | NR | 5.74 |
| S059 | NR | NR | 2.31 |
| S115 | NR | NR | 3.21 |
| S 5 | NR | NR | 4.70 |
| S 3 | NR | NR | 2.22 |
| S 33 | NR | NR | 1.70 |
| S 109 | NR | NR | 1.48 |
| S 148 | NR | NR | 1.45 |
| S 45 | NR | NR | 1.37 |

*S/CO = sample to cutoff value > 1.0 is considered reactive for antibodies to that peptide. The cutoff was determined as 10 times the signal for the negative control value.
**Non-reactive Samples reactive with pooled peptides were retested with individual peptides from the reactive peptide pool as shown below. All 200 samples were also tested with individual Peptide 15 and Peptide 16. Data below indicate that 8 samples were reactive with two or more individual peptides and 16 samples were reactive only with single peptides (Table 5). A total of 24 samples were reactive with one or more of the synthetic peptides that were evaluated: 176 of the 200 samples were non-reactive for the peptides used in the assay.

An antibody positive result for any HPgV-2 peptide is consistent with previous or current infection with HPgV-2; the prevalence in this population may be as high as 12% (24 reactive samples among 200 samples).

It can be uncertain as to which results indicate past or current infection with HPgV-2. Confirmatory tests are often utilized to provide supportive evidence that a given serologic result correlates to infection with the agent being studied. In many cases, RT-PCR testing is utilized determine if an antibody positive individual is actively infected with a given agent. A positive RT-PCR result supports that idea that the serologic test is correct. However, a negative RT-PCR result however, does not over rule the serologic test, as some seropositive individuals may have cleared the infection, thus producing a negative RT-PCR result.

RT-PCR testing was performed on all 200 samples from ProMedDx using the primer and probe sets described in Example 3. Three samples were determined to be positive by RT-PCR (ABT0070P, ABT0096P, ABT0188P) and have subsequently been confirmed by next generation sequencing (Example 5).

Serology Tests with UC0125.US Case

An aliquot of the index case (UC0125.US) was tested for antibodies to peptides 4 and 9, as both of these peptides, as noted above having shown some positive predictive value for HPgV-2 RNA positivity. It was found that this case was positive for antibodies to both peptides 4 and 9, with S/N values of 12.5 and 94.7, respectively. Thus, providing further support that detection of antibodies to selected peptides may predict active HPgV-2 infection as detected by RT-PCR.

TABLE 5

Individual peptide results on ProMedDx samples reactive with peptide pools.

| | Abbott ID | 1 | 2 | 3 | 4 | 5 | 6 | 7 | 8 | 9 | 10 | 11 | 12 | 13 | 14 | 15 | 16 | PCR result |
|---|---|---|---|---|---|---|---|---|---|---|---|---|---|---|---|---|---|---|
| 200 HCV RNA and AB positive samples from PreMedDx | S188 | | | 1.7 | 5.2 | | | | | 1.9 | | | 4.8 | | | 1.3 | | positive |
| | S182 | 4.2 | | | | | | | | | | | | | | | | negative |
| | S080 | | | | 4.3 | | | | | 9.6 | | | | | | | 16.5 | negative |
| | S164 | | | 1.5 | 1.2 | 1.9 | 3.9 | 2.6 | | 1.1 | 3.2 | | 5.5 | | | | | negative |
| | S066 | 4.9 | | | | | | | | | | | | | | | | negative |
| | S147 | 2 | | | 1.5 | | | | | | | | | | | | | negative |
| | S096 | | | 1.6 | 3.5 | | 1.1 | | | 1 | | | | | | 20.7 | | positive |
| | S070 | | | | | | | | | 5.3 | | | | | | 1.1 | | positive |
| | S027 | | | | | | | | | 4.3 | | | | | | 4.6 | | negative |
| | S089 | | | | | | | | | 5.4 | | | | | | 2.5 | | negative |
| | "S192" | | | 4.6 | | | | | | | | | | | | | | negative |
| | "S005" | | | 4.3 | | | | | | | | | | | | | | negative |
| | "S115" | | | | | | 1.5 | | | | | | | | | | | negative |
| | "S059" | | | | | | 2.5 | | | | | | | | | | | negative |
| | "S003" | | | | | | 1.3 | | | | | | | | | | | negative |
| | "S033" | | | 1.2 | | | | | | | | | | | | | | negative |
| | "S109" | | | 1.3 | | | | | | | | | | | | | | negative |
| | "S148" | | | 2.1 | | | | | | | | | | | | | | negative |
| | "S045" | | | | | | | | | | | | 4.7 | | | | | negative |
| | S093 | | | | | | | | | | | | | | | 16.6 | | negative |
| | S133 | | | | | | | | | | | | | | | 1.4 | | negative |
| | S020 | | | | | | | | | | | | | | | 1.1 | | negative |
| | S123 | | | | | | | | | | | | | | | | 7.8 | negative |
| | S044 | | | | | | | | | | | | | | | | 2.4 | negative |
| | S065 | | | | | | | | | | | | | | | | | negative |
| | S114 | | | | | | | | | | | | | | | | | negative |

*S/CO = sample to cutoff value > 1.0 is considered reactive for antibodies to that peptide.
The cutoff was determined as 10 times the signal for the negative control value.

Correlation between Antibody Reactivity and RT-PCR Results

There appears to be a correlation between antibody reactivity to certain peptides, and a positive HPgV-2 RT-PCR result (Table 6). Reactivity to peptides 3, 4, 9, and 16 occurred in at least 2 of the 4 HPgV-2 RNA positives including the index case. Whereas reactivity to other peptides was absent or only occurred in 1 of the HPgV-2 RNA positive samples.

TABLE 6

Correlation of Antibody Test results and RT-PCR(qPCR) results for ProMedDx panel of plasmapheresis donors.

| 200 HCV RNA and Ab positive samples from ProMedDx | HPgV-2 PCR positive | HPgV-2 PCR negative | Postive predicitve value* |
|---|---|---|---|
| Antibody Positive for any HPgV-2 peptide (N = 24) | 3 | 21 | 12.5% |
| Antibody Negative for all HPgV-2 peptides (N = 176) | 0 | 176 | 0.0% |
| Antibody Positive for HPgV-2 Peptide 3 (N = 8) | 2 | 6 | 25.0% |
| Antibody Positive for HPgV-2 Peptide 4 (N = 5) | 2 | 3 | 40.0% |
| Antibody Positive for HPgV-2 Peptide 9 (N = 6) | 2 | 4 | 33.3% |
| Antibody Positive for HPgV-2 Peptide 16 (N = 7) | 2 | 5 | 28.6% |

*Positive predictive value was determined as the number of samples that were HPgV-2 RNA positive and antibody positive for HPgV-2 peptides divided by the total number of antibody positive samples for each peptide.

Strategy to Identify RT-PCR Positive Samples

The discussion above indicates that antibody reactivity has a positive predictive value for identifying RT-PCR positive samples. Thus, several populations of samples, as described below, are tested with the three peptide pools described below, followed by individual peptide testing. Samples that are reactive with individual peptides are selected for RT-PCR testing. For RT-PCR positive samples, sequencing can be performed across the genome.

Peptide Pools for Continued Testing:

The peptide pool composition has been modified as shown below:
Pool 1 contained the following peptides: P 1, 5, 7, 8, 10
Pool 2 contained the following peptides: P 2, 3, 4, 6, 9
Pool 3 contained the following peptides: P 11, 12, 13, 14

HCV RNA Positive/Anti-HCV Negative Blood Donor Samples.

A panel of 240 blood donor samples were obtained from the American Red Cross (Gaithersburg, Md.) having been identified as NAT yield samples (i.e., samples that tested as antibody negative for HCV, but were RT-PCR positive via minipool nucleic acid testing). When tested with the three peptide pools, a total of 11 samples were detected as reactive (Table 7).

TABLE 7

240 ARC Samples that were HCV RNA positive but anti-HCV antibody negative: List of sample ID numbers with positive result.

| HCV NAT Yield Samples (ARC) Sample ID | Peptide Pool 1 S/CO* | Peptide Pool 2 S/CO* | Peptide Pool 3 S/CO* |
|---|---|---|---|
| S0217 | 3.6 | NR** | NR |
| S0159 | 1.8 | NR | NR |
| S049 | 1.5 | NR | NR |
| S0078 | 1.5 | NR | NR |
| S0226 | 1.4 | NR | NR |
| S0111 | NR | 4.3 | NR |
| S0079 | NR | 1.8 | NR |
| S0061 | NR | 1.7 | NR |
| S0177 | NR | 1.3 | NR |
| S0108 | NR | NR | 1.3 |
| S0145 | NR | NR | 1.0 |

*S/CO = sample to cutoff value > 1.0 is considered reactive for antibodies to that peptide. The cutoff was determined as 10 times the signal for the negative control value.
**Non-reactive Samples reactive with pooled peptides were retested with individual peptides from the reactive peptide pool as shown below. Data below indicate that 1 sample was reactive with two or more individual peptides and 11 samples were reactive only with single peptides (Table 8).

TABLE 8

Individual peptide results on HCV NAT yield samples reactive with peptide pools. Shown are signal to noise (S/N) values compared to the negative control for each peptide tested individually. RT-PCR was performed and results are indicated.

| | Abbott ID | 1 | 2 | 3 | 4 | 5 | 6 | 7 | 8 | 9 | 10 | 11 | 12 | 13 | 14 | 15 | 16 | PCR result |
|---|---|---|---|---|---|---|---|---|---|---|---|---|---|---|---|---|---|---|
| 240 HCV RNA | S0111 | | | 28 | | | | | | | | | | | | | | negative |
| positive | S0079 | | | | | 45 | | | | | | | | | | | | negative |
| samples | S0061 | | | 21 | | | | | | | | | | | | | | negative |
| from ARC | S0177 | 14 | | | | 15 | | 20 | | | | | | | | | | negative |
| | S0217 | | | | 38 | | | | | | | | | | | | | negative |
| | S0159 | | | | 19 | | | | | | | | | | | | | negative |
| | S0049 | | | | 21 | | | | | | | | | | | | | negative |
| | S0078 | | | | 20 | | | | | | | | | | | | | negative |
| | S0226 | | | | 18 | | | | | | | | | | | | | negative |
| | S0108 | | | | | | | | | | | | | 19 | | | | negative |
| | S0162 | | | | | | | | | | | | | | | | 55 | negative |
| | S0145 | | | | | | | | | | | | | 26 | | | | negative |

HCV RNA Positive/Anti-HCV Positive Blood Donor Samples.

A panel of 240 blood donor samples obtained from the American Red Cross (Gaithersburg Md.) were identified as HCV infected (being both antibody positive for HCV and RT-PCR positive via minipool nucleic acid testing) were tested via peptide pools. A total of 12 samples were reactive with one or more peptide pools as listed in Table 9.

TABLE 9

List of sample ID numbers with positive results from HCV RNA positive/anti-HCV positive blood donors from ARC.

| HCV Antibody Positive/HCV RT-PCR Positive Samples (ARC) Sample ID | Peptide Pool 1 S/CO* | Peptide Pool 2 S/CO* | Peptide Pool 3 S/CO* |
|---|---|---|---|
| S0127 | 6.8 | NR | NR |
| S0104 | 4.4 | NR | NR |
| S0046 | 1.5 | NR | NR |
| S0128 | NR | 3.6 | NR |
| S0045 | NR | 2.6 | NR |
| S0178 | NR | 2.3 | NR |
| S0044 | NR | 2.2 | NR |
| S0220 | NR | 1.9 | NR |
| S0238 | NR | 1.2 | NR |
| S0141 | NR | 1.1 | NR |
| S0077 | NR | NR | 1.5 |
| S0202 | NR | NR | 1.5 |

*S/CO = sample to cutoff value > 1.0 is considered reactive for antibodies to that peptide. The cutoff was determined as 10 times the signal for the negative control value.
**Non-reactive Samples reactive with pooled peptides were re-tested with individual peptides from the reactive peptide pool as shown below. Data below indicate that 5 samples were reactive with two or more individual peptides and 9 samples were reactive with single peptides (Table 10).

positive. The three HPgV-2 RNA positive samples showed reactivity to peptide 16, 2 out of 3 were reactive for peptide 9, 1 was reactive for peptide 4, and 1 was reactive for peptide 3. Whereas sample ABT0029A.US was reactive to 13 of the peptides, sample ABT0055A.US was only reactive for peptide 16, and sample ABT0128A.US was reactive to both peptide 9 and 16. The peptide reactivity data supports the utility of peptides 3, 4, 9, and 16 in detecting HPgV-2 RNA positives. Seventeen additional samples that were antibody negative for these 14 peptides were also tested by RT-PCR: all 17 samples were negative by RT-PCR.

Blood Donor Samples from Thailand

A total of 145 HIV positive blood donor samples (obtained from Thailand) were tested via the three peptide pools. A total of 6 samples were detected as reactive with one or more peptide pools as listed in Table 11.

TABLE 11

List of sample ID numbers with positive results from 145 samples collected in Thailand

| Thailand Samples Sample ID | Peptide Pool 1 S/CO* | Peptide Pool 2 S/CO* | Peptide Pool 3 S/CO* |
|---|---|---|---|
| S0116 | 17.6 | NR | NR |
| S0068 | NR | 18.4 | NR |
| S0145 | NR | 17.0 | NR |
| S0027 | NR | NR | 38.1 |
| S0136 | NR | NR | 16.1 |
| S0016 | NR | NR | 10.1 |

*S/CO = sample to cutoff value > 1.0 is considered reactive for antibodies to that peptide. The cutoff was determined as 10 times the signal for the negative control value.
**Non-reactive

TABLE 10

Individual peptide results on HCV RNA positive/anti-HCV positive on ARC blood donor samples reactive with peptide pools. Shown are signal to noise (S/N) values compared to the negative control for each peptide tested individually. RT-PCR was performed and results are indicated.

| | Abbott ID | 1 | 2 | 3 | 4 | 5 | 6 | 7 | 8 | 9 | 10 | 11 | 12 | 13 | 14 | 15 | 16 | PCR result |
|---|---|---|---|---|---|---|---|---|---|---|---|---|---|---|---|---|---|---|
| 240 HCV RNA and Ab positive samples from ARC | S0029 | 7 | 19 | 11 | 12 | 25 | 46 | 16 | 15 | 12 | 30 | | 35 | | 23 | | 28 | positive |
| | S0055 | | | | | | | | | | | | | | | | 15 | positive |
| | S0127 | | | | | 164 | | | | | | | | | | | | negative |
| | S0104 | | | | | 152 | | | | | | | | | | | | negative |
| | S0046 | | | | | | | | | 136 | | | | | | | | negative |
| | S0128 | | | | | | | | | 69 | | | | | | | 24 | positive |
| | S0045 | | | 30 | | | | | | | | | | | | | | negative |
| | S0178 | | | 21 | | | | | | | | | | | | | | negative |
| | S0044 | | | | | 12 | | | | 18 | | | | | | | 71 | negative |
| | S0220 | | 59 | | | | | | | | | | | | | | | negative |
| | S0238 | | | | 30 | | | | | 46 | | | | | | | | negative |
| | S0141 | | | 30 | | | | | | | | | | | | | | negative |
| | S0077 | | | | | | | | | | | | | 15 | | | | negative |
| | S0202 | | | | | | 14 | | | | | | | 21 | | | | negative |

RT-PCR testing was performed on the 14 samples. Three samples (S029, ABT0029A.US; S0055, ABT0055A.US; and S128, ABT0128A.US) were found to be HPgV-2 RNA Samples reactive with pooled peptides were retested with individual peptides from the reactive peptide pool as shown below. Data below indicate that all samples were reactive only single peptides (Table 12).

TABLE 12

Individual peptide results on Thailand samples reactive with peptide pools.

For 145 Thailand sample: reactive to (S/CO)

| Run ID | P1 | p2 | p3 | p4 | p5 | p6 | p7 | p8 | p9 | p10 | p11 | p12 | p13 | 14 |
|---|---|---|---|---|---|---|---|---|---|---|---|---|---|---|
| S0116 |  | 2.8 |  |  |  |  |  |  |  |  |  |  |  |  |
| S0068 |  |  |  |  | 1.0 |  |  |  |  |  |  |  |  |  |
| S0145 |  |  |  |  | 1.6 |  |  |  |  |  |  |  |  |  |
| S0027 |  |  |  |  |  |  |  |  |  |  | 9.4 |  |  |  |
| S0136 |  |  |  |  |  |  |  |  |  |  |  | 2.1 |  |  |
| S0016 |  |  |  |  |  |  |  |  |  | 1.1 |  |  |  |  |

HIV Positive Blood Donor Samples from South Africa.

A total of 73 HIV donor samples (obtained from South Africa) that were tested with the three peptide pools. Most of the samples were from HIV-infected blood donors. A total of 4 samples were detected as reactive with one or more peptide pools as listed in Table 13.

TABLE 13

List of sample ID numbers with positive results from HIV positive blood donors from South Africa.

| South African Blood Donors (anti-HCV positive) Sample ID | Peptide Pool 1 S/CO* | Peptide Pool 2 S/CO* | Peptide Pool 3 S/CO* |
|---|---|---|---|
| S0027 | 1.3 | NR | NR |
| S0009 | NR | 2.2 | NR |
| S0004 | NR | 1.6 | NR |
| S0008 | NR | NR | 3.4 |

*S/CO = sample to cutoff value > 1.0 is considered reactive for antibodies to that peptide. The cutoff was determined as 10 times the signal for the negative control value.
**Non-reactive Samples reactive with pooled peptides were re-tested with individual peptides from the reactive peptide pool as shown below. Data below indicate that all four samples were reactive with only single peptides (Table 14).

TABLE 14

List of ID numbers with positive results on individual peptides.

For 73 S. Africa sample: reactive to (S/CO)

| Run ID | P1 | p2 | p3 | p4 | p5 | p6 | p7 | p8 | p9 | p10 | p11 | p12 | p13 | 14 |
|---|---|---|---|---|---|---|---|---|---|---|---|---|---|---|
| S0027 |  |  |  | 2.1 |  |  |  |  |  |  |  |  |  |  |
| S0009 |  |  |  |  | 17.0 |  |  |  |  |  |  |  |  |  |
| S0004 |  |  |  |  | 3.2 |  |  |  |  |  |  |  |  |  |
| S0008 |  |  |  |  |  |  |  |  |  |  | 14.9 |  |  |  |

Expanded HPgV-2 Prevalence Studies

The first seven isolates (ABT0096P, ABT0070P, ABT0188P, ABT0029A, ABT0055A, and ABT0128A), besides index case, showed a positive correlation between having an antibody response to peptides 3, 4, 9, or 16 and the presence of HPgV-2 RNA. Continued studies to investigate the presence of HPgV-2 in different populations was performed using a combination of antibody testing with a pool of peptides 3, 4, 9, 16 and the RT-PCR assay described in Example 3.

A total of 542 samples were positive for both HCV RNA and antibodies to HCV (including 200 ProMedDx samples, 240 HCV samples from ARC and a second set of 100 samples from ProMedDx). Eight of these 540 samples (1.5%) were positive for HPgV-2 RNA when screened with the KEYS qPCR multiplex assay. Six of the 8 HPgV-2 RNA positives samples from this group were reactive with one or more HPgV-2 peptides. (Two HPgV-2 RNA positive samples were obtained from individuals co-infected with HIV and HCV and were tested as negative for antibodies to HPgV-2 peptides). Overall 24 of the 540 (4.4%) samples were reactive with one or more HPgV-2 peptides: six of these 24 (25.0%) were HPgV-2 RNA positive, indicating a positive predictive value of 25.0%. The negative predictive was calculated to be 99.6%. A total of 13 of the 542 (2.4%) samples were reactive with two or more peptides and 5 of the 13 (38.5%) samples, indicating a positive predictive value for HPgV-2 RNA positivity as being 38.5%, and a negative predictive value of 99.6%.

There was a fourth set of 240 HCV RNA samples obtained from the American Red Cross (Gaithersburg, Md.) that were anti-HCV negative, and thus, were recent infections, within the preseroconversion window period. There was 1 sample among 240 (0.4%) samples that was HPgV-2 RNA positive. This sample was not reactive with any of the HPgV-2 peptides. Overall, a total of 5 of 240 (2.1%) samples were reactive with one or more HPgV-2 peptides, but none of the samples were reactive with two or more peptides.

A total of 188 samples were positive for both HBsAg and HBV DNA. None of these samples were positive for HPgV-2 RNA and a total of 3 of 188 (1.6%) samples were reactive with one or more HPgV-2 peptides. One sample was reactive with two or more peptides.

A total of 298 samples were positive for both HIV RNA and antibodies to HIV. A total of 4 of 298 (1.3%) were reactive to one or more HPgV-2 peptides and one sample was reactive for two or more peptides. One sample was positive for HPgV-2 RNA, and was reactive with on HPgV-2 peptide. Two additional samples were identified by RT-PCR screening that not detected with the peptides. The 3 RT-PCR positive samples were confirmed by RT-PCR assay but not next generation sequencing. Upon further testing it was noted that the two HPgV-2 RNA samples that were negative for HPgV-2 peptides were positive for anti-HCV (Abbott ARCHITECT anti-HCV) and HCV antigen (Abbott ARCHITECT HCV Ag). Therefore these samples are categorized as co-infected with HCV and were removed from this sample group and included in the HCV antibody positive HCV RNA positive group (Table 15 below).

A total of 463 samples were obtained from volunteer blood donors, considered to be at low risk for parenterally transmitted viruses like HCV. A total of 13 of 463 (2.8%) of the groups tested. HPgV-2 RNA was found more frequently in HCV infected individuals than in volunteer blood donors, HBV positive individuals, and HIV infected individuals not co-infected with HCV. The frequency of HPgV-2 infection (as noted by HPgV-2 RNA or antibody detection to HPgV-2 peptides) was higher among HCV seropositive individuals, than in HCV infected individuals who are seronegative. Reactivity to two or more of peptides 4, 9, or 16 had a positive predictive value of having HPgV-2 RNA. The negative predictive value for reactivity to peptides was high in all of the groups tested.

TABLE 15

Number of samples reactive to at least one peptide from the peptide pool (3, 4, 9, 16) for the indicated sample groups.

| | | | Antibody Reactive to one or more peptides(%) | | |
|---|---|---|---|---|---|
| Group | HPgV-1 RNA positive (%) | HPgV-2 RNA positive (%) | Positive (%) | Positive Predictive value* | Negative Predictive Value** |
| HCV Ab+/PCR+ (n = 542*) | 40 (7.4%) | 8 (1.5%) | 24 (4.4%) | 6/24 (25%) | 518/520 (99.6%) |
| HCV Ab−/PCR+ (n = 240) | nt | 1 (0.4%) | 5 (2.1%) | 0/5 (0%) | 239/240 (99.6%) |
| HIV (n = 296) | 29/275 (10.5%) | 1 (0.3%) | 4 (1.3%) | 1/4 (25.0%) | 288/292 (98.6%) |
| HBV (n = 188) | 6 (3.2%) | 0/0 (0%) | 3 (1.6%) | N/A | 185/188 (98.4%) |
| Blood donors (n = 463) | 19/452 (4.2%) | 0/0 (0%) | 13 (2.8%) | N/A | 450/463 (97.2%) |
| Grand total (n = 1729) | 94/1457 (6.4%) | 10 (0.6%) | 40 (2.3%) | | |

| | Antibody reactive to two or more peptides (%) | | | |
|---|---|---|---|---|
| Group | Positive (%) | Positive Predictive value* | Negative Predictive Value** | Antibody Reactive/PCR negative− |
| HCV Ab+/PCR+ (n = 542*) | 13 (2.4%) | 5/13 (38.5%) | 529/531 (99.6%) | 18/534 (3.4%) |
| HCV Ab−/PCR+ (n = 240) | 0 (0%) | N/A | 239/240 (99.6%) | 5/239 (2.1%) |
| HIV (n = 296) | 1 (0.3%) | 0/1 | 294/295 (99. %) | 1/295 (0.3%) |
| HBV (n = 188) | 0/0 (0.0%) | N/A | 188/188 (100%)-- | 3/188 (1.6%) |
| Blood donors (n = 463) | 2 (0.4%) | N/A | 461/463 (99.4%)-- | 13/463 (2.8%) |
| Grand total (n = 1729) | 7/10 (70%) | | | 40/1708 (2.3%) |

*Positive predictive value was determined as the number of samples that were HPgV-2 RNA positive and antibody positive for HPgV-2 peptides divided by the total number of antibody positive samples
**Negative predictive value was determine as the number of samples that were negative for antibodies to HPgV-2 peptides minus the number of HPgV-2 RNA positive samplesdivided by the total number samples negative for antibodies to HPgV-2 peptides
***Includes co-infected HCV/HIV samples (n = 2), not confirmed by NGS.

samples were reactive with one or more HPgV-2 peptides. Two of the 463 (0.4%) samples were reactive with two or more peptides. None of the samples were positive for HPgV-2 RNA. (However, not all of the samples were tested using the same methodology. All 450 of the samples that were negative for antibody detection using HPgV-2 peptides were tested as negative via the multiplex RT-PCR assay. Among the 13 samples that were reactive for peptides only two were tested with the multiplex assay, both being negative. The remaining 11 samples were all tested for HPgV-2 RNA using the NS2/3 primer set and 7 of the 11 were also tested with other primer sets (E1, 5'UTR): all samples were negative for HPgV-2 RNA, as described in example 3)

A summary of the testing performed on various sample groups is found below. The frequency of HPgV-1 RNA positivity was higher than HPgV-2 RNA positivity in all of A total of 11 HPgV-2 RNA positive samples (including the index case) have been identified among 1729 samples tested (Table 16). A total of 782 of the 1729 (45.2%) of samples were obtained from HCV infected individuals. Ten of the 11 HPgV-2 RNA positive samples were found among individuals infected with HCV, suggesting that this virus may share a similar transmission pattern as HCV (parenteral exposure). For HPgV-1, the prevalence of HPgV-1 RNA was highest in the HIV population (10.5%), was relatively high in HCV infected persons (7.4%), and was detected in volunteer blood donors (4.2%), indicating that active infection with HPgV-1 is much more common than HPgV-2, for the populations studied.

As noted above, there were 40 samples among 1729 samples that were reactive to antibodies to HPgV-2 peptides. Seven of these 40 samples were HPgV-2 RNA positive. A total of 7 of the 10 (70%) HPgV-2 RNA positives were antibody reactive. The remaining 33 antibody reactive results were noted among 1719 tested samples, resulting in a frequency of 1.9%. As noted below, several of the HPgV-2 RNA positive samples are reactive to 2 or more peptides.

with traditional RT-PCR and Sanger sequencing, the current genome sequence coverage of each strain is reported. The 5'ends of viruses were obtained by SMARTer PCR cDNA synthesis (see FIG. 23A). The 3'end of ABT0070P.US was determined by 3'RACE and for ABT0029A.US and ABT0239AN.US by using RT-PCR, supplementing reactions with 2% DMSO (see FIG. 23DD-EE).

TABLE 22

| HPgV-2 isolate | HCV Ab/RNA | HCV RNA only | GBV-C RNA | HIV RNA | Peptide reactivity (S/CO) 3 | 4 | 9 | 16 | HPgV-2 Viral load Log RNA copies/ml |
|---|---|---|---|---|---|---|---|---|---|
| UC0125.US | + | − | nt | − | nt | 1.3 | 9.7 | nt | 6.2 |
| ABT0096P.US | + | − | − | − | 1.6 | 3.5 | 9.0 | 20.7 | 3.5 |
| ABT0070P.US | + | − | − | − | − | − | 5.3 | 1.1 | 5.2 |
| ABT0188P.US | + | − | − | − | 1.7 | 5.2 | − | − | 2.5 |
| ABT0055A.US | + | − | − | − | 1.0 | − | − | 1.5 | 3.8 |
| ABT0029A.US | + | − | + | − | − | 1.0 | 1.2 | 2.8 | 4.6 |
| ABT0128A.US | + | − | − | − | − | − | 6.9 | 2.4 | 4.5 |
| ABT0239.AN.US | − | + | − | − | − | − | − | − | 5.8 |
| ABT0100P.US | − | − | − | + | − | − | 16.3 | − | nt |
| ABT0030P.US | + | − | − | + | − | − | − | − | nt |
| ABT0035P.US | + | − | + | + | − | − | − | − | nt |

Example 5

Next Generation Sequencing of ABT0070P.US, ABT0096P.US and ABT0128A.US

The qPCR positive samples in Example 3.1 were probed by conventional RT-PCR as described in Example 2. Only ABT0070P.US was reactive with primers in NS5A: 6914F and 7213R (SEQ IDs 44 & 45) and in NS2-NS3: 3334F & 3708R (SEQ IDs 34 & 35) and products subsequently shown by Sanger sequencing to align to UC0125.US. All three samples were extracted and prepared for NGS as described in Example 2. Read mappings from multiple MiSeq runs were extracted and combined.

A total of 98,017 NGS reads from sample ABT0070P.US mapped to SEQ ID NO:1, covering 93% of the HPg-V2 genome. Coverage depth was 1133X±1364 reads/nucleotide, with a short gap (>20 nt) present at the 5' end, four internal gaps within the region of nt 2600-3400 in SEQ ID 1 totaling approximately 300 missing bases, and the final 354 nt lacking at the 3'end. The missing 5' end was filled in by PCR and Sanger sequencing of products from 44F-342R (SEQ ID NO: 12 &13) reactions. The internal gaps were covered by 10 overlapping amplicons located in the X-NS3 region using the primers listed in Table 1 (SEQ ID NO: 16-35). The resulting consensus sequence (SEQ ID NO: 75) combining the NGS and Sanger data is shown in FIG. 9 and annotated in FIG. 10. Table 16 reports the number of amino acid mismatches and the percentage identity compared to UC0125.US, which ranged from 90-97%, depending on the protein.

Figure 11A:
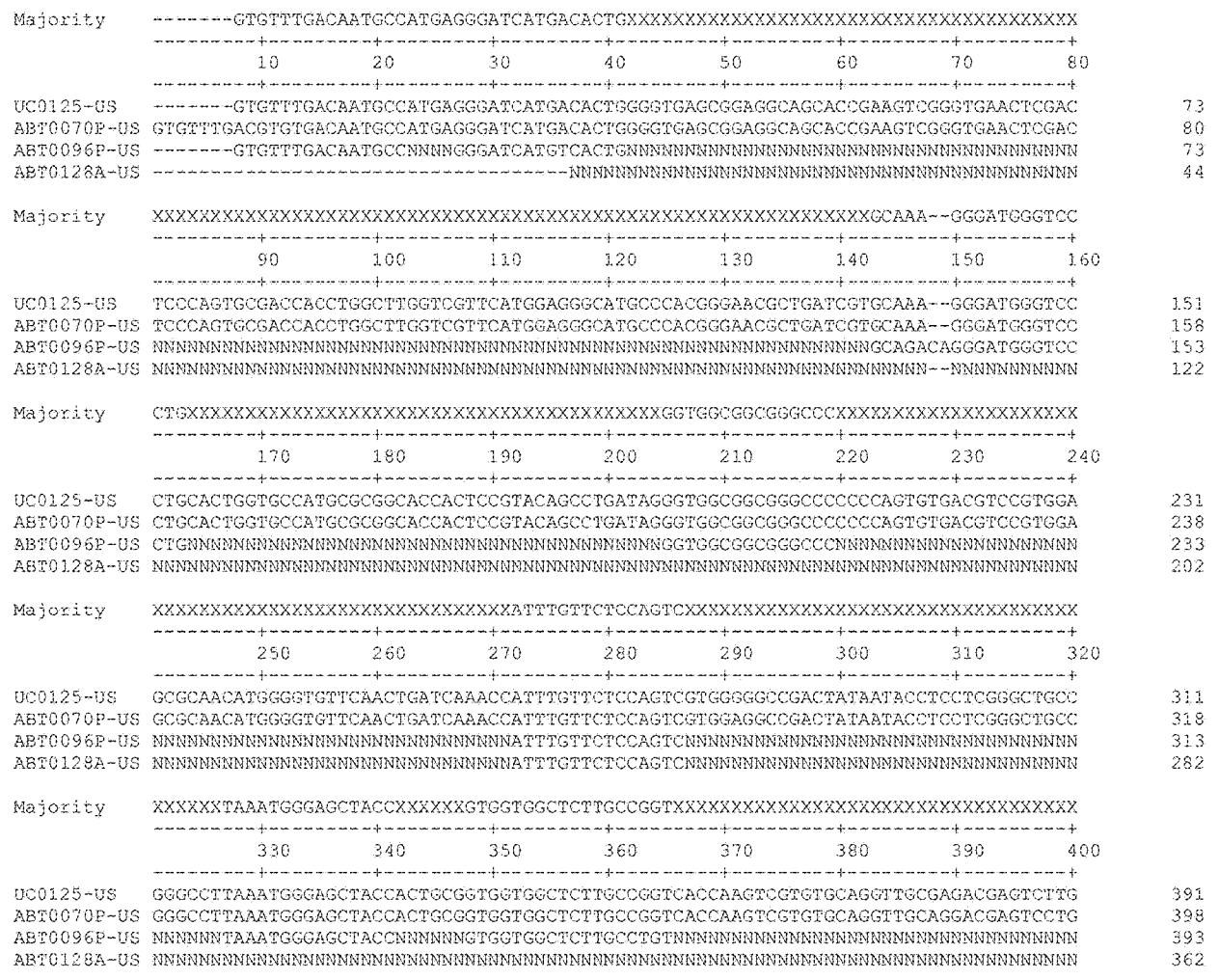
Figure 11B:
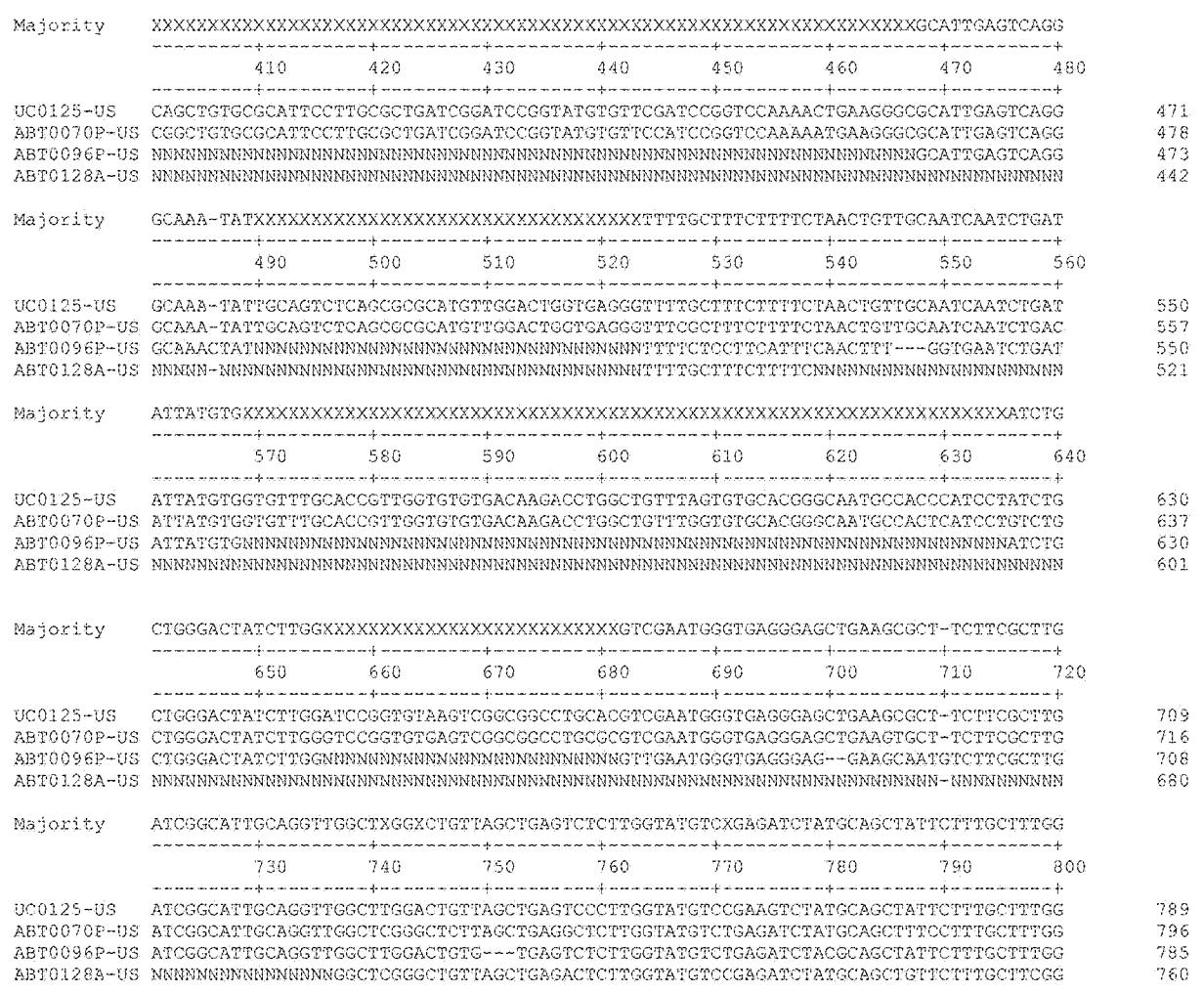
Figure 11C:
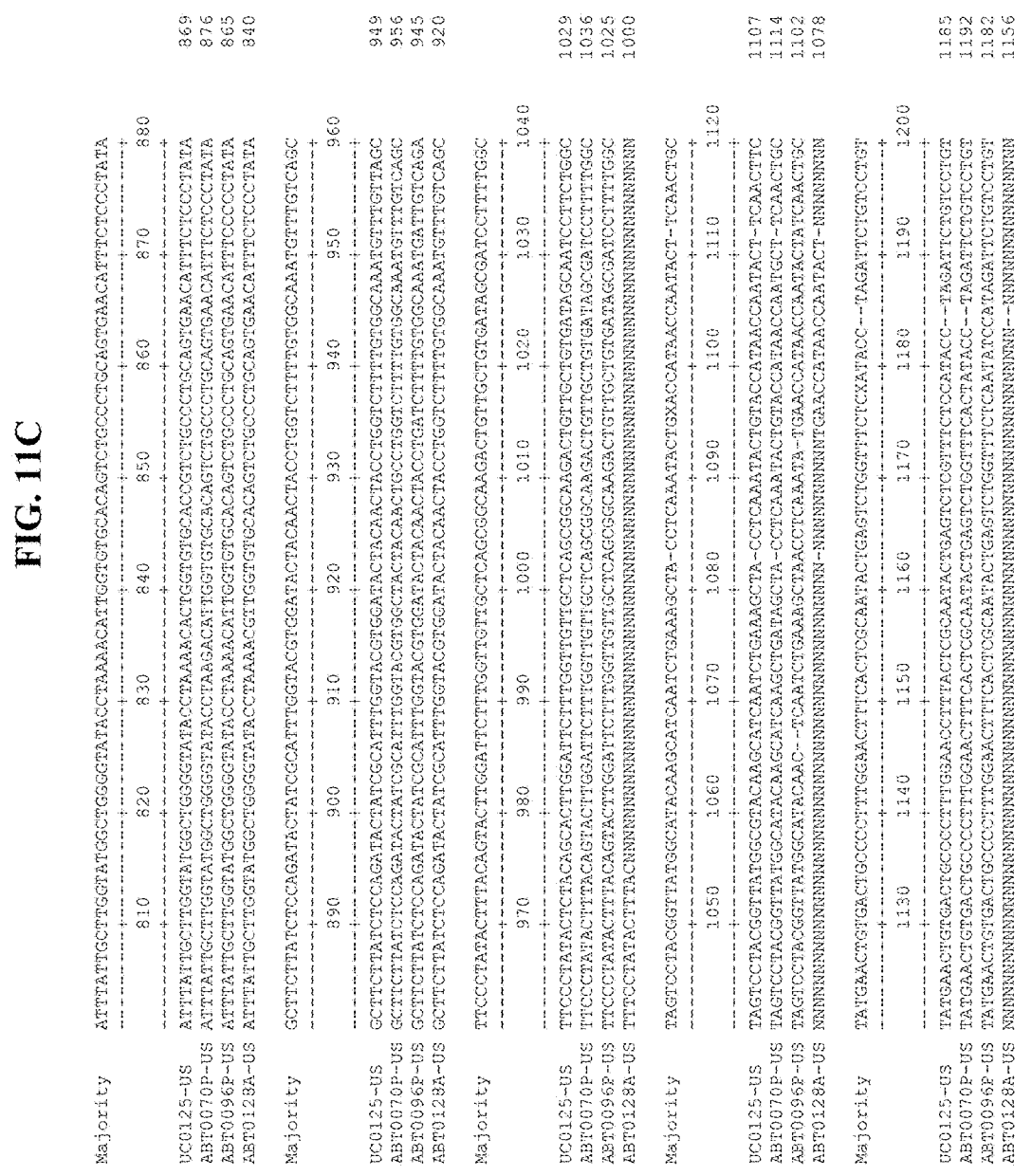
Figure 11D:
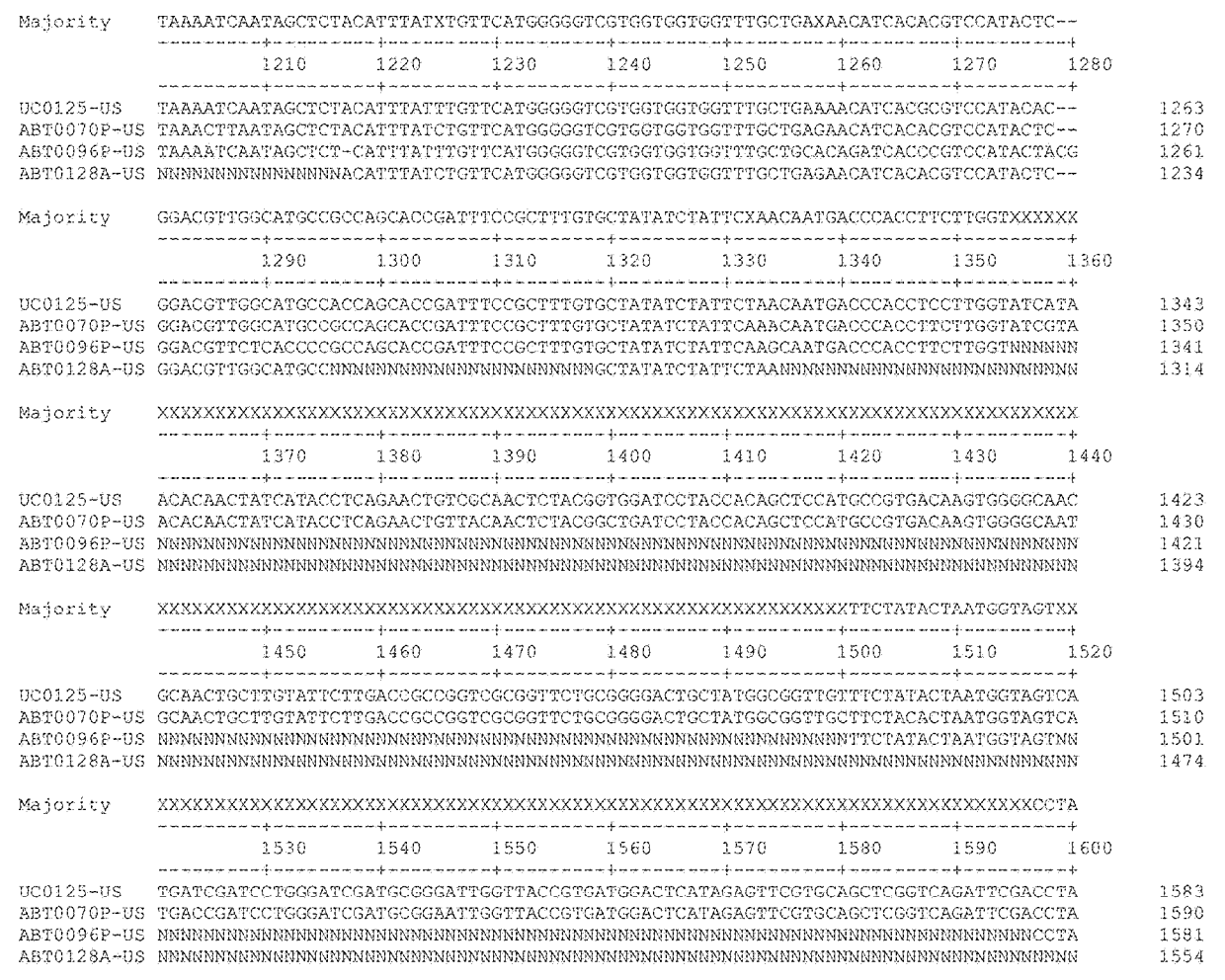
Figure 11E:
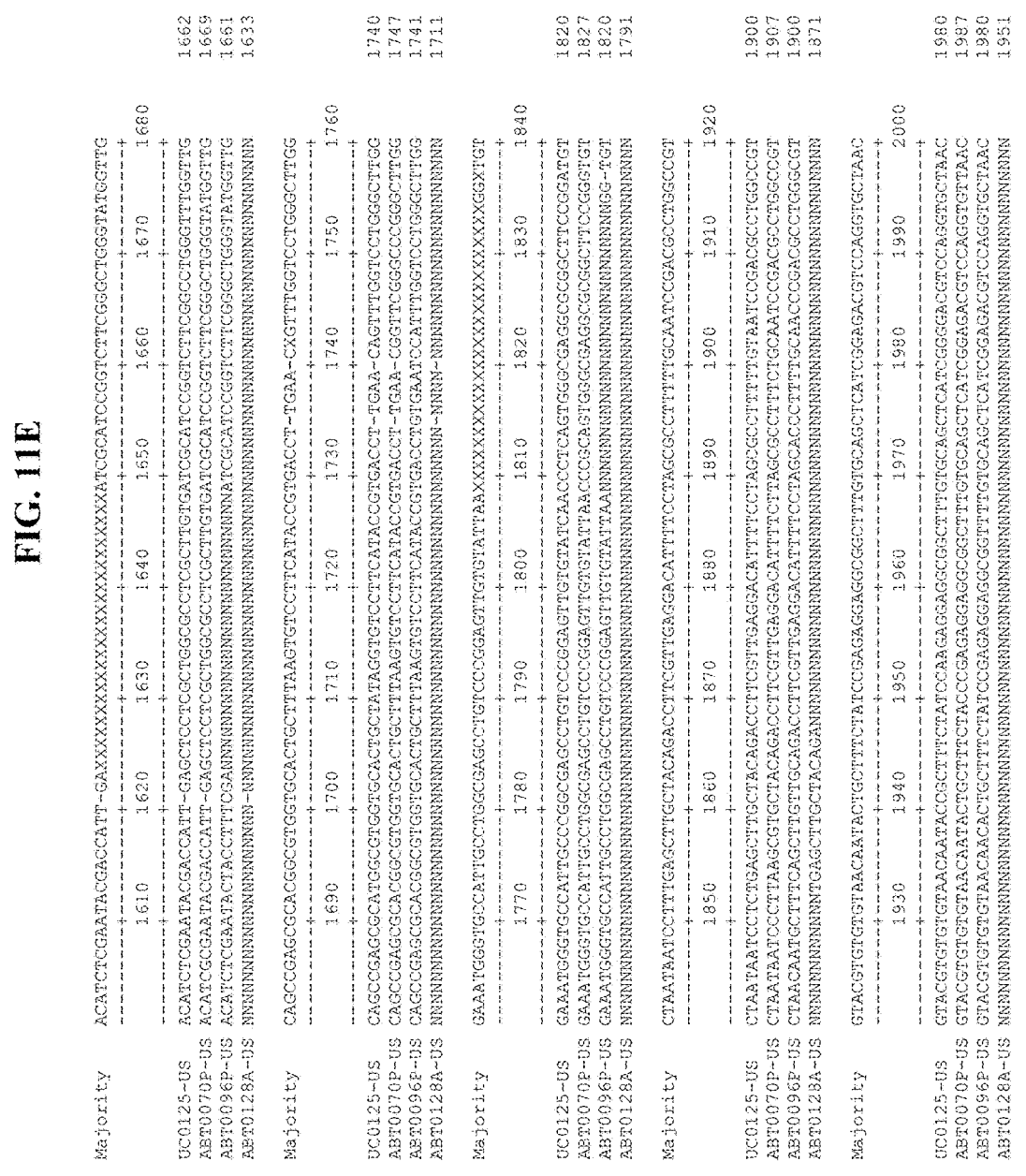
Figure 11F:
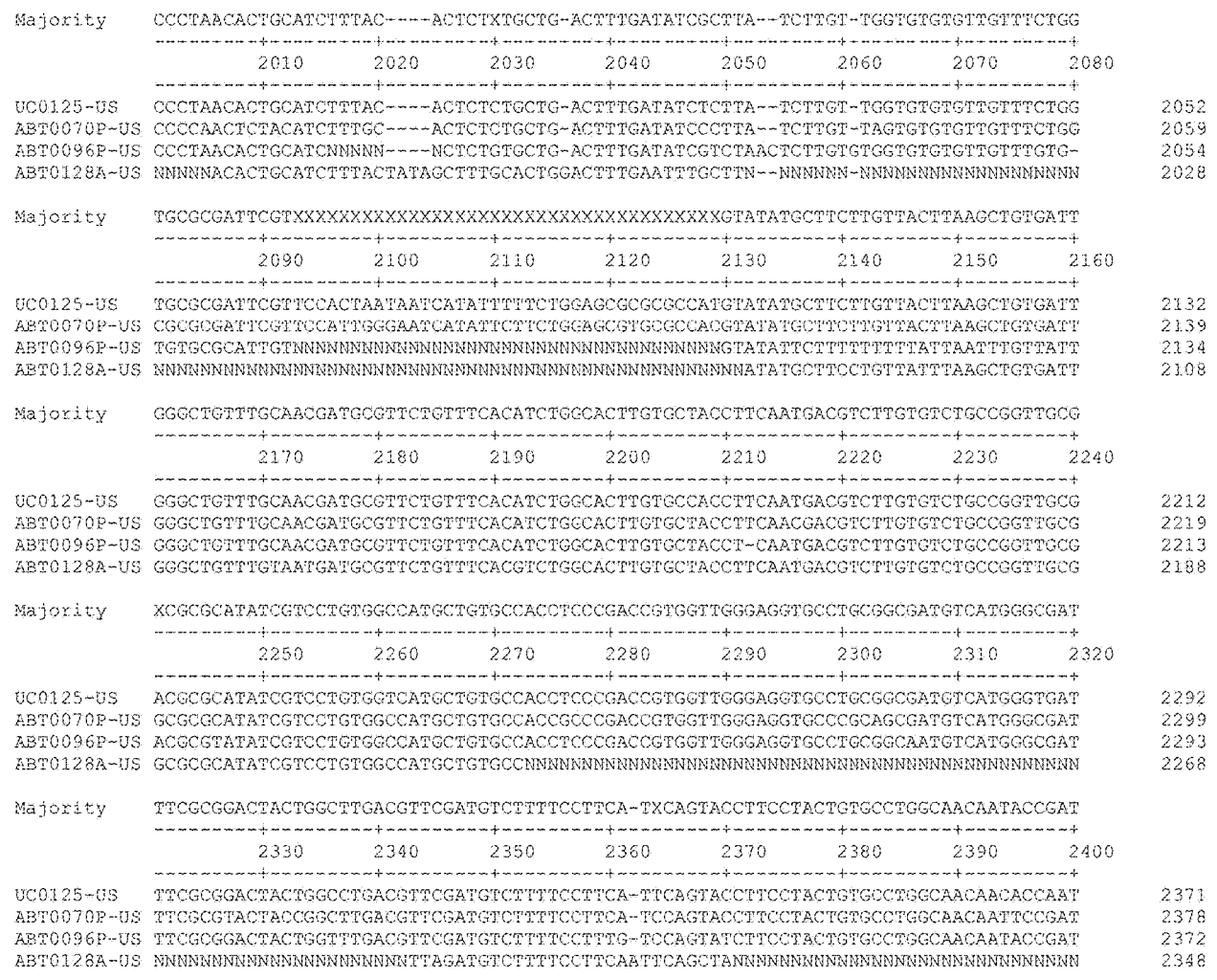
Figure 11G:
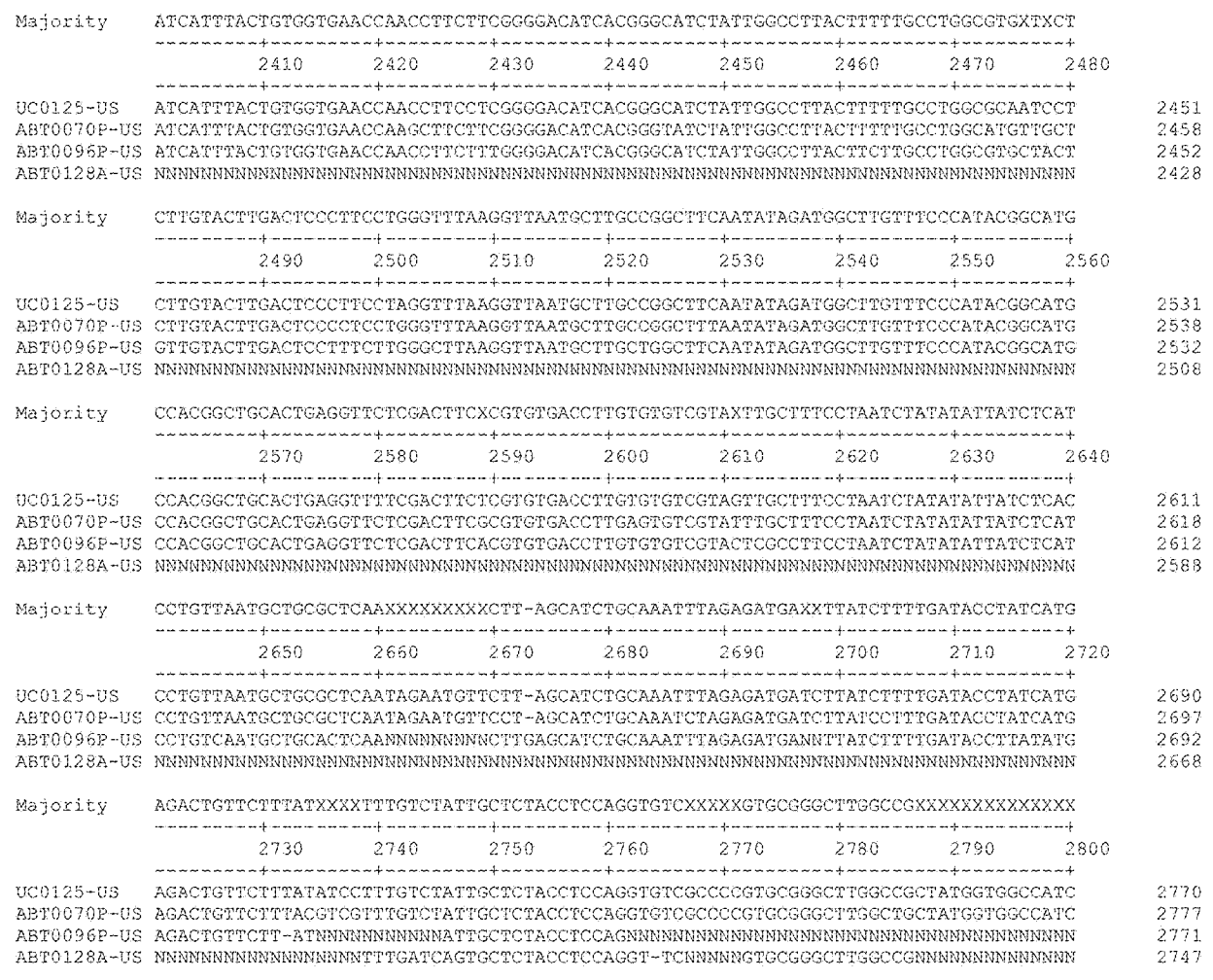
Figure 11H:
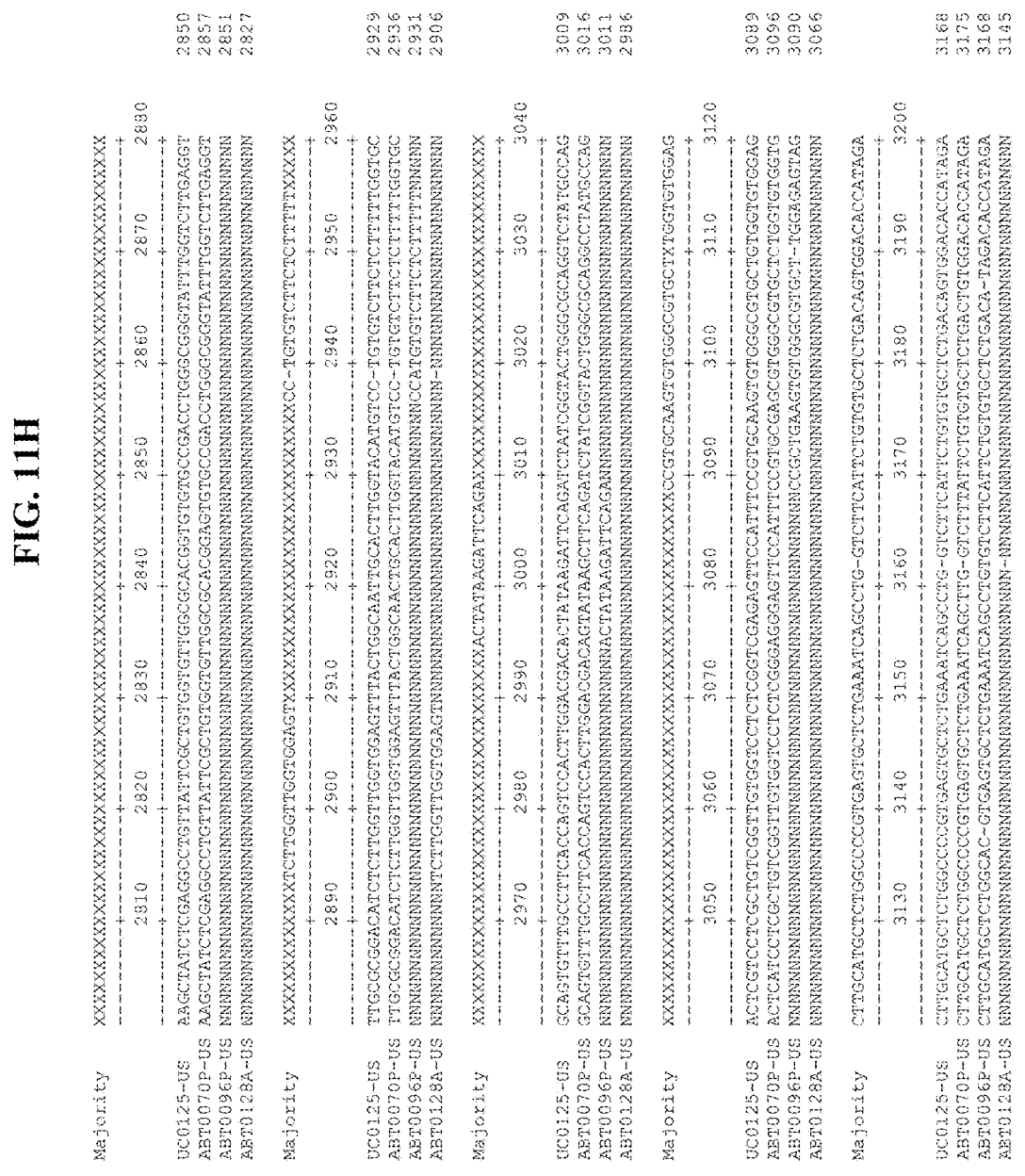
Figure 11I:
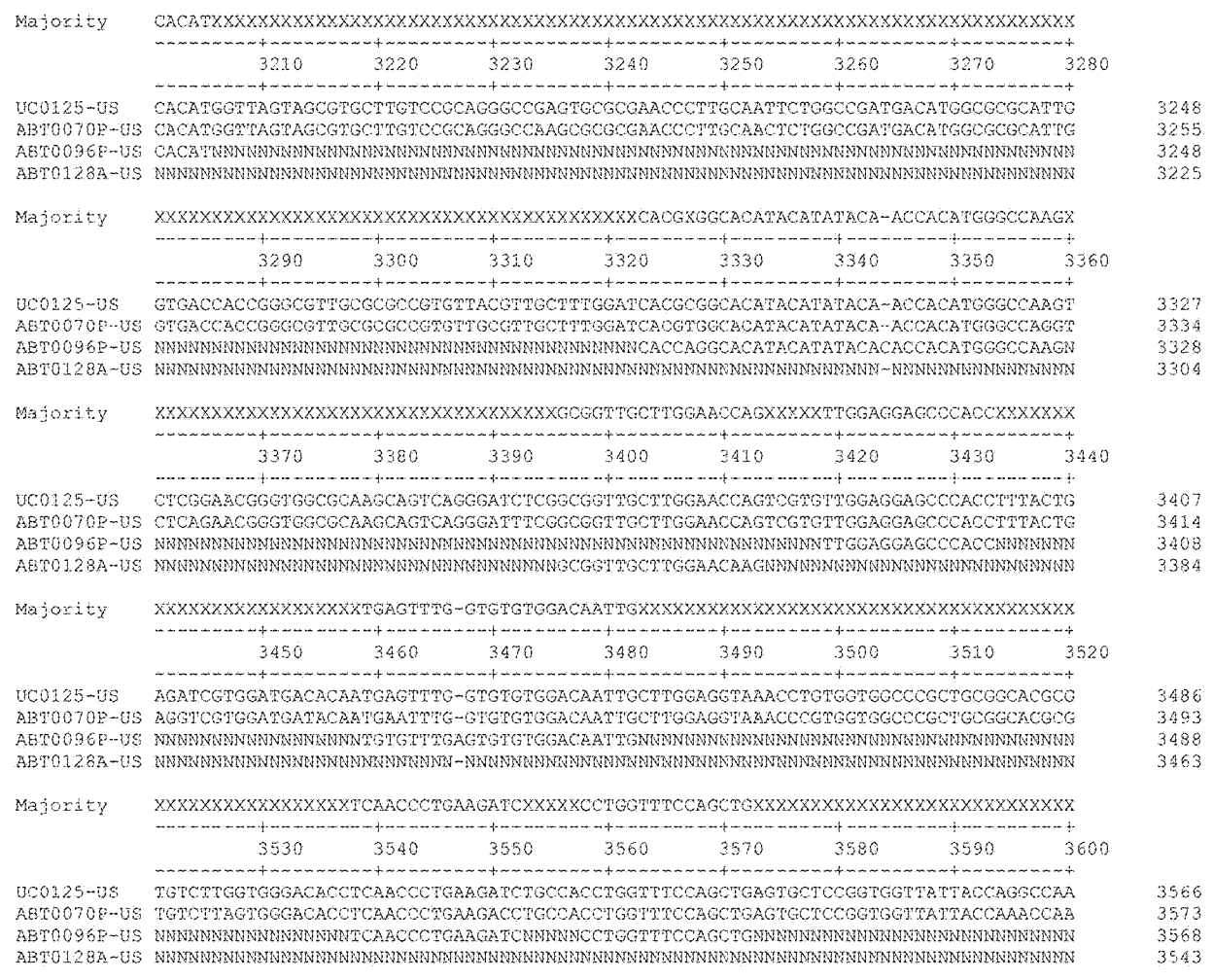
Figure 11K:
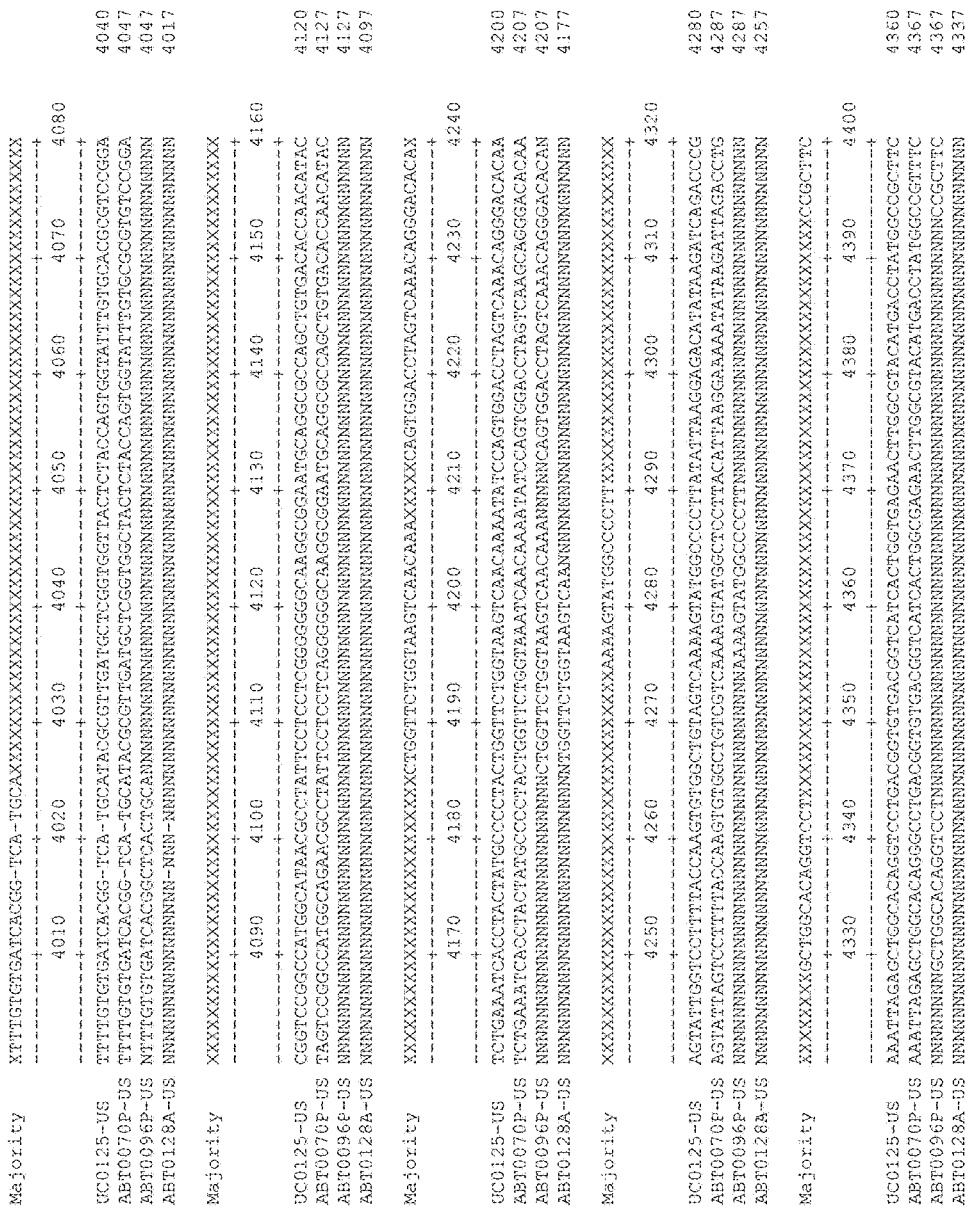
FIGS. 11A-Y show an alignment of the genomes or partial genomes of HPgV-2 variants UC0125.US, ABT0070P.US, ABT0096P.US (SEQ ID NO:354), and ABT0128A.US (SEQ ID NO:355), along with a majority consensus sequence (SEQ ID NO:356).
Figure 11L:
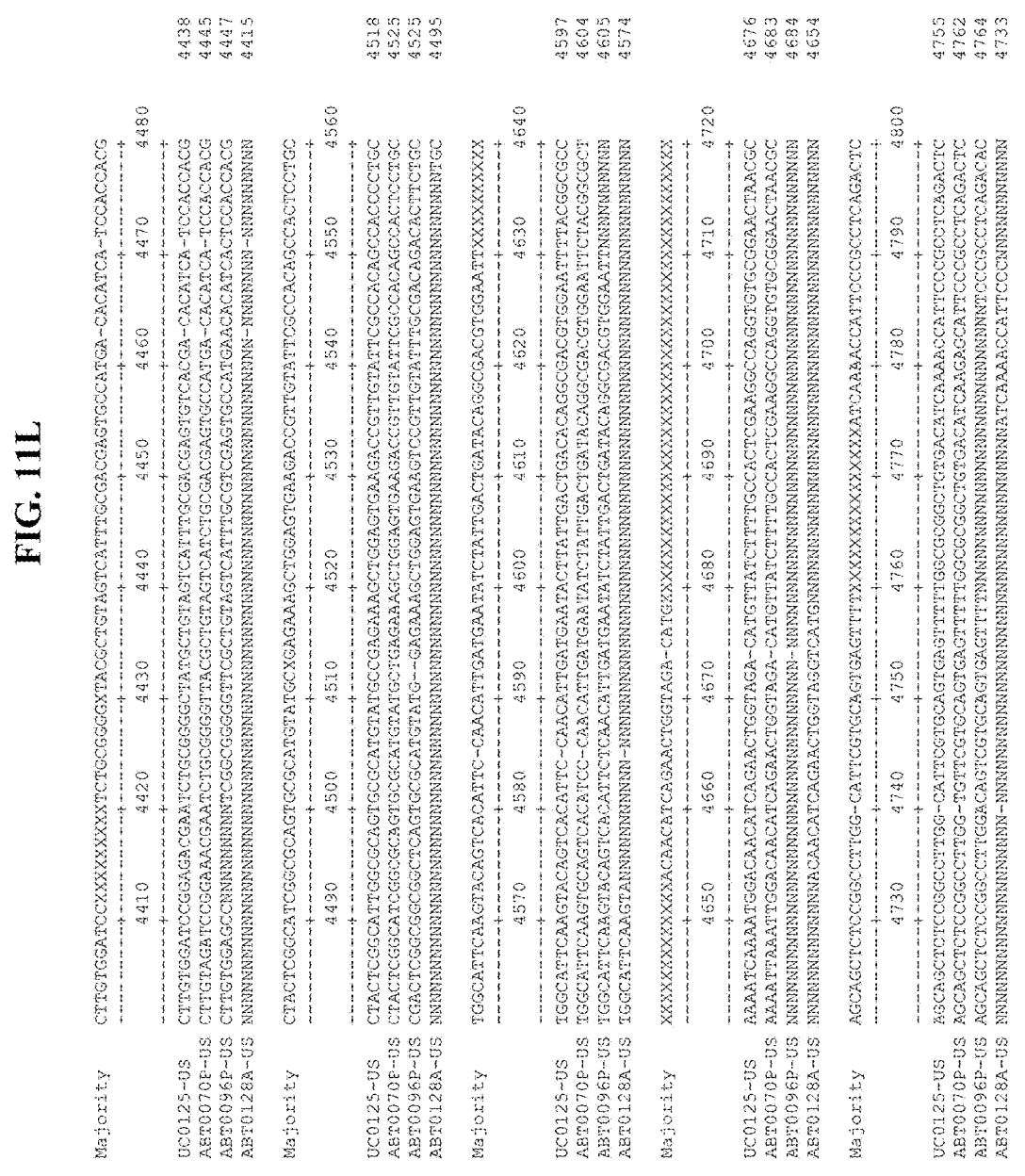
Figure 11M:
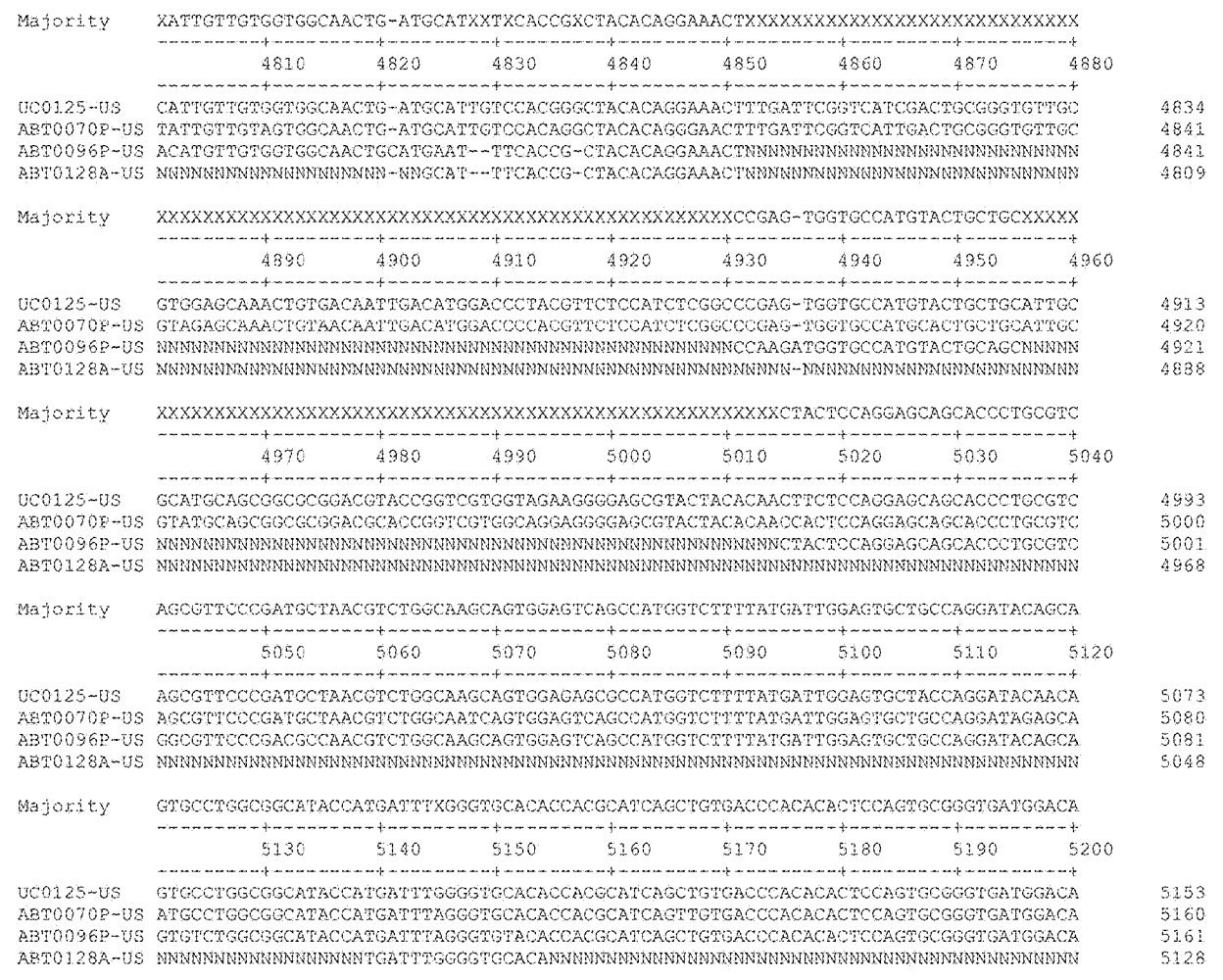
Figure 11N:
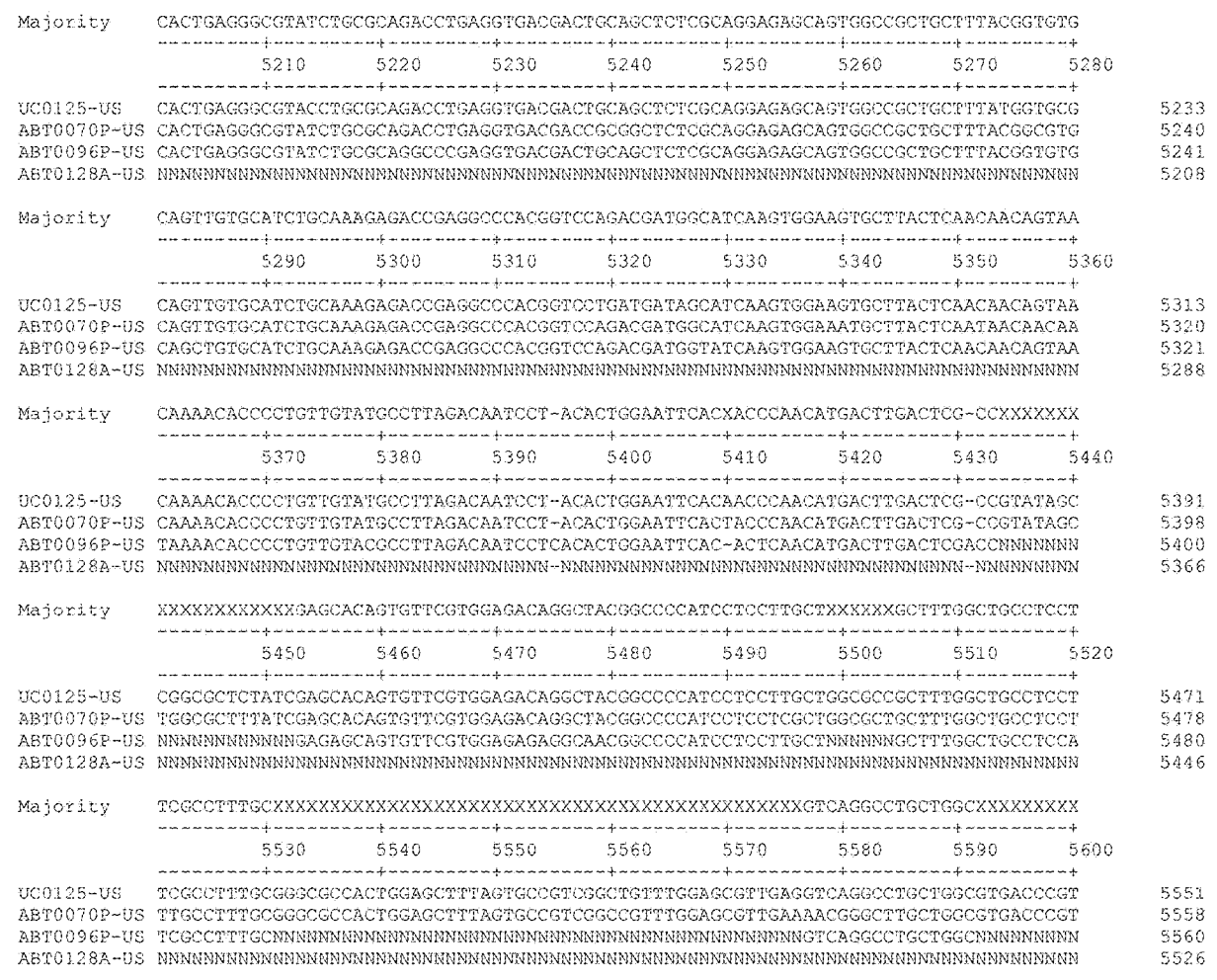
Figure 11P:
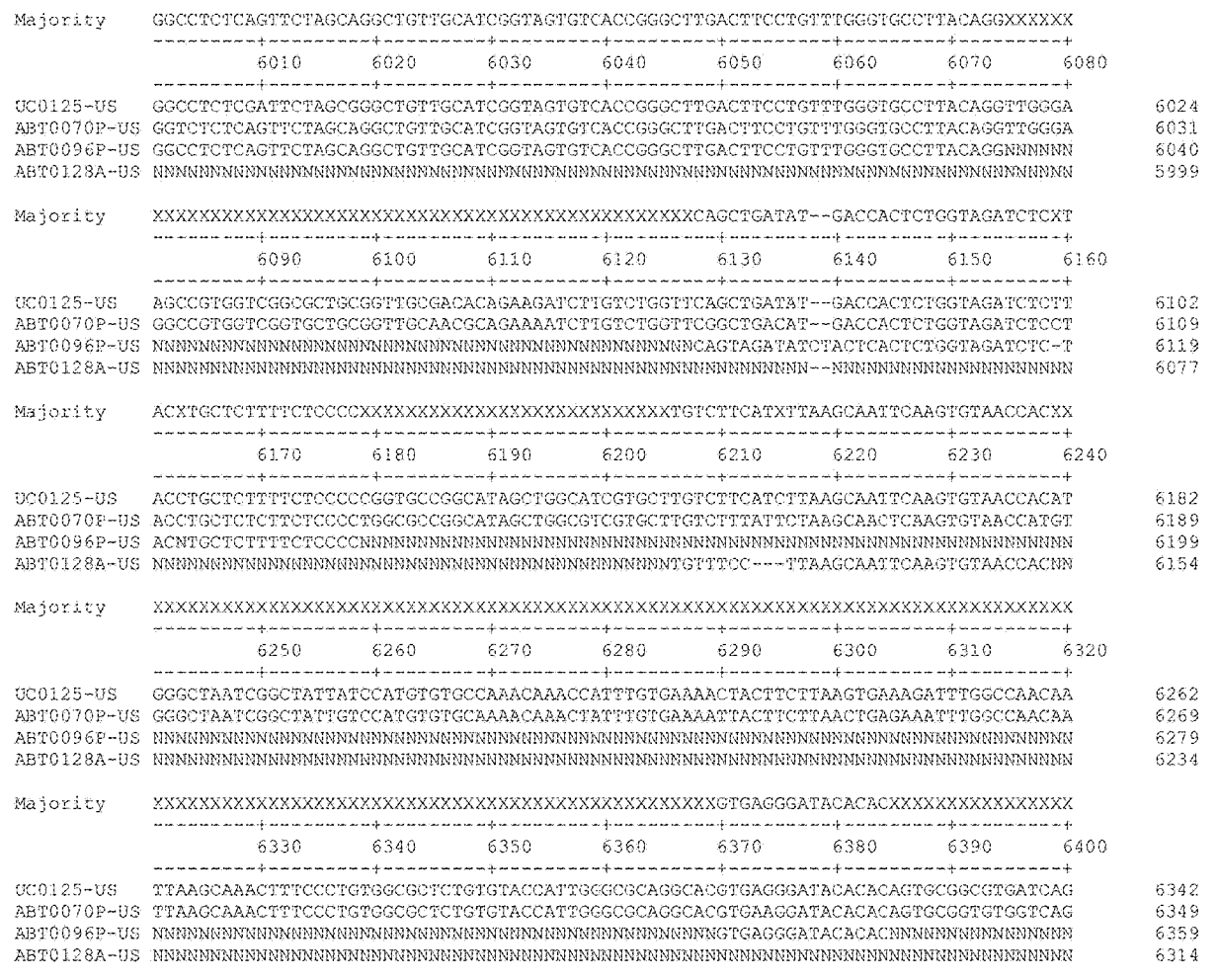
Figure 11Q:
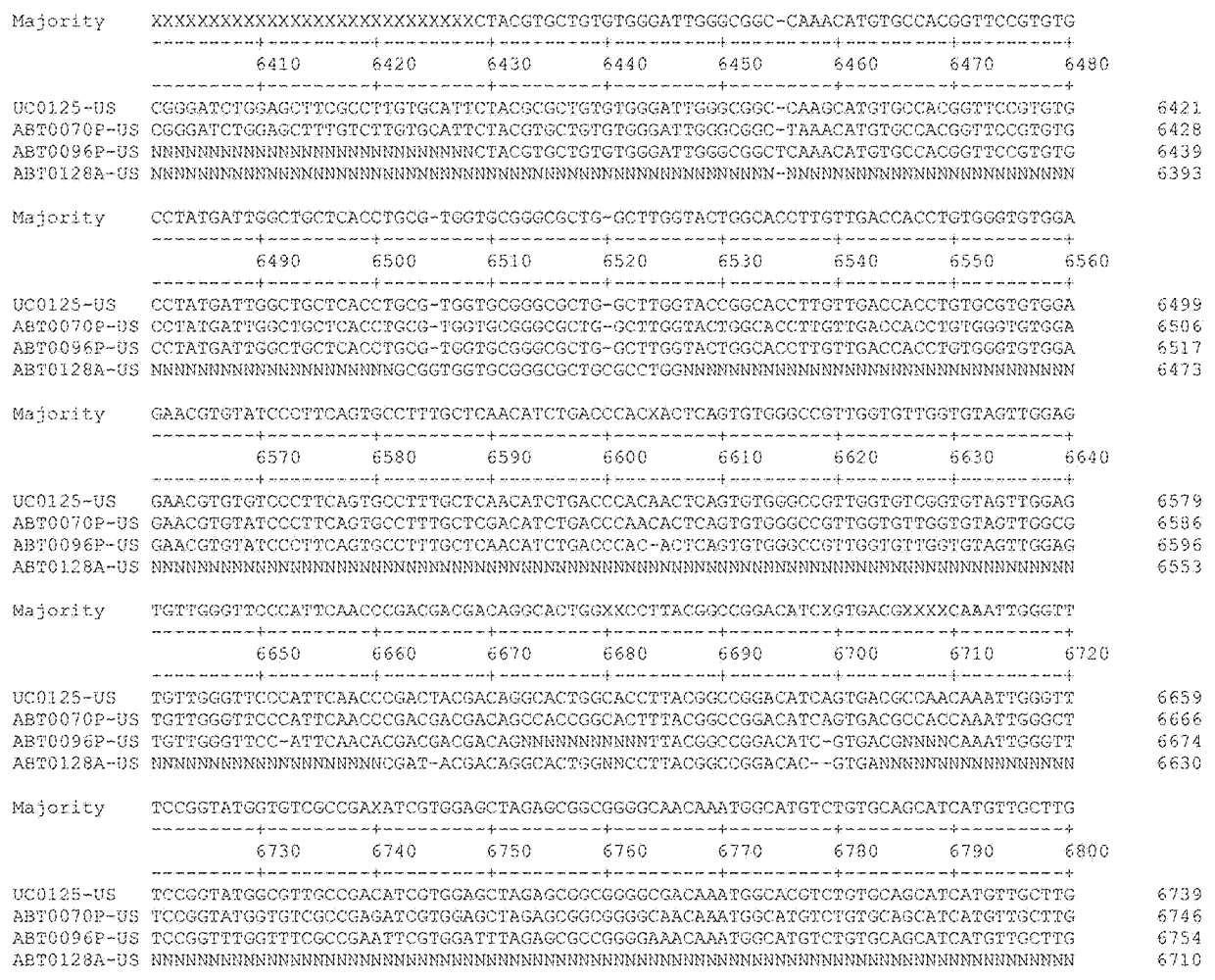
Figure 11R:
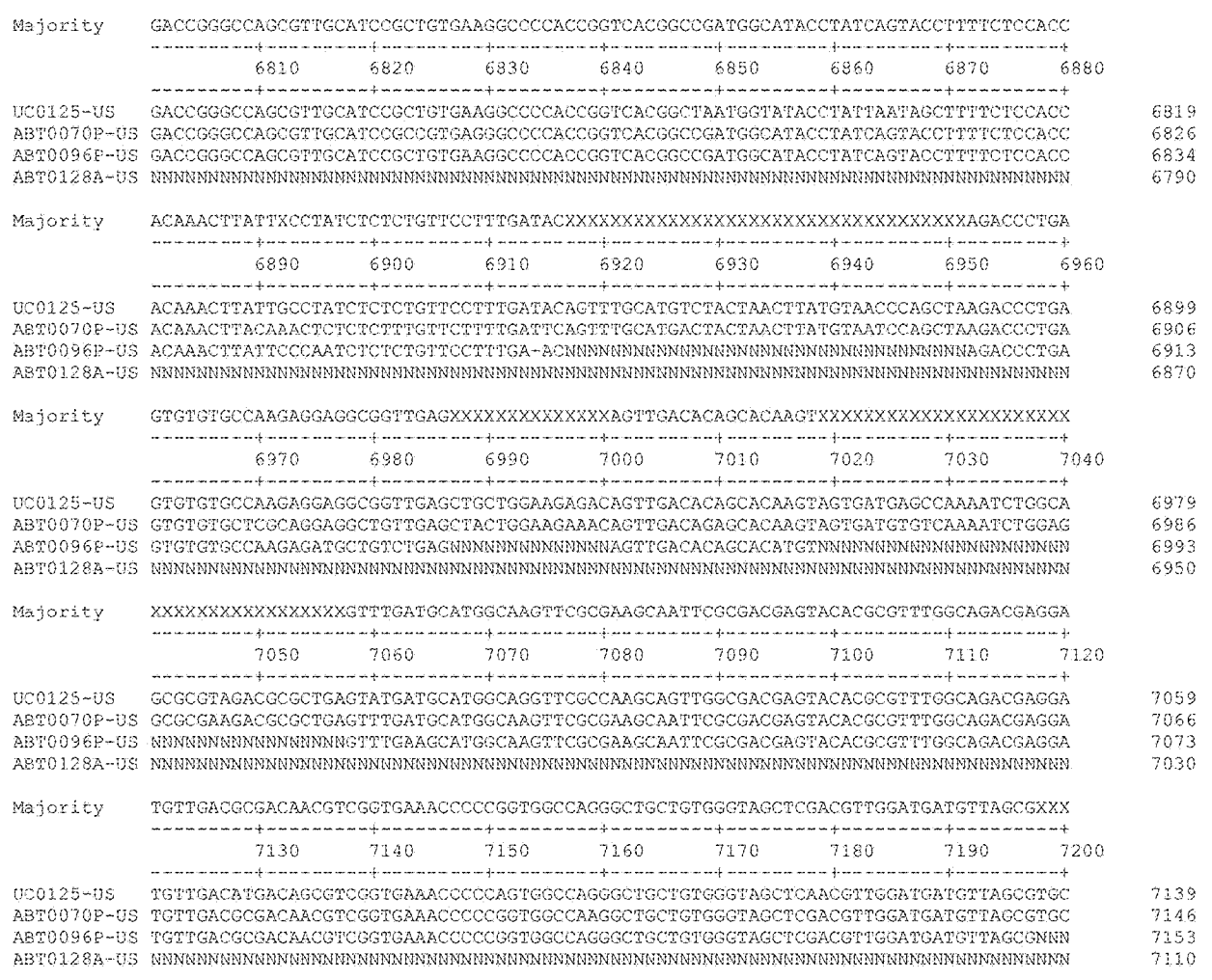
Figure 11U:
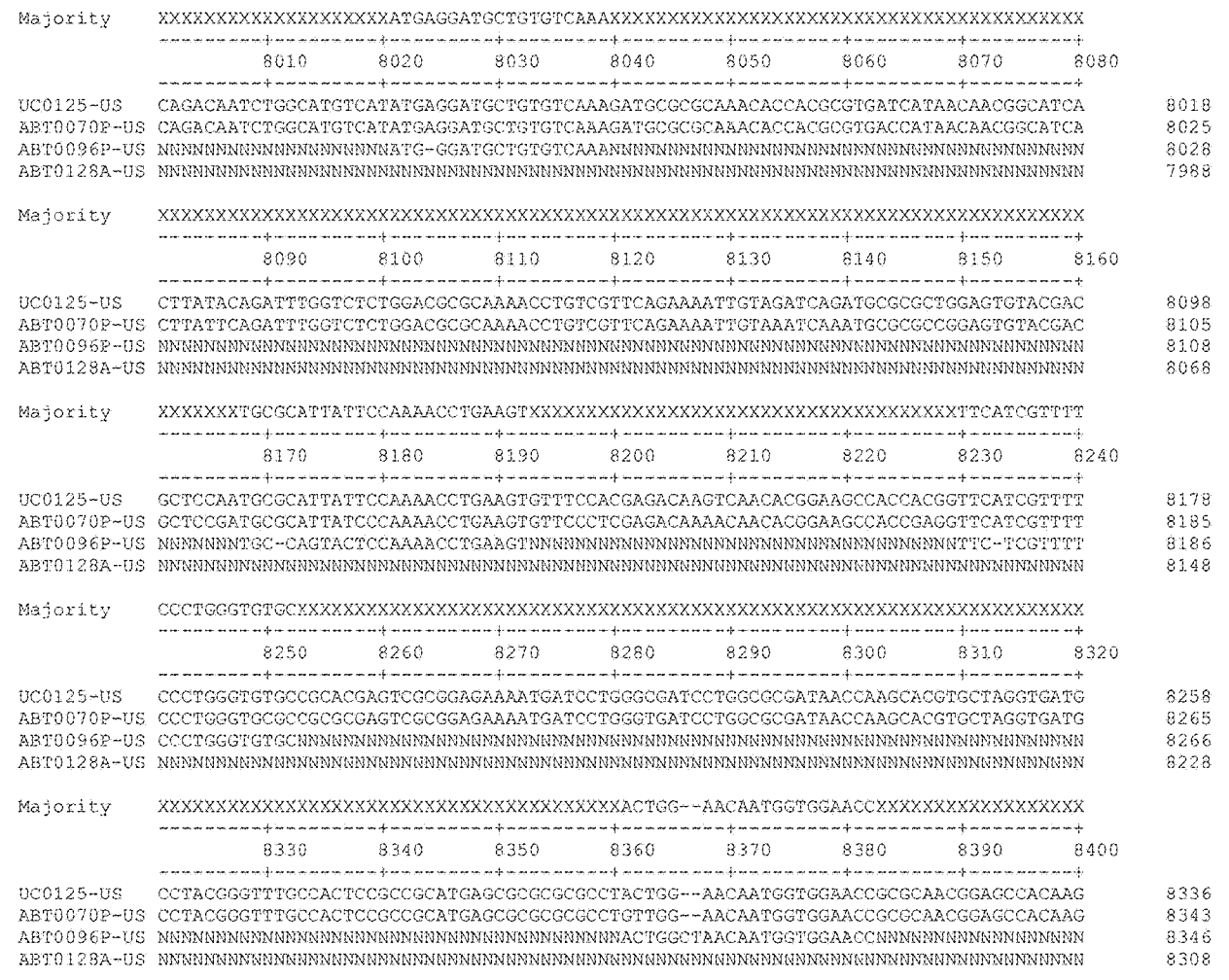
Figure 11V:
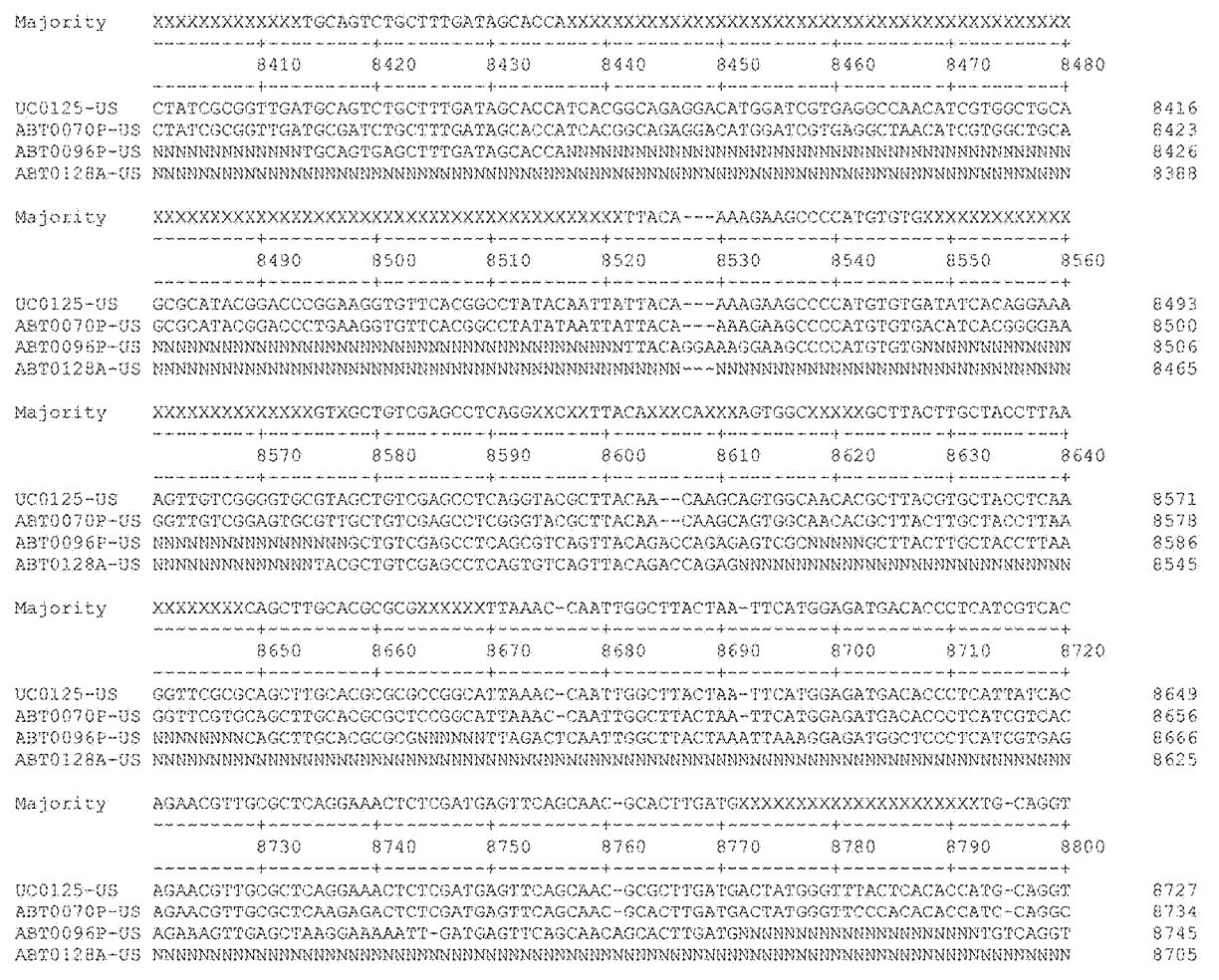
Figure 11W:
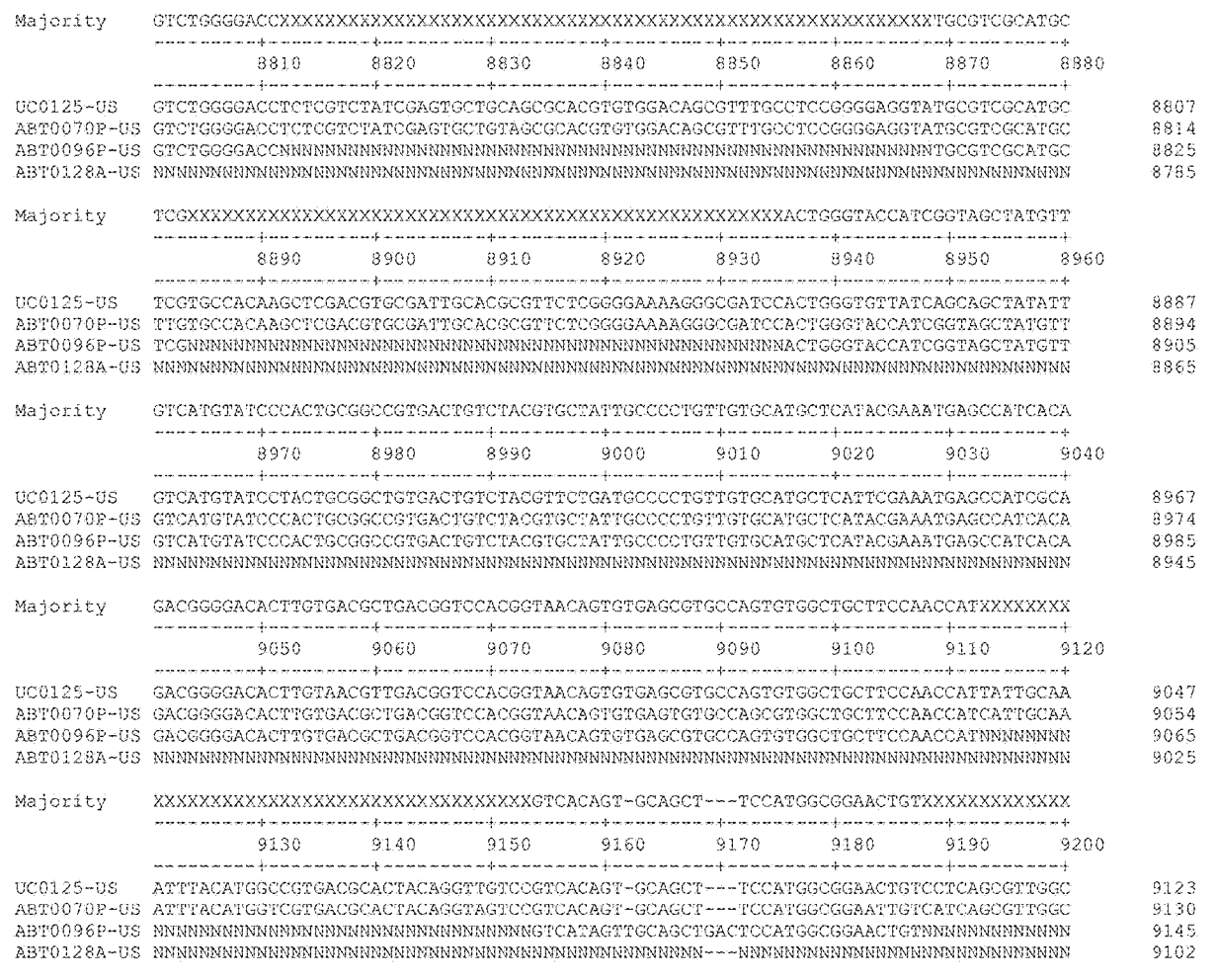

A total of 5,099 NGS reads from sample ABT0096P.US mapped to SEQ ID NO:1, covering 57% of the HPg-V2 genome. Coverage depth was 33X±112 reads/nucleotide, with gaps seen throughout the length of the genome. Sample 128 only had 116 NGS reads, primarily concentrated into 2 regions: 740-975 and 2130-2270. A nucleotide alignment of these 3 additional cases to UC0125.US is shown in FIG. 11.

Four additional strains of HPgV-2 in HCV co-infected patients have been uncovered through our screening efforts and sequenced by NGS (see below). Using both gene-specific and random-primed NGS approaches, in concert

TABLE 17

| HCV positive specimens | % Genome Coverage | Length |
|---|---|---|
| UC0125.US | 99.8 | 9847 nt |
| ABT0070P.US | 100.0 | 9867 nt |
| ABT0029A.US | 100.0 | 9867 nt |
| ABT0239AN.US | 100.0 | 9867 nt |
| ABT0128A.US | 92.3 | 9109 nt |
| ABT0055A.US | 78.3 | 7724 nt |
| ABT0096P.US | 58.0 | 5726 nt |
| ABT0188P.US | 4.0 | 394 nt |
| ABT0030P.US | 99.4 | 9812 nt |
| ABT0041P.US | 97.7 | 9645 nt |

A total of eight HPgV-2 isolates have now been identified in patients co-infected with HCV (above). Recent screening in a US population of HIV+ patients from ProMedDx has revealed 6 additional strains that have been confirmed by RT-PCR and Sanger sequencing: ABT0084H.US, ABT0086H.US, ABT0100H.US, ABT0198H.US, ABT0030P.US, and ABT0041P.US (sequences not shown).

A total of ten HPgV-2 isolates have now been identified in patients co-infected with HCV (above). Recent screening in a US population of HIV+ patients from ProMedDx has revealed 4 additional strains that have been confirmed by RT-PCR and Sanger sequencing: ABT0084H.US, ABT0086H.US, ABT0100H.US, and ABT0198H.US (sequences not shown).

TABLE 21

| HIV positive specimens | % Genome Coverage | Length |
|---|---|---|
| ABT0084H.US | 3.3 | 325 nt |
| ABT0086H.US | 1.6 | 163 nt |
| ABT0100H.US | 4.3 | 421 nt |
| ABT0198H.US | 1.7 | 168 nt |

This brings the total to 14 isolates of HPgV-2 and demonstrates that infection with this virus, for example, is not restricted to individuals co-infected with HCV as originally believed. An alignment of some of the full and nearly complete genomes is shown in FIG. 23.

Figure 12B:
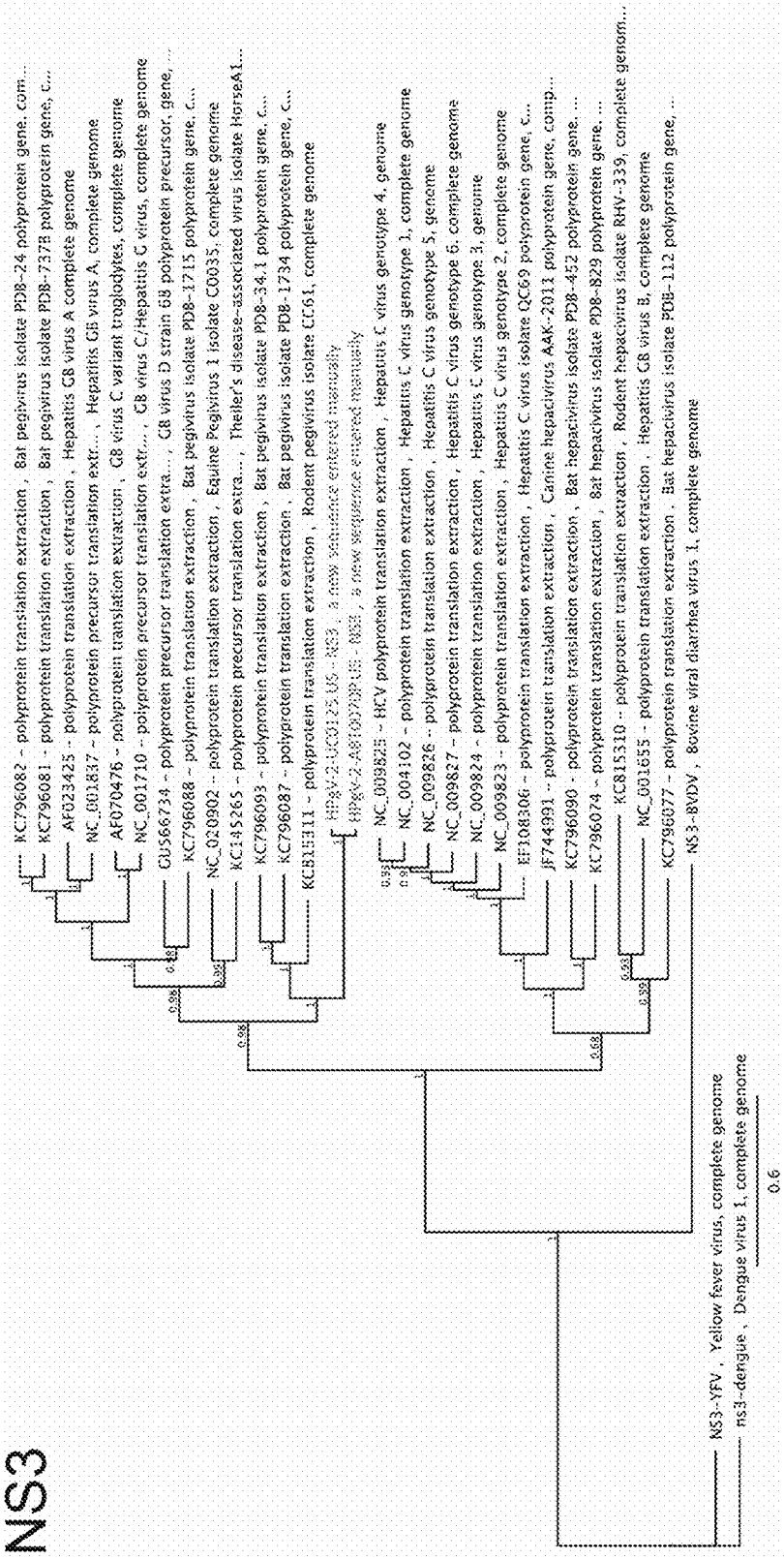
Figure 12C:
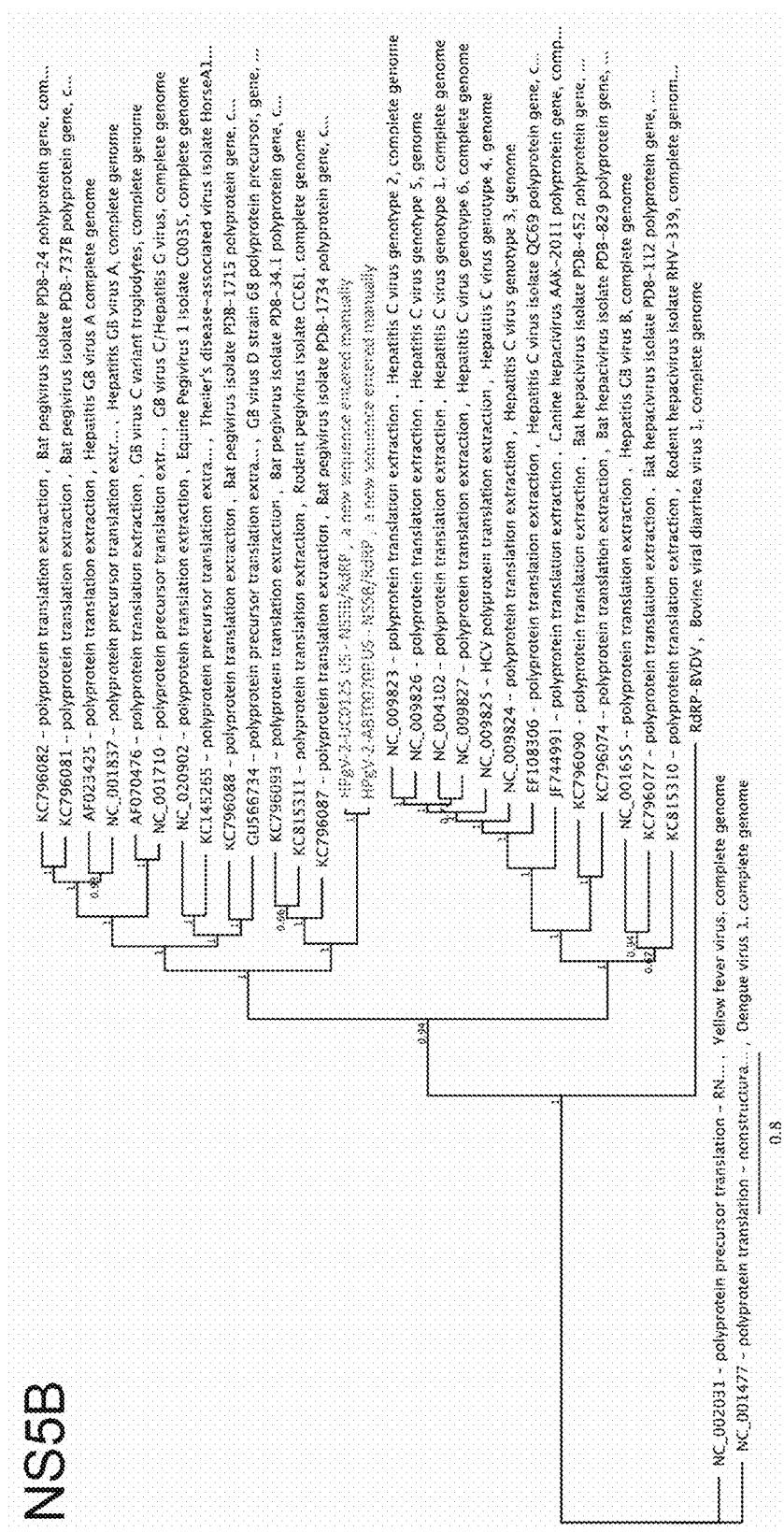
Figure 23A:
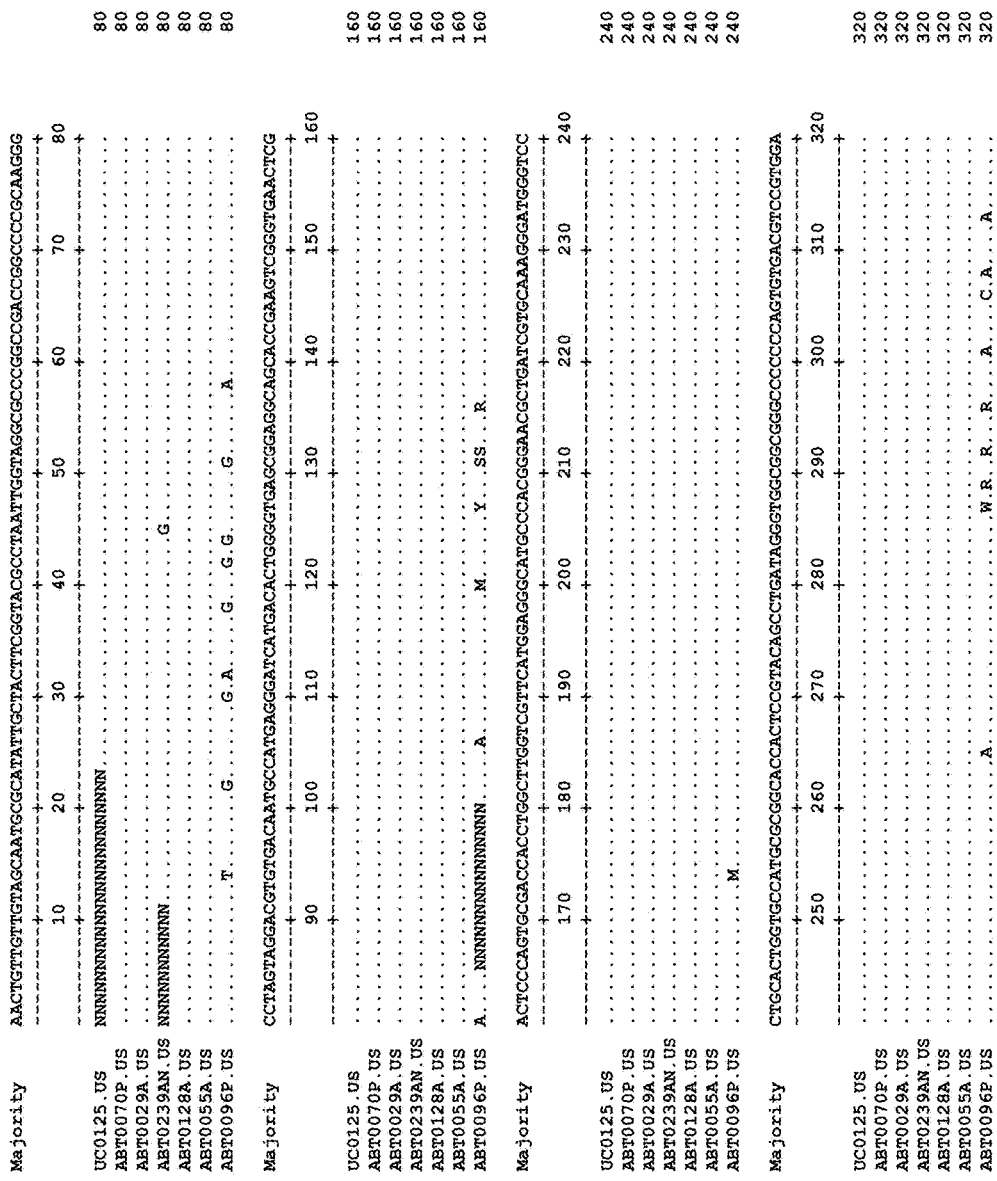
FIGS. 23A-EE show an alignment of the genomes or partial genomes of HPgV-2 variants UC0125, ABT0070P, ARC29v36 (ABT0029A), ARCNAT239 (ABT0239AN), ARC 128 (ABT0128A), PMDx96 (ABT0096P), and ARC55 (ABT0055A), along with a majority consensus sequence (SEQ ID NO:299).
Figure 23B:
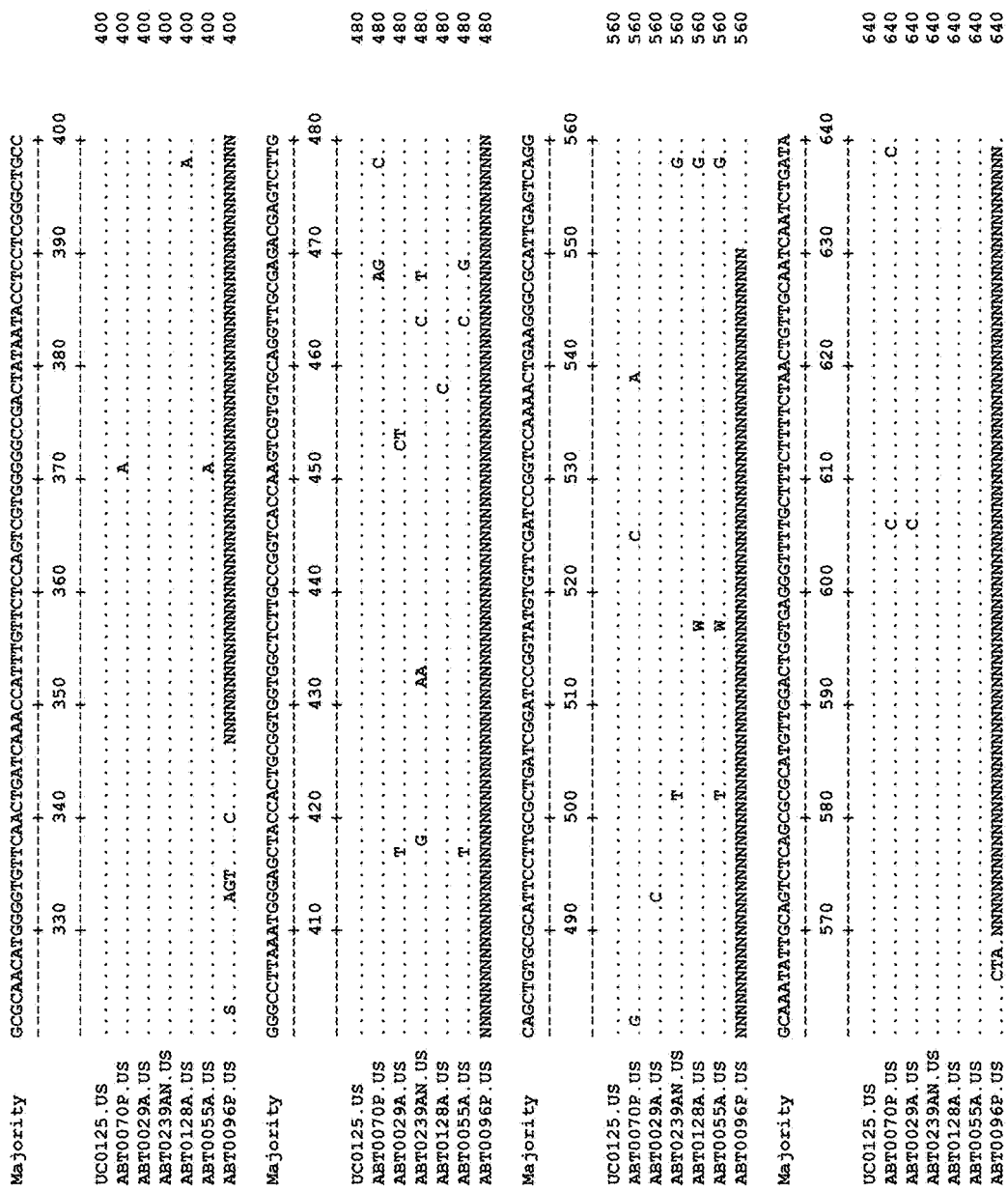
Figure 23C:
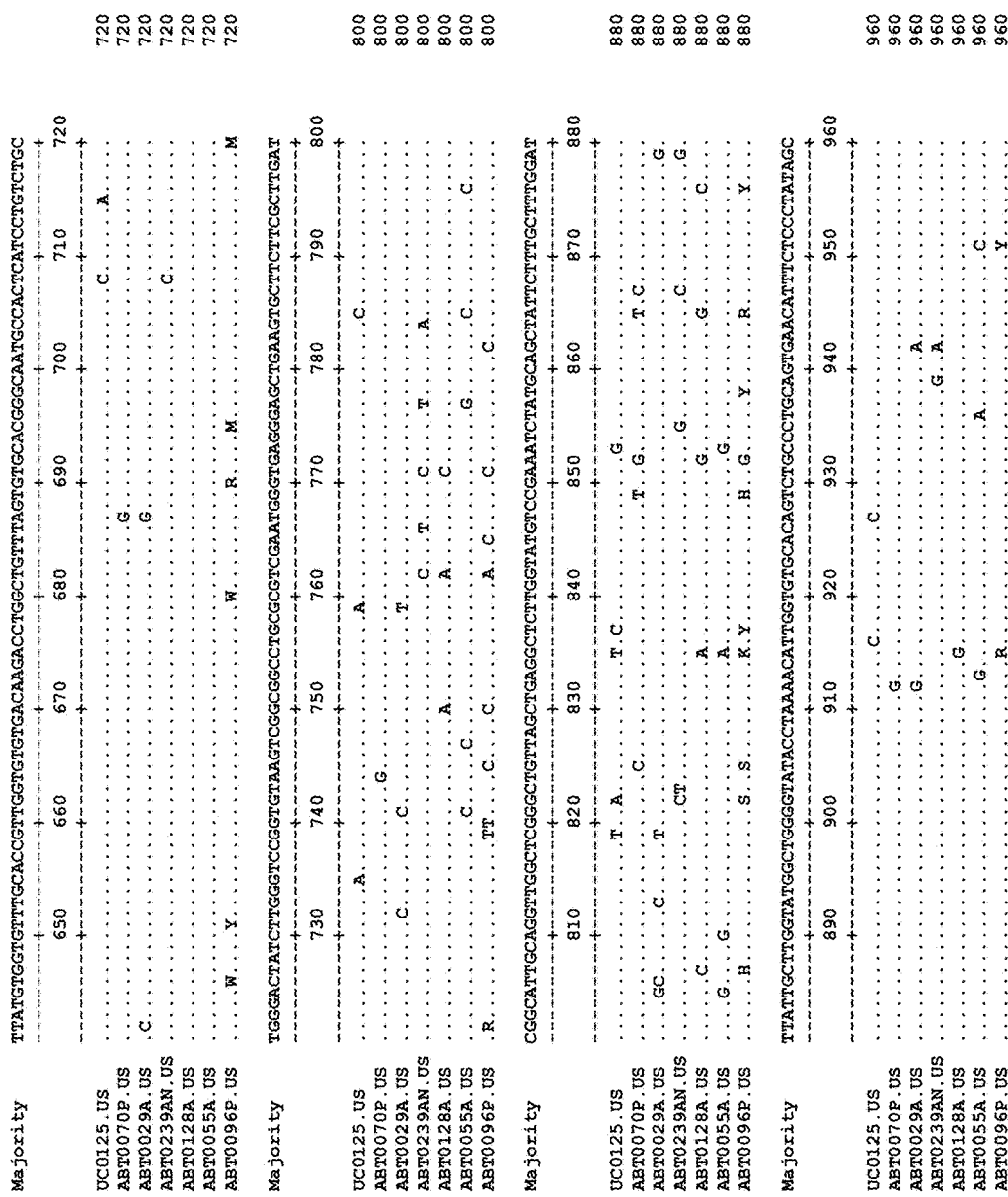
Figure 23D:
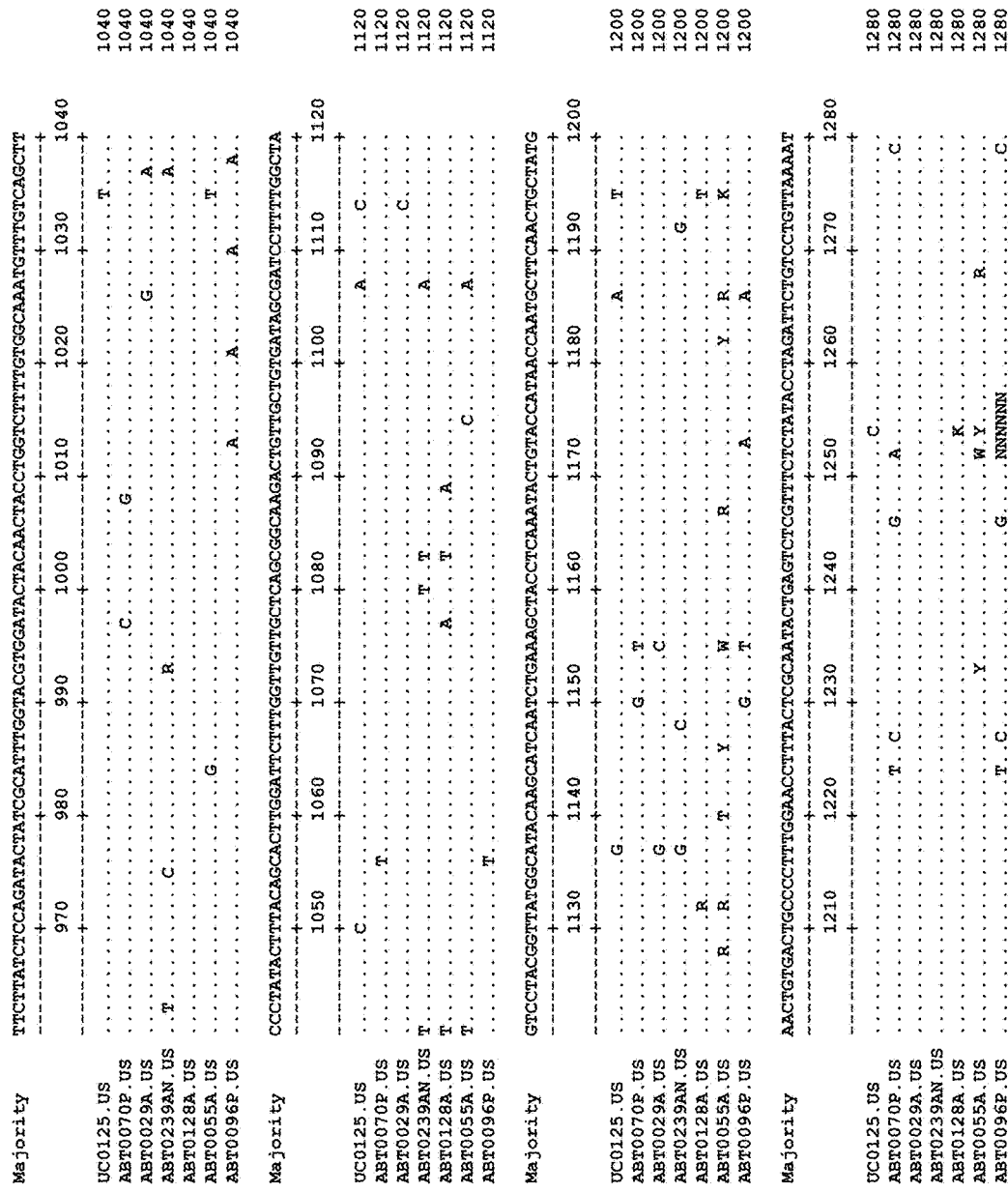
Figure 23E:
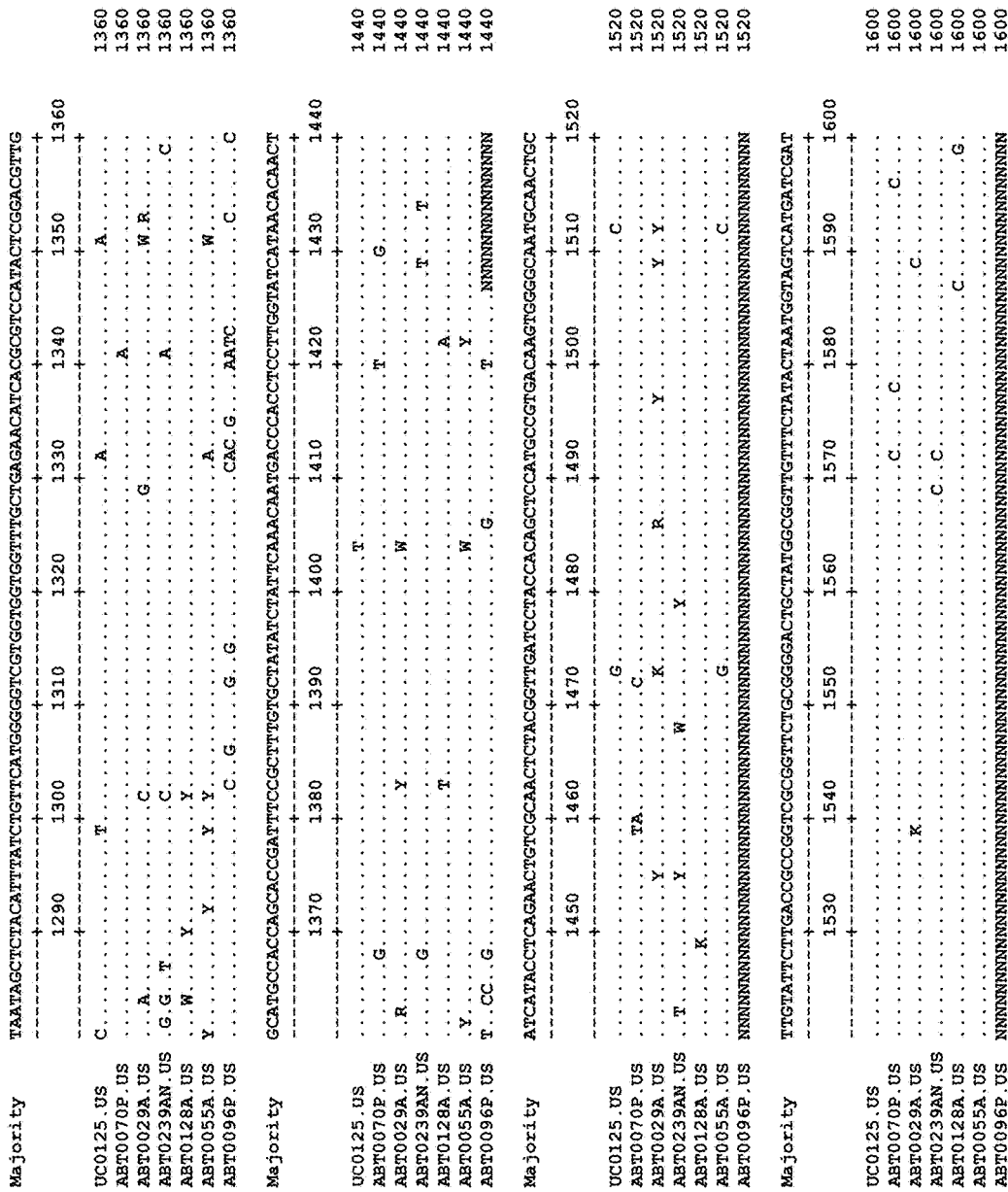
Figure 23F:
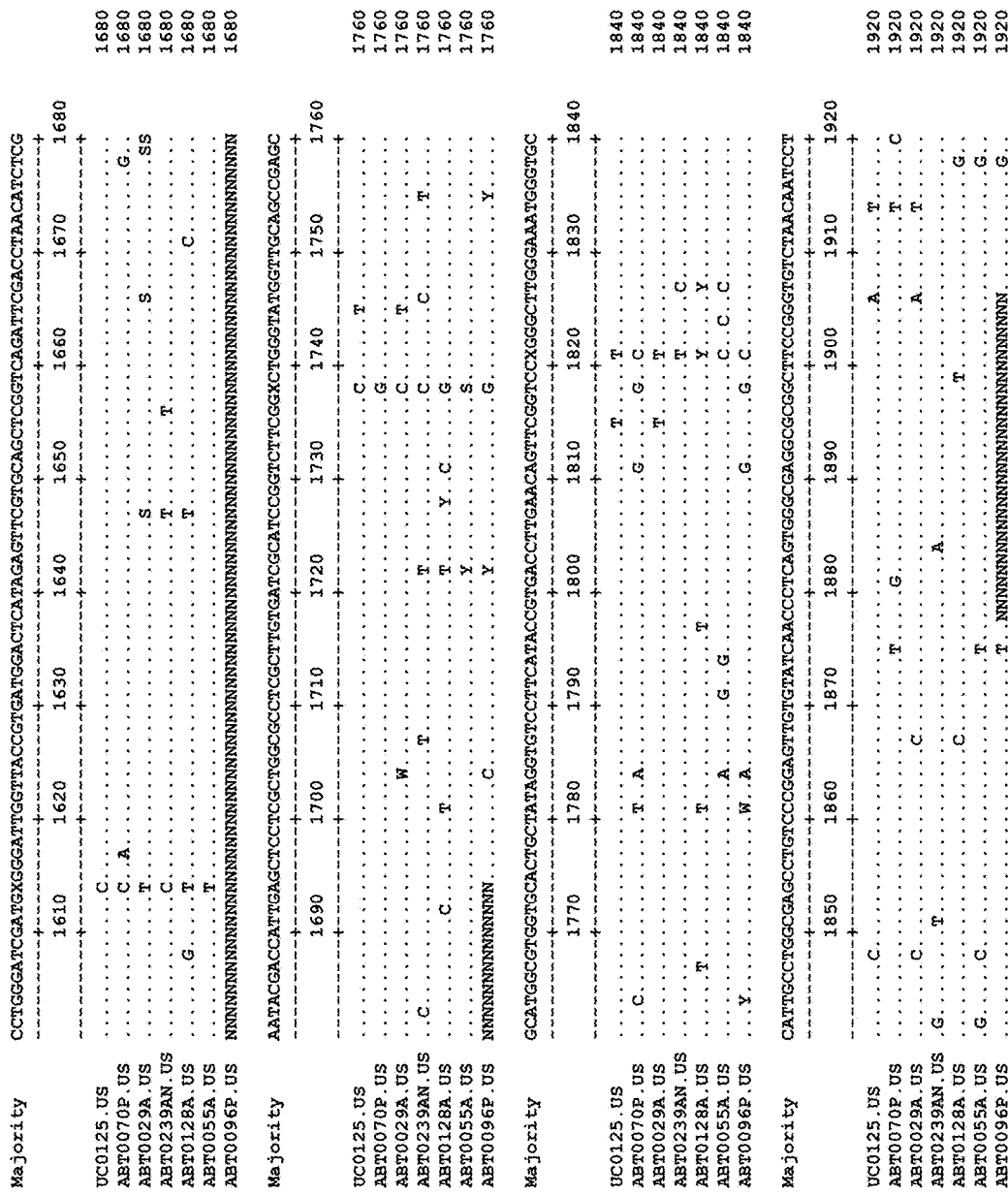
Figure 23G:
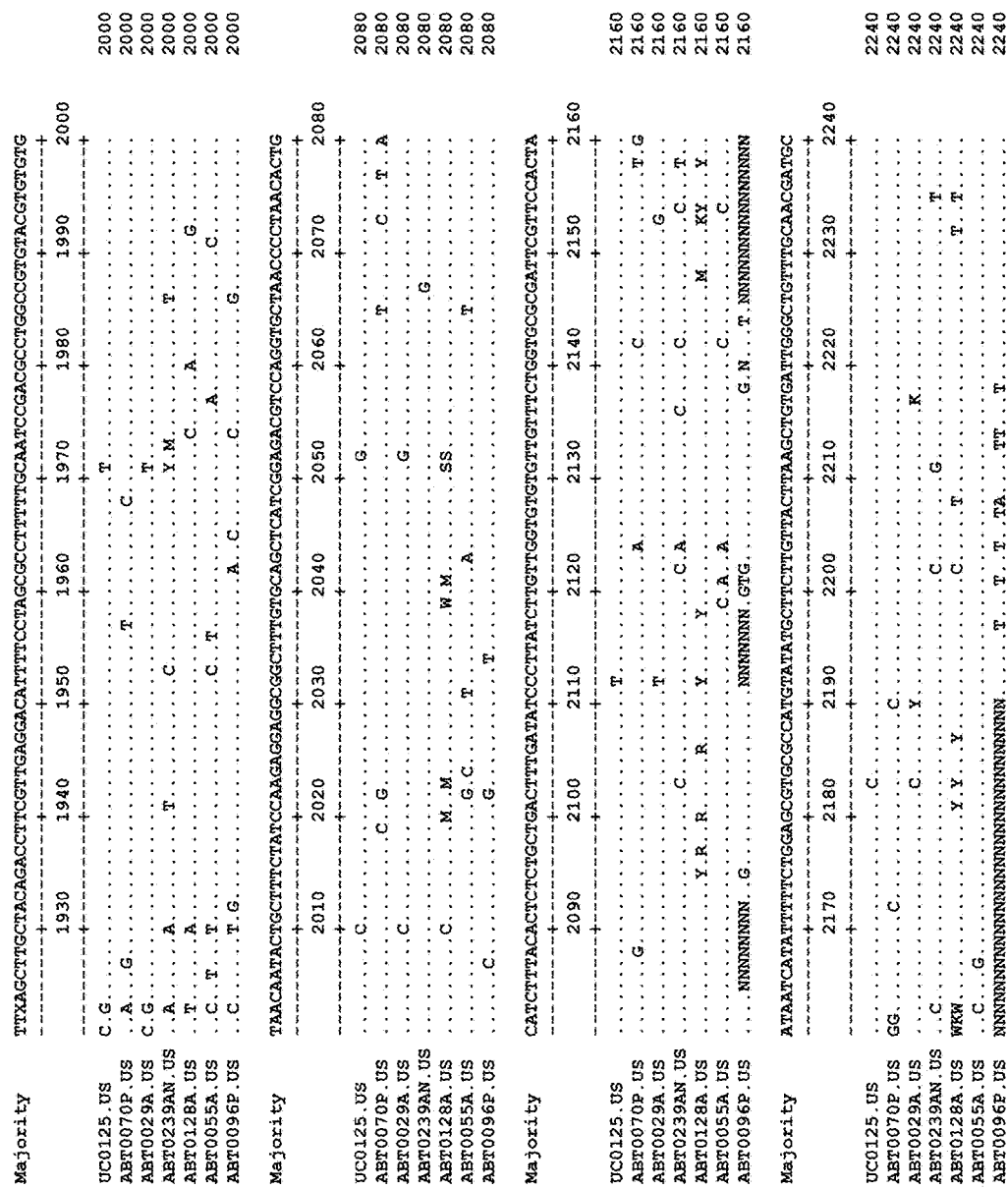
Figure 23I:
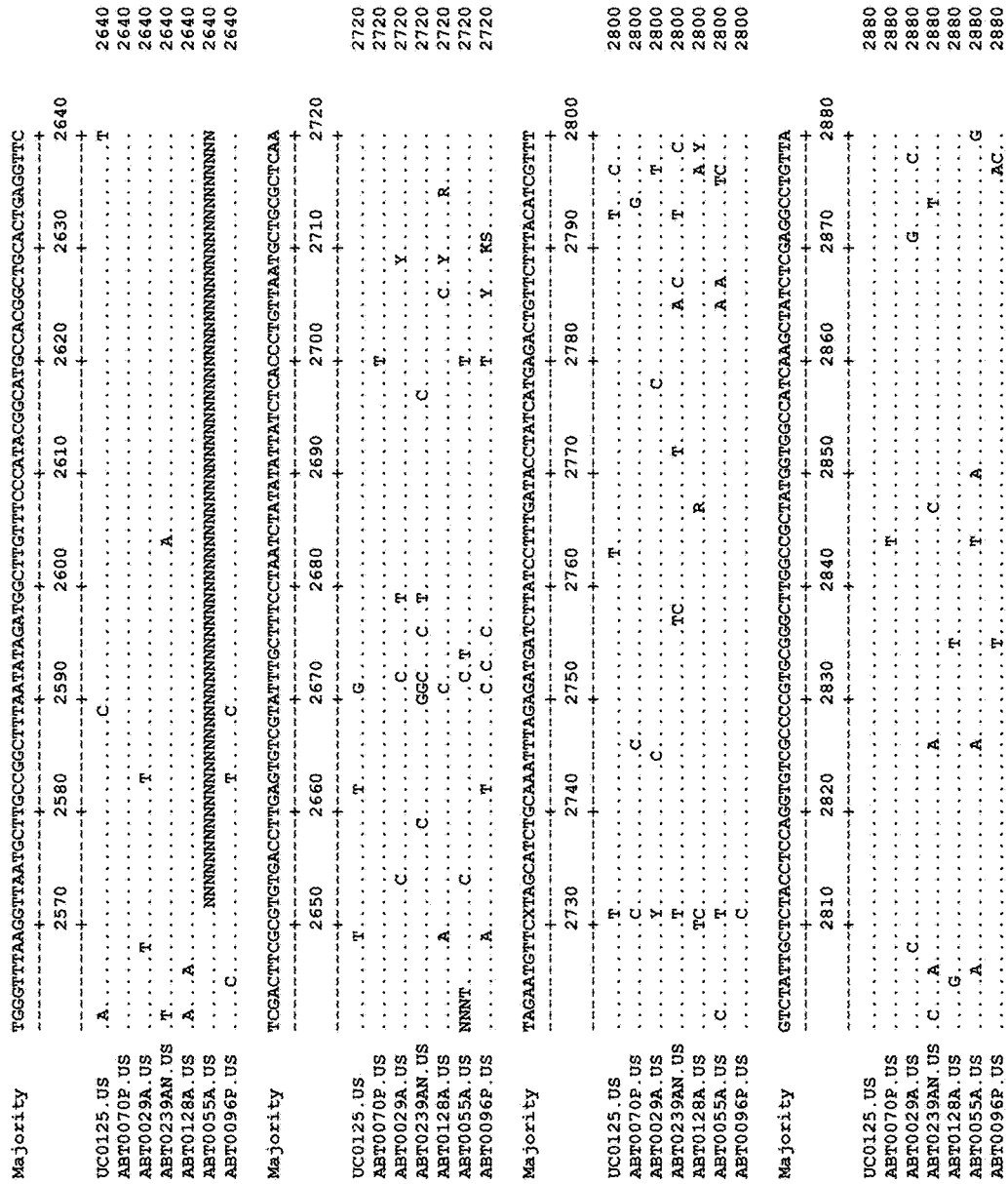
Figure 23J:
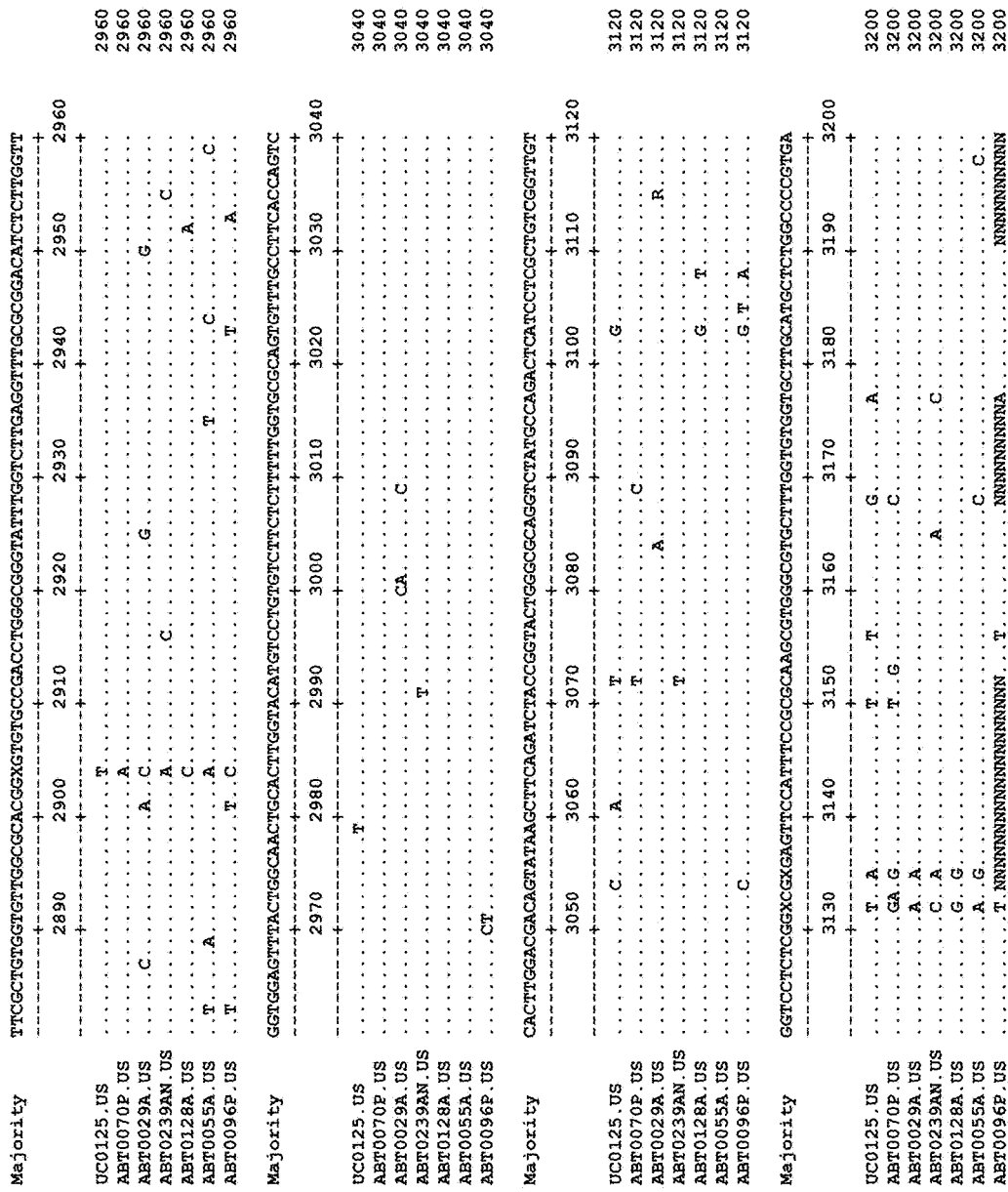
Figure 23K:
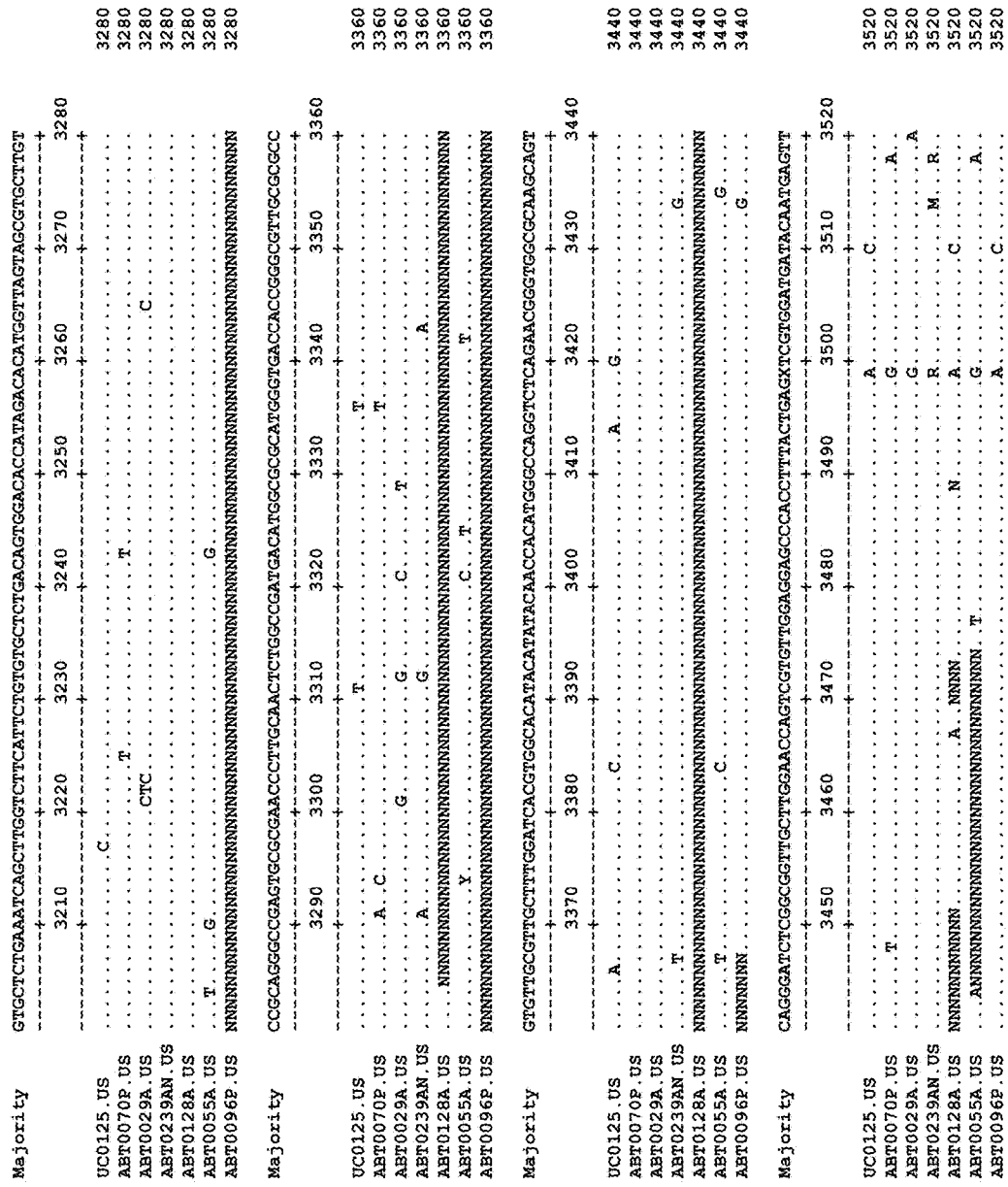
Figure 23L:
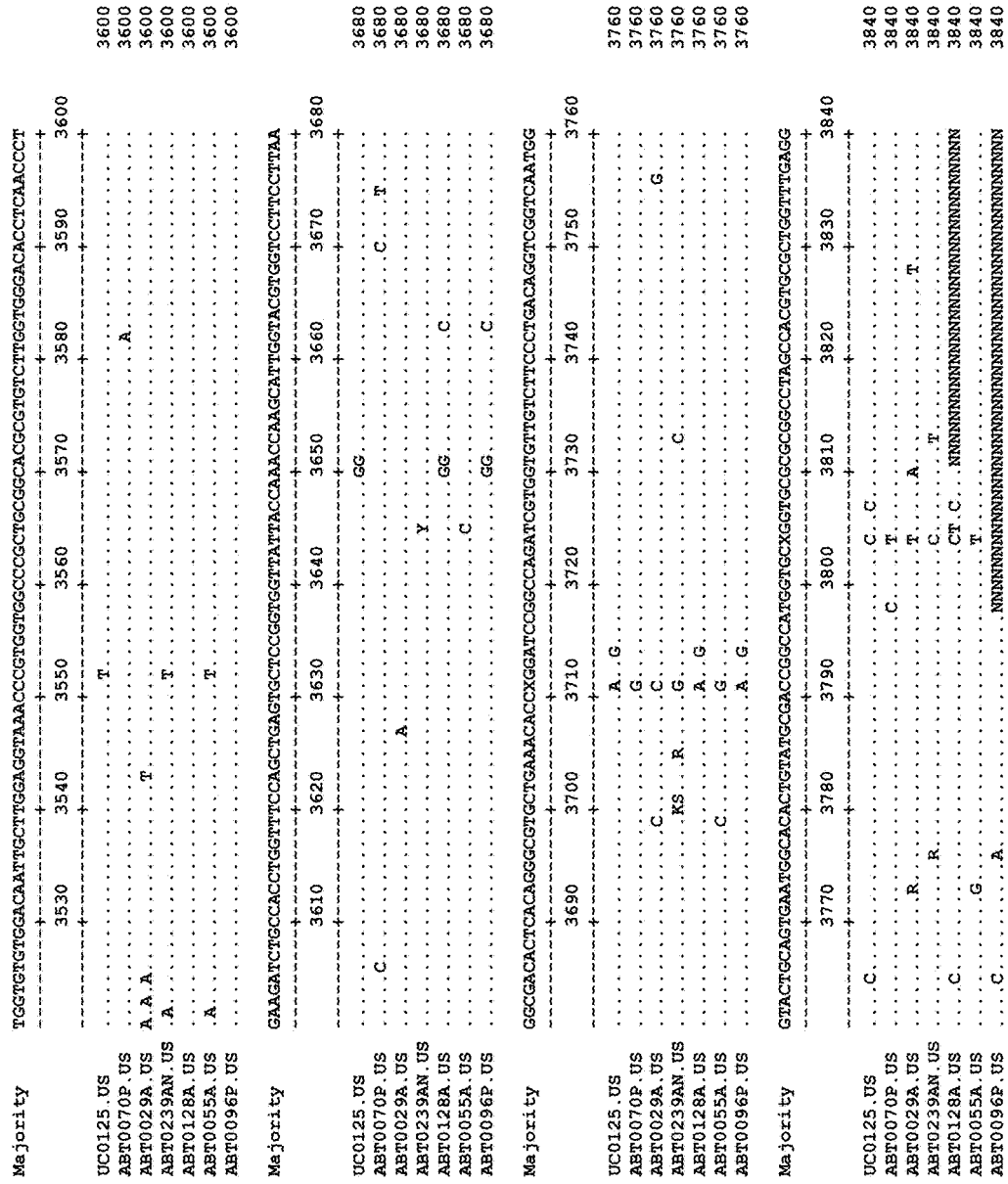
Figure 23M:
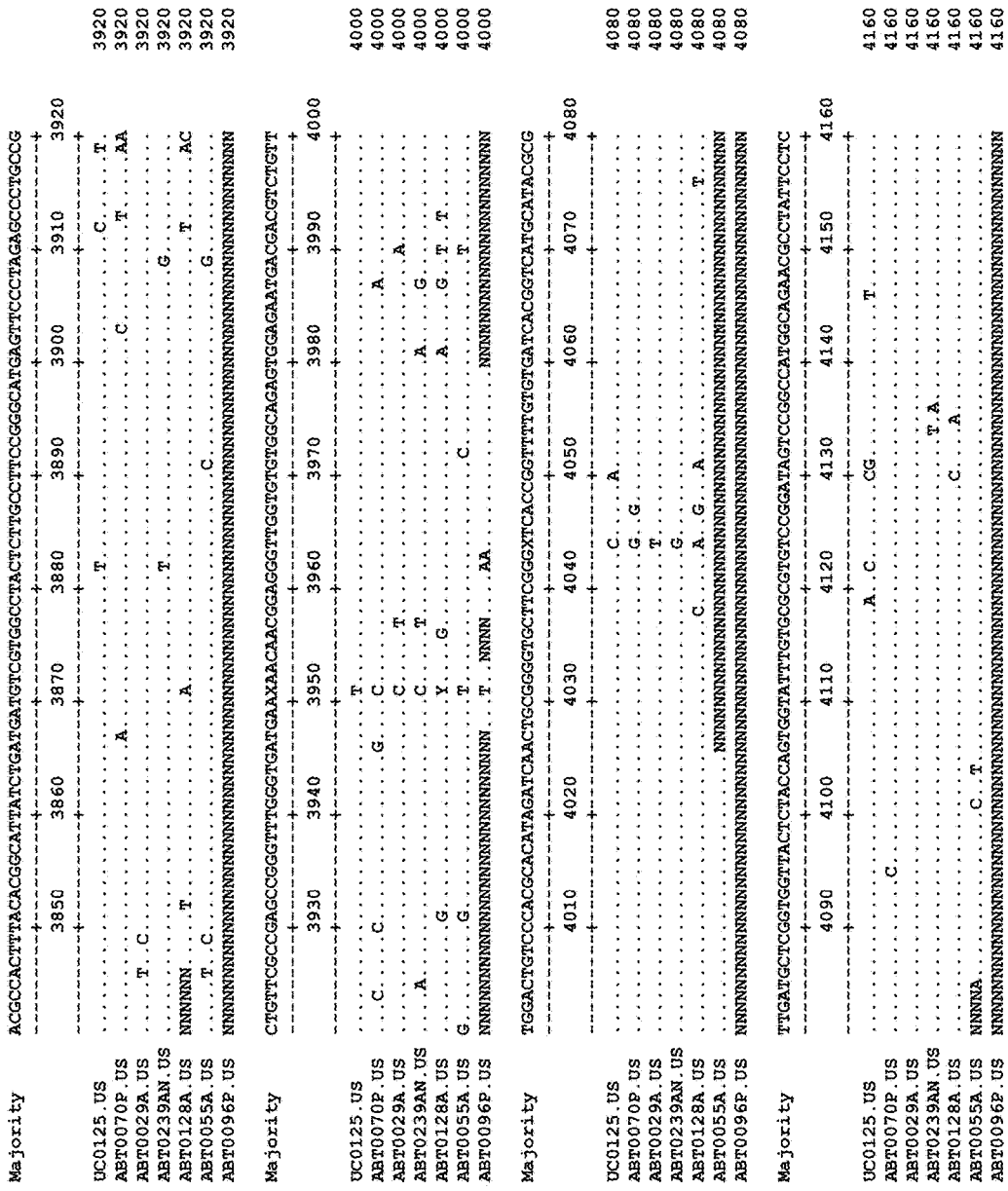
Figure 23N:
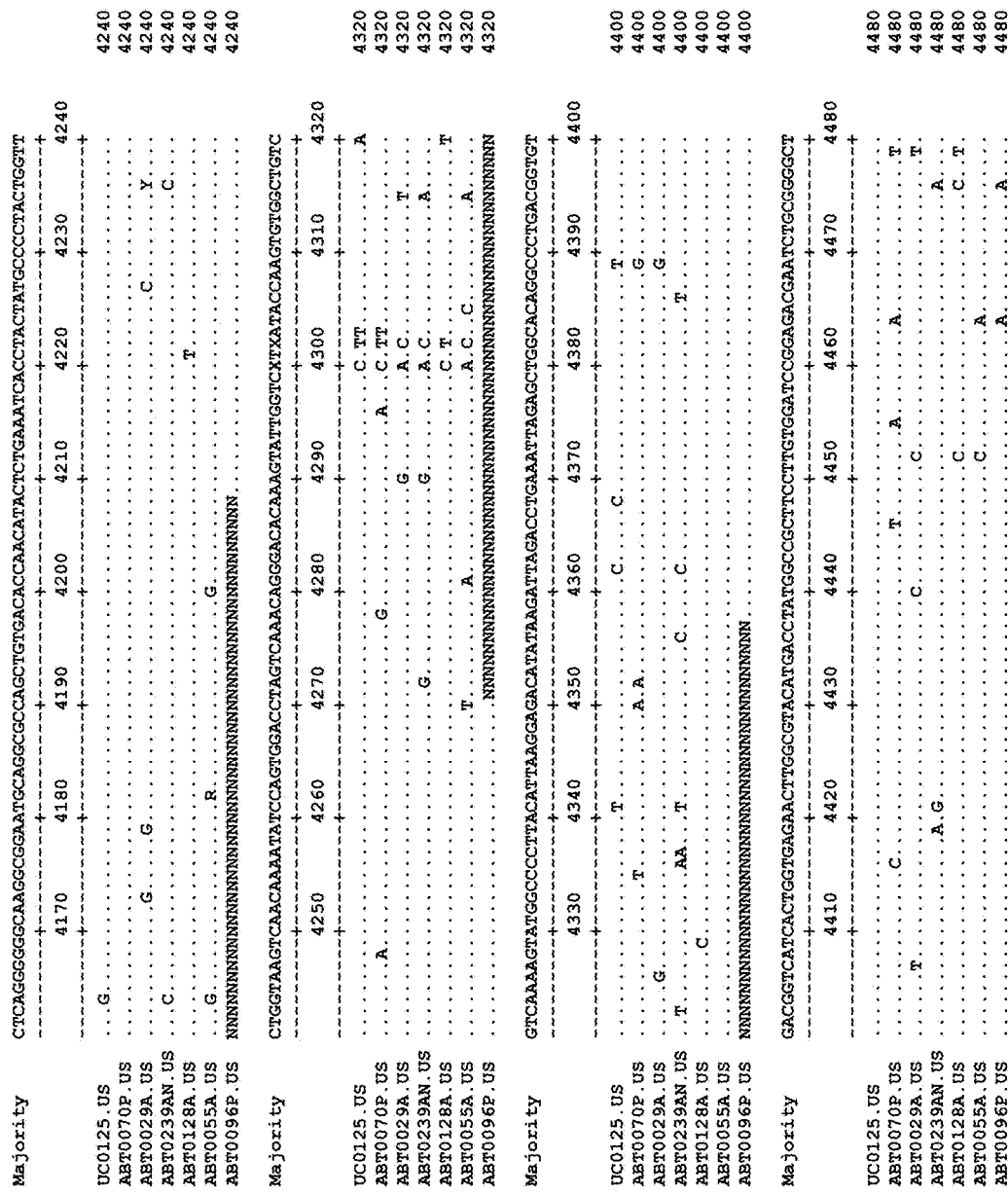
Figure 23O:
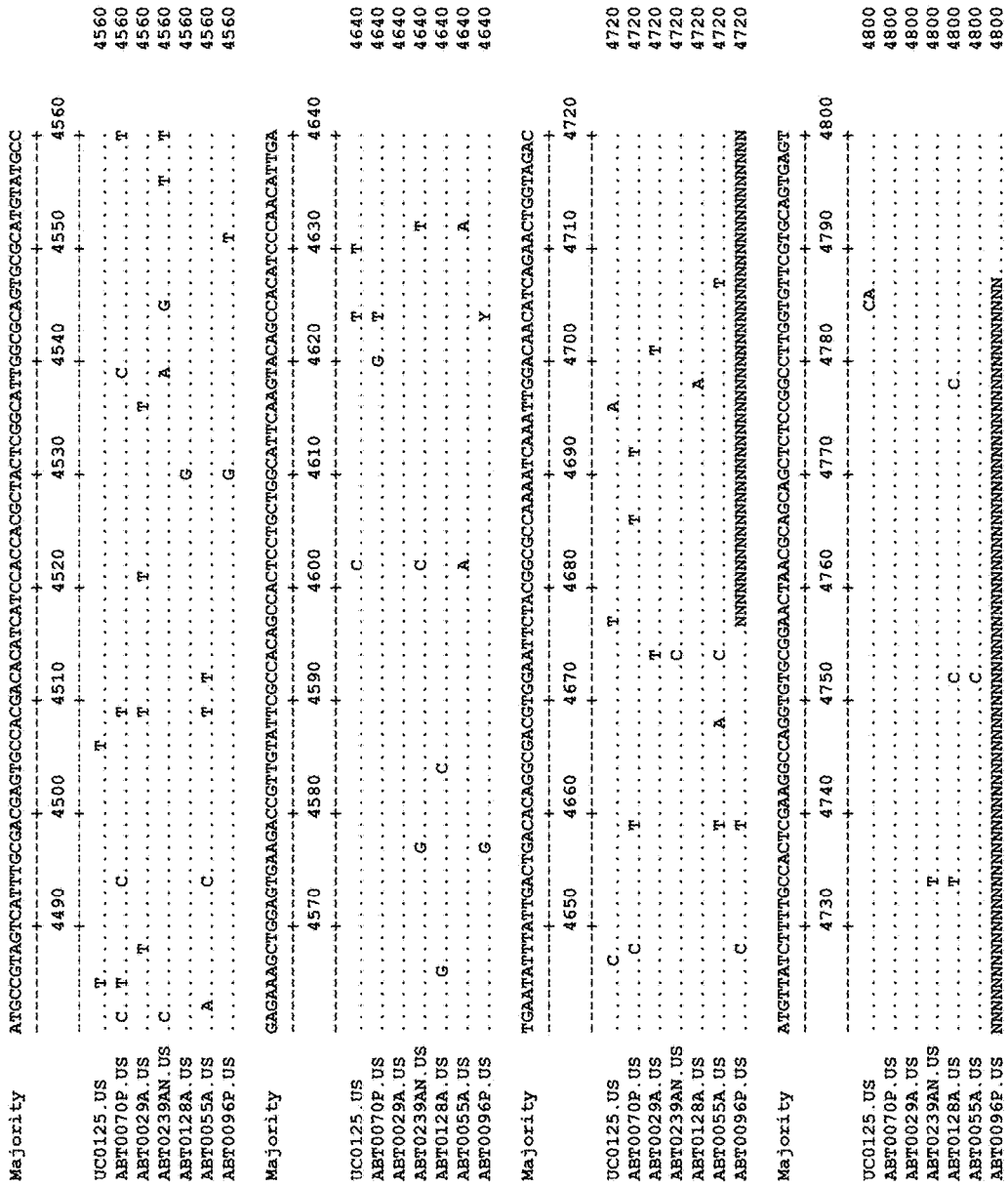
Figure 23Q:
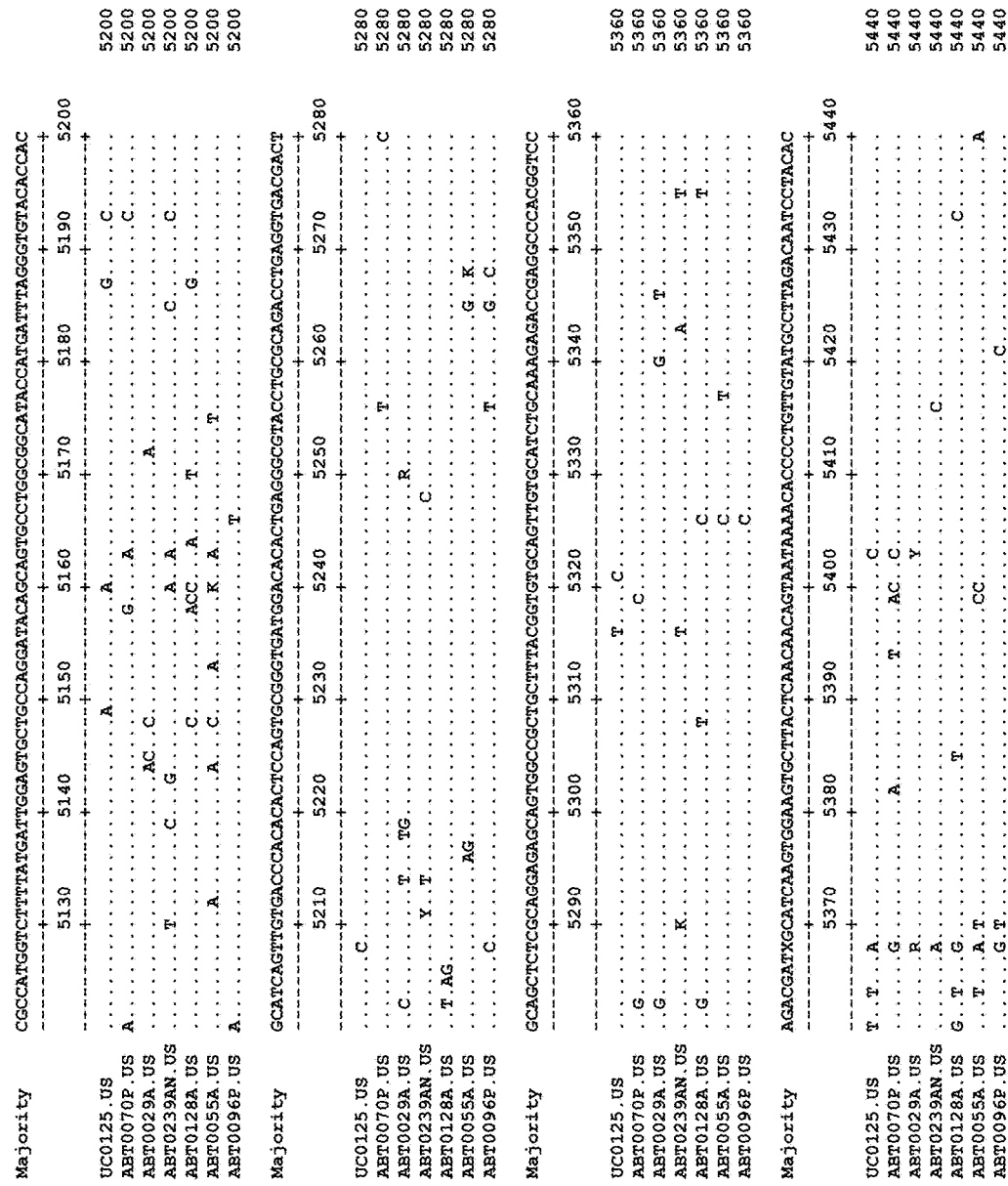
Figure 23S:
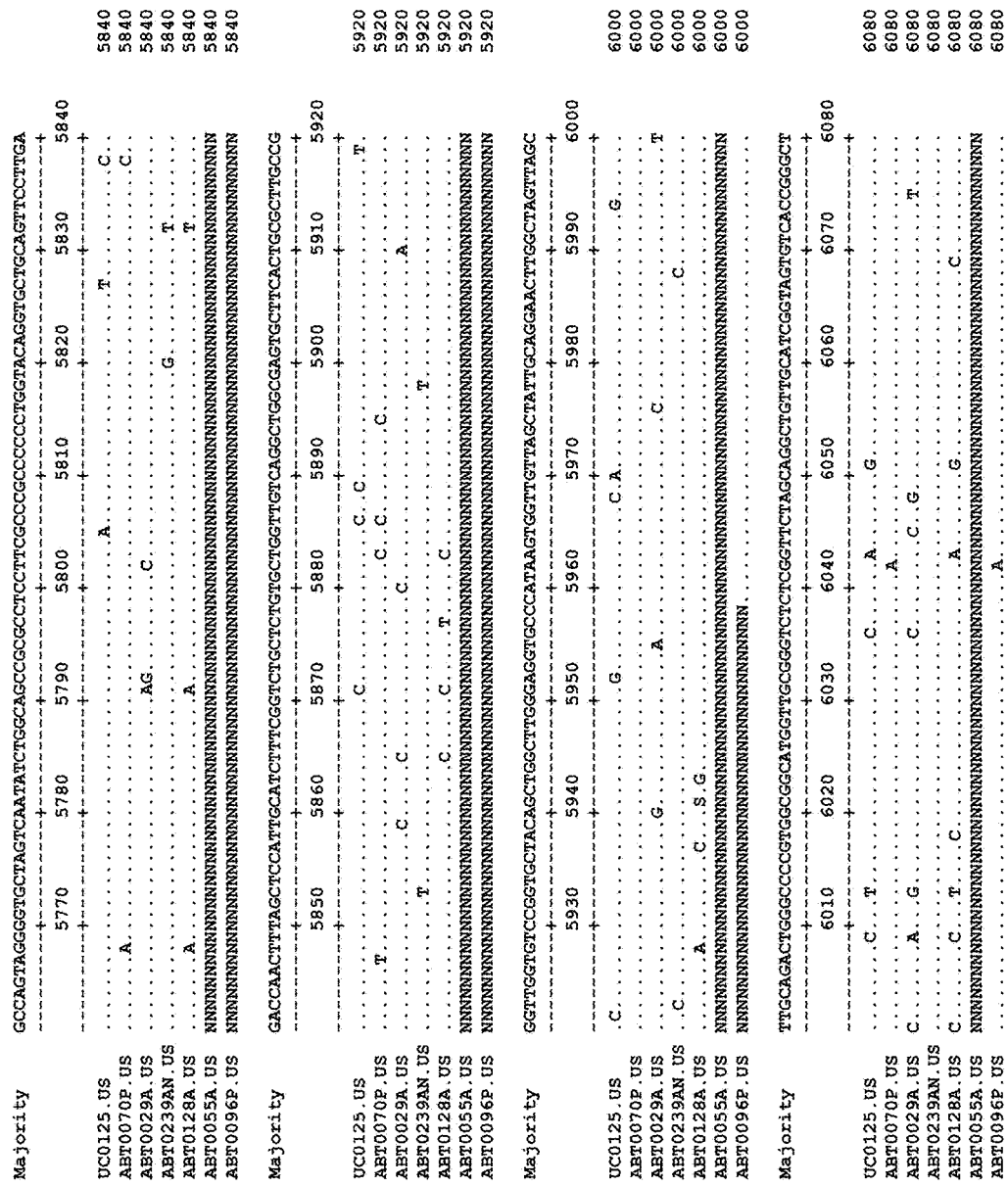
Figure 23T:
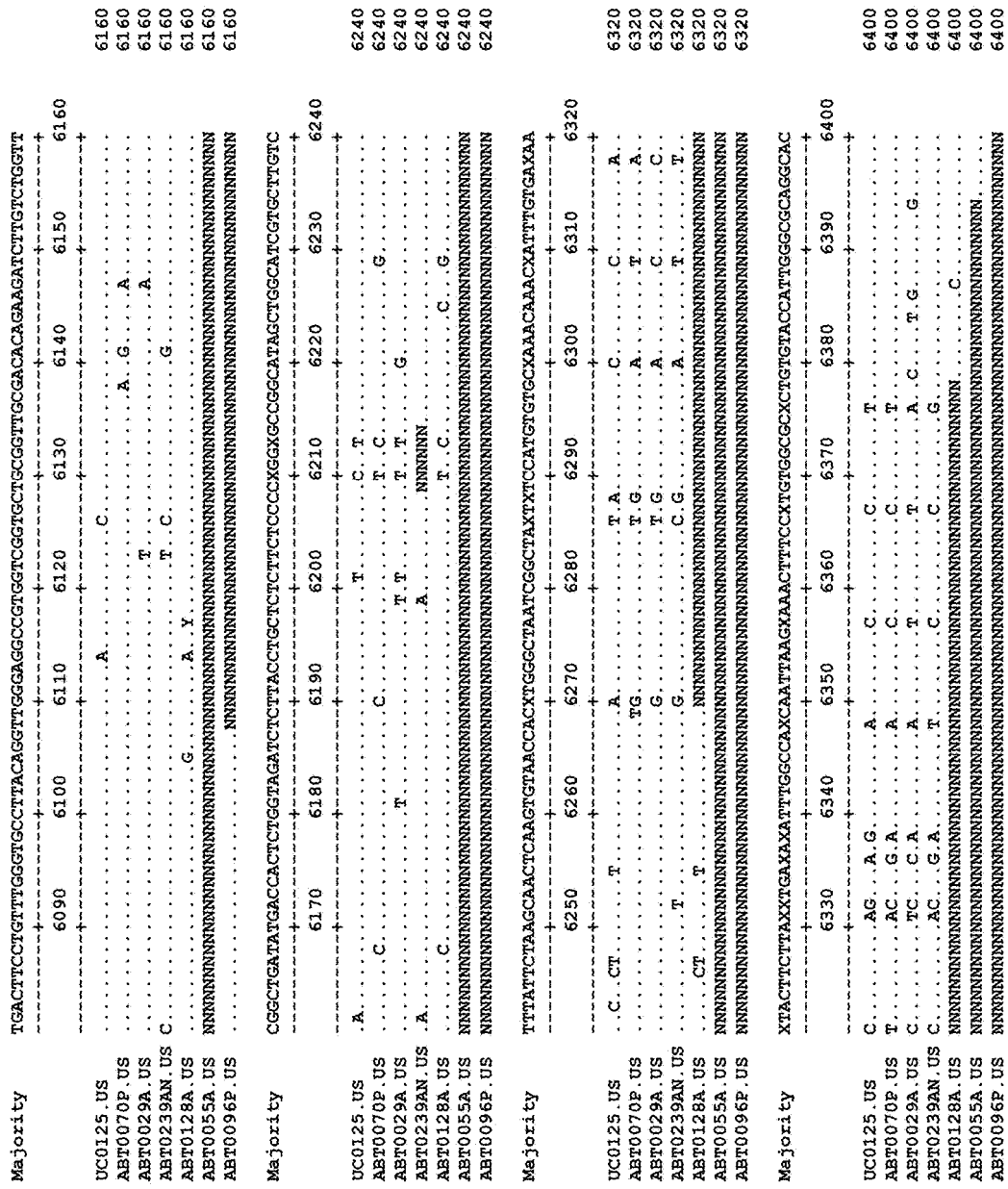
Figure 23U:
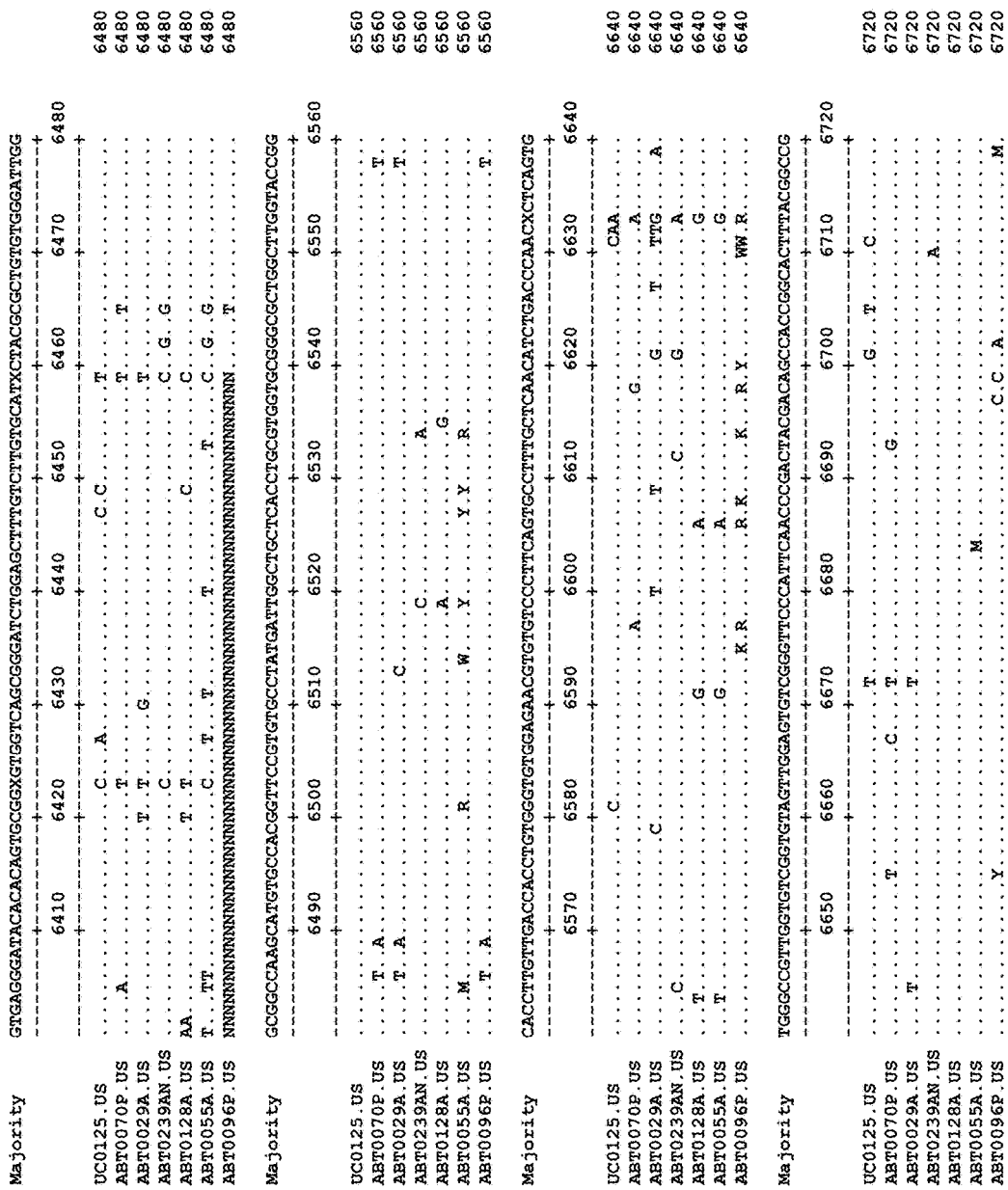
Figure 23X:
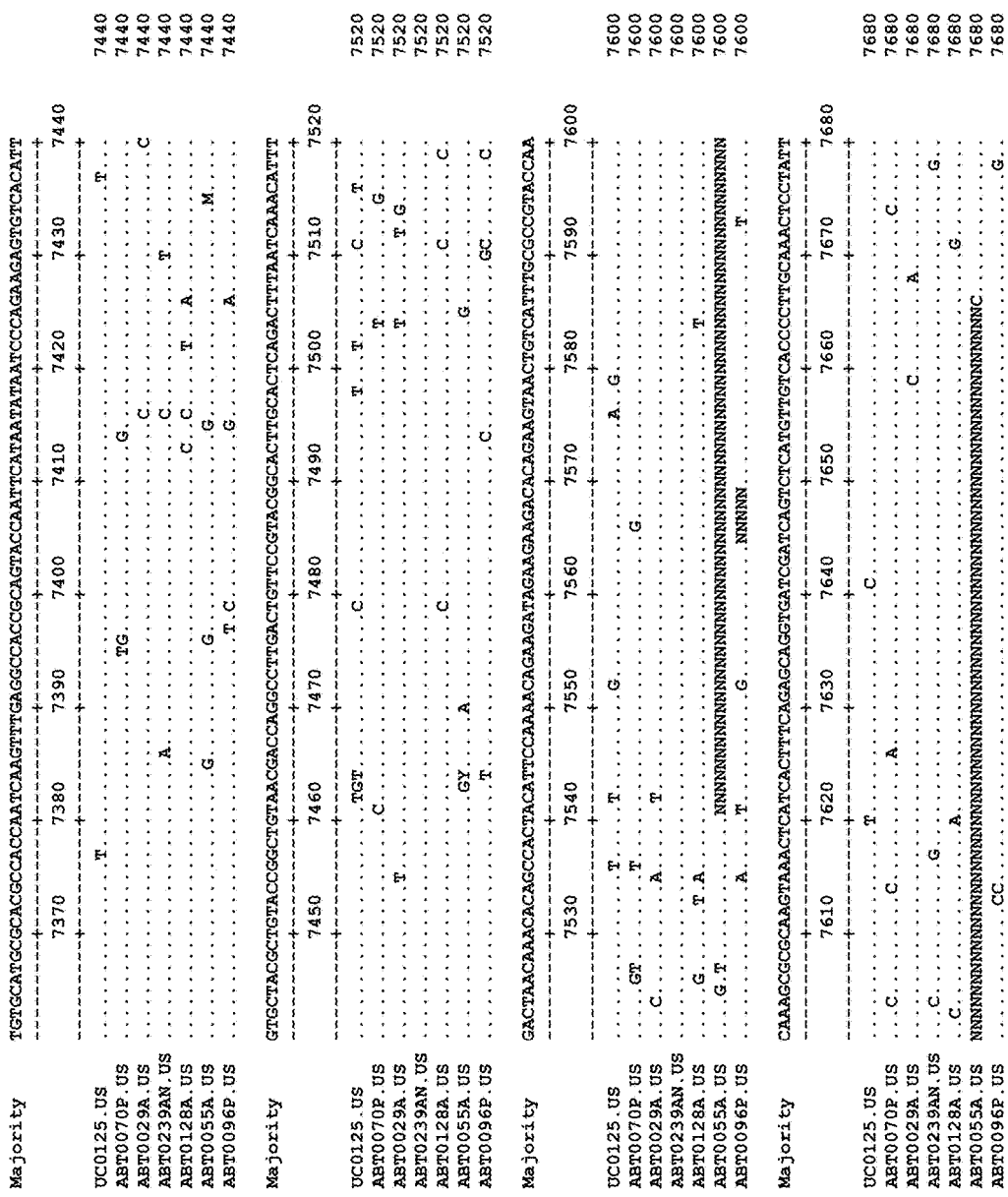
Figure 23Y:
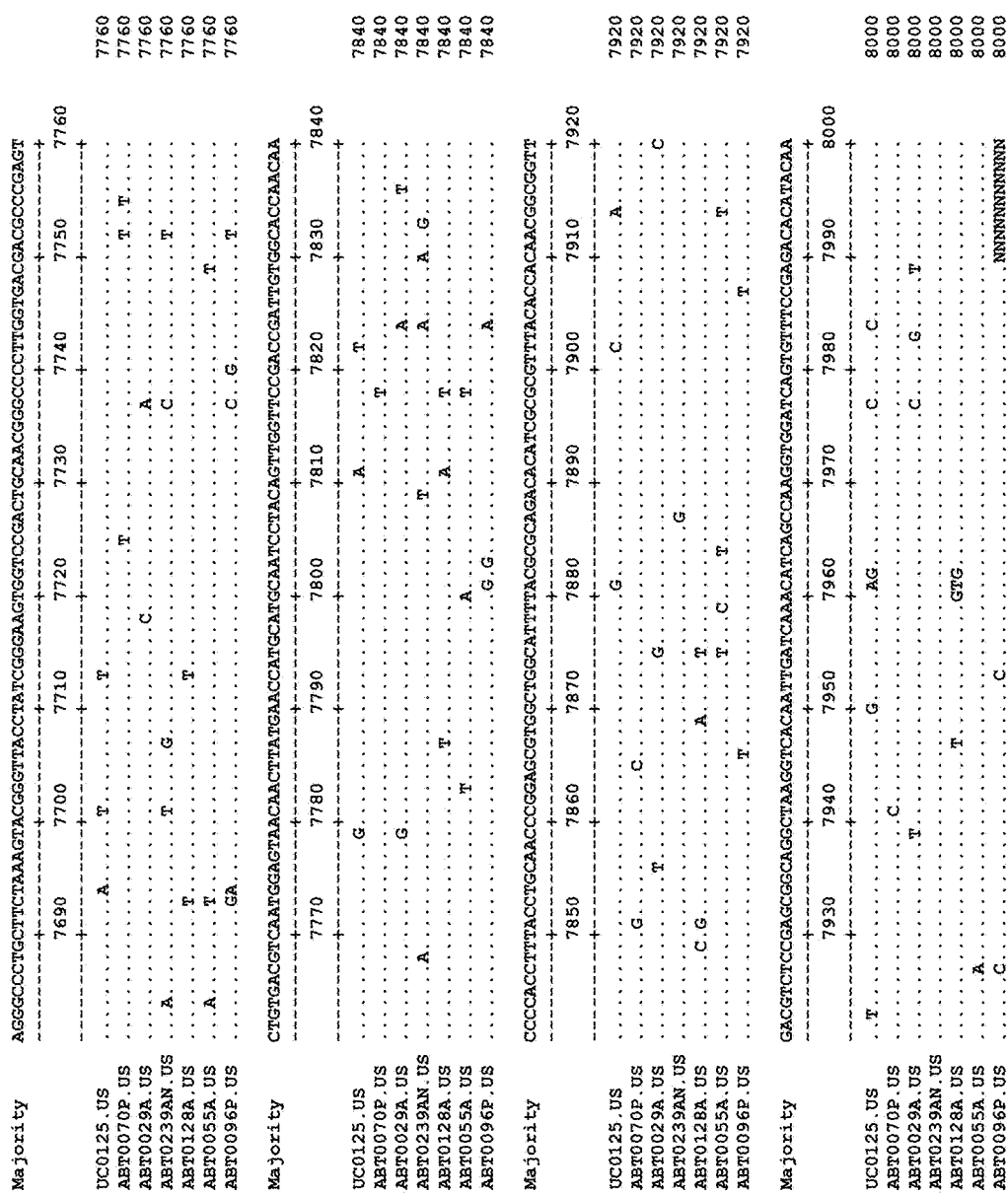
Figure 23Z:
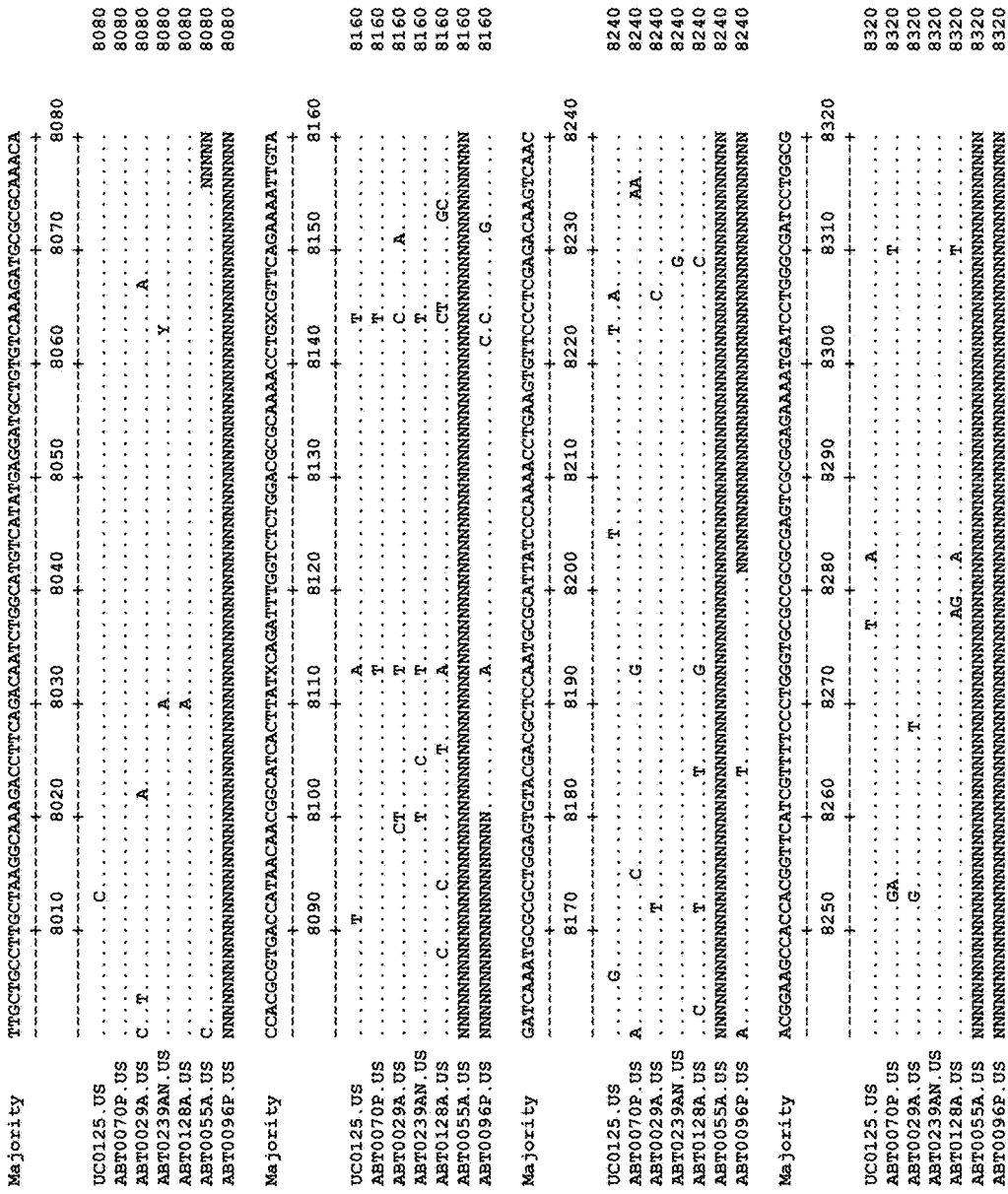
Figure 23A:
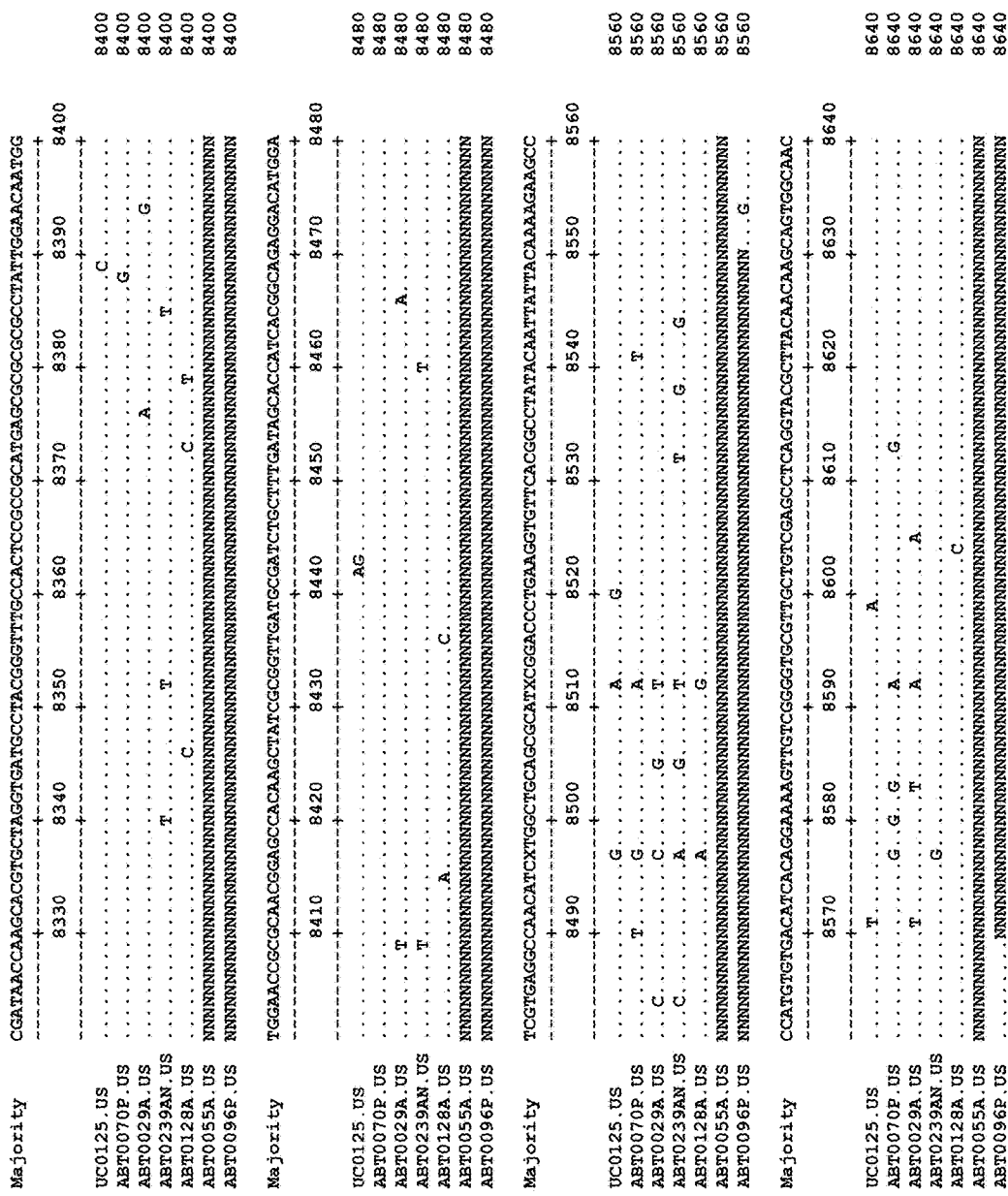
Figure 23D:
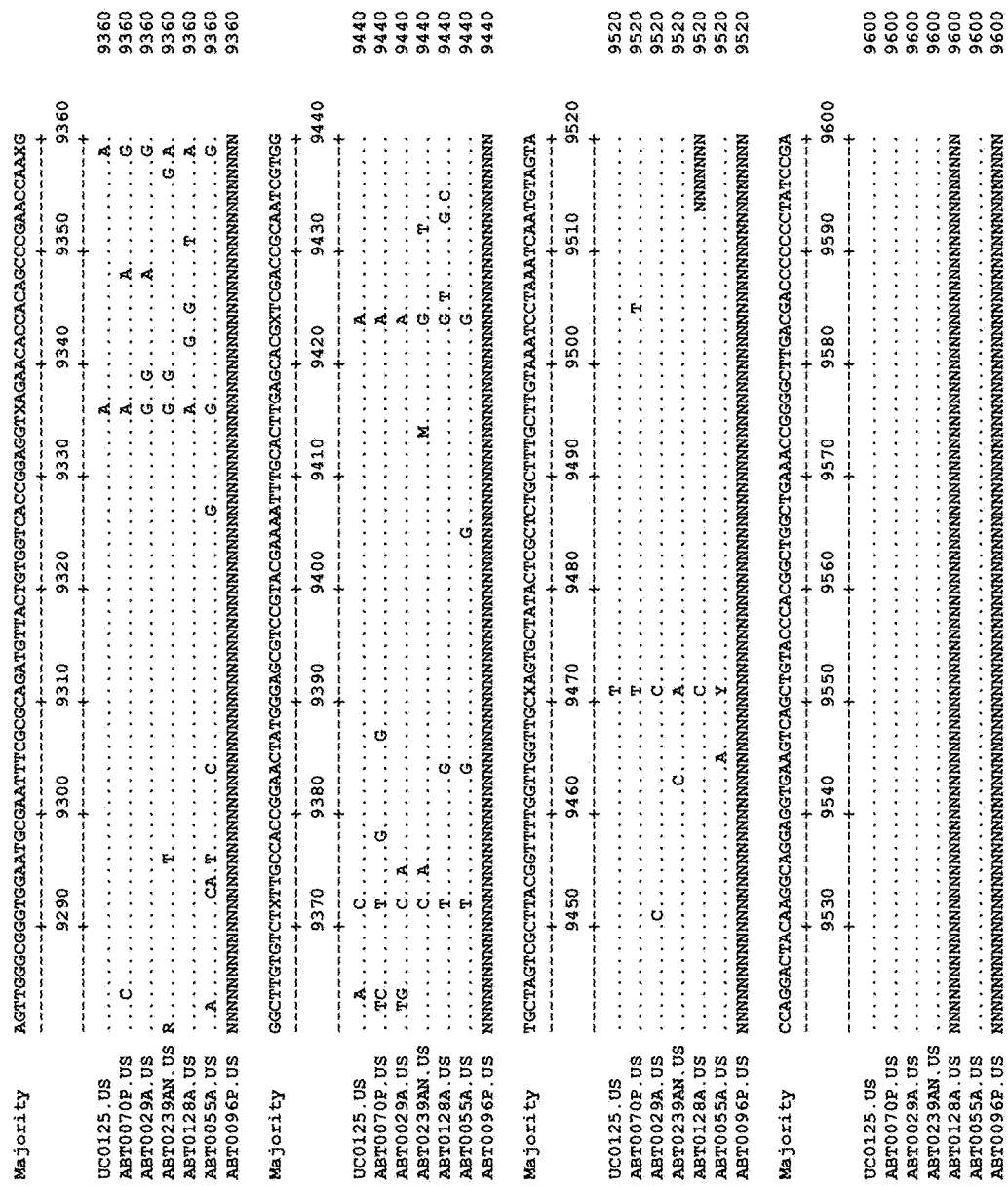
Figure 23E:
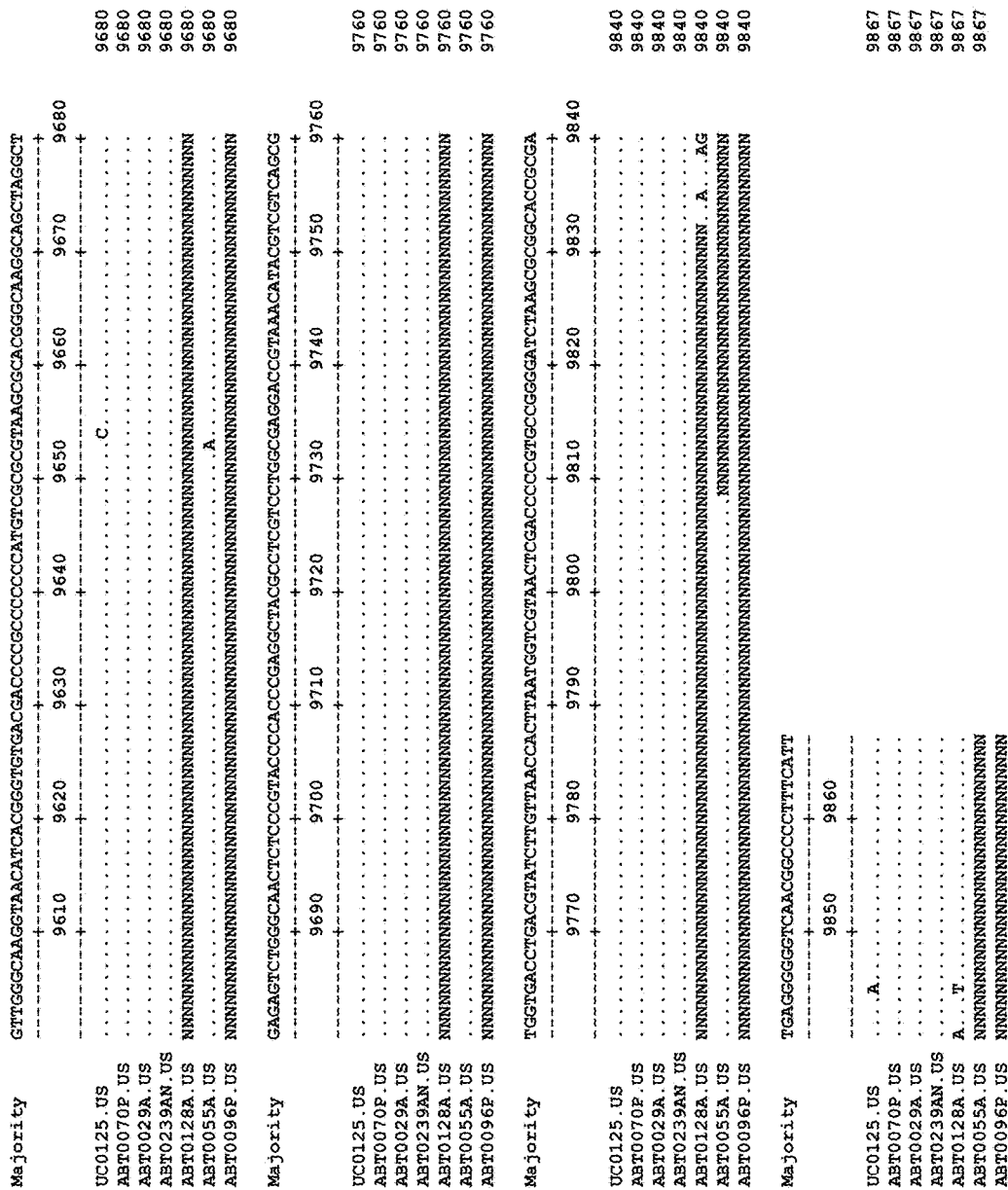

A multiple sequence alignment of HPgV-2 (UC0125.US) and ABT0070P.US along with 29 representative flaviviruses was performed in Geneious v6.1 (Kearse, et al., 2012, Bioinformatics), using MAFFT v7.0 with the E-INS-I algorithm and at default parameters Katoh, et al., Mol Biol Evol, 2013), followed by refinement using MUSCLE v3.8 with 10 maximum iterative cycles (Edgar, Nuc Acids Res, 2004). Phylogenetic trees were constructed in Geneious using the Jukes-Cantor model and neighbor joining algorithm with 10,000 bootstrap replicates used to calculate branch supports. These tree topologies were then refined using a maximum likelihood Bayesian approach with MrBayes V3.2 software (1,000,000 sample trees, 10% of trees discarded as burn-in, convergence defined at an average standard deviation of <0.01). Each tree was rooted with dengue virus type 1 (DENV1) and yellow fever virus (YFV) as outgroups. Analysis was performed on entire polyprotein sequences, as well as on NS3 and NS5B proteins individually (FIG. 12). Two major branches distinguish pegiviruses from hepaciviruses in the Flavivirus family. Within the *pegivirus* branch, ABT0070P.US clusters tightly with UC0125.US, with the branch supported by a bootstrap value of 100%. Both strains share a common, albeit distant, ancestor with bat and rodent pegiviruses, with a bootstrap value of 99.95%. This demonstrates that HPgV-2 is a human *pegivirus* distinct from pegiviruses previously identified in mammals.

Example 6

Purification of HPgV-2 E2 Glycoprotein and Serology with HPgV-2 PCR+/Ab+ Samples Expression, Purification, Characterization of HPgV-2 E2 in Mammalian Cells.

This example describes the design, expression, and purification of the HPgV-2 glycoprotein E2 from mammalian cells. An expression plasmid encoding the E2 ORF sequence up to the predicted transmembrane region (SEQ ID NO:406) was constructed using a pcDNA3.1 derived vector containing a mouse Ig kappa light chain leader sequence for protein secretion.

```
SEQ ID 406: Coding sequence of E2-cassette
atgagagttcctgcacaattattaggattattattattatggtttcctgg atctaggtgctacaagcaccagagcgagagctacctgaagtattgtacaa ttacaaatacatctacaagcatgaactgcgattgcccttttggcaccttc accaggaatacagagtctagattttctattcctagattttgtccagtgaa gatcaatagcagcaccttcatctgctcttggggatcttggtggtggtttg ctgaaaatattacaagaccttatacagatgtgggaatgcctccagctcca atttctgctctgtgttacatctacagcaataatgatcctcctccttggta tcataataccaccatcattcctcagaactgcagaaatagcaccgttgatc ctacaacagctccttgtagagataaatggggaaatgctacagcttgtatt cttgacagaagaagcagattttgcggcgattgttatggaggatgctttta cacaaatggaagccatgatagatcttgggatagatgtggaatcggctaca gagatggactgattgaatttgttcagttaggccagattagacccaatatc agcaatacaaccatcgaactgcttgctggagcttctttagttattgcttc
```

-continued
```
tggattaagacctggatttggatgttctagagctcatggagttgtgcact gctatagatgtccttcttacagagatttagagcaatttggacctggactt ggaaaatgggtgcctttacctggagaacctgttcctgaattatgtattaa tcctcaatgggctagaagaggattcagaatgagcaataaccctctgtctc tgctgcagacatttgttgaagatatctttcttgcccctttctgtaatcct acacctggaagagttagagtgtgcaacaatacagccttttatcctagagg aggaggatttgttcaacttattggcgatgttcaggttctgacccctaata caggatctggatctggacatcatcatcatcatcatcatcactaa
```

An 8× Histidine tag was cloned in frame at the carboxy terminus of the E2 ORF for purification. The plasmid encoding HPgV-2 E2 was transiently transfected into HEK293-6E (human embryonic kidney—6E) suspension cells using Lipofectamine 2000 transfection reagent (Life Technologies, Carlsbad, Calif., USA). After 6 days the cell cultures were centrifuged (1200 rpm 10 min) and the supernatant was collected. The supernatant was concentrated using an Amicon Ultra filter (EMD Millipore, Billerica, Mass., USA). Cells were lysed on ice for 30 minutes using phospho-buffered saline (PBS) with 1% triton X-100. Cell debris was spun down by centrifugation for 10 minutes at 15000 rpm, the supernatant was collected. Cell lysates and concentrated supernatants were run on a 4-20% SDS PAGE gradient gel (Novex by Life Technologies Carlsbad, Calif., USA) and Western blot was performed using the Western-Breeze kit (Novex by Life Technologies) in conjunction with an anti-His alkaline phosphatase (AP) conjugated primary antibody (Novex by Life Technologies, Carlsbad, Calif., USA). Protein was visualized using the BCIP/NBT chromagen staining (Novex by Life Technologies) and the Bio-Rad Imager (BioRad GelDoc EZ Imager using Image Lab v4.0 software). The predicted molecular weight of the expressed HPgV-2 E2 construct is 39.6 kDa. HPgV-2 E2 from the cell lysate ran at approximately 50 kDa and the concentrated HPgV-2 E2 from the supernatant ran a range of molecular weights between 50-75 kDa suggesting glycosylation of the secreted form of the protein (FIG. 24A), which may cause the protein to migrate more slowly during electrophoresis.

Figure 24A:
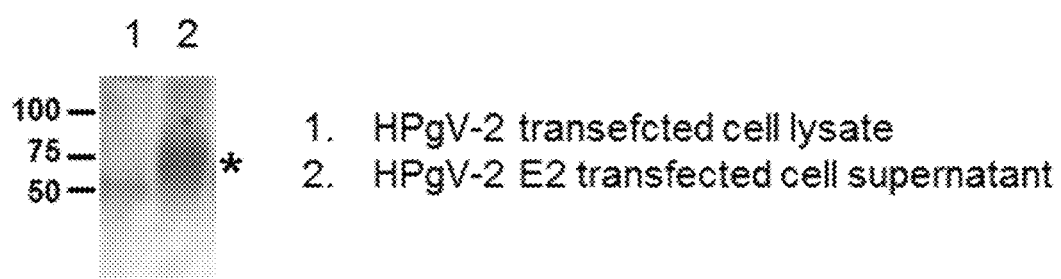
FIG. 24A shows anti-His Western blot of 293F cells transfected with HPgV-2 E-E2 expression plasmid. Supernatants were collected and concentrated. Cells were lysed in sample buffer (2× Laemmli sample buffer+2-mercaptoethanol (BioRad, Hercules, Calif., USA). Samples were run on a 4-12% SDS-PAGE gel and transferred to a PDVF membrane. Western blot was performed using the Western Breeze kit and an anti-His (C-term)/Alkaline phosphatase primary antibody (Novex by Life Technologies, Carlsbad, Calif., USA).
Figure 24B:
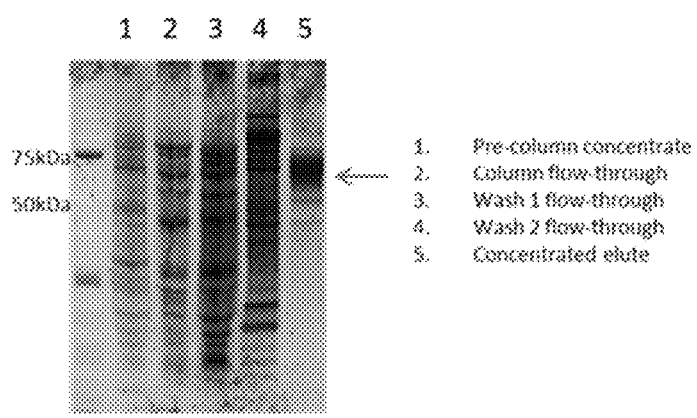
FIG. 24B shows purification of HPgV-2 E2. Concentrated HPgV-2 E2 supernatant was run over a Nickel column and eluted with 250 mM imidazole. Fraction of pre-column concentrate, flow-through, washes, and eluted protein were diluted 1:2 with Laemelli sample buffer containing beta-mercaptoethanol and run on a 4-12% SDS-PAGE gel followed by visualizing with Oriole protein stain (BioRad, Hercules, Calif., USA). Arrow indicates purified HPgV-2 E2.
Figure 24C:
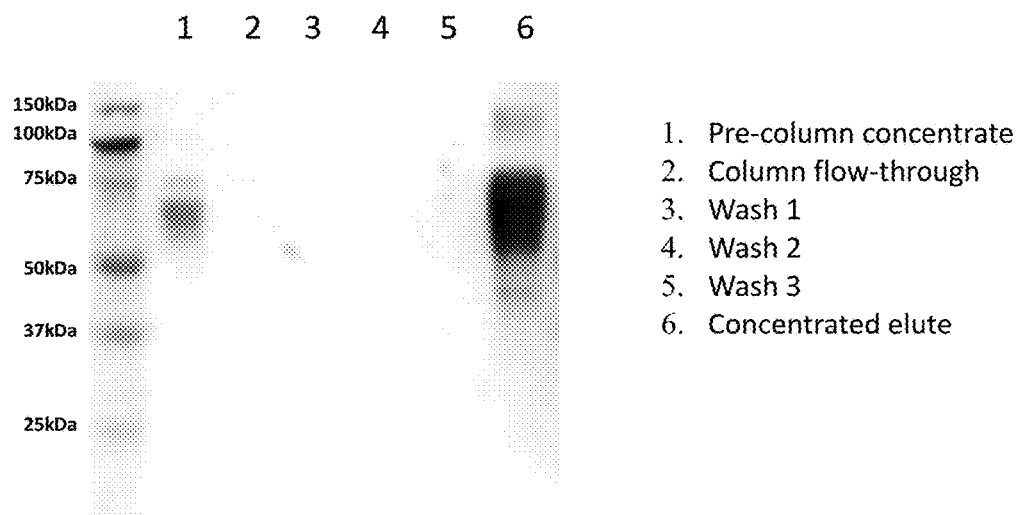
FIG. 24C shows western blot of purified HPgV-2 E2. Fractions diluted 1:2 in Laemelli sample buffer with beta-mercaptoethanol and run on 4-12% SDS-PAGE gel as above and transferred to PDVF membrane. Western blot was performed using the Western Breeze kit and an anti-His (C-term)/Alkaline phosphatase primary antibody (Novex by Life Technologies, Carlsbad, Calif., USA). Arrow indicates purified HPgV-2 E2.

HPgV-2 E2 from concentrated supernatant was purified under native conditions using a nickel (Ni+) agarose packed affinity column (His Bind resin, Novagen, EMD Millipore, Billerica, Mass., USA). Unbound material (flow-through) and eluted bound material was run on a 4-20% SDS-PAGE gel followed by staining with Oriole protein stain (Bio-Rad) or Western blotted using an anti-His-AP antibody (Western-Breeze, Novex by Life Technologies, Carlsbad, Calif., USA). Protein staining showed multiple molecule weights of bound and eluted material between 50-70 kDa (FIG. 24B), consistent with size detected by initial Western blot of HPgV-2 E2 transfected cell supernatants (FIG. 24A). Western blot showed multiple molecular weight bands between 60-70 kDa (FIG. 24C).

Figure 24D:
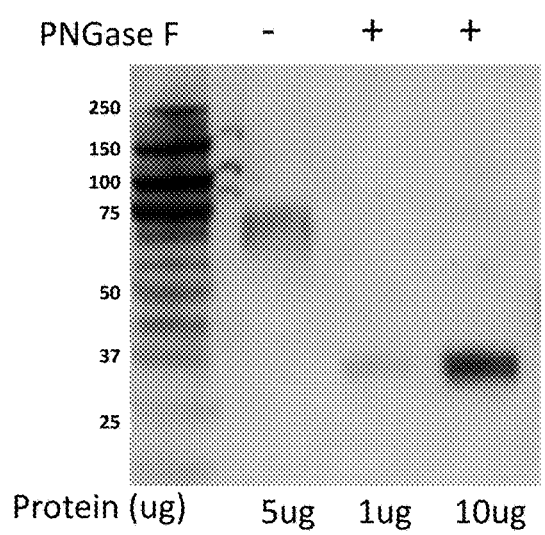
FIG. 24D shows PNGase F removal of HPgV-2 E2 glycosylation. Purified HPgV-2 E2 was denatured and incubated with PNGase F followed by resolution by electrophoresis on a 10% SDS-PAGE gel.

PNGase F (Peptide-N-Glycosidase F) treatment of purified HPgV-2 E2 was performed to confirm the larger than estimated molecular weight of the purified protein was due to post-translational glycosylation. HPgV-2 has 10 potential asparagine-linked glycosylation sites which can shift electrophoretic mobility of the 39.6 kDa predicted molecular weight. PNGase F is an enzyme that specifically cleaves between the innermost GlcNAc and asparagine residues of N-linked glycoproteins. Purified HPgV-2 E2 was denatured and incubated with PNGase F (New England Biolabs (NEB), Ipswich, Mass., USA) for 1 hour at 37° C. followed by SDS-PAGE analysis of treated and untreated proteins (FIG. 24D). Purified HPgV-2 E2 untreated with PNGase F had a molecular weight 60-70 kDa, PNGase F treated HPgV-2 E2 had a molecular weight closer to the 37 kDa marker by SDS-PAGE gel. The PNGase F treated E2 ran closer to the predicted molecular weight suggesting the majority of the protein was deglycosylated.

Additionally, a plasmid encoding HPgV-1 (GBV-C) E2 without the carboxy terminal transmembrane domain was also expressed in a mammalian expression vector as described above. Upon expression in mammalian cells the protein is secreted as a fusion with a 8× hisitidine tag at the carboxy terminus.

Serology Testing of Purified HpGV-2 E2 with PCR+/Ab+ Samples.

Figure 25:
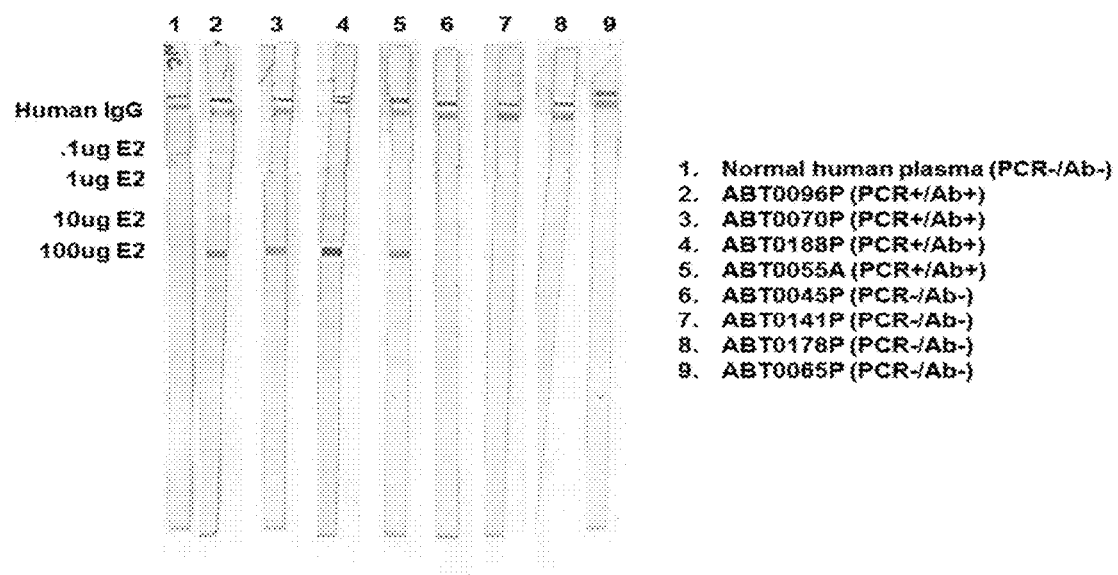
FIG. 25 shows seroreactivity of HPgV-2 PCR+ samples for glycoprotein E2. Purified HPgV-2 E2 was bound to nitrocellulose membrane and probed with a 1:100 dilution of serum (samples indicated above). Strip blots were washed and visualized using a goat-anti-Human alkaline phosphatase secondary antibody and BCIP/NBT chromogen substrate. All samples were reactive with human IgG on the membrane but only the HPgV-2 PCR+ samples were reactive with purified E2. Samples ABT0096P, ABT0070P, ABT0188P were from ProMedDx and ABT0055A was from the American Red Cross (ARC).

Antibodies against the purified HPgV-2 E2 in PCR+/Ab+ samples were assessed by performing a slot blot containing dilutions of HPgV-2 purified E2 protein. Purified protein was bound to nitrocellulose membrane at a titration of 0.1 ug/ml, 1 ug/ml, 10 ug/ml, and 100 ug/ml. Unbound protein was washed away and membranes were air-dried. 1:100 dilutions of PCR+/Ab+ samples ABT0096P, ABT0070P, ABT0188P, and ABT0055A were incubated with the slot blots. These samples were reactive to a pool of HPgV-2 peptides (3, 4, 9, and 16). Negative controls were normal human plasma and samples negative for HPgV-2 RNA and negative for antibodies to the pool of HPgV-2 peptides 3, 4, 9, and 16. Antibodies were visualized using a goat anti-human secondary antibody conjugated to alkaline phosphatase and BCIP/NBT chromogen substrate (FIG. 25). The HPgV-2 PCR+/Ab+ samples tested had strongly detectable antibodies to the 100 ug band and were faintly reactive to the 10 ug E2 band. This data shows that PCR+ individuals make antibodies to the native form of HPgV-2 E2. Further studies need to be done to determine if E2 antibodies are present following viremia. Also this data indicates that HPgV-2 is a serologic marker of infection. Additionally a panel of samples from first-time plasmapheresis donors, testing positive for, both by an antibody test for HCV (Abbott Laboratories, Abbott Park Ill. 60064) and a HCV RNA test (Bayer Versant HCV RNA 3.0 assay (from ProMedDx, Norton, Mass.)) were used to probe the slot blots (FIG. 25—samples ABT0045P, ABT0141P, ABT0178P, ABT0065P).

Samples which were HPgV-2 RNA positive and positive for antibodies to the peptides were used to validate the utility of purified HPgV-2 E2 when coated onto a solid phase microparticle and used in an ARCHITECT assay (See Example 4). Briefly, Spherotech magnetic microparticles (Lake Forest, Ill., USA) were coated with 100 ug/ml of purified E2 protein using N-(3-Dimethylaminopropyl)-N'-ethylcarbodiimide hydrochloride (EDAC, Sigma-Aldrich, St. Louis, Mo. 63103) to crosslink the purified protein to the magnetic microparticle. The E2 coupled microparticles were run with selected HPgV-2 RNA positive samples in an indirect immunoassay using the ABBOTT ARCHITECT instrument (described above, Example 3) where bound antibodies from the sample were detected with a mouse anti-human acridinium conjugated secondary antibody (Table 18). Additionally samples negative for HPgV-2 RNA and antibody response were tested with the E2 coated microparticles. Samples reactive on the slot blot were also reactive when HPgV-2 E2 was coated onto microparticles and used in an ARCHITECT assay (Table 18).

TABLE 18

ARCHITECT assay using HPgV-2 coated microparticles. Signal to cut-off (S/CO) was set at 10 times NC. A sample was considered positive (reactive) for antibodies to HPgV-2 E2 when the S/CO > 1. Samples ABT0029A and ABT0128A had elevated signals but not over the cut-off.

| sample | HPgV-2 RNA+ | Abs to HPgV-2 peptide pool 3, 4, 9, 16 S/CO | Abs to purified HPgV-2 E2 S/CO |
|---|---|---|---|
| NC | Neg | Neg | — |
| ABT0029A | Pos | Pos | 0.6 |
| ABT0055A | Pos | Pos | 6.6 |
| ABT0070P | Pos | Pos | 4.1 |
| ABT0096P | Pos | Pos | 6.4 |
| ABT0128A | Pos | Pos | 0.9 |
| ABT0188P | Pos | Pos | 15.7 |
| ABT0239A | Pos | Neg | .05 |
| HPgV-2 RNA negative/Antibody negative samples | | | |
| ABT0045P | Neg | Neg | .07 |
| ABT0141P | Neg | Neg | .004 |
| ABT0178P | Neg | Neg | .02 |
| ABT0065P | Neg | Neg | .007 |

Within the HPgV-2 RNA positive samples, the correlation between having antibodies to the peptides and antibodies to the E2 protein was high. 4 out of 6 HPgV-2 RNA positive samples had a detectable antibody response which was over 10 times the negative control signal to the E2 recombinant protein coated microparticles. The remaining 2 samples had elevated signals over background suggesting there is a mild antibody response, which may be detected upon further optimization of the assay A population of normal human donor plasma (n=100) was also screened for reactivity to HPgV-2 E2 to indicate current or past infection. No samples were detected with a signal to cutoff (S/CO) greater than 1 suggesting HPgV-2 is a low frequency endemic virus in the US population.

Figure 26:
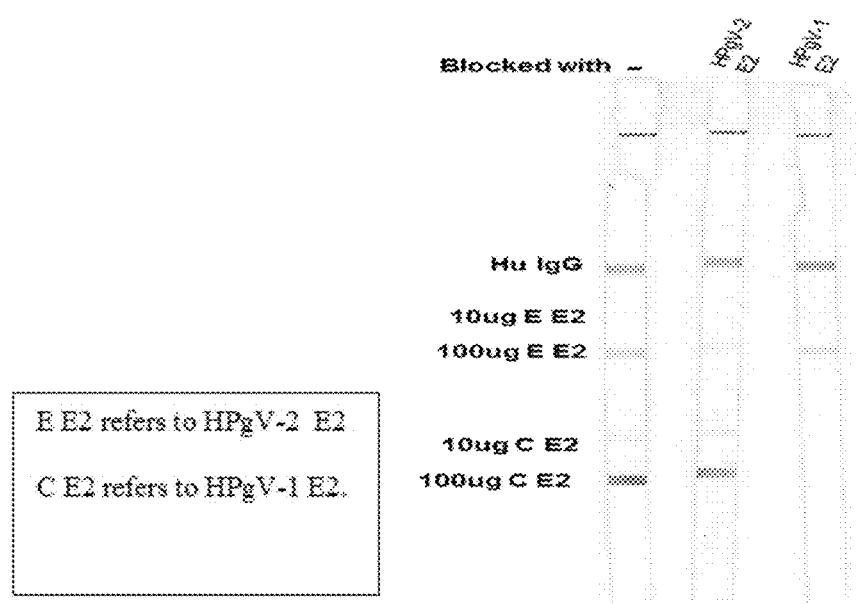
FIG. 26 shows blocking immunoreactivity on slot blot with homologous, not heterologous, proteins. 15 ul of sample ABT0055A was incubated with PBS, 10 µg of HPgV-2 E2, or 10 µg of HPgV-1 E2 in a total of 100 µl of sample diluent (20 mM TRIS-HCl, 0.5M NaCl, 0.3% Tween-20 pH 8, 5% non-fat dry milk, 10% heat inactivated newborn bovine serum) for 1 hour at room temperature (25° C.) with rotation. Samples were diluted with 1.4 mls of sample diluent then incubated with pre-made slot blots bound with human IgG, HPgV-2 E2 (10 µg and 100 µg), and HPgV-1 E2 (10 µg and 100 µg). Bound antibodies were detected with an anti-human IgG conjugated to alkaline phosphatase.

Because many of the HPgV-2 RNA+ samples also have antibodies to HPgV-1 E2, cross-reactivity to either HPgV-1 or -2 E2 was evaluated. A blocking experiment was performed where purified HPgV-1 or -2 E2 was prebound to a sample that was HPgV-1 E2 Ab+ and HPgV-2 RNA+/E2Ab+. The sample prebound to with either HPgV-1 or HPgV-2 was used to probe a slot blot containing both purified HPgV-1 and HPgV-2 E2 glycoproteins. Pre-binding with HPgV-2 E2 reduced binding to the purified HPgV-2 E2 on the slot blot and pre-binding with HPgV-1 E2 reduced binding of the sample to HPgV-1 E2 (FIG. 26). There was a minimal decrease in binding to the heterologous proteins not used in the pre-binding suggesting the immunoreactivity detected by slot blot analysis is specific.

Example 7

Expression, Purification, and Serology Using HPgV-2 NS4A/4B Fusion Protein.

Design, Expression, and Purification of Plasmid Containing NS4A/4B Fusion in *Esherichia coli* (*E. coli*).

This example describes the design of a maltose binding protein fusion to domains of the HPgV-2 proteins NS4A and NS4B and the subsequent expression and purification from *E. coli*. Briefly, using the Protean 3D program (DNASTAR, Madison, Wis., USA) a 81 amino acid segment of HPgV-2 NS4A-4B was predicted to have cytoplasmic localization (SEQ ID NO:407).

Nucleic acid sequence of encoded 81 amino acid HPgV-2 NS4A-4B peptide (SEQ:407):

```
ATG GCC CTT GTT CCC AGC GCT GTG TGG AGT GTT GAA
GTC CGC CCC GCA GGC GTG ACG CGC CCT GAT GCC ACC
GAT GAA ACC GCT GCG TAC GCT CAA CGC TTG TAT CAG
GCC TGC GCC GAT TCA GGT ATC TTT GCG TCA CTT CAA
GGA ACC GCG AGT GCG GCG TTG GGC AAG CTG GCG GAT
GCC TCG CGT GGC GCG AGT CAA TAC CTG GCA GCC GCC
CCA CCA TCA CCT GCC CCA CTG GTG CAG GTA TTA
```

Figure 27:
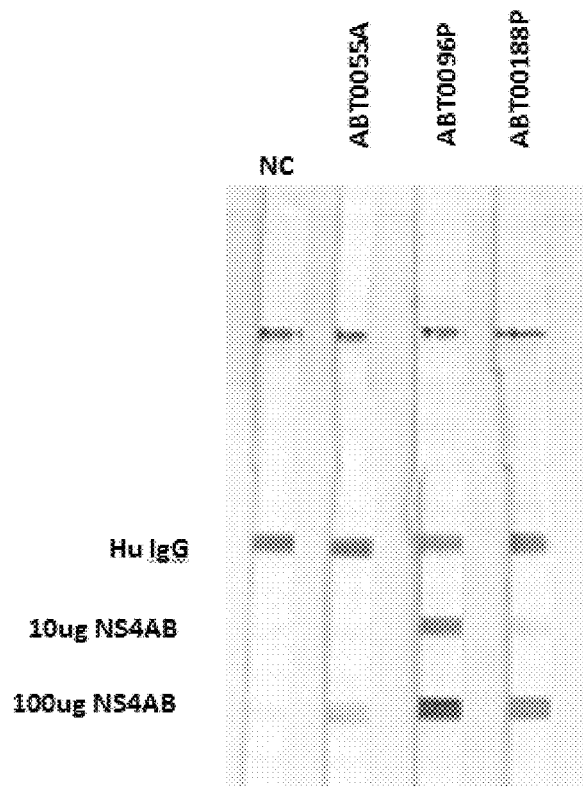
FIG. 27 shows samples ABT0055A, ABT0096P, ABT0188P were incubated with nitrocellulose membrane containing bound NS4AB protein. Antibodies against the indicated proteins are shown as dark lines for each sample.

This region was chosen for expression in the pMAL-C5X vector that allows for an amino-terminal maltose binding fusion and a 6× histidine tag was designed at the C-terminal end of the construct, all under an IPTG inducible promoter (Genscript, Piscataway, N.J., USA). The construct was expressed in the BL21 E. coli strain and following IPTG induction for four hours at 37 C the cells were lysed and the soluble protein was purified using Probond nickel purification system (Invitrogen, Grand Island, N.Y., USA). A Western blot was performed (WesternBreeze, Invitrogen, Grand Island, N.Y., USA) using an anti-His antibody (Invitrogen, Grand Island, N.Y., USA) and a single band at 50 kDa was detected (42 kDa MBP+8 kDa NS4AB) in the eluted material (FIG. 27A).

To validate the purified material both slot blot and an indirect ARCHITECT immunoassay were performed using known HPgV-2 RNA positive samples. For the slot blot, 10 and 100 ug of purified material was passively bound to a nitrocellulose membrane (Invitrogen, Grand Island, N.Y., USA) followed by washing away unbound protein and blocking of the membrane. Antibodies to the purified NS4AB were detected using slot blots containing bound NS4AB for the samples ABT0055A, ABT0096P, ABT0188P and not for the negative control plasma (FIG. 27B). Bound antibodies were detected using a goat anti-human alkaline phosphatase conjugated secondary antibody (SouthernBiotech, Birmingham, Ala., USA) conjugated to alkaline phosphatase, colormeric detection was provided by BCIP/NBT substrate (SigmaFAST, Sigma-Aldrich, St. Louis, Mo. 63103).

To test the purified NS4AB protein in an automated immunoassay, Spherotech magnetic microparticles (Lake Forest, Ill., USA) were coated with 50 ug/ml of purified NS4AB protein using N-(3-Dimethylaminopropyl)-N'-ethylcarbodimide hydrochloride (EDAC, Sigma-Aldrich, St. Louis, Mo. 63103) to crosslink the purified protein to the magnetic microparticle. The NS4AB coupled microparticles were run with selected HPgV-2 RNA positive samples in an indirect immunoassay using the ABBOTT ARCHITECT instrument (described above, Example 3) where bound antibodies from the sample were detected with a mouse anti-human acridinium conjugated secondary antibody (Table 19).

TABLE 19

Indirect assay of antibodies to NS4AB in HPgV-2 RNA positive samples.

| sample | S/CO* |
|---|---|
| ABT0029A | 1.4 |
| ABT0055A | 0.4 |
| ABT0070P | 14.8 |
| ABT0096P | 9.8 |
| ABT0128A | 0.8 |
| ABT0188P | 1.9 |

*S/CO = signal/cut-off. S/CO > 1 is considered reactive for antibodies to NS4AB protein. The cut-off was determined as 10 times the signal for the negative control.

A population of normal human donor plasma (n=100) was also screened for reactivity to HPgV-2 NS4AB to indicate current or past infection. No samples were detected with a signal to cutoff (S/CO) greater than 1 suggesting HPgV-2 is a low frequency endemic virus in the US population.

Example 8

Detection of HPgV-2 Antigens and Generation of Hyperimmune Serum in Rabbits

New Zealand Rabbits approximately 1 year of age were selected for the generation of antibodies to HPgV-2 peptides. For the first immunization, each rabbit was inoculated with 1.0 mg of peptides (peptides 4, 5, and 9 from Table 3, Example 4) solubilized in 0.9% saline mixed with 0.5 ml of adjuvant. Approximately 10 weeks after the first immunization serum was obtained from the rabbits and tested for antibodies to the immugens. The rabbits were immunized five additional times over the next 8 months.

Antibody production was determined for each rabbit by using an indirect assay on the ARCHITECT. The assay format utilized 800 ng/ml of each respective biotinylated peptide diluted into a buffered solution along with 10 ul of rabbit serum and 0.05% of microparticles coated with streptavidin for capturing peptide/antibody complexes via the biotin tag on each peptide. After an 18 minute incubation, the magnetic microparticles were washed and reacted with a conjugate diluent containing 10 ng/ml of acridinylated goat anti-rabbit IgG to detect rabbit antibodies bound to the solid phased via immunocomplex. Samples were diluted 1:100 in ARCHITECT wash buffer solution prior to testing. The signal (S) expressed in relative light units (rlu) for the negative control (NC) rabbit (not inoculated with any of the HPgV-2 peptides) ran between 197 and 251. The S/N values were obtained for the five rabbits immunized with HPgV-2 peptides are found in Table 20. The S/N values for rabbits 13212 and 13213 were 1195 and 1131.1 for reactivity to peptide 4, rabbits 13214 and 13215 were 1056 and 1160 for peptide 5, and rabbit 13216 was 849 for peptide 9, all rabbits were negative for peptides they were not immunized against. Rabbits showed specific antibodies for the immunogen peptides (Table 20) and antibodies were not cross reactive to the other HPgV-2 peptides. Thus these hyperimmune sera can be utilized to determine the presence of HPgV-2 antigens in various tissues (blood) or organs (liver, etc) and may be useful in determining the cell tropism of this virus.

TABLE 20

Serum from rabbits immunized with HPgV-2 peptides show specific reactivity to the immunogen sequence.

| Rabbit Number | Immunogen peptide (Genscript) | Testing with 800 ng/ml BT-peptides | | |
|---|---|---|---|---|
| | | peptide 4 1st bleed | peptide 5 | peptide 9 |
| 13212 | PV4A (peptide 4) | 1195.0 | 0.7 | 0.5 |
| 13213 | PV4A (peptide 4) | 1131.1 | 1.5 | 1.0 |
| 13214 | PV5A (peptide 5) | 1.2 | 1055.9 | 0.6 |
| 13215 | PV5A (peptide 5) | 1.6 | 1160.0 | 0.8 |
| 13216 | PV9A (peptide 9) | 1.1 | 1.4 | 849.4 |

Bleeds from HPgV-2 peptide immunized, or non-immunized rabbit serum (NC) were assayed for peptide specific antibodies by ARCHITECT indirect assay. Shown are the relative light units (rlus) for the negative control (non-immunized rabbit serum) and the signal to noise (S/N) for each rabbit immunized with the indicated peptides.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a synthetic DNA nucleic acid molecule,
    wherein said synthetic DNA nucleic acid molecule comprises a nucleotide sequence at least 12 nucleotides in length that hybridizes under stringent conditions to a portion of an HPgV-2 genomic sequence selected from the group consisting of: the NS2 gene, the 5' UTR, the S gene, the E1 gene, the E2 gene, the NS4a gene, the NS4b gene, and the 3' UTR, and
    wherein said genomic sequence of HPgV-2 is shown in SEQ ID NO:1, 75, or 299-303.

2. The composition of claim 1, wherein said synthetic DNA nucleic acid molecule comprises a detectable label.

3. The composition of claim 1, wherein said synthetic DNA nucleic acid molecule hybridizes to said NS2 gene.

4. The composition of claim 1, wherein said synthetic DNA nucleic acid molecule comprises at least one modified base.

5. The composition of claim 1, further comprising a heterologous nucleic acid sequence, and wherein said synthetic nucleic acid molecule is linked to said heterologous nucleic acid sequence.

6. The composition of claim 1, wherein said synthetic DNA nucleic acid molecule hybridizes to said S gene.

7. The composition of claim 1, wherein said synthetic DNA nucleic acid molecule hybridizes to said E1 gene.

8. The composition of claim 1, wherein said synthetic DNA nucleic acid molecule hybridizes to said E2 gene.

9. The composition of claim 1, wherein said synthetic DNA nucleic acid molecule hybridizes to said NS4a gene.

10. The composition of claim 1, wherein said synthetic DNA nucleic acid molecule comprises a primer that hybridizes to the NS2 gene of HPgV-2, wherein said primer comprises the nucleic acid sequence GTGGGACACCT-CAACCCTGAAG (SEQ ID NO: 413).

11. The composition of claim 1, wherein said synthetic DNA nucleic acid molecule comprises a primer that hybridizes to the 5' UTR of HPgV-2, wherein said primer comprises the nucleic acid sequence CGCTGATCGTG-CAAAGGGATG (SEQ ID NO: 416).

12. The composition of claim 1, wherein said synthetic DNA nucleic acid molecule comprises a primer that hybridizes to the 5' UTR of HPgV-2, wherein said primer comprises the nucleic acid sequence GCTCCACGGACGTCA-CACTGG (SEQ ID NO: 417).

13. The composition of claim 1, wherein said synthetic DNA nucleic acid molecule comprises a labeled probe that hybridizes to the 5' UTR of HPgV-2, wherein said probe comprises the nucleic acid sequence GCACCACTCCGTA-CAGCCTGAT (SEQ ID NO: 418).

14. The composition of claim 1, wherein said synthetic DNA nucleic acid molecule hybridizes to said NS4b gene.

15. The composition of claim 1, wherein said synthetic DNA nucleic acid molecule hybridizes to said 5' UTR.

16. The composition of claim 1, wherein said synthetic DNA nucleic acid molecule hybridizes to said 3' UTR.

17. The composition of claim 1, wherein said at synthetic DNA nucleic acid molecule is least 15 nucleotides in length.

18. The composition of claim 1, wherein said genomic sequence of HPgV-2 is shown in SEQ ID NO:303.

19. The composition of claim 1, wherein said genomic sequence of HPgV-2 is shown in SEQ ID NO:300.

20. The composition of claim 1, wherein said genomic sequence of HPgV-2 is shown in SEQ ID NO:301.

21. The composition of claim 1, wherein said genomic sequence of HPgV-2 is shown in SEQ ID NO:299.

22. The composition of claim 1, wherein said genomic sequence of HPgV-2 is shown in SEQ ID NO:302.

23. A composition comprising a synthetic nucleic acid molecule,
    wherein said synthetic nucleic acid molecule comprises a nucleotide sequence at least 12 nucleotides in length that hybridizes under stringent conditions to a portion of an HPgV-2 genomic sequence selected from the group consisting of: the NS2 gene, the 5' UTR, the S gene, the E1 gene, the E2 gene, the NS4a gene, the NS4b gene, and the 3' UTR, and wherein said genomic sequence of HPgV-2 is shown in SEQ ID NO: 1, 75, or 299-303;
    wherein the synthetic nucleic acid molecule is linked to a fluorescent label, chemiluminescent label or enzymatic label, a heterologous nucleic acid sequence or a solid support or the synthetic nucleic acid molecule comprises at least one modified base selected from the group consisting of: phosphorothioate, boranophosphate, 4'-thio-ribose, locked nucleic acid, 2'-0-(2'-methoxyethyl), 2'-0-methyl, 2'-fluoro, 2'-deoxy-T-fluoro-b-D-arabinonucleic acid, phosphonoacetate, 2'-3'-seco-RNA, Morpholino nucleic acid analog, Peptide nucleic acid analog, phosphorodithioate, phosphoramidate, methylphosphonate, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, 2-aminopurine, 5-amino-allyluracil, 5-hydroxymethylcytosine, 5-iodouracil, 5-nitroindole, 5-propynylcytosine, 5-propynyluracil, hypoxanthine, N3-methyluracil, N6,N6-dimethyladenine, purine, C-5-propynyl cytosine, C-5-propynyl uracil, and difluorotouyl.

24. The composition of claim 23, wherein said synthetic nucleic acid molecule hybridizes to said NS2 gene.

25. The composition of claim 23, wherein said synthetic nucleic acid molecule hybridizes to said S gene.

26. The composition of claim 23, wherein said synthetic nucleic acid molecule hybridizes to said E1 gene.

27. The composition of claim 23, wherein said synthetic nucleic acid molecule hybridizes to said E2 gene.

28. The composition of claim 23, wherein said synthetic nucleic acid molecule hybridizes to said NS4a gene.

29. The composition of claim 23, wherein said synthetic nucleic acid molecule hybridizes to said NS4b gene.

30. The composition of claim 23, wherein said synthetic nucleic acid molecule hybridizes to said 5' UTR.

31. The composition of claim 23, wherein said synthetic nucleic acid molecule hybridizes to said 3' UTR.

32. The composition of claim 23, wherein said synthetic nucleic acid molecule is at least 15 nucleotides in length.

33. The composition of claim 23, wherein said genomic sequence of HPgV-2 is shown in SEQ ID NO: 303.

34. The composition of claim 23, wherein said genomic sequence of HPgV-2 is shown in SEQ ID NO: 300.

35. The composition of claim 23, wherein said genomic sequence of HPgV-2 is shown in SEQ ID NO: 301.

36. The composition of claim 23, wherein said genomic sequence of HPgV-2 is shown in SEQ ID NO: 299.

37. The composition of claim 23, wherein said genomic sequence of HPgV-2 is shown in SEQ ID NO: 302.

* * * * *